(12) United States Patent
Lang et al.

(10) Patent No.: US 12,404,315 B2
(45) Date of Patent: Sep. 2, 2025

(54) PROTEASE-ACTIVATING CD45-GATE CAR

(71) Applicants: ALLOGENE THERAPEUTICS, INC., South San Francisco, CA (US); PFIZER INC., New York, NY (US)

(72) Inventors: Shanshan Lang, San Mateo, CA (US); Thomas John Van Blarcom, Oakland, CA (US); Michael Thomas Bethune, Castro Valley, CA (US); Siler Panowski, Berkeley, CA (US); Nguyen Tan, Berkeley, CA (US); Yi Zhang, Foster City, CA (US); Barbra Johnson Sasu, San Francisco, CA (US); Zhe Li, Burlingame, CA (US)

(73) Assignees: Allogene Therapeutics, Inc., South San Francisco, CA (US); Pfizer Inc., New York, NY (US)

(*) Notice: Subject to any disclaimer, the term of this patent is extended or adjusted under 35 U.S.C. 154(b) by 663 days.

(21) Appl. No.: 17/557,654

(22) Filed: Dec. 21, 2021

(65) Prior Publication Data
US 2022/0227832 A1    Jul. 21, 2022

Related U.S. Application Data

(60) Provisional application No. 63/289,984, filed on Dec. 15, 2021, provisional application No. 63/128,667, filed on Dec. 21, 2020.

(51) Int. Cl.
| | |
|---|---|
| C07K 16/28 | (2006.01) |
| A61K 39/395 | (2006.01) |
| A61K 40/11 | (2025.01) |
| A61K 40/15 | (2025.01) |
| A61K 40/31 | (2025.01) |
| A61K 40/42 | (2025.01) |
| C07K 14/705 | (2006.01) |
| C07K 14/725 | (2006.01) |
| C07K 19/00 | (2006.01) |
| C12N 5/078 | (2010.01) |
| C12N 5/0783 | (2010.01) |
| C12N 5/10 | (2006.01) |
| C12N 15/79 | (2006.01) |

(52) U.S. Cl.
CPC .......... *C07K 14/7051* (2013.01); *A61K 40/11* (2025.01); *A61K 40/15* (2025.01); *A61K 40/31* (2025.01); *A61K 40/4224* (2025.01); *A61K 40/4252* (2025.01); *A61K 40/4257* (2025.01); *C07K 14/70521* (2013.01); *C07K 14/70596* (2013.01); *C07K 16/28* (2013.01); *C07K 16/289* (2013.01); *C07K 19/00* (2013.01); *C12N 5/0634* (2013.01); *C12N 5/0636* (2013.01); *C12N 5/10* (2013.01); *C12N 15/79* (2013.01); *A61K 2239/31* (2023.05); *A61K 2239/38* (2023.05); *A61K 2239/49* (2023.05); *A61K 2239/55* (2023.05); *A61K 2239/59* (2023.05); *C07K 2317/22* (2013.01); *C07K 2317/24* (2013.01); *C07K 2317/31* (2013.01); *C07K 2317/569* (2013.01); *C07K 2319/01* (2013.01); *C07K 2319/31* (2013.01); *C07K 2319/50* (2013.01)

(58) Field of Classification Search
CPC ........ C07K 16/18; C07K 16/24; C07K 16/28; C07K 16/26; C07K 16/30; C07K 19/00; C07K 2319/01; C07K 2319/31; C07K 2319/50; C07K 2317/22; C07K 2317/24; C07K 2317/31; C07K 2317/569; C07K 2319/00; C07K 16/289; A61K 2039/505; A61K 39/3955; A61K 39/39558
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |

(Continued)

FOREIGN PATENT DOCUMENTS

| | | |
|---|---|---|
| CN | 1568198 A | 1/2005 |
| CN | 109628492 A | 4/2019 |

(Continued)

OTHER PUBLICATIONS

Abbott et al. To go or not to go? Biological logic gating engineered T cells. Immunother Cancer 10: e004185, 2022 (11 total pages).*
Bhattacharya et al. Impact of genetic variation on three dimensional structure and function of proteins. PLoS ONE 12(3): e0171355, 2017.*

(Continued)

*Primary Examiner* — Bridget E Bunner
(74) *Attorney, Agent, or Firm* — Allogene Therapeutics, Inc.

(57) ABSTRACT

A reversibly gated effector polypeptide e.g. a chimeric antigen receptor (protease-activating CD45-gate CAR) comprising an extracellular CD45 recruiting domain, a protease-cleavable linker, and a polypeptide comprising an extracellular ligand binding domain, a transmembrane domain, and an intracellular domain. Nucleic acids including vectors and expression vectors that encode the protease-activating CD45-gate CAR and cells including immune cells such as T cells that comprise and express the nucleic acids. Methods of treatment of various conditions including various forms of cancer comprising administering the cells including CAR T cell therapy. In some embodiments, the CD45 gate at least partially inhibits activation of the protease-activating CD45-gate CAR when the protease-activating CD45-gate CAR binds antigen. The inhibition is at least partially diminished, relieved and/or eliminated when the protease-activating CD45-gate CAR is exposed to a protease that can cleave the linker.

35 Claims, 27 Drawing Sheets

Specification includes a Sequence Listing.

(56) References Cited

U.S. PATENT DOCUMENTS

| | | | |
|---|---|---|---|
| 4,754,065 | A | 6/1988 | Levenson et al. |
| 4,800,159 | A | 1/1989 | Mullis et al. |
| 5,037,743 | A | 8/1991 | Welch et al. |
| 5,143,830 | A | 9/1992 | Holland et al. |
| 5,858,358 | A | 1/1999 | June et al. |
| 5,883,223 | A | 3/1999 | Gray et al. |
| 6,011,138 | A | 1/2000 | Reff et al. |
| 6,106,834 | A | 8/2000 | Lazarovits et al. |
| 6,352,694 | B1 | 3/2002 | June et al. |
| 6,534,055 | B1 | 3/2003 | June et al. |
| 6,692,964 | B1 | 2/2004 | June et al. |
| 6,797,514 | B2 | 9/2004 | Brenson et al. |
| 6,867,041 | B2 | 3/2005 | Berenson et al. |
| 6,887,466 | B2 | 5/2005 | June et al. |
| 6,905,680 | B2 | 6/2005 | June et al. |
| 6,905,681 | B1 | 6/2005 | June et al. |
| 6,905,874 | B2 | 6/2005 | Berenson et al. |
| 7,067,318 | B2 | 6/2006 | June et al. |
| 7,144,575 | B2 | 12/2006 | June et al. |
| 7,172,869 | B2 | 2/2007 | June et al. |
| 7,175,843 | B2 | 2/2007 | June et al. |
| 7,232,566 | B2 | 6/2007 | June et al. |
| 7,622,119 | B2 | 11/2009 | Sugiyama |
| 7,709,226 | B2 | 5/2010 | Foote |
| 9,169,328 | B2 | 10/2015 | Springgs et al. |
| 10,808,035 | B2 | 10/2020 | Chmielewsk et al. |
| 10,815,301 | B2 | 10/2020 | Kochenderfer et al. |
| 11,077,144 | B2 | 8/2021 | Galetto et al. |
| 2006/0121005 | A1 | 6/2006 | Berenson et al. |
| 2013/0165389 | A1 | 6/2013 | Schellenberger et al. |
| 2016/0152725 | A1 | 6/2016 | Cheung |
| 2017/0204139 | A1 | 7/2017 | Moore et al. |
| 2018/0148503 | A1 | 5/2018 | Scheinberg et al. |
| 2020/0231699 | A1 | 7/2020 | Terrett et al. |
| 2020/0246383 | A1 | 8/2020 | Lebeau et al. |
| 2021/0115102 | A1 | 4/2021 | Winston et al. |
| 2021/0206848 | A1 * | 7/2021 | Garcia ............... C07K 16/2818 |
| 2021/0269501 | A1 | 9/2021 | Powell et al. |
| 2021/0277141 | A1 | 9/2021 | Zhao et al. |
| 2022/0023346 | A1 | 1/2022 | Bethune et al. |
| 2023/0357424 | A1 * | 11/2023 | Lupardus ............ C07K 16/289 |

FOREIGN PATENT DOCUMENTS

| | | |
|---|---|---|
| CN | 109680002 A | 4/2019 |
| EP | 1664122 B1 | 3/2010 |
| WO | 2002077029 A2 | 10/2002 |
| WO | 2005026210 A2 | 3/2005 |
| WO | 2013104804 A2 | 7/2013 |
| WO | 2013130683 A2 | 9/2013 |
| WO | 2016014565 A2 | 1/2016 |
| WO | 2016014576 A1 | 1/2016 |
| WO | 2016016341 A1 | 2/2016 |
| WO | 2016115559 A1 | 7/2016 |
| WO | 2016118629 A1 | 7/2016 |
| WO | 2016149368 A1 | 9/2016 |
| WO | 2016166630 A1 | 10/2016 |
| WO | 2017009473 A1 | 1/2017 |
| WO | 2017025038 A1 | 2/2017 |
| WO | 2017025323 A1 | 2/2017 |
| WO | 2017125830 A1 | 7/2017 |
| WO | 2017173410 A1 | 10/2017 |
| WO | 2018006882 A1 | 1/2018 |
| WO | 2018072025 A1 | 4/2018 |
| WO | 2018145649 A1 | 8/2018 |
| WO | 2018152181 A1 | 8/2018 |
| WO | 2018222935 A1 | 12/2018 |
| WO | 2019030240 A1 | 2/2019 |
| WO | 2020150339 A1 | 4/2019 |
| WO | 2019196713 A1 | 10/2019 |
| WO | 2019222275 A2 | 11/2019 |
| WO | 2020010235 A1 | 1/2020 |
| WO | 2020010284 A1 | 1/2020 |
| WO | 2020023888 A2 | 1/2020 |
| WO | 2020092654 A1 | 5/2020 |
| WO | 2020108646 A1 | 6/2020 |
| WO | 2020123691 A2 | 6/2020 |
| WO | 2020180591 A1 | 9/2020 |
| WO | 2020186204 A1 | 9/2020 |
| WO | WO-2020247670 A1 * | 12/2020 |
| WO | 2021008463 A1 | 1/2021 |
| WO | 2019152742 A1 | 8/2021 |
| WO | 2021179353 A1 | 9/2021 |

OTHER PUBLICATIONS

Bork, P. Powers and pitfalls in sequence analysis: the 70% hurdle. Genome Res 10: 398-400, 2000.*

Bork, P. Go hunting in sequence databases but watch out for the traps. Trends in Genetics 12(10): 425-427, 1996.*

Brenner. S.E. Errors in genome annotation. Trends in Genetics 15:132-133, 1999.*

Celichowski et al. Tuning CARs: recent advances in modulating chimeric antigen receptor (CAR) T cell activity for improved safety, efcacy, and fexibility. J Translat Med 21: 197, 2023 (24 total pages).*

Doerks et al. Protein annotation: detective work for function prediction. Trends in Genetics 14:248-250, 1998.*

Fenton et al. Rheostat positions: a new classification of protein positions relevant to pharmacogenomics. Medicinal Chem Res 29: 1133-1146, 2020.*

Guo et al. Protein tolerance to random amino acid change. Proc Natl Acad Sci USA 101(25): 9205-9210, 2004.*

Lin et al. Genetically Engineered Anti-CD45 Single-Chain AntibodyStreptavidin Fusion Protein for Pretargeted Radioimmunotherapy of Hematologic Malignancies. Cancer Res 66(7): 3884-3892, 2006.*

Moradi-Kalbolandi et al. Development of an anti-CD45RA-quantum dots conjugated scFv to detect leukemic cancer stem cells. Mol Biol Reports 47: 225-234, 2020.*

Ngo et al. "Computational complexity, protein structure prediction, and the Levinthal paradox" in The Protein Folding Problem and Tertiary Structure Prediction, pp. 492-495, 1994.*

Rheinlander et al. CD45 in human physiology and clinical medicine. Immunol Lett 196: 22-32, 2018.*

Rhodes et al. Activation of Human γδ T Cells by Cytosolic Interactions of BTN3A1 with Soluble Phosphoantigens and the Cytoskeletal Adaptor Periplakin. J Immunol 194: 2390-2398, 2015.*

Rossotti et al. Streamlined method for parallel identification of single domain antibodies to membrane receptors on whole cells. Biochim Biophys Acta 1850: 1397-1404, 2015.*

Shin et al. Characterization of Monoclonal Antibodies against Human Leukocyte Common Antigen (CD45). Immune Network 11(2): 114-122, 2011.*

Shipley et al. Genome-Wide Surveillance of Genital Herpes Simplex Virus Type 1 From Multiple Anatomic Sites Over Time. J Infect Dis 218: 595-605, 2018.*

Skolnick et al. From genes to protein structure and function: novel applications of computational approaches in the genomic era. Trends Biotechnol 18(I):34-39 2000.*

Smith et al. The challenges of genome sequence annotation or "the devil is in the details". Nature Biotechnol 15: 1222-1223, 1997.*

Tokuriki et al. Stability effects of mutations and protein evolvability. Curr Opin Structural Biol 19: 596-604, 2009.*

Wells, J.A. Additivity of mutational effects in proteins. Biochemistry 29(37): 8509-8517, 1990.*

Shepherd, Philip, et al., "Monoclonal Antibodies: A Practical Approach", Oxford University Press, 2000 (TOC).

Sommer, Cesar, et al., "Allogeneic FLT3 CAR T Cells with an Off-Switch Exhibit Potent Activity against AML and Can Be Depleted to Expedite Bone Marrow Recovery", Molecular Therapy; Oct. 7, 2020;28(10):2237-2251. doi: 10.1016/j.ymthe.2020.06.022. Epub Jun. 19, 2020.

Sommer, Cesar, et al., "Preclinical Evaluation of Allogeneic CAR T Cells Targeting BCMA for the Treatment of Multiple Myeloma", Molecular Therapy; Jun. 5, 2019;27(6):1126-1138. doi: 10.1016/j.ymthe.2019.04.001. Epub Apr. 8, 2019.

Thiel, Nadine, et al., "Viral Interference with Functions of the Cellular Receptor Tyrosine Phosphatase CD45", Viruses 2015, 7, 1540-1557; doi:10.3390/v7031540.
Tramontano, Anna, et al., "Framework Residue 71 is a Major Determinant of the Position and Conformation of the Second Hypervariable Region in the V H Domains of Immunoglobulins", J. Mol. Biol. (1990) 215, 175-182.
Weidle, Ulrich, et al., "Proteases as Activators for Cytotoxic Prodrugs in Antitumor Therapy", Cancer Genomics & Proteomics 11: 67-80 (2014).
Whitlow, Marc, et al., "An improved linker for single-chain Fv with reduced aggregation and enhanced proteolytic stability", Protein Engineering; Nov. 1993;6(8):989-95. doi: 10.1093/protein/6.8.989.
Zanetti, Maurizio, et al., "The Antibodies", vol. 1, Harwood Academic Publisher, 1995, Luxembourg (TOC).
Al-Lazikani, Bissan, et al., "Standard Conformations for the Canonical Structures of Immunoglobulins", J. Mol. Biol. (1997) 273, 927-948.
Atkins, J. F., et al., "A case for "StopGo": Reprogramming translation to augment codon meaning of GGN by promoting unconventional termination (Stop) after addition of glycine and then allowing continued translation (Go)", RNA (2007), 13:803-810., Cold Spring Harbor Laboratory Press.
Ausubel, Frederick M., et al., "Short Protocols in Molecular Biology", A Compendium of Methods from Current Protocols in Molecular Biology; 4th ED.; Wiley and Sons, 1999; (TOC).
Bakalar, Matthew H., et al., "Size-dependent segregation controls macrophage phagocytosis of antibody-opsonized targets", Cell. Jun. 28, 2018; 174(1): 131-142.e13. doi:10.1016/j.cell.2018.05.059.
Bierer, B., et al., "Cyclosporin A and FK506: molecular mechanisms of immunosuppression and probes for transplantation biology", Current Opinion in Immunology; 1993; 5:763-773.
Catty, D., "Antibodies: a practical approach", IRL Press Ltd. 1988, Oxford England (TOC).
Celis, Julio E., "Cell Biology: A Laboratory Hnadbook", Academic Press, 1998 (TOC).
Chang, Veronica T., et al., "Initiation of T cell signaling by CD45 segregation at 'close-contacts'", Nat Immunol. May 2016 ; 17(5): 574-582. doi: 10.1038/ni.3392.
Cho, Jae-Ho, et al., "CD45-mediated control of TCR tuning in naïve and memory CD8 + T cells", Nat Commununications; Nov. 14, 2016;7:13373. doi: 10.1038/ncomms13373.
Chothia, Cyrus, et al., "Canonical structures for the hypervariable regions of immunoglobulins", J Mol Biol; Aug. 20, 1987;196(4):901-17. doi: 10.1016/0022-2836(87)90412-8.
Chothia, Cyrus, et al., "Conformations of immunoglobulin hypervariable regions", Nature. vol. 342 . 21/ Dec. 28, 1989.
Chothia, Cyrus, et al., "Structural Repertoire of the Human VH Segments", J. Mol. Biol. (1992) 227, 799-917.
Clark, Mike, "Antibody humanization: a case of the 'Emperor's new clothes'?", Immunol Today; . Aug. 2000;21 (8):397-402. doi: 10.1016/s0167-5699(00)01680-7.
Coligan, John E., et al., "Current Protocols in Immunology", vol. 1, 1991, John Wiley & Sons, Inc.(TOC).
Courtney, Adam H., et al., "CD45 functions as a signaling gate-keeper in T cells", Sci Signal; Oct. 22, 2019;12(604):eaaw8151. doi: 10.1126/scisignal.aaw8151.
Davis, Simon, et al., "The kinetic-segregation model: TCR triggering and beyond", Nature Immunology; vol. 7, No. 8, Aug. 2006.
Desnoyers, Luc R., "Tumor-Specific Activation of an EGFR-Targeting Probody Enhances Therapeutic Index", Sci Transl Med. 2013. doi:10.1126/scitranslmed.3006682.
Donnelly, Michelle, et al., "Fluorescent Tagging of Herpes Simplex Virus Tegument Protein VP13/14 in Virus Infection", Journal of Virology, vol. 75, No. 6, Mar. 2001, p. 2575-2583.
Donnelly, Michelle, et al., "Nuclear Localization and Shuttling of Herpes Simplex Virus Tegument Protein VP13/14", Journal of Virology, vol. 75, No. 6, Mar. 2001, p. 2566-2574.
Doronina, Victoria A., et al., "Site-Specific Release of Nascent Chains from Ribosomes at a Sense Codon", Molecular and Cellular Biology, vol. 28, No. 13, Jul. 2008, p. 4227-4239.

Doyle, Alan, et al., "Cell and Tissue Culture: Laboratory Procedures in Biotechnology", John Wiley & Sons, Ltd., West Sussex, England, 1998 (TOC).
EPO, "International Search Report & Written Opinion", mailed on Jun. 7, 2022 for International Application No. PCT/US2021/064615 36 pages.
Eshhar, Zelig, et al., "Specific activation and targeting of cytotoxic lymphocytes through chimeric single chains consisting of antibody-binding domains and the gamma or zeta subunits of the immunoglobulin and T-cell receptors.", Immunology; Proc Natl Acad Sci U S A. Jan. 15, 1993; 90(2): 720-724.
Felberg, Jackie, et al., "Characterization of Recombinant CD45 Cytoplasmic Domain Proteins", The Journal of Biological Chemistry; vol. 273, No. 28, Issue of Jul. 10, pp. 17839-17845, 1998.
Fellouse, F. A., "High-throughput Generation of Synthetic Antibodies from Highly Functional Minimalist Phage-displayed Libraries", J. Mol. Biol.; 2007; 373; 924-940.
Finch, Peter, "Antibodies", 1st Ed., Stride Publications, 1997 (TOC).
Gait, M. J., "Oligonucleotide Synthesis: A Practical Approach", IRL Press Ltd., Oxford, England, 1984 (TOC).
Gaj, Thomas, et al., "Genome-Editing Technologies: Principles and Applications", Cold Spring Harbor Perspective in Biology; 2016;8:a023754.
Geiger, Martina, et al., "Protease-activation using anti-idiotypic masks enables tumor specificity of a folate receptor 1-T cell bispecific antibody", Nature Communications; (2020) 11:3196 | https://doi.org/10.1038/s41467-020-16838-w.
Gialeli, Chrisostomi, et al., "Roles of matrix metalloproteinases in cancer progression and their pharmacological targeting", FEBS Journal 278 (2011) 16-27.
Han, Xiaolu, et al., "Masked Chimeric Antigen Receptor for Tumor-Specific Activation", Mol Therapy; Jan. 4, 2017;25 (1):274-284. doi: 10.1016/j.ymthe.2016.10.011. Epub Jan. 4, 2017.
Harlow, Ed, et al., "Epitope Mapping", Using Antibodies: A Laboratory Manual, Chapter 11, Cold Spring Harbor aboratory Press, NY, 1998.
Henderson, D. J., et al., "Comparison of the effects of FK-506, cyclosporin A and rapamycin on IL-2 production", Immunology. Jul. 1991; 73(3):316-21.
Janeway, Charles A., et al., "Immunobiology", Churchill Livingstone; 2nd Edition, Sep. 1, 1997, (TOC).
Jayasena, S. D., et al., "Aptamers: an emerging class of molecules that rival antibodies in diagnostics", Clin Chem. Sep. 1999;45(9):1628-50.
Kabat, Elvin A., et al., "Sequences of Proteins of Immunological Interest", 5th Ed. NIH publication, No. 91-3242; 1992 (TOC).
Ledbetter, Jeffrey A., et al., "CD45 regulates signal transduction and lymphocyte activation by specific association with receptor molecules on T or B cells", Proc. Nati. Acad. Sci. USA; vol. 85, pp. 8628-8632, Nov. 1988.
Liu, J., et al., "Inhibition of T Cell Signaling by Immunophilin-Ligand Complexes Correlates with Loss of Calcineurin Phosphatase Activity", Biochemistry, 1992, 31, 3891-3901.
Makabe, Koki, et al., "Thermodynamic Consequences of Mutations in Vernier Zone Residues of a Humanized Anti-human Epidermal Growth Factor Receptor Murine Antibody, 528", The Journal of Biological Chemistry vol. 283, No. 2, pp. 1156-1166, Jan. 11, 2008.
Mather, Jennie P., et al., "Introduction to Cell and Tissue Culture: Theory and Techique", Plem Press, New Yord, NY, 1998, (TOC).
Mcneill, Louise, et al., "The Differential Regulation of Lck Kinase Phosphorylation Sites by CD45 Is Critical for T Cell Receptor Signaling Responses", Immunity 27, 425-437, Sep. 2007; DOI 10.1016/j.immuni.2007.07.015.
Miller, Jeffrey H., et al., "Gene Transfer Vectors for Mammalian Cells", Current Communications in Molecular Biology, Cold Spring Harbor Laboratory, 1987 (TOC).
Mullis, et al., "PCR: The Polymerase Chain Reaction", Birkauswer Press, Boston, 1994 (Table of Contents).
Payne, Kyle K., et al., "BTN3A1 governs anti-tumor responses by coordinating alpha-beta and gamma-delta T cells", Science. Aug. 21, 2020; 369(6506): 942-949. doi:10.1126/science.aay2767.

Penninger, Josef M., et al., "CD45: new jobs for an old acquaintance", Nature Immunology; May 2001;2 (5):389-96. doi: 10.1038/87687.

Poreba, Marcin, et al., "Protease-activated prodrugs: strategies, challenges, and future directions", The FEBS Journal; vol. 287, Issue10; May 2020; pp. 1936-1969.

Razvag, Yair, et al., "Nanoscale kinetic segregation of TCR and CD45 in engaged microvilli facilitates early T cell activation", Nature Communications; 2018, 9732; DOI: 10.1038/s41467-018-03127-w.

Remington, "The Science and Practice of Pharmacy", 21st Ed. Mack Publishing, 2005, Table of Contents.

Sadelain, Michel, et al., "The promise and potential pitfalls of chimeric antigen receptors", Current Opinion in Immunology 2009, 21:215-223.

Sambrook, J., et al., "Molecular Cloning: A Laboratory Manual", Second Ed., Cold Spring Harbor Laboratory Press, 1989 (TOC).

* cited by examiner

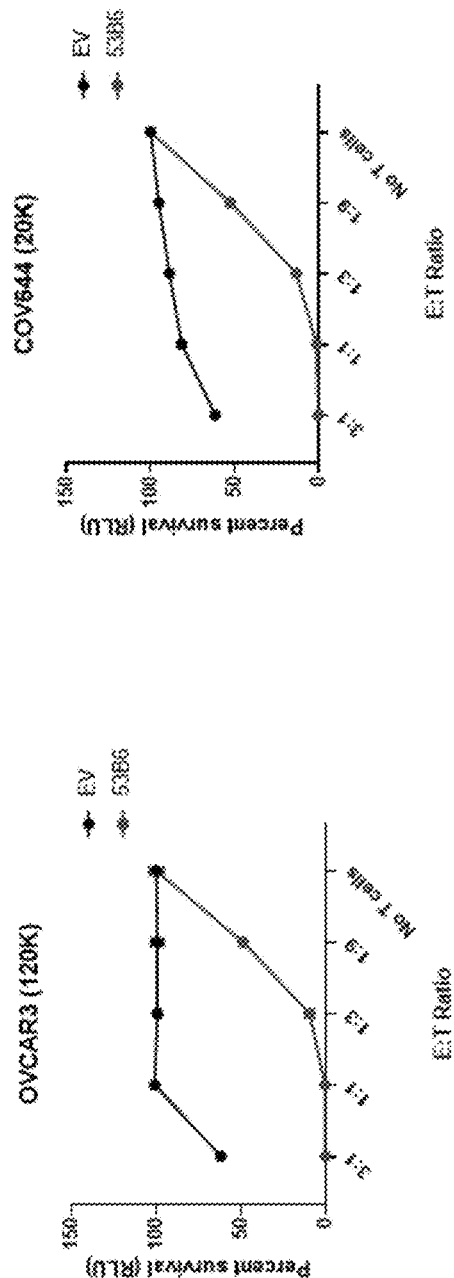
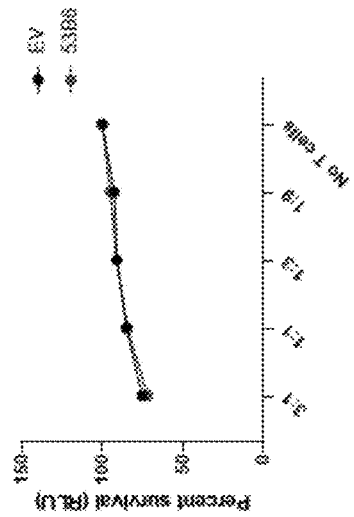
Fig. 8A
Fig. 8B
Fig. 8C

FIG. 11

| Description | Matriptase cleavage site | MMP cleavage site | uPA cleavage site | Linker length | Schematic |
|---|---|---|---|---|---|
| 53B6 naked CAR | | | | None | |
| Non-cleavable GS | | | | 30aa | |
| Non-cleavable V5 | | | | 45aa | |
| 2xTPS3 | | ✓ | ✓ | 45aa | |
| TPS4 | ✓ | ✓ | | 45aa | |
| TPS6 | ✓ | | | 45aa | |
| 2xTPS6 | ✓ | | | 45aa | |
| 2xTPS6 | ✓ | | | 40aa | |
| 2xTPS6 | ✓ | | | 35aa | |
| 2xTPS6 | ✓ | | | 30aa | |
| 2xTPS6 | ✓ | | | 25aa | |

| Target expression | | Protease detection in vitro | | |
|---|---|---|---|---|
| | MUC16 | Matriptase (membrane-bound) | uPA | MMP-9 |
| OVCAR3 | Endogenous (122K) | +/++ | + | - |
| MDA-MB-231-Muc16 | Overexpressed | ++ | +++ | - |
| H292-Muc16 | Overexpressed | ++ | - | - |

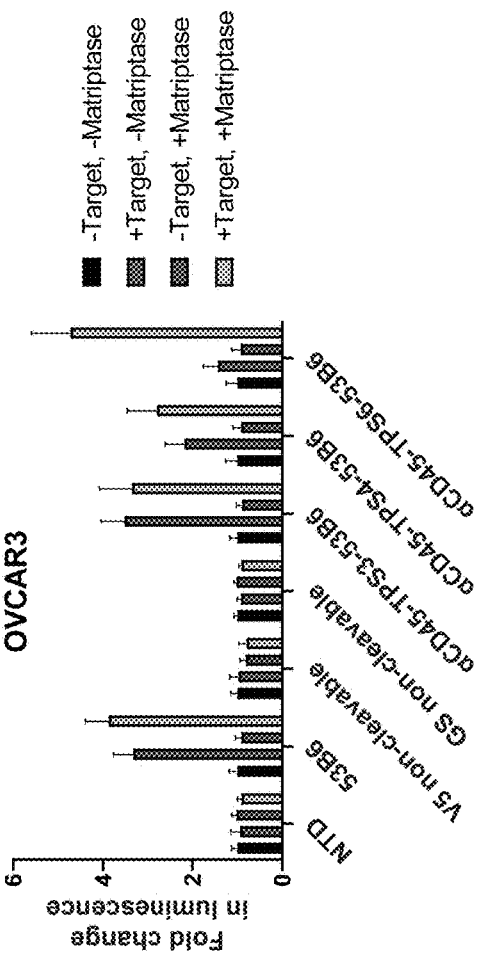
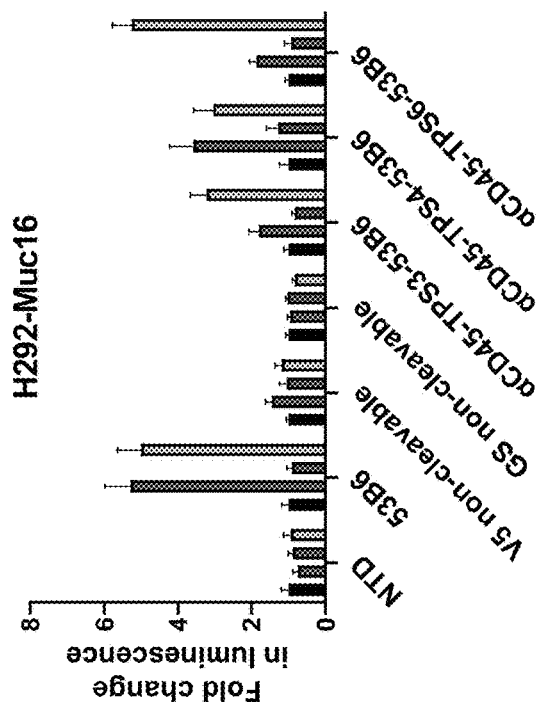
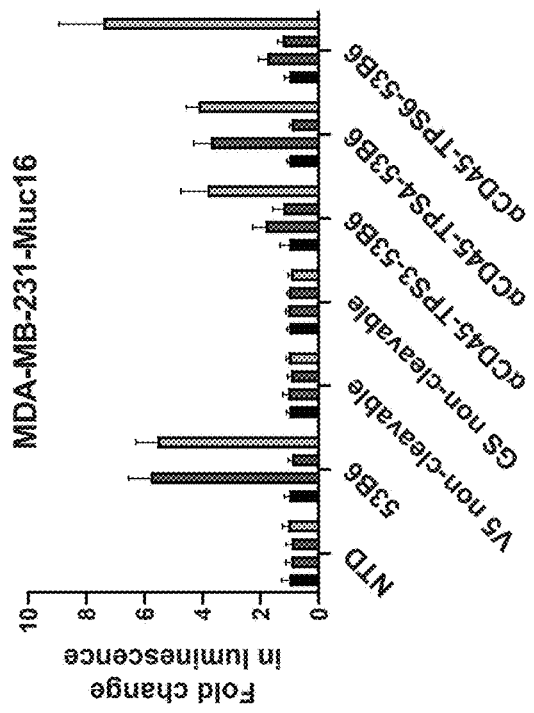
FIG. 15A
FIG. 15B
FIG. 15C

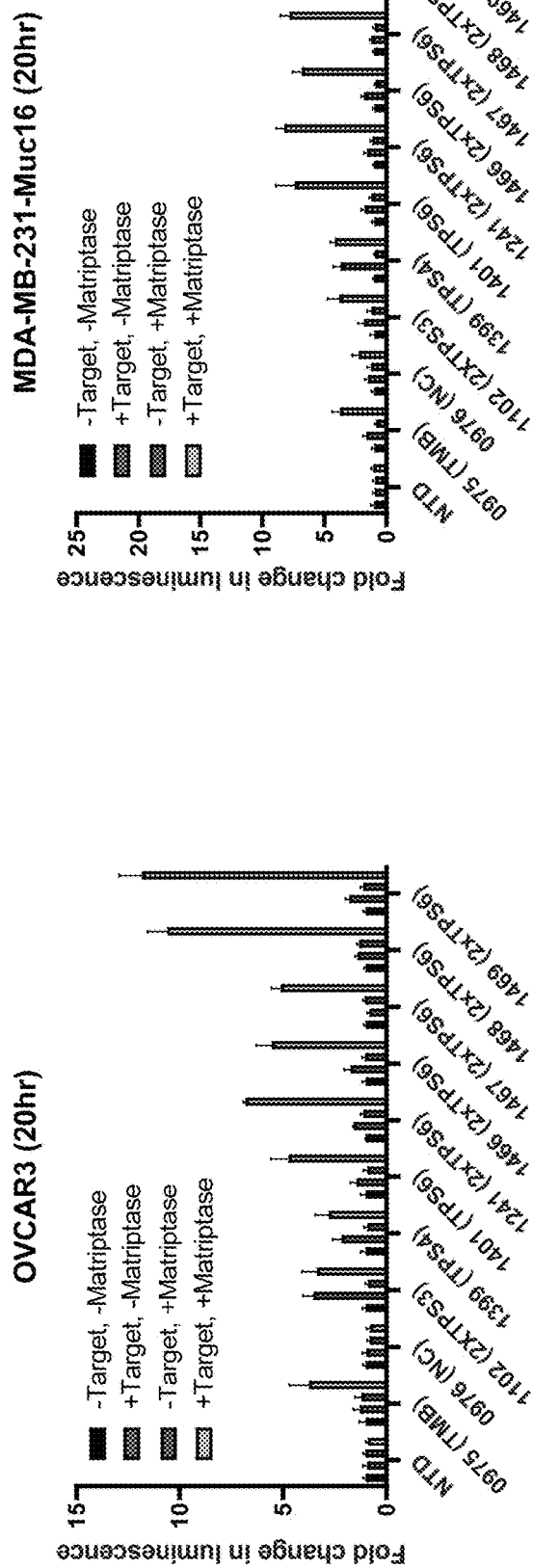
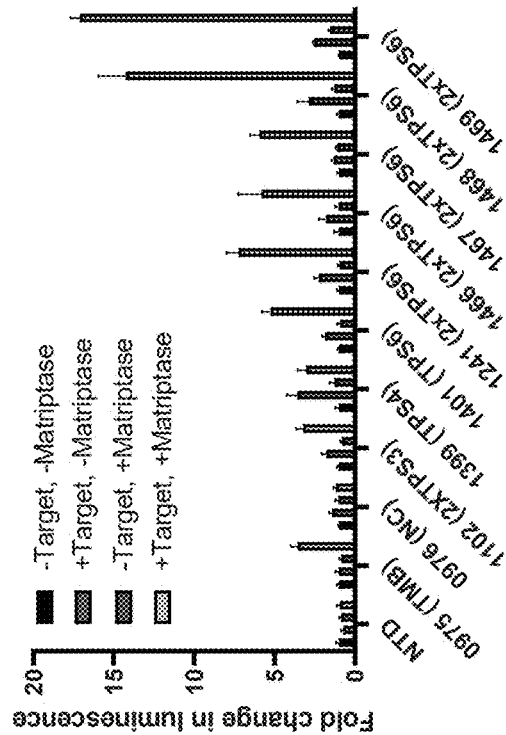
FIG. 15D
FIG. 15E
FIG. 15F

SEQUENCE LISTING

```
<160> NUMBER OF SEQ ID NOS: 187

<210> SEQ ID NO 1
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Met Ala Leu Pro Val Thr Ala Leu Leu Leu Pro Leu Ala Leu Leu Leu
1               5                   10                  15

His Ala Ala Arg Pro
            20

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Tyr Pro Tyr Asp Val Pro Asp Tyr Ala
1               5                   10

<210> SEQ ID NO 3
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Asp Ile Val Met Thr Gln Thr Pro Ala Ser Val Ser Glu Pro Val Gly
1               5                   10                  15

Gly Ser Val Thr Ile Lys Cys Gln Ala Ser Gln Ser Phe Tyr Asn Leu
                20                  25                  30

Leu Ala Trp Tyr Gln Gln Lys Pro Gly Gln Pro Pro Lys Leu Leu Ile
            35                  40                  45

Tyr Asp Ala Ser Asp Leu Ala Ser Gly Val Pro Ser Arg Phe Lys Gly
        50                  55                  60

Ser Gly Ser Gly Thr Asp Phe Thr Leu Thr Ile Ser Asp Leu Glu Cys
65                  70                  75                  80

Ala Asp Ala Ala Ala Tyr Tyr Cys Gln Ser Ala Asp Gly Ser Ser Tyr
```

```
                    85                  90                  95
Ala Phe Gly Gly Gly Thr Glu Val Val Lys Gly Gly Gly Gly
                100                 105                 110
Ser Gly Gly Gly Gly Ser Gly Gly Gly Ser Gly Gly Gly Ser
                115                 120                 125
Gln Glu Gln Leu Glu Glu Ser Gly Gly Leu Val Lys Pro Gly
            130                 135                 140
Ser Leu Thr Leu Thr Cys Thr Ala Ser Gly Val Ser Phe Ser Ser
145                 150                 155                 160
Tyr Trp Ile Tyr Trp Val Arg Gln Ala Pro Gly Lys Gly Leu Glu Trp
                165                 170                 175
Ile Ala Cys Ile Tyr Thr Gly Ser Ser Gly Ser Thr Tyr Tyr Ala Ser
                180                 185                 190
Trp Ala Lys Gly Arg Phe Thr Val Ser Glu Thr Ser Thr Thr Val
                195                 200                 205
Thr Leu Gln Met Thr Ser Leu Thr Ala Ala Asp Thr Ala Thr Tyr Phe
            210                 215                 220
Cys Ala Arg Ala Ser Ala Trp Thr Tyr Gly Met Asp Leu Trp Gly Pro
225                 230                 235                 240
Gly Thr Leu Val Thr Val Ser Ser
                245

<210> SEQ ID NO 4
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Asp Ile Val Met Thr Gln Thr Pro Ala Ser Val Ser Glu Pro Val Gly
1               5                   10                  15
Gly Thr Val Thr Ile Met Cys Gln Ala Ser Gln Ser Ile Ser Asn Trp
                20                  25                  30
Leu Ala Trp Tyr Gln Gln Lys Pro Gly Gln Pro Pro Lys Leu Leu Ile
            35                  40                  45
Tyr Gln Ala Ser Lys Leu Ala Ser Gly Val Pro Ser Arg Phe Lys Gly
        50                  55                  60
Ser Gly Ser Gly Thr Glu Tyr Thr Leu Thr Ile Ser Asp Leu Glu Cys
65                  70                  75                  80
Ala Asp Ala Ala Thr Tyr Tyr Cys Gln Ser Tyr Tyr Asp Ser Gly Ser
                85                  90                  95
Asn Val Phe Phe Ala Phe Gly Gly Gly Thr Lys Val Val Val Glu Gly
                100                 105                 110
Gly Gly Gly Gly Ser Gly Gly Gly Gly Ser Gly Gly Gly Ser Gly
                115                 120                 125
Gly Gly Gly Ser Leu Ser Leu Glu Glu Ser Gly Gly Asp Leu Val Lys
            130                 135                 140
Pro Gly Ala Ser Leu Thr Leu Thr Cys Thr Ala Ser Gly Phe Ser Phe
145                 150                 155                 160
Ser Ala Gly Tyr Trp Ile Cys Trp Val Arg Gln Ala Pro Gly Lys Gly
                165                 170                 175
Leu Glu Trp Ile Ala Cys Thr Tyr Ala Gly Arg Ser Gly Ser Thr Tyr
                180                 185                 190
```

```
Tyr Ala Asn Trp Val Asn Gly Arg Phe Thr Ile Pro Lys Thr Ser Ser
            195                 200                 205

Thr Thr Val Thr Leu Gln Met Thr Ser Leu Ser Gly Ala Asp Thr Ala
    210                 215                 220

Ser Tyr Phe Cys Ala Arg Gly Asn Ala Gly Val Ala Val Gly Ala Leu
225                 230                 235                 240

Trp Gly Pro Gly Thr Leu Val Thr Val Ser Ser
                245                 250

<210> SEQ ID NO 5
<211> LENGTH: 264
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Asp Ile Val Met Thr Gln Thr Pro Ala Ser Val Ser Glu Pro Val Gly
1               5                   10                  15

Gly Ser Val Thr Ile Lys Cys Gln Ala Ser Gln Ser Phe Tyr Asn Leu
            20                  25                  30

Leu Ala Trp Tyr Gln Gln Lys Pro Gly Gln Pro Lys Leu Leu Ile
        35                  40                  45

Tyr Asp Ala Ser Asp Leu Ala Ser Gly Val Pro Ser Arg Phe Lys Gly
    50                  55                  60

Ser Gly Ser Gly Thr Asp Phe Thr Leu Thr Ile Ser Asp Leu Glu Cys
65                  70                  75                  80

Ala Asp Ala Ala Ala Tyr Tyr Cys Gln Ser Ala Asp Gly Ser Ser Tyr
                85                  90                  95

Ala Phe Gly Gly Gly Thr Glu Val Val Lys Gly Gly Gly Gly
            100                 105                 110

Ser Gly Gly Gly Gly Ser Leu Ser Gly Arg Ser Asp Asn His Ser Pro
            115                 120                 125

Leu Gly Leu Ala Gly Ser Gly Gly Gly Ser Gly Gly Gly Ser
    130                 135                 140

Gln Glu Gln Leu Glu Glu Ser Gly Gly Gly Leu Val Lys Pro Glu Gly
145                 150                 155                 160

Ser Leu Thr Leu Thr Cys Thr Ala Ser Gly Val Ser Phe Ser Ser Ser
                165                 170                 175

Tyr Trp Ile Tyr Trp Val Arg Gln Ala Pro Gly Lys Gly Leu Glu Trp
            180                 185                 190

Ile Ala Cys Ile Tyr Thr Gly Ser Ser Gly Ser Thr Tyr Tyr Ala Ser
            195                 200                 205

Trp Ala Lys Gly Arg Phe Thr Val Ser Glu Thr Ser Ser Thr Thr Val
        210                 215                 220

Thr Leu Gln Met Thr Ser Leu Thr Ala Ala Asp Thr Ala Thr Tyr Phe
225                 230                 235                 240

Cys Ala Arg Ala Ser Ala Trp Thr Tyr Gly Met Asp Leu Trp Gly Pro
                245                 250                 255

Gly Thr Leu Val Thr Val Ser Ser
            260

<210> SEQ ID NO 6
<211> LENGTH: 267
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 6

Asp Ile Val Met Thr Gln Thr Pro Ala Ser Val Ser Glu Pro Val Gly
1               5                   10                  15

Gly Thr Val Thr Ile Met Cys Gln Ala Ser Gln Ser Ile Ser Asn Trp
            20                  25                  30

Leu Ala Trp Tyr Gln Gln Lys Pro Gly Gln Pro Pro Lys Leu Leu Ile
        35                  40                  45

Tyr Gln Ala Ser Lys Leu Ala Ser Gly Val Pro Ser Arg Phe Lys Gly
50                  55                  60

Ser Gly Ser Gly Thr Glu Tyr Thr Leu Thr Ile Ser Asp Leu Glu Cys
65                  70                  75                  80

Ala Asp Ala Ala Thr Tyr Tyr Cys Gln Ser Tyr Tyr Asp Ser Gly Ser
                85                  90                  95

Asn Val Phe Phe Ala Phe Gly Gly Gly Thr Lys Val Val Val Glu Gly
            100                 105                 110

Gly Gly Gly Gly Ser Gly Gly Gly Ser Leu Ser Gly Arg Ser Asp
        115                 120                 125            Asp

Asn His Ser Pro Leu Gly Leu Ala Gly Ser Gly Gly Gly Ser Gly
            130                 135                 140

Gly Gly Gly Ser Leu Ser Leu Glu Glu Ser Gly Gly Asp Leu Val Lys
145                 150                 155                 160

Pro Gly Ala Ser Leu Thr Leu Thr Cys Thr Ala Ser Gly Phe Ser Phe
                165                 170                 175

Ser Ala Gly Tyr Trp Ile Cys Trp Val Arg Gln Ala Pro Gly Lys Gly
            180                 185                 190

Leu Glu Trp Ile Ala Cys Thr Tyr Ala Gly Arg Ser Gly Ser Thr Tyr
        195                 200                 205

Tyr Ala Asn Trp Val Asn Gly Arg Phe Thr Ile Pro Lys Thr Ser Ser
    210                 215                 220

Thr Thr Val Thr Leu Gln Met Thr Ser Leu Ser Gly Ala Asp Thr Ala
225                 230                 235                 240

Ser Tyr Phe Cys Ala Arg Gly Asn Ala Gly Val Ala Val Gly Ala Leu
                245                 250                 255

Trp Gly Pro Gly Thr Leu Val Thr Val Ser Ser
            260                 265

<210> SEQ ID NO 7
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gly Gly Gly Gly Ser Gly Gly Gly Ser Gly Gly Ser Gly Ser
1               5                   10                  15

Lys Pro Ile Pro Asn Pro Leu Leu Gly Leu Asp Ser Thr Gly Gly
            20                  25                  30

Ser Gly Ser Gly Gly Gly Gly Ser Gly Gly Gly Gly Ser
        35                  40                  45

<210> SEQ ID NO 8
```

<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Gly Gly Gly Gly Ser Gly Gly Gly Ser Leu Val Pro Arg Gly Ser
1               5                   10                  15

Lys Pro Ile Pro Asn Pro Leu Leu Gly Leu Asp Ser Thr Leu Val Pro
            20                  25                  30

Arg Gly Ser Gly Gly Gly Gly Ser Gly Gly Gly Gly Ser
        35                  40                  45

<210> SEQ ID NO 9
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gly Gly Gly Gly Ser Gly Gly Gly Ser Gly Gly Gly Ser Gly Leu
1               5                   10                  15

Ser Gly Arg Ser Asp Asn His Ser Pro Leu Gly Leu Ala Gly Ser Gly
            20                  25                  30

Gly Gly Ser Gly Gly Gly Gly Ser Gly Gly Gly Gly Ser
        35                  40                  45

<210> SEQ ID NO 10
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gly Gly Gly Gly Ser Leu Ser Gly Arg Ser Asp Asn His Ser Pro Leu
1               5                   10                  15

Gly Leu Ala Gly Ser Lys Pro Ile Pro Asn Pro Leu Leu Gly Leu Asp
            20                  25                  30

Ser Thr Leu Ser Gly Arg Ser Asp Asn His Ser Pro Leu Gly Leu Ala
        35                  40                  45

Gly Ser Gly Gly Gly Gly Ser
    50                  55

<210> SEQ ID NO 11
<211> LENGTH: 469
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Tyr Tyr
            20                  25                  30

Ser Trp Thr Trp Val Arg Gln Pro Ala Gly Gln Gly Leu Glu Trp Ile

```
                35                  40                  45
Gly Arg Ile His Ile Ser Gly Val Thr Asn His Asn Pro Ser Leu Lys
 50                  55                  60

Ser Arg Val Ser Met Ser Ile Asp Thr Ser Arg Thr Gln Phe Ser Leu
 65                  70                  75                  80

Arg Leu Thr Ser Val Thr Ala Ala Asp Thr Ala Val Tyr Phe Cys Ala
                 85                  90                  95

Arg Ser Gly Gly Thr Tyr Ser Ala Phe Asp Ile Trp Gly Gln Gly Thr
                100                 105                 110

Met Val Thr Val Ser Ser Gly Gly Gly Gly Ser Gly Gly Gly Gly Ser
                115                 120                 125

Gly Gly Gly Gly Ser Gly Gly Gly Ser Glu Ile Val Leu Thr Gln
                130                 135                 140

Ser Pro Gly Thr Leu Ser Leu Ser Pro Gly Glu Arg Ser Thr Leu Ser
145                 150                 155                 160

Cys Arg Ala Ser Gln Ser Phe Thr Ser Asn Tyr Leu Ala Trp Tyr Gln
                165                 170                 175

Gln Arg Pro Gly Gln Ala Pro Arg Leu Leu Ile Tyr Gly Ala Ser Thr
                180                 185                 190

Arg Ala Ile Gly Ile Pro Asp Arg Phe Ser Gly Ser Gly Ser Gly Thr
                195                 200                 205

Asp Phe Thr Leu Thr Ile Ser Arg Leu Glu Pro Glu Asp Phe Ala Val
210                 215                 220

Tyr Tyr Cys Gln Gln Tyr Gly Ser Ser Pro Trp Thr Phe Gly Gln Gly
225                 230                 235                 240

Thr Lys Val Glu Ile Lys Thr Thr Thr Pro Ala Pro Arg Pro Pro Thr
                245                 250                 255

Pro Ala Pro Thr Ile Ala Ser Gln Pro Leu Ser Leu Arg Pro Glu Ala
                260                 265                 270

Cys Arg Pro Ala Ala Gly Gly Ala Val His Thr Arg Gly Leu Asp Phe
                275                 280                 285

Ala Cys Asp Ile Tyr Ile Trp Ala Pro Leu Ala Gly Thr Cys Gly Val
                290                 295                 300

Leu Leu Leu Ser Leu Val Ile Thr Leu Tyr Cys Lys Arg Gly Arg Lys
305                 310                 315                 320

Lys Leu Leu Tyr Ile Phe Lys Gln Pro Phe Met Arg Pro Val Gln Thr
                325                 330                 335

Thr Gln Glu Glu Asp Gly Cys Ser Cys Arg Phe Pro Glu Glu Glu Glu
                340                 345                 350

Gly Gly Cys Glu Leu Arg Val Lys Phe Ser Arg Ser Ala Asp Ala Pro
                355                 360                 365

Ala Tyr Gln Gln Gly Gln Asn Gln Leu Tyr Asn Glu Leu Asn Leu Gly
                370                 375                 380

Arg Arg Glu Glu Tyr Asp Val Leu Asp Lys Arg Arg Gly Arg Asp Pro
385                 390                 395                 400

Glu Met Gly Gly Lys Pro Arg Arg Lys Asn Pro Gln Glu Gly Leu Tyr
                405                 410                 415

Asn Glu Leu Gln Lys Asp Lys Met Ala Glu Ala Tyr Ser Glu Ile Gly
                420                 425                 430

Met Lys Gly Glu Arg Arg Arg Gly Lys Gly His Asp Gly Leu Tyr Gln
                435                 440                 445

Gly Leu Ser Thr Ala Thr Lys Asp Thr Tyr Asp Ala Leu His Met Gln
                450                 455                 460
```

Ala Leu Pro Pro Arg
465

<210> SEQ ID NO 12
<211> LENGTH: 363
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gly Phe His Thr Ile Asn Ala Thr Trp Trp Ala Asn Ile Thr Leu Val
1               5                   10                  15

Gly Pro Pro Asp Thr Pro Val Thr Trp Tyr Asp Thr Gln Gly Leu Trp
                20                  25                  30

Phe Cys Asn Gly Ser Arg Val Lys Asn Pro Gln Ile Arg His Thr Cys
            35                  40                  45

Asn Asp Gln Asn Leu Thr Leu Ile His Val Asn Lys Thr Tyr Glu Arg
        50                  55                  60

Thr Tyr Met Gly Tyr Asn Arg Gln Gly Thr Lys Lys Glu Asp Tyr Lys
65                  70                  75                  80

Val Val Val Ile Pro Pro Pro Ala Thr Val Lys Pro Gln Pro Glu
                85                  90                  95

Pro Glu Tyr Val Phe Val Tyr Met Gly Glu Asn Lys Thr Leu Glu Gly
                100                 105                 110

Pro Pro Gly Thr Pro Val Thr Trp Phe Asn Gln Asp Gly Lys Lys Phe
            115                 120                 125

Cys Glu Gly Glu Lys Val Leu His Pro Glu Phe Asn His Thr Cys Asp
        130                 135                 140

Lys Gln Asn Leu Ile Leu Leu Phe Val Asn Phe Thr His Asp Gly Ala
145                 150                 155                 160

Tyr Leu Gly Tyr Asn His Gln Gly Thr Gln Arg Thr His Tyr Glu Val
                165                 170                 175

Thr Val Leu Asp Leu Phe Pro Asp Ser Gly Gln Met Lys Ile Glu Asn
                180                 185                 190

His Ser Glu Glu Thr Glu Gln Lys Asn Asp Glu His His Asn Trp Gln
            195                 200                 205

Lys Gln Gly Gly Gln Lys Gly Gly Gln Lys Thr Asn Gln Thr Lys
        210                 215                 220

Val Asn Asp Arg Arg Lys Thr Ala Gln Lys Arg Pro Ser Lys Leu Lys
225                 230                 235                 240

Pro Ala Thr Ile Glu Ala Met Leu Val Thr Val Thr Ala Gly Ser Asn
                245                 250                 255

Leu Thr Leu Val Gly Pro Lys Ala Glu Gly Lys Val Thr Trp Phe Asp
            260                 265                 270

Gly Asp Leu Lys Arg Pro Cys Glu Pro Asn Tyr Arg Leu Arg His Glu
        275                 280                 285

Cys Asn Asn Gln Asn Leu Thr Leu Ile Asn Val Thr Lys Asp Tyr Glu
    290                 295                 300

Gly Thr Tyr Tyr Gly Thr Asn Asp Lys Asp Gly Lys Arg Tyr Arg
305                 310                 315                 320

Val Lys Val Asn Thr Thr Asn Ser Gln Ser Val Lys Ile Gln Pro Tyr
                325                 330                 335

Thr Arg Gln Thr Thr Pro Asp Gln Glu His Lys Phe Glu Leu Gln Phe

```
                         340                 345                 350
Glu Thr Asn Gly Asn Tyr Asp Ser Lys Ile Pro
            355                 360

<210> SEQ ID NO 13
<211> LENGTH: 200
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

His Asp Ala Cys Ile Pro Val Val Gly Lys Ile Gly Thr Asn Val Thr
1               5                   10                  15

Leu Asn Ala Val Asp Phe His Pro Gly Asp His Val Arg Trp Ser Tyr
            20                  25                  30

Gly Pro Gly Gly Ala Gly Tyr Met Leu Cys Val Tyr Thr Gly Ser Trp
        35                  40                  45

Thr Glu Tyr Lys Lys Pro Asp Ile Ile Phe Lys Cys Leu Ser Asn Asn
    50                  55                  60

Ser Leu Leu Leu Ile Asn Val Thr Val Asn Tyr Thr Asn Thr Tyr Arg
65                  70                  75                  80

Thr Leu Thr Ser Leu Asn Asn Trp Val His Asn Gln His His His Lys
                85                  90                  95

Phe Pro Gly Trp Asn Leu Asp Thr Cys Tyr Ser Leu Thr Val Asn Glu
            100                 105                 110

Asn Gly Thr Phe Pro Thr Thr Thr Lys Lys Pro Thr Thr Thr Thr
        115                 120                 125

Arg Thr Thr Thr Thr Thr Thr Lys Lys Thr Thr Thr Thr Arg Thr
    130                 135                 140

Thr Thr Ala Ala Lys Lys Thr Thr Ile Ser Thr Thr His His Lys His
145                 150                 155                 160

Ser Ser Pro Lys Lys Ser Ser Thr Pro Asn Ser His Val Glu His His
                165                 170                 175

Val Gly Phe Glu Ala Thr Ala Ala Glu Thr Pro Leu Gln Pro Ser Pro
            180                 185                 190

Gln His Gln His Val Ala Thr His
        195                 200

<210> SEQ ID NO 14
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gln Phe Ser Val Leu Gly Pro Ser Gly Pro Ile Leu Ala Met Val Gly
1               5                   10                  15

Glu Asp Ala Asp Leu Pro Cys His Leu Phe Pro Thr Met Ser Ala Glu
            20                  25                  30

Thr Met Glu Leu Lys Trp Val Ser Ser Ser Leu Arg Gln Val Val Asn
        35                  40                  45

Val Tyr Ala Asp Gly Lys Glu Val Glu Asp Arg Gln Ser Ala Pro Tyr
    50                  55                  60

Arg Gly Arg Thr Ser Ile Leu Arg Asp Gly Ile Thr Ala Gly Lys Ala
```

```
                65                  70                  75                  80
Ala Leu Arg Ile His Asn Val Thr Ala Ser Asp Ser Gly Lys Tyr Leu
                    85                  90                  95

Cys Tyr Phe Gln Asp Gly Asp Phe Tyr Glu Lys Ala Leu Val Glu Leu
                    100                 105                 110

Lys Val Ala
        115

<210> SEQ ID NO 15
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Ala Leu Gly Ser Asp Leu His Val Asp Val Lys Gly Tyr Lys Asp Gly
1               5                   10                  15

Gly Ile His Leu Glu Cys Arg Ser Thr Gly Trp Tyr Pro Gln Pro Gln
                20                  25                  30

Ile Gln Trp Ser Asn Asn Lys Gly Glu Asn Ile Pro Thr Val Glu Ala
            35                  40                  45

Pro Val Val Ala Asp Gly Val Gly Leu Tyr Ala Val Ala Ala Ser Val
        50                  55                  60

Ile Met Arg Gly Ser Ser Gly Glu Gly Val Ser Cys Thr Ile Arg Ser
65                  70                  75                  80

Ser Leu Leu Gly Leu Glu Lys Thr Ala Ser Ile Ser Ile Ala Asp Pro
                85                  90                  95

Phe Phe Arg Ser Ala Gln Arg Trp Ile Ala Ala Leu Ala Gly Thr
                100                 105                 110

<210> SEQ ID NO 16
<211> LENGTH: 793
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Met Ala Leu Pro Val Thr Ala Leu Leu Leu Pro Leu Ala Leu Leu Leu
1               5                   10                  15

His Ala Ala Arg Pro Gly Tyr Pro Tyr Asp Val Pro Asp Tyr Ala Asp
                20                  25                  30

Ile Val Met Thr Gln Thr Pro Ala Ser Val Ser Glu Pro Val Gly Gly
            35                  40                  45

Ser Val Thr Ile Lys Cys Gln Ala Ser Gln Ser Phe Tyr Asn Leu Leu
        50                  55                  60

Ala Trp Tyr Gln Gln Lys Pro Gly Gln Pro Pro Lys Leu Leu Ile Tyr
65                  70                  75                  80

Asp Ala Ser Asp Leu Ala Ser Gly Val Pro Ser Arg Phe Lys Gly Ser
                85                  90                  95

Gly Ser Gly Thr Asp Phe Thr Leu Thr Ile Ser Asp Leu Glu Cys Ala
                100                 105                 110

Asp Ala Ala Ala Tyr Tyr Cys Gln Ser Ala Asp Gly Ser Ser Tyr Ala
                115                 120                 125

Phe Gly Gly Gly Thr Glu Val Val Val Lys Gly Gly Gly Gly Ser
```

```
              130                 135                 140
Gly Gly Gly Gly Ser Gly Gly Gly Ser Gly Gly Gly Ser Gln
145                 150                 155                 160

Glu Gln Leu Glu Glu Ser Gly Gly Gly Leu Val Lys Pro Glu Gly Ser
                    165                 170                 175

Leu Thr Leu Thr Cys Thr Ala Ser Gly Val Ser Phe Ser Ser Ser Tyr
                    180                 185                 190

Trp Ile Tyr Trp Val Arg Gln Ala Pro Gly Lys Gly Leu Glu Trp Ile
                195                 200                 205

Ala Cys Ile Tyr Thr Gly Ser Ser Gly Ser Thr Tyr Tyr Ala Ser Trp
            210                 215                 220

Ala Lys Gly Arg Phe Thr Val Ser Glu Thr Ser Ser Thr Thr Val Thr
225                 230                 235                 240

Leu Gln Met Thr Ser Leu Thr Ala Ala Asp Thr Ala Thr Tyr Phe Cys
                    245                 250                 255

Ala Arg Ala Ser Ala Trp Thr Tyr Gly Met Asp Leu Trp Gly Pro Gly
                260                 265                 270

Thr Leu Val Thr Val Ser Ser Gly Gly Gly Ser Gly Gly Gly Gly
            275                 280                 285

Ser Leu Val Pro Arg Gly Ser Lys Pro Ile Pro Asn Pro Leu Leu Gly
            290                 295                 300

Leu Asp Ser Thr Leu Val Pro Arg Gly Ser Gly Gly Gly Gly Ser Gly
305                 310                 315                 320

Gly Gly Ser Gln Val Gln Leu Gln Glu Ser Gly Pro Gly Leu Val
                    325                 330                 335

Lys Pro Ser Glu Thr Leu Ser Leu Thr Cys Thr Val Ser Gly Gly Ser
                340                 345                 350

Ile Ser Tyr Tyr Ser Trp Thr Trp Val Arg Gln Pro Ala Gly Gln Gly
            355                 360                 365

Leu Glu Trp Ile Gly Arg Ile His Ile Ser Gly Val Thr Asn His Asn
        370                 375                 380

Pro Ser Leu Lys Ser Arg Val Ser Met Ser Ile Asp Thr Ser Arg Thr
385                 390                 395                 400

Gln Phe Ser Leu Arg Leu Thr Ser Val Thr Ala Ala Asp Thr Ala Val
                405                 410                 415

Tyr Phe Cys Ala Arg Ser Gly Gly Thr Tyr Ser Ala Phe Asp Ile Trp
            420                 425                 430

Gly Gln Gly Thr Met Val Thr Val Ser Ser Gly Gly Gly Gly Ser Gly
            435                 440                 445

Gly Gly Ser Gly Gly Gly Ser Gly Gly Gly Ser Glu Ile
        450                 455                 460

Val Leu Thr Gln Ser Pro Gly Thr Leu Ser Leu Ser Pro Gly Glu Arg
465                 470                 475                 480

Ser Thr Leu Ser Cys Arg Ala Ser Gln Ser Phe Thr Ser Asn Tyr Leu
                485                 490                 495

Ala Trp Tyr Gln Gln Arg Pro Gly Gln Ala Pro Arg Leu Leu Ile Tyr
            500                 505                 510

Gly Ala Ser Thr Arg Ala Ile Gly Ile Pro Asp Arg Phe Ser Gly Ser
            515                 520                 525

Gly Ser Gly Thr Asp Phe Thr Leu Thr Ile Ser Arg Leu Glu Pro Glu
        530                 535                 540

Asp Phe Ala Val Tyr Tyr Cys Gln Gln Tyr Gly Ser Ser Pro Trp Thr
545                 550                 555                 560
```

-continued

```
Phe Gly Gln Gly Thr Lys Val Glu Ile Lys Thr Thr Pro Ala Pro
                565                 570                 575

Arg Pro Pro Thr Pro Ala Pro Thr Ile Ala Ser Gln Pro Leu Ser Leu
            580                 585                 590

Arg Pro Glu Ala Cys Arg Pro Ala Ala Gly Gly Ala Val His Thr Arg
        595                 600                 605

Gly Leu Asp Phe Ala Cys Asp Ile Tyr Ile Trp Ala Pro Leu Ala Gly
    610                 615                 620

Thr Cys Gly Val Leu Leu Leu Ser Leu Val Ile Thr Leu Tyr Cys Lys
625                 630                 635                 640

Arg Gly Arg Lys Lys Leu Leu Tyr Ile Phe Lys Gln Pro Phe Met Arg
                645                 650                 655

Pro Val Gln Thr Thr Gln Glu Glu Asp Gly Cys Ser Cys Arg Phe Pro
            660                 665                 670

Glu Glu Glu Glu Gly Gly Cys Glu Leu Arg Val Lys Phe Ser Arg Ser
        675                 680                 685

Ala Asp Ala Pro Ala Tyr Gln Gln Gly Gln Asn Gln Leu Tyr Asn Glu
    690                 695                 700

Leu Asn Leu Gly Arg Arg Glu Glu Tyr Asp Val Leu Asp Lys Arg Arg
705                 710                 715                 720

Gly Arg Asp Pro Glu Met Gly Gly Lys Pro Arg Arg Lys Asn Pro Gln
                725                 730                 735

Glu Gly Leu Tyr Asn Glu Leu Gln Lys Asp Lys Met Ala Glu Ala Tyr
            740                 745                 750

Ser Glu Ile Gly Met Lys Gly Glu Arg Arg Arg Gly Lys Gly His Asp
        755                 760                 765

Gly Leu Tyr Gln Gly Leu Ser Thr Ala Thr Lys Asp Thr Tyr Asp Ala
    770                 775                 780

Leu His Met Gln Ala Leu Pro Pro Arg
785                 790

<210> SEQ ID NO 17
<211> LENGTH: 793
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met Ala Leu Pro Val Thr Ala Leu Leu Leu Pro Leu Ala Leu Leu Leu
1               5                   10                  15

His Ala Ala Arg Pro Gly Tyr Pro Tyr Asp Val Pro Asp Tyr Ala Asp
                20                  25                  30

Ile Val Met Thr Gln Thr Pro Ala Ser Val Ser Glu Pro Val Gly Gly
            35                  40                  45

Ser Val Thr Ile Lys Cys Gln Ala Ser Gln Ser Phe Tyr Asn Leu Leu
        50                  55                  60

Ala Trp Tyr Gln Gln Lys Pro Gly Gln Pro Lys Leu Leu Ile Tyr
65                  70                  75                  80

Asp Ala Ser Asp Leu Ala Ser Gly Val Pro Ser Arg Phe Lys Gly Ser
                85                  90                  95

Gly Ser Gly Thr Asp Phe Thr Leu Thr Ile Ser Asp Leu Glu Cys Ala
            100                 105                 110

Asp Ala Ala Ala Tyr Tyr Cys Gln Ser Ala Asp Gly Ser Ser Tyr Ala
```

```
            115                 120                 125
Phe Gly Gly Gly Thr Glu Val Val Lys Gly Gly Gly Gly Ser
        130                 135                 140
Gly Gly Gly Gly Ser Gly Gly Gly Ser Gly Gly Gly Ser Gln
145                 150                 155                 160
Glu Gln Leu Glu Glu Ser Gly Gly Leu Val Lys Pro Glu Gly Ser
                165                 170                 175
Leu Thr Leu Thr Cys Thr Ala Ser Gly Val Ser Phe Ser Ser Tyr
            180                 185                 190
Trp Ile Tyr Trp Val Arg Gln Ala Pro Gly Lys Gly Leu Glu Trp Ile
        195                 200                 205
Ala Cys Ile Tyr Thr Gly Ser Ser Gly Ser Thr Tyr Tyr Ala Ser Trp
        210                 215                 220
Ala Lys Gly Arg Phe Thr Val Ser Glu Thr Ser Ser Thr Val Thr
225                 230                 235                 240
Leu Gln Met Thr Ser Leu Thr Ala Ala Asp Thr Ala Thr Tyr Phe Cys
                245                 250                 255
Ala Arg Ala Ser Ala Trp Thr Tyr Gly Met Asp Leu Trp Gly Pro Gly
            260                 265                 270
Thr Leu Val Thr Val Ser Ser Gly Gly Gly Ser Gly Gly Gly
        275                 280                 285
Ser Gly Gly Gly Ser Gly Ser Lys Pro Ile Pro Asn Pro Leu Leu Gly
290                 295                 300
Leu Asp Ser Thr Gly Gly Gly Ser Gly Gly Gly Gly Ser Gly
305                 310                 315                 320
Gly Gly Gly Ser Gln Val Gln Leu Gln Glu Ser Gly Pro Gly Leu Val
                325                 330                 335
Lys Pro Ser Glu Thr Leu Ser Leu Thr Cys Thr Val Ser Gly Gly Ser
            340                 345                 350
Ile Ser Tyr Tyr Ser Trp Thr Trp Val Arg Gln Pro Ala Gly Gln Gly
        355                 360                 365
Leu Glu Trp Ile Gly Arg Ile His Ile Ser Gly Val Thr Asn His Asn
        370                 375                 380
Pro Ser Leu Lys Ser Arg Val Ser Met Ser Ile Asp Thr Ser Arg Thr
385                 390                 395                 400
Gln Phe Ser Leu Arg Leu Thr Ser Val Thr Ala Ala Asp Thr Ala Val
                405                 410                 415
Tyr Phe Cys Ala Arg Ser Gly Gly Thr Tyr Ser Ala Phe Asp Ile Trp
            420                 425                 430
Gly Gln Gly Thr Met Val Thr Val Ser Ser Gly Gly Gly Gly Ser Gly
        435                 440                 445
Gly Gly Gly Ser Gly Gly Gly Ser Gly Gly Gly Ser Glu Ile
        450                 455                 460
Val Leu Thr Gln Ser Pro Gly Thr Leu Ser Leu Ser Pro Gly Glu Arg
465                 470                 475                 480
Ser Thr Leu Ser Cys Arg Ala Ser Gln Ser Phe Thr Ser Asn Tyr Leu
                485                 490                 495
Ala Trp Tyr Gln Gln Arg Pro Gly Gln Ala Pro Arg Leu Leu Ile Tyr
            500                 505                 510
Gly Ala Ser Thr Arg Ala Ile Gly Ile Pro Asp Arg Phe Ser Gly Ser
        515                 520                 525
Gly Ser Gly Thr Asp Phe Thr Leu Thr Ile Ser Arg Leu Glu Pro Glu
        530                 535                 540
```

Asp Phe Ala Val Tyr Tyr Cys Gln Gln Tyr Gly Ser Ser Pro Trp Thr
545                 550                 555                 560

Phe Gly Gln Gly Thr Lys Val Glu Ile Lys Thr Thr Pro Ala Pro
            565                 570                 575

Arg Pro Pro Thr Pro Ala Pro Thr Ile Ala Ser Gln Pro Leu Ser Leu
        580                 585                 590

Arg Pro Glu Ala Cys Arg Pro Ala Ala Gly Gly Ala Val His Thr Arg
            595                 600                 605

Gly Leu Asp Phe Ala Cys Asp Ile Tyr Ile Trp Ala Pro Leu Ala Gly
            610                 615                 620

Thr Cys Gly Val Leu Leu Leu Ser Leu Val Ile Thr Leu Tyr Cys Lys
625                 630                 635                 640

Arg Gly Arg Lys Lys Leu Leu Tyr Ile Phe Lys Gln Pro Phe Met Arg
            645                 650                 655

Pro Val Gln Thr Thr Gln Glu Glu Asp Gly Cys Ser Cys Arg Phe Pro
            660                 665                 670

Glu Glu Glu Glu Gly Gly Cys Glu Leu Arg Val Lys Phe Ser Arg Ser
            675                 680                 685

Ala Asp Ala Pro Ala Tyr Gln Gln Gly Gln Asn Gln Leu Tyr Asn Glu
            690                 695                 700

Leu Asn Leu Gly Arg Arg Glu Glu Tyr Asp Val Leu Asp Lys Arg Arg
705                 710                 715                 720

Gly Arg Asp Pro Glu Met Gly Gly Lys Pro Arg Arg Lys Asn Pro Gln
            725                 730                 735

Glu Gly Leu Tyr Asn Glu Leu Gln Lys Asp Lys Met Ala Glu Ala Tyr
            740                 745                 750

Ser Glu Ile Gly Met Lys Gly Glu Arg Arg Arg Gly Lys Gly His Asp
            755                 760                 765

Gly Leu Tyr Gln Gly Leu Ser Thr Ala Thr Lys Asp Thr Tyr Asp Ala
            770                 775                 780

Leu His Met Gln Ala Leu Pro Pro Arg
785                 790

<210> SEQ ID NO 18
<211> LENGTH: 796
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Met Ala Leu Pro Val Thr Ala Leu Leu Leu Pro Leu Ala Leu Leu Leu
1               5                   10                  15

His Ala Ala Arg Pro Gly Tyr Pro Tyr Asp Val Pro Asp Tyr Ala Asp
            20                  25                  30

Ile Val Met Thr Gln Thr Pro Ala Ser Val Ser Glu Pro Val Gly Gly
        35                  40                  45

Thr Val Thr Ile Met Cys Gln Ala Ser Gln Ser Ile Ser Asn Trp Leu
50                  55                  60

Ala Trp Tyr Gln Gln Lys Pro Gly Gln Pro Pro Lys Leu Leu Ile Tyr
65                  70                  75                  80

Gln Ala Ser Lys Leu Ala Ser Gly Val Pro Ser Arg Phe Lys Gly Ser
            85                  90                  95

Gly Ser Gly Thr Glu Tyr Thr Leu Thr Ile Ser Asp Leu Glu Cys Ala

-continued

```
                100                 105                 110
Asp Ala Ala Thr Tyr Tyr Cys Gln Ser Tyr Tyr Asp Ser Gly Ser Asn
            115                 120                 125
Val Phe Phe Ala Phe Gly Gly Gly Thr Lys Val Val Glu Gly Gly
        130                 135                 140
Gly Gly Gly Ser Gly Gly Gly Ser Gly Gly Gly Ser Gly Gly
145                 150                 155                 160
Gly Gly Ser Leu Ser Leu Glu Glu Ser Gly Asp Leu Val Lys Pro
                165                 170                 175
Gly Ala Ser Leu Thr Leu Thr Cys Thr Ala Ser Gly Phe Ser Phe Ser
            180                 185                 190
Ala Gly Tyr Trp Ile Cys Trp Val Arg Gln Ala Pro Gly Lys Gly Leu
        195                 200                 205
Glu Trp Ile Ala Cys Thr Tyr Ala Gly Arg Ser Gly Ser Thr Tyr Tyr
    210                 215                 220
Ala Asn Trp Val Asn Gly Arg Phe Thr Ile Pro Lys Thr Ser Ser Thr
225                 230                 235                 240
Thr Val Thr Leu Gln Met Thr Ser Leu Ser Gly Ala Asp Thr Ala Ser
                245                 250                 255
Tyr Phe Cys Ala Arg Gly Asn Ala Gly Val Ala Val Gly Ala Leu Trp
            260                 265                 270
Gly Pro Gly Thr Leu Val Thr Val Ser Ser Gly Gly Gly Ser Gly
        275                 280                 285
Gly Gly Gly Ser Leu Val Pro Arg Gly Ser Lys Pro Ile Pro Asn Pro
    290                 295                 300
Leu Leu Gly Leu Asp Ser Thr Leu Val Pro Arg Gly Ser Gly Gly Gly
305                 310                 315                 320
Gly Ser Gly Gly Gly Ser Gln Val Gln Leu Gln Glu Ser Gly Pro
                325                 330                 335
Gly Leu Val Lys Pro Ser Glu Thr Leu Ser Leu Thr Cys Thr Val Ser
            340                 345                 350
Gly Gly Ser Ile Ser Tyr Tyr Ser Trp Thr Trp Val Arg Gln Pro Ala
        355                 360                 365
Gly Gln Gly Leu Glu Trp Ile Gly Arg Ile His Ile Ser Gly Val Thr
    370                 375                 380
Asn His Asn Pro Ser Leu Lys Ser Arg Val Ser Met Ser Ile Asp Thr
385                 390                 395                 400
Ser Arg Thr Gln Phe Ser Leu Arg Leu Thr Ser Val Thr Ala Ala Asp
                405                 410                 415
Thr Ala Val Tyr Phe Cys Ala Arg Ser Gly Gly Thr Tyr Ser Ala Phe
            420                 425                 430
Asp Ile Trp Gly Gln Gly Thr Met Val Thr Val Ser Ser Gly Gly Gly
        435                 440                 445
Gly Ser Gly Gly Gly Gly Ser Gly Gly Gly Ser Gly Gly Gly Gly
    450                 455                 460
Ser Glu Ile Val Leu Thr Gln Ser Pro Gly Thr Leu Ser Leu Ser Pro
465                 470                 475                 480
Gly Glu Arg Ser Thr Leu Ser Cys Arg Ala Ser Gln Ser Phe Thr Ser
                485                 490                 495
Asn Tyr Leu Ala Trp Tyr Gln Gln Arg Pro Gly Gln Ala Pro Arg Leu
            500                 505                 510
Leu Ile Tyr Gly Ala Ser Thr Arg Ala Ile Gly Ile Pro Asp Arg Phe
        515                 520                 525
```

```
Ser Gly Ser Gly Ser Gly Thr Asp Phe Thr Leu Thr Ile Ser Arg Leu
            530                 535                 540

Glu Pro Glu Asp Phe Ala Val Tyr Tyr Cys Gln Gln Tyr Gly Ser Ser
545                 550                 555                 560

Pro Trp Thr Phe Gly Gln Gly Thr Lys Val Glu Ile Lys Thr Thr Thr
                565                 570                 575

Pro Ala Pro Arg Pro Thr Pro Ala Pro Thr Ile Ala Ser Gln Pro
            580                 585                 590

Leu Ser Leu Arg Pro Glu Ala Cys Arg Pro Ala Ala Gly Gly Ala Val
            595                 600                 605

His Thr Arg Gly Leu Asp Phe Ala Cys Asp Ile Tyr Ile Trp Ala Pro
            610                 615                 620

Leu Ala Gly Thr Cys Gly Val Leu Leu Leu Ser Leu Val Ile Thr Leu
625                 630                 635                 640

Tyr Cys Lys Arg Gly Arg Lys Lys Leu Leu Tyr Ile Phe Lys Gln Pro
                645                 650                 655

Phe Met Arg Pro Val Gln Thr Thr Gln Glu Glu Asp Gly Cys Ser Cys
            660                 665                 670

Arg Phe Pro Glu Glu Glu Glu Gly Gly Cys Glu Leu Arg Val Lys Phe
            675                 680                 685

Ser Arg Ser Ala Asp Ala Pro Ala Tyr Gln Gln Gly Gln Asn Gln Leu
690                 695                 700

Tyr Asn Glu Leu Asn Leu Gly Arg Arg Glu Glu Tyr Asp Val Leu Asp
705                 710                 715                 720

Lys Arg Arg Gly Arg Asp Pro Glu Met Gly Gly Lys Pro Arg Arg Lys
                725                 730                 735

Asn Pro Gln Glu Gly Leu Tyr Asn Glu Leu Gln Lys Asp Lys Met Ala
            740                 745                 750

Glu Ala Tyr Ser Glu Ile Gly Met Lys Gly Glu Arg Arg Gly Lys
                755                 760                 765

Gly His Asp Gly Leu Tyr Gln Gly Leu Ser Thr Ala Thr Lys Asp Thr
            770                 775                 780

Tyr Asp Ala Leu His Met Gln Ala Leu Pro Pro Arg
785                 790                 795

<210> SEQ ID NO 19
<211> LENGTH: 796
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Met Ala Leu Pro Val Thr Ala Leu Leu Leu Pro Leu Ala Leu Leu Leu
1               5                   10                  15

His Ala Ala Arg Pro Gly Tyr Pro Tyr Asp Val Pro Asp Tyr Ala Asp
                20                  25                  30

Ile Val Met Thr Gln Thr Pro Ala Ser Val Ser Glu Pro Val Gly Gly
            35                  40                  45

Thr Val Thr Ile Met Cys Gln Ala Ser Gln Ser Ile Ser Asn Trp Leu
        50                  55                  60

Ala Trp Tyr Gln Gln Lys Pro Gly Gln Pro Lys Leu Leu Ile Tyr
65                  70                  75                  80

Gln Ala Ser Lys Leu Ala Ser Gly Val Pro Ser Arg Phe Lys Gly Ser
```

```
                    85                  90                  95
Gly Ser Gly Thr Glu Tyr Thr Leu Thr Ile Ser Asp Leu Glu Cys Ala
            100                 105                 110

Asp Ala Ala Thr Tyr Tyr Cys Gln Ser Tyr Tyr Asp Ser Gly Ser Asn
            115                 120                 125

Val Phe Phe Ala Phe Gly Gly Gly Thr Lys Val Val Val Glu Gly Gly
            130                 135                 140

Gly Gly Gly Ser Gly Gly Gly Ser Gly Gly Gly Ser Gly Gly Gly Gly
145                 150                 155                 160

Gly Gly Ser Leu Ser Leu Glu Glu Ser Gly Gly Asp Leu Val Lys Pro
            165                 170                 175

Gly Ala Ser Leu Thr Leu Thr Cys Thr Ala Ser Gly Phe Ser Phe Ser
            180                 185                 190

Ala Gly Tyr Trp Ile Cys Trp Val Arg Gln Ala Pro Gly Lys Gly Leu
            195                 200                 205

Glu Trp Ile Ala Cys Thr Tyr Ala Gly Arg Ser Gly Ser Thr Tyr Tyr
            210                 215                 220

Ala Asn Trp Val Asn Gly Arg Phe Thr Ile Pro Lys Thr Ser Ser Thr
225                 230                 235                 240

Thr Val Thr Leu Gln Met Thr Ser Leu Ser Gly Ala Asp Thr Ala Ser
            245                 250                 255

Tyr Phe Cys Ala Arg Gly Asn Ala Gly Val Ala Val Gly Ala Leu Trp
            260                 265                 270

Gly Pro Gly Thr Leu Val Thr Val Ser Ser Gly Gly Gly Gly Ser Gly
            275                 280                 285

Gly Gly Gly Ser Gly Gly Gly Ser Gly Ser Lys Pro Ile Pro Asn Pro
            290                 295                 300

Leu Leu Gly Leu Asp Ser Thr Gly Gly Ser Gly Ser Gly Gly Gly Gly
305                 310                 315                 320

Gly Ser Gly Gly Gly Ser Gln Val Gln Leu Gln Glu Ser Gly Pro Gly
            325                 330                 335

Gly Leu Val Lys Pro Ser Glu Thr Leu Ser Leu Thr Cys Thr Val Ser
            340                 345                 350

Gly Gly Ser Ile Ser Tyr Tyr Ser Trp Thr Trp Val Arg Gln Pro Ala
            355                 360                 365

Gly Gln Gly Leu Glu Trp Ile Gly Arg Ile His Ile Ser Gly Val Thr
            370                 375                 380

Asn His Asn Pro Ser Leu Lys Ser Arg Val Ser Met Ser Ile Asp Thr
385                 390                 395                 400

Ser Arg Thr Gln Phe Ser Leu Arg Leu Thr Ser Val Thr Ala Ala Asp
            405                 410                 415

Thr Ala Val Tyr Phe Cys Ala Arg Ser Gly Gly Thr Tyr Ser Ala Phe
            420                 425                 430

Asp Ile Trp Gly Gln Gly Thr Met Val Thr Val Ser Ser Gly Gly Gly
            435                 440                 445

Gly Ser Gly Gly Gly Gly Ser Gly Gly Gly Gly Ser Gly Gly Gly Gly
            450                 455                 460

Ser Glu Ile Val Leu Thr Gln Ser Pro Gly Thr Leu Ser Leu Ser Pro
465                 470                 475                 480

Gly Glu Arg Ser Thr Leu Ser Cys Arg Ala Ser Gln Ser Phe Thr Ser
            485                 490                 495

Asn Tyr Leu Ala Trp Tyr Gln Gln Arg Pro Gly Gln Ala Pro Arg Leu
            500                 505                 510
```

```
Leu Ile Tyr Gly Ala Ser Thr Arg Ala Ile Gly Ile Pro Asp Arg Phe
            515                 520                 525

Ser Gly Ser Gly Ser Gly Thr Asp Phe Thr Leu Thr Ile Ser Arg Leu
        530                 535                 540

Glu Pro Glu Asp Phe Ala Val Tyr Tyr Cys Gln Gln Tyr Gly Ser Ser
545                 550                 555                 560

Pro Trp Thr Phe Gly Gln Gly Thr Lys Val Glu Ile Lys Thr Thr Thr
                565                 570                 575

Pro Ala Pro Arg Pro Pro Thr Pro Ala Pro Thr Ile Ala Ser Gln Pro
                580                 585                 590

Leu Ser Leu Arg Pro Glu Ala Cys Arg Pro Ala Ala Gly Gly Ala Val
        595                 600                 605

His Thr Arg Gly Leu Asp Phe Ala Cys Asp Ile Tyr Ile Trp Ala Pro
    610                 615                 620

Leu Ala Gly Thr Cys Gly Val Leu Leu Leu Ser Leu Val Ile Thr Leu
625                 630                 635                 640

Tyr Cys Lys Arg Gly Arg Lys Lys Leu Leu Tyr Ile Phe Lys Gln Pro
                645                 650                 655

Phe Met Arg Pro Val Gln Thr Thr Gln Glu Glu Asp Gly Cys Ser Cys
                660                 665                 670

Arg Phe Pro Glu Glu Glu Glu Gly Gly Cys Glu Leu Arg Val Lys Phe
                675                 680                 685

Ser Arg Ser Ala Asp Ala Pro Ala Tyr Gln Gln Gly Gln Asn Gln Leu
        690                 695                 700

Tyr Asn Glu Leu Asn Leu Gly Arg Arg Glu Glu Tyr Asp Val Leu Asp
705                 710                 715                 720

Lys Arg Arg Gly Arg Asp Pro Glu Met Gly Gly Lys Pro Arg Arg Lys
                725                 730                 735

Asn Pro Gln Glu Gly Leu Tyr Asn Glu Leu Gln Lys Asp Lys Met Ala
                740                 745                 750

Glu Ala Tyr Ser Glu Ile Gly Met Lys Gly Glu Arg Arg Arg Gly Lys
        755                 760                 765

Gly His Asp Gly Leu Tyr Gln Gly Leu Ser Thr Ala Thr Lys Asp Thr
    770                 775                 780

Tyr Asp Ala Leu His Met Gln Ala Leu Pro Pro Arg
785                 790                 795

<210> SEQ ID NO 20
<211> LENGTH: 793
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Met Ala Leu Pro Val Thr Ala Leu Leu Leu Pro Leu Ala Leu Leu Leu
1               5                   10                  15

His Ala Ala Arg Pro Gly Tyr Pro Tyr Asp Val Pro Asp Tyr Ala Asp
                20                  25                  30

Ile Val Met Thr Gln Thr Pro Ala Ser Val Ser Glu Pro Val Gly Gly
            35                  40                  45

Ser Val Thr Ile Lys Cys Gln Ala Ser Gln Ser Phe Tyr Asn Leu Leu
        50                  55                  60

Ala Trp Tyr Gln Gln Lys Pro Gly Gln Pro Pro Lys Leu Leu Ile Tyr
```

-continued

```
        65                  70                  75                  80
Asp Ala Ser Asp Leu Ala Ser Gly Val Pro Ser Arg Phe Lys Gly Ser
                    85                  90                  95
Gly Ser Gly Thr Asp Phe Thr Leu Thr Ile Ser Asp Leu Glu Cys Ala
                100                 105                 110
Asp Ala Ala Tyr Tyr Cys Gln Ser Ala Asp Gly Ser Ser Tyr Ala
                115                 120                 125
Phe Gly Gly Gly Thr Glu Val Val Lys Gly Gly Gly Gly Ser
    130                 135                 140
Gly Gly Gly Ser Gly Gly Gly Ser Gly Gly Gly Ser Gln
145                 150                 155                 160
Glu Gln Leu Glu Glu Ser Gly Gly Leu Val Lys Pro Glu Gly Ser
                165                 170                 175
Leu Thr Leu Thr Cys Thr Ala Ser Gly Val Ser Phe Ser Ser Tyr
                180                 185                 190
Trp Ile Tyr Trp Val Arg Gln Ala Pro Gly Lys Gly Leu Glu Trp Ile
            195                 200                 205
Ala Cys Ile Tyr Thr Gly Ser Ser Gly Ser Thr Tyr Tyr Ala Ser Trp
    210                 215                 220
Ala Lys Gly Arg Phe Thr Val Ser Glu Thr Ser Ser Thr Val Thr
225                 230                 235                 240
Leu Gln Met Thr Ser Leu Thr Ala Ala Asp Thr Ala Thr Tyr Phe Cys
                245                 250                 255
Ala Arg Ala Ser Ala Trp Thr Tyr Gly Met Asp Leu Trp Gly Pro Gly
                260                 265                 270
Thr Leu Val Thr Val Ser Ser Gly Gly Gly Ser Gly Gly Gly Gly
            275                 280                 285
Ser Gly Gly Gly Ser Gly Leu Ser Gly Arg Ser Asp Asn His Ser Pro
    290                 295                 300
Leu Gly Leu Ala Gly Ser Gly Gly Ser Gly Gly Gly Ser Gly
305                 310                 315                 320
Gly Gly Gly Ser Gln Val Gln Leu Gln Glu Ser Gly Pro Gly Leu Val
                325                 330                 335
Lys Pro Ser Glu Thr Leu Ser Leu Thr Cys Thr Val Ser Gly Gly Ser
                340                 345                 350
Ile Ser Tyr Tyr Ser Trp Thr Trp Val Arg Gln Pro Ala Gly Gln Gly
            355                 360                 365
Leu Glu Trp Ile Gly Arg Ile His Ile Ser Gly Val Thr Asn His Asn
    370                 375                 380
Pro Ser Leu Lys Ser Arg Val Ser Met Ser Ile Asp Thr Ser Arg Thr
385                 390                 395                 400
Gln Phe Ser Leu Arg Leu Thr Ser Val Thr Ala Ala Asp Thr Ala Val
                405                 410                 415
Tyr Phe Cys Ala Arg Ser Gly Gly Thr Tyr Ser Ala Phe Asp Ile Trp
            420                 425                 430
Gly Gln Gly Thr Met Val Thr Val Ser Ser Gly Gly Gly Ser Gly
    435                 440                 445
Gly Gly Gly Ser Gly Gly Gly Ser Gly Gly Gly Ser Glu Ile
450                 455                 460
Val Leu Thr Gln Ser Pro Gly Thr Leu Ser Leu Ser Pro Gly Glu Arg
                470                 475                 480
Ser Thr Leu Ser Cys Arg Ala Ser Gln Ser Phe Thr Ser Asn Tyr Leu
                485                 490                 495
```

```
Ala Trp Tyr Gln Gln Arg Pro Gly Gln Ala Pro Arg Leu Leu Ile Tyr
            500                 505                 510

Gly Ala Ser Thr Arg Ala Ile Gly Ile Pro Asp Arg Phe Ser Gly Ser
            515                 520                 525

Gly Ser Gly Thr Asp Phe Thr Leu Thr Ile Ser Arg Leu Glu Pro Glu
        530                 535                 540

Asp Phe Ala Val Tyr Tyr Cys Gln Gln Tyr Gly Ser Ser Pro Trp Thr
545                 550                 555                 560

Phe Gly Gln Gly Thr Lys Val Glu Ile Lys Thr Thr Thr Pro Ala Pro
                565                 570                 575

Arg Pro Pro Thr Pro Ala Pro Thr Ile Ala Ser Gln Pro Leu Ser Leu
            580                 585                 590

Arg Pro Glu Ala Cys Arg Pro Ala Ala Gly Gly Ala Val His Thr Arg
        595                 600                 605

Gly Leu Asp Phe Ala Cys Asp Ile Tyr Ile Trp Ala Pro Leu Ala Gly
        610                 615                 620

Thr Cys Gly Val Leu Leu Leu Ser Leu Val Ile Thr Leu Tyr Cys Lys
625                 630                 635                 640

Arg Gly Arg Lys Lys Leu Leu Tyr Ile Phe Lys Gln Pro Phe Met Arg
                645                 650                 655

Pro Val Gln Thr Thr Gln Glu Glu Asp Gly Cys Ser Cys Arg Phe Pro
            660                 665                 670

Glu Glu Glu Glu Gly Gly Cys Glu Leu Arg Val Lys Phe Ser Arg Ser
        675                 680                 685

Ala Asp Ala Pro Ala Tyr Gln Gln Gly Gln Asn Gln Leu Tyr Asn Glu
        690                 695                 700

Leu Asn Leu Gly Arg Arg Glu Glu Tyr Asp Val Leu Asp Lys Arg Arg
705                 710                 715                 720

Gly Arg Asp Pro Glu Met Gly Gly Lys Pro Arg Arg Lys Asn Pro Gln
                725                 730                 735

Glu Gly Leu Tyr Asn Glu Leu Gln Lys Asp Lys Met Ala Glu Ala Tyr
            740                 745                 750

Ser Glu Ile Gly Met Lys Gly Glu Arg Arg Arg Gly Lys Gly His Asp
        755                 760                 765

Gly Leu Tyr Gln Gly Leu Ser Thr Ala Thr Lys Asp Thr Tyr Asp Ala
        770                 775                 780

Leu His Met Gln Ala Leu Pro Pro Arg
785                 790

<210> SEQ ID NO 21
<211> LENGTH: 796
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Met Ala Leu Pro Val Thr Ala Leu Leu Leu Pro Leu Ala Leu Leu Leu
1               5                   10                  15

His Ala Ala Arg Pro Gly Tyr Pro Tyr Asp Val Pro Asp Tyr Ala Asp
                20                  25                  30

Ile Val Met Thr Gln Thr Pro Ala Ser Val Ser Glu Pro Val Gly Gly
            35                  40                  45

Thr Val Thr Ile Met Cys Gln Ala Ser Gln Ser Ile Ser Asn Trp Leu
```

-continued

```
            50                  55                  60
Ala Trp Tyr Gln Gln Lys Pro Gly Gln Pro Pro Lys Leu Leu Ile Tyr
 65                  70                  75                  80

Gln Ala Ser Lys Leu Ala Ser Gly Val Pro Ser Arg Phe Lys Gly Ser
                 85                  90                  95

Gly Ser Gly Thr Glu Tyr Thr Leu Thr Ile Ser Asp Leu Glu Cys Ala
                100                 105                 110

Asp Ala Ala Thr Tyr Tyr Cys Gln Ser Tyr Tyr Asp Ser Gly Ser Asn
                115                 120                 125

Val Phe Phe Ala Phe Gly Gly Thr Lys Val Val Glu Gly Gly
            130                 135                 140

Gly Gly Gly Ser Gly Gly Gly Ser Gly Gly Gly Ser Gly Gly
145                 150                 155                 160

Gly Gly Ser Leu Ser Leu Glu Glu Ser Gly Gly Asp Leu Val Lys Pro
                165                 170                 175

Gly Ala Ser Leu Thr Leu Thr Cys Thr Ala Ser Gly Phe Ser Phe Ser
                180                 185                 190

Ala Gly Tyr Trp Ile Cys Trp Val Arg Gln Ala Pro Gly Lys Gly Leu
            195                 200                 205

Glu Trp Ile Ala Cys Thr Tyr Ala Gly Arg Ser Gly Ser Thr Tyr Tyr
            210                 215                 220

Ala Asn Trp Val Asn Gly Arg Phe Thr Ile Pro Lys Thr Ser Ser Thr
225                 230                 235                 240

Thr Val Thr Leu Gln Met Thr Ser Leu Ser Gly Ala Asp Thr Ala Ser
                245                 250                 255

Tyr Phe Cys Ala Arg Gly Asn Ala Gly Val Ala Val Gly Ala Leu Trp
                260                 265                 270

Gly Pro Gly Thr Leu Val Thr Val Ser Gly Gly Gly Gly Ser Gly
            275                 280                 285

Gly Gly Gly Ser Gly Gly Gly Ser Gly Leu Ser Gly Arg Ser Asp Asn
            290                 295                 300

His Ser Pro Leu Gly Leu Ala Gly Ser Gly Gly Ser Gly Gly Gly
305                 310                 315                 320

Gly Ser Gly Gly Gly Ser Gln Val Gln Leu Gln Glu Ser Gly Pro
                325                 330                 335

Gly Leu Val Lys Pro Ser Glu Thr Leu Ser Leu Thr Cys Thr Val Ser
            340                 345                 350

Gly Gly Ser Ile Ser Tyr Tyr Ser Trp Thr Trp Val Arg Gln Pro Ala
            355                 360                 365

Gly Gln Gly Leu Glu Trp Ile Gly Arg Ile His Ile Ser Gly Val Thr
370                 375                 380

Asn His Asn Pro Ser Leu Lys Ser Arg Val Ser Met Ser Ile Asp Thr
385                 390                 395                 400

Ser Arg Thr Gln Phe Ser Leu Arg Leu Thr Ser Val Thr Ala Ala Asp
                405                 410                 415

Thr Ala Val Tyr Phe Cys Ala Arg Ser Gly Gly Thr Tyr Ser Ala Phe
                420                 425                 430

Asp Ile Trp Gly Gln Gly Thr Met Val Thr Val Ser Ser Gly Gly Gly
            435                 440                 445

Gly Ser Gly Gly Gly Gly Ser Gly Gly Gly Ser Gly Gly Gly Gly
        450                 455                 460

Ser Glu Ile Val Leu Thr Gln Ser Pro Gly Thr Leu Ser Leu Ser Pro
465                 470                 475                 480
```

```
Gly Glu Arg Ser Thr Leu Ser Cys Arg Ala Ser Gln Ser Phe Thr Ser
                485                 490                 495

Asn Tyr Leu Ala Trp Tyr Gln Gln Arg Pro Gly Gln Ala Pro Arg Leu
            500                 505                 510

Leu Ile Tyr Gly Ala Ser Thr Arg Ala Ile Gly Ile Pro Asp Arg Phe
        515                 520                 525

Ser Gly Ser Gly Ser Gly Thr Asp Phe Thr Leu Thr Ile Ser Arg Leu
    530                 535                 540

Glu Pro Glu Asp Phe Ala Val Tyr Tyr Cys Gln Gln Tyr Gly Ser Ser
545                 550                 555                 560

Pro Trp Thr Phe Gly Gln Gly Thr Lys Val Glu Ile Lys Thr Thr Thr
                565                 570                 575

Pro Ala Pro Arg Pro Pro Thr Pro Ala Pro Thr Ile Ala Ser Gln Pro
            580                 585                 590

Leu Ser Leu Arg Pro Glu Ala Cys Arg Pro Ala Ala Gly Gly Ala Val
        595                 600                 605

His Thr Arg Gly Leu Asp Phe Ala Cys Asp Ile Tyr Ile Trp Ala Pro
    610                 615                 620

Leu Ala Gly Thr Cys Gly Val Leu Leu Leu Ser Leu Val Ile Thr Leu
625                 630                 635                 640

Tyr Cys Lys Arg Gly Arg Lys Lys Leu Leu Tyr Ile Phe Lys Gln Pro
                645                 650                 655

Phe Met Arg Pro Val Gln Thr Thr Gln Glu Glu Asp Gly Cys Ser Cys
            660                 665                 670

Arg Phe Pro Glu Glu Glu Glu Gly Gly Cys Glu Leu Arg Val Lys Phe
        675                 680                 685

Ser Arg Ser Ala Asp Ala Pro Ala Tyr Gln Gln Gly Gln Asn Gln Leu
    690                 695                 700

Tyr Asn Glu Leu Asn Leu Gly Arg Arg Glu Glu Tyr Asp Val Leu Asp
705                 710                 715                 720

Lys Arg Arg Gly Arg Asp Pro Glu Met Gly Gly Lys Pro Arg Arg Lys
                725                 730                 735

Asn Pro Gln Glu Gly Leu Tyr Asn Glu Leu Gln Lys Asp Lys Met Ala
            740                 745                 750

Glu Ala Tyr Ser Glu Ile Gly Met Lys Gly Glu Arg Arg Arg Gly Lys
        755                 760                 765

Gly His Asp Gly Leu Tyr Gln Gly Leu Ser Thr Ala Thr Lys Asp Thr
    770                 775                 780

Tyr Asp Ala Leu His Met Gln Ala Leu Pro Pro Arg
785                 790                 795

<210> SEQ ID NO 22
<211> LENGTH: 803
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Met Ala Leu Pro Val Thr Ala Leu Leu Leu Pro Leu Ala Leu Leu Leu
1               5                   10                  15

His Ala Ala Arg Pro Gly Tyr Pro Tyr Asp Val Pro Asp Tyr Ala Asp
            20                  25                  30

Ile Val Met Thr Gln Thr Pro Ala Ser Val Ser Glu Pro Val Gly Gly
```

```
              35                  40                  45
Ser Val Thr Ile Lys Cys Gln Ala Ser Gln Ser Phe Tyr Asn Leu Leu
 50                  55                  60
Ala Trp Tyr Gln Gln Lys Pro Gly Gln Pro Pro Lys Leu Leu Ile Tyr
 65                  70                  75                  80
Asp Ala Ser Asp Leu Ala Ser Gly Val Pro Ser Arg Phe Lys Gly Ser
                     85                  90                  95
Gly Ser Gly Thr Asp Phe Thr Leu Thr Ile Ser Asp Leu Glu Cys Ala
                100                 105                 110
Asp Ala Ala Tyr Tyr Cys Gln Ser Ala Asp Gly Ser Ser Tyr Ala
                115                 120                 125
Phe Gly Gly Gly Thr Glu Val Val Lys Gly Gly Gly Gly Ser
130                 135                 140
Gly Gly Gly Gly Ser Gly Gly Gly Ser Gly Gly Gly Ser Gln
145                 150                 155                 160
Glu Gln Leu Glu Glu Ser Gly Gly Leu Val Lys Pro Gly Ser
                165                 170                 175
Leu Thr Leu Thr Cys Thr Ala Ser Gly Val Ser Phe Ser Ser Ser Tyr
                180                 185                 190
Trp Ile Tyr Trp Val Arg Gln Ala Pro Gly Lys Gly Leu Glu Trp Ile
                195                 200                 205
Ala Cys Ile Tyr Thr Gly Ser Ser Gly Ser Thr Tyr Tyr Ala Ser Trp
210                 215                 220
Ala Lys Gly Arg Phe Thr Val Ser Glu Thr Ser Ser Thr Val Thr
225                 230                 235                 240
Leu Gln Met Thr Ser Leu Thr Ala Ala Asp Thr Ala Thr Tyr Phe Cys
                245                 250                 255
Ala Arg Ala Ser Ala Trp Thr Tyr Gly Met Asp Leu Trp Gly Pro Gly
                260                 265                 270
Thr Leu Val Thr Val Ser Ser Gly Gly Gly Ser Leu Ser Gly Arg
                275                 280                 285
Ser Asp Asn His Ser Pro Leu Gly Leu Ala Gly Ser Lys Pro Ile Pro
290                 295                 300
Asn Pro Leu Leu Gly Leu Asp Ser Thr Leu Ser Gly Arg Ser Asp Asn
305                 310                 315                 320
His Ser Pro Leu Gly Leu Ala Gly Ser Gly Gly Gly Ser Gln Val
                325                 330                 335
Gln Leu Gln Glu Ser Gly Pro Gly Leu Val Lys Pro Ser Glu Thr Leu
                340                 345                 350
Ser Leu Thr Cys Thr Val Ser Gly Gly Ser Ile Ser Tyr Tyr Ser Trp
                355                 360                 365
Thr Trp Val Arg Gln Pro Ala Gly Gln Gly Leu Glu Trp Ile Gly Arg
                370                 375                 380
Ile His Ile Ser Gly Val Thr Asn His Asn Pro Ser Leu Lys Ser Arg
385                 390                 395                 400
Val Ser Met Ser Ile Asp Thr Ser Arg Thr Gln Phe Ser Leu Arg Leu
                405                 410                 415
Thr Ser Val Thr Ala Ala Asp Thr Ala Val Tyr Phe Cys Ala Arg Ser
                420                 425                 430
Gly Gly Thr Tyr Ser Ala Phe Asp Ile Trp Gly Gln Gly Thr Met Val
                435                 440                 445
Thr Val Ser Ser Gly Gly Gly Gly Ser Gly Gly Gly Gly Ser Gly Gly
450                 455                 460
```

Gly Gly Ser Gly Gly Gly Ser Glu Ile Val Leu Thr Gln Ser Pro
465                 470                 475                 480

Gly Thr Leu Ser Leu Ser Pro Gly Glu Arg Ser Thr Leu Ser Cys Arg
                485                 490                 495

Ala Ser Gln Ser Phe Thr Ser Asn Tyr Leu Ala Trp Tyr Gln Gln Arg
            500                 505                 510

Pro Gly Gln Ala Pro Arg Leu Leu Ile Tyr Gly Ala Ser Thr Arg Ala
        515                 520                 525

Ile Gly Ile Pro Asp Arg Phe Ser Gly Ser Gly Ser Gly Thr Asp Phe
530                 535                 540

Thr Leu Thr Ile Ser Arg Leu Glu Pro Glu Asp Phe Ala Val Tyr Tyr
545                 550                 555                 560

Cys Gln Gln Tyr Gly Ser Ser Pro Trp Thr Phe Gly Gln Gly Thr Lys
                565                 570                 575

Val Glu Ile Lys Thr Thr Thr Pro Ala Pro Arg Pro Pro Thr Pro Ala
            580                 585                 590

Pro Thr Ile Ala Ser Gln Pro Leu Ser Leu Arg Pro Glu Ala Cys Arg
        595                 600                 605

Pro Ala Ala Gly Gly Ala Val His Thr Arg Gly Leu Asp Phe Ala Cys
610                 615                 620

Asp Ile Tyr Ile Trp Ala Pro Leu Ala Gly Thr Cys Gly Val Leu Leu
625                 630                 635                 640

Leu Ser Leu Val Ile Thr Leu Tyr Cys Lys Arg Gly Arg Lys Lys Leu
                645                 650                 655

Leu Tyr Ile Phe Lys Gln Pro Phe Met Arg Pro Val Gln Thr Thr Gln
            660                 665                 670

Glu Glu Asp Gly Cys Ser Cys Arg Phe Pro Glu Glu Glu Glu Gly Gly
        675                 680                 685

Cys Glu Leu Arg Val Lys Phe Ser Arg Ser Ala Asp Ala Pro Ala Tyr
690                 695                 700

Gln Gln Gly Gln Asn Gln Leu Tyr Asn Glu Leu Asn Leu Gly Arg Arg
705                 710                 715                 720

Glu Glu Tyr Asp Val Leu Asp Lys Arg Gly Arg Asp Pro Glu Met
                725                 730                 735

Gly Gly Lys Pro Arg Arg Lys Asn Pro Gln Glu Gly Leu Tyr Asn Glu
            740                 745                 750

Leu Gln Lys Asp Lys Met Ala Glu Ala Tyr Ser Glu Ile Gly Met Lys
        755                 760                 765

Gly Glu Arg Arg Arg Gly Lys Gly His Asp Gly Leu Tyr Gln Gly Leu
770                 775                 780

Ser Thr Ala Thr Lys Asp Thr Tyr Asp Ala Leu His Met Gln Ala Leu
785                 790                 795                 800

Pro Pro Arg

<210> SEQ ID NO 23
<211> LENGTH: 806
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Met Ala Leu Pro Val Thr Ala Leu Leu Leu Pro Leu Ala Leu Leu Leu
1               5                   10                  15

-continued

```
His Ala Ala Arg Pro Gly Tyr Pro Tyr Asp Val Pro Asp Tyr Ala Asp
            20                  25                  30

Ile Val Met Thr Gln Thr Pro Ala Ser Val Ser Glu Pro Val Gly Gly
        35                  40                  45

Thr Val Thr Ile Met Cys Gln Ala Ser Gln Ser Ile Ser Asn Trp Leu
    50                  55                  60

Ala Trp Tyr Gln Gln Lys Pro Gly Gln Pro Lys Leu Leu Ile Tyr
65                  70                  75                  80

Gln Ala Ser Lys Leu Ala Ser Gly Val Pro Ser Arg Phe Lys Gly Ser
                85                  90                  95

Gly Ser Gly Thr Glu Tyr Thr Leu Thr Ile Ser Asp Leu Glu Cys Ala
            100                 105                 110

Asp Ala Ala Thr Tyr Tyr Cys Gln Ser Tyr Tyr Asp Ser Gly Ser Asn
        115                 120                 125

Val Phe Phe Ala Phe Gly Gly Thr Lys Val Val Glu Gly Gly
    130                 135                 140

Gly Gly Gly Ser Gly Gly Gly Ser Gly Gly Gly Ser Gly Gly
145                 150                 155                 160

Gly Gly Ser Leu Ser Leu Glu Glu Ser Gly Asp Leu Val Lys Pro
                165                 170                 175

Gly Ala Ser Leu Thr Leu Thr Cys Thr Ala Ser Gly Phe Ser Phe Ser
            180                 185                 190

Ala Gly Tyr Trp Ile Cys Trp Val Arg Gln Ala Pro Gly Lys Gly Leu
        195                 200                 205

Glu Trp Ile Ala Cys Thr Tyr Ala Gly Arg Ser Gly Ser Thr Tyr Tyr
    210                 215                 220

Ala Asn Trp Val Asn Gly Arg Phe Thr Ile Pro Lys Thr Ser Ser Thr
225                 230                 235                 240

Thr Val Thr Leu Gln Met Thr Ser Leu Ser Gly Ala Asp Thr Ala Ser
                245                 250                 255

Tyr Phe Cys Ala Arg Gly Asn Ala Gly Val Ala Val Gly Ala Leu Trp
            260                 265                 270

Gly Pro Gly Thr Leu Val Thr Val Ser Ser Gly Gly Gly Ser Leu
        275                 280                 285

Ser Gly Arg Ser Asp Asn His Ser Pro Leu Gly Leu Ala Gly Ser Lys
    290                 295                 300

Pro Ile Pro Asn Pro Leu Leu Gly Leu Asp Ser Thr Leu Ser Gly Arg
305                 310                 315                 320

Ser Asp Asn His Ser Pro Leu Gly Leu Ala Gly Ser Gly Gly Gly Gly
                325                 330                 335

Ser Gln Val Gln Leu Gln Glu Ser Gly Pro Gly Leu Val Lys Pro Ser
            340                 345                 350

Glu Thr Leu Ser Leu Thr Cys Thr Val Ser Gly Gly Ser Ile Ser Tyr
        355                 360                 365

Tyr Ser Trp Thr Trp Val Arg Gln Pro Ala Gly Gln Gly Leu Glu Trp
    370                 375                 380

Ile Gly Arg Ile His Ile Ser Gly Val Thr Asn His Asn Pro Ser Leu
385                 390                 395                 400

Lys Ser Arg Val Ser Met Ser Ile Asp Thr Ser Arg Thr Gln Phe Ser
                405                 410                 415

Leu Arg Leu Thr Ser Val Thr Ala Ala Asp Thr Ala Val Tyr Phe Cys
            420                 425                 430
```

Ala Arg Ser Gly Gly Thr Tyr Ser Ala Phe Asp Ile Trp Gly Gln Gly
            435                 440                 445

Thr Met Val Thr Val Ser Ser Gly Gly Gly Ser Gly Gly Gly Gly
450                 455                 460

Ser Gly Gly Gly Ser Gly Gly Gly Gly Ser Glu Ile Val Leu Thr
465                 470                 475                 480

Gln Ser Pro Gly Thr Leu Ser Leu Ser Pro Gly Glu Arg Ser Thr Leu
                485                 490                 495

Ser Cys Arg Ala Ser Gln Ser Phe Thr Ser Asn Tyr Leu Ala Trp Tyr
            500                 505                 510

Gln Gln Arg Pro Gly Gln Ala Pro Arg Leu Leu Ile Tyr Gly Ala Ser
            515                 520                 525

Thr Arg Ala Ile Gly Ile Pro Asp Arg Phe Ser Gly Ser Gly Ser Gly
530                 535                 540

Thr Asp Phe Thr Leu Thr Ile Ser Arg Leu Glu Pro Glu Asp Phe Ala
545                 550                 555                 560

Val Tyr Tyr Cys Gln Gln Tyr Gly Ser Ser Pro Trp Thr Phe Gly Gln
                565                 570                 575

Gly Thr Lys Val Glu Ile Lys Thr Thr Thr Pro Ala Pro Arg Pro Pro
            580                 585                 590

Thr Pro Ala Pro Thr Ile Ala Ser Gln Pro Leu Ser Leu Arg Pro Glu
            595                 600                 605

Ala Cys Arg Pro Ala Ala Gly Gly Ala Val His Thr Arg Gly Leu Asp
            610                 615                 620

Phe Ala Cys Asp Ile Tyr Ile Trp Ala Pro Leu Ala Gly Thr Cys Gly
625                 630                 635                 640

Val Leu Leu Leu Ser Leu Val Ile Thr Leu Tyr Cys Lys Arg Gly Arg
                645                 650                 655

Lys Lys Leu Leu Tyr Ile Phe Lys Gln Pro Phe Met Arg Pro Val Gln
            660                 665                 670

Thr Thr Gln Glu Glu Asp Gly Cys Ser Cys Arg Phe Pro Glu Glu Glu
            675                 680                 685

Glu Gly Gly Cys Glu Leu Arg Val Lys Phe Ser Arg Ser Ala Asp Ala
690                 695                 700

Pro Ala Tyr Gln Gln Gly Gln Asn Gln Leu Tyr Asn Glu Leu Asn Leu
705                 710                 715                 720

Gly Arg Arg Glu Glu Tyr Asp Val Leu Asp Lys Arg Arg Gly Arg Asp
                725                 730                 735

Pro Glu Met Gly Gly Lys Pro Arg Arg Lys Asn Pro Gln Glu Gly Leu
            740                 745                 750

Tyr Asn Glu Leu Gln Lys Asp Lys Met Ala Glu Ala Tyr Ser Glu Ile
            755                 760                 765

Gly Met Lys Gly Glu Arg Arg Arg Gly Lys Gly His Asp Gly Leu Tyr
770                 775                 780

Gln Gly Leu Ser Thr Ala Thr Lys Asp Thr Tyr Asp Ala Leu His Met
785                 790                 795                 800

Gln Ala Leu Pro Pro Arg
                805

<210> SEQ ID NO 24
<211> LENGTH: 809
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 24

```
Met Ala Leu Pro Val Thr Ala Leu Leu Leu Pro Leu Ala Leu Leu Leu
1               5                   10                  15

His Ala Ala Arg Pro Gly Tyr Pro Tyr Asp Val Pro Asp Tyr Ala Asp
            20                  25                  30

Ile Val Met Thr Gln Thr Pro Ala Ser Val Ser Glu Pro Val Gly Gly
        35                  40                  45

Ser Val Thr Ile Lys Cys Gln Ala Ser Gln Ser Phe Tyr Asn Leu Leu
    50                  55                  60

Ala Trp Tyr Gln Gln Lys Pro Gly Gln Pro Pro Lys Leu Leu Ile Tyr
65                  70                  75                  80

Asp Ala Ser Asp Leu Ala Ser Gly Val Pro Ser Arg Phe Lys Gly Ser
                85                  90                  95

Gly Ser Gly Thr Asp Phe Thr Leu Thr Ile Ser Asp Leu Glu Cys Ala
            100                 105                 110

Asp Ala Ala Ala Tyr Tyr Cys Gln Ser Ala Asp Gly Ser Ser Tyr Ala
        115                 120                 125

Phe Gly Gly Gly Thr Glu Val Val Lys Gly Gly Gly Gly Ser
    130                 135                 140

Gly Gly Gly Gly Ser Leu Ser Gly Arg Ser Asp Asn His Ser Pro Leu
145                 150                 155                 160

Gly Leu Ala Gly Ser Gly Gly Gly Ser Gly Gly Gly Ser Gln
                165                 170                 175

Glu Gln Leu Glu Glu Ser Gly Gly Gly Leu Val Lys Pro Glu Gly Ser
            180                 185                 190

Leu Thr Leu Thr Cys Thr Ala Ser Gly Val Ser Phe Ser Ser Ser Tyr
        195                 200                 205

Trp Ile Tyr Trp Val Arg Gln Ala Pro Gly Lys Gly Leu Glu Trp Ile
210                 215                 220

Ala Cys Ile Tyr Thr Gly Ser Ser Gly Ser Thr Tyr Tyr Ala Ser Trp
225                 230                 235                 240

Ala Lys Gly Arg Phe Thr Val Ser Glu Thr Ser Ser Thr Thr Val Thr
                245                 250                 255

Leu Gln Met Thr Ser Leu Thr Ala Ala Asp Thr Ala Thr Tyr Phe Cys
            260                 265                 270

Ala Arg Ala Ser Ala Trp Thr Tyr Gly Met Asp Leu Trp Gly Pro Gly
        275                 280                 285

Thr Leu Val Thr Val Ser Ser Gly Gly Gly Ser Gly Gly Gly Gly
    290                 295                 300

Ser Gly Gly Gly Ser Gly Leu Ser Gly Arg Ser Asp Asn His Ser Pro
305                 310                 315                 320

Leu Gly Leu Ala Gly Ser Gly Gly Ser Gly Gly Gly Ser Gly
                325                 330                 335

Gly Gly Gly Ser Gln Val Gln Leu Gln Glu Ser Gly Pro Gly Leu Val
            340                 345                 350

Lys Pro Ser Glu Thr Leu Ser Leu Thr Cys Thr Val Ser Gly Gly Ser
        355                 360                 365

Ile Ser Tyr Tyr Ser Trp Thr Trp Val Arg Gln Pro Ala Gly Gln Gly
    370                 375                 380

Leu Glu Trp Ile Gly Arg Ile His Ile Ser Gly Val Thr Asn His Asn
385                 390                 395                 400
```

```
Pro Ser Leu Lys Ser Arg Val Ser Met Ser Ile Asp Thr Ser Arg Thr
                405                 410                 415

Gln Phe Ser Leu Arg Leu Thr Ser Val Thr Ala Ala Asp Thr Ala Val
            420                 425                 430

Tyr Phe Cys Ala Arg Ser Gly Gly Thr Tyr Ser Ala Phe Asp Ile Trp
            435                 440                 445

Gly Gln Gly Thr Met Val Thr Val Ser Ser Gly Gly Gly Gly Ser Gly
        450                 455                 460

Gly Gly Gly Ser Gly Gly Gly Ser Gly Gly Gly Gly Ser Glu Ile
465                 470                 475                 480

Val Leu Thr Gln Ser Pro Gly Thr Leu Ser Leu Ser Pro Gly Glu Arg
                485                 490                 495

Ser Thr Leu Ser Cys Arg Ala Ser Gln Ser Phe Thr Ser Asn Tyr Leu
            500                 505                 510

Ala Trp Tyr Gln Gln Arg Pro Gly Gln Ala Pro Arg Leu Leu Ile Tyr
        515                 520                 525

Gly Ala Ser Thr Arg Ala Ile Gly Ile Pro Asp Arg Phe Ser Gly Ser
        530                 535                 540

Gly Ser Gly Thr Asp Phe Thr Leu Thr Ile Ser Arg Leu Glu Pro Glu
545                 550                 555                 560

Asp Phe Ala Val Tyr Tyr Cys Gln Gln Tyr Gly Ser Ser Pro Trp Thr
                565                 570                 575

Phe Gly Gln Gly Thr Lys Val Glu Ile Lys Thr Thr Thr Pro Ala Pro
            580                 585                 590

Arg Pro Pro Thr Pro Ala Pro Thr Ile Ala Ser Gln Pro Leu Ser Leu
        595                 600                 605

Arg Pro Glu Ala Cys Arg Pro Ala Ala Gly Gly Ala Val His Thr Arg
        610                 615                 620

Gly Leu Asp Phe Ala Cys Asp Ile Tyr Ile Trp Ala Pro Leu Ala Gly
625                 630                 635                 640

Thr Cys Gly Val Leu Leu Leu Ser Leu Val Ile Thr Leu Tyr Cys Lys
                645                 650                 655

Arg Gly Arg Lys Lys Leu Leu Tyr Ile Phe Lys Gln Pro Phe Met Arg
            660                 665                 670

Pro Val Gln Thr Thr Gln Glu Glu Asp Gly Cys Ser Cys Arg Phe Pro
        675                 680                 685

Glu Glu Glu Glu Gly Gly Cys Glu Leu Arg Val Lys Phe Ser Arg Ser
        690                 695                 700

Ala Asp Ala Pro Ala Tyr Gln Gln Gly Gln Asn Gln Leu Tyr Asn Glu
705                 710                 715                 720

Leu Asn Leu Gly Arg Arg Glu Glu Tyr Asp Val Leu Asp Lys Arg Arg
                725                 730                 735

Gly Arg Asp Pro Glu Met Gly Gly Lys Pro Arg Arg Lys Asn Pro Gln
            740                 745                 750

Glu Gly Leu Tyr Asn Glu Leu Gln Lys Asp Lys Met Ala Glu Ala Tyr
        755                 760                 765

Ser Glu Ile Gly Met Lys Gly Glu Arg Arg Gly Lys Gly His Asp
        770                 775                 780

Gly Leu Tyr Gln Gly Leu Ser Thr Ala Thr Lys Asp Thr Tyr Asp Ala
785                 790                 795                 800

Leu His Met Gln Ala Leu Pro Pro Arg
                805
```

<210> SEQ ID NO 25
<211> LENGTH: 812
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 25

```
Met Ala Leu Pro Val Thr Ala Leu Leu Leu Pro Leu Ala Leu Leu Leu
1               5                   10                  15

His Ala Ala Arg Pro Gly Tyr Pro Tyr Asp Val Pro Asp Tyr Ala Asp
            20                  25                  30

Ile Val Met Thr Gln Thr Pro Ala Ser Val Ser Glu Pro Val Gly Gly
        35                  40                  45

Thr Val Thr Ile Met Cys Gln Ala Ser Gln Ser Ile Ser Asn Trp Leu
    50                  55                  60

Ala Trp Tyr Gln Gln Lys Pro Gly Gln Pro Pro Lys Leu Leu Ile Tyr
65                  70                  75                  80

Gln Ala Ser Lys Leu Ala Ser Gly Val Pro Ser Arg Phe Lys Gly Ser
                85                  90                  95

Gly Ser Gly Thr Glu Tyr Thr Leu Thr Ile Ser Asp Leu Glu Cys Ala
            100                 105                 110

Asp Ala Ala Thr Tyr Tyr Cys Gln Ser Tyr Tyr Asp Ser Gly Ser Asn
        115                 120                 125

Val Phe Phe Ala Phe Gly Gly Gly Thr Lys Val Val Glu Gly Gly Gly
    130                 135                 140

Gly Gly Gly Ser Gly Gly Gly Gly Ser Leu Ser Gly Arg Ser Asp Asn
145                 150                 155                 160

His Ser Pro Leu Gly Leu Ala Gly Ser Gly Gly Gly Ser Gly Gly
                165                 170                 175

Gly Gly Ser Leu Ser Leu Glu Glu Ser Gly Gly Asp Leu Val Lys Pro
            180                 185                 190

Gly Ala Ser Leu Thr Leu Thr Cys Thr Ala Ser Gly Phe Ser Phe Ser
        195                 200                 205

Ala Gly Tyr Trp Ile Cys Trp Val Arg Gln Ala Pro Gly Lys Gly Leu
    210                 215                 220

Glu Trp Ile Ala Cys Thr Tyr Ala Gly Arg Ser Gly Ser Thr Tyr Tyr
225                 230                 235                 240

Ala Asn Trp Val Asn Gly Arg Phe Thr Ile Pro Lys Thr Ser Ser Thr
                245                 250                 255

Thr Val Thr Leu Gln Met Thr Ser Leu Ser Gly Ala Asp Thr Ala Ser
            260                 265                 270

Tyr Phe Cys Ala Arg Gly Asn Ala Gly Val Ala Val Gly Ala Leu Trp
        275                 280                 285

Gly Pro Gly Thr Leu Val Thr Val Ser Ser Gly Gly Gly Gly Ser Gly
    290                 295                 300

Gly Gly Gly Ser Gly Gly Gly Ser Leu Ser Gly Arg Ser Asp Asn
305                 310                 315                 320

His Ser Pro Leu Gly Leu Ala Gly Ser Gly Gly Gly Ser Gly Gly
                325                 330                 335

Gly Ser Gly Gly Gly Gly Ser Gln Val Gln Leu Gln Glu Ser Gly Pro
            340                 345                 350

Gly Leu Val Lys Pro Ser Glu Thr Leu Ser Leu Thr Cys Thr Val Ser
        355                 360                 365
```

```
Gly Gly Ser Ile Ser Tyr Tyr Ser Trp Thr Trp Val Arg Gln Pro Ala
        370             375             380
Gly Gln Gly Leu Glu Trp Ile Gly Arg Ile His Ile Ser Gly Val Thr
385             390             395             400
Asn His Asn Pro Ser Leu Lys Ser Arg Val Ser Met Ser Ile Asp Thr
                405             410             415
Ser Arg Thr Gln Phe Ser Leu Arg Leu Thr Ser Val Thr Ala Ala Asp
            420             425             430
Thr Ala Val Tyr Phe Cys Ala Arg Ser Gly Gly Thr Tyr Ser Ala Phe
        435             440             445
Asp Ile Trp Gly Gln Gly Thr Met Val Thr Val Ser Ser Gly Gly Gly
450             455             460
Gly Ser Gly Gly Gly Ser Gly Gly Gly Ser Gly Gly Gly Gly
465             470             475             480
Ser Glu Ile Val Leu Thr Gln Ser Pro Gly Thr Leu Ser Leu Ser Pro
                485             490             495
Gly Glu Arg Ser Thr Leu Ser Cys Arg Ala Ser Gln Ser Phe Thr Ser
            500             505             510
Asn Tyr Leu Ala Trp Tyr Gln Gln Arg Pro Gly Gln Ala Pro Arg Leu
        515             520             525
Leu Ile Tyr Gly Ala Ser Thr Arg Ala Ile Gly Ile Pro Asp Arg Phe
530             535             540
Ser Gly Ser Gly Ser Gly Thr Asp Phe Thr Leu Thr Ile Ser Arg Leu
545             550             555             560
Glu Pro Glu Asp Phe Ala Val Tyr Tyr Cys Gln Gln Tyr Gly Ser Ser
                565             570             575
Pro Trp Thr Phe Gly Gln Gly Thr Lys Val Glu Ile Lys Thr Thr Thr
            580             585             590
Pro Ala Pro Arg Pro Pro Thr Pro Ala Pro Thr Ile Ala Ser Gln Pro
        595             600             605
Leu Ser Leu Arg Pro Glu Ala Cys Arg Pro Ala Ala Gly Gly Ala Val
610             615             620
His Thr Arg Gly Leu Asp Phe Ala Cys Asp Ile Tyr Ile Trp Ala Pro
625             630             635             640
Leu Ala Gly Thr Cys Gly Val Leu Leu Leu Ser Leu Val Ile Thr Leu
                645             650             655
Tyr Cys Lys Arg Gly Arg Lys Lys Leu Leu Tyr Ile Phe Lys Gln Pro
            660             665             670
Phe Met Arg Pro Val Gln Thr Thr Gln Glu Glu Asp Gly Cys Ser Cys
        675             680             685
Arg Phe Pro Glu Glu Glu Glu Gly Gly Cys Glu Leu Arg Val Lys Phe
690             695             700
Ser Arg Ser Ala Asp Ala Pro Ala Tyr Gln Gln Gly Gln Asn Gln Leu
705             710             715             720
Tyr Asn Glu Leu Asn Leu Gly Arg Arg Glu Glu Tyr Asp Val Leu Asp
                725             730             735
Lys Arg Arg Gly Arg Asp Pro Glu Met Gly Gly Lys Pro Arg Arg Lys
            740             745             750
Asn Pro Gln Glu Gly Leu Tyr Asn Glu Leu Gln Lys Asp Lys Met Ala
        755             760             765
Glu Ala Tyr Ser Glu Ile Gly Met Lys Gly Glu Arg Arg Arg Gly Lys
770             775             780
Gly His Asp Gly Leu Tyr Gln Gly Leu Ser Thr Ala Thr Lys Asp Thr
```

```
                785                 790                 795                 800
Tyr Asp Ala Leu His Met Gln Ala Leu Pro Pro Arg
                    805                 810

<210> SEQ ID NO 26
<211> LENGTH: 799
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Met Ala Leu Pro Val Thr Ala Leu Leu Leu Pro Leu Ala Leu Leu Leu
1               5                   10                  15

His Ala Ala Arg Pro Gly Tyr Pro Tyr Asp Val Pro Asp Tyr Ala Asp
                20                  25                  30

Ile Val Met Thr Gln Thr Pro Ala Ser Val Ser Glu Pro Val Gly Gly
            35                  40                  45

Ser Val Thr Ile Lys Cys Gln Ala Ser Gln Ser Phe Tyr Asn Leu Leu
    50                  55                  60

Ala Trp Tyr Gln Gln Lys Pro Gly Gln Pro Pro Lys Leu Leu Ile Tyr
65                  70                  75                  80

Asp Ala Ser Asp Leu Ala Ser Gly Val Pro Ser Arg Phe Lys Gly Ser
                85                  90                  95

Gly Ser Gly Thr Asp Phe Thr Leu Thr Ile Ser Asp Leu Glu Cys Ala
            100                 105                 110

Asp Ala Ala Tyr Tyr Cys Gln Ser Ala Asp Gly Ser Ser Tyr Ala
        115                 120                 125

Phe Gly Gly Gly Thr Glu Val Val Val Lys Gly Gly Gly Gly Ser
130                 135                 140

Gly Gly Gly Gly Ser Leu Val Pro Arg Gly Ser Gly Gly Gly Gly Ser
145                 150                 155                 160

Gly Gly Gly Gly Ser Gln Glu Gln Leu Glu Glu Ser Gly Gly Gly Leu
                165                 170                 175

Val Lys Pro Glu Gly Ser Leu Thr Leu Thr Cys Thr Ala Ser Gly Val
            180                 185                 190

Ser Phe Ser Ser Ser Tyr Trp Ile Tyr Trp Val Arg Gln Ala Pro Gly
        195                 200                 205

Lys Gly Leu Glu Trp Ile Ala Cys Ile Tyr Thr Gly Ser Ser Gly Ser
    210                 215                 220

Thr Tyr Tyr Ala Ser Trp Ala Lys Gly Arg Phe Thr Val Ser Glu Thr
225                 230                 235                 240

Ser Ser Thr Thr Val Thr Leu Gln Met Thr Ser Leu Thr Ala Ala Asp
                245                 250                 255

Thr Ala Thr Tyr Phe Cys Ala Arg Ala Ser Ala Trp Thr Tyr Gly Met
            260                 265                 270

Asp Leu Trp Gly Pro Gly Thr Leu Val Thr Val Ser Ser Gly Gly Gly
        275                 280                 285

Gly Ser Gly Gly Gly Gly Ser Leu Val Pro Arg Gly Ser Lys Pro Ile
    290                 295                 300

Pro Asn Pro Leu Leu Gly Leu Asp Ser Thr Leu Val Pro Arg Gly Ser
305                 310                 315                 320

Gly Gly Gly Gly Ser Gly Gly Gly Ser Gln Val Gln Leu Gln Glu
                325                 330                 335
```

```
Ser Gly Pro Gly Leu Val Lys Pro Ser Glu Thr Leu Ser Leu Thr Cys
            340                 345                 350

Thr Val Ser Gly Gly Ser Ile Ser Tyr Tyr Ser Trp Thr Trp Val Arg
        355                 360                 365

Gln Pro Ala Gly Gln Gly Leu Glu Trp Ile Gly Arg Ile His Ile Ser
    370                 375                 380

Gly Val Thr Asn His Asn Pro Ser Leu Lys Ser Arg Val Ser Met Ser
385                 390                 395                 400

Ile Asp Thr Ser Arg Thr Gln Phe Ser Leu Arg Leu Thr Ser Val Thr
                405                 410                 415

Ala Ala Asp Thr Ala Val Tyr Phe Cys Ala Arg Ser Gly Gly Thr Tyr
            420                 425                 430

Ser Ala Phe Asp Ile Trp Gly Gln Gly Thr Met Val Thr Val Ser Ser
            435                 440                 445

Gly Gly Gly Gly Ser Gly Gly Gly Gly Ser Gly Gly Gly Gly Ser Gly
            450                 455                 460

Gly Gly Gly Ser Glu Ile Val Leu Thr Gln Ser Pro Gly Thr Leu Ser
465                 470                 475                 480

Leu Ser Pro Gly Glu Arg Ser Thr Leu Ser Cys Arg Ala Ser Gln Ser
                485                 490                 495

Phe Thr Ser Asn Tyr Leu Ala Trp Tyr Gln Gln Arg Pro Gly Gln Ala
            500                 505                 510

Pro Arg Leu Leu Ile Tyr Gly Ala Ser Thr Arg Ala Ile Gly Ile Pro
            515                 520                 525

Asp Arg Phe Ser Gly Ser Gly Ser Gly Thr Asp Phe Thr Leu Thr Ile
530                 535                 540

Ser Arg Leu Glu Pro Glu Asp Phe Ala Val Tyr Tyr Cys Gln Gln Tyr
545                 550                 555                 560

Gly Ser Ser Pro Trp Thr Phe Gly Gln Gly Thr Lys Val Glu Ile Lys
                565                 570                 575

Thr Thr Thr Pro Ala Pro Arg Pro Pro Thr Pro Ala Pro Thr Ile Ala
            580                 585                 590

Ser Gln Pro Leu Ser Leu Arg Pro Glu Ala Cys Arg Pro Ala Ala Gly
            595                 600                 605

Gly Ala Val His Thr Arg Gly Leu Asp Phe Ala Cys Asp Ile Tyr Ile
        610                 615                 620

Trp Ala Pro Leu Ala Gly Thr Cys Gly Val Leu Leu Leu Ser Leu Val
625                 630                 635                 640

Ile Thr Leu Tyr Cys Lys Arg Gly Arg Lys Lys Leu Leu Tyr Ile Phe
                645                 650                 655

Lys Gln Pro Phe Met Arg Pro Val Gln Thr Thr Gln Glu Glu Asp Gly
            660                 665                 670

Cys Ser Cys Arg Phe Pro Glu Glu Glu Glu Gly Gly Cys Glu Leu Arg
            675                 680                 685

Val Lys Phe Ser Arg Ser Ala Asp Ala Pro Ala Tyr Gln Gln Gly Gln
            690                 695                 700

Asn Gln Leu Tyr Asn Glu Leu Asn Leu Gly Arg Arg Glu Glu Tyr Asp
705                 710                 715                 720

Val Leu Asp Lys Arg Arg Gly Arg Asp Pro Glu Met Gly Gly Lys Pro
                725                 730                 735

Arg Arg Lys Asn Pro Gln Glu Gly Leu Tyr Asn Glu Leu Gln Lys Asp
            740                 745                 750

Lys Met Ala Glu Ala Tyr Ser Glu Ile Gly Met Lys Gly Glu Arg Arg
```

```
                    755                 760                 765
Arg Gly Lys Gly His Asp Gly Leu Tyr Gln Gly Leu Ser Thr Ala Thr
            770                 775                 780

Lys Asp Thr Tyr Asp Ala Leu His Met Gln Ala Leu Pro Pro Arg
785                 790                 795
```

<210> SEQ ID NO 27
<211> LENGTH: 802
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

```
Met Ala Leu Pro Val Thr Ala Leu Leu Leu Pro Leu Ala Leu Leu Leu
1               5                   10                  15

His Ala Ala Arg Pro Gly Tyr Pro Tyr Asp Val Pro Asp Tyr Ala Asp
            20                  25                  30

Ile Val Met Thr Gln Thr Pro Ala Ser Val Ser Glu Pro Val Gly Gly
        35                  40                  45

Thr Val Thr Ile Met Cys Gln Ala Ser Gln Ser Ile Ser Asn Trp Leu
    50                  55                  60

Ala Trp Tyr Gln Gln Lys Pro Gly Gln Pro Lys Leu Leu Ile Tyr
65                  70                  75                  80

Gln Ala Ser Lys Leu Ala Ser Gly Val Pro Ser Arg Phe Lys Gly Ser
                85                  90                  95

Gly Ser Gly Thr Glu Tyr Thr Leu Thr Ile Ser Asp Leu Glu Cys Ala
            100                 105                 110

Asp Ala Ala Thr Tyr Tyr Cys Gln Ser Tyr Tyr Asp Ser Gly Ser Asn
        115                 120                 125

Val Phe Phe Ala Phe Gly Gly Gly Thr Lys Val Val Val Glu Gly Gly
    130                 135                 140

Gly Gly Gly Ser Gly Gly Gly Gly Ser Leu Val Pro Arg Gly Ser Gly
145                 150                 155                 160

Gly Gly Gly Ser Gly Gly Gly Gly Ser Leu Ser Leu Glu Glu Ser Gly
                165                 170                 175

Gly Asp Leu Val Lys Pro Gly Ala Ser Leu Thr Leu Thr Cys Thr Ala
            180                 185                 190

Ser Gly Phe Ser Phe Ser Ala Gly Tyr Trp Ile Cys Trp Val Arg Gln
        195                 200                 205

Ala Pro Gly Lys Gly Leu Glu Trp Ile Ala Cys Thr Tyr Ala Gly Arg
    210                 215                 220

Ser Gly Ser Thr Tyr Tyr Ala Asn Trp Val Asn Gly Arg Phe Thr Ile
225                 230                 235                 240

Pro Lys Thr Ser Ser Thr Thr Val Thr Leu Gln Met Thr Ser Leu Ser
                245                 250                 255

Gly Ala Asp Thr Ala Ser Tyr Phe Cys Ala Arg Gly Asn Ala Gly Val
            260                 265                 270

Ala Val Gly Ala Leu Trp Gly Pro Gly Thr Leu Val Thr Val Ser Ser
        275                 280                 285

Gly Gly Gly Gly Ser Gly Gly Gly Gly Ser Leu Val Pro Arg Gly Ser
    290                 295                 300

Lys Pro Ile Pro Asn Pro Leu Leu Gly Leu Asp Ser Thr Leu Val Pro
305                 310                 315                 320
```

-continued

Arg Gly Ser Gly Gly Gly Ser Gly Gly Gly Ser Gln Val Gln
              325                 330             335

Leu Gln Glu Ser Gly Pro Gly Leu Val Lys Pro Ser Glu Thr Leu Ser
        340                 345                 350

Leu Thr Cys Thr Val Ser Gly Gly Ser Ile Ser Tyr Tyr Ser Trp Thr
            355                 360                 365

Trp Val Arg Gln Pro Ala Gly Gln Gly Leu Glu Trp Ile Gly Arg Ile
370                 375                 380

His Ile Ser Gly Val Thr Asn His Asn Pro Ser Leu Lys Ser Arg Val
385                 390                 395                 400

Ser Met Ser Ile Asp Thr Ser Arg Thr Gln Phe Ser Leu Arg Leu Thr
                405                 410                 415

Ser Val Thr Ala Ala Asp Thr Ala Val Tyr Phe Cys Ala Arg Ser Gly
            420                 425                 430

Gly Thr Tyr Ser Ala Phe Asp Ile Trp Gly Gln Gly Thr Met Val Thr
            435                 440                 445

Val Ser Ser Gly Gly Gly Gly Ser Gly Gly Gly Gly Ser Gly Gly Gly
450                 455                 460

Gly Ser Gly Gly Gly Ser Glu Ile Val Leu Thr Gln Ser Pro Gly
465                 470                 475                 480

Thr Leu Ser Leu Ser Pro Gly Glu Arg Ser Thr Leu Ser Cys Arg Ala
                485                 490                 495

Ser Gln Ser Phe Thr Ser Asn Tyr Leu Ala Trp Tyr Gln Gln Arg Pro
            500                 505                 510

Gly Gln Ala Pro Arg Leu Leu Ile Tyr Gly Ala Ser Thr Arg Ala Ile
            515                 520                 525

Gly Ile Pro Asp Arg Phe Ser Gly Ser Gly Ser Gly Thr Asp Phe Thr
530                 535                 540

Leu Thr Ile Ser Arg Leu Glu Pro Glu Asp Phe Ala Val Tyr Tyr Cys
545                 550                 555                 560

Gln Gln Tyr Gly Ser Ser Pro Trp Thr Phe Gly Gln Gly Thr Lys Val
                565                 570                 575

Glu Ile Lys Thr Thr Thr Pro Ala Pro Arg Pro Pro Thr Pro Ala Pro
            580                 585                 590

Thr Ile Ala Ser Gln Pro Leu Ser Leu Arg Pro Glu Ala Cys Arg Pro
            595                 600                 605

Ala Ala Gly Gly Ala Val His Thr Arg Gly Leu Asp Phe Ala Cys Asp
            610                 615                 620

Ile Tyr Ile Trp Ala Pro Leu Ala Gly Thr Cys Gly Val Leu Leu Leu
625                 630                 635                 640

Ser Leu Val Ile Thr Leu Tyr Cys Lys Arg Gly Arg Lys Lys Leu Leu
                645                 650                 655

Tyr Ile Phe Lys Gln Pro Phe Met Arg Pro Val Gln Thr Thr Gln Glu
            660                 665                 670

Glu Asp Gly Cys Ser Cys Arg Phe Pro Glu Glu Glu Gly Gly Cys
            675                 680                 685

Glu Leu Arg Val Lys Phe Ser Arg Ser Ala Asp Ala Pro Ala Tyr Gln
            690                 695                 700

Gln Gly Gln Asn Gln Leu Tyr Asn Glu Leu Asn Leu Gly Arg Arg Glu
705                 710                 715                 720

Glu Tyr Asp Val Leu Asp Lys Arg Arg Gly Arg Asp Pro Glu Met Gly
                725                 730                 735

Gly Lys Pro Arg Arg Lys Asn Pro Gln Glu Gly Leu Tyr Asn Glu Leu

```
                    740                 745                 750
Gln Lys Asp Lys Met Ala Glu Ala Tyr Ser Glu Ile Gly Met Lys Gly
            755                 760                 765

Glu Arg Arg Gly Lys Gly His Asp Gly Leu Tyr Gln Gly Leu Ser
        770                 775                 780

Thr Ala Thr Lys Asp Thr Tyr Asp Ala Leu His Met Gln Ala Leu Pro
785                 790                 795                 800

Pro Arg

<210> SEQ ID NO 28
<211> LENGTH: 908
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Met Ala Leu Pro Val Thr Ala Leu Leu Leu Pro Leu Ala Leu Leu Leu
1               5                   10                  15

His Ala Ala Arg Pro Gly Tyr Pro Tyr Asp Val Pro Asp Tyr Ala Gly
            20                  25                  30

Phe His Thr Ile Asn Ala Thr Trp Trp Ala Asn Ile Thr Leu Val Gly
        35                  40                  45

Pro Pro Asp Thr Pro Val Thr Trp Tyr Asp Thr Gln Gly Leu Trp Phe
    50                  55                  60

Cys Asn Gly Ser Arg Val Lys Asn Pro Gln Ile Arg His Thr Cys Asn
65                  70                  75                  80

Asp Gln Asn Leu Thr Leu Ile His Val Asn Lys Thr Tyr Glu Arg Thr
                85                  90                  95

Tyr Met Gly Tyr Asn Arg Gln Gly Thr Lys Lys Glu Asp Tyr Lys Val
            100                 105                 110

Val Val Ile Pro Pro Pro Ala Thr Val Lys Pro Gln Pro Glu Pro
        115                 120                 125

Glu Tyr Val Phe Val Tyr Met Gly Glu Asn Lys Thr Leu Glu Gly Pro
    130                 135                 140

Pro Gly Thr Pro Val Thr Trp Phe Asn Gln Asp Gly Lys Lys Phe Cys
145                 150                 155                 160

Glu Gly Glu Lys Val Leu His Pro Glu Phe Asn His Thr Cys Asp Lys
                165                 170                 175

Gln Asn Leu Ile Leu Leu Phe Val Asn Phe Thr His Asp Gly Ala Tyr
            180                 185                 190

Leu Gly Tyr Asn His Gln Gly Thr Gln Arg Thr His Tyr Glu Val Thr
        195                 200                 205

Val Leu Asp Leu Phe Pro Asp Ser Gly Gln Met Lys Ile Glu Asn His
    210                 215                 220

Ser Glu Glu Thr Glu Gln Lys Asn Asp Glu His His Asn Trp Gln Lys
225                 230                 235                 240

Gln Gly Gly Gln Lys Gln Gly Gln Lys Thr Asn Gln Thr Lys Val
                245                 250                 255

Asn Asp Arg Arg Lys Thr Ala Gln Arg Pro Ser Lys Leu Lys Pro
            260                 265                 270

Ala Thr Ile Glu Ala Met Leu Val Thr Val Thr Ala Gly Ser Asn Leu
        275                 280                 285

Thr Leu Val Gly Pro Lys Ala Glu Gly Lys Val Thr Trp Phe Asp Gly
```

```
            290                 295                 300
Asp Leu Lys Arg Pro Cys Glu Pro Asn Tyr Arg Leu Arg His Glu Cys
305                 310                 315                 320

Asn Asn Gln Asn Leu Thr Leu Ile Asn Val Thr Lys Asp Tyr Glu Gly
                325                 330                 335

Thr Tyr Tyr Gly Thr Asn Asp Lys Asp Glu Gly Lys Arg Tyr Arg Val
                340                 345                 350

Lys Val Asn Thr Thr Asn Ser Gln Ser Val Lys Ile Gln Pro Tyr Thr
                355                 360                 365

Arg Gln Thr Thr Pro Asp Gln Glu His Lys Phe Glu Leu Gln Phe Glu
            370                 375                 380

Thr Asn Gly Asn Tyr Asp Ser Lys Ile Pro Gly Gly Gly Ser Gly
385                 390                 395                 400

Gly Gly Gly Ser Leu Val Pro Arg Gly Ser Lys Pro Ile Pro Asn Pro
                405                 410                 415

Leu Leu Gly Leu Asp Ser Thr Leu Val Pro Arg Gly Ser Gly Gly Gly
                420                 425                 430

Gly Ser Gly Gly Gly Ser Gln Val Gln Leu Gln Glu Ser Gly Pro
            435                 440                 445

Gly Leu Val Lys Pro Ser Glu Thr Leu Ser Leu Thr Cys Thr Val Ser
            450                 455                 460

Gly Gly Ser Ile Ser Tyr Tyr Ser Trp Thr Trp Val Arg Gln Pro Ala
465                 470                 475                 480

Gly Gln Gly Leu Glu Trp Ile Gly Arg Ile His Ile Ser Gly Val Thr
                485                 490                 495

Asn His Asn Pro Ser Leu Lys Ser Arg Val Ser Met Ser Ile Asp Thr
                500                 505                 510

Ser Arg Thr Gln Phe Ser Leu Arg Leu Thr Ser Val Thr Ala Ala Asp
            515                 520                 525

Thr Ala Val Tyr Phe Cys Ala Arg Ser Gly Gly Thr Tyr Ser Ala Phe
            530                 535                 540

Asp Ile Trp Gly Gln Gly Thr Met Val Thr Val Ser Ser Gly Gly Gly
545                 550                 555                 560

Gly Ser Gly Gly Gly Gly Ser Gly Gly Gly Ser Gly Gly Gly Gly
                565                 570                 575

Ser Glu Ile Val Leu Thr Gln Ser Pro Gly Thr Leu Ser Leu Ser Pro
                580                 585                 590

Gly Glu Arg Ser Thr Leu Ser Cys Arg Ala Ser Gln Ser Phe Thr Ser
            595                 600                 605

Asn Tyr Leu Ala Trp Tyr Gln Gln Arg Pro Gly Gln Ala Pro Arg Leu
            610                 615                 620

Leu Ile Tyr Gly Ala Ser Thr Arg Ala Ile Gly Ile Pro Asp Arg Phe
625                 630                 635                 640

Ser Gly Ser Gly Ser Gly Thr Asp Phe Thr Leu Thr Ile Ser Arg Leu
                645                 650                 655

Glu Pro Glu Asp Phe Ala Val Tyr Tyr Cys Gln Gln Tyr Gly Ser Ser
                660                 665                 670

Pro Trp Thr Phe Gly Gln Gly Thr Lys Val Glu Ile Lys Thr Thr Thr
            675                 680                 685

Pro Ala Pro Arg Pro Pro Thr Pro Ala Pro Thr Ile Ala Ser Gln Pro
            690                 695                 700

Leu Ser Leu Arg Pro Glu Ala Cys Arg Pro Ala Ala Gly Gly Ala Val
705                 710                 715                 720
```

His Thr Arg Gly Leu Asp Phe Ala Cys Asp Ile Tyr Ile Trp Ala Pro
                725                 730                 735

Leu Ala Gly Thr Cys Gly Val Leu Leu Ser Leu Val Ile Thr Leu
            740                 745                 750

Tyr Cys Lys Arg Gly Arg Lys Lys Leu Leu Tyr Ile Phe Lys Gln Pro
            755                 760                 765

Phe Met Arg Pro Val Gln Thr Thr Gln Glu Glu Asp Gly Cys Ser Cys
    770                 775                 780

Arg Phe Pro Glu Glu Glu Glu Gly Gly Cys Glu Leu Arg Val Lys Phe
785                 790                 795                 800

Ser Arg Ser Ala Asp Ala Pro Ala Tyr Gln Gln Gly Gln Asn Gln Leu
                805                 810                 815

Tyr Asn Glu Leu Asn Leu Gly Arg Arg Glu Glu Tyr Asp Val Leu Asp
            820                 825                 830

Lys Arg Arg Gly Arg Asp Pro Glu Met Gly Gly Lys Pro Arg Arg Lys
            835                 840                 845

Asn Pro Gln Glu Gly Leu Tyr Asn Glu Leu Gln Lys Asp Lys Met Ala
    850                 855                 860

Glu Ala Tyr Ser Glu Ile Gly Met Lys Gly Glu Arg Arg Arg Gly Lys
865                 870                 875                 880

Gly His Asp Gly Leu Tyr Gln Gly Leu Ser Thr Ala Thr Lys Asp Thr
                885                 890                 895

Tyr Asp Ala Leu His Met Gln Ala Leu Pro Pro Arg
            900                 905

<210> SEQ ID NO 29
<211> LENGTH: 745
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Met Ala Leu Pro Val Thr Ala Leu Leu Leu Pro Leu Ala Leu Leu Leu
1               5                   10                  15

His Ala Ala Arg Pro Gly Tyr Pro Tyr Asp Val Pro Asp Tyr Ala His
                20                  25                  30

Asp Ala Cys Ile Pro Val Val Gly Lys Ile Gly Thr Asn Val Thr Leu
            35                  40                  45

Asn Ala Val Asp Phe His Pro Gly Asp His Val Arg Trp Ser Tyr Gly
    50                  55                  60

Pro Gly Gly Ala Gly Tyr Met Leu Cys Val Tyr Thr Gly Ser Trp Thr
65                  70                  75                  80

Glu Tyr Lys Lys Pro Asp Ile Ile Phe Lys Cys Leu Ser Asn Asn Ser
                85                  90                  95

Leu Leu Leu Ile Asn Val Thr Val Asn Tyr Thr Asn Tyr Arg Thr
            100                 105                 110

Leu Thr Ser Leu Asn Asn Trp Val His Asn Gln His His Lys Phe
            115                 120                 125

Pro Gly Trp Asn Leu Asp Thr Cys Tyr Ser Leu Thr Val Asn Glu Asn
    130                 135                 140

Gly Thr Phe Pro Thr Thr Thr Lys Lys Pro Thr Thr Thr Arg
145                 150                 155                 160

Thr Thr Thr Thr Thr Thr Thr Lys Lys Thr Thr Thr Thr Arg Thr Thr

```
                    165                 170                 175
Thr Ala Ala Lys Lys Thr Thr Ile Ser Thr Thr His His Lys His Ser
                180                 185                 190

Ser Pro Lys Lys Ser Ser Thr Pro Asn Ser His Val Glu His His Val
                195                 200                 205

Gly Phe Glu Ala Thr Ala Ala Glu Thr Pro Leu Gln Pro Ser Pro Gln
                210                 215                 220

His Gln His Val Ala Thr His Gly Gly Gly Ser Gly Gly Gly Gly
225                 230                 235                 240

Ser Leu Val Pro Arg Gly Ser Lys Pro Ile Pro Asn Pro Leu Leu Gly
                245                 250                 255

Leu Asp Ser Thr Leu Val Pro Arg Gly Ser Gly Gly Gly Ser Gly
                260                 265                 270

Gly Gly Gly Ser Gln Val Gln Leu Gln Glu Ser Gly Pro Gly Leu Val
                275                 280                 285

Lys Pro Ser Glu Thr Leu Ser Leu Thr Cys Thr Val Ser Gly Gly Ser
                290                 295                 300

Ile Ser Tyr Tyr Ser Trp Thr Trp Val Arg Gln Pro Ala Gly Gln Gly
305                 310                 315                 320

Leu Glu Trp Ile Gly Arg Ile His Ile Ser Gly Val Thr Asn His Asn
                325                 330                 335

Pro Ser Leu Lys Ser Arg Val Ser Met Ser Ile Asp Thr Ser Arg Thr
                340                 345                 350

Gln Phe Ser Leu Arg Leu Thr Ser Val Thr Ala Ala Asp Thr Ala Val
                355                 360                 365

Tyr Phe Cys Ala Arg Ser Gly Gly Thr Tyr Ser Ala Phe Asp Ile Trp
                370                 375                 380

Gly Gln Gly Thr Met Val Thr Val Ser Ser Gly Gly Gly Gly Ser Gly
385                 390                 395                 400

Gly Gly Gly Ser Gly Gly Gly Ser Gly Gly Gly Gly Ser Glu Ile
                405                 410                 415

Val Leu Thr Gln Ser Pro Gly Thr Leu Ser Leu Ser Pro Gly Glu Arg
                420                 425                 430

Ser Thr Leu Ser Cys Arg Ala Ser Gln Ser Phe Thr Ser Asn Tyr Leu
                435                 440                 445

Ala Trp Tyr Gln Gln Arg Pro Gly Gln Ala Pro Arg Leu Leu Ile Tyr
                450                 455                 460

Gly Ala Ser Thr Arg Ala Ile Gly Ile Pro Asp Arg Phe Ser Gly Ser
465                 470                 475                 480

Gly Ser Gly Thr Asp Phe Thr Leu Thr Ile Ser Arg Leu Glu Pro Glu
                485                 490                 495

Asp Phe Ala Val Tyr Tyr Cys Gln Gln Tyr Gly Ser Ser Pro Trp Thr
                500                 505                 510

Phe Gly Gln Gly Thr Lys Val Glu Ile Lys Thr Thr Pro Ala Pro
                515                 520                 525

Arg Pro Pro Thr Pro Ala Pro Thr Ile Ala Ser Gln Pro Leu Ser Leu
                530                 535                 540

Arg Pro Glu Ala Cys Arg Pro Ala Ala Gly Gly Ala Val His Thr Arg
545                 550                 555                 560

Gly Leu Asp Phe Ala Cys Asp Ile Tyr Ile Trp Ala Pro Leu Ala Gly
                565                 570                 575

Thr Cys Gly Val Leu Leu Leu Ser Leu Val Ile Thr Leu Tyr Cys Lys
                580                 585                 590
```

```
Arg Gly Arg Lys Lys Leu Leu Tyr Ile Phe Lys Gln Pro Phe Met Arg
        595                 600                 605

Pro Val Gln Thr Thr Gln Glu Glu Asp Gly Cys Ser Cys Arg Phe Pro
    610                 615                 620

Glu Glu Glu Glu Gly Gly Cys Glu Leu Arg Val Lys Phe Ser Arg Ser
625                 630                 635                 640

Ala Asp Ala Pro Ala Tyr Gln Gln Gly Gln Asn Gln Leu Tyr Asn Glu
            645                 650                 655

Leu Asn Leu Gly Arg Arg Glu Glu Tyr Asp Val Leu Asp Lys Arg Arg
        660                 665                 670

Gly Arg Asp Pro Glu Met Gly Gly Lys Pro Arg Arg Lys Asn Pro Gln
        675                 680                 685

Glu Gly Leu Tyr Asn Glu Leu Gln Lys Asp Lys Met Ala Glu Ala Tyr
    690                 695                 700

Ser Glu Ile Gly Met Lys Gly Glu Arg Arg Arg Gly Lys Gly His Asp
705                 710                 715                 720

Gly Leu Tyr Gln Gly Leu Ser Thr Ala Thr Lys Asp Thr Tyr Asp Ala
            725                 730                 735

Leu His Met Gln Ala Leu Pro Pro Arg
        740                 745

<210> SEQ ID NO 30
<211> LENGTH: 660
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Met Ala Leu Pro Val Thr Ala Leu Leu Leu Pro Leu Ala Leu Leu Leu
1               5                   10                  15

His Ala Ala Arg Pro Gly Tyr Pro Tyr Asp Val Pro Asp Tyr Ala Gln
            20                  25                  30

Phe Ser Val Leu Gly Pro Ser Gly Pro Ile Leu Ala Met Val Gly Glu
        35                  40                  45

Asp Ala Asp Leu Pro Cys His Leu Phe Pro Thr Met Ser Ala Glu Thr
    50                  55                  60

Met Glu Leu Lys Trp Val Ser Ser Ser Leu Arg Gln Val Val Asn Val
65                  70                  75                  80

Tyr Ala Asp Gly Lys Glu Val Glu Asp Arg Gln Ser Ala Pro Tyr Arg
            85                  90                  95

Gly Arg Thr Ser Ile Leu Arg Asp Gly Ile Thr Ala Gly Lys Ala Ala
        100                 105                 110

Leu Arg Ile His Asn Val Thr Ala Ser Asp Ser Gly Lys Tyr Leu Cys
    115                 120                 125

Tyr Phe Gln Asp Gly Asp Phe Tyr Glu Lys Ala Leu Val Glu Leu Lys
        130                 135                 140

Val Ala Gly Gly Gly Gly Ser Gly Gly Gly Gly Ser Leu Val Pro Arg
145                 150                 155                 160

Gly Ser Lys Pro Ile Pro Asn Pro Leu Leu Gly Leu Asp Ser Thr Leu
            165                 170                 175

Val Pro Arg Gly Ser Gly Gly Gly Gly Ser Gly Gly Gly Gly Ser Gln
        180                 185                 190

Val Gln Leu Gln Glu Ser Gly Pro Gly Leu Val Lys Pro Ser Glu Thr
```

```
                195                 200                 205
Leu Ser Leu Thr Cys Thr Val Ser Gly Gly Ser Ile Ser Tyr Tyr Ser
    210                 215                 220
Trp Thr Trp Val Arg Gln Pro Ala Gly Gln Gly Leu Glu Trp Ile Gly
225                 230                 235                 240
Arg Ile His Ile Ser Gly Val Thr Asn His Asn Pro Ser Leu Lys Ser
                245                 250                 255
Arg Val Ser Met Ser Ile Asp Thr Ser Arg Thr Gln Phe Ser Leu Arg
                260                 265                 270
Leu Thr Ser Val Thr Ala Ala Asp Thr Ala Val Tyr Phe Cys Ala Arg
            275                 280                 285
Ser Gly Gly Thr Tyr Ser Ala Phe Asp Ile Trp Gly Gln Gly Thr Met
        290                 295                 300
Val Thr Val Ser Ser Gly Gly Gly Gly Ser Gly Gly Gly Gly Ser Gly
305                 310                 315                 320
Gly Gly Gly Ser Gly Gly Gly Gly Ser Glu Ile Val Leu Thr Gln Ser
                325                 330                 335
Pro Gly Thr Leu Ser Leu Ser Pro Gly Glu Arg Ser Thr Leu Ser Cys
                340                 345                 350
Arg Ala Ser Gln Ser Phe Thr Ser Asn Tyr Leu Ala Trp Tyr Gln Gln
            355                 360                 365
Arg Pro Gly Gln Ala Pro Arg Leu Leu Ile Tyr Gly Ala Ser Thr Arg
        370                 375                 380
Ala Ile Gly Ile Pro Asp Arg Phe Ser Gly Ser Gly Ser Gly Thr Asp
385                 390                 395                 400
Phe Thr Leu Thr Ile Ser Arg Leu Glu Pro Glu Asp Phe Ala Val Tyr
                405                 410                 415
Tyr Cys Gln Gln Tyr Gly Ser Ser Pro Trp Thr Phe Gly Gln Gly Thr
            420                 425                 430
Lys Val Glu Ile Lys Thr Thr Thr Pro Ala Pro Arg Pro Pro Thr Pro
        435                 440                 445
Ala Pro Thr Ile Ala Ser Gln Pro Leu Ser Leu Arg Pro Glu Ala Cys
    450                 455                 460
Arg Pro Ala Ala Gly Gly Ala Val His Thr Arg Gly Leu Asp Phe Ala
465                 470                 475                 480
Cys Asp Ile Tyr Ile Trp Ala Pro Leu Ala Gly Thr Cys Gly Val Leu
                485                 490                 495
Leu Leu Ser Leu Val Ile Thr Leu Tyr Cys Lys Arg Gly Arg Lys Lys
                500                 505                 510
Leu Leu Tyr Ile Phe Lys Gln Pro Phe Met Arg Pro Val Gln Thr Thr
            515                 520                 525
Gln Glu Glu Asp Gly Cys Ser Cys Arg Phe Pro Glu Glu Glu Glu Gly
        530                 535                 540
Gly Cys Glu Leu Arg Val Lys Phe Ser Arg Ser Ala Asp Ala Pro Ala
545                 550                 555                 560
Tyr Gln Gln Gly Gln Asn Gln Leu Tyr Asn Glu Leu Asn Leu Gly Arg
                565                 570                 575
Arg Glu Glu Tyr Asp Val Leu Asp Lys Arg Arg Gly Arg Asp Pro Glu
                580                 585                 590
Met Gly Gly Lys Pro Arg Arg Lys Asn Pro Gln Glu Gly Leu Tyr Asn
            595                 600                 605
Glu Leu Gln Lys Asp Lys Met Ala Glu Ala Tyr Ser Glu Ile Gly Met
        610                 615                 620
```

```
Lys Gly Glu Arg Arg Gly Lys Gly His Asp Gly Leu Tyr Gln Gly
625                 630                 635                 640

Leu Ser Thr Ala Thr Lys Asp Thr Tyr Asp Ala Leu His Met Gln Ala
            645                 650                 655

Leu Pro Pro Arg
            660

<210> SEQ ID NO 31
<211> LENGTH: 656
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Met Ala Leu Pro Val Thr Ala Leu Leu Leu Pro Leu Ala Leu Leu Leu
1               5                   10                  15

His Ala Ala Arg Pro Gly Tyr Pro Tyr Asp Val Pro Asp Tyr Ala Ala
            20                  25                  30

Leu Gly Ser Asp Leu His Val Asp Val Lys Gly Tyr Lys Asp Gly Gly
        35                  40                  45

Ile His Leu Glu Cys Arg Ser Thr Gly Trp Tyr Pro Gln Pro Gln Ile
    50                  55                  60

Gln Trp Ser Asn Asn Lys Gly Glu Asn Ile Pro Thr Val Glu Ala Pro
65                  70                  75                  80

Val Val Ala Asp Gly Val Gly Leu Tyr Ala Val Ala Ala Ser Val Ile
                85                  90                  95

Met Arg Gly Ser Ser Gly Glu Gly Val Ser Cys Thr Ile Arg Ser Ser
            100                 105                 110

Leu Leu Gly Leu Glu Lys Thr Ala Ser Ile Ser Ile Ala Asp Pro Phe
        115                 120                 125

Phe Arg Ser Ala Gln Arg Trp Ile Ala Ala Leu Ala Gly Thr Gly Gly
    130                 135                 140

Gly Gly Ser Gly Gly Gly Gly Ser Leu Val Pro Arg Gly Ser Lys Pro
145                 150                 155                 160

Ile Pro Asn Pro Leu Leu Gly Leu Asp Ser Thr Leu Val Pro Arg Gly
                165                 170                 175

Ser Gly Gly Gly Gly Ser Gly Gly Gly Ser Gln Val Gln Leu Gln
            180                 185                 190

Glu Ser Gly Pro Gly Leu Val Lys Pro Ser Glu Thr Leu Ser Leu Thr
        195                 200                 205

Cys Thr Val Ser Gly Gly Ser Ile Ser Tyr Tyr Ser Trp Thr Trp Val
    210                 215                 220

Arg Gln Pro Ala Gly Gln Gly Leu Glu Trp Ile Gly Arg Ile His Ile
225                 230                 235                 240

Ser Gly Val Thr Asn His Asn Pro Ser Leu Lys Ser Arg Val Ser Met
                245                 250                 255

Ser Ile Asp Thr Ser Arg Thr Gln Phe Ser Leu Arg Leu Thr Ser Val
            260                 265                 270

Thr Ala Ala Asp Thr Ala Val Tyr Phe Cys Ala Arg Ser Gly Gly Thr
        275                 280                 285

Tyr Ser Ala Phe Asp Ile Trp Gly Gln Gly Thr Met Val Thr Val Ser
    290                 295                 300

Ser Gly Gly Gly Gly Ser Gly Gly Gly Gly Ser Gly Gly Gly Gly Ser
```

```
                305                 310                 315                 320
Gly Gly Gly Gly Ser Glu Ile Val Leu Thr Gln Ser Pro Gly Thr Leu
                325                 330                 335

Ser Leu Ser Pro Gly Glu Arg Ser Thr Leu Ser Cys Arg Ala Ser Gln
                340                 345                 350

Ser Phe Thr Ser Asn Tyr Leu Ala Trp Tyr Gln Gln Arg Pro Gly Gln
                355                 360                 365

Ala Pro Arg Leu Leu Ile Tyr Gly Ala Ser Thr Arg Ala Ile Gly Ile
370                 375                 380

Pro Asp Arg Phe Ser Gly Ser Gly Ser Gly Thr Asp Phe Thr Leu Thr
385                 390                 395                 400

Ile Ser Arg Leu Glu Pro Glu Asp Phe Ala Val Tyr Tyr Cys Gln Gln
                405                 410                 415

Tyr Gly Ser Ser Pro Trp Thr Phe Gly Gln Gly Thr Lys Val Glu Ile
                420                 425                 430

Lys Thr Thr Thr Pro Ala Pro Arg Pro Pro Thr Pro Ala Pro Thr Ile
                435                 440                 445

Ala Ser Gln Pro Leu Ser Leu Arg Pro Glu Ala Cys Arg Pro Ala Ala
            450                 455                 460

Gly Gly Ala Val His Thr Arg Gly Leu Asp Phe Ala Cys Asp Ile Tyr
465                 470                 475                 480

Ile Trp Ala Pro Leu Ala Gly Thr Cys Gly Val Leu Leu Leu Ser Leu
                485                 490                 495

Val Ile Thr Leu Tyr Cys Lys Arg Gly Arg Lys Lys Leu Leu Tyr Ile
                500                 505                 510

Phe Lys Gln Pro Phe Met Arg Pro Val Gln Thr Thr Gln Glu Glu Asp
            515                 520                 525

Gly Cys Ser Cys Arg Phe Pro Glu Glu Glu Gly Gly Cys Glu Leu
            530                 535                 540

Arg Val Lys Phe Ser Arg Ser Ala Asp Ala Pro Ala Tyr Gln Gln Gly
545                 550                 555                 560

Gln Asn Gln Leu Tyr Asn Glu Leu Asn Leu Gly Arg Arg Glu Glu Tyr
                565                 570                 575

Asp Val Leu Asp Lys Arg Arg Gly Arg Asp Pro Glu Met Gly Gly Lys
                580                 585                 590

Pro Arg Arg Lys Asn Pro Gln Glu Gly Leu Tyr Asn Glu Leu Gln Lys
                595                 600                 605

Asp Lys Met Ala Glu Ala Tyr Ser Glu Ile Gly Met Lys Gly Glu Arg
            610                 615                 620

Arg Arg Gly Lys Gly His Asp Gly Leu Tyr Gln Gly Leu Ser Thr Ala
625                 630                 635                 640

Thr Lys Asp Thr Tyr Asp Ala Leu His Met Gln Ala Leu Pro Pro Arg
                645                 650                 655

<210> SEQ ID NO 32
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Leu Val Pro Arg Gly Ser
1               5
```

```
<210> SEQ ID NO 33
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 34
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 35
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Arg Ser Lys Arg Ser Arg Gly Gly His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 36
<211> LENGTH: 16
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 36

Gly Leu Ala Val Ser Thr Ile Ser Ser Phe Phe Pro Pro Gly Tyr Gln
1               5                   10                  15

<210> SEQ ID NO 37
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
                20                  25                  30

Gly Ala Val His Thr Arg Gly Leu Asp Phe Ala Cys Asp
                35                  40                  45

<210> SEQ ID NO 38
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Glu Pro Lys Ser Pro Asp Lys Thr His Thr Cys Pro Pro Cys Pro Ala
1               5                   10                  15

Pro Pro Val Ala Gly Pro Ser Val Phe Leu Phe Pro Pro Lys Pro Lys
                20                  25                  30

Asp Thr Leu Met Ile Ala Arg Thr Pro Glu Val Thr Cys Val Val Val
                35                  40                  45

Asp Val Ser His Glu Asp Pro Glu Val Lys Phe Asn Trp Tyr Val Asp
50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
                100                 105                 110

Pro Ala Pro Ile Glu Lys Thr Ile Ser Lys Ala Lys Gly Gln Pro Arg
                115                 120                 125

Glu Pro Gln Val Tyr Thr Leu Pro Pro Ser Arg Asp Glu Leu Thr Lys
                130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
                180                 185                 190

Lys Leu Thr Val Asp Lys Ser Arg Trp Gln Gln Gly Asn Val Phe Ser
                195                 200                 205

Cys Ser Val Met His Glu Ala Leu His Asn His Tyr Thr Gln Lys Ser
                210                 215                 220

```
Leu Ser Leu Ser Pro Gly Lys
225                 230

<210> SEQ ID NO 39
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Ile Tyr Ile Trp Ala Pro Leu Ala Gly Thr Cys Gly Val Leu Leu Leu
1               5                   10                  15

Ser Leu Val Ile Thr Leu Tyr Cys
                20

<210> SEQ ID NO 40
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
        50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
                100                 105                 110

<210> SEQ ID NO 41
<211> LENGTH: 52
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Phe Phe Ile Pro Leu Leu Val Val Ile Leu Phe Ala Val Asp Thr Gly
1               5                   10                  15

Leu Phe Ile Ser Thr Gln Gln Gln Val Thr Phe Leu Leu Lys Ile Lys
                20                  25                  30

Arg Thr Arg Lys Gly Phe Arg Leu Leu Asn Pro His Pro Lys Pro Asn
            35                  40                  45

Pro Lys Asn Asn
    50

<210> SEQ ID NO 42
<211> LENGTH: 215
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Met Asp Thr Glu Ser Asn Arg Arg Ala Asn Leu Ala Leu Pro Gln Glu
1               5                   10                  15

Pro Ser Ser Val Pro Ala Phe Glu Val Leu Glu Ile Ser Pro Gln Glu
                20                  25                  30

Val Ser Ser Gly Arg Leu Leu Lys Ser Ala Ser Ser Pro Pro Leu His
            35                  40                  45

Thr Trp Leu Thr Val Leu Lys Lys Glu Gln Glu Phe Leu Gly Val Thr
        50                  55                  60

Gln Ile Leu Thr Ala Met Ile Cys Leu Cys Phe Gly Thr Val Val Cys
65                  70                  75                  80

Ser Val Leu Asp Ile Ser His Ile Glu Gly Asp Ile Phe Ser Ser Phe
                85                  90                  95

Lys Ala Gly Tyr Pro Phe Trp Gly Ala Ile Phe Phe Ser Ile Ser Gly
            100                 105                 110

Met Leu Ser Ile Ile Ser Glu Arg Arg Asn Ala Thr Tyr Leu Val Arg
        115                 120                 125

Gly Ser Leu Gly Ala Asn Thr Ala Ser Ser Ile Ala Gly Gly Thr Gly
130                 135                 140

Ile Thr Ile Leu Ile Ile Asn Leu Lys Lys Ser Leu Ala Tyr Ile His
145                 150                 155                 160

Ile His Ser Cys Gln Lys Phe Phe Glu Thr Lys Cys Phe Met Ala Ser
                165                 170                 175

Phe Ser Thr Glu Ile Val Val Met Met Leu Phe Leu Thr Ile Leu Gly
            180                 185                 190

Leu Gly Ser Ala Val Ser Leu Thr Ile Cys Gly Ala Gly Glu Glu Leu
        195                 200                 205

Lys Gly Asn Lys Val Pro Glu
        210                 215

<210> SEQ ID NO 43
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Arg Ser Lys Arg Ser Arg Gly Gly His Ser Asp Tyr Met Asn Met Thr
1               5                   10                  15

Pro Arg Arg Pro Gly Pro Thr Arg Lys His Tyr Gln Pro Tyr Ala Pro
                20                  25                  30

Pro Arg Asp Phe Ala Ala Tyr Arg Ser
            35                  40

<210> SEQ ID NO 44
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide -continued

```
<400> SEQUENCE: 44

Met Ile Pro Ala Val Val Leu Leu Leu Leu Val Glu Gln Ala
1               5                   10                  15

Ala Ala

<210> SEQ ID NO 45
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Leu Gly Glu Pro Gln Leu Cys Tyr Ile Leu Asp Ala Ile Leu Phe Leu
1               5                   10                  15

Tyr Gly Ile Val Leu Thr Leu Leu Tyr Cys Arg Leu Lys Ile Gln Val
                20                  25                  30

Arg Lys Ala Ala Ile Thr Ser Tyr Glu Lys Ser
        35                  40

<210> SEQ ID NO 46
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 47
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 48
<211> LENGTH: 136
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Cys Pro Tyr Ser Asn Pro Ser Leu Cys Ser Gly Gly Gly Gly Ser Glu
1               5                   10                  15

Leu Pro Thr Gln Gly Thr Phe Ser Asn Val Ser Thr Asn Val Ser Pro
                20                  25                  30

Ala Lys Pro Thr Thr Thr Ala Cys Pro Tyr Ser Asn Pro Ser Leu Cys
```

```
                35                  40                  45
Ser Gly Gly Gly Gly Ser Pro Ala Pro Arg Pro Pro Thr Pro Ala Pro
 50                  55                  60

Thr Ile Ala Ser Gln Pro Leu Ser Leu Arg Pro Glu Ala Cys Arg Pro
65                  70                  75                  80

Ala Ala Gly Gly Ala Val His Thr Arg Gly Leu Asp Phe Ala Cys Asp
                85                  90                  95

Ile Tyr Ile Trp Ala Pro Leu Ala Gly Thr Cys Gly Val Leu Leu Leu
            100                 105                 110

Ser Leu Val Ile Thr Leu Tyr Cys Asn His Arg Asn Arg Arg Arg Val
        115                 120                 125

Cys Lys Cys Pro Arg Pro Val Val
    130                 135

<210> SEQ ID NO 49
<211> LENGTH: 157
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Met Gly Thr Ser Leu Leu Cys Trp Met Ala Leu Cys Leu Leu Gly Ala
1               5                  10                  15

Asp His Ala Asp Ala Cys Pro Tyr Ser Asn Pro Ser Leu Cys Ser Gly
            20                  25                  30

Gly Gly Gly Ser Glu Leu Pro Thr Gln Gly Thr Phe Ser Asn Val Ser
        35                  40                  45

Thr Asn Val Ser Pro Ala Lys Pro Thr Thr Thr Ala Cys Pro Tyr Ser
    50                  55                  60

Asn Pro Ser Leu Cys Ser Gly Gly Gly Ser Pro Ala Pro Arg Pro
65                  70                  75                  80

Pro Thr Pro Ala Pro Thr Ile Ala Ser Gln Pro Leu Ser Leu Arg Pro
                85                  90                  95

Glu Ala Cys Arg Pro Ala Ala Gly Gly Ala Val His Thr Arg Gly Leu
            100                 105                 110

Asp Phe Ala Cys Asp Ile Tyr Ile Trp Ala Pro Leu Ala Gly Thr Cys
        115                 120                 125

Gly Val Leu Leu Leu Ser Leu Val Ile Thr Leu Tyr Cys Asn His Arg
    130                 135                 140

Asn Arg Arg Arg Val Cys Lys Cys Pro Arg Pro Val Val
145                 150                 155

<210> SEQ ID NO 50
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Cys Pro Tyr Ser Asn Pro Ser Leu Cys
1               5

<210> SEQ ID NO 51
<211> LENGTH: 37
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 51

Gly Ser Gly Gly Gly Gly Ser Cys Pro Tyr Ser Asn Pro Ser Leu Cys
1               5                   10                  15

Ser Gly Gly Gly Gly Ser Cys Pro Tyr Ser Asn Pro Ser Leu Cys Ser
            20                  25                  30

Gly Gly Gly Gly Ser
        35

<210> SEQ ID NO 52
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gly Gly Gly Gly Ser Gly Gly Gly Ser Gly Gly Gly Ser Gly
1               5                   10                  15

<210> SEQ ID NO 53
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Leu Ser Gly Arg Ser Asp Asn His Ser Pro Leu Gly Leu Ala Gly Ser
1               5                   10                  15

<210> SEQ ID NO 54
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gly Gly Gly Ser Gly Gly Gly Ser Gly Gly Gly Ser
1               5                   10

<210> SEQ ID NO 55
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Lys Pro Ile Pro Asn Pro Leu Leu Gly Leu Asp Ser Thr
1               5                   10

<210> SEQ ID NO 56
<211> LENGTH: 267
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 56

Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Glu Thr Leu Ser Leu Thr Cys Thr Val Ser Gly Gly
        35                  40                  45

Ser Ile Ser Tyr Tyr Ser Trp Thr Trp Val Arg Gln Pro Ala Gly Gln
    50                  55                  60

Gly Leu Glu Trp Ile Gly Arg Ile His Ile Ser Gly Val Thr Asn His
65                  70                  75                  80

Asn Pro Ser Leu Lys Ser Arg Val Ser Met Ser Ile Asp Thr Ser Arg
                85                  90                  95

Thr Gln Phe Ser Leu Arg Leu Thr Ser Val Thr Ala Ala Asp Thr Ala
            100                 105                 110

Val Tyr Phe Cys Ala Arg Ser Gly Gly Thr Tyr Ser Ala Phe Asp Ile
        115                 120                 125

Trp Gly Gln Gly Thr Met Val Thr Val Ser Ser Gly Gly Gly Gly Ser
    130                 135                 140

Gly Gly Gly Gly Ser Gly Gly Gly Ser Gly Gly Gly Gly Ser Glu
145                 150                 155                 160

Ile Val Leu Thr Gln Ser Pro Gly Thr Leu Ser Leu Ser Pro Gly Glu
                165                 170                 175

Arg Ser Thr Leu Ser Cys Arg Ala Ser Gln Ser Phe Thr Ser Asn Tyr
            180                 185                 190

Leu Ala Trp Tyr Gln Gln Arg Pro Gly Gln Ala Pro Arg Leu Leu Ile
        195                 200                 205

Tyr Gly Ala Ser Thr Arg Ala Ile Gly Ile Pro Asp Arg Phe Ser Gly
    210                 215                 220

Ser Gly Ser Gly Thr Asp Phe Thr Leu Thr Ile Ser Arg Leu Glu Pro
225                 230                 235                 240

Glu Asp Phe Ala Val Tyr Tyr Cys Gln Gln Tyr Gly Ser Ser Pro Trp
                245                 250                 255

Thr Phe Gly Gln Gly Thr Lys Val Glu Ile Lys
            260                 265

<210> SEQ ID NO 57
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gly Gly Gly Gly Ser Gly Gly Gly Gly Ser Gly Gly Gly Gly Ser
1               5                   10                  15

<210> SEQ ID NO 58
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Tyr Tyr
            20                  25                  30

Ser Trp Thr Trp Val Arg Gln Pro Ala Gly Gln Gly Leu Glu Trp Ile
        35                  40                  45

Gly Arg Ile His Ile Ser Gly Val Thr Asn His Asn Pro Ser Leu Lys
    50                  55                  60

Ser Arg Val Ser Met Ser Ile Asp Thr Ser Arg Thr Gln Phe Ser Leu
65                  70                  75                  80

Arg Leu Thr Ser Val Thr Ala Ala Asp Thr Ala Val Tyr Phe Cys Ala
                85                  90                  95

Arg Ser Gly Gly Thr Tyr Ser Ala Phe Asp Ile Trp Gly Gln Gly Thr
                100                 105                 110

Met Val Thr Val Ser Ser
        115

<210> SEQ ID NO 59
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Glu Ile Val Leu Thr Gln Ser Pro Gly Thr Leu Ser Leu Ser Pro Gly
1               5                   10                  15

Glu Arg Ser Thr Leu Ser Cys Arg Ala Ser Gln Ser Phe Thr Ser Asn
            20                  25                  30

Tyr Leu Ala Trp Tyr Gln Gln Arg Pro Gly Gln Ala Pro Arg Leu Leu
        35                  40                  45

Ile Tyr Gly Ala Ser Thr Arg Ala Ile Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105

<210> SEQ ID NO 60
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Tyr Tyr Ser Trp Thr
1               5

<210> SEQ ID NO 61
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 61

Arg Ile His Ile Ser Gly Val Thr Asn His Asn Pro Ser Leu Lys Ser
1               5                   10                  15

<210> SEQ ID NO 62
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Ser Gly Gly Thr Tyr Ser Ala Phe Asp Ile
1               5                   10

<210> SEQ ID NO 63
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Ser Gly Gly Ser Ile Ser Tyr Tyr
1               5

<210> SEQ ID NO 64
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

His Ile Ser Gly Val
1               5

<210> SEQ ID NO 65
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ser Gly Gly Thr Tyr Ser Ala Phe Asp Ile
1               5                   10

<210> SEQ ID NO 66
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Arg Ala Ser Gln Ser Phe Thr Ser Asn Tyr Leu Ala
1               5                   10

<210> SEQ ID NO 67
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gly Ala Ser Thr Arg Ala Ile
1               5

<210> SEQ ID NO 68
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Gln Gln Tyr Gly Ser Ser Pro Trp Thr
1               5

<210> SEQ ID NO 69
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Arg Ala Ser Gln Ser Phe Thr Ser Asn Tyr Leu Ala
1               5                   10

<210> SEQ ID NO 70
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gly Ala Ser Thr Arg Ala Ile
1               5

<210> SEQ ID NO 71
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gln Gln Tyr Gly Ser Ser Pro Trp Thr
1               5

<210> SEQ ID NO 72
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Gly Gly Gly Gly Ser Gly Gly Gly Gly Ser Gly Gly Gly Gly Ser Gly
```

-continued

```
                1               5                  10                  15

Gly Gly Gly Ser
            20

<210> SEQ ID NO 73
<211> LENGTH: 66
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr Ile
        35                  40                  45

Trp Ala Pro Leu Ala Gly Thr Cys Gly Val Leu Leu Leu Ser Leu Val
    50                  55                  60

Ile Thr
65

<210> SEQ ID NO 74
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Glu Leu Pro Thr Gln Gly Thr Phe Ser Asn Val Ser Thr Asn Val Ser
1               5                   10                  15

Pro Ala Lys Pro Thr Thr Thr Ala
            20

<210> SEQ ID NO 75
<211> LENGTH: 490
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Glu Thr Leu Ser Leu Thr Cys Thr Val Ser Gly Gly
        35                  40                  45

Ser Ile Ser Tyr Tyr Ser Trp Thr Trp Val Arg Gln Pro Ala Gly Gln
    50                  55                  60

Gly Leu Glu Trp Ile Gly Arg Ile His Ile Ser Gly Val Thr Asn His
65                  70                  75                  80

Asn Pro Ser Leu Lys Ser Arg Val Ser Met Ser Ile Asp Thr Ser Arg
                85                  90                  95

Thr Gln Phe Ser Leu Arg Leu Thr Ser Val Thr Ala Ala Asp Thr Ala
            100                 105                 110
```

Val Tyr Phe Cys Ala Arg Ser Gly Gly Thr Tyr Ser Ala Phe Asp Ile
                115                 120                 125

Trp Gly Gln Gly Thr Met Val Thr Val Ser Ser Gly Gly Gly Gly Ser
            130                 135                 140

Gly Gly Gly Gly Ser Gly Gly Gly Ser Gly Gly Gly Gly Ser Glu
            145                 150                 155                 160

Ile Val Leu Thr Gln Ser Pro Gly Thr Leu Ser Leu Ser Pro Gly Glu
                            165                 170                 175

Arg Ser Thr Leu Ser Cys Arg Ala Ser Gln Ser Phe Thr Ser Asn Tyr
                            180                 185                 190

Leu Ala Trp Tyr Gln Gln Arg Pro Gly Gln Ala Pro Arg Leu Leu Ile
                        195                 200                 205

Tyr Gly Ala Ser Thr Arg Ala Ile Gly Ile Pro Asp Arg Phe Ser Gly
                    210                 215                 220

Ser Gly Ser Gly Thr Asp Phe Thr Leu Thr Ile Ser Arg Leu Glu Pro
            225                 230                 235                 240

Glu Asp Phe Ala Val Tyr Tyr Cys Gln Gln Tyr Gly Ser Ser Pro Trp
                            245                 250                 255

Thr Phe Gly Gln Gly Thr Lys Val Glu Ile Lys Thr Thr Thr Pro Ala
                        260                 265                 270

Pro Arg Pro Pro Thr Pro Ala Pro Thr Ile Ala Ser Gln Pro Leu Ser
                    275                 280                 285

Leu Arg Pro Glu Ala Cys Arg Pro Ala Ala Gly Gly Ala Val His Thr
                290                 295                 300

Arg Gly Leu Asp Phe Ala Cys Asp Ile Tyr Ile Trp Ala Pro Leu Ala
            305                 310                 315                 320

Gly Thr Cys Gly Val Leu Leu Leu Ser Leu Val Ile Thr Leu Tyr Cys
                            325                 330                 335

Lys Arg Gly Arg Lys Lys Leu Leu Tyr Ile Phe Lys Gln Pro Phe Met
                        340                 345                 350

Arg Pro Val Gln Thr Thr Gln Glu Glu Asp Gly Cys Ser Cys Arg Phe
                    355                 360                 365

Pro Glu Glu Glu Glu Gly Gly Cys Glu Leu Arg Val Lys Phe Ser Arg
                370                 375                 380

Ser Ala Asp Ala Pro Ala Tyr Gln Gln Gly Gln Asn Gln Leu Tyr Asn
            385                 390                 395                 400

Glu Leu Asn Leu Gly Arg Arg Glu Glu Tyr Asp Val Leu Asp Lys Arg
                            405                 410                 415

Arg Gly Arg Asp Pro Glu Met Gly Gly Lys Pro Arg Arg Lys Asn Pro
                        420                 425                 430

Gln Glu Gly Leu Tyr Asn Glu Leu Gln Lys Asp Lys Met Ala Glu Ala
                    435                 440                 445

Tyr Ser Glu Ile Gly Met Lys Gly Glu Arg Arg Arg Gly Lys Gly His
                450                 455                 460

Asp Gly Leu Tyr Gln Gly Leu Ser Thr Ala Thr Lys Asp Thr Tyr Asp
            465                 470                 475                 480

Ala Leu His Met Gln Ala Leu Pro Pro Arg
                            485                 490

<210> SEQ ID NO 76
<211> LENGTH: 527
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 76

Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Glu Thr Leu Ser Leu Thr Cys Thr Val Ser Gly Gly
        35                  40                  45

Ser Ile Ser Tyr Tyr Ser Trp Thr Trp Val Arg Gln Pro Ala Gly Gln
    50                  55                  60

Gly Leu Glu Trp Ile Gly Arg Ile His Ile Ser Gly Val Thr Asn His
65                  70                  75                  80

Asn Pro Ser Leu Lys Ser Arg Val Ser Met Ser Ile Asp Thr Ser Arg
                85                  90                  95

Thr Gln Phe Ser Leu Arg Leu Thr Ser Val Thr Ala Ala Asp Thr Ala
            100                 105                 110

Val Tyr Phe Cys Ala Arg Ser Gly Gly Thr Tyr Ser Ala Phe Asp Ile
        115                 120                 125

Trp Gly Gln Gly Thr Met Val Thr Val Ser Ser Gly Gly Gly Gly Ser
130                 135                 140

Gly Gly Gly Gly Ser Gly Gly Gly Ser Gly Gly Gly Gly Ser Glu
145                 150                 155                 160

Ile Val Leu Thr Gln Ser Pro Gly Thr Leu Ser Leu Ser Pro Gly Glu
                165                 170                 175

Arg Ser Thr Leu Ser Cys Arg Ala Ser Gln Ser Phe Thr Ser Asn Tyr
            180                 185                 190

Leu Ala Trp Tyr Gln Gln Arg Pro Gly Gln Ala Pro Arg Leu Leu Ile
        195                 200                 205

Tyr Gly Ala Ser Thr Arg Ala Ile Gly Ile Pro Asp Arg Phe Ser Gly
    210                 215                 220

Ser Gly Ser Gly Thr Asp Phe Thr Leu Thr Ile Ser Arg Leu Glu Pro
225                 230                 235                 240

Glu Asp Phe Ala Val Tyr Tyr Cys Gln Gln Tyr Gly Ser Ser Pro Trp
                245                 250                 255

Thr Phe Gly Gln Gly Thr Lys Val Glu Ile Lys Gly Ser Gly Gly Gly
            260                 265                 270

Gly Ser Cys Pro Tyr Ser Asn Pro Ser Leu Cys Ser Gly Gly Gly Gly
        275                 280                 285

Ser Cys Pro Tyr Ser Asn Pro Ser Leu Cys Ser Gly Gly Gly Gly Ser
    290                 295                 300

Thr Thr Thr Pro Ala Pro Arg Pro Pro Thr Pro Ala Pro Thr Ile Ala
305                 310                 315                 320

Ser Gln Pro Leu Ser Leu Arg Pro Glu Ala Cys Arg Pro Ala Ala Gly
                325                 330                 335

Gly Ala Val His Thr Arg Gly Leu Asp Phe Ala Cys Asp Ile Tyr Ile
            340                 345                 350

Trp Ala Pro Leu Ala Gly Thr Cys Gly Val Leu Leu Leu Ser Leu Val
        355                 360                 365

Ile Thr Leu Tyr Cys Lys Arg Gly Arg Lys Lys Leu Leu Tyr Ile Phe
    370                 375                 380

Lys Gln Pro Phe Met Arg Pro Val Gln Thr Thr Gln Glu Glu Asp Gly
385                 390                 395                 400

```
Cys Ser Cys Arg Phe Pro Glu Glu Glu Gly Gly Cys Glu Leu Arg
                405                 410                 415

Val Lys Phe Ser Arg Ser Ala Asp Ala Pro Ala Tyr Gln Gln Gly Gln
            420                 425                 430

Asn Gln Leu Tyr Asn Glu Leu Asn Leu Gly Arg Arg Glu Glu Tyr Asp
                435                 440                 445

Val Leu Asp Lys Arg Arg Gly Arg Asp Pro Glu Met Gly Gly Lys Pro
    450                 455                 460

Arg Arg Lys Asn Pro Gln Glu Gly Leu Tyr Asn Glu Leu Gln Lys Asp
465                 470                 475                 480

Lys Met Ala Glu Ala Tyr Ser Glu Ile Gly Met Lys Gly Glu Arg Arg
                485                 490                 495

Arg Gly Lys Gly His Asp Gly Leu Tyr Gln Gly Leu Ser Thr Ala Thr
                500                 505                 510

Lys Asp Thr Tyr Asp Ala Leu His Met Gln Ala Leu Pro Pro Arg
                515                 520                 525

<210> SEQ ID NO 77
<211> LENGTH: 523
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Met Ala Leu Pro Val Thr Ala Leu Leu Leu Pro Leu Ala Leu Leu Leu
1               5                   10                  15

His Ala Ala Arg Pro Gly Gly Gly Ser Cys Pro Tyr Ser Asn Pro
                20                  25                  30

Ser Leu Cys Gly Gly Gly Gly Ser Gln Val Gln Leu Gln Glu Ser Gly
                35                  40                  45

Pro Gly Leu Val Lys Pro Ser Glu Thr Leu Ser Leu Thr Cys Thr Val
            50                  55                  60

Ser Gly Gly Ser Ile Ser Tyr Tyr Ser Trp Thr Trp Val Arg Gln Pro
65                  70                  75                  80

Ala Gly Gln Gly Leu Glu Trp Ile Gly Arg Ile His Ile Ser Gly Val
                85                  90                  95

Thr Asn His Asn Pro Ser Leu Lys Ser Arg Val Ser Met Ser Ile Asp
                100                 105                 110

Thr Ser Arg Thr Gln Phe Ser Leu Arg Leu Thr Ser Val Thr Ala Ala
            115                 120                 125

Asp Thr Ala Val Tyr Phe Cys Ala Arg Ser Gly Gly Thr Tyr Ser Ala
            130                 135                 140

Phe Asp Ile Trp Gly Gln Gly Thr Met Val Thr Val Ser Ser Gly Gly
145                 150                 155                 160

Gly Gly Ser Gly Gly Gly Gly Ser Gly Gly Gly Gly Ser Gly Gly Gly
                165                 170                 175

Gly Ser Glu Ile Val Leu Thr Gln Ser Pro Gly Thr Leu Ser Leu Ser
                180                 185                 190

Pro Gly Glu Arg Ser Thr Leu Ser Cys Arg Ala Ser Gln Ser Phe Thr
            195                 200                 205

Ser Asn Tyr Leu Ala Trp Tyr Gln Gln Arg Pro Gly Gln Ala Pro Arg
            210                 215                 220

Leu Leu Ile Tyr Gly Ala Ser Thr Arg Ala Ile Gly Ile Pro Asp Arg
```

225                 230                 235                 240
Phe Ser Gly Ser Gly Ser Gly Thr Asp Phe Thr Leu Thr Ile Ser Arg
                245                 250                 255

Leu Glu Pro Glu Asp Phe Ala Val Tyr Tyr Cys Gln Gln Tyr Gly Ser
                260                 265                 270

Ser Pro Trp Thr Phe Gly Gln Gly Thr Lys Val Glu Ile Lys Gly Gly
                275                 280                 285

Gly Gly Ser Cys Pro Tyr Ser Asn Pro Ser Leu Cys Thr Thr Thr Pro
                290                 295                 300

Ala Pro Arg Pro Pro Thr Pro Ala Pro Thr Ile Ala Ser Gln Pro Leu
305                 310                 315                 320

Ser Leu Arg Pro Glu Ala Cys Arg Pro Ala Ala Gly Gly Ala Val His
                325                 330                 335

Thr Arg Gly Leu Asp Phe Ala Cys Asp Ile Tyr Ile Trp Ala Pro Leu
                340                 345                 350

Ala Gly Thr Cys Gly Val Leu Leu Leu Ser Leu Val Ile Thr Leu Tyr
                355                 360                 365

Cys Lys Arg Gly Arg Lys Lys Leu Leu Tyr Ile Phe Lys Gln Pro Phe
                370                 375                 380

Met Arg Pro Val Gln Thr Thr Gln Glu Glu Asp Gly Cys Ser Cys Arg
385                 390                 395                 400

Phe Pro Glu Glu Glu Glu Gly Gly Cys Glu Leu Arg Val Lys Phe Ser
                405                 410                 415

Arg Ser Ala Asp Ala Pro Ala Tyr Gln Gln Gly Gln Asn Gln Leu Tyr
                420                 425                 430

Asn Glu Leu Asn Leu Gly Arg Arg Glu Glu Tyr Asp Val Leu Asp Lys
                435                 440                 445

Arg Arg Gly Arg Asp Pro Glu Met Gly Gly Lys Pro Arg Arg Lys Asn
                450                 455                 460

Pro Gln Glu Gly Leu Tyr Asn Glu Leu Gln Lys Asp Lys Met Ala Glu
465                 470                 475                 480

Ala Tyr Ser Glu Ile Gly Met Lys Gly Glu Arg Arg Arg Gly Lys Gly
                485                 490                 495

His Asp Gly Leu Tyr Gln Gly Leu Ser Thr Ala Thr Lys Asp Thr Tyr
                500                 505                 510

Asp Ala Leu His Met Gln Ala Leu Pro Pro Arg
                515                 520

<210> SEQ ID NO 78
<211> LENGTH: 523
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Met Ala Leu Pro Val Thr Ala Leu Leu Leu Pro Leu Ala Leu Leu Leu
1               5                   10                  15

His Ala Ala Arg Pro Gly Gly Gly Gly Ser Cys Pro Tyr Ser Asn Pro
                20                  25                  30

Ser Leu Cys Gly Gly Gly Gly Ser Cys Pro Tyr Ser Asn Pro Ser Leu
            35                  40                  45

Cys Gly Gly Gly Gly Ser Gln Val Gln Leu Gln Glu Ser Gly Pro Gly
        50                  55                  60

-continued

Leu Val Lys Pro Ser Glu Thr Leu Ser Leu Thr Cys Thr Val Ser Gly
65                  70                  75                  80

Gly Ser Ile Ser Tyr Tyr Ser Trp Thr Trp Val Arg Gln Pro Ala Gly
            85                  90                  95

Gln Gly Leu Glu Trp Ile Gly Arg Ile His Ile Ser Gly Val Thr Asn
        100                 105                 110

His Asn Pro Ser Leu Lys Ser Arg Val Ser Met Ser Ile Asp Thr Ser
        115                 120                 125

Arg Thr Gln Phe Ser Leu Arg Leu Thr Ser Val Thr Ala Ala Asp Thr
        130                 135                 140

Ala Val Tyr Phe Cys Ala Arg Ser Gly Gly Thr Tyr Ser Ala Phe Asp
145                 150                 155                 160

Ile Trp Gly Gln Gly Thr Met Val Thr Val Ser Ser Gly Gly Gly Gly
                165                 170                 175

Ser Gly Gly Gly Gly Ser Gly Gly Gly Ser Gly Gly Gly Gly Gly Ser
            180                 185                 190

Glu Ile Val Leu Thr Gln Ser Pro Gly Thr Leu Ser Leu Ser Pro Gly
        195                 200                 205

Glu Arg Ser Thr Leu Ser Cys Arg Ala Ser Gln Ser Phe Thr Ser Asn
        210                 215                 220

Tyr Leu Ala Trp Tyr Gln Gln Arg Pro Gly Gln Ala Pro Arg Leu Leu
225                 230                 235                 240

Ile Tyr Gly Ala Ser Thr Arg Ala Ile Gly Ile Pro Asp Arg Phe Ser
                245                 250                 255

Gly Ser Gly Ser Gly Thr Asp Phe Thr Leu Thr Ile Ser Arg Leu Glu
            260                 265                 270

Pro Glu Asp Phe Ala Val Tyr Tyr Cys Gln Gln Tyr Gly Ser Ser Pro
        275                 280                 285

Trp Thr Phe Gly Gln Gly Thr Lys Val Glu Ile Lys Thr Thr Thr Pro
        290                 295                 300

Ala Pro Arg Pro Pro Thr Pro Ala Pro Thr Ile Ala Ser Gln Pro Leu
305                 310                 315                 320

Ser Leu Arg Pro Glu Ala Cys Arg Pro Ala Ala Gly Gly Ala Val His
                325                 330                 335

Thr Arg Gly Leu Asp Phe Ala Cys Asp Ile Tyr Ile Trp Ala Pro Leu
            340                 345                 350

Ala Gly Thr Cys Gly Val Leu Leu Leu Ser Leu Val Ile Thr Leu Tyr
        355                 360                 365

Cys Lys Arg Gly Arg Lys Lys Leu Leu Tyr Ile Phe Lys Gln Pro Phe
370                 375                 380

Met Arg Pro Val Gln Thr Thr Gln Glu Glu Asp Gly Cys Ser Cys Arg
385                 390                 395                 400

Phe Pro Glu Glu Glu Glu Gly Gly Cys Glu Leu Arg Val Lys Phe Ser
                405                 410                 415

Arg Ser Ala Asp Ala Pro Ala Tyr Gln Gln Gly Gln Asn Gln Leu Tyr
            420                 425                 430

Asn Glu Leu Asn Leu Gly Arg Arg Glu Glu Tyr Asp Val Leu Asp Lys
        435                 440                 445

Arg Arg Gly Arg Asp Pro Glu Met Gly Gly Lys Pro Arg Arg Lys Asn
        450                 455                 460

Pro Gln Glu Gly Leu Tyr Asn Glu Leu Gln Lys Asp Lys Met Ala Glu
465                 470                 475                 480

Ala Tyr Ser Glu Ile Gly Met Lys Gly Glu Arg Arg Arg Gly Lys Gly

```
                    485                 490                 495
His Asp Gly Leu Tyr Gln Gly Leu Ser Thr Ala Thr Lys Asp Thr Tyr
                500                 505                 510

Asp Ala Leu His Met Gln Ala Leu Pro Pro Arg
            515                 520

<210> SEQ ID NO 79
<211> LENGTH: 571
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Met Ala Leu Pro Val Thr Ala Leu Leu Leu Pro Leu Ala Leu Leu Leu
1               5                   10                  15

His Ala Ala Arg Pro Gly Gly Gly Ser Cys Pro Tyr Ser Asn Pro
                20                  25                  30

Ser Leu Cys Ser Gly Gly Gly Gly Ser Gly Gly Gly Ser Gln Val
            35                  40                  45

Gln Leu Gln Glu Ser Gly Pro Gly Leu Val Lys Pro Ser Glu Thr Leu
50                  55                  60

Ser Leu Thr Cys Thr Val Ser Gly Gly Ser Ile Ser Tyr Tyr Ser Trp
65                  70                  75                  80

Thr Trp Val Arg Gln Pro Ala Gly Gln Gly Leu Glu Trp Ile Gly Arg
                85                  90                  95

Ile His Ile Ser Gly Val Thr Asn His Asn Pro Ser Leu Lys Ser Arg
            100                 105                 110

Val Ser Met Ser Ile Asp Thr Ser Arg Thr Gln Phe Ser Leu Arg Leu
        115                 120                 125

Thr Ser Val Thr Ala Ala Asp Thr Ala Val Tyr Phe Cys Ala Arg Ser
130                 135                 140

Gly Gly Thr Tyr Ser Ala Phe Asp Ile Trp Gly Gln Gly Thr Met Val
145                 150                 155                 160

Thr Val Ser Ser Gly Gly Gly Gly Ser Gly Gly Gly Gly Ser Gly Gly
                165                 170                 175

Gly Gly Ser Gly Gly Gly Gly Ser Glu Ile Val Leu Thr Gln Ser Pro
            180                 185                 190

Gly Thr Leu Ser Leu Ser Pro Gly Glu Arg Ser Thr Leu Ser Cys Arg
        195                 200                 205

Ala Ser Gln Ser Phe Thr Ser Asn Tyr Leu Ala Trp Tyr Gln Gln Arg
    210                 215                 220

Pro Gly Gln Ala Pro Arg Leu Leu Ile Tyr Gly Ala Ser Thr Arg Ala
225                 230                 235                 240

Ile Gly Ile Pro Asp Arg Phe Ser Gly Ser Gly Ser Gly Thr Asp Phe
                245                 250                 255

Thr Leu Thr Ile Ser Arg Leu Glu Pro Glu Asp Phe Ala Val Tyr Tyr
            260                 265                 270

Cys Gln Gln Tyr Gly Ser Ser Pro Trp Thr Phe Gly Gln Gly Thr Lys
        275                 280                 285

Val Glu Ile Lys Gly Ser Gly Gly Gly Ser Cys Pro Tyr Ser Asn
    290                 295                 300

Pro Ser Leu Cys Ser Gly Gly Gly Gly Ser Glu Leu Pro Thr Gln Gly
305                 310                 315                 320
```

```
Thr Phe Ser Asn Val Ser Thr Asn Val Ser Pro Ala Lys Pro Thr Thr
                325                 330                 335

Thr Ala Cys Pro Tyr Ser Asn Pro Ser Leu Cys Thr Thr Pro Ala
        340                 345                 350

Pro Arg Pro Pro Thr Pro Ala Pro Thr Ile Ala Ser Gln Pro Leu Ser
        355                 360                 365

Leu Arg Pro Glu Ala Cys Arg Pro Ala Ala Gly Gly Ala Val His Thr
    370                 375                 380

Arg Gly Leu Asp Phe Ala Cys Asp Ile Tyr Ile Trp Ala Pro Leu Ala
385                 390                 395                 400

Gly Thr Cys Gly Val Leu Leu Leu Ser Leu Val Ile Thr Leu Tyr Cys
                405                 410                 415

Lys Arg Gly Arg Lys Lys Leu Leu Tyr Ile Phe Lys Gln Pro Phe Met
                420                 425                 430

Arg Pro Val Gln Thr Thr Gln Glu Glu Asp Gly Cys Ser Cys Arg Phe
                435                 440                 445

Pro Glu Glu Glu Glu Gly Gly Cys Glu Leu Leu Arg Val Lys Phe Ser
                450                 455                 460

Arg Ser Ala Asp Ala Pro Ala Tyr Gln Gln Gly Gln Asn Gln Leu Tyr
465                 470                 475                 480

Asn Glu Leu Asn Leu Gly Arg Arg Glu Glu Tyr Asp Val Leu Asp Lys
                485                 490                 495

Arg Arg Gly Arg Asp Pro Glu Met Gly Gly Lys Pro Arg Arg Lys Asn
                500                 505                 510

Pro Gln Glu Gly Leu Tyr Asn Glu Leu Gln Lys Asp Lys Met Ala Glu
                515                 520                 525

Ala Tyr Ser Glu Ile Gly Met Lys Gly Glu Arg Arg Arg Gly Lys Gly
                530                 535                 540

His Asp Gly Leu Tyr Gln Gly Leu Ser Thr Ala Thr Lys Asp Thr Tyr
545                 550                 555                 560

Asp Ala Leu His Met Gln Ala Leu Pro Pro Arg
                565                 570

<210> SEQ ID NO 80
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Asn Ser Glu Leu Leu Ser Leu Ile Asn Asp Met Pro Ile Thr Asn Asp
1               5                   10                  15

Gln Lys Lys Leu Met Ser Asn Asn
            20

<210> SEQ ID NO 81
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Cys Gln Phe Asp Leu Ser Thr Arg Arg Leu Lys Cys
1               5                   10
```

<210> SEQ ID NO 82
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Cys Gln Tyr Asn Leu Ser Ser Arg Ala Leu Lys Cys
1               5                   10

<210> SEQ ID NO 83
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Cys Val Trp Gln Arg Trp Gln Lys Ser Tyr Val Cys
1               5                   10

<210> SEQ ID NO 84
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Cys Met Trp Asp Arg Phe Ser Arg Trp Tyr Lys Cys
1               5                   10

<210> SEQ ID NO 85
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Ser Phe Val Leu Asn Trp Tyr Arg Met Ser Pro Ser Asn Gln Thr Asp
1               5                   10                  15

Lys Leu Ala Ala Phe Pro Glu Asp Arg
            20                  25

<210> SEQ ID NO 86
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Ser Gly Thr Tyr Leu Cys Gly Ala Ile Ser Leu Ala Pro Lys Ala Gln
1               5                   10                  15

Ile Lys Glu

<210> SEQ ID NO 87
<211> LENGTH: 24
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 87

Glu Leu Pro Thr Gln Gly Thr Phe Ser Asn Val Ser Thr Asn Val Ser
1               5                   10                  15

Pro Ala Lys Pro Thr Thr Thr Ala
            20

<210> SEQ ID NO 88
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Gly Gln Asn Asp Thr Ser Gln Thr Ser Ser Pro Ser
1               5                   10

<210> SEQ ID NO 89
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Val His Met Pro Leu Gly Phe Leu Gly Pro Arg Gln Ala Arg Val Val
1               5                   10                  15

Asn Gly

<210> SEQ ID NO 90
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Val His Met Pro Leu Gly Phe Leu Gly Pro Gly Ser Ala Arg Val Val
1               5                   10                  15

Asn Gly

<210> SEQ ID NO 91
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Arg Gln Ala Arg Val Val Asn Gly
1               5

<210> SEQ ID NO 92
<211> LENGTH: 8
<212> TYPE: PRT
<213> ORGANISM: Artificial Sequence
<220> FEATURE:
```

```
-continued

<223> OTHER INFORMATION: Description of Artificial Sequence: Synthetic
      peptide

<400> SEQUENCE: 92

Arg Gln Ala Arg Val Gly Ser Gly
1               5

<210> SEQ ID NO 93
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Val His Met Pro Leu Gly Phe Leu Gly Pro
1               5                   10

<210> SEQ ID NO 94
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Val His Met Pro Leu Ser Phe Leu Gly Pro
1               5                   10

<210> SEQ ID NO 95
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Pro Met Ala Lys Lys
1               5

<210> SEQ ID NO 96
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Pro Met Ala Lys Gly Ser
1               5

<210> SEQ ID NO 97
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Leu Ser Gly Arg Ser Asp Asn His
1               5
```

-continued

```
<210> SEQ ID NO 98
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Leu Ser Gly Arg Ser Asp Ser His
1               5

<210> SEQ ID NO 99
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Gly Gly Gly Gly Ser Val His Met Pro Leu Gly Phe Leu Gly Pro Arg
1               5                  10                  15

Gln Ala Arg Val Val Asn Gly Gly Ser
            20                  25

<210> SEQ ID NO 100
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Gly Gly Gly Gly Ser Val His Met Pro Leu Gly Phe Leu Gly Pro Gly
1               5                  10                  15

Ser Ala Arg Val Val Asn Gly Gly Ser
            20                  25

<210> SEQ ID NO 101
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Gly Gly Gly Gly Ser Gly Gly Gly Ser Pro Met Ala Lys Lys Gly
1               5                  10                  15

Gly Gly Gly Ser Gly Gly Gly Gly Ser
            20                  25

<210> SEQ ID NO 102
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Gly Gly Gly Gly Ser Gly Gly Gly Gly Ser Pro Met Ala Lys Gly Ser
1               5                  10                  15

Gly Gly Gly Ser Gly Gly Gly Gly Ser
```

<210> SEQ ID NO 103
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Ser Pro Leu Gly Leu Ala Gly Ser
1               5

<210> SEQ ID NO 104
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Pro Leu Gly Val Arg Gly Lys
1               5

<210> SEQ ID NO 105
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Pro Met Ala Lys Gly
1               5

<210> SEQ ID NO 106
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Gly Ser Ala Arg Val Val Asn Gly
1               5

<210> SEQ ID NO 107
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Gly Gly Gly Gly Ser Gly Gly Gly Gly Ser Gly Gly Gly Gly Ser Val
1               5                   10                  15

His Met Pro Leu Gly Phe Leu Gly Pro Arg Gln Ala Arg Val Val Asn
                20                  25                  30

Gly Gly Ser Gly Gly Gly Gly Ser Gly Gly Gly Gly Ser
            35                  40                  45

<210> SEQ ID NO 108
<211> LENGTH: 45
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 108

Gly Gly Gly Gly Ser Gly Gly Gly Ser Gly Gly Gly Gly Ser Val
1               5                   10                  15

His Met Pro Leu Gly Phe Leu Gly Pro Gly Ser Ala Arg Val Val Asn
            20                  25                  30

Gly Gly Ser Gly Gly Gly Gly Ser Gly Gly Gly Gly Ser
        35                  40                  45

<210> SEQ ID NO 109
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 109

Gly Gly Gly Gly Ser Pro Met Ala Lys Lys Gly Gly Gly Ser Gly
1               5                   10                  15

Gly Gly Gly Ser
            20

<210> SEQ ID NO 110
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 110

Gly Gly Gly Gly Ser Gly Gly Gly Gly Ser Pro Met Ala Lys Lys Gly
1               5                   10                  15

Gly Gly Gly Ser Gly Gly Gly Gly Ser
            20                  25

<210> SEQ ID NO 111
<211> LENGTH: 30
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 111

Gly Gly Gly Gly Ser Gly Gly Gly Gly Ser Pro Met Ala Lys Lys Gly
1               5                   10                  15

Gly Gly Gly Ser Gly Gly Gly Gly Ser Gly Gly Gly Gly Ser
            20                  25                  30

<210> SEQ ID NO 112
<211> LENGTH: 35
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 112

Gly Gly Gly Gly Ser Gly Gly Gly Ser Gly Gly Gly Ser Pro
1               5                   10                  15

Met Ala Lys Lys Gly Gly Gly Ser Gly Gly Gly Ser Gly Gly
            20                  25                  30

Gly Gly Ser
        35

<210> SEQ ID NO 113
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Gly Gly Gly Gly Ser Gly Gly Gly Ser Gly Gly Gly Ser Gly
1               5                   10                  15

Gly Gly Ser Pro Met Ala Lys Lys Gly Gly Gly Ser Gly Gly
            20                  25                  30

Gly Gly Ser Gly Gly Gly Ser Gly Gly Gly Ser
        35                  40                  45

<210> SEQ ID NO 114
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Gly Gly Gly Gly Ser Gly Gly Gly Ser Gly Gly Gly Ser Gly
1               5                   10                  15

Gly Gly Ser Pro Met Ala Lys Gly Ser Gly Gly Ser Gly Gly
            20                  25                  30

Gly Gly Ser Gly Gly Gly Ser Gly Gly Gly Ser
        35                  40                  45

<210> SEQ ID NO 115
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Gly Gly Gly Gly Ser Gly Gly Gly Ser Gly Ser Ser Pro Leu Gly
1               5                   10                  15

Leu Ala Gly Ser Gly Gly Gly Ser Gly Gly Gly Ser Pro Met
            20                  25                  30

Ala Lys Lys Gly Gly Gly Ser Gly Gly Gly Ser
        35                  40                  45

<210> SEQ ID NO 116
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 116

Gly Gly Gly Gly Ser Gly Gly Gly Ser Gly Gly Ser Val His Met
1               5                   10                  15

Pro Leu Gly Phe Leu Gly Pro Gly Ser Gly Gly Ser Pro Met
            20                  25                  30

Ala Lys Lys Gly Gly Gly Ser Gly Gly Gly Gly Ser
        35                  40                  45

<210> SEQ ID NO 117
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Gly Gly Gly Gly Ser Gly Gly Gly Ser Gly Gly Ser Pro Leu Gly
1               5                   10                  15

Val Arg Gly Lys Gly Gly Gly Ser Gly Gly Gly Ser Pro Met
            20                  25                  30

Ala Lys Lys Gly Gly Gly Ser Gly Gly Gly Gly Ser
        35                  40                  45

<210> SEQ ID NO 118
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Gly Gly Gly Gly Ser Gly Gly Gly Ser Gly Gly Ser Ser Pro Leu
1               5                   10                  15

Gly Leu Ala Gly Ser Gly Ser Gly Gly Ser Arg Gln Ala Arg Val
            20                  25                  30

Val Asn Gly Gly Gly Gly Gly Ser Gly Gly Gly Gly Ser
        35                  40                  45

<210> SEQ ID NO 119
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Gly Gly Gly Gly Ser Gly Gly Gly Ser Gly Gly Ser Val His Met
1               5                   10                  15

Pro Leu Gly Phe Leu Gly Pro Gly Gly Ser Arg Gln Ala Arg Val
            20                  25                  30

Val Asn Gly Gly Gly Gly Gly Ser Gly Gly Gly Gly Ser
        35                  40                  45

<210> SEQ ID NO 120
<211> LENGTH: 45
<212> TYPE: PRT
<213> ORGANISM: Artificial Sequence
<220> FEATURE:
<223> OTHER INFORMATION: Description of Artificial Sequence: Synthetic
```

-continued

```
       polypeptide

<400> SEQUENCE: 120

Gly Gly Gly Gly Ser Gly Gly Gly Ser Gly Gly Ser Pro Leu Gly
1               5                   10                  15

Val Arg Gly Lys Gly Gly Ser Gly Gly Ser Arg Gln Ala Arg Val
            20                  25                  30

Val Asn Gly Gly Gly Gly Gly Ser Gly Gly Gly Gly Ser
        35                  40                  45

<210> SEQ ID NO 121
<211> LENGTH: 793
<212> TYPE: PRT
<213> ORGANISM: Artificial Sequence
<220> FEATURE:
<223> OTHER INFORMATION: Description of Artificial Sequence: Synthetic
       polypeptide

<400> SEQUENCE: 121

Met Ala Leu Pro Val Thr Ala Leu Leu Leu Pro Leu Ala Leu Leu
1               5                   10                  15

His Ala Ala Arg Pro Gly Tyr Pro Tyr Asp Val Pro Asp Tyr Ala Asp
            20                  25                  30

Ile Val Met Thr Gln Thr Pro Ala Ser Val Ser Glu Pro Val Gly Gly
        35                  40                  45

Ser Val Thr Ile Lys Cys Gln Ala Ser Gln Ser Phe Tyr Asn Leu Leu
    50                  55                  60

Ala Trp Tyr Gln Gln Lys Pro Gly Gln Pro Pro Lys Leu Leu Ile Tyr
65                  70                  75                  80

Asp Ala Ser Asp Leu Ala Ser Gly Val Pro Ser Arg Phe Lys Gly Ser
                85                  90                  95

Gly Ser Gly Thr Asp Phe Thr Leu Thr Ile Ser Asp Leu Glu Cys Ala
            100                 105                 110

Asp Ala Ala Ala Tyr Tyr Cys Gln Ser Ala Asp Gly Ser Ser Tyr Ala
            115                 120                 125

Phe Gly Gly Gly Thr Glu Val Val Val Lys Gly Gly Gly Gly Ser
        130                 135                 140

Gly Gly Gly Gly Ser Gly Gly Gly Ser Gly Gly Gly Gly Ser Gln
145                 150                 155                 160

Glu Gln Leu Glu Glu Ser Gly Gly Leu Val Lys Pro Glu Gly Ser
                165                 170                 175

Leu Thr Leu Thr Cys Thr Ala Ser Gly Val Ser Phe Ser Ser Ser Tyr
            180                 185                 190

Trp Ile Tyr Trp Val Arg Gln Ala Pro Gly Lys Gly Leu Glu Trp Ile
        195                 200                 205

Ala Cys Ile Tyr Thr Gly Ser Ser Gly Ser Thr Tyr Tyr Ala Ser Trp
    210                 215                 220

Ala Lys Gly Arg Phe Thr Val Ser Glu Thr Ser Ser Thr Thr Val Thr
225                 230                 235                 240

Leu Gln Met Thr Ser Leu Thr Ala Ala Asp Thr Ala Thr Tyr Phe Cys
                245                 250                 255

Ala Arg Ala Ser Ala Trp Thr Tyr Gly Met Asp Leu Trp Gly Pro Gly
            260                 265                 270

Thr Leu Val Thr Val Ser Ser Gly Gly Gly Ser Gly Gly Gly Gly
        275                 280                 285

Ser Gly Gly Gly Gly Ser Val His Met Pro Leu Gly Phe Leu Gly Pro
```

```
              290                 295                 300
Arg Gln Ala Arg Val Val Asn Gly Gly Ser Gly Gly Gly Ser Gly
305                 310                 315                 320

Gly Gly Gly Ser Gln Val Gln Leu Gln Glu Ser Gly Pro Gly Leu Val
                325                 330                 335

Lys Pro Ser Glu Thr Leu Ser Leu Thr Cys Thr Val Ser Gly Gly Ser
                340                 345                 350

Ile Ser Tyr Tyr Ser Trp Thr Trp Val Arg Gln Pro Ala Gly Gln Gly
                355                 360                 365

Leu Glu Trp Ile Gly Arg Ile His Ile Ser Gly Val Thr Asn His Asn
            370                 375                 380

Pro Ser Leu Lys Ser Arg Val Ser Met Ser Ile Asp Thr Ser Arg Thr
385                 390                 395                 400

Gln Phe Ser Leu Arg Leu Thr Ser Val Thr Ala Ala Asp Thr Ala Val
                405                 410                 415

Tyr Phe Cys Ala Arg Ser Gly Gly Thr Tyr Ser Ala Phe Asp Ile Trp
                420                 425                 430

Gly Gln Gly Thr Met Val Thr Val Ser Ser Gly Gly Gly Gly Ser Gly
                435                 440                 445

Gly Gly Gly Ser Gly Gly Gly Gly Ser Gly Gly Gly Gly Ser Glu Ile
            450                 455                 460

Val Leu Thr Gln Ser Pro Gly Thr Leu Ser Leu Ser Pro Gly Glu Arg
465                 470                 475                 480

Ser Thr Leu Ser Cys Arg Ala Ser Gln Ser Phe Thr Ser Asn Tyr Leu
                485                 490                 495

Ala Trp Tyr Gln Gln Arg Pro Gly Gln Ala Pro Arg Leu Leu Ile Tyr
                500                 505                 510

Gly Ala Ser Thr Arg Ala Ile Gly Ile Pro Asp Arg Phe Ser Gly Ser
                515                 520                 525

Gly Ser Gly Thr Asp Phe Thr Leu Thr Ile Ser Arg Leu Glu Pro Glu
            530                 535                 540

Asp Phe Ala Val Tyr Tyr Cys Gln Gln Tyr Gly Ser Ser Pro Trp Thr
545                 550                 555                 560

Phe Gly Gln Gly Thr Lys Val Glu Ile Lys Thr Thr Thr Pro Ala Pro
                565                 570                 575

Arg Pro Pro Thr Pro Ala Pro Thr Ile Ala Ser Gln Pro Leu Ser Leu
                580                 585                 590

Arg Pro Glu Ala Cys Arg Pro Ala Ala Gly Gly Ala Val His Thr Arg
                595                 600                 605

Gly Leu Asp Phe Ala Cys Asp Ile Tyr Ile Trp Ala Pro Leu Ala Gly
            610                 615                 620

Thr Cys Gly Val Leu Leu Leu Ser Leu Val Ile Thr Leu Tyr Cys Lys
625                 630                 635                 640

Arg Gly Arg Lys Lys Leu Leu Tyr Ile Phe Lys Gln Pro Phe Met Arg
                645                 650                 655

Pro Val Gln Thr Thr Gln Glu Glu Asp Gly Cys Ser Cys Arg Phe Pro
                660                 665                 670

Glu Glu Glu Glu Gly Gly Cys Glu Leu Arg Val Lys Phe Ser Arg Ser
                675                 680                 685

Ala Asp Ala Pro Ala Tyr Gln Gln Gly Gln Asn Gln Leu Tyr Asn Glu
            690                 695                 700

Leu Asn Leu Gly Arg Arg Glu Glu Tyr Asp Val Leu Asp Lys Arg Arg
705                 710                 715                 720
```

```
Gly Arg Asp Pro Glu Met Gly Lys Pro Arg Arg Lys Asn Pro Gln
                725                 730                 735

Glu Gly Leu Tyr Asn Glu Leu Gln Lys Asp Lys Met Ala Glu Ala Tyr
            740                 745                 750

Ser Glu Ile Gly Met Lys Gly Glu Arg Arg Arg Gly Lys Gly His Asp
        755                 760                 765

Gly Leu Tyr Gln Gly Leu Ser Thr Ala Thr Lys Asp Thr Tyr Asp Ala
    770                 775                 780

Leu His Met Gln Ala Leu Pro Pro Arg
785                 790

<210> SEQ ID NO 122
<211> LENGTH: 793
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Met Ala Leu Pro Val Thr Ala Leu Leu Leu Pro Leu Ala Leu Leu Leu
1               5                   10                  15

His Ala Ala Arg Pro Gly Tyr Pro Tyr Asp Val Pro Asp Tyr Ala Asp
            20                  25                  30

Ile Val Met Thr Gln Thr Pro Ala Ser Val Ser Glu Pro Val Gly Gly
        35                  40                  45

Ser Val Thr Ile Lys Cys Gln Ala Ser Gln Ser Phe Tyr Asn Leu Leu
    50                  55                  60

Ala Trp Tyr Gln Gln Lys Pro Gly Gln Pro Pro Lys Leu Leu Ile Tyr
65                  70                  75                  80

Asp Ala Ser Asp Leu Ala Ser Gly Val Pro Ser Arg Phe Lys Gly Ser
                85                  90                  95

Gly Ser Gly Thr Asp Phe Thr Leu Thr Ile Ser Asp Leu Glu Cys Ala
            100                 105                 110

Asp Ala Ala Thr Tyr Cys Gln Ser Ala Asp Gly Ser Ser Tyr Ala
        115                 120                 125

Phe Gly Gly Gly Thr Glu Val Val Lys Gly Gly Gly Gly Ser
    130                 135                 140

Gly Gly Gly Gly Ser Gly Gly Gly Ser Gly Gly Gly Gly Ser Gln
145                 150                 155                 160

Glu Gln Leu Glu Glu Ser Gly Gly Leu Val Lys Pro Glu Gly Ser
                165                 170                 175

Leu Thr Leu Thr Cys Thr Ala Ser Gly Val Ser Phe Ser Ser Ser Tyr
            180                 185                 190

Trp Ile Tyr Trp Val Arg Gln Ala Pro Gly Lys Gly Leu Glu Trp Ile
        195                 200                 205

Ala Cys Ile Tyr Thr Gly Ser Ser Gly Ser Thr Tyr Tyr Ala Ser Trp
    210                 215                 220

Ala Lys Gly Arg Phe Thr Val Ser Glu Thr Ser Ser Thr Thr Val Thr
225                 230                 235                 240

Leu Gln Met Thr Ser Leu Thr Ala Ala Asp Thr Ala Thr Tyr Phe Cys
                245                 250                 255

Ala Arg Ala Ser Ala Trp Thr Tyr Gly Met Asp Leu Trp Gly Pro Gly
            260                 265                 270

Thr Leu Val Thr Val Ser Ser Gly Gly Gly Gly Ser Gly Gly Gly Gly
```

```
                275                 280                 285
Ser Gly Gly Gly Ser Val His Met Pro Leu Gly Phe Leu Gly Pro
    290                 295                 300
Gly Ser Ala Arg Val Val Asn Gly Gly Ser Gly Gly Gly Ser Gly
305                 310                 315                 320
Gly Gly Gly Ser Gln Val Gln Leu Gln Glu Ser Gly Pro Gly Leu Val
                325                 330                 335
Lys Pro Ser Glu Thr Leu Ser Leu Thr Cys Thr Val Ser Gly Gly Ser
                340                 345                 350
Ile Ser Tyr Tyr Ser Trp Thr Trp Val Arg Gln Pro Ala Gly Gln Gly
                355                 360                 365
Leu Glu Trp Ile Gly Arg Ile His Ile Ser Gly Val Thr Asn His Asn
    370                 375                 380
Pro Ser Leu Lys Ser Arg Val Ser Met Ser Ile Asp Thr Ser Arg Thr
385                 390                 395                 400
Gln Phe Ser Leu Arg Leu Thr Ser Val Thr Ala Ala Asp Thr Ala Val
                405                 410                 415
Tyr Phe Cys Ala Arg Ser Gly Gly Thr Tyr Ser Ala Phe Asp Ile Trp
                420                 425                 430
Gly Gln Gly Thr Met Val Thr Val Ser Ser Gly Gly Gly Ser Gly
                435                 440                 445
Gly Gly Gly Ser Gly Gly Gly Ser Gly Gly Gly Gly Ser Glu Ile
450                 455                 460
Val Leu Thr Gln Ser Pro Gly Thr Leu Ser Leu Ser Pro Gly Glu Arg
465                 470                 475                 480
Ser Thr Leu Ser Cys Arg Ala Ser Gln Ser Phe Thr Ser Asn Tyr Leu
                485                 490                 495
Ala Trp Tyr Gln Gln Arg Pro Gly Gln Ala Pro Arg Leu Leu Ile Tyr
                500                 505                 510
Gly Ala Ser Thr Arg Ala Ile Gly Ile Pro Asp Arg Phe Ser Gly Ser
                515                 520                 525
Gly Ser Gly Thr Asp Phe Thr Leu Thr Ile Ser Arg Leu Glu Pro Glu
                530                 535                 540
Asp Phe Ala Val Tyr Tyr Cys Gln Gln Tyr Gly Ser Ser Pro Trp Thr
545                 550                 555                 560
Phe Gly Gln Gly Thr Lys Val Glu Ile Lys Thr Thr Thr Pro Ala Pro
                565                 570                 575
Arg Pro Pro Thr Pro Ala Pro Thr Ile Ala Ser Gln Pro Leu Ser Leu
                580                 585                 590
Arg Pro Glu Ala Cys Arg Pro Ala Ala Gly Gly Ala Val His Thr Arg
                595                 600                 605
Gly Leu Asp Phe Ala Cys Asp Ile Tyr Ile Trp Ala Pro Leu Ala Gly
                610                 615                 620
Thr Cys Gly Val Leu Leu Leu Ser Leu Val Ile Thr Leu Tyr Cys Lys
625                 630                 635                 640
Arg Gly Arg Lys Lys Leu Leu Tyr Ile Phe Lys Gln Pro Phe Met Arg
                645                 650                 655
Pro Val Gln Thr Thr Gln Glu Glu Asp Gly Cys Ser Cys Arg Phe Pro
                660                 665                 670
Glu Glu Glu Glu Gly Gly Cys Glu Leu Arg Val Lys Phe Ser Arg Ser
                675                 680                 685
Ala Asp Ala Pro Ala Tyr Gln Gln Gly Gln Asn Gln Leu Tyr Asn Glu
                690                 695                 700
```

```
Leu Asn Leu Gly Arg Arg Glu Glu Tyr Asp Val Leu Asp Lys Arg Arg
705                 710                 715                 720

Gly Arg Asp Pro Glu Met Gly Gly Lys Pro Arg Arg Lys Asn Pro Gln
            725                 730                 735

Glu Gly Leu Tyr Asn Glu Leu Gln Lys Asp Lys Met Ala Glu Ala Tyr
            740                 745                 750

Ser Glu Ile Gly Met Lys Gly Glu Arg Arg Arg Gly Lys Gly His Asp
        755                 760                 765

Gly Leu Tyr Gln Gly Leu Ser Thr Ala Thr Lys Asp Thr Tyr Asp Ala
    770                 775                 780

Leu His Met Gln Ala Leu Pro Pro Arg
785                 790
```

<210> SEQ ID NO 123
<211> LENGTH: 793
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

```
Met Ala Leu Pro Val Thr Ala Leu Leu Leu Pro Leu Ala Leu Leu Leu
1               5                   10                  15

His Ala Ala Arg Pro Gly Tyr Pro Tyr Asp Val Pro Asp Tyr Ala Asp
            20                  25                  30

Ile Val Met Thr Gln Thr Pro Ala Ser Val Ser Glu Pro Val Gly Gly
        35                  40                  45

Ser Val Thr Ile Lys Cys Gln Ala Ser Gln Ser Phe Tyr Asn Leu Leu
    50                  55                  60

Ala Trp Tyr Gln Gln Lys Pro Gly Gln Pro Pro Lys Leu Leu Ile Tyr
65              70                  75                  80

Asp Ala Ser Asp Leu Ala Ser Gly Val Pro Ser Arg Phe Lys Gly Ser
                85                  90                  95

Gly Ser Gly Thr Asp Phe Thr Leu Thr Ile Ser Asp Leu Glu Cys Ala
            100                 105                 110

Asp Ala Ala Ala Tyr Tyr Cys Gln Ser Ala Asp Gly Ser Ser Tyr Ala
        115                 120                 125

Phe Gly Gly Gly Thr Glu Val Val Lys Gly Gly Gly Gly Ser
    130                 135                 140

Gly Gly Gly Gly Ser Gly Gly Gly Ser Gly Gly Gly Gly Ser Gln
145                 150                 155                 160

Glu Gln Leu Glu Glu Ser Gly Gly Gly Leu Val Lys Pro Glu Gly Ser
                165                 170                 175

Leu Thr Leu Thr Cys Thr Ala Ser Gly Val Ser Phe Ser Ser Ser Tyr
            180                 185                 190

Trp Ile Tyr Trp Val Arg Gln Ala Pro Gly Lys Gly Leu Glu Trp Ile
        195                 200                 205

Ala Cys Ile Tyr Thr Gly Ser Ser Gly Ser Thr Tyr Tyr Ala Ser Trp
    210                 215                 220

Ala Lys Gly Arg Phe Thr Val Ser Glu Thr Ser Ser Thr Thr Val Thr
225                 230                 235                 240

Leu Gln Met Thr Ser Leu Thr Ala Ala Asp Thr Ala Thr Tyr Phe Cys
                245                 250                 255

Ala Arg Ala Ser Ala Trp Thr Tyr Gly Met Asp Leu Trp Gly Pro Gly
```

```
                260                 265                 270
Thr Leu Val Thr Val Ser Ser Gly Gly Gly Ser Gly Gly Gly
            275                 280                 285
Ser Gly Gly Gly Ser Gly Gly Gly Ser Pro Met Ala Lys Lys
            290                 295                 300
Gly Gly Gly Ser Gly Gly Gly Ser Gly Gly Gly Ser Gly
305                 310                 315                 320
Gly Gly Ser Gln Val Gln Leu Gln Glu Ser Gly Pro Gly Leu Val
                325                 330                 335
Lys Pro Ser Glu Thr Leu Ser Leu Thr Cys Thr Val Ser Gly Gly Ser
            340                 345                 350
Ile Ser Tyr Tyr Ser Trp Thr Trp Val Arg Gln Pro Ala Gly Gln Gly
            355                 360                 365
Leu Glu Trp Ile Gly Arg Ile His Ile Ser Gly Val Thr Asn His Asn
            370                 375                 380
Pro Ser Leu Lys Ser Arg Val Ser Met Ser Ile Asp Thr Ser Arg Thr
385                 390                 395                 400
Gln Phe Ser Leu Arg Leu Thr Ser Val Thr Ala Ala Asp Thr Ala Val
                405                 410                 415
Tyr Phe Cys Ala Arg Ser Gly Gly Thr Tyr Ser Ala Phe Asp Ile Trp
            420                 425                 430
Gly Gln Gly Thr Met Val Thr Val Ser Ser Gly Gly Gly Gly Ser Gly
            435                 440                 445
Gly Gly Gly Ser Gly Gly Gly Gly Ser Gly Gly Gly Gly Ser Glu Ile
            450                 455                 460
Val Leu Thr Gln Ser Pro Gly Thr Leu Ser Leu Ser Pro Gly Glu Arg
465                 470                 475                 480
Ser Thr Leu Ser Cys Arg Ala Ser Gln Ser Phe Thr Ser Asn Tyr Leu
                485                 490                 495
Ala Trp Tyr Gln Gln Arg Pro Gly Gln Ala Pro Arg Leu Leu Ile Tyr
            500                 505                 510
Gly Ala Ser Thr Arg Ala Ile Gly Ile Pro Asp Arg Phe Ser Gly Ser
            515                 520                 525
Gly Ser Gly Thr Asp Phe Thr Leu Thr Ile Ser Arg Leu Glu Pro Glu
            530                 535                 540
Asp Phe Ala Val Tyr Tyr Cys Gln Gln Tyr Gly Ser Ser Pro Trp Thr
545                 550                 555                 560
Phe Gly Gln Gly Thr Lys Val Glu Ile Lys Thr Thr Thr Pro Ala Pro
                565                 570                 575
Arg Pro Pro Thr Pro Ala Pro Thr Ile Ala Ser Gln Pro Leu Ser Leu
            580                 585                 590
Arg Pro Glu Ala Cys Arg Pro Ala Ala Gly Gly Ala Val His Thr Arg
            595                 600                 605
Gly Leu Asp Phe Ala Cys Asp Ile Tyr Ile Trp Ala Pro Leu Ala Gly
            610                 615                 620
Thr Cys Gly Val Leu Leu Leu Ser Leu Val Ile Thr Leu Tyr Cys Lys
625                 630                 635                 640
Arg Gly Arg Lys Lys Leu Leu Tyr Ile Phe Lys Gln Pro Phe Met Arg
                645                 650                 655
Pro Val Gln Thr Thr Gln Glu Glu Asp Gly Cys Ser Cys Arg Phe Pro
            660                 665                 670
Glu Glu Glu Glu Gly Gly Cys Glu Leu Arg Val Lys Phe Ser Arg Ser
            675                 680                 685
```

```
Ala Asp Ala Pro Ala Tyr Gln Gln Gly Gln Asn Gln Leu Tyr Asn Glu
    690             695                 700

Leu Asn Leu Gly Arg Arg Glu Glu Tyr Asp Val Leu Asp Lys Arg Arg
705             710                 715                 720

Gly Arg Asp Pro Glu Met Gly Gly Lys Pro Arg Arg Lys Asn Pro Gln
            725                 730                 735

Glu Gly Leu Tyr Asn Glu Leu Gln Lys Asp Lys Met Ala Glu Ala Tyr
            740                 745                 750

Ser Glu Ile Gly Met Lys Gly Glu Arg Arg Arg Gly Lys Gly His Asp
        755                 760                 765

Gly Leu Tyr Gln Gly Leu Ser Thr Ala Thr Lys Asp Thr Tyr Asp Ala
    770                 775                 780

Leu His Met Gln Ala Leu Pro Pro Arg
785                 790
```

<210> SEQ ID NO 124
<211> LENGTH: 793
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

```
Met Ala Leu Pro Val Thr Ala Leu Leu Leu Pro Leu Ala Leu Leu Leu
1               5                   10                  15

His Ala Ala Arg Pro Gly Tyr Pro Tyr Asp Val Pro Asp Tyr Ala Asp
                20                  25                  30

Ile Val Met Thr Gln Thr Pro Ala Ser Val Ser Glu Pro Val Gly Gly
            35                  40                  45

Ser Val Thr Ile Lys Cys Gln Ala Ser Gln Ser Phe Tyr Asn Leu Leu
    50                  55                  60

Ala Trp Tyr Gln Gln Lys Pro Gly Gln Pro Pro Lys Leu Leu Ile Tyr
65                  70                  75                  80

Asp Ala Ser Asp Leu Ala Ser Gly Val Pro Ser Arg Phe Lys Gly Ser
                85                  90                  95

Gly Ser Gly Thr Asp Phe Thr Leu Thr Ile Ser Asp Leu Glu Cys Ala
            100                 105                 110

Asp Ala Ala Tyr Tyr Cys Gln Ser Ala Asp Gly Ser Ser Tyr Ala
            115                 120                 125

Phe Gly Gly Gly Thr Glu Val Val Lys Gly Gly Gly Gly Ser
            130                 135                 140

Gly Gly Gly Gly Ser Gly Gly Gly Ser Gly Gly Gly Ser Gln
145                 150                 155                 160

Glu Gln Leu Glu Glu Ser Gly Gly Leu Val Lys Pro Glu Gly Ser
                165                 170                 175

Leu Thr Leu Thr Cys Thr Ala Ser Gly Val Ser Phe Ser Ser Ser Tyr
            180                 185                 190

Trp Ile Tyr Trp Val Arg Gln Ala Pro Gly Lys Gly Leu Glu Trp Ile
        195                 200                 205

Ala Cys Ile Tyr Thr Gly Ser Ser Gly Ser Thr Tyr Tyr Ala Ser Trp
    210                 215                 220

Ala Lys Gly Arg Phe Thr Val Ser Glu Thr Ser Ser Thr Thr Val Thr
225                 230                 235                 240

Leu Gln Met Thr Ser Leu Thr Ala Ala Asp Thr Ala Thr Tyr Phe Cys
```

-continued

```
                245                 250                 255
Ala Arg Ala Ser Ala Trp Thr Tyr Gly Met Asp Leu Trp Gly Pro Gly
            260                 265                 270

Thr Leu Val Thr Val Ser Ser Gly Gly Gly Ser Gly Gly Gly Gly
            275                 280                 285

Ser Gly Gly Gly Gly Ser Gly Gly Gly Ser Pro Met Ala Lys Gly
            290                 295                 300

Ser Gly Gly Ser Gly Gly Gly Ser Gly Gly Gly Ser Gly
305                 310                 315                 320

Gly Gly Ser Gln Val Gln Leu Gln Glu Ser Gly Pro Gly Leu Val
            325                 330                 335

Lys Pro Ser Glu Thr Leu Ser Leu Thr Cys Thr Val Ser Gly Gly Ser
            340                 345                 350

Ile Ser Tyr Tyr Ser Trp Thr Trp Val Arg Gln Pro Ala Gly Gln Gly
            355                 360                 365

Leu Glu Trp Ile Gly Arg Ile His Ile Ser Gly Val Thr Asn His Asn
            370                 375                 380

Pro Ser Leu Lys Ser Arg Val Ser Met Ser Ile Asp Thr Ser Arg Thr
385                 390                 395                 400

Gln Phe Ser Leu Arg Leu Thr Ser Val Thr Ala Ala Asp Thr Ala Val
            405                 410                 415

Tyr Phe Cys Ala Arg Ser Gly Gly Thr Tyr Ser Ala Phe Asp Ile Trp
            420                 425                 430

Gly Gln Gly Thr Met Val Thr Val Ser Ser Gly Gly Gly Gly Ser Gly
            435                 440                 445

Gly Gly Gly Ser Gly Gly Gly Gly Ser Gly Gly Gly Gly Ser Glu Ile
            450                 455                 460

Val Leu Thr Gln Ser Pro Gly Thr Leu Ser Leu Ser Pro Gly Glu Arg
465                 470                 475                 480

Ser Thr Leu Ser Cys Arg Ala Ser Gln Ser Phe Thr Ser Asn Tyr Leu
            485                 490                 495

Ala Trp Tyr Gln Gln Arg Pro Gly Gln Ala Pro Arg Leu Leu Ile Tyr
            500                 505                 510

Gly Ala Ser Thr Arg Ala Ile Gly Ile Pro Asp Arg Phe Ser Gly Ser
            515                 520                 525

Gly Ser Gly Thr Asp Phe Thr Leu Thr Ile Ser Arg Leu Glu Pro Glu
            530                 535                 540

Asp Phe Ala Val Tyr Tyr Cys Gln Gln Tyr Gly Ser Ser Pro Trp Thr
545                 550                 555                 560

Phe Gly Gln Gly Thr Lys Val Glu Ile Lys Thr Thr Pro Ala Pro
            565                 570                 575

Arg Pro Pro Thr Pro Ala Pro Thr Ile Ala Ser Gln Pro Leu Ser Leu
            580                 585                 590

Arg Pro Glu Ala Cys Arg Pro Ala Ala Gly Gly Ala Val His Thr Arg
            595                 600                 605

Gly Leu Asp Phe Ala Cys Asp Ile Tyr Ile Trp Ala Pro Leu Ala Gly
            610                 615                 620

Thr Cys Gly Val Leu Leu Leu Ser Leu Val Ile Thr Leu Tyr Cys Lys
625                 630                 635                 640

Arg Gly Arg Lys Lys Leu Leu Tyr Ile Phe Lys Gln Pro Phe Met Arg
            645                 650                 655

Pro Val Gln Thr Thr Gln Glu Glu Asp Gly Cys Ser Cys Arg Phe Pro
            660                 665                 670
```

```
Glu Glu Glu Glu Gly Gly Cys Glu Leu Arg Val Lys Phe Ser Arg Ser
            675                 680                 685

Ala Asp Ala Pro Ala Tyr Gln Gln Gly Gln Asn Gln Leu Tyr Asn Glu
690                 695                 700

Leu Asn Leu Gly Arg Arg Glu Glu Tyr Asp Val Leu Asp Lys Arg Arg
705                 710                 715                 720

Gly Arg Asp Pro Glu Met Gly Gly Lys Pro Arg Arg Lys Asn Pro Gln
            725                 730                 735

Glu Gly Leu Tyr Asn Glu Leu Gln Lys Asp Lys Met Ala Glu Ala Tyr
            740                 745                 750

Ser Glu Ile Gly Met Lys Gly Glu Arg Arg Arg Gly Lys Gly His Asp
            755                 760                 765

Gly Leu Tyr Gln Gly Leu Ser Thr Ala Thr Lys Asp Thr Tyr Asp Ala
770                 775                 780

Leu His Met Gln Ala Leu Pro Pro Arg
785                 790

<210> SEQ ID NO 125
<211> LENGTH: 808
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Met Ala Leu Pro Val Thr Ala Leu Leu Leu Pro Leu Ala Leu Leu Leu
1               5                   10                  15

His Ala Ala Arg Pro Gly Tyr Pro Tyr Asp Val Pro Asp Tyr Ala Asp
            20                  25                  30

Ile Val Met Thr Gln Thr Pro Ala Ser Val Ser Glu Pro Val Gly Gly
            35                  40                  45

Ser Val Thr Ile Lys Cys Gln Ala Ser Gln Ser Phe Tyr Asn Leu Leu
        50                  55                  60

Ala Trp Tyr Gln Gln Lys Pro Gly Gln Pro Pro Lys Leu Leu Ile Tyr
65                  70                  75                  80

Asp Ala Ser Asp Leu Ala Ser Gly Val Pro Ser Arg Phe Lys Gly Ser
                85                  90                  95

Gly Ser Gly Thr Asp Phe Thr Leu Thr Ile Ser Asp Leu Glu Cys Ala
            100                 105                 110

Asp Ala Ala Ala Tyr Tyr Cys Gln Ser Ala Asp Gly Ser Ser Tyr Ala
            115                 120                 125

Phe Gly Gly Gly Thr Glu Val Val Lys Gly Gly Gly Gly Ser
130                 135                 140

Gly Gly Gly Gly Ser Val His Met Pro Leu Gly Phe Leu Gly Pro Arg
145                 150                 155                 160

Gln Ala Arg Val Val Asn Gly Ser Gly Gly Gly Ser Gln Glu
            165                 170                 175

Gln Leu Glu Glu Ser Gly Gly Gly Leu Val Lys Pro Glu Gly Ser Leu
            180                 185                 190

Thr Leu Thr Cys Thr Ala Ser Gly Val Ser Phe Ser Ser Tyr Trp
                195                 200                 205

Ile Tyr Trp Val Arg Gln Ala Pro Gly Lys Gly Leu Glu Trp Ile Ala
        210                 215                 220

Cys Ile Tyr Thr Gly Ser Ser Gly Ser Thr Tyr Tyr Ala Ser Trp Ala
```

```
              225                 230                 235                 240
Lys Gly Arg Phe Thr Val Ser Glu Thr Ser Thr Thr Val Thr Leu
                245                 250                 255
Gln Met Thr Ser Leu Thr Ala Ala Asp Thr Ala Thr Tyr Phe Cys Ala
                260                 265                 270
Arg Ala Ser Ala Trp Thr Tyr Gly Met Asp Leu Trp Gly Pro Gly Thr
                275                 280                 285
Leu Val Thr Val Ser Ser Gly Gly Gly Ser Gly Gly Gly Gly Ser
                290                 295                 300
Gly Gly Gly Gly Ser Val His Met Pro Leu Gly Phe Leu Gly Pro Arg
305                 310                 315                 320
Gln Ala Arg Val Val Asn Gly Gly Ser Gly Gly Gly Ser Gly Gly
                325                 330                 335
Gly Gly Ser Gln Val Gln Leu Gln Glu Ser Gly Pro Gly Leu Val Lys
                340                 345                 350
Pro Ser Glu Thr Leu Ser Leu Thr Cys Thr Val Ser Gly Gly Ser Ile
                355                 360                 365
Ser Tyr Tyr Ser Trp Thr Trp Val Arg Gln Pro Ala Gly Gln Gly Leu
                370                 375                 380
Glu Trp Ile Gly Arg Ile His Ile Ser Gly Val Thr Asn His Asn Pro
385                 390                 395                 400
Ser Leu Lys Ser Arg Val Ser Met Ser Ile Asp Thr Ser Arg Thr Gln
                405                 410                 415
Phe Ser Leu Arg Leu Thr Ser Val Thr Ala Ala Asp Thr Ala Val Tyr
                420                 425                 430
Phe Cys Ala Arg Ser Gly Gly Thr Tyr Ser Ala Phe Asp Ile Trp Gly
                435                 440                 445
Gln Gly Thr Met Val Thr Val Ser Ser Gly Gly Gly Ser Gly Gly
                450                 455                 460
Gly Gly Ser Gly Gly Gly Gly Ser Gly Gly Gly Gly Ser Glu Ile Val
465                 470                 475                 480
Leu Thr Gln Ser Pro Gly Thr Leu Ser Leu Ser Pro Gly Glu Arg Ser
                485                 490                 495
Thr Leu Ser Cys Arg Ala Ser Gln Ser Phe Thr Ser Asn Tyr Leu Ala
                500                 505                 510
Trp Tyr Gln Gln Arg Pro Gly Gln Ala Pro Arg Leu Leu Ile Tyr Gly
                515                 520                 525
Ala Ser Thr Arg Ala Ile Gly Ile Pro Asp Arg Phe Ser Gly Ser Gly
                530                 535                 540
Ser Gly Thr Asp Phe Thr Leu Thr Ile Ser Arg Leu Glu Pro Glu Asp
545                 550                 555                 560
Phe Ala Val Tyr Tyr Cys Gln Gln Tyr Gly Ser Ser Pro Trp Thr Phe
                565                 570                 575
Gly Gln Gly Thr Lys Val Glu Ile Lys Thr Thr Thr Pro Ala Pro Arg
                580                 585                 590
Pro Pro Thr Pro Ala Pro Thr Ile Ala Ser Gln Pro Leu Ser Leu Arg
                595                 600                 605
Pro Glu Ala Cys Arg Pro Ala Ala Gly Gly Ala Val His Thr Arg Gly
                610                 615                 620
Leu Asp Phe Ala Cys Asp Ile Tyr Ile Trp Ala Pro Leu Ala Gly Thr
625                 630                 635                 640
Cys Gly Val Leu Leu Leu Ser Leu Val Ile Thr Leu Tyr Cys Lys Arg
                645                 650                 655
```

```
Gly Arg Lys Lys Leu Leu Tyr Ile Phe Lys Gln Pro Phe Met Arg Pro
            660                 665                 670

Val Gln Thr Thr Gln Glu Glu Asp Gly Cys Ser Cys Arg Phe Pro Glu
        675                 680                 685

Glu Glu Glu Gly Gly Cys Glu Leu Arg Val Lys Phe Ser Arg Ser Ala
690                 695                 700

Asp Ala Pro Ala Tyr Gln Gln Gly Gln Asn Gln Leu Tyr Asn Glu Leu
705                 710                 715                 720

Asn Leu Gly Arg Arg Glu Glu Tyr Asp Val Leu Asp Lys Arg Arg Gly
            725                 730                 735

Arg Asp Pro Glu Met Gly Gly Lys Pro Arg Arg Lys Asn Pro Gln Glu
            740                 745                 750

Gly Leu Tyr Asn Glu Leu Gln Lys Asp Lys Met Ala Glu Ala Tyr Ser
            755                 760                 765

Glu Ile Gly Met Lys Gly Glu Arg Arg Arg Gly Lys Gly His Asp Gly
        770                 775                 780

Leu Tyr Gln Gly Leu Ser Thr Ala Thr Lys Asp Thr Tyr Asp Ala Leu
785                 790                 795                 800

His Met Gln Ala Leu Pro Pro Arg
                805

<210> SEQ ID NO 126
<211> LENGTH: 808
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Met Ala Leu Pro Val Thr Ala Leu Leu Leu Pro Leu Ala Leu Leu Leu
1               5                   10                  15

His Ala Ala Arg Pro Gly Tyr Pro Tyr Asp Val Pro Asp Tyr Ala Asp
            20                  25                  30

Ile Val Met Thr Gln Thr Pro Ala Ser Val Ser Glu Pro Val Gly Gly
        35                  40                  45

Ser Val Thr Ile Lys Cys Gln Ala Ser Gln Ser Phe Tyr Asn Leu Leu
50                  55                  60

Ala Trp Tyr Gln Gln Lys Pro Gly Gln Pro Pro Lys Leu Leu Ile Tyr
65                  70                  75                  80

Asp Ala Ser Asp Leu Ala Ser Gly Val Pro Ser Arg Phe Lys Gly Ser
            85                  90                  95

Gly Ser Gly Thr Asp Phe Thr Leu Thr Ile Ser Asp Leu Glu Cys Ala
        100                 105                 110

Asp Ala Ala Tyr Tyr Cys Gln Ser Ala Asp Gly Ser Ser Tyr Ala
            115                 120                 125

Phe Gly Gly Gly Thr Glu Val Val Lys Gly Gly Gly Gly Ser
        130                 135                 140

Gly Gly Gly Gly Ser Val His Met Pro Leu Gly Phe Leu Gly Pro Gly
145                 150                 155                 160

Ser Ala Arg Val Val Asn Gly Ser Gly Gly Gly Ser Gln Glu
            165                 170                 175

Gln Leu Glu Glu Ser Gly Gly Leu Val Lys Pro Glu Gly Ser Leu
        180                 185                 190

Thr Leu Thr Cys Thr Ala Ser Gly Val Ser Phe Ser Ser Ser Tyr Trp
```

```
                      195                 200                 205
Ile Tyr Trp Val Arg Gln Ala Pro Gly Lys Gly Leu Glu Trp Ile Ala
210                 215                 220

Cys Ile Tyr Thr Gly Ser Ser Gly Ser Thr Tyr Tyr Ala Ser Trp Ala
225                 230                 235                 240

Lys Gly Arg Phe Thr Val Ser Glu Thr Ser Ser Thr Thr Val Thr Leu
                245                 250                 255

Gln Met Thr Ser Leu Thr Ala Ala Asp Thr Ala Thr Tyr Phe Cys Ala
            260                 265                 270

Arg Ala Ser Ala Trp Thr Tyr Gly Met Asp Leu Trp Gly Pro Gly Thr
        275                 280                 285

Leu Val Thr Val Ser Ser Gly Gly Gly Ser Gly Gly Gly Gly Gly Ser
    290                 295                 300

Gly Gly Gly Gly Ser Val His Met Pro Leu Gly Phe Leu Gly Pro Gly
305                 310                 315                 320

Ser Ala Arg Val Val Asn Gly Gly Ser Gly Gly Gly Ser Gly Gly
                325                 330                 335

Gly Gly Ser Gln Val Gln Leu Gln Glu Ser Gly Pro Gly Leu Val Lys
            340                 345                 350

Pro Ser Glu Thr Leu Ser Leu Thr Cys Thr Val Ser Gly Gly Ser Ile
        355                 360                 365

Ser Tyr Tyr Ser Trp Thr Trp Val Arg Gln Pro Ala Gly Gln Gly Leu
    370                 375                 380

Glu Trp Ile Gly Arg Ile His Ile Ser Gly Val Thr Asn His Asn Pro
385                 390                 395                 400

Ser Leu Lys Ser Arg Val Ser Met Ser Ile Asp Thr Ser Arg Thr Gln
                405                 410                 415

Phe Ser Leu Arg Leu Thr Ser Val Thr Ala Ala Asp Thr Ala Val Tyr
            420                 425                 430

Phe Cys Ala Arg Ser Gly Gly Thr Tyr Ser Ala Phe Asp Ile Trp Gly
        435                 440                 445

Gln Gly Thr Met Val Thr Val Ser Ser Gly Gly Gly Ser Gly Gly
    450                 455                 460

Gly Gly Ser Gly Gly Gly Ser Gly Gly Gly Ser Glu Ile Val
465                 470                 475                 480

Leu Thr Gln Ser Pro Gly Thr Leu Ser Leu Ser Pro Gly Glu Arg Ser
                485                 490                 495

Thr Leu Ser Cys Arg Ala Ser Gln Ser Phe Thr Ser Asn Tyr Leu Ala
            500                 505                 510

Trp Tyr Gln Gln Arg Pro Gly Gln Ala Pro Arg Leu Leu Ile Tyr Gly
        515                 520                 525

Ala Ser Thr Arg Ala Ile Gly Ile Pro Asp Arg Phe Ser Gly Ser Gly
    530                 535                 540

Ser Gly Thr Asp Phe Thr Leu Thr Ile Ser Arg Leu Glu Pro Glu Asp
545                 550                 555                 560

Phe Ala Val Tyr Tyr Cys Gln Gln Tyr Gly Ser Ser Pro Trp Thr Phe
                565                 570                 575

Gly Gln Gly Thr Lys Val Glu Ile Lys Thr Thr Thr Pro Ala Pro Arg
            580                 585                 590

Pro Pro Thr Pro Ala Pro Thr Ile Ala Ser Gln Pro Leu Ser Leu Arg
        595                 600                 605

Pro Glu Ala Cys Arg Pro Ala Ala Gly Gly Ala Val His Thr Arg Gly
    610                 615                 620
```

Leu Asp Phe Ala Cys Asp Ile Tyr Ile Trp Ala Pro Leu Ala Gly Thr
625                 630                 635                 640

Cys Gly Val Leu Leu Leu Ser Leu Val Ile Thr Leu Tyr Cys Lys Arg
            645                 650                 655

Gly Arg Lys Lys Leu Leu Tyr Ile Phe Lys Gln Pro Phe Met Arg Pro
                660                 665                 670

Val Gln Thr Thr Gln Glu Glu Asp Gly Cys Ser Cys Arg Phe Pro Glu
            675                 680                 685

Glu Glu Glu Gly Gly Cys Glu Leu Arg Val Lys Phe Ser Arg Ser Ala
        690                 695                 700

Asp Ala Pro Ala Tyr Gln Gln Gly Gln Asn Gln Leu Tyr Asn Glu Leu
705                 710                 715                 720

Asn Leu Gly Arg Arg Glu Glu Tyr Asp Val Leu Asp Lys Arg Arg Gly
                725                 730                 735

Arg Asp Pro Glu Met Gly Gly Lys Pro Arg Arg Lys Asn Pro Gln Glu
                740                 745                 750

Gly Leu Tyr Asn Glu Leu Gln Lys Asp Lys Met Ala Glu Ala Tyr Ser
            755                 760                 765

Glu Ile Gly Met Lys Gly Glu Arg Arg Arg Gly Lys Gly His Asp Gly
770                 775                 780

Leu Tyr Gln Gly Leu Ser Thr Ala Thr Lys Asp Thr Tyr Asp Ala Leu
785                 790                 795                 800

His Met Gln Ala Leu Pro Pro Arg
                805

<210> SEQ ID NO 127
<211> LENGTH: 808
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Met Ala Leu Pro Val Thr Ala Leu Leu Leu Pro Leu Ala Leu Leu Leu
1               5                   10                  15

His Ala Ala Arg Pro Gly Tyr Pro Tyr Asp Val Pro Asp Tyr Ala Asp
                20                  25                  30

Ile Val Met Thr Gln Thr Pro Ala Ser Val Ser Glu Pro Val Gly Gly
            35                  40                  45

Ser Val Thr Ile Lys Cys Gln Ala Ser Gln Ser Phe Tyr Asn Leu Leu
        50                  55                  60

Ala Trp Tyr Gln Gln Lys Pro Gly Gln Pro Lys Leu Leu Ile Tyr
65                  70                  75                  80

Asp Ala Ser Asp Leu Ala Ser Gly Val Pro Ser Arg Phe Lys Gly Ser
                85                  90                  95

Gly Ser Gly Thr Asp Phe Thr Leu Thr Ile Ser Asp Leu Glu Cys Ala
            100                 105                 110

Asp Ala Ala Ala Tyr Tyr Cys Gln Ser Ala Asp Gly Ser Ser Tyr Ala
        115                 120                 125

Phe Gly Gly Gly Thr Glu Val Val Lys Gly Gly Gly Gly Ser
    130                 135                 140

Gly Gly Gly Gly Ser Gly Gly Gly Ser Pro Met Ala Lys Lys Gly
145                 150                 155                 160

Gly Gly Gly Ser Gly Gly Gly Gly Ser Gly Gly Gly Gly Ser Gln Glu

-continued

```
                165                 170                 175
Gln Leu Glu Glu Ser Gly Gly Leu Val Lys Pro Glu Gly Ser Leu
            180                 185                 190

Thr Leu Thr Cys Thr Ala Ser Gly Val Ser Phe Ser Ser Tyr Trp
            195                 200                 205

Ile Tyr Trp Val Arg Gln Ala Pro Gly Lys Gly Leu Glu Trp Ile Ala
            210                 215                 220

Cys Ile Tyr Thr Gly Ser Gly Ser Thr Tyr Tyr Ala Ser Trp Ala
225                 230                 235                 240

Lys Gly Arg Phe Thr Val Ser Glu Thr Ser Ser Thr Val Thr Leu
                245                 250                 255

Gln Met Thr Ser Leu Thr Ala Ala Asp Thr Ala Thr Tyr Phe Cys Ala
            260                 265                 270

Arg Ala Ser Ala Trp Thr Tyr Gly Met Asp Leu Trp Gly Pro Gly Thr
            275                 280                 285

Leu Val Thr Val Ser Ser Gly Gly Gly Ser Gly Gly Gly Gly Ser
            290                 295                 300

Gly Gly Gly Gly Ser Gly Gly Gly Ser Pro Met Ala Lys Lys Gly
305                 310                 315                 320

Gly Gly Gly Ser Gly Gly Gly Ser Gly Gly Gly Ser Gly Gly
                325                 330                 335

Gly Gly Ser Gln Val Gln Leu Gln Glu Ser Gly Pro Gly Leu Val Lys
            340                 345                 350

Pro Ser Glu Thr Leu Ser Leu Thr Cys Thr Val Ser Gly Gly Ser Ile
            355                 360                 365

Ser Tyr Tyr Ser Trp Thr Trp Val Arg Gln Pro Ala Gly Gln Gly Leu
            370                 375                 380

Glu Trp Ile Gly Arg Ile His Ile Ser Gly Val Thr Asn His Asn Pro
385                 390                 395                 400

Ser Leu Lys Ser Arg Val Ser Met Ser Ile Asp Thr Ser Arg Thr Gln
                405                 410                 415

Phe Ser Leu Arg Leu Thr Ser Val Thr Ala Ala Asp Thr Ala Val Tyr
            420                 425                 430

Phe Cys Ala Arg Ser Gly Gly Thr Tyr Ser Ala Phe Asp Ile Trp Gly
            435                 440                 445

Gln Gly Thr Met Val Thr Val Ser Ser Gly Gly Gly Gly Ser Gly Gly
            450                 455                 460

Gly Gly Ser Gly Gly Gly Gly Ser Gly Gly Gly Gly Ser Glu Ile Val
465                 470                 475                 480

Leu Thr Gln Ser Pro Gly Thr Leu Ser Leu Ser Pro Gly Glu Arg Ser
                485                 490                 495

Thr Leu Ser Cys Arg Ala Ser Gln Ser Phe Thr Ser Asn Tyr Leu Ala
            500                 505                 510

Trp Tyr Gln Gln Arg Pro Gly Gln Ala Pro Arg Leu Leu Ile Tyr Gly
            515                 520                 525

Ala Ser Thr Arg Ala Ile Gly Ile Pro Asp Arg Phe Ser Gly Ser Gly
            530                 535                 540

Ser Gly Thr Asp Phe Thr Leu Thr Ile Ser Arg Leu Glu Pro Glu Asp
545                 550                 555                 560

Phe Ala Val Tyr Tyr Cys Gln Gln Tyr Gly Ser Ser Pro Trp Thr Phe
                565                 570                 575

Gly Gln Gly Thr Lys Val Glu Ile Lys Thr Thr Thr Pro Ala Pro Arg
            580                 585                 590
```

```
Pro Pro Thr Pro Ala Pro Thr Ile Ala Ser Gln Pro Leu Ser Leu Arg
        595                 600                 605

Pro Glu Ala Cys Arg Pro Ala Ala Gly Gly Ala Val His Thr Arg Gly
        610                 615                 620

Leu Asp Phe Ala Cys Asp Ile Tyr Ile Trp Ala Pro Leu Ala Gly Thr
625                 630                 635                 640

Cys Gly Val Leu Leu Leu Ser Leu Val Ile Thr Leu Tyr Cys Lys Arg
                645                 650                 655

Gly Arg Lys Lys Leu Leu Tyr Ile Phe Lys Gln Pro Phe Met Arg Pro
                660                 665                 670

Val Gln Thr Thr Gln Glu Glu Asp Gly Cys Ser Cys Arg Phe Pro Glu
                675                 680                 685

Glu Glu Glu Gly Gly Cys Glu Leu Arg Val Lys Phe Ser Arg Ser Ala
        690                 695                 700

Asp Ala Pro Ala Tyr Gln Gln Gly Gln Asn Gln Leu Tyr Asn Glu Leu
705                 710                 715                 720

Asn Leu Gly Arg Arg Glu Glu Tyr Asp Val Leu Asp Lys Arg Arg Gly
                725                 730                 735

Arg Asp Pro Glu Met Gly Gly Lys Pro Arg Arg Lys Asn Pro Gln Glu
                740                 745                 750

Gly Leu Tyr Asn Glu Leu Gln Lys Asp Lys Met Ala Glu Ala Tyr Ser
        755                 760                 765

Glu Ile Gly Met Lys Gly Glu Arg Arg Arg Gly Lys Gly His Asp Gly
        770                 775                 780

Leu Tyr Gln Gly Leu Ser Thr Ala Thr Lys Asp Thr Tyr Asp Ala Leu
785                 790                 795                 800

His Met Gln Ala Leu Pro Pro Arg
                805

<210> SEQ ID NO 128
<211> LENGTH: 808
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Met Ala Leu Pro Val Thr Ala Leu Leu Leu Pro Leu Ala Leu Leu Leu
1               5                   10                  15

His Ala Ala Arg Pro Gly Tyr Pro Tyr Asp Val Pro Asp Tyr Ala Asp
                20                  25                  30

Ile Val Met Thr Gln Thr Pro Ala Ser Val Ser Glu Pro Val Gly Gly
        35                  40                  45

Ser Val Thr Ile Lys Cys Gln Ala Ser Gln Ser Phe Tyr Asn Leu Leu
    50                  55                  60

Ala Trp Tyr Gln Gln Lys Pro Gly Gln Pro Pro Lys Leu Leu Ile Tyr
65                  70                  75                  80

Asp Ala Ser Asp Leu Ala Ser Gly Val Pro Ser Arg Phe Lys Gly Ser
                85                  90                  95

Gly Ser Gly Thr Asp Phe Thr Leu Thr Ile Ser Asp Leu Glu Cys Ala
                100                 105                 110

Asp Ala Ala Ala Tyr Tyr Cys Gln Ser Ala Asp Gly Ser Ser Tyr Ala
            115                 120                 125

Phe Gly Gly Gly Thr Glu Val Val Val Lys Gly Gly Gly Gly Gly Ser
```

```
            130                 135                 140
Gly Gly Gly Gly Ser Gly Gly Gly Ser Pro Met Ala Lys Gly Ser
145                 150                 155                 160

Gly Gly Gly Ser Gly Gly Gly Ser Gly Gly Gly Ser Gln Glu
            165                 170                 175

Gln Leu Glu Glu Ser Gly Gly Gly Leu Val Lys Pro Gly Ser Leu
            180                 185                 190

Thr Leu Thr Cys Thr Ala Ser Gly Val Ser Phe Ser Ser Tyr Trp
            195                 200                 205

Ile Tyr Trp Val Arg Gln Ala Pro Gly Lys Gly Leu Glu Trp Ile Ala
    210                 215                 220

Cys Ile Tyr Thr Gly Ser Ser Gly Ser Thr Tyr Tyr Ala Ser Trp Ala
225                 230                 235                 240

Lys Gly Arg Phe Thr Val Ser Glu Thr Ser Ser Thr Val Thr Leu
                245                 250                 255

Gln Met Thr Ser Leu Thr Ala Ala Asp Thr Ala Thr Tyr Phe Cys Ala
                260                 265                 270

Arg Ala Ser Ala Trp Thr Tyr Gly Met Asp Leu Trp Gly Pro Gly Thr
            275                 280                 285

Leu Val Thr Val Ser Ser Gly Gly Gly Ser Gly Gly Gly Ser
    290                 295                 300

Gly Gly Gly Gly Ser Gly Gly Gly Ser Pro Met Ala Lys Gly Ser
305                 310                 315                 320

Gly Gly Gly Ser Gly Gly Gly Ser Gly Gly Gly Ser Gly Gly
            325                 330                 335

Gly Gly Ser Gln Val Gln Leu Gln Glu Ser Gly Pro Gly Leu Val Lys
            340                 345                 350

Pro Ser Glu Thr Leu Ser Leu Thr Cys Thr Val Ser Gly Gly Ser Ile
            355                 360                 365

Ser Tyr Tyr Ser Trp Thr Trp Val Arg Gln Pro Ala Gly Gln Gly Leu
    370                 375                 380

Glu Trp Ile Gly Arg Ile His Ile Ser Gly Val Thr Asn His Asn Pro
385                 390                 395                 400

Ser Leu Lys Ser Arg Val Ser Met Ser Ile Asp Thr Ser Arg Thr Gln
                405                 410                 415

Phe Ser Leu Arg Leu Thr Ser Val Thr Ala Ala Asp Thr Ala Val Tyr
            420                 425                 430

Phe Cys Ala Arg Ser Gly Gly Thr Tyr Ser Ala Phe Asp Ile Trp Gly
            435                 440                 445

Gln Gly Thr Met Val Thr Val Ser Ser Gly Gly Gly Ser Gly Gly
            450                 455                 460

Gly Gly Ser Gly Gly Gly Ser Gly Gly Gly Ser Glu Ile Val
465                 470                 475                 480

Leu Thr Gln Ser Pro Gly Thr Leu Ser Leu Ser Pro Gly Glu Arg Ser
                485                 490                 495

Thr Leu Ser Cys Arg Ala Ser Gln Ser Phe Thr Ser Asn Tyr Leu Ala
                500                 505                 510

Trp Tyr Gln Gln Arg Pro Gly Gln Ala Pro Arg Leu Leu Ile Tyr Gly
            515                 520                 525

Ala Ser Thr Arg Ala Ile Gly Ile Pro Asp Arg Phe Ser Gly Ser Gly
            530                 535                 540

Ser Gly Thr Asp Phe Thr Leu Thr Ile Ser Arg Leu Glu Pro Glu Asp
545                 550                 555                 560
```

Phe Ala Val Tyr Tyr Cys Gln Gln Tyr Gly Ser Ser Pro Trp Thr Phe
                565                 570                 575

Gly Gln Gly Thr Lys Val Glu Ile Lys Thr Thr Pro Ala Pro Arg
            580                 585                 590

Pro Pro Thr Pro Ala Pro Thr Ile Ala Ser Gln Pro Leu Ser Leu Arg
            595                 600                 605

Pro Glu Ala Cys Arg Pro Ala Ala Gly Gly Ala Val His Thr Arg Gly
            610                 615                 620

Leu Asp Phe Ala Cys Asp Ile Tyr Ile Trp Ala Pro Leu Ala Gly Thr
625                 630                 635                 640

Cys Gly Val Leu Leu Leu Ser Leu Val Ile Thr Leu Tyr Cys Lys Arg
                645                 650                 655

Gly Arg Lys Lys Leu Leu Tyr Ile Phe Lys Gln Pro Phe Met Arg Pro
            660                 665                 670

Val Gln Thr Thr Gln Glu Glu Asp Gly Cys Ser Cys Arg Phe Pro Glu
            675                 680                 685

Glu Glu Glu Gly Gly Cys Glu Leu Arg Val Lys Phe Ser Arg Ser Ala
            690                 695                 700

Asp Ala Pro Ala Tyr Gln Gln Gly Gln Asn Gln Leu Tyr Asn Glu Leu
705                 710                 715                 720

Asn Leu Gly Arg Arg Glu Glu Tyr Asp Val Leu Asp Lys Arg Arg Gly
                725                 730                 735

Arg Asp Pro Glu Met Gly Gly Lys Pro Arg Arg Lys Asn Pro Gln Glu
            740                 745                 750

Gly Leu Tyr Asn Glu Leu Gln Lys Asp Lys Met Ala Glu Ala Tyr Ser
            755                 760                 765

Glu Ile Gly Met Lys Gly Glu Arg Arg Arg Gly Lys Gly His Asp Gly
            770                 775                 780

Leu Tyr Gln Gly Leu Ser Thr Ala Thr Lys Asp Thr Tyr Asp Ala Leu
785                 790                 795                 800

His Met Gln Ala Leu Pro Pro Arg
                805

<210> SEQ ID NO 129
<211> LENGTH: 771
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Met Ala Leu Pro Val Thr Ala Leu Leu Leu Pro Leu Ala Leu Leu Leu
1               5                   10                  15

His Ala Ala Arg Pro Gly Tyr Pro Tyr Asp Val Pro Asp Tyr Ala Gln
            20                  25                  30

Phe Ser Val Leu Gly Pro Ser Gly Pro Ile Leu Ala Met Val Gly Glu
            35                  40                  45

Asp Ala Asp Leu Pro Cys His Leu Phe Pro Thr Met Ser Ala Glu Thr
50                  55                  60

Met Glu Leu Lys Trp Val Ser Ser Ser Leu Arg Gln Val Val Asn Val
65                  70                  75                  80

Tyr Ala Asp Gly Lys Glu Val Glu Asp Arg Gln Ser Ala Pro Tyr Arg
                85                  90                  95

Gly Arg Thr Ser Ile Leu Arg Asp Gly Ile Thr Ala Gly Lys Ala Ala

-continued

```
               100                 105                 110
Leu Arg Ile His Asn Val Thr Ala Ser Asp Ser Gly Lys Tyr Leu Cys
            115                 120                 125

Tyr Phe Gln Asp Gly Asp Phe Tyr Glu Lys Ala Leu Val Glu Leu Lys
        130                 135                 140

Val Ala Ala Leu Gly Ser Asp Leu His Val Asp Val Lys Gly Tyr Lys
145                 150                 155                 160

Asp Gly Gly Ile His Leu Glu Cys Arg Ser Thr Gly Trp Tyr Pro Gln
                165                 170                 175

Pro Gln Ile Gln Trp Ser Asn Asn Lys Gly Glu Asn Ile Pro Thr Val
            180                 185                 190

Glu Ala Pro Val Val Ala Asp Gly Val Gly Leu Tyr Ala Val Ala Ala
        195                 200                 205

Ser Val Ile Met Arg Gly Ser Ser Gly Glu Gly Val Ser Cys Thr Ile
210                 215                 220

Arg Ser Ser Leu Leu Gly Leu Glu Lys Thr Ala Ser Ile Ser Ile Ala
225                 230                 235                 240

Asp Pro Phe Phe Arg Ser Ala Gln Arg Trp Ile Ala Ala Leu Ala Gly
                245                 250                 255

Thr Gly Gly Gly Gly Ser Gly Gly Gly Gly Ser Leu Val Pro Arg Gly
                260                 265                 270

Ser Lys Pro Ile Pro Asn Pro Leu Leu Gly Leu Asp Ser Thr Leu Val
        275                 280                 285

Pro Arg Gly Ser Gly Gly Gly Ser Gly Gly Gly Gly Ser Gln Val
290                 295                 300

Gln Leu Gln Glu Ser Gly Pro Gly Leu Val Lys Pro Ser Glu Thr Leu
305                 310                 315                 320

Ser Leu Thr Cys Thr Val Ser Gly Gly Ser Ile Ser Tyr Tyr Ser Trp
                325                 330                 335

Thr Trp Val Arg Gln Pro Ala Gly Gln Gly Leu Glu Trp Ile Gly Arg
            340                 345                 350

Ile His Ile Ser Gly Val Thr Asn His Asn Pro Ser Leu Lys Ser Arg
        355                 360                 365

Val Ser Met Ser Ile Asp Thr Ser Arg Thr Gln Phe Ser Leu Arg Leu
370                 375                 380

Thr Ser Val Thr Ala Ala Asp Thr Ala Val Tyr Phe Cys Ala Arg Ser
385                 390                 395                 400

Gly Gly Thr Tyr Ser Ala Phe Asp Ile Trp Gly Gln Gly Thr Met Val
                405                 410                 415

Thr Val Ser Ser Gly Gly Gly Ser Gly Gly Gly Gly Ser Gly Gly
            420                 425                 430

Gly Gly Ser Gly Gly Gly Ser Glu Ile Val Leu Thr Gln Ser Pro
            435                 440                 445

Gly Thr Leu Ser Leu Ser Pro Gly Glu Arg Ser Thr Leu Ser Cys Arg
        450                 455                 460

Ala Ser Gln Ser Phe Thr Ser Asn Tyr Leu Ala Trp Tyr Gln Gln Arg
465                 470                 475                 480

Pro Gly Gln Ala Pro Arg Leu Leu Ile Tyr Gly Ala Ser Thr Arg Ala
                485                 490                 495

Ile Gly Ile Pro Asp Arg Phe Ser Gly Ser Gly Ser Gly Thr Asp Phe
            500                 505                 510

Thr Leu Thr Ile Ser Arg Leu Glu Pro Glu Asp Phe Ala Val Tyr Tyr
        515                 520                 525
```

```
Cys Gln Gln Tyr Gly Ser Ser Pro Trp Thr Phe Gly Gln Gly Thr Lys
            530                 535                 540

Val Glu Ile Lys Thr Thr Pro Ala Pro Arg Pro Pro Thr Pro Ala
545                 550                 555                 560

Pro Thr Ile Ala Ser Gln Pro Leu Ser Leu Arg Pro Glu Ala Cys Arg
                565                 570                 575

Pro Ala Ala Gly Gly Ala Val His Thr Arg Gly Leu Asp Phe Ala Cys
                580                 585                 590

Asp Ile Tyr Ile Trp Ala Pro Leu Ala Gly Thr Cys Gly Val Leu Leu
                595                 600                 605

Leu Ser Leu Val Ile Thr Leu Tyr Cys Lys Arg Gly Arg Lys Lys Leu
            610                 615                 620

Leu Tyr Ile Phe Lys Gln Pro Phe Met Arg Pro Val Gln Thr Thr Gln
625                 630                 635                 640

Glu Glu Asp Gly Cys Ser Cys Arg Phe Pro Glu Glu Glu Gly Gly
                645                 650                 655

Cys Glu Leu Arg Val Lys Phe Ser Arg Ser Ala Asp Ala Pro Ala Tyr
                660                 665                 670

Gln Gln Gly Gln Asn Gln Leu Tyr Asn Glu Leu Asn Leu Gly Arg Arg
            675                 680                 685

Glu Glu Tyr Asp Val Leu Asp Lys Arg Arg Gly Arg Asp Pro Glu Met
            690                 695                 700

Gly Gly Lys Pro Arg Arg Lys Asn Pro Gln Glu Gly Leu Tyr Asn Glu
705                 710                 715                 720

Leu Gln Lys Asp Lys Met Ala Glu Ala Tyr Ser Glu Ile Gly Met Lys
                725                 730                 735

Gly Glu Arg Arg Arg Gly Lys Gly His Asp Gly Leu Tyr Gln Gly Leu
            740                 745                 750

Ser Thr Ala Thr Lys Asp Thr Tyr Asp Ala Leu His Met Gln Ala Leu
                755                 760                 765

Pro Pro Arg
    770

<210> SEQ ID NO 130
<211> LENGTH: 790
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Met Ala Leu Pro Val Thr Ala Leu Leu Leu Pro Leu Ala Leu Leu Leu
1               5                   10                  15

His Ala Ala Arg Pro Gly Tyr Pro Tyr Asp Val Pro Asp Tyr Ala Asp
                20                  25                  30

Ile Leu Leu Thr Gln Ser Pro Ala Thr Leu Ser Leu Ser Pro Gly Glu
                35                  40                  45

Arg Ala Thr Leu Ser Cys Arg Ala Ser Gln Asn Ile Gly Thr Ser Ile
            50                  55                  60

Gln Trp Tyr Gln Gln Lys Pro Gly Gln Ala Pro Arg Leu Leu Ile Arg
65                  70                  75                  80

Ser Ser Ser Glu Ser Ile Ser Gly Ile Pro Ser Arg Phe Ser Gly Ser
                85                  90                  95

Gly Ser Gly Thr Asp Phe Thr Leu Thr Ile Ser Ser Leu Glu Pro Glu
```

```
                    100                 105                 110
Asp Phe Ala Val Tyr Tyr Cys Gln Gln Ser Asn Thr Trp Pro Phe Thr
            115                 120                 125

Phe Gly Gln Gly Thr Lys Leu Glu Ile Lys Gly Gly Gly Gly Ser Gly
    130                 135                 140

Gly Gly Gly Ser Gly Gly Gly Gly Ser Gly Gly Gly Ser Glu Val
145                 150                 155                 160

Gln Leu Val Glu Ser Gly Ala Glu Val Lys Lys Pro Gly Ala Ser Val
                165                 170                 175

Lys Val Ser Cys Lys Ala Ser Gly Tyr Thr Phe Thr Asn Tyr Ile Ile
            180                 185                 190

His Trp Val Lys Gln Glu Pro Gly Gln Gly Leu Glu Trp Ile Gly Tyr
        195                 200                 205

Phe Asn Pro Tyr Asn His Gly Thr Lys Tyr Asn Glu Lys Phe Lys Gly
    210                 215                 220

Arg Ala Thr Leu Thr Ala Asp Lys Ser Ile Ser Thr Ala Tyr Met Glu
225                 230                 235                 240

Leu Ser Ser Leu Arg Ser Glu Asp Thr Ala Val Tyr Tyr Cys Ala Arg
                245                 250                 255

Ser Gly Pro Tyr Ala Trp Phe Asp Thr Trp Gly Gln Gly Thr Thr Val
            260                 265                 270

Thr Val Ser Ser Gly Gly Gly Gly Ser Gly Gly Gly Gly Ser Leu Val
        275                 280                 285

Pro Arg Gly Ser Lys Pro Ile Pro Asn Pro Leu Leu Gly Leu Asp Ser
    290                 295                 300

Thr Leu Val Pro Arg Gly Ser Gly Gly Gly Ser Gly Gly Gly Gly
305                 310                 315                 320

Ser Gln Val Gln Leu Gln Glu Ser Gly Pro Gly Leu Val Lys Pro Ser
                325                 330                 335

Glu Thr Leu Ser Leu Thr Cys Thr Val Ser Gly Gly Ser Ile Ser Tyr
            340                 345                 350

Tyr Ser Trp Thr Trp Val Arg Gln Pro Ala Gly Gln Gly Leu Glu Trp
        355                 360                 365

Ile Gly Arg Ile His Ile Ser Gly Val Thr Asn His Asn Pro Ser Leu
    370                 375                 380

Lys Ser Arg Val Ser Met Ser Ile Asp Thr Ser Arg Thr Gln Phe Ser
385                 390                 395                 400

Leu Arg Leu Thr Ser Val Thr Ala Ala Asp Thr Ala Val Tyr Phe Cys
                405                 410                 415

Ala Arg Ser Gly Gly Thr Tyr Ser Ala Phe Asp Ile Trp Gly Gln Gly
            420                 425                 430

Thr Met Val Thr Val Ser Ser Gly Gly Gly Gly Ser Gly Gly Gly Gly
        435                 440                 445

Ser Gly Gly Gly Ser Gly Gly Gly Gly Ser Glu Ile Val Leu Thr
450                 455                 460

Gln Ser Pro Gly Thr Leu Ser Leu Ser Pro Gly Glu Arg Ser Thr Leu
465                 470                 475                 480

Ser Cys Arg Ala Ser Gln Ser Phe Thr Ser Asn Tyr Leu Ala Trp Tyr
                485                 490                 495

Gln Gln Arg Pro Gly Gln Ala Pro Arg Leu Leu Ile Tyr Gly Ala Ser
            500                 505                 510

Thr Arg Ala Ile Gly Ile Pro Asp Arg Phe Ser Gly Ser Gly Ser Gly
        515                 520                 525
```

```
Thr Asp Phe Thr Leu Thr Ile Ser Arg Leu Glu Pro Glu Asp Phe Ala
            530                 535                 540

Val Tyr Tyr Cys Gln Gln Tyr Gly Ser Ser Pro Trp Thr Phe Gly Gln
545                 550                 555                 560

Gly Thr Lys Val Glu Ile Lys Thr Thr Thr Pro Ala Pro Arg Pro Pro
                565                 570                 575

Thr Pro Ala Pro Thr Ile Ala Ser Gln Pro Leu Ser Leu Arg Pro Glu
            580                 585                 590

Ala Cys Arg Pro Ala Ala Gly Gly Ala Val His Thr Arg Gly Leu Asp
        595                 600                 605

Phe Ala Cys Asp Ile Tyr Ile Trp Ala Pro Leu Ala Gly Thr Cys Gly
        610                 615                 620

Val Leu Leu Leu Ser Leu Val Ile Thr Leu Tyr Cys Lys Arg Gly Arg
625                 630                 635                 640

Lys Lys Leu Leu Tyr Ile Phe Lys Gln Pro Phe Met Arg Pro Val Gln
                645                 650                 655

Thr Thr Gln Glu Glu Asp Gly Cys Ser Cys Arg Phe Pro Glu Glu Glu
            660                 665                 670

Glu Gly Gly Cys Glu Leu Arg Val Lys Phe Ser Arg Ser Ala Asp Ala
        675                 680                 685

Pro Ala Tyr Gln Gln Gly Gln Asn Gln Leu Tyr Asn Glu Leu Asn Leu
        690                 695                 700

Gly Arg Arg Glu Glu Tyr Asp Val Leu Asp Lys Arg Arg Gly Arg Asp
705                 710                 715                 720

Pro Glu Met Gly Gly Lys Pro Arg Arg Lys Asn Pro Gln Glu Gly Leu
                725                 730                 735

Tyr Asn Glu Leu Gln Lys Asp Lys Met Ala Glu Ala Tyr Ser Glu Ile
            740                 745                 750

Gly Met Lys Gly Glu Arg Arg Arg Gly Lys Gly His Asp Gly Leu Tyr
        755                 760                 765

Gln Gly Leu Ser Thr Ala Thr Lys Asp Thr Tyr Asp Ala Leu His Met
        770                 775                 780

Gln Ala Leu Pro Pro Arg
785                 790

<210> SEQ ID NO 131
<211> LENGTH: 790
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Met Ala Leu Pro Val Thr Ala Leu Leu Leu Pro Leu Ala Leu Leu Leu
1               5                   10                  15

His Ala Ala Arg Pro Gly Tyr Pro Tyr Asp Val Pro Asp Tyr Ala Asp
            20                  25                  30

Ile Leu Leu Thr Gln Ser Pro Ala Thr Leu Ser Leu Ser Pro Gly Glu
        35                  40                  45

Arg Ala Thr Leu Ser Cys Arg Ala Ser Gln Asn Ile Gly Thr Ser Ile
    50                  55                  60

Gln Trp Tyr Gln Gln Lys Pro Gly Gln Ala Pro Arg Leu Leu Ile Arg
65                  70                  75                  80

Ser Ser Ser Glu Ser Ile Ser Gly Ile Pro Ser Arg Phe Ser Gly Ser
```

-continued

```
                85                  90                  95
Gly Ser Gly Thr Asp Phe Thr Leu Thr Ile Ser Ser Leu Glu Pro Glu
                   100                 105                 110

Asp Phe Ala Val Tyr Tyr Cys Gln Gln Ser Asn Thr Trp Pro Phe Thr
                   115                 120                 125

Phe Gly Gln Gly Thr Lys Leu Glu Ile Lys Gly Gly Gly Gly Ser Gly
                   130                 135                 140

Gly Gly Gly Ser Gly Gly Gly Ser Gly Gly Gly Ser Glu Val
145                 150                 155                 160

Gln Leu Val Glu Ser Gly Ala Glu Val Lys Lys Pro Gly Ala Ser Val
                   165                 170                 175

Lys Val Ser Cys Lys Ala Ser Gly Tyr Thr Phe Thr Asn Tyr Ile Ile
                   180                 185                 190

His Trp Val Lys Gln Glu Pro Gly Gln Gly Leu Glu Trp Ile Gly Tyr
                   195                 200                 205

Phe Asn Pro Tyr Asn His Gly Thr Lys Tyr Asn Glu Lys Phe Lys Gly
                   210                 215                 220

Arg Ala Thr Leu Thr Ala Asp Lys Ser Ile Ser Thr Ala Tyr Met Glu
225                 230                 235                 240

Leu Ser Ser Leu Arg Ser Glu Asp Thr Ala Val Tyr Tyr Cys Ala Arg
                   245                 250                 255

Ser Gly Pro Tyr Ala Trp Phe Asp Thr Trp Gly Gln Gly Thr Thr Val
                   260                 265                 270

Thr Val Ser Ser Gly Gly Gly Gly Ser Gly Gly Gly Gly Ser Gly Gly
                   275                 280                 285

Gly Ser Gly Ser Lys Pro Ile Pro Asn Pro Leu Leu Gly Leu Asp Ser
290                 295                 300

Thr Gly Gly Gly Ser Gly Ser Gly Gly Gly Ser Gly Gly Gly Gly
305                 310                 315                 320

Ser Gln Val Gln Leu Gln Glu Ser Gly Pro Gly Leu Val Lys Pro Ser
                   325                 330                 335

Glu Thr Leu Ser Leu Thr Cys Thr Val Ser Gly Gly Ser Ile Ser Tyr
                   340                 345                 350

Tyr Ser Trp Thr Trp Val Arg Gln Pro Ala Gly Gln Gly Leu Glu Trp
                   355                 360                 365

Ile Gly Arg Ile His Ile Ser Gly Val Thr Asn His Asn Pro Ser Leu
                   370                 375                 380

Lys Ser Arg Val Ser Met Ser Ile Asp Thr Ser Arg Thr Gln Phe Ser
385                 390                 395                 400

Leu Arg Leu Thr Ser Val Thr Ala Ala Asp Thr Ala Val Tyr Phe Cys
                   405                 410                 415

Ala Arg Ser Gly Gly Thr Tyr Ser Ala Phe Asp Ile Trp Gly Gln Gly
                   420                 425                 430

Thr Met Val Thr Val Ser Ser Gly Gly Gly Gly Ser Gly Gly Gly Gly
                   435                 440                 445

Ser Gly Gly Gly Gly Ser Gly Gly Gly Ser Glu Ile Val Leu Thr
                   450                 455                 460

Gln Ser Pro Gly Thr Leu Ser Leu Ser Pro Gly Glu Arg Ser Thr Leu
465                 470                 475                 480

Ser Cys Arg Ala Ser Gln Ser Phe Thr Ser Asn Tyr Leu Ala Trp Tyr
                   485                 490                 495

Gln Gln Arg Pro Gly Gln Ala Pro Arg Leu Leu Ile Tyr Gly Ala Ser
                   500                 505                 510
```

Thr Arg Ala Ile Gly Ile Pro Asp Arg Phe Ser Gly Ser Gly Ser Gly
            515                 520                 525

Thr Asp Phe Thr Leu Thr Ile Ser Arg Leu Glu Pro Glu Asp Phe Ala
            530                 535                 540

Val Tyr Tyr Cys Gln Gln Tyr Gly Ser Ser Pro Trp Thr Phe Gly Gln
545                 550                 555                 560

Gly Thr Lys Val Glu Ile Lys Thr Thr Thr Pro Ala Pro Arg Pro Pro
            565                 570                 575

Thr Pro Ala Pro Thr Ile Ala Ser Gln Pro Leu Ser Leu Arg Pro Glu
            580                 585                 590

Ala Cys Arg Pro Ala Ala Gly Gly Ala Val His Thr Arg Gly Leu Asp
            595                 600                 605

Phe Ala Cys Asp Ile Tyr Ile Trp Ala Pro Leu Ala Gly Thr Cys Gly
            610                 615                 620

Val Leu Leu Leu Ser Leu Val Ile Thr Leu Tyr Cys Lys Arg Gly Arg
625                 630                 635                 640

Lys Lys Leu Leu Tyr Ile Phe Lys Gln Pro Phe Met Arg Pro Val Gln
                645                 650                 655

Thr Thr Gln Glu Glu Asp Gly Cys Ser Cys Arg Phe Pro Glu Glu Glu
            660                 665                 670

Glu Gly Gly Cys Glu Leu Arg Val Lys Phe Ser Arg Ser Ala Asp Ala
            675                 680                 685

Pro Ala Tyr Gln Gln Gly Gln Asn Gln Leu Tyr Asn Glu Leu Asn Leu
            690                 695                 700

Gly Arg Arg Glu Glu Tyr Asp Val Leu Asp Lys Arg Arg Gly Arg Asp
705                 710                 715                 720

Pro Glu Met Gly Gly Lys Pro Arg Arg Lys Asn Pro Gln Glu Gly Leu
            725                 730                 735

Tyr Asn Glu Leu Gln Lys Asp Lys Met Ala Glu Ala Tyr Ser Glu Ile
            740                 745                 750

Gly Met Lys Gly Glu Arg Arg Arg Gly Lys Gly His Asp Gly Leu Tyr
            755                 760                 765

Gln Gly Leu Ser Thr Ala Thr Lys Asp Thr Tyr Asp Ala Leu His Met
            770                 775                 780

Gln Ala Leu Pro Pro Arg
785                 790

<210> SEQ ID NO 132
<211> LENGTH: 790
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Met Ala Leu Pro Val Thr Ala Leu Leu Leu Pro Leu Ala Leu Leu Leu
1               5                   10                  15

His Ala Ala Arg Pro Gly Tyr Pro Tyr Asp Val Pro Asp Tyr Ala Asp
            20                  25                  30

Ile Leu Leu Thr Gln Ser Pro Ala Thr Leu Ser Leu Ser Pro Gly Glu
            35                  40                  45

Arg Ala Thr Leu Ser Cys Arg Ala Ser Gln Asn Ile Gly Thr Ser Ile
        50                  55                  60

Gln Trp Tyr Gln Gln Lys Pro Gly Gln Ala Pro Arg Leu Leu Ile Arg

```
                65                  70                  75                  80
Ser Ser Ser Glu Ser Ile Ser Gly Ile Pro Ser Arg Phe Ser Gly Ser
                    85                  90                  95

Gly Ser Gly Thr Asp Phe Thr Leu Thr Ile Ser Ser Leu Glu Pro Glu
                100                 105                 110

Asp Phe Ala Val Tyr Tyr Cys Gln Gln Ser Asn Thr Trp Pro Phe Thr
                115                 120                 125

Phe Gly Gln Gly Thr Lys Leu Glu Ile Lys Gly Gly Gly Ser Gly
        130                 135                 140

Gly Gly Gly Ser Gly Gly Gly Ser Gly Gly Gly Ser Glu Val
145                 150                 155                 160

Gln Leu Val Glu Ser Gly Ala Glu Val Lys Lys Pro Gly Ala Ser Val
                165                 170                 175

Lys Val Ser Cys Lys Ala Ser Gly Tyr Thr Phe Thr Asn Tyr Ile Ile
                180                 185                 190

His Trp Val Lys Gln Glu Pro Gly Gln Gly Leu Glu Trp Ile Gly Tyr
                195                 200                 205

Phe Asn Pro Tyr Asn His Gly Thr Lys Tyr Asn Glu Lys Phe Lys Gly
        210                 215                 220

Arg Ala Thr Leu Thr Ala Asp Lys Ser Ile Ser Thr Ala Tyr Met Glu
225                 230                 235                 240

Leu Ser Ser Leu Arg Ser Glu Asp Thr Ala Val Tyr Tyr Cys Ala Arg
                245                 250                 255

Ser Gly Pro Tyr Ala Trp Phe Asp Thr Trp Gly Gln Gly Thr Thr Val
                260                 265                 270

Thr Val Ser Ser Gly Gly Gly Gly Ser Gly Gly Gly Ser Gly Gly
        275                 280                 285

Gly Gly Ser Val His Met Pro Leu Gly Phe Leu Gly Pro Arg Gln Ala
        290                 295                 300

Arg Val Val Asn Gly Gly Ser Gly Gly Gly Gly Ser Gly Gly Gly Gly
305                 310                 315                 320

Ser Gln Val Gln Leu Gln Glu Ser Gly Pro Gly Leu Val Lys Pro Ser
                325                 330                 335

Glu Thr Leu Ser Leu Thr Cys Thr Val Ser Gly Gly Ser Ile Ser Tyr
                340                 345                 350

Tyr Ser Trp Thr Trp Val Arg Gln Pro Ala Gly Gln Gly Leu Glu Trp
        355                 360                 365

Ile Gly Arg Ile His Ile Ser Gly Val Thr Asn His Asn Pro Ser Leu
        370                 375                 380

Lys Ser Arg Val Ser Met Ser Ile Asp Thr Ser Arg Thr Gln Phe Ser
385                 390                 395                 400

Leu Arg Leu Thr Ser Val Thr Ala Ala Asp Thr Ala Val Tyr Phe Cys
                405                 410                 415

Ala Arg Ser Gly Gly Thr Tyr Ser Ala Phe Asp Ile Trp Gly Gln Gly
                420                 425                 430

Thr Met Val Thr Val Ser Ser Gly Gly Gly Ser Gly Gly Gly Gly
        435                 440                 445

Ser Gly Gly Gly Ser Gly Gly Gly Ser Glu Ile Val Leu Thr
        450                 455                 460

Gln Ser Pro Gly Thr Leu Ser Leu Ser Pro Gly Glu Arg Ser Thr Leu
465                 470                 475                 480

Ser Cys Arg Ala Ser Gln Ser Phe Thr Ser Asn Tyr Leu Ala Trp Tyr
                485                 490                 495
```

-continued

```
Gln Gln Arg Pro Gly Gln Ala Pro Arg Leu Leu Ile Tyr Gly Ala Ser
                500                 505                 510

Thr Arg Ala Ile Gly Ile Pro Asp Arg Phe Ser Gly Ser Gly Ser Gly
            515                 520                 525

Thr Asp Phe Thr Leu Thr Ile Ser Arg Leu Glu Pro Glu Asp Phe Ala
            530                 535                 540

Val Tyr Tyr Cys Gln Gln Tyr Gly Ser Ser Pro Trp Thr Phe Gly Gln
545                 550                 555                 560

Gly Thr Lys Val Glu Ile Lys Thr Thr Thr Pro Ala Pro Arg Pro Pro
                565                 570                 575

Thr Pro Ala Pro Thr Ile Ala Ser Gln Pro Leu Ser Leu Arg Pro Glu
            580                 585                 590

Ala Cys Arg Pro Ala Ala Gly Gly Ala Val His Thr Arg Gly Leu Asp
            595                 600                 605

Phe Ala Cys Asp Ile Tyr Ile Trp Ala Pro Leu Ala Gly Thr Cys Gly
            610                 615                 620

Val Leu Leu Leu Ser Leu Val Ile Thr Leu Tyr Cys Lys Arg Gly Arg
625                 630                 635                 640

Lys Lys Leu Leu Tyr Ile Phe Lys Gln Pro Phe Met Arg Pro Val Gln
                645                 650                 655

Thr Thr Gln Glu Glu Asp Gly Cys Ser Cys Arg Phe Pro Glu Glu Glu
            660                 665                 670

Glu Gly Gly Cys Glu Leu Arg Val Lys Phe Ser Arg Ser Ala Asp Ala
            675                 680                 685

Pro Ala Tyr Gln Gln Gly Gln Asn Gln Leu Tyr Asn Glu Leu Asn Leu
            690                 695                 700

Gly Arg Arg Glu Glu Tyr Asp Val Leu Asp Lys Arg Arg Gly Arg Asp
705                 710                 715                 720

Pro Glu Met Gly Gly Lys Pro Arg Arg Lys Asn Pro Gln Glu Gly Leu
                725                 730                 735

Tyr Asn Glu Leu Gln Lys Asp Lys Met Ala Glu Ala Tyr Ser Glu Ile
            740                 745                 750

Gly Met Lys Gly Glu Arg Arg Arg Gly Lys Gly His Asp Gly Leu Tyr
            755                 760                 765

Gln Gly Leu Ser Thr Ala Thr Lys Asp Thr Tyr Asp Ala Leu His Met
            770                 775                 780

Gln Ala Leu Pro Pro Arg
785                 790

<210> SEQ ID NO 133
<211> LENGTH: 790
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Met Ala Leu Pro Val Thr Ala Leu Leu Leu Pro Leu Ala Leu Leu Leu
1               5                   10                  15

His Ala Ala Arg Pro Gly Tyr Pro Tyr Asp Val Pro Asp Tyr Ala Asp
                20                  25                  30

Ile Leu Leu Thr Gln Ser Pro Ala Thr Leu Ser Leu Ser Pro Gly Glu
            35                  40                  45

Arg Ala Thr Leu Ser Cys Arg Ala Ser Gln Asn Ile Gly Thr Ser Ile
```

-continued

```
                50                  55                  60
Gln Trp Tyr Gln Gln Lys Pro Gly Gln Ala Pro Arg Leu Leu Ile Arg
 65                  70                  75                  80

Ser Ser Ser Glu Ser Ile Ser Gly Ile Pro Ser Arg Phe Ser Gly Ser
                     85                  90                  95

Gly Ser Gly Thr Asp Phe Thr Leu Thr Ile Ser Ser Leu Glu Pro Glu
                100                 105                 110

Asp Phe Ala Val Tyr Tyr Cys Gln Gln Ser Asn Thr Trp Pro Phe Thr
                115                 120                 125

Phe Gly Gln Gly Thr Lys Leu Glu Ile Lys Gly Gly Gly Gly Ser Gly
                130                 135                 140

Gly Gly Gly Ser Gly Gly Gly Gly Ser Gly Gly Gly Gly Ser Glu Val
145                 150                 155                 160

Gln Leu Val Glu Ser Gly Ala Glu Val Lys Lys Pro Gly Ala Ser Val
                165                 170                 175

Lys Val Ser Cys Lys Ala Ser Gly Tyr Thr Phe Thr Asn Tyr Ile Ile
                180                 185                 190

His Trp Val Lys Gln Glu Pro Gly Gln Gly Leu Glu Trp Ile Gly Tyr
                195                 200                 205

Phe Asn Pro Tyr Asn His Gly Thr Lys Tyr Asn Glu Lys Phe Lys Gly
210                 215                 220

Arg Ala Thr Leu Thr Ala Asp Lys Ser Ile Ser Thr Ala Tyr Met Glu
225                 230                 235                 240

Leu Ser Ser Leu Arg Ser Glu Asp Thr Ala Val Tyr Tyr Cys Ala Arg
                245                 250                 255

Ser Gly Pro Tyr Ala Trp Phe Asp Thr Trp Gly Gln Gly Thr Thr Val
                260                 265                 270

Thr Val Ser Ser Gly Gly Gly Gly Ser Gly Gly Gly Gly Ser Gly Gly
                275                 280                 285

Gly Gly Ser Gly Gly Gly Gly Ser Pro Met Ala Lys Lys Gly Gly Gly
                290                 295                 300

Gly Ser Gly Gly Gly Gly Ser Gly Gly Gly Ser Gly Gly Gly Gly
305                 310                 315                 320

Ser Gln Val Gln Leu Gln Glu Ser Gly Pro Gly Leu Val Lys Pro Ser
                325                 330                 335

Glu Thr Leu Ser Leu Thr Cys Thr Val Ser Gly Gly Ser Ile Ser Tyr
                340                 345                 350

Tyr Ser Trp Thr Trp Val Arg Gln Pro Ala Gly Gln Gly Leu Glu Trp
                355                 360                 365

Ile Gly Arg Ile His Ile Ser Gly Val Thr Asn His Asn Pro Ser Leu
                370                 375                 380

Lys Ser Arg Val Ser Met Ser Ile Asp Thr Arg Thr Gln Phe Ser
385                 390                 395                 400

Leu Arg Leu Thr Ser Val Thr Ala Ala Asp Thr Ala Val Tyr Phe Cys
                405                 410                 415

Ala Arg Ser Gly Gly Thr Tyr Ser Ala Phe Asp Ile Trp Gly Gln Gly
                420                 425                 430

Thr Met Val Thr Val Ser Ser Gly Gly Gly Gly Ser Gly Gly Gly Gly
                435                 440                 445

Ser Gly Gly Gly Gly Ser Gly Gly Gly Gly Ser Glu Ile Val Leu Thr
450                 455                 460

Gln Ser Pro Gly Thr Leu Ser Leu Ser Pro Gly Glu Arg Ser Thr Leu
465                 470                 475                 480
```

```
Ser Cys Arg Ala Ser Gln Ser Phe Thr Ser Asn Tyr Leu Ala Trp Tyr
            485                 490                 495

Gln Gln Arg Pro Gly Gln Ala Pro Arg Leu Leu Ile Tyr Gly Ala Ser
            500                 505                 510

Thr Arg Ala Ile Gly Ile Pro Asp Arg Phe Ser Gly Ser Gly Ser Gly
            515                 520                 525

Thr Asp Phe Thr Leu Thr Ile Ser Arg Leu Glu Pro Glu Asp Phe Ala
            530                 535                 540

Val Tyr Tyr Cys Gln Gln Tyr Gly Ser Ser Pro Trp Thr Phe Gly Gln
545                 550                 555                 560

Gly Thr Lys Val Glu Ile Lys Thr Thr Thr Pro Ala Pro Arg Pro Pro
                565                 570                 575

Thr Pro Ala Pro Thr Ile Ala Ser Gln Pro Leu Ser Leu Arg Pro Glu
            580                 585                 590

Ala Cys Arg Pro Ala Ala Gly Gly Ala Val His Thr Arg Gly Leu Asp
            595                 600                 605

Phe Ala Cys Asp Ile Tyr Ile Trp Ala Pro Leu Ala Gly Thr Cys Gly
            610                 615                 620

Val Leu Leu Leu Ser Leu Val Ile Thr Leu Tyr Cys Lys Arg Gly Arg
625                 630                 635                 640

Lys Lys Leu Leu Tyr Ile Phe Lys Gln Pro Phe Met Arg Pro Val Gln
                645                 650                 655

Thr Thr Gln Glu Glu Asp Gly Cys Ser Cys Arg Phe Pro Glu Glu Glu
            660                 665                 670

Glu Gly Gly Cys Glu Leu Arg Val Lys Phe Ser Arg Ser Ala Asp Ala
            675                 680                 685

Pro Ala Tyr Gln Gln Gly Gln Asn Gln Leu Tyr Asn Glu Leu Asn Leu
            690                 695                 700

Gly Arg Arg Glu Glu Tyr Asp Val Leu Asp Lys Arg Arg Gly Arg Asp
705                 710                 715                 720

Pro Glu Met Gly Gly Lys Pro Arg Arg Lys Asn Pro Gln Glu Gly Leu
                725                 730                 735

Tyr Asn Glu Leu Gln Lys Asp Lys Met Ala Glu Ala Tyr Ser Glu Ile
            740                 745                 750

Gly Met Lys Gly Glu Arg Arg Arg Gly Lys Gly His Asp Gly Leu Tyr
            755                 760                 765

Gln Gly Leu Ser Thr Ala Thr Lys Asp Thr Tyr Asp Ala Leu His Met
            770                 775                 780

Gln Ala Leu Pro Pro Arg
785                 790

<210> SEQ ID NO 134
<211> LENGTH: 805
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Met Ala Leu Pro Val Thr Ala Leu Leu Leu Pro Leu Ala Leu Leu Leu
1               5                   10                  15

His Ala Ala Arg Pro Gly Tyr Pro Tyr Asp Val Pro Asp Tyr Ala Asp
            20                  25                  30

Ile Leu Leu Thr Gln Ser Pro Ala Thr Leu Ser Leu Ser Pro Gly Glu
```

-continued

```
                35                  40                  45
Arg Ala Thr Leu Ser Cys Arg Ala Ser Gln Asn Ile Gly Thr Ser Ile
 50                  55                  60
Gln Trp Tyr Gln Gln Lys Pro Gly Gln Ala Pro Arg Leu Leu Ile Arg
 65                  70                  75                  80
Ser Ser Ser Glu Ser Ile Ser Gly Ile Pro Ser Arg Phe Ser Gly Ser
                 85                  90                  95
Gly Ser Gly Thr Asp Phe Thr Leu Thr Ile Ser Ser Leu Glu Pro Glu
                100                 105                 110
Asp Phe Ala Val Tyr Tyr Cys Gln Gln Ser Asn Thr Trp Pro Phe Thr
                115                 120                 125
Phe Gly Gln Gly Thr Lys Leu Glu Ile Lys Gly Gly Gly Ser Gly
                130                 135                 140
Gly Gly Gly Ser Val His Met Pro Leu Gly Phe Leu Gly Pro Arg Gln
145                 150                 155                 160
Ala Arg Val Val Asn Gly Gly Ser Gly Gly Gly Ser Glu Val Gln
                165                 170                 175
Leu Val Glu Ser Gly Ala Glu Val Lys Lys Pro Gly Ala Ser Val Lys
                180                 185                 190
Val Ser Cys Lys Ala Ser Gly Tyr Thr Phe Thr Asn Tyr Ile Ile His
                195                 200                 205
Trp Val Lys Gln Glu Pro Gly Gln Gly Leu Glu Trp Ile Gly Tyr Phe
                210                 215                 220
Asn Pro Tyr Asn His Gly Thr Lys Tyr Asn Glu Lys Phe Lys Gly Arg
225                 230                 235                 240
Ala Thr Leu Thr Ala Asp Lys Ser Ile Ser Thr Ala Tyr Met Glu Leu
                245                 250                 255
Ser Ser Leu Arg Ser Glu Asp Thr Ala Val Tyr Tyr Cys Ala Arg Ser
                260                 265                 270
Gly Pro Tyr Ala Trp Phe Asp Thr Trp Gly Gln Gly Thr Thr Val Thr
                275                 280                 285
Val Ser Ser Gly Gly Gly Gly Ser Gly Gly Gly Gly Ser Gly Gly Gly
                290                 295                 300
Gly Ser Val His Met Pro Leu Gly Phe Leu Gly Pro Arg Gln Ala Arg
305                 310                 315                 320
Val Val Asn Gly Gly Ser Gly Gly Gly Ser Gly Gly Gly Gly Ser
                325                 330                 335
Gln Val Gln Leu Gln Glu Ser Gly Pro Gly Leu Val Lys Pro Ser Glu
                340                 345                 350
Thr Leu Ser Leu Thr Cys Thr Val Ser Gly Gly Ser Ile Ser Tyr Tyr
                355                 360                 365
Ser Trp Thr Trp Val Arg Gln Pro Ala Gly Gln Gly Leu Glu Trp Ile
                370                 375                 380
Gly Arg Ile His Ile Ser Gly Val Thr Asn His Asn Pro Ser Leu Lys
385                 390                 395                 400
Ser Arg Val Ser Met Ser Ile Asp Thr Ser Arg Thr Gln Phe Ser Leu
                405                 410                 415
Arg Leu Thr Ser Val Thr Ala Ala Asp Thr Ala Val Tyr Phe Cys Ala
                420                 425                 430
Arg Ser Gly Gly Thr Tyr Ser Ala Phe Asp Ile Trp Gly Gln Gly Thr
                435                 440                 445
Met Val Thr Val Ser Ser Gly Gly Gly Gly Ser Gly Gly Gly Gly Ser
450                 455                 460
```

Gly Gly Gly Gly Ser Gly Gly Gly Ser Glu Ile Val Leu Thr Gln
465                 470                 475                 480

Ser Pro Gly Thr Leu Ser Leu Ser Pro Gly Glu Arg Ser Thr Leu Ser
            485                 490                 495

Cys Arg Ala Ser Gln Ser Phe Thr Ser Asn Tyr Leu Ala Trp Tyr Gln
                500                 505                 510

Gln Arg Pro Gly Gln Ala Pro Arg Leu Leu Ile Tyr Gly Ala Ser Thr
            515                 520                 525

Arg Ala Ile Gly Ile Pro Asp Arg Phe Ser Gly Ser Gly Ser Gly Thr
530                 535                 540

Asp Phe Thr Leu Thr Ile Ser Arg Leu Glu Pro Glu Asp Phe Ala Val
545                 550                 555                 560

Tyr Tyr Cys Gln Gln Tyr Gly Ser Ser Pro Trp Thr Phe Gly Gln Gly
                565                 570                 575

Thr Lys Val Glu Ile Lys Thr Thr Thr Pro Ala Pro Arg Pro Pro Thr
            580                 585                 590

Pro Ala Pro Thr Ile Ala Ser Gln Pro Leu Ser Leu Arg Pro Glu Ala
            595                 600                 605

Cys Arg Pro Ala Ala Gly Gly Ala Val His Thr Arg Gly Leu Asp Phe
610                 615                 620

Ala Cys Asp Ile Tyr Ile Trp Ala Pro Leu Ala Gly Thr Cys Gly Val
625                 630                 635                 640

Leu Leu Leu Ser Leu Val Ile Thr Leu Tyr Cys Lys Arg Gly Arg Lys
                645                 650                 655

Lys Leu Leu Tyr Ile Phe Lys Gln Pro Phe Met Arg Pro Val Gln Thr
            660                 665                 670

Thr Gln Glu Glu Asp Gly Cys Ser Cys Arg Phe Pro Glu Glu Glu Glu
            675                 680                 685

Gly Gly Cys Glu Leu Arg Val Lys Phe Ser Arg Ser Ala Asp Ala Pro
690                 695                 700

Ala Tyr Gln Gln Gly Gln Asn Gln Leu Tyr Asn Glu Leu Asn Leu Gly
705                 710                 715                 720

Arg Arg Glu Glu Tyr Asp Val Leu Asp Lys Arg Arg Gly Arg Asp Pro
                725                 730                 735

Glu Met Gly Gly Lys Pro Arg Arg Lys Asn Pro Gln Glu Gly Leu Tyr
            740                 745                 750

Asn Glu Leu Gln Lys Asp Lys Met Ala Glu Ala Tyr Ser Glu Ile Gly
            755                 760                 765

Met Lys Gly Glu Arg Arg Arg Gly Lys Gly His Asp Gly Leu Tyr Gln
770                 775                 780

Gly Leu Ser Thr Ala Thr Lys Asp Thr Tyr Asp Ala Leu His Met Gln
785                 790                 795                 800

Ala Leu Pro Pro Arg
            805

<210> SEQ ID NO 135
<211> LENGTH: 805
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Met Ala Leu Pro Val Thr Ala Leu Leu Leu Pro Leu Ala Leu Leu Leu

-continued

```
1               5                   10                  15
His Ala Ala Arg Pro Gly Tyr Pro Tyr Asp Val Pro Asp Tyr Ala Asp
                20                  25                  30
Ile Leu Leu Thr Gln Ser Pro Ala Thr Leu Ser Leu Ser Pro Gly Glu
                35                  40                  45
Arg Ala Thr Leu Ser Cys Arg Ala Ser Gln Asn Ile Gly Thr Ser Ile
        50                  55                  60
Gln Trp Tyr Gln Gln Lys Pro Gly Gln Ala Pro Arg Leu Leu Ile Arg
65                  70                  75                  80
Ser Ser Ser Glu Ser Ile Ser Gly Ile Pro Ser Arg Phe Ser Gly Ser
                85                  90                  95
Gly Ser Gly Thr Asp Phe Thr Leu Thr Ile Ser Ser Leu Glu Pro Glu
                100                 105                 110
Asp Phe Ala Val Tyr Tyr Cys Gln Gln Ser Asn Thr Trp Pro Phe Thr
            115                 120                 125
Phe Gly Gln Gly Thr Lys Leu Glu Ile Lys Gly Gly Gly Gly Ser Gly
130                 135                 140
Gly Gly Gly Ser Gly Gly Gly Gly Ser Pro Met Ala Lys Lys Gly Gly
145                 150                 155                 160
Gly Gly Ser Gly Gly Gly Gly Ser Gly Gly Gly Ser Glu Val Gln
                165                 170                 175
Leu Val Glu Ser Gly Ala Glu Val Lys Lys Pro Gly Ala Ser Val Lys
            180                 185                 190
Val Ser Cys Lys Ala Ser Gly Tyr Thr Phe Thr Asn Tyr Ile Ile His
        195                 200                 205
Trp Val Lys Gln Glu Pro Gly Gln Gly Leu Glu Trp Ile Gly Tyr Phe
210                 215                 220
Asn Pro Tyr Asn His Gly Thr Lys Tyr Asn Glu Lys Phe Lys Gly Arg
225                 230                 235                 240
Ala Thr Leu Thr Ala Asp Lys Ser Ile Ser Thr Ala Tyr Met Glu Leu
                245                 250                 255
Ser Ser Leu Arg Ser Glu Asp Thr Ala Val Tyr Tyr Cys Ala Arg Ser
                260                 265                 270
Gly Pro Tyr Ala Trp Phe Asp Thr Trp Gly Gln Gly Thr Thr Val Thr
            275                 280                 285
Val Ser Ser Gly Gly Gly Gly Ser Gly Gly Gly Gly Ser Gly Gly Gly
290                 295                 300
Gly Ser Gly Gly Gly Gly Ser Pro Met Ala Lys Lys Gly Gly Gly Gly
305                 310                 315                 320
Ser Gly Gly Gly Gly Ser Gly Gly Gly Gly Ser Gly Gly Gly Gly Ser
                325                 330                 335
Gln Val Gln Leu Gln Glu Ser Gly Pro Gly Leu Val Lys Pro Ser Glu
            340                 345                 350
Thr Leu Ser Leu Thr Cys Thr Val Ser Gly Gly Ser Ile Ser Tyr Tyr
        355                 360                 365
Ser Trp Thr Trp Val Arg Gln Pro Ala Gly Gln Gly Leu Glu Trp Ile
370                 375                 380
Gly Arg Ile His Ile Ser Gly Val Thr Asn His Asn Pro Ser Leu Lys
385                 390                 395                 400
Ser Arg Val Ser Met Ser Ile Asp Thr Ser Arg Thr Gln Phe Ser Leu
                405                 410                 415
Arg Leu Thr Ser Val Thr Ala Ala Asp Thr Ala Val Tyr Phe Cys Ala
            420                 425                 430
```

```
Arg Ser Gly Gly Thr Tyr Ser Ala Phe Asp Ile Trp Gly Gln Gly Thr
            435                 440                 445

Met Val Thr Val Ser Ser Gly Gly Gly Ser Gly Gly Gly Gly Ser
    450                 455                 460

Gly Gly Gly Gly Ser Gly Gly Gly Ser Glu Ile Val Leu Thr Gln
465                 470                 475                 480

Ser Pro Gly Thr Leu Ser Leu Ser Pro Gly Glu Arg Ser Thr Leu Ser
                485                 490                 495

Cys Arg Ala Ser Gln Ser Phe Thr Ser Asn Tyr Leu Ala Trp Tyr Gln
                500                 505                 510

Gln Arg Pro Gly Gln Ala Pro Arg Leu Leu Ile Tyr Gly Ala Ser Thr
            515                 520                 525

Arg Ala Ile Gly Ile Pro Asp Arg Phe Ser Gly Ser Gly Ser Gly Thr
            530                 535                 540

Asp Phe Thr Leu Thr Ile Ser Arg Leu Glu Pro Glu Asp Phe Ala Val
545                 550                 555                 560

Tyr Tyr Cys Gln Gln Tyr Gly Ser Ser Pro Trp Thr Phe Gly Gln Gly
                565                 570                 575

Thr Lys Val Glu Ile Lys Thr Thr Thr Pro Ala Pro Arg Pro Pro Thr
            580                 585                 590

Pro Ala Pro Thr Ile Ala Ser Gln Pro Leu Ser Leu Arg Pro Glu Ala
            595                 600                 605

Cys Arg Pro Ala Ala Gly Gly Ala Val His Thr Arg Gly Leu Asp Phe
            610                 615                 620

Ala Cys Asp Ile Tyr Ile Trp Ala Pro Leu Ala Gly Thr Cys Gly Val
625                 630                 635                 640

Leu Leu Leu Ser Leu Val Ile Thr Leu Tyr Cys Lys Arg Gly Arg Lys
                645                 650                 655

Lys Leu Leu Tyr Ile Phe Lys Gln Pro Phe Met Arg Pro Val Gln Thr
                660                 665                 670

Thr Gln Glu Glu Asp Gly Cys Ser Cys Arg Phe Pro Glu Glu Glu Glu
            675                 680                 685

Gly Gly Cys Glu Leu Arg Val Lys Phe Ser Arg Ser Ala Asp Ala Pro
            690                 695                 700

Ala Tyr Gln Gln Gly Gln Asn Gln Leu Tyr Asn Glu Leu Asn Leu Gly
705                 710                 715                 720

Arg Arg Glu Glu Tyr Asp Val Leu Asp Lys Arg Arg Gly Arg Asp Pro
                725                 730                 735

Glu Met Gly Gly Lys Pro Arg Arg Lys Asn Pro Gln Glu Gly Leu Tyr
            740                 745                 750

Asn Glu Leu Gln Lys Asp Lys Met Ala Glu Ala Tyr Ser Glu Ile Gly
            755                 760                 765

Met Lys Gly Glu Arg Arg Arg Gly Lys Gly His Asp Gly Leu Tyr Gln
770                 775                 780

Gly Leu Ser Thr Ala Thr Lys Asp Thr Tyr Asp Ala Leu His Met Gln
785                 790                 795                 800

Ala Leu Pro Pro Arg
                805

<210> SEQ ID NO 136
<211> LENGTH: 817
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 136

Met Ala Leu Pro Val Thr Ala Leu Leu Leu Pro Leu Ala Leu Leu Leu
1               5                   10                  15

His Ala Ala Arg Pro Gly Lys Pro Ile Pro Asn Pro Leu Leu Gly Leu
            20                  25                  30

Asp Ser Thr Gly Gly Gly Gly Ser Gly Gly Gly Gly Ser Gly Gly Gly
        35                  40                  45

Gly Ser Gly Gly Gly Gly Ser Asp Ile Val Met Thr Gln Thr Pro Ala
    50                  55                  60

Ser Val Ser Glu Pro Val Gly Gly Ser Val Thr Ile Lys Cys Gln Ala
65              70                  75                  80

Ser Gln Ser Phe Tyr Asn Leu Leu Ala Trp Tyr Gln Gln Lys Pro Gly
                85                  90                  95

Gln Pro Pro Lys Leu Leu Ile Tyr Asp Ala Ser Asp Leu Ala Ser Gly
            100                 105                 110

Val Pro Ser Arg Phe Lys Gly Ser Gly Ser Gly Thr Asp Phe Thr Leu
        115                 120                 125

Thr Ile Ser Asp Leu Glu Cys Ala Asp Ala Ala Tyr Tyr Cys Gln
130                 135                 140

Ser Ala Asp Gly Ser Ser Tyr Ala Phe Gly Gly Gly Thr Glu Val Val
145                 150                 155                 160

Val Lys Gly Gly Gly Gly Ser Gly Gly Gly Gly Ser Gly Gly Gly
            165                 170                 175

Gly Ser Gly Gly Gly Gly Ser Gln Glu Gln Leu Glu Glu Ser Gly Gly
            180                 185                 190

Gly Leu Val Lys Pro Glu Gly Ser Leu Thr Leu Thr Cys Thr Ala Ser
        195                 200                 205

Gly Val Ser Phe Ser Ser Ser Tyr Trp Ile Tyr Trp Val Arg Gln Ala
    210                 215                 220

Pro Gly Lys Gly Leu Glu Trp Ile Ala Cys Ile Tyr Thr Gly Ser Ser
225                 230                 235                 240

Gly Ser Thr Tyr Tyr Ala Ser Trp Ala Lys Gly Arg Phe Thr Val Ser
                245                 250                 255

Glu Thr Ser Ser Thr Thr Val Thr Leu Gln Met Thr Ser Leu Thr Ala
            260                 265                 270

Ala Asp Thr Ala Thr Tyr Phe Cys Ala Arg Ala Ser Ala Trp Thr Tyr
        275                 280                 285

Gly Met Asp Leu Trp Gly Pro Gly Thr Leu Val Thr Val Ser Ser Gly
    290                 295                 300

Gly Gly Gly Ser Gly Gly Gly Gly Ser Gly Gly Gly Gly Ser Leu Ser
305                 310                 315                 320

Gly Arg Ser Asp Asn His Ser Pro Leu Gly Leu Ala Gly Ser Gly Gly
                325                 330                 335

Gly Ser Gly Gly Gly Gly Ser Gly Gly Gly Gly Ser Gln Val Gln Leu
            340                 345                 350

Gln Glu Ser Gly Pro Gly Leu Val Lys Pro Ser Glu Thr Leu Ser Leu
        355                 360                 365

Thr Cys Thr Val Ser Gly Gly Ser Ile Ser Tyr Tyr Ser Trp Thr Trp
    370                 375                 380

Val Arg Gln Pro Ala Gly Gln Gly Leu Glu Trp Ile Gly Arg Ile His
385                 390                 395                 400

```
Ile Ser Gly Val Thr Asn His Asn Pro Ser Leu Lys Ser Arg Val Ser
            405                 410                 415

Met Ser Ile Asp Thr Ser Arg Thr Gln Phe Ser Leu Arg Leu Thr Ser
            420                 425                 430

Val Thr Ala Ala Asp Thr Ala Val Tyr Phe Cys Ala Arg Ser Gly Gly
            435                 440                 445

Thr Tyr Ser Ala Phe Asp Ile Trp Gly Gln Gly Thr Met Val Thr Val
            450                 455                 460

Ser Ser Gly Gly Gly Gly Ser Gly Gly Gly Gly Ser Gly Gly Gly Gly
465                 470                 475                 480

Ser Gly Gly Gly Gly Ser Glu Ile Val Leu Thr Gln Ser Pro Gly Thr
            485                 490                 495

Leu Ser Leu Ser Pro Gly Glu Arg Ser Thr Leu Ser Cys Arg Ala Ser
            500                 505                 510

Gln Ser Phe Thr Ser Asn Tyr Leu Ala Trp Tyr Gln Gln Arg Pro Gly
            515                 520                 525

Gln Ala Pro Arg Leu Leu Ile Tyr Gly Ala Ser Thr Arg Ala Ile Gly
            530                 535                 540

Ile Pro Asp Arg Phe Ser Gly Ser Gly Ser Gly Thr Asp Phe Thr Leu
545                 550                 555                 560

Thr Ile Ser Arg Leu Glu Pro Glu Asp Phe Ala Val Tyr Tyr Cys Gln
            565                 570                 575

Gln Tyr Gly Ser Ser Pro Trp Thr Phe Gly Gln Gly Thr Lys Val Glu
            580                 585                 590

Ile Lys Thr Thr Thr Pro Ala Pro Arg Pro Pro Thr Pro Ala Pro Thr
            595                 600                 605

Ile Ala Ser Gln Pro Leu Ser Leu Arg Pro Glu Ala Cys Arg Pro Ala
610                 615                 620

Ala Gly Gly Ala Val His Thr Arg Gly Leu Asp Phe Ala Cys Asp Ile
625                 630                 635                 640

Tyr Ile Trp Ala Pro Leu Ala Gly Thr Cys Gly Val Leu Leu Leu Ser
            645                 650                 655

Leu Val Ile Thr Leu Tyr Cys Lys Arg Gly Arg Lys Lys Leu Leu Tyr
            660                 665                 670

Ile Phe Lys Gln Pro Phe Met Arg Pro Val Gln Thr Thr Gln Glu Glu
            675                 680                 685

Asp Gly Cys Ser Cys Arg Phe Pro Glu Glu Glu Glu Gly Gly Cys Glu
            690                 695                 700

Leu Arg Val Lys Phe Ser Arg Ser Ala Asp Ala Pro Ala Tyr Gln Gln
705                 710                 715                 720

Gly Gln Asn Gln Leu Tyr Asn Glu Leu Asn Leu Gly Arg Arg Glu Glu
            725                 730                 735

Tyr Asp Val Leu Asp Lys Arg Gly Arg Asp Pro Glu Met Gly Gly
            740                 745                 750

Lys Pro Arg Arg Lys Asn Pro Gln Glu Gly Leu Tyr Asn Glu Leu Gln
            755                 760                 765

Lys Asp Lys Met Ala Glu Ala Tyr Ser Glu Ile Gly Met Lys Gly Glu
            770                 775                 780

Arg Arg Arg Gly Lys Gly His Asp Gly Leu Tyr Gln Gly Leu Ser Thr
785                 790                 795                 800

Ala Thr Lys Asp Thr Tyr Asp Ala Leu His Met Gln Ala Leu Pro Pro
            805                 810                 815
```

Arg

```
<210> SEQ ID NO 137
<211> LENGTH: 817
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137
```

| Met | Ala | Leu | Pro | Val | Thr | Ala | Leu | Leu | Leu | Pro | Leu | Ala | Leu | Leu | Leu |
|---|---|---|---|---|---|---|---|---|---|---|---|---|---|---|---|
| 1 | | | | 5 | | | | | 10 | | | | | 15 | |

| His | Ala | Ala | Arg | Pro | Gly | Lys | Pro | Ile | Pro | Asn | Pro | Leu | Leu | Gly | Leu |
|---|---|---|---|---|---|---|---|---|---|---|---|---|---|---|---|
| | | | 20 | | | | | 25 | | | | | 30 | | |

| Asp | Ser | Thr | Gly | Gly | Gly | Gly | Ser | Gly | Gly | Gly | Gly | Ser | Gly | Gly | Gly |
|---|---|---|---|---|---|---|---|---|---|---|---|---|---|---|---|
| | | 35 | | | | | 40 | | | | | 45 | | | |

| Gly | Ser | Gly | Gly | Gly | Gly | Ser | Asp | Ile | Val | Met | Thr | Gln | Thr | Pro | Ala |
|---|---|---|---|---|---|---|---|---|---|---|---|---|---|---|---|
| 50 | | | | | 55 | | | | | 60 | | | | | |

| Ser | Val | Ser | Glu | Pro | Val | Gly | Gly | Ser | Val | Thr | Ile | Lys | Cys | Gln | Ala |
|---|---|---|---|---|---|---|---|---|---|---|---|---|---|---|---|
| 65 | | | | 70 | | | | | 75 | | | | | 80 | |

| Ser | Gln | Ser | Phe | Tyr | Asn | Leu | Leu | Ala | Trp | Tyr | Gln | Gln | Lys | Pro | Gly |
|---|---|---|---|---|---|---|---|---|---|---|---|---|---|---|---|
| | | | | 85 | | | | | 90 | | | | | 95 | |

| Gln | Pro | Pro | Lys | Leu | Leu | Ile | Tyr | Asp | Ala | Ser | Asp | Leu | Ala | Ser | Gly |
|---|---|---|---|---|---|---|---|---|---|---|---|---|---|---|---|
| | | | 100 | | | | | 105 | | | | | 110 | | |

| Val | Pro | Ser | Arg | Phe | Lys | Gly | Ser | Gly | Ser | Gly | Thr | Asp | Phe | Thr | Leu |
|---|---|---|---|---|---|---|---|---|---|---|---|---|---|---|---|
| | | 115 | | | | | 120 | | | | | 125 | | | |

| Thr | Ile | Ser | Asp | Leu | Glu | Cys | Ala | Asp | Ala | Ala | Tyr | Tyr | Cys | Gln |
|---|---|---|---|---|---|---|---|---|---|---|---|---|---|---|
| 130 | | | | | 135 | | | | | 140 | | | | |

| Ser | Ala | Asp | Gly | Ser | Ser | Tyr | Ala | Phe | Gly | Gly | Gly | Thr | Glu | Val | Val |
|---|---|---|---|---|---|---|---|---|---|---|---|---|---|---|---|
| 145 | | | | | 150 | | | | | 155 | | | | | 160 |

| Val | Lys | Gly | Gly | Gly | Gly | Ser | Gly | Gly | Gly | Gly | Ser | Gly | Gly | Gly |
|---|---|---|---|---|---|---|---|---|---|---|---|---|---|---|
| | | | 165 | | | | | 170 | | | | | 175 | |

| Gly | Ser | Gly | Gly | Gly | Gly | Ser | Gln | Glu | Gln | Leu | Glu | Glu | Ser | Gly | Gly |
|---|---|---|---|---|---|---|---|---|---|---|---|---|---|---|---|
| | | | 180 | | | | | 185 | | | | | 190 | | |

| Gly | Leu | Val | Lys | Pro | Glu | Gly | Ser | Leu | Thr | Leu | Thr | Cys | Thr | Ala | Ser |
|---|---|---|---|---|---|---|---|---|---|---|---|---|---|---|---|
| | | 195 | | | | | 200 | | | | | 205 | | | |

| Gly | Val | Ser | Phe | Ser | Ser | Ser | Tyr | Trp | Ile | Tyr | Trp | Val | Arg | Gln | Ala |
|---|---|---|---|---|---|---|---|---|---|---|---|---|---|---|---|
| | 210 | | | | | 215 | | | | | 220 | | | | |

| Pro | Gly | Lys | Gly | Leu | Glu | Trp | Ile | Ala | Cys | Ile | Tyr | Thr | Gly | Ser | Ser |
|---|---|---|---|---|---|---|---|---|---|---|---|---|---|---|---|
| 225 | | | | | 230 | | | | | 235 | | | | | 240 |

| Gly | Ser | Thr | Tyr | Tyr | Ala | Ser | Trp | Ala | Lys | Gly | Arg | Phe | Thr | Val | Ser |
|---|---|---|---|---|---|---|---|---|---|---|---|---|---|---|---|
| | | | | 245 | | | | | 250 | | | | | 255 | |

| Glu | Thr | Ser | Ser | Thr | Thr | Val | Thr | Leu | Gln | Met | Thr | Ser | Leu | Thr | Ala |
|---|---|---|---|---|---|---|---|---|---|---|---|---|---|---|---|
| | | | 260 | | | | | 265 | | | | | 270 | | |

| Ala | Asp | Thr | Ala | Thr | Tyr | Phe | Cys | Ala | Arg | Ala | Ser | Ala | Trp | Thr | Tyr |
|---|---|---|---|---|---|---|---|---|---|---|---|---|---|---|---|
| | | 275 | | | | | 280 | | | | | 285 | | | |

| Gly | Met | Asp | Leu | Trp | Gly | Pro | Gly | Thr | Leu | Val | Thr | Val | Ser | Ser | Gly |
|---|---|---|---|---|---|---|---|---|---|---|---|---|---|---|---|
| | 290 | | | | | 295 | | | | | 300 | | | | |

| Gly | Gly | Gly | Ser | Gly | Gly | Gly | Ser | Gly | Gly | Gly | Ser | Val | His |
|---|---|---|---|---|---|---|---|---|---|---|---|---|---|
| 305 | | | | | 310 | | | | | 315 | | | 320 |

| Met | Pro | Leu | Gly | Phe | Leu | Gly | Pro | Arg | Gln | Ala | Arg | Val | Val | Asn | Gly |
|---|---|---|---|---|---|---|---|---|---|---|---|---|---|---|---|
| | | | 325 | | | | | 330 | | | | | 335 | | |

| Gly | Ser | Gly | Gly | Gly | Gly | Ser | Gly | Gly | Gly | Gly | Ser | Gln | Val | Gln | Leu |
|---|---|---|---|---|---|---|---|---|---|---|---|---|---|---|---|
| | | 340 | | | | | 345 | | | | | 350 | | | |

-continued

```
Gln Glu Ser Gly Pro Gly Leu Val Lys Pro Ser Glu Thr Leu Ser Leu
            355                 360                 365

Thr Cys Thr Val Ser Gly Gly Ser Ile Ser Tyr Tyr Ser Trp Thr Trp
        370                 375                 380

Val Arg Gln Pro Ala Gly Gln Gly Leu Glu Trp Ile Gly Arg Ile His
385                 390                 395                 400

Ile Ser Gly Val Thr Asn His Asn Pro Ser Leu Lys Ser Arg Val Ser
                405                 410                 415

Met Ser Ile Asp Thr Ser Arg Thr Gln Phe Ser Leu Arg Leu Thr Ser
            420                 425                 430

Val Thr Ala Ala Asp Thr Ala Val Tyr Phe Cys Ala Arg Ser Gly Gly
        435                 440                 445

Thr Tyr Ser Ala Phe Asp Ile Trp Gly Gln Gly Thr Met Val Thr Val
    450                 455                 460

Ser Ser Gly Gly Gly Gly Ser Gly Gly Gly Gly Ser Gly Gly Gly Gly
465                 470                 475                 480

Ser Gly Gly Gly Gly Ser Glu Ile Val Leu Thr Gln Ser Pro Gly Thr
                485                 490                 495

Leu Ser Leu Ser Pro Gly Glu Arg Ser Thr Leu Ser Cys Arg Ala Ser
            500                 505                 510

Gln Ser Phe Thr Ser Asn Tyr Leu Ala Trp Tyr Gln Gln Arg Pro Gly
        515                 520                 525

Gln Ala Pro Arg Leu Leu Ile Tyr Gly Ala Ser Thr Arg Ala Ile Gly
    530                 535                 540

Ile Pro Asp Arg Phe Ser Gly Ser Gly Ser Gly Thr Asp Phe Thr Leu
545                 550                 555                 560

Thr Ile Ser Arg Leu Glu Pro Glu Asp Phe Ala Val Tyr Tyr Cys Gln
                565                 570                 575

Gln Tyr Gly Ser Ser Pro Trp Thr Phe Gly Gln Gly Thr Lys Val Glu
            580                 585                 590

Ile Lys Thr Thr Thr Pro Ala Pro Arg Pro Thr Pro Ala Pro Thr
        595                 600                 605

Ile Ala Ser Gln Pro Leu Ser Leu Arg Pro Glu Ala Cys Arg Pro Ala
    610                 615                 620

Ala Gly Gly Ala Val His Thr Arg Gly Leu Asp Phe Ala Cys Asp Ile
625                 630                 635                 640

Tyr Ile Trp Ala Pro Leu Ala Gly Thr Cys Gly Val Leu Leu Leu Ser
                645                 650                 655

Leu Val Ile Thr Leu Tyr Cys Lys Arg Gly Arg Lys Lys Leu Leu Tyr
            660                 665                 670

Ile Phe Lys Gln Pro Phe Met Arg Pro Val Gln Thr Thr Gln Glu Glu
        675                 680                 685

Asp Gly Cys Ser Cys Arg Phe Pro Glu Glu Glu Glu Gly Gly Cys Glu
    690                 695                 700

Leu Arg Val Lys Phe Ser Arg Ser Ala Asp Ala Pro Ala Tyr Gln Gln
705                 710                 715                 720

Gly Gln Asn Gln Leu Tyr Asn Glu Leu Asn Leu Gly Arg Arg Glu Glu
                725                 730                 735

Tyr Asp Val Leu Asp Lys Arg Arg Gly Arg Asp Pro Glu Met Gly Gly
            740                 745                 750

Lys Pro Arg Arg Lys Asn Pro Gln Glu Gly Leu Tyr Asn Glu Leu Gln
        755                 760                 765

Lys Asp Lys Met Ala Glu Ala Tyr Ser Glu Ile Gly Met Lys Gly Glu
```

```
                    770                 775                 780
Arg Arg Arg Gly Lys Gly His Asp Gly Leu Tyr Gln Gly Leu Ser Thr
785                 790                 795                 800

Ala Thr Lys Asp Thr Tyr Asp Ala Leu His Met Gln Ala Leu Pro Pro
                805                 810                 815

Arg

<210> SEQ ID NO 138
<211> LENGTH: 817
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Met Ala Leu Pro Val Thr Ala Leu Leu Leu Pro Leu Ala Leu Leu Leu
1               5                   10                  15

His Ala Ala Arg Pro Gly Lys Pro Ile Pro Asn Pro Leu Leu Gly Leu
                20                  25                  30

Asp Ser Thr Gly Gly Gly Gly Ser Gly Gly Gly Gly Ser Gly Gly Gly
            35                  40                  45

Gly Ser Gly Gly Gly Gly Ser Asp Ile Val Met Thr Gln Thr Pro Ala
        50                  55                  60

Ser Val Ser Glu Pro Val Gly Gly Ser Val Thr Ile Lys Cys Gln Ala
65                  70                  75                  80

Ser Gln Ser Phe Tyr Asn Leu Leu Ala Trp Tyr Gln Gln Lys Pro Gly
                85                  90                  95

Gln Pro Pro Lys Leu Leu Ile Tyr Asp Ala Ser Asp Leu Ala Ser Gly
                100                 105                 110

Val Pro Ser Arg Phe Lys Gly Ser Gly Ser Gly Thr Asp Phe Thr Leu
            115                 120                 125

Thr Ile Ser Asp Leu Glu Cys Ala Asp Ala Ala Tyr Tyr Cys Gln
        130                 135                 140

Ser Ala Asp Gly Ser Ser Tyr Ala Phe Gly Gly Gly Thr Glu Val Val
145                 150                 155                 160

Val Lys Gly Gly Gly Gly Ser Gly Gly Gly Ser Gly Gly Gly
                165                 170                 175

Gly Ser Gly Gly Gly Gly Ser Gln Glu Gln Leu Glu Ser Gly Gly
                180                 185                 190

Gly Leu Val Lys Pro Glu Gly Ser Leu Thr Leu Thr Cys Thr Ala Ser
            195                 200                 205

Gly Val Ser Phe Ser Ser Tyr Trp Ile Tyr Trp Val Arg Gln Ala
        210                 215                 220

Pro Gly Lys Gly Leu Glu Trp Ile Ala Cys Ile Tyr Thr Gly Ser Ser
225                 230                 235                 240

Gly Ser Thr Tyr Tyr Ala Ser Trp Ala Lys Gly Arg Phe Thr Val Ser
                245                 250                 255

Glu Thr Ser Ser Thr Thr Val Thr Leu Gln Met Thr Ser Leu Thr Ala
                260                 265                 270

Ala Asp Thr Ala Thr Tyr Phe Cys Ala Arg Ala Ser Ala Trp Thr Tyr
            275                 280                 285

Gly Met Asp Leu Trp Gly Pro Gly Thr Leu Val Thr Val Ser Ser Gly
        290                 295                 300

Gly Gly Gly Ser Gly Gly Gly Gly Ser Gly Gly Gly Gly Ser Gly Gly
```

```
             305                 310                 315                 320
Gly Gly Ser Pro Met Ala Lys Lys Gly Gly Gly Ser Gly Gly Gly
                325                 330                 335
Gly Ser Gly Gly Gly Ser Gly Gly Gly Ser Gln Val Gln Leu
            340                 345                 350
Gln Glu Ser Gly Pro Gly Leu Val Lys Pro Ser Glu Thr Leu Ser Leu
            355                 360                 365
Thr Cys Thr Val Ser Gly Gly Ser Ile Ser Tyr Tyr Ser Trp Thr Trp
    370                 375                 380
Val Arg Gln Pro Ala Gly Gln Gly Leu Glu Trp Ile Gly Arg Ile His
385                 390                 395                 400
Ile Ser Gly Val Thr Asn His Asn Pro Ser Leu Lys Ser Arg Val Ser
                405                 410                 415
Met Ser Ile Asp Thr Ser Arg Thr Gln Phe Ser Leu Arg Leu Thr Ser
                420                 425                 430
Val Thr Ala Ala Asp Thr Ala Val Tyr Phe Cys Ala Arg Ser Gly Gly
            435                 440                 445
Thr Tyr Ser Ala Phe Asp Ile Trp Gly Gln Gly Thr Met Val Thr Val
    450                 455                 460
Ser Ser Gly Gly Gly Gly Ser Gly Gly Gly Gly Ser Gly Gly Gly Gly
465                 470                 475                 480
Ser Gly Gly Gly Gly Ser Glu Ile Val Leu Thr Gln Ser Pro Gly Thr
                485                 490                 495
Leu Ser Leu Ser Pro Gly Glu Arg Ser Thr Leu Ser Cys Arg Ala Ser
                500                 505                 510
Gln Ser Phe Thr Ser Asn Tyr Leu Ala Trp Tyr Gln Gln Arg Pro Gly
    515                 520                 525
Gln Ala Pro Arg Leu Leu Ile Tyr Gly Ala Ser Thr Arg Ala Ile Gly
    530                 535                 540
Ile Pro Asp Arg Phe Ser Gly Ser Gly Ser Gly Thr Asp Phe Thr Leu
545                 550                 555                 560
Thr Ile Ser Arg Leu Glu Pro Glu Asp Phe Ala Val Tyr Tyr Cys Gln
                565                 570                 575
Gln Tyr Gly Ser Ser Pro Trp Thr Phe Gly Gln Gly Thr Lys Val Glu
            580                 585                 590
Ile Lys Thr Thr Thr Pro Ala Pro Arg Pro Pro Thr Pro Ala Pro Thr
            595                 600                 605
Ile Ala Ser Gln Pro Leu Ser Leu Arg Pro Glu Ala Cys Arg Pro Ala
    610                 615                 620
Ala Gly Gly Ala Val His Thr Arg Gly Leu Asp Phe Ala Cys Asp Ile
625                 630                 635                 640
Tyr Ile Trp Ala Pro Leu Ala Gly Thr Cys Gly Val Leu Leu Leu Ser
                645                 650                 655
Leu Val Ile Thr Leu Tyr Cys Lys Arg Gly Arg Lys Lys Leu Leu Tyr
                660                 665                 670
Ile Phe Lys Gln Pro Phe Met Arg Pro Val Gln Thr Thr Gln Glu Glu
    675                 680                 685
Asp Gly Cys Ser Cys Arg Phe Pro Glu Glu Glu Gly Gly Cys Glu
    690                 695                 700
Leu Arg Val Lys Phe Ser Arg Ser Ala Asp Ala Pro Ala Tyr Gln Gln
705                 710                 715                 720
Gly Gln Asn Gln Leu Tyr Asn Glu Leu Asn Leu Gly Arg Arg Glu Glu
            725                 730                 735
```

```
Tyr Asp Val Leu Asp Lys Arg Arg Gly Arg Asp Pro Glu Met Gly Gly
            740                 745                 750

Lys Pro Arg Arg Lys Asn Pro Gln Glu Gly Leu Tyr Asn Glu Leu Gln
            755                 760                 765

Lys Asp Lys Met Ala Glu Ala Tyr Ser Glu Ile Gly Met Lys Gly Glu
            770                 775                 780

Arg Arg Arg Gly Lys Gly His Asp Gly Leu Tyr Gln Gly Leu Ser Thr
785                 790                 795                 800

Ala Thr Lys Asp Thr Tyr Asp Ala Leu His Met Gln Ala Leu Pro Pro
            805                 810                 815

Arg

<210> SEQ ID NO 139
<211> LENGTH: 832
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Met Ala Leu Pro Val Thr Ala Leu Leu Leu Pro Leu Ala Leu Leu Leu
1               5                   10                  15

His Ala Ala Arg Pro Gly Lys Pro Ile Pro Asn Pro Leu Leu Gly Leu
            20                  25                  30

Asp Ser Thr Gly Gly Gly Gly Ser Gly Gly Gly Gly Ser Gly Gly Gly
            35                  40                  45

Gly Ser Gly Gly Gly Gly Ser Asp Ile Val Met Thr Gln Thr Pro Ala
50                  55                  60

Ser Val Ser Glu Pro Val Gly Gly Ser Val Thr Ile Lys Cys Gln Ala
65                  70                  75                  80

Ser Gln Ser Phe Tyr Asn Leu Leu Ala Trp Tyr Gln Gln Lys Pro Gly
            85                  90                  95

Gln Pro Pro Lys Leu Leu Ile Tyr Asp Ala Ser Asp Leu Ala Ser Gly
            100                 105                 110

Val Pro Ser Arg Phe Lys Gly Ser Gly Ser Gly Thr Asp Phe Thr Leu
            115                 120                 125

Thr Ile Ser Asp Leu Glu Cys Ala Asp Ala Ala Tyr Tyr Cys Gln
            130                 135                 140

Ser Ala Asp Gly Ser Ser Tyr Ala Phe Gly Gly Gly Thr Glu Val Val
145                 150                 155                 160

Val Lys Gly Gly Gly Gly Ser Gly Gly Gly Ser Gly Gly Gly
            165                 170                 175

Gly Ser Pro Met Ala Lys Lys Gly Gly Gly Ser Gly Gly Gly Gly
            180                 185                 190

Ser Gly Gly Gly Ser Gln Glu Gln Leu Glu Glu Ser Gly Gly Gly
            195                 200                 205

Leu Val Lys Pro Glu Gly Ser Leu Thr Leu Thr Cys Thr Ala Ser Gly
            210                 215                 220

Val Ser Phe Ser Ser Tyr Trp Ile Tyr Trp Val Arg Gln Ala Pro
225                 230                 235                 240

Gly Lys Gly Leu Glu Trp Ile Ala Cys Ile Tyr Thr Gly Ser Ser Gly
            245                 250                 255

Ser Thr Tyr Tyr Ala Ser Trp Ala Lys Gly Arg Phe Thr Val Ser Glu
            260                 265                 270
```

```
Thr Ser Ser Thr Thr Val Thr Leu Gln Met Thr Ser Leu Thr Ala Ala
        275                 280                 285

Asp Thr Ala Thr Tyr Phe Cys Ala Arg Ala Ser Ala Trp Thr Tyr Gly
    290                 295                 300

Met Asp Leu Trp Gly Pro Gly Thr Leu Val Thr Val Ser Ser Gly Gly
305                 310                 315                 320

Gly Gly Ser Gly Gly Gly Gly Ser Gly Gly Gly Ser Gly Gly Gly
            325                 330                 335

Gly Ser Pro Met Ala Lys Lys Gly Gly Gly Ser Gly Gly Gly Gly
                340                 345                 350

Ser Gly Gly Gly Ser Gly Gly Gly Ser Gln Val Gln Leu Gln
        355                 360                 365

Glu Ser Gly Pro Gly Leu Val Lys Pro Ser Glu Thr Leu Ser Leu Thr
    370                 375                 380

Cys Thr Val Ser Gly Gly Ser Ile Ser Tyr Tyr Ser Trp Thr Trp Val
385                 390                 395                 400

Arg Gln Pro Ala Gly Gln Gly Leu Glu Trp Ile Gly Arg Ile His Ile
                405                 410                 415

Ser Gly Val Thr Asn His Asn Pro Ser Leu Lys Ser Arg Val Ser Met
            420                 425                 430

Ser Ile Asp Thr Ser Arg Thr Gln Phe Ser Leu Arg Leu Thr Ser Val
        435                 440                 445

Thr Ala Ala Asp Thr Ala Val Tyr Phe Cys Ala Arg Ser Gly Gly Thr
    450                 455                 460

Tyr Ser Ala Phe Asp Ile Trp Gly Gln Gly Thr Met Val Thr Val Ser
465                 470                 475                 480

Ser Gly Gly Gly Gly Ser Gly Gly Gly Gly Ser Gly Gly Gly Gly Ser
                485                 490                 495

Gly Gly Gly Gly Ser Glu Ile Val Leu Thr Gln Ser Pro Gly Thr Leu
            500                 505                 510

Ser Leu Ser Pro Gly Glu Arg Ser Thr Leu Ser Cys Arg Ala Ser Gln
        515                 520                 525

Ser Phe Thr Ser Asn Tyr Leu Ala Trp Tyr Gln Gln Arg Pro Gly Gln
    530                 535                 540

Ala Pro Arg Leu Leu Ile Tyr Gly Ala Ser Thr Arg Ala Ile Gly Ile
545                 550                 555                 560

Pro Asp Arg Phe Ser Gly Ser Gly Ser Gly Thr Asp Phe Thr Leu Thr
                565                 570                 575

Ile Ser Arg Leu Glu Pro Glu Asp Phe Ala Val Tyr Tyr Cys Gln Gln
            580                 585                 590

Tyr Gly Ser Ser Pro Trp Thr Phe Gly Gln Gly Thr Lys Val Glu Ile
        595                 600                 605

Lys Thr Thr Thr Pro Ala Pro Arg Pro Pro Thr Pro Ala Pro Thr Ile
    610                 615                 620

Ala Ser Gln Pro Leu Ser Leu Arg Pro Glu Ala Cys Arg Pro Ala Ala
625                 630                 635                 640

Gly Gly Ala Val His Thr Arg Gly Leu Asp Phe Ala Cys Asp Ile Tyr
                645                 650                 655

Ile Trp Ala Pro Leu Ala Gly Thr Cys Gly Val Leu Leu Leu Ser Leu
            660                 665                 670

Val Ile Thr Leu Tyr Cys Lys Arg Gly Arg Lys Lys Leu Leu Tyr Ile
        675                 680                 685
```

```
Phe Lys Gln Pro Phe Met Arg Pro Val Gln Thr Thr Gln Glu Glu Asp
        690                 695                 700

Gly Cys Ser Cys Arg Phe Pro Glu Glu Glu Gly Gly Cys Glu Leu
705                 710                 715                 720

Arg Val Lys Phe Ser Arg Ser Ala Asp Ala Pro Ala Tyr Gln Gln Gly
                725                 730                 735

Gln Asn Gln Leu Tyr Asn Glu Leu Asn Leu Gly Arg Arg Glu Glu Tyr
            740                 745                 750

Asp Val Leu Asp Lys Arg Arg Gly Arg Asp Pro Glu Met Gly Gly Lys
        755                 760                 765

Pro Arg Arg Lys Asn Pro Gln Glu Gly Leu Tyr Asn Glu Leu Gln Lys
770                 775                 780

Asp Lys Met Ala Glu Ala Tyr Ser Glu Ile Gly Met Lys Gly Glu Arg
785                 790                 795                 800

Arg Arg Gly Lys Gly His Asp Gly Leu Tyr Gln Gly Leu Ser Thr Ala
                805                 810                 815

Thr Lys Asp Thr Tyr Asp Ala Leu His Met Gln Ala Leu Pro Pro Arg
            820                 825                 830

<210> SEQ ID NO 140
<211> LENGTH: 817
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Met Ala Leu Pro Val Thr Ala Leu Leu Leu Pro Leu Ala Leu Leu Leu
1               5                   10                  15

His Ala Ala Arg Pro Gly Lys Pro Ile Pro Asn Pro Leu Leu Gly Leu
            20                  25                  30

Asp Ser Thr Gly Gly Gly Gly Ser Gly Gly Gly Gly Ser Gly Gly Gly
        35                  40                  45

Gly Ser Gly Gly Gly Gly Ser Asp Ile Val Met Thr Gln Thr Pro Ala
50                  55                  60

Ser Val Ser Glu Pro Val Gly Gly Ser Val Thr Ile Lys Cys Gln Ala
65                  70                  75                  80

Ser Gln Ser Phe Tyr Asn Leu Leu Ala Trp Tyr Gln Gln Lys Pro Gly
                85                  90                  95

Gln Pro Pro Lys Leu Leu Ile Tyr Asp Ala Ser Asp Leu Ala Ser Gly
            100                 105                 110

Val Pro Ser Arg Phe Lys Gly Ser Gly Ser Gly Thr Asp Phe Thr Leu
        115                 120                 125

Thr Ile Ser Asp Leu Glu Cys Ala Asp Ala Ala Tyr Tyr Cys Gln
    130                 135                 140

Ser Ala Asp Gly Ser Ser Tyr Ala Phe Gly Gly Gly Thr Glu Val Val
145                 150                 155                 160

Val Lys Gly Gly Gly Gly Ser Gly Gly Gly Ser Gly Gly Gly
                165                 170                 175

Gly Ser Gly Gly Gly Ser Gln Glu Gln Leu Glu Glu Ser Gly Gly
            180                 185                 190

Gly Leu Val Lys Pro Glu Gly Ser Leu Thr Leu Thr Cys Thr Ala Ser
        195                 200                 205

Gly Val Ser Phe Ser Ser Ser Tyr Trp Ile Tyr Trp Val Arg Gln Ala
    210                 215                 220
```

Pro Gly Lys Gly Leu Glu Trp Ile Ala Cys Ile Tyr Thr Gly Ser Ser
225                 230                 235                 240

Gly Ser Thr Tyr Tyr Ala Ser Trp Ala Lys Gly Arg Phe Thr Val Ser
            245                 250                 255

Glu Thr Ser Ser Thr Thr Val Thr Leu Gln Met Thr Ser Leu Thr Ala
        260                 265                 270

Ala Asp Thr Ala Thr Tyr Phe Cys Ala Arg Ala Ser Ala Trp Thr Tyr
        275                 280                 285

Gly Met Asp Leu Trp Gly Pro Gly Thr Leu Val Thr Val Ser Ser Gly
        290                 295                 300

Gly Gly Gly Ser Gly Gly Gly Ser Gly Gly Ser Gly Ser Gly
305                 310                 315                 320

Gly Gly Gly Ser Gly Gly Gly Ser Gly Gly Gly Ser Gly Gly Gly Ser
                325                 330                 335

Gly Ser Gly Gly Gly Gly Ser Gly Gly Gly Gly Ser Gln Val Gln Leu
            340                 345                 350

Gln Glu Ser Gly Pro Gly Leu Val Lys Pro Ser Glu Thr Leu Ser Leu
        355                 360                 365

Thr Cys Thr Val Ser Gly Gly Ser Ile Ser Tyr Tyr Ser Trp Thr Trp
        370                 375                 380

Val Arg Gln Pro Ala Gly Gln Gly Leu Glu Trp Ile Gly Arg Ile His
385                 390                 395                 400

Ile Ser Gly Val Thr Asn His Asn Pro Ser Leu Lys Ser Arg Val Ser
                405                 410                 415

Met Ser Ile Asp Thr Ser Arg Thr Gln Phe Ser Leu Arg Leu Thr Ser
            420                 425                 430

Val Thr Ala Ala Asp Thr Ala Val Tyr Phe Cys Ala Arg Ser Gly Gly
        435                 440                 445

Thr Tyr Ser Ala Phe Asp Ile Trp Gly Gln Gly Thr Met Val Thr Val
        450                 455                 460

Ser Ser Gly Gly Gly Gly Ser Gly Gly Gly Gly Ser Gly Gly Gly Gly
465                 470                 475                 480

Ser Gly Gly Gly Gly Ser Glu Ile Val Leu Thr Gln Ser Pro Gly Thr
                485                 490                 495

Leu Ser Leu Ser Pro Gly Glu Arg Ser Thr Leu Ser Cys Arg Ala Ser
            500                 505                 510

Gln Ser Phe Thr Ser Asn Tyr Leu Ala Trp Tyr Gln Gln Arg Pro Gly
        515                 520                 525

Gln Ala Pro Arg Leu Leu Ile Tyr Gly Ala Ser Thr Arg Ala Ile Gly
        530                 535                 540

Ile Pro Asp Arg Phe Ser Gly Ser Gly Ser Gly Thr Asp Phe Thr Leu
545                 550                 555                 560

Thr Ile Ser Arg Leu Glu Pro Glu Asp Phe Ala Val Tyr Tyr Cys Gln
                565                 570                 575

Gln Tyr Gly Ser Ser Pro Trp Thr Phe Gly Gln Gly Thr Lys Val Glu
            580                 585                 590

Ile Lys Thr Thr Thr Pro Ala Pro Arg Pro Pro Thr Pro Ala Pro Thr
        595                 600                 605

Ile Ala Ser Gln Pro Leu Ser Leu Arg Pro Glu Ala Cys Arg Pro Ala
        610                 615                 620

Ala Gly Gly Ala Val His Thr Arg Gly Leu Asp Phe Ala Cys Asp Ile
625                 630                 635                 640

Tyr Ile Trp Ala Pro Leu Ala Gly Thr Cys Gly Val Leu Leu Leu Ser
                645                 650                 655

Leu Val Ile Thr Leu Tyr Cys Lys Arg Gly Arg Lys Lys Leu Leu Tyr
            660                 665                 670

Ile Phe Lys Gln Pro Phe Met Arg Pro Val Gln Thr Thr Gln Glu Glu
            675                 680                 685

Asp Gly Cys Ser Cys Arg Phe Pro Glu Glu Glu Glu Gly Gly Cys Glu
            690                 695                 700

Leu Arg Val Lys Phe Ser Arg Ser Ala Asp Ala Pro Ala Tyr Gln Gln
705                 710                 715                 720

Gly Gln Asn Gln Leu Tyr Asn Glu Leu Asn Leu Gly Arg Arg Glu Glu
                725                 730                 735

Tyr Asp Val Leu Asp Lys Arg Arg Gly Arg Asp Pro Glu Met Gly Gly
            740                 745                 750

Lys Pro Arg Arg Lys Asn Pro Gln Glu Gly Leu Tyr Asn Glu Leu Gln
            755                 760                 765

Lys Asp Lys Met Ala Glu Ala Tyr Ser Glu Ile Gly Met Lys Gly Glu
            770                 775                 780

Arg Arg Arg Gly Lys Gly His Asp Gly Leu Tyr Gln Gly Leu Ser Thr
785                 790                 795                 800

Ala Thr Lys Asp Thr Tyr Asp Ala Leu His Met Gln Ala Leu Pro Pro
                805                 810                 815

Arg

<210> SEQ ID NO 141
<211> LENGTH: 822
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Met Ala Leu Pro Val Thr Ala Leu Leu Leu Pro Leu Ala Leu Leu Leu
1               5                   10                  15

His Ala Ala Arg Pro Gly Tyr Pro Tyr Asp Val Pro Asp Tyr Ala Asp
            20                  25                  30

Ile Val Met Thr Gln Thr Pro Ala Ser Val Ser Glu Pro Val Gly Gly
            35                  40                  45

Ser Val Thr Ile Lys Cys Gln Ala Ser Gln Ser Phe Tyr Asn Leu Leu
        50                  55                  60

Ala Trp Tyr Gln Gln Lys Pro Gly Gln Pro Pro Lys Leu Leu Ile Tyr
65                  70                  75                  80

Asp Ala Ser Asp Leu Ala Ser Gly Val Pro Ser Arg Phe Lys Gly Ser
                85                  90                  95

Gly Ser Gly Thr Asp Phe Thr Leu Thr Ile Ser Asp Leu Glu Cys Ala
            100                 105                 110

Asp Ala Ala Thr Tyr Tyr Cys Gln Ser Ala Asp Gly Ser Ser Tyr Ala
            115                 120                 125

Phe Gly Gly Gly Thr Glu Val Val Val Lys Gly Gly Gly Gly Ser
            130                 135                 140

Gly Gly Gly Gly Ser Leu Ser Gly Arg Ser Asp Asn His Ser Pro Leu
145                 150                 155                 160

Gly Leu Ala Gly Ser Gly Gly Gly Ser Gly Gly Gly Gly Ser Gln
                165                 170                 175

```
Glu Gln Leu Glu Glu Ser Gly Gly Gly Leu Val Lys Pro Glu Gly Ser
            180                 185                 190

Leu Thr Leu Thr Cys Thr Ala Ser Gly Val Ser Phe Ser Ser Ser Tyr
            195                 200                 205

Trp Ile Tyr Trp Val Arg Gln Ala Pro Gly Lys Gly Leu Glu Trp Ile
            210                 215                 220

Ala Cys Ile Tyr Thr Gly Ser Ser Gly Ser Thr Tyr Tyr Ala Ser Trp
225                 230                 235                 240

Ala Lys Gly Arg Phe Thr Val Ser Glu Thr Ser Ser Thr Thr Val Thr
            245                 250                 255

Leu Gln Met Thr Ser Leu Thr Ala Ala Asp Thr Ala Thr Tyr Phe Cys
            260                 265                 270

Ala Arg Ala Ser Ala Trp Thr Tyr Gly Met Asp Leu Trp Gly Pro Gly
            275                 280                 285

Thr Leu Val Thr Val Ser Ser Gly Gly Gly Ser Gly Gly Gly Gly
            290                 295                 300

Ser Lys Pro Ile Pro Asn Pro Leu Leu Gly Leu Asp Ser Thr Gly Gly
305                 310                 315                 320

Gly Ser Gly Leu Ser Gly Arg Ser Asp Asn His Ser Pro Leu Gly Leu
            325                 330                 335

Ala Gly Ser Gly Gly Gly Ser Gly Gly Gly Ser Gly Gly Gly Gly
            340                 345                 350

Ser Gln Val Gln Leu Gln Glu Ser Gly Pro Gly Leu Val Lys Pro Ser
            355                 360                 365

Glu Thr Leu Ser Leu Thr Cys Thr Val Ser Gly Gly Ser Ile Ser Tyr
            370                 375                 380

Tyr Ser Trp Thr Trp Val Arg Gln Pro Ala Gly Gln Gly Leu Glu Trp
385                 390                 395                 400

Ile Gly Arg Ile His Ile Ser Gly Val Thr Asn His Asn Pro Ser Leu
            405                 410                 415

Lys Ser Arg Val Ser Met Ser Ile Asp Thr Ser Arg Thr Gln Phe Ser
            420                 425                 430

Leu Arg Leu Thr Ser Val Thr Ala Ala Asp Thr Ala Val Tyr Phe Cys
            435                 440                 445

Ala Arg Ser Gly Gly Thr Tyr Ser Ala Phe Asp Ile Trp Gly Gln Gly
450                 455                 460

Thr Met Val Thr Val Ser Ser Gly Gly Gly Ser Gly Gly Gly Gly
465                 470                 475                 480

Ser Gly Gly Gly Ser Gly Gly Gly Gly Ser Glu Ile Val Leu Thr
            485                 490                 495

Gln Ser Pro Gly Thr Leu Ser Leu Ser Pro Gly Glu Arg Ser Thr Leu
            500                 505                 510

Ser Cys Arg Ala Ser Gln Ser Phe Thr Ser Asn Tyr Leu Ala Trp Tyr
            515                 520                 525

Gln Gln Arg Pro Gly Gln Ala Pro Arg Leu Leu Ile Tyr Gly Ala Ser
            530                 535                 540

Thr Arg Ala Ile Gly Ile Pro Asp Arg Phe Ser Gly Ser Gly Ser Gly
545                 550                 555                 560

Thr Asp Phe Thr Leu Thr Ile Ser Arg Leu Glu Pro Glu Asp Phe Ala
            565                 570                 575

Val Tyr Tyr Cys Gln Gln Tyr Gly Ser Ser Pro Trp Thr Phe Gly Gln
            580                 585                 590

Gly Thr Lys Val Glu Ile Lys Thr Thr Thr Pro Ala Pro Arg Pro Pro
```

595                 600                 605
Thr Pro Ala Pro Thr Ile Ala Ser Gln Pro Leu Ser Leu Arg Pro Glu
            610                 615                 620

Ala Cys Arg Pro Ala Ala Gly Gly Ala Val His Thr Arg Gly Leu Asp
625                 630                 635                 640

Phe Ala Cys Asp Ile Tyr Ile Trp Ala Pro Leu Ala Gly Thr Cys Gly
            645                 650                 655

Val Leu Leu Leu Ser Leu Val Ile Thr Leu Tyr Cys Lys Arg Gly Arg
            660                 665                 670

Lys Lys Leu Leu Tyr Ile Phe Lys Gln Pro Phe Met Arg Pro Val Gln
            675                 680                 685

Thr Thr Gln Glu Glu Asp Gly Cys Ser Cys Arg Phe Pro Glu Glu Glu
            690                 695                 700

Glu Gly Gly Cys Glu Leu Arg Val Lys Phe Ser Arg Ser Ala Asp Ala
705                 710                 715                 720

Pro Ala Tyr Gln Gln Gly Gln Asn Gln Leu Tyr Asn Glu Leu Asn Leu
            725                 730                 735

Gly Arg Arg Glu Glu Tyr Asp Val Leu Asp Lys Arg Arg Gly Arg Asp
            740                 745                 750

Pro Glu Met Gly Gly Lys Pro Arg Arg Lys Asn Pro Gln Glu Gly Leu
            755                 760                 765

Tyr Asn Glu Leu Gln Lys Asp Lys Met Ala Glu Ala Tyr Ser Glu Ile
            770                 775                 780

Gly Met Lys Gly Glu Arg Arg Arg Gly Lys Gly His Asp Gly Leu Tyr
785                 790                 795                 800

Gln Gly Leu Ser Thr Ala Thr Lys Asp Thr Tyr Asp Ala Leu His Met
            805                 810                 815

Gln Ala Leu Pro Pro Arg
            820

<210> SEQ ID NO 142
<211> LENGTH: 821
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Met Ala Leu Pro Val Thr Ala Leu Leu Leu Pro Leu Ala Leu Leu Leu
1               5                   10                  15

His Ala Ala Arg Pro Gly Tyr Pro Tyr Asp Val Pro Asp Tyr Ala Asp
            20                  25                  30

Ile Val Met Thr Gln Thr Pro Ala Ser Val Ser Glu Pro Val Gly Gly
            35                  40                  45

Ser Val Thr Ile Lys Cys Gln Ala Ser Gln Ser Phe Tyr Asn Leu Leu
        50                  55                  60

Ala Trp Tyr Gln Gln Lys Pro Gly Gln Pro Pro Lys Leu Leu Ile Tyr
65              70                  75                  80

Asp Ala Ser Asp Leu Ala Ser Gly Val Pro Ser Arg Phe Lys Gly Ser
            85                  90                  95

Gly Ser Gly Thr Asp Phe Thr Leu Thr Ile Ser Asp Leu Glu Cys Ala
            100                 105                 110

Asp Ala Ala Ala Tyr Tyr Cys Gln Ser Ala Asp Gly Ser Ser Tyr Ala
        115                 120                 125

```
Phe Gly Gly Gly Thr Glu Val Val Lys Gly Gly Gly Ser
    130                 135                 140

Gly Gly Gly Gly Ser Val His Met Pro Leu Gly Phe Leu Gly Pro Arg
145                 150                 155                 160

Gln Ala Arg Val Val Asn Gly Gly Ser Gly Gly Gly Ser Gln Glu
                165                 170                 175

Gln Leu Glu Glu Ser Gly Gly Gly Leu Val Lys Pro Glu Gly Ser Leu
            180                 185                 190

Thr Leu Thr Cys Thr Ala Ser Gly Val Ser Phe Ser Ser Ser Tyr Trp
            195                 200                 205

Ile Tyr Trp Val Arg Gln Ala Pro Gly Lys Gly Leu Glu Trp Ile Ala
    210                 215                 220

Cys Ile Tyr Thr Gly Ser Ser Gly Ser Thr Tyr Tyr Ala Ser Trp Ala
225                 230                 235                 240

Lys Gly Arg Phe Thr Val Ser Glu Thr Ser Ser Thr Thr Val Thr Leu
                245                 250                 255

Gln Met Thr Ser Leu Thr Ala Ala Asp Thr Ala Thr Tyr Phe Cys Ala
            260                 265                 270

Arg Ala Ser Ala Trp Thr Tyr Gly Met Asp Leu Trp Gly Pro Gly Thr
    275                 280                 285

Leu Val Thr Val Ser Ser Gly Gly Gly Ser Gly Gly Gly Gly Ser
290                 295                 300

Lys Pro Ile Pro Asn Pro Leu Leu Gly Leu Asp Ser Thr Gly Gly Gly
305                 310                 315                 320

Gly Ser Val His Met Pro Leu Gly Phe Leu Gly Pro Arg Gln Ala Arg
            325                 330                 335

Val Val Asn Gly Gly Ser Gly Gly Gly Ser Gly Gly Gly Gly Ser
            340                 345                 350

Gln Val Gln Leu Gln Glu Ser Gly Pro Gly Leu Val Lys Pro Ser Glu
            355                 360                 365

Thr Leu Ser Leu Thr Cys Thr Val Ser Gly Gly Ser Ile Ser Tyr Tyr
            370                 375                 380

Ser Trp Thr Trp Val Arg Gln Pro Ala Gly Gln Gly Leu Glu Trp Ile
385                 390                 395                 400

Gly Arg Ile His Ile Ser Gly Val Thr Asn His Asn Pro Ser Leu Lys
                405                 410                 415

Ser Arg Val Ser Met Ser Ile Asp Thr Ser Arg Thr Gln Phe Ser Leu
                420                 425                 430

Arg Leu Thr Ser Val Thr Ala Ala Asp Thr Ala Val Tyr Phe Cys Ala
            435                 440                 445

Arg Ser Gly Gly Thr Tyr Ser Ala Phe Asp Ile Trp Gly Gln Gly Thr
    450                 455                 460

Met Val Thr Val Ser Ser Gly Gly Gly Gly Ser Gly Gly Gly Gly Ser
465                 470                 475                 480

Gly Gly Gly Gly Ser Gly Gly Gly Gly Ser Glu Ile Val Leu Thr Gln
                485                 490                 495

Ser Pro Gly Thr Leu Ser Leu Ser Pro Gly Glu Arg Ser Thr Leu Ser
            500                 505                 510

Cys Arg Ala Ser Gln Ser Phe Thr Ser Asn Tyr Leu Ala Trp Tyr Gln
            515                 520                 525

Gln Arg Pro Gly Gln Ala Pro Arg Leu Leu Ile Tyr Gly Ala Ser Thr
            530                 535                 540

Arg Ala Ile Gly Ile Pro Asp Arg Phe Ser Gly Ser Gly Ser Gly Thr
```

```
                545                 550                 555                 560
Asp Phe Thr Leu Thr Ile Ser Arg Leu Glu Pro Glu Asp Phe Ala Val
                565                 570                 575

Tyr Tyr Cys Gln Gln Tyr Gly Ser Ser Pro Trp Thr Phe Gly Gln Gly
                580                 585                 590

Thr Lys Val Glu Ile Lys Thr Thr Pro Ala Pro Arg Pro Pro Thr
                595                 600                 605

Pro Ala Pro Thr Ile Ala Ser Gln Pro Leu Ser Leu Arg Pro Glu Ala
                610                 615                 620

Cys Arg Pro Ala Ala Gly Gly Ala Val His Thr Arg Gly Leu Asp Phe
625                 630                 635                 640

Ala Cys Asp Ile Tyr Ile Trp Ala Pro Leu Ala Gly Thr Cys Gly Val
                645                 650                 655

Leu Leu Leu Ser Leu Val Ile Thr Leu Tyr Cys Lys Arg Gly Arg Lys
                660                 665                 670

Lys Leu Leu Tyr Ile Phe Lys Gln Pro Phe Met Arg Pro Val Gln Thr
                675                 680                 685

Thr Gln Glu Glu Asp Gly Cys Ser Cys Arg Phe Pro Glu Glu Glu Glu
                690                 695                 700

Gly Gly Cys Glu Leu Arg Val Lys Phe Ser Arg Ser Ala Asp Ala Pro
705                 710                 715                 720

Ala Tyr Gln Gln Gly Gln Asn Gln Leu Tyr Asn Glu Leu Asn Leu Gly
                725                 730                 735

Arg Arg Glu Glu Tyr Asp Val Leu Asp Lys Arg Arg Gly Arg Asp Pro
                740                 745                 750

Glu Met Gly Gly Lys Pro Arg Arg Lys Asn Pro Gln Glu Gly Leu Tyr
                755                 760                 765

Asn Glu Leu Gln Lys Asp Lys Met Ala Glu Ala Tyr Ser Glu Ile Gly
                770                 775                 780

Met Lys Gly Glu Arg Arg Arg Gly Lys Gly His Asp Gly Leu Tyr Gln
785                 790                 795                 800

Gly Leu Ser Thr Ala Thr Lys Asp Thr Tyr Asp Ala Leu His Met Gln
                805                 810                 815

Ala Leu Pro Pro Arg
                820

<210> SEQ ID NO 143
<211> LENGTH: 821
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Met Ala Leu Pro Val Thr Ala Leu Leu Leu Pro Leu Ala Leu Leu Leu
1               5                   10                  15

His Ala Ala Arg Pro Gly Tyr Pro Tyr Asp Val Pro Asp Tyr Ala Asp
                20                  25                  30

Ile Val Met Thr Gln Thr Pro Ala Ser Val Ser Glu Pro Val Gly Gly
                35                  40                  45

Ser Val Thr Ile Lys Cys Gln Ala Ser Gln Ser Phe Tyr Asn Leu Leu
                50                  55                  60

Ala Trp Tyr Gln Gln Lys Pro Gly Gln Pro Pro Lys Leu Leu Ile Tyr
65                  70                  75                  80
```

```
Asp Ala Ser Asp Leu Ala Ser Gly Val Pro Ser Arg Phe Lys Gly Ser
                85                  90                  95

Gly Ser Gly Thr Asp Phe Thr Leu Thr Ile Ser Asp Leu Glu Cys Ala
            100                 105                 110

Asp Ala Ala Tyr Tyr Cys Gln Ser Ala Asp Gly Ser Ser Tyr Ala
        115                 120                 125

Phe Gly Gly Gly Thr Glu Val Val Lys Gly Gly Gly Gly Ser
130                 135                 140

Gly Gly Gly Gly Ser Val His Met Pro Leu Gly Phe Leu Gly Pro Gly
145                 150                 155                 160

Ser Ala Arg Val Val Asn Gly Gly Ser Gly Gly Gly Ser Gln Glu
                165                 170                 175

Gln Leu Glu Glu Ser Gly Gly Gly Leu Val Lys Pro Glu Gly Ser Leu
            180                 185                 190

Thr Leu Thr Cys Thr Ala Ser Gly Val Ser Phe Ser Ser Tyr Trp
        195                 200                 205

Ile Tyr Trp Val Arg Gln Ala Pro Gly Lys Gly Leu Glu Trp Ile Ala
    210                 215                 220

Cys Ile Tyr Thr Gly Ser Ser Gly Ser Thr Tyr Tyr Ala Ser Trp Ala
225                 230                 235                 240

Lys Gly Arg Phe Thr Val Ser Glu Thr Ser Ser Thr Val Thr Leu
                245                 250                 255

Gln Met Thr Ser Leu Thr Ala Ala Asp Thr Ala Thr Tyr Phe Cys Ala
            260                 265                 270

Arg Ala Ser Ala Trp Thr Tyr Gly Met Asp Leu Trp Gly Pro Gly Thr
        275                 280                 285

Leu Val Thr Val Ser Ser Gly Gly Gly Ser Gly Gly Gly Gly Ser
290                 295                 300

Lys Pro Ile Pro Asn Pro Leu Leu Gly Leu Asp Ser Thr Gly Gly Gly
305                 310                 315                 320

Gly Ser Val His Met Pro Leu Gly Phe Leu Gly Pro Gly Ser Ala Arg
                325                 330                 335

Val Val Asn Gly Gly Ser Gly Gly Gly Gly Ser Gly Gly Gly Gly Ser
            340                 345                 350

Gln Val Gln Leu Gln Glu Ser Gly Pro Gly Leu Val Lys Pro Ser Glu
        355                 360                 365

Thr Leu Ser Leu Thr Cys Thr Val Ser Gly Gly Ser Ile Ser Tyr Tyr
370                 375                 380

Ser Trp Thr Trp Val Arg Gln Pro Ala Gly Gln Gly Leu Glu Trp Ile
385                 390                 395                 400

Gly Arg Ile His Ile Ser Gly Val Thr Asn His Asn Pro Ser Leu Lys
                405                 410                 415

Ser Arg Val Ser Met Ser Ile Asp Thr Ser Arg Thr Gln Phe Ser Leu
            420                 425                 430

Arg Leu Thr Ser Val Thr Ala Ala Asp Thr Ala Val Tyr Phe Cys Ala
        435                 440                 445

Arg Ser Gly Gly Thr Tyr Ser Ala Phe Asp Ile Trp Gly Gln Gly Thr
450                 455                 460

Met Val Thr Val Ser Ser Gly Gly Gly Gly Ser Gly Gly Gly Gly Ser
465                 470                 475                 480

Gly Gly Gly Gly Ser Gly Gly Gly Gly Ser Glu Ile Val Leu Thr Gln
                485                 490                 495

Ser Pro Gly Thr Leu Ser Leu Ser Pro Gly Glu Arg Ser Thr Leu Ser
```

```
                  500                 505                 510
Cys Arg Ala Ser Gln Ser Phe Thr Ser Asn Tyr Leu Ala Trp Tyr Gln
            515                 520                 525

Gln Arg Pro Gly Gln Ala Pro Arg Leu Leu Ile Tyr Gly Ala Ser Thr
        530                 535                 540

Arg Ala Ile Gly Ile Pro Asp Arg Phe Ser Gly Ser Gly Ser Gly Thr
545                 550                 555                 560

Asp Phe Thr Leu Thr Ile Ser Arg Leu Glu Pro Glu Asp Phe Ala Val
                565                 570                 575

Tyr Tyr Cys Gln Gln Tyr Gly Ser Ser Pro Trp Thr Phe Gly Gln Gly
            580                 585                 590

Thr Lys Val Glu Ile Lys Thr Thr Pro Ala Pro Arg Pro Pro Thr
        595                 600                 605

Pro Ala Pro Thr Ile Ala Ser Gln Pro Leu Ser Leu Arg Pro Glu Ala
        610                 615                 620

Cys Arg Pro Ala Ala Gly Gly Ala Val His Thr Arg Gly Leu Asp Phe
625                 630                 635                 640

Ala Cys Asp Ile Tyr Ile Trp Ala Pro Leu Ala Gly Thr Cys Gly Val
                645                 650                 655

Leu Leu Leu Ser Leu Val Ile Thr Leu Tyr Cys Lys Arg Gly Arg Lys
            660                 665                 670

Lys Leu Leu Tyr Ile Phe Lys Gln Pro Phe Met Arg Pro Val Gln Thr
        675                 680                 685

Thr Gln Glu Glu Asp Gly Cys Ser Cys Arg Phe Pro Glu Glu Glu Glu
        690                 695                 700

Gly Gly Cys Glu Leu Arg Val Lys Phe Ser Arg Ser Ala Asp Ala Pro
705                 710                 715                 720

Ala Tyr Gln Gln Gly Gln Asn Gln Leu Tyr Asn Glu Leu Asn Leu Gly
            725                 730                 735

Arg Arg Glu Glu Tyr Asp Val Leu Asp Lys Arg Arg Gly Arg Asp Pro
        740                 745                 750

Glu Met Gly Gly Lys Pro Arg Arg Lys Asn Pro Gln Glu Gly Leu Tyr
        755                 760                 765

Asn Glu Leu Gln Lys Asp Lys Met Ala Glu Ala Tyr Ser Glu Ile Gly
        770                 775                 780

Met Lys Gly Glu Arg Arg Arg Gly Lys Gly His Asp Gly Leu Tyr Gln
785                 790                 795                 800

Gly Leu Ser Thr Ala Thr Lys Asp Thr Tyr Asp Ala Leu His Met Gln
                805                 810                 815

Ala Leu Pro Pro Arg
            820

<210> SEQ ID NO 144
<211> LENGTH: 816
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Met Ala Leu Pro Val Thr Ala Leu Leu Leu Pro Leu Ala Leu Leu Leu
1               5                   10                  15

His Ala Ala Arg Pro Gly Tyr Pro Tyr Asp Val Pro Asp Tyr Ala Asp
            20                  25                  30
```

```
Ile Val Met Thr Gln Thr Pro Ala Ser Val Ser Glu Pro Val Gly Gly
            35                  40                  45

Ser Val Thr Ile Lys Cys Gln Ala Ser Gln Ser Phe Tyr Asn Leu Leu
 50                  55                  60

Ala Trp Tyr Gln Gln Lys Pro Gly Gln Pro Lys Leu Leu Ile Tyr
 65                  70                  75                  80

Asp Ala Ser Asp Leu Ala Ser Gly Val Pro Ser Arg Phe Lys Gly Ser
                 85                  90                  95

Gly Ser Gly Thr Asp Phe Thr Leu Thr Ile Ser Asp Leu Glu Cys Ala
                100                 105                 110

Asp Ala Ala Tyr Tyr Cys Gln Ser Ala Asp Gly Ser Ser Tyr Ala
                115                 120                 125

Phe Gly Gly Gly Thr Glu Val Val Lys Gly Gly Gly Gly Ser
 130                 135                 140

Gly Gly Gly Gly Ser Gly Gly Gly Ser Pro Met Ala Lys Lys Gly
 145                 150                 155                 160

Gly Gly Gly Ser Gly Gly Gly Ser Gly Gly Gly Ser Gln Glu
                165                 170                 175

Gln Leu Glu Glu Ser Gly Gly Gly Leu Val Lys Pro Glu Gly Ser Leu
                180                 185                 190

Thr Leu Thr Cys Thr Ala Ser Gly Val Ser Phe Ser Ser Tyr Trp
                195                 200                 205

Ile Tyr Trp Val Arg Gln Ala Pro Gly Lys Gly Leu Glu Trp Ile Ala
 210                 215                 220

Cys Ile Tyr Thr Gly Ser Ser Gly Ser Thr Tyr Tyr Ala Ser Trp Ala
225                 230                 235                 240

Lys Gly Arg Phe Thr Val Ser Glu Thr Ser Thr Thr Val Thr Leu
                245                 250                 255

Gln Met Thr Ser Leu Thr Ala Ala Asp Thr Ala Thr Tyr Phe Cys Ala
                260                 265                 270

Arg Ala Ser Ala Trp Thr Tyr Gly Met Asp Leu Trp Gly Pro Gly Thr
                275                 280                 285

Leu Val Thr Val Ser Ser Gly Gly Gly Ser Gly Gly Gly Gly Ser
 290                 295                 300

Lys Pro Ile Pro Asn Pro Leu Leu Gly Leu Asp Ser Thr Gly Gly
305                 310                 315                 320

Gly Ser Pro Met Ala Lys Lys Gly Gly Gly Ser Gly Gly Gly Gly
                325                 330                 335

Ser Gly Gly Gly Ser Gly Gly Gly Ser Gln Val Gln Leu Gln
                340                 345                 350

Glu Ser Gly Pro Gly Leu Val Lys Pro Ser Glu Thr Leu Ser Leu Thr
                355                 360                 365

Cys Thr Val Ser Gly Gly Ser Ile Ser Tyr Tyr Ser Trp Thr Trp Val
                370                 375                 380

Arg Gln Pro Ala Gly Gln Gly Leu Glu Trp Ile Gly Arg Ile His Ile
385                 390                 395                 400

Ser Gly Val Thr Asn His Asn Pro Ser Leu Lys Ser Arg Val Ser Met
                405                 410                 415

Ser Ile Asp Thr Ser Arg Thr Gln Phe Ser Leu Arg Leu Thr Ser Val
                420                 425                 430

Thr Ala Ala Asp Thr Ala Val Tyr Phe Cys Ala Arg Ser Gly Gly Thr
                435                 440                 445

Tyr Ser Ala Phe Asp Ile Trp Gly Gln Gly Thr Met Val Thr Val Ser
```

450                 455                 460
Ser Gly Gly Gly Ser Gly Gly Gly Ser Gly Gly Gly Ser
465                 470                 475                 480

Gly Gly Gly Gly Ser Glu Ile Val Leu Thr Gln Ser Pro Gly Thr Leu
                485                 490                 495

Ser Leu Ser Pro Gly Glu Arg Ser Thr Leu Ser Cys Arg Ala Ser Gln
            500                 505                 510

Ser Phe Thr Ser Asn Tyr Leu Ala Trp Tyr Gln Gln Arg Pro Gly Gln
        515                 520                 525

Ala Pro Arg Leu Leu Ile Tyr Gly Ala Ser Thr Arg Ala Ile Gly Ile
530                 535                 540

Pro Asp Arg Phe Ser Gly Ser Gly Ser Gly Thr Asp Phe Thr Leu Thr
545                 550                 555                 560

Ile Ser Arg Leu Glu Pro Glu Asp Phe Ala Val Tyr Tyr Cys Gln Gln
                565                 570                 575

Tyr Gly Ser Ser Pro Trp Thr Phe Gly Gln Gly Thr Lys Val Glu Ile
            580                 585                 590

Lys Thr Thr Thr Pro Ala Pro Arg Pro Pro Thr Pro Ala Pro Thr Ile
        595                 600                 605

Ala Ser Gln Pro Leu Ser Leu Arg Pro Glu Ala Cys Arg Pro Ala Ala
610                 615                 620

Gly Gly Ala Val His Thr Arg Gly Leu Asp Phe Ala Cys Asp Ile Tyr
625                 630                 635                 640

Ile Trp Ala Pro Leu Ala Gly Thr Cys Gly Val Leu Leu Leu Ser Leu
                645                 650                 655

Val Ile Thr Leu Tyr Cys Lys Arg Gly Arg Lys Lys Leu Leu Tyr Ile
            660                 665                 670

Phe Lys Gln Pro Phe Met Arg Pro Val Gln Thr Thr Gln Glu Glu Asp
        675                 680                 685

Gly Cys Ser Cys Arg Phe Pro Glu Glu Glu Glu Gly Gly Cys Glu Leu
690                 695                 700

Arg Val Lys Phe Ser Arg Ser Ala Asp Ala Pro Ala Tyr Gln Gln Gly
705                 710                 715                 720

Gln Asn Gln Leu Tyr Asn Glu Leu Asn Leu Gly Arg Arg Glu Glu Tyr
                725                 730                 735

Asp Val Leu Asp Lys Arg Arg Gly Arg Asp Pro Glu Met Gly Gly Lys
            740                 745                 750

Pro Arg Arg Lys Asn Pro Gln Glu Gly Leu Tyr Asn Glu Leu Gln Lys
        755                 760                 765

Asp Lys Met Ala Glu Ala Tyr Ser Glu Ile Gly Met Lys Gly Glu Arg
770                 775                 780

Arg Arg Gly Lys Gly His Asp Gly Leu Tyr Gln Gly Leu Ser Thr Ala
785                 790                 795                 800

Thr Lys Asp Thr Tyr Asp Ala Leu His Met Gln Ala Leu Pro Pro Arg
                805                 810                 815

<210> SEQ ID NO 145
<211> LENGTH: 816
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

```
Met Ala Leu Pro Val Thr Ala Leu Leu Leu Pro Leu Ala Leu Leu Leu
1               5                   10                  15

His Ala Ala Arg Pro Gly Tyr Pro Tyr Asp Val Pro Asp Tyr Ala Asp
            20                  25                  30

Ile Val Met Thr Gln Thr Pro Ala Ser Val Ser Glu Pro Val Gly Gly
        35                  40                  45

Ser Val Thr Ile Lys Cys Gln Ala Ser Gln Ser Phe Tyr Asn Leu Leu
    50                  55                  60

Ala Trp Tyr Gln Gln Lys Pro Gly Gln Pro Pro Lys Leu Leu Ile Tyr
65                  70                  75                  80

Asp Ala Ser Asp Leu Ala Ser Gly Val Pro Ser Arg Phe Lys Gly Ser
                85                  90                  95

Gly Ser Gly Thr Asp Phe Thr Leu Thr Ile Ser Asp Leu Glu Cys Ala
            100                 105                 110

Asp Ala Ala Tyr Tyr Cys Gln Ser Ala Asp Gly Ser Ser Tyr Ala
            115                 120                 125

Phe Gly Gly Gly Thr Glu Val Val Lys Gly Gly Gly Gly Ser
    130                 135                 140

Gly Gly Gly Gly Ser Gly Gly Gly Ser Pro Met Ala Lys Gly Ser
145                 150                 155                 160

Gly Gly Gly Ser Gly Gly Gly Ser Gly Gly Gly Ser Gln Glu
                165                 170                 175

Gln Leu Glu Glu Ser Gly Gly Gly Leu Val Lys Pro Glu Gly Ser Leu
            180                 185                 190

Thr Leu Thr Cys Thr Ala Ser Gly Val Ser Phe Ser Ser Ser Tyr Trp
        195                 200                 205

Ile Tyr Trp Val Arg Gln Ala Pro Gly Lys Gly Leu Glu Trp Ile Ala
    210                 215                 220

Cys Ile Tyr Thr Gly Ser Ser Gly Ser Thr Tyr Tyr Ala Ser Trp Ala
225                 230                 235                 240

Lys Gly Arg Phe Thr Val Ser Glu Thr Ser Ser Thr Val Thr Leu
            245                 250                 255

Gln Met Thr Ser Leu Thr Ala Ala Asp Thr Ala Thr Tyr Phe Cys Ala
            260                 265                 270

Arg Ala Ser Ala Trp Thr Tyr Gly Met Asp Leu Trp Gly Pro Gly Thr
    275                 280                 285

Leu Val Thr Val Ser Ser Gly Gly Gly Ser Gly Gly Gly Gly Ser
    290                 295                 300

Lys Pro Ile Pro Asn Pro Leu Leu Gly Leu Asp Ser Thr Gly Gly
305                 310                 315                 320

Gly Ser Pro Met Ala Lys Gly Ser Gly Gly Ser Gly Gly Gly Gly
            325                 330                 335

Ser Gly Gly Gly Gly Ser Gly Gly Gly Ser Gln Val Gln Leu Gln
            340                 345                 350

Glu Ser Gly Pro Gly Leu Val Lys Pro Ser Glu Thr Leu Ser Leu Thr
            355                 360                 365

Cys Thr Val Ser Gly Gly Ser Ile Ser Tyr Tyr Ser Trp Thr Trp Val
    370                 375                 380

Arg Gln Pro Ala Gly Gly Leu Glu Trp Ile Gly Arg Ile His Ile
385                 390                 395                 400

Ser Gly Val Thr Asn His Asn Pro Ser Leu Lys Ser Arg Val Ser Met
            405                 410                 415

Ser Ile Asp Thr Ser Arg Thr Gln Phe Ser Leu Arg Leu Thr Ser Val
```

```
                420             425             430
Thr Ala Ala Asp Thr Ala Val Tyr Phe Cys Ala Arg Ser Gly Gly Thr
            435                 440                 445
Tyr Ser Ala Phe Asp Ile Trp Gly Gln Gly Thr Met Val Thr Val Ser
450                 455                 460
Ser Gly Gly Gly Gly Ser Gly Gly Gly Gly Ser Gly Gly Gly Gly Ser
465                 470                 475                 480
Gly Gly Gly Gly Ser Glu Ile Val Leu Thr Gln Ser Pro Gly Thr Leu
                485                 490                 495
Ser Leu Ser Pro Gly Glu Arg Ser Thr Leu Ser Cys Arg Ala Ser Gln
            500                 505                 510
Ser Phe Thr Ser Asn Tyr Leu Ala Trp Tyr Gln Gln Arg Pro Gly Gln
            515                 520                 525
Ala Pro Arg Leu Leu Ile Tyr Gly Ala Ser Thr Arg Ala Ile Gly Ile
            530                 535                 540
Pro Asp Arg Phe Ser Gly Ser Gly Ser Gly Thr Asp Phe Thr Leu Thr
545                 550                 555                 560
Ile Ser Arg Leu Glu Pro Glu Asp Phe Ala Val Tyr Tyr Cys Gln Gln
                565                 570                 575
Tyr Gly Ser Ser Pro Trp Thr Phe Gly Gln Gly Thr Lys Val Glu Ile
            580                 585                 590
Lys Thr Thr Thr Pro Ala Pro Arg Pro Pro Thr Pro Ala Pro Thr Ile
            595                 600                 605
Ala Ser Gln Pro Leu Ser Leu Arg Pro Glu Ala Cys Arg Pro Ala Ala
            610                 615                 620
Gly Gly Ala Val His Thr Arg Gly Leu Asp Phe Ala Cys Asp Ile Tyr
625                 630                 635                 640
Ile Trp Ala Pro Leu Ala Gly Thr Cys Gly Val Leu Leu Leu Ser Leu
                645                 650                 655
Val Ile Thr Leu Tyr Cys Lys Arg Gly Arg Lys Lys Leu Leu Tyr Ile
            660                 665                 670
Phe Lys Gln Pro Phe Met Arg Pro Val Gln Thr Thr Gln Glu Glu Asp
            675                 680                 685
Gly Cys Ser Cys Arg Phe Pro Glu Glu Glu Glu Gly Gly Cys Glu Leu
            690                 695                 700
Arg Val Lys Phe Ser Arg Ser Ala Asp Ala Pro Ala Tyr Gln Gln Gly
705                 710                 715                 720
Gln Asn Gln Leu Tyr Asn Glu Leu Asn Leu Gly Arg Arg Glu Glu Tyr
                725                 730                 735
Asp Val Leu Asp Lys Arg Arg Gly Arg Asp Pro Glu Met Gly Gly Lys
            740                 745                 750
Pro Arg Arg Lys Asn Pro Gln Glu Gly Leu Tyr Asn Glu Leu Gln Lys
            755                 760                 765
Asp Lys Met Ala Glu Ala Tyr Ser Glu Ile Gly Met Lys Gly Glu Arg
            770                 775                 780
Arg Arg Gly Lys Gly His Asp Gly Leu Tyr Gln Gly Leu Ser Thr Ala
785                 790                 795                 800
Thr Lys Asp Thr Tyr Asp Ala Leu His Met Gln Ala Leu Pro Pro Arg
                805                 810                 815

<210> SEQ ID NO 146
<211> LENGTH: 778
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 146

Met Ala Leu Pro Val Thr Ala Leu Leu Leu Pro Leu Ala Leu Leu Leu
1               5                   10                  15

His Ala Ala Arg Pro Gly Tyr Pro Tyr Asp Val Pro Asp Tyr Ala Asp
            20                  25                  30

Ile Val Met Thr Gln Thr Pro Ala Ser Val Ser Glu Pro Val Gly Gly
        35                  40                  45

Ser Val Thr Ile Lys Cys Gln Ala Ser Gln Ser Phe Tyr Asn Leu Leu
    50                  55                  60

Ala Trp Tyr Gln Gln Lys Pro Gly Gln Pro Lys Leu Leu Ile Tyr
65                  70                  75                  80

Asp Ala Ser Asp Leu Ala Ser Gly Val Pro Ser Arg Phe Lys Gly Ser
                85                  90                  95

Gly Ser Gly Thr Asp Phe Thr Leu Thr Ile Ser Asp Leu Glu Cys Ala
            100                 105                 110

Asp Ala Ala Tyr Tyr Cys Gln Ser Ala Asp Gly Ser Ser Tyr Ala
        115                 120                 125

Phe Gly Gly Gly Thr Glu Val Val Lys Gly Gly Gly Gly Ser
    130                 135                 140

Gly Gly Gly Gly Ser Gly Gly Gly Ser Gly Gly Gly Ser Gln
145                 150                 155                 160

Glu Gln Leu Glu Glu Ser Gly Gly Leu Val Lys Pro Glu Gly Ser
                165                 170                 175

Leu Thr Leu Thr Cys Thr Ala Ser Gly Val Ser Phe Ser Ser Ser Tyr
            180                 185                 190

Trp Ile Tyr Trp Val Arg Gln Ala Pro Gly Lys Gly Leu Glu Trp Ile
        195                 200                 205

Ala Cys Ile Tyr Thr Gly Ser Ser Gly Ser Thr Tyr Tyr Ala Ser Trp
    210                 215                 220

Ala Lys Gly Arg Phe Thr Val Ser Glu Thr Ser Ser Thr Thr Val Thr
225                 230                 235                 240

Leu Gln Met Thr Ser Leu Thr Ala Ala Asp Thr Ala Thr Tyr Phe Cys
                245                 250                 255

Ala Arg Ala Ser Ala Trp Thr Tyr Gly Met Asp Leu Trp Gly Pro Gly
            260                 265                 270

Thr Leu Val Thr Val Ser Ser Gly Gly Gly Ser Gly Gly Gly Gly
        275                 280                 285

Ser Gly Gly Gly Ser Gly Gly Gly Ser Gly Gly Gly Gly Ser
    290                 295                 300

Gly Gly Gly Gly Ser Gln Val Gln Leu Gln Glu Ser Gly Pro Gly Leu
305                 310                 315                 320

Val Lys Pro Ser Glu Thr Leu Ser Leu Thr Cys Thr Val Ser Gly Gly
                325                 330                 335

Ser Ile Ser Tyr Tyr Ser Trp Thr Trp Val Arg Gln Pro Ala Gly Gln
            340                 345                 350

Gly Leu Glu Trp Ile Gly Arg Ile His Ile Ser Gly Val Thr Asn His
        355                 360                 365

Asn Pro Ser Leu Lys Ser Arg Val Ser Met Ser Ile Asp Thr Ser Arg
    370                 375                 380

Thr Gln Phe Ser Leu Arg Leu Thr Ser Val Thr Ala Ala Asp Thr Ala

```
            385                 390                 395                 400
Val Tyr Phe Cys Ala Arg Ser Gly Gly Thr Tyr Ser Ala Phe Asp Ile
                    405                 410                 415
Trp Gly Gln Gly Thr Met Val Thr Val Ser Ser Gly Gly Gly Gly Ser
                420                 425                 430
Gly Gly Gly Gly Ser Gly Gly Gly Ser Gly Gly Gly Gly Ser Glu
            435                 440                 445
Ile Val Leu Thr Gln Ser Pro Gly Thr Leu Ser Leu Ser Pro Gly Glu
    450                 455                 460
Arg Ser Thr Leu Ser Cys Arg Ala Ser Gln Ser Phe Thr Ser Asn Tyr
465                 470                 475                 480
Leu Ala Trp Tyr Gln Gln Arg Pro Gly Gln Ala Pro Arg Leu Leu Ile
                485                 490                 495
Tyr Gly Ala Ser Thr Arg Ala Ile Gly Ile Pro Asp Arg Phe Ser Gly
                500                 505                 510
Ser Gly Ser Gly Thr Asp Phe Thr Leu Thr Ile Ser Arg Leu Glu Pro
                515                 520                 525
Glu Asp Phe Ala Val Tyr Tyr Cys Gln Gln Tyr Gly Ser Ser Pro Trp
        530                 535                 540
Thr Phe Gly Gln Gly Thr Lys Val Glu Ile Lys Thr Thr Thr Pro Ala
545                 550                 555                 560
Pro Arg Pro Pro Thr Pro Ala Pro Thr Ile Ala Ser Gln Pro Leu Ser
                    565                 570                 575
Leu Arg Pro Glu Ala Cys Arg Pro Ala Ala Gly Gly Ala Val His Thr
                580                 585                 590
Arg Gly Leu Asp Phe Ala Cys Asp Ile Tyr Ile Trp Ala Pro Leu Ala
            595                 600                 605
Gly Thr Cys Gly Val Leu Leu Leu Ser Leu Val Ile Thr Leu Tyr Cys
        610                 615                 620
Lys Arg Gly Arg Lys Lys Leu Leu Tyr Ile Phe Lys Gln Pro Phe Met
625                 630                 635                 640
Arg Pro Val Gln Thr Thr Gln Glu Glu Asp Gly Cys Ser Cys Arg Phe
                    645                 650                 655
Pro Glu Glu Glu Glu Gly Gly Cys Glu Leu Arg Val Lys Phe Ser Arg
                660                 665                 670
Ser Ala Asp Ala Pro Ala Tyr Gln Gln Gly Gln Asn Gln Leu Tyr Asn
            675                 680                 685
Glu Leu Asn Leu Gly Arg Arg Glu Glu Tyr Asp Val Leu Asp Lys Arg
        690                 695                 700
Arg Gly Arg Asp Pro Glu Met Gly Gly Lys Pro Arg Arg Lys Asn Pro
705                 710                 715                 720
Gln Glu Gly Leu Tyr Asn Glu Leu Gln Lys Asp Lys Met Ala Glu Ala
                    725                 730                 735
Tyr Ser Glu Ile Gly Met Lys Gly Glu Arg Arg Arg Gly Lys Gly His
                740                 745                 750
Asp Gly Leu Tyr Gln Gly Leu Ser Thr Ala Thr Lys Asp Thr Tyr Asp
            755                 760                 765
Ala Leu His Met Gln Ala Leu Pro Pro Arg
        770                 775

<210> SEQ ID NO 147
<211> LENGTH: 768
<212> TYPE: PRT
<213> ORGANISM: Artificial Sequence
```

-continued

```
<220> FEATURE:
<223> OTHER INFORMATION: Description of Artificial Sequence: Synthetic
      polypeptide

<400> SEQUENCE: 147

Met Ala Leu Pro Val Thr Ala Leu Leu Leu Pro Leu Ala Leu Leu Leu
1               5                   10                  15

His Ala Ala Arg Pro Gly Tyr Pro Tyr Asp Val Pro Asp Tyr Ala Asp
            20                  25                  30

Ile Val Met Thr Gln Thr Pro Ala Ser Val Ser Glu Pro Val Gly Gly
        35                  40                  45

Ser Val Thr Ile Lys Cys Gln Ala Ser Gln Ser Phe Tyr Asn Leu Leu
50                  55                  60

Ala Trp Tyr Gln Gln Lys Pro Gly Gln Pro Lys Leu Leu Ile Tyr
65                  70                  75                  80

Asp Ala Ser Asp Leu Ala Ser Gly Val Pro Ser Arg Phe Lys Gly Ser
                85                  90                  95

Gly Ser Gly Thr Asp Phe Thr Leu Thr Ile Ser Asp Leu Glu Cys Ala
            100                 105                 110

Asp Ala Ala Tyr Tyr Cys Gln Ser Ala Asp Gly Ser Ser Tyr Ala
        115                 120                 125

Phe Gly Gly Gly Thr Glu Val Val Lys Gly Gly Gly Gly Ser
130                 135                 140

Gly Gly Gly Ser Gly Gly Gly Ser Gly Gly Gly Ser Gln
145                 150                 155                 160

Glu Gln Leu Glu Glu Ser Gly Gly Leu Val Lys Pro Glu Gly Ser
            165                 170                 175

Leu Thr Leu Thr Cys Thr Ala Ser Gly Val Ser Phe Ser Ser Ser Tyr
            180                 185                 190

Trp Ile Tyr Trp Val Arg Gln Ala Pro Gly Lys Gly Leu Glu Trp Ile
        195                 200                 205

Ala Cys Ile Tyr Thr Gly Ser Ser Gly Ser Thr Tyr Tyr Ala Ser Trp
        210                 215                 220

Ala Lys Gly Arg Phe Thr Val Ser Glu Thr Ser Ser Thr Thr Val Thr
225                 230                 235                 240

Leu Gln Met Thr Ser Leu Thr Ala Ala Asp Thr Ala Thr Tyr Phe Cys
                245                 250                 255

Ala Arg Ala Ser Ala Trp Thr Tyr Gly Met Asp Leu Trp Gly Pro Gly
            260                 265                 270

Thr Leu Val Thr Val Ser Ser Gly Gly Gly Ser Gly Gly Gly Gly
        275                 280                 285

Ser Gly Gly Gly Ser Gly Gly Gly Gly Ser Gln Val Gln Leu Gln
        290                 295                 300

Glu Ser Gly Pro Gly Leu Val Lys Pro Ser Glu Thr Leu Ser Leu Thr
305                 310                 315                 320

Cys Thr Val Ser Gly Gly Ser Ile Ser Tyr Tyr Ser Trp Thr Trp Val
                325                 330                 335

Arg Gln Pro Ala Gly Gln Gly Leu Glu Trp Ile Gly Arg Ile His Ile
            340                 345                 350

Ser Gly Val Thr Asn His Asn Pro Ser Leu Lys Ser Arg Val Ser Met
        355                 360                 365

Ser Ile Asp Thr Ser Arg Thr Gln Phe Ser Leu Arg Leu Thr Ser Val
        370                 375                 380

Thr Ala Ala Asp Thr Ala Val Tyr Phe Cys Ala Arg Ser Gly Gly Thr
```

```
                385                 390                 395                 400
Tyr Ser Ala Phe Asp Ile Trp Gly Gln Gly Thr Met Val Thr Val Ser
                    405                 410                 415
Ser Gly Gly Gly Gly Ser Gly Gly Gly Ser Gly Gly Gly Gly Ser
                420                 425                 430
Gly Gly Gly Gly Ser Glu Ile Val Leu Thr Gln Ser Pro Gly Thr Leu
                435                 440                 445
Ser Leu Ser Pro Gly Glu Arg Ser Thr Leu Ser Cys Arg Ala Ser Gln
450                 455                 460
Ser Phe Thr Ser Asn Tyr Leu Ala Trp Tyr Gln Gln Arg Pro Gly Gln
465                 470                 475                 480
Ala Pro Arg Leu Leu Ile Tyr Gly Ala Ser Thr Arg Ala Ile Gly Ile
                    485                 490                 495
Pro Asp Arg Phe Ser Gly Ser Gly Ser Gly Thr Asp Phe Thr Leu Thr
                500                 505                 510
Ile Ser Arg Leu Glu Pro Glu Asp Phe Ala Val Tyr Tyr Cys Gln Gln
                515                 520                 525
Tyr Gly Ser Ser Pro Trp Thr Phe Gly Gln Gly Thr Lys Val Glu Ile
                530                 535                 540
Lys Thr Thr Thr Pro Ala Pro Arg Pro Pro Thr Pro Ala Pro Thr Ile
545                 550                 555                 560
Ala Ser Gln Pro Leu Ser Leu Arg Pro Glu Ala Cys Arg Pro Ala Ala
                    565                 570                 575
Gly Gly Ala Val His Thr Arg Gly Leu Asp Phe Ala Cys Asp Ile Tyr
                580                 585                 590
Ile Trp Ala Pro Leu Ala Gly Thr Cys Gly Val Leu Leu Leu Ser Leu
                595                 600                 605
Val Ile Thr Leu Tyr Cys Lys Arg Gly Arg Lys Lys Leu Leu Tyr Ile
                610                 615                 620
Phe Lys Gln Pro Phe Met Arg Pro Val Gln Thr Thr Gln Glu Glu Asp
625                 630                 635                 640
Gly Cys Ser Cys Arg Phe Pro Glu Glu Glu Gly Gly Cys Glu Leu
                    645                 650                 655
Arg Val Lys Phe Ser Arg Ser Ala Asp Ala Pro Ala Tyr Gln Gln Gly
                660                 665                 670
Gln Asn Gln Leu Tyr Asn Glu Leu Asn Leu Gly Arg Arg Glu Glu Tyr
                675                 680                 685
Asp Val Leu Asp Lys Arg Arg Gly Arg Asp Pro Glu Met Gly Gly Lys
                690                 695                 700
Pro Arg Arg Lys Asn Pro Gln Glu Gly Leu Tyr Asn Glu Leu Gln Lys
705                 710                 715                 720
Asp Lys Met Ala Glu Ala Tyr Ser Glu Ile Gly Met Lys Gly Glu Arg
                    725                 730                 735
Arg Arg Gly Lys Gly His Asp Gly Leu Tyr Gln Gly Leu Ser Thr Ala
                740                 745                 750
Thr Lys Asp Thr Tyr Asp Ala Leu His Met Gln Ala Leu Pro Pro Arg
                755                 760                 765

<210> SEQ ID NO 148
<211> LENGTH: 758
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 148

| | | | | | | | | | | | | | | |
|---|---|---|---|---|---|---|---|---|---|---|---|---|---|---|
|Met|Ala|Leu|Pro|Val|Thr|Ala|Leu|Leu|Pro|Leu|Ala|Leu|Leu|Leu|
|1| | | |5| | | | |10| | | | |15|

His Ala Ala Arg Pro Gly Tyr Pro Tyr Asp Val Pro Asp Tyr Ala Asp
          20                    25                30

Ile Val Met Thr Gln Thr Pro Ala Ser Val Ser Glu Pro Val Gly Gly
          35                    40                45

Ser Val Thr Ile Lys Cys Gln Ala Ser Gln Ser Phe Tyr Asn Leu Leu
50                      55                    60

Ala Trp Tyr Gln Gln Lys Pro Gly Gln Pro Pro Lys Leu Leu Ile Tyr
65                      70                75                80

Asp Ala Ser Asp Leu Ala Ser Gly Val Pro Ser Arg Phe Lys Gly Ser
          85                    90                95

Gly Ser Gly Thr Asp Phe Thr Leu Thr Ile Ser Asp Leu Glu Cys Ala
          100                  105              110

Asp Ala Ala Ala Tyr Tyr Cys Gln Ser Ala Asp Gly Ser Ser Tyr Ala
          115                  120              125

Phe Gly Gly Gly Thr Glu Val Val Val Lys Gly Gly Gly Gly Gly Ser
      130                  135              140

Gly Gly Gly Gly Ser Gly Gly Gly Ser Gly Gly Gly Ser Gln
145                    150                155              160

Glu Gln Leu Glu Glu Ser Gly Gly Gly Leu Val Lys Pro Glu Gly Ser
          165                  170              175

Leu Thr Leu Thr Cys Thr Ala Ser Gly Val Ser Phe Ser Ser Ser Tyr
          180                  185              190

Trp Ile Tyr Trp Val Arg Gln Ala Pro Gly Lys Gly Leu Glu Trp Ile
      195                  200              205

Ala Cys Ile Tyr Thr Gly Ser Ser Gly Ser Thr Tyr Tyr Ala Ser Trp
          210                  215              220

Ala Lys Gly Arg Phe Thr Val Ser Glu Thr Ser Ser Thr Thr Val Thr
225                    230                235              240

Leu Gln Met Thr Ser Leu Thr Ala Ala Asp Thr Ala Thr Tyr Phe Cys
          245                  250              255

Ala Arg Ala Ser Ala Trp Thr Tyr Gly Met Asp Leu Trp Gly Pro Gly
          260                  265              270

Thr Leu Val Thr Val Ser Ser Gly Gly Gly Ser Gly Gly Gly Gly
      275                  280              285

Ser Gln Val Gln Leu Gln Glu Ser Gly Pro Gly Leu Val Lys Pro Ser
          290                  295              300

Glu Thr Leu Ser Leu Thr Cys Thr Val Ser Gly Gly Ser Ile Ser Tyr
305                    310                315              320

Tyr Ser Trp Thr Trp Val Arg Gln Pro Ala Gly Gln Gly Leu Glu Trp
              325                330              335

Ile Gly Arg Ile His Ile Ser Gly Val Thr Asn His Asn Pro Ser Leu
          340                  345              350

Lys Ser Arg Val Ser Met Ser Ile Asp Thr Ser Arg Thr Gln Phe Ser
          355                  360              365

Leu Arg Leu Thr Ser Val Thr Ala Ala Asp Thr Ala Val Tyr Phe Cys
          370                  375              380

Ala Arg Ser Gly Gly Thr Tyr Ser Ala Phe Asp Ile Trp Gly Gln Gly
385                    390                395              400

Thr Met Val Thr Val Ser Ser Gly Gly Gly Gly Ser Gly Gly Gly Gly

Ser Gly Gly Gly Ser Gly Gly Gly Ser Glu Ile Val Leu Thr
            405                 410                 415

Gln Ser Pro Gly Thr Leu Ser Leu Ser Pro Gly Glu Arg Ser Thr Leu
        420                 425                 430

Ser Cys Arg Ala Ser Gln Ser Phe Thr Ser Asn Tyr Leu Ala Trp Tyr
    450                 455                 460

Gln Gln Arg Pro Gly Gln Ala Pro Arg Leu Leu Ile Tyr Gly Ala Ser
465                 470                 475                 480

Thr Arg Ala Ile Gly Ile Pro Asp Arg Phe Ser Gly Ser Gly Ser Gly
                485                 490                 495

Thr Asp Phe Thr Leu Thr Ile Ser Arg Leu Glu Pro Glu Asp Phe Ala
            500                 505                 510

Val Tyr Tyr Cys Gln Gln Tyr Gly Ser Ser Pro Trp Thr Phe Gly Gln
        515                 520                 525

Gly Thr Lys Val Glu Ile Lys Thr Thr Thr Pro Ala Pro Arg Pro Pro
    530                 535                 540

Thr Pro Ala Pro Thr Ile Ala Ser Gln Pro Leu Ser Leu Arg Pro Glu
545                 550                 555                 560

Ala Cys Arg Pro Ala Ala Gly Gly Ala Val His Thr Arg Gly Leu Asp
                565                 570                 575

Phe Ala Cys Asp Ile Tyr Ile Trp Ala Pro Leu Ala Gly Thr Cys Gly
            580                 585                 590

Val Leu Leu Leu Ser Leu Val Ile Thr Leu Tyr Cys Lys Arg Gly Arg
        595                 600                 605

Lys Lys Leu Leu Tyr Ile Phe Lys Gln Pro Phe Met Arg Pro Val Gln
    610                 615                 620

Thr Thr Gln Glu Glu Asp Gly Cys Ser Cys Arg Phe Pro Glu Glu Glu
625                 630                 635                 640

Glu Gly Gly Cys Glu Leu Arg Val Lys Phe Ser Arg Ser Ala Asp Ala
                645                 650                 655

Pro Ala Tyr Gln Gln Gly Gln Asn Gln Leu Tyr Asn Glu Leu Asn Leu
            660                 665                 670

Gly Arg Arg Glu Glu Tyr Asp Val Leu Asp Lys Arg Arg Gly Arg Asp
        675                 680                 685

Pro Glu Met Gly Gly Lys Pro Arg Arg Lys Asn Pro Gln Glu Gly Leu
    690                 695                 700

Tyr Asn Glu Leu Gln Lys Asp Lys Met Ala Glu Ala Tyr Ser Glu Ile
705                 710                 715                 720

Gly Met Lys Gly Glu Arg Arg Arg Gly Lys Gly His Asp Gly Leu Tyr
                725                 730                 735

Gln Gly Leu Ser Thr Ala Thr Lys Asp Thr Tyr Asp Ala Leu His Met
            740                 745                 750

Gln Ala Leu Pro Pro Arg
            755

<210> SEQ ID NO 149
<211> LENGTH: 807
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

```
Met Ala Leu Pro Val Thr Ala Leu Leu Leu Pro Leu Ala Leu Leu Leu
1               5                   10                  15

His Ala Ala Arg Pro Gly Lys Pro Ile Pro Asn Pro Leu Leu Gly Leu
            20                  25                  30

Asp Ser Thr Gly Gly Gly Gly Ser Gly Gly Gly Gly Ser Gly Gly Gly
                35                  40                  45

Gly Ser Gly Gly Gly Gly Ser Asp Ile Val Met Thr Gln Thr Pro Ala
        50                  55                  60

Ser Val Ser Glu Pro Val Gly Gly Ser Val Thr Ile Lys Cys Gln Ala
65                  70                  75                  80

Ser Gln Ser Phe Tyr Asn Leu Leu Ala Trp Tyr Gln Gln Lys Pro Gly
                85                  90                  95

Gln Pro Pro Lys Leu Leu Ile Tyr Asp Ala Ser Asp Leu Ala Ser Gly
            100                 105                 110

Val Pro Ser Arg Phe Lys Gly Ser Gly Ser Gly Thr Asp Phe Thr Leu
                115                 120                 125

Thr Ile Ser Asp Leu Glu Cys Ala Asp Ala Ala Tyr Tyr Cys Gln
        130                 135                 140

Ser Ala Asp Gly Ser Ser Tyr Ala Phe Gly Gly Gly Thr Glu Val Val
145                 150                 155                 160

Val Lys Gly Gly Gly Gly Ser Gly Gly Gly Ser Gly Gly Gly
                165                 170                 175

Gly Ser Gly Gly Gly Gly Ser Gln Glu Gln Leu Glu Glu Ser Gly Gly
        180                 185                 190

Gly Leu Val Lys Pro Glu Gly Ser Leu Thr Leu Thr Cys Thr Ala Ser
        195                 200                 205

Gly Val Ser Phe Ser Ser Ser Tyr Trp Ile Tyr Trp Val Arg Gln Ala
        210                 215                 220

Pro Gly Lys Gly Leu Glu Trp Ile Ala Cys Ile Tyr Thr Gly Ser Ser
225                 230                 235                 240

Gly Ser Thr Tyr Tyr Ala Ser Trp Ala Lys Gly Arg Phe Thr Val Ser
                245                 250                 255

Glu Thr Ser Ser Thr Thr Val Thr Leu Gln Met Thr Ser Leu Thr Ala
            260                 265                 270

Ala Asp Thr Ala Thr Tyr Phe Cys Ala Arg Ala Ser Ala Trp Thr Tyr
        275                 280                 285

Gly Met Asp Leu Trp Gly Pro Gly Thr Leu Val Thr Val Ser Ser Gly
        290                 295                 300

Gly Gly Gly Ser Gly Gly Gly Gly Ser Gly Gly Gly Gly Ser Pro Met
305                 310                 315                 320

Ala Lys Lys Gly Gly Gly Gly Ser Gly Gly Gly Gly Ser Gly Gly Gly
                325                 330                 335

Gly Ser Gln Val Gln Leu Gln Glu Ser Gly Pro Gly Leu Val Lys Pro
        340                 345                 350

Ser Glu Thr Leu Ser Leu Thr Cys Thr Val Ser Gly Gly Ser Ile Ser
            355                 360                 365

Tyr Tyr Ser Trp Thr Trp Val Arg Gln Pro Ala Gly Gln Gly Leu Glu
370                 375                 380

Trp Ile Gly Arg Ile His Ile Ser Gly Val Thr Asn His Asn Pro Ser
385                 390                 395                 400

Leu Lys Ser Arg Val Ser Met Ser Ile Asp Thr Ser Arg Thr Gln Phe
            405                 410                 415

Ser Leu Arg Leu Thr Ser Val Thr Ala Ala Asp Thr Ala Val Tyr Phe
```

```
                420             425             430
Cys Ala Arg Ser Gly Gly Thr Tyr Ser Ala Phe Asp Ile Trp Gly Gln
            435             440             445
Gly Thr Met Val Thr Val Ser Ser Gly Gly Gly Ser Gly Gly Gly
        450             455             460
Gly Ser Gly Gly Gly Ser Gly Gly Gly Ser Glu Ile Val Leu
465             470             475             480
Thr Gln Ser Pro Gly Thr Leu Ser Leu Ser Pro Gly Glu Arg Ser Thr
            485             490             495
Leu Ser Cys Arg Ala Ser Gln Ser Phe Thr Ser Asn Tyr Leu Ala Trp
            500             505             510
Tyr Gln Gln Arg Pro Gly Gln Ala Pro Arg Leu Leu Ile Tyr Gly Ala
            515             520             525
Ser Thr Arg Ala Ile Gly Ile Pro Asp Arg Phe Ser Gly Ser Gly Ser
            530             535             540
Gly Thr Asp Phe Thr Leu Thr Ile Ser Arg Leu Glu Pro Glu Asp Phe
545             550             555             560
Ala Val Tyr Tyr Cys Gln Gln Tyr Gly Ser Ser Pro Trp Thr Phe Gly
                565             570             575
Gln Gly Thr Lys Val Glu Ile Lys Thr Thr Pro Ala Pro Arg Pro
            580             585             590
Pro Thr Pro Ala Pro Thr Ile Ala Ser Gln Pro Leu Ser Leu Arg Pro
            595             600             605
Glu Ala Cys Arg Pro Ala Ala Gly Gly Ala Val His Thr Arg Gly Leu
            610             615             620
Asp Phe Ala Cys Asp Ile Tyr Ile Trp Ala Pro Leu Ala Gly Thr Cys
625             630             635             640
Gly Val Leu Leu Leu Ser Leu Val Ile Thr Leu Tyr Cys Lys Arg Gly
                645             650             655
Arg Lys Lys Leu Leu Tyr Ile Phe Lys Gln Pro Phe Met Arg Pro Val
            660             665             670
Gln Thr Thr Gln Glu Glu Asp Gly Cys Ser Cys Arg Phe Pro Glu Glu
            675             680             685
Glu Glu Gly Gly Cys Glu Leu Arg Val Lys Phe Ser Arg Ser Ala Asp
            690             695             700
Ala Pro Ala Tyr Gln Gln Gly Gln Asn Gln Leu Tyr Asn Glu Leu Asn
705             710             715             720
Leu Gly Arg Arg Glu Glu Tyr Asp Val Leu Asp Lys Arg Arg Gly Arg
                725             730             735
Asp Pro Glu Met Gly Gly Lys Pro Arg Arg Lys Asn Pro Gln Glu Gly
            740             745             750
Leu Tyr Asn Glu Leu Gln Lys Asp Lys Met Ala Glu Ala Tyr Ser Glu
            755             760             765
Ile Gly Met Lys Gly Glu Arg Arg Arg Gly Lys Gly His Asp Gly Leu
            770             775             780
Tyr Gln Gly Leu Ser Thr Ala Thr Lys Asp Thr Tyr Asp Ala Leu His
785             790             795             800
Met Gln Ala Leu Pro Pro Arg
                805

<210> SEQ ID NO 150
<211> LENGTH: 802
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 150

```
Met Ala Leu Pro Val Thr Ala Leu Leu Leu Pro Leu Ala Leu Leu Leu
1               5                   10                  15

His Ala Ala Arg Pro Gly Lys Pro Ile Pro Asn Pro Leu Leu Gly Leu
            20                  25                  30

Asp Ser Thr Gly Gly Gly Gly Ser Gly Gly Gly Ser Gly Gly Gly
        35                  40                  45

Gly Ser Gly Gly Gly Gly Ser Asp Ile Val Met Thr Gln Thr Pro Ala
    50                  55                  60

Ser Val Ser Glu Pro Val Gly Gly Ser Val Thr Ile Lys Cys Gln Ala
65              70                  75                  80

Ser Gln Ser Phe Tyr Asn Leu Leu Ala Trp Tyr Gln Lys Pro Gly
                85                  90                  95

Gln Pro Pro Lys Leu Leu Ile Tyr Asp Ala Ser Asp Leu Ala Ser Gly
            100                 105                 110

Val Pro Ser Arg Phe Lys Gly Ser Gly Ser Gly Thr Asp Phe Thr Leu
        115                 120                 125

Thr Ile Ser Asp Leu Glu Cys Ala Asp Ala Ala Tyr Tyr Cys Gln
130                 135                 140

Ser Ala Asp Gly Ser Ser Tyr Ala Phe Gly Gly Gly Thr Glu Val Val
145                 150                 155                 160

Val Lys Gly Gly Gly Gly Ser Gly Gly Gly Gly Ser Gly Gly Gly
                165                 170                 175

Gly Ser Gly Gly Gly Gly Ser Gln Glu Gln Leu Glu Glu Ser Gly Gly
            180                 185                 190

Gly Leu Val Lys Pro Glu Gly Ser Leu Thr Leu Thr Cys Thr Ala Ser
        195                 200                 205

Gly Val Ser Phe Ser Ser Tyr Trp Ile Tyr Trp Val Arg Gln Ala
210                 215                 220

Pro Gly Lys Gly Leu Glu Trp Ile Ala Cys Ile Tyr Thr Gly Ser Ser
225                 230                 235                 240

Gly Ser Thr Tyr Tyr Ala Ser Trp Ala Lys Gly Arg Phe Thr Val Ser
                245                 250                 255

Glu Thr Ser Ser Thr Thr Val Thr Leu Gln Met Thr Ser Leu Thr Ala
            260                 265                 270

Ala Asp Thr Ala Thr Tyr Phe Cys Ala Arg Ala Ser Ala Trp Thr Tyr
        275                 280                 285

Gly Met Asp Leu Trp Gly Pro Gly Thr Leu Val Thr Val Ser Ser Gly
290                 295                 300

Gly Gly Gly Ser Gly Gly Gly Gly Ser Pro Met Ala Lys Lys Gly Gly
305                 310                 315                 320

Gly Gly Ser Gly Gly Gly Gly Ser Gly Gly Gly Ser Gln Val Gln
                325                 330                 335

Leu Gln Glu Ser Gly Pro Gly Leu Val Lys Pro Ser Glu Thr Leu Ser
            340                 345                 350

Leu Thr Cys Thr Val Ser Gly Gly Ser Ile Ser Tyr Tyr Ser Trp Thr
        355                 360                 365

Trp Val Arg Gln Pro Ala Gly Gln Gly Leu Glu Trp Ile Gly Arg Ile
370                 375                 380

His Ile Ser Gly Val Thr Asn His Asn Pro Ser Leu Lys Ser Arg Val
```

-continued

```
            385                 390                 395                 400
        Ser Met Ser Ile Asp Thr Ser Arg Thr Gln Phe Ser Leu Arg Leu Thr
                        405                 410                 415

Ser Val Thr Ala Ala Asp Thr Ala Val Tyr Phe Cys Ala Arg Ser Gly
                        420                 425                 430

Gly Thr Tyr Ser Ala Phe Asp Ile Trp Gly Gln Gly Thr Met Val Thr
                        435                 440                 445

Val Ser Ser Gly Gly Gly Ser Gly Gly Gly Ser Gly Gly Gly
            450                 455                 460

Gly Ser Gly Gly Gly Ser Glu Ile Val Leu Thr Gln Ser Pro Gly
        465                 470                 475                 480

Thr Leu Ser Leu Ser Pro Gly Glu Arg Ser Thr Leu Ser Cys Arg Ala
                        485                 490                 495

Ser Gln Ser Phe Thr Ser Asn Tyr Leu Ala Trp Tyr Gln Arg Pro
                    500                 505                 510

Gly Gln Ala Pro Arg Leu Leu Ile Tyr Gly Ala Ser Thr Arg Ala Ile
                        515                 520                 525

Gly Ile Pro Asp Arg Phe Ser Gly Ser Gly Ser Gly Thr Asp Phe Thr
        530                 535                 540

Leu Thr Ile Ser Arg Leu Glu Pro Glu Asp Phe Ala Val Tyr Tyr Cys
        545                 550                 555                 560

Gln Gln Tyr Gly Ser Ser Pro Trp Thr Phe Gly Gln Gly Thr Lys Val
                        565                 570                 575

Glu Ile Lys Thr Thr Thr Pro Ala Pro Arg Pro Pro Thr Pro Ala Pro
                        580                 585                 590

Thr Ile Ala Ser Gln Pro Leu Ser Leu Arg Pro Glu Ala Cys Arg Pro
                        595                 600                 605

Ala Ala Gly Gly Ala Val His Thr Arg Gly Leu Asp Phe Ala Cys Asp
                        610                 615                 620

Ile Tyr Ile Trp Ala Pro Leu Ala Gly Thr Cys Gly Val Leu Leu Leu
        625                 630                 635                 640

Ser Leu Val Ile Thr Leu Tyr Cys Lys Arg Gly Arg Lys Lys Leu Leu
                        645                 650                 655

Tyr Ile Phe Lys Gln Pro Phe Met Arg Pro Val Gln Thr Thr Gln Glu
                        660                 665                 670

Glu Asp Gly Cys Ser Cys Arg Phe Pro Glu Glu Glu Glu Gly Gly Cys
                        675                 680                 685

Glu Leu Arg Val Lys Phe Ser Arg Ser Ala Asp Ala Pro Ala Tyr Gln
                        690                 695                 700

Gln Gly Gln Asn Gln Leu Tyr Asn Glu Leu Asn Leu Gly Arg Arg Glu
        705                 710                 715                 720

Glu Tyr Asp Val Leu Asp Lys Arg Arg Gly Arg Asp Pro Glu Met Gly
                        725                 730                 735

Gly Lys Pro Arg Arg Lys Asn Pro Gln Glu Gly Leu Tyr Asn Glu Leu
                        740                 745                 750

Gln Lys Asp Lys Met Ala Glu Ala Tyr Ser Glu Ile Gly Met Lys Gly
                        755                 760                 765

Glu Arg Arg Arg Gly Lys Gly His Asp Gly Leu Tyr Gln Gly Leu Ser
                        770                 775                 780

Thr Ala Thr Lys Asp Thr Tyr Asp Ala Leu His Met Gln Ala Leu Pro
        785                 790                 795                 800

Pro Arg
```

<210> SEQ ID NO 151
<211> LENGTH: 797
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 151

| Met | Ala | Leu | Pro | Val | Thr | Ala | Leu | Leu | Leu | Pro | Leu | Ala | Leu | Leu | Leu |
|---|---|---|---|---|---|---|---|---|---|---|---|---|---|---|---|
| 1 | | | | 5 | | | | | 10 | | | | | 15 | |

| His | Ala | Ala | Arg | Pro | Gly | Lys | Pro | Ile | Pro | Asn | Pro | Leu | Leu | Gly | Leu |
| | | 20 | | | | | 25 | | | | | 30 | | | |

| Asp | Ser | Thr | Gly | Gly | Gly | Gly | Ser | Gly | Gly | Gly | Ser | Gly | Gly | Gly |
| | | 35 | | | | 40 | | | | | 45 | | | |

| Gly | Ser | Gly | Gly | Gly | Gly | Ser | Asp | Ile | Val | Met | Thr | Gln | Thr | Pro | Ala |
| | 50 | | | | | 55 | | | | | 60 | | | | |

| Ser | Val | Ser | Glu | Pro | Val | Gly | Gly | Ser | Val | Thr | Ile | Lys | Cys | Gln | Ala |
| 65 | | | | | 70 | | | | | 75 | | | | | 80 |

| Ser | Gln | Ser | Phe | Tyr | Asn | Leu | Leu | Ala | Trp | Tyr | Gln | Gln | Lys | Pro | Gly |
| | | | | 85 | | | | | 90 | | | | | 95 | |

| Gln | Pro | Pro | Lys | Leu | Leu | Ile | Tyr | Asp | Ala | Ser | Asp | Leu | Ala | Ser | Gly |
| | | | 100 | | | | | 105 | | | | | 110 | | |

| Val | Pro | Ser | Arg | Phe | Lys | Gly | Ser | Gly | Ser | Gly | Thr | Asp | Phe | Thr | Leu |
| | | | 115 | | | | | 120 | | | | | 125 | | |

| Thr | Ile | Ser | Asp | Leu | Glu | Cys | Ala | Asp | Ala | Ala | Tyr | Tyr | Cys | Gln |
| | 130 | | | | | 135 | | | | | 140 | | | | |

| Ser | Ala | Asp | Gly | Ser | Ser | Tyr | Ala | Phe | Gly | Gly | Gly | Thr | Glu | Val | Val |
| 145 | | | | | 150 | | | | | 155 | | | | | 160 |

| Val | Lys | Gly | Gly | Gly | Gly | Ser | Gly | Gly | Gly | Ser | Gly | Gly | Gly |
| | | | | 165 | | | | | 170 | | | | | 175 | |

| Gly | Ser | Gly | Gly | Gly | Gly | Ser | Gln | Glu | Gln | Leu | Glu | Glu | Ser | Gly | Gly |
| | | | 180 | | | | | 185 | | | | | 190 | | |

| Gly | Leu | Val | Lys | Pro | Glu | Gly | Ser | Leu | Thr | Leu | Thr | Cys | Thr | Ala | Ser |
| | | | 195 | | | | | 200 | | | | | 205 | | |

| Gly | Val | Ser | Phe | Ser | Ser | Ser | Tyr | Trp | Ile | Tyr | Trp | Val | Arg | Gln | Ala |
| | 210 | | | | | 215 | | | | | 220 | | | | |

| Pro | Gly | Lys | Gly | Leu | Glu | Trp | Ile | Ala | Cys | Ile | Tyr | Thr | Gly | Ser | Ser |
| 225 | | | | | 230 | | | | | 235 | | | | | 240 |

| Gly | Ser | Thr | Tyr | Tyr | Ala | Ser | Trp | Ala | Lys | Gly | Arg | Phe | Thr | Val | Ser |
| | | | | 245 | | | | | 250 | | | | | 255 | |

| Glu | Thr | Ser | Ser | Thr | Thr | Val | Thr | Leu | Gln | Met | Thr | Ser | Leu | Thr | Ala |
| | | | 260 | | | | | 265 | | | | | 270 | | |

| Ala | Asp | Thr | Ala | Thr | Tyr | Phe | Cys | Ala | Arg | Ala | Ser | Ala | Trp | Thr | Tyr |
| | | | 275 | | | | | 280 | | | | | 285 | | |

| Gly | Met | Asp | Leu | Trp | Gly | Pro | Gly | Thr | Leu | Val | Thr | Val | Ser | Ser | Gly |
| | 290 | | | | | 295 | | | | | 300 | | | | |

| Gly | Gly | Gly | Ser | Gly | Gly | Gly | Ser | Pro | Met | Ala | Lys | Lys | Gly | Gly |
| 305 | | | | | 310 | | | | | 315 | | | | | 320 |

| Gly | Gly | Ser | Gly | Gly | Gly | Ser | Gln | Val | Gln | Leu | Gln | Glu | Ser | Gly |
| | | | | 325 | | | | | 330 | | | | | 335 | |

| Pro | Gly | Leu | Val | Lys | Pro | Ser | Glu | Thr | Leu | Ser | Leu | Thr | Cys | Thr | Val |
| | | | 340 | | | | | 345 | | | | | 350 | | |

| Ser | Gly | Gly | Ser | Ile | Ser | Tyr | Tyr | Ser | Trp | Thr | Trp | Val | Arg | Gln | Pro |
| | | | 355 | | | | | 360 | | | | | 365 | | |

```
Ala Gly Gln Gly Leu Glu Trp Ile Gly Arg Ile His Ile Ser Gly Val
    370                 375                 380

Thr Asn His Asn Pro Ser Leu Lys Ser Arg Val Ser Met Ser Ile Asp
385                 390                 395                 400

Thr Ser Arg Thr Gln Phe Ser Leu Arg Leu Thr Ser Val Thr Ala Ala
                405                 410                 415

Asp Thr Ala Val Tyr Phe Cys Ala Arg Ser Gly Gly Thr Tyr Ser Ala
                420                 425                 430

Phe Asp Ile Trp Gly Gln Gly Thr Met Val Thr Val Ser Ser Gly Gly
            435                 440                 445

Gly Gly Ser Gly Gly Gly Gly Ser Gly Gly Gly Gly Ser Gly Gly Gly
            450                 455                 460

Gly Ser Glu Ile Val Leu Thr Gln Ser Pro Gly Thr Leu Ser Leu Ser
465                 470                 475                 480

Pro Gly Glu Arg Ser Thr Leu Ser Cys Arg Ala Ser Gln Ser Phe Thr
                485                 490                 495

Ser Asn Tyr Leu Ala Trp Tyr Gln Gln Arg Pro Gly Gln Ala Pro Arg
            500                 505                 510

Leu Leu Ile Tyr Gly Ala Ser Thr Arg Ala Ile Gly Ile Pro Asp Arg
        515                 520                 525

Phe Ser Gly Ser Gly Ser Gly Thr Asp Phe Thr Leu Thr Ile Ser Arg
    530                 535                 540

Leu Glu Pro Glu Asp Phe Ala Val Tyr Tyr Cys Gln Gln Tyr Gly Ser
545                 550                 555                 560

Ser Pro Trp Thr Phe Gly Gln Gly Thr Lys Val Glu Ile Lys Thr Thr
                565                 570                 575

Thr Pro Ala Pro Arg Pro Pro Thr Pro Ala Pro Thr Ile Ala Ser Gln
            580                 585                 590

Pro Leu Ser Leu Arg Pro Glu Ala Cys Arg Pro Ala Ala Gly Gly Ala
        595                 600                 605

Val His Thr Arg Gly Leu Asp Phe Ala Cys Asp Ile Tyr Ile Trp Ala
    610                 615                 620

Pro Leu Ala Gly Thr Cys Gly Val Leu Leu Leu Ser Leu Val Ile Thr
625                 630                 635                 640

Leu Tyr Cys Lys Arg Gly Arg Lys Lys Leu Leu Tyr Ile Phe Lys Gln
                645                 650                 655

Pro Phe Met Arg Pro Val Gln Thr Thr Gln Glu Glu Asp Gly Cys Ser
            660                 665                 670

Cys Arg Phe Pro Glu Glu Glu Glu Gly Gly Cys Glu Leu Arg Val Lys
        675                 680                 685

Phe Ser Arg Ser Ala Asp Ala Pro Ala Tyr Gln Gln Gly Gln Asn Gln
    690                 695                 700

Leu Tyr Asn Glu Leu Asn Leu Gly Arg Arg Glu Glu Tyr Asp Val Leu
705                 710                 715                 720

Asp Lys Arg Arg Gly Arg Asp Pro Glu Met Gly Gly Lys Pro Arg Arg
                725                 730                 735

Lys Asn Pro Gln Glu Gly Leu Tyr Asn Glu Leu Gln Lys Asp Lys Met
            740                 745                 750

Ala Glu Ala Tyr Ser Glu Ile Gly Met Lys Gly Glu Arg Arg Arg Gly
        755                 760                 765

Lys Gly His Asp Gly Leu Tyr Gln Gly Leu Ser Thr Ala Thr Lys Asp
    770                 775                 780
```

```
Thr Tyr Asp Ala Leu His Met Gln Ala Leu Pro Pro Arg
785                 790                 795

<210> SEQ ID NO 152
<211> LENGTH: 792
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Met Ala Leu Pro Val Thr Ala Leu Leu Leu Pro Leu Ala Leu Leu Leu
1               5                   10                  15

His Ala Ala Arg Pro Gly Lys Pro Ile Pro Asn Pro Leu Leu Gly Leu
                20                  25                  30

Asp Ser Thr Gly Gly Gly Gly Ser Gly Gly Gly Ser Gly Gly Gly
            35                  40                  45

Gly Ser Gly Gly Gly Gly Ser Asp Ile Val Met Thr Gln Thr Pro Ala
    50                  55                  60

Ser Val Ser Glu Pro Val Gly Gly Ser Val Thr Ile Lys Cys Gln Ala
65                  70                  75                  80

Ser Gln Ser Phe Tyr Asn Leu Leu Ala Trp Tyr Gln Gln Lys Pro Gly
                85                  90                  95

Gln Pro Pro Lys Leu Leu Ile Tyr Asp Ala Ser Asp Leu Ala Ser Gly
                100                 105                 110

Val Pro Ser Arg Phe Lys Gly Ser Gly Ser Gly Thr Asp Phe Thr Leu
            115                 120                 125

Thr Ile Ser Asp Leu Glu Cys Ala Asp Ala Ala Tyr Tyr Cys Gln
130                 135                 140

Ser Ala Asp Gly Ser Ser Tyr Ala Phe Gly Gly Gly Thr Glu Val Val
145                 150                 155                 160

Val Lys Gly Gly Gly Gly Ser Gly Gly Gly Gly Ser Gly Gly Gly
                165                 170                 175

Gly Ser Gly Gly Gly Gly Ser Gln Glu Gln Leu Glu Glu Ser Gly Gly
            180                 185                 190

Gly Leu Val Lys Pro Glu Gly Ser Leu Thr Leu Thr Cys Thr Ala Ser
        195                 200                 205

Gly Val Ser Phe Ser Ser Tyr Trp Ile Tyr Trp Val Arg Gln Ala
    210                 215                 220

Pro Gly Lys Gly Leu Glu Trp Ile Ala Cys Ile Tyr Thr Gly Ser Ser
225                 230                 235                 240

Gly Ser Thr Tyr Tyr Ala Ser Trp Ala Lys Gly Arg Phe Thr Val Ser
                245                 250                 255

Glu Thr Ser Ser Thr Thr Val Thr Leu Gln Met Thr Ser Leu Thr Ala
                260                 265                 270

Ala Asp Thr Ala Thr Tyr Phe Cys Ala Arg Ala Ser Ala Trp Thr Tyr
            275                 280                 285

Gly Met Asp Leu Trp Gly Pro Gly Thr Leu Val Thr Val Ser Ser Gly
        290                 295                 300

Gly Gly Gly Ser Pro Met Ala Lys Lys Gly Gly Gly Ser Gly Gly
305                 310                 315                 320

Gly Gly Ser Gln Val Gln Leu Gln Glu Ser Gly Pro Gly Leu Val Lys
                325                 330                 335

Pro Ser Glu Thr Leu Ser Leu Thr Cys Thr Val Ser Gly Gly Ser Ile
            340                 345                 350
```

```
Ser Tyr Tyr Ser Trp Thr Trp Val Arg Gln Pro Ala Gly Gln Gly Leu
        355                 360                 365

Glu Trp Ile Gly Arg Ile His Ile Ser Gly Val Thr Asn His Asn Pro
    370                 375                 380

Ser Leu Lys Ser Arg Val Ser Met Ser Ile Asp Thr Ser Arg Thr Gln
385                 390                 395                 400

Phe Ser Leu Arg Leu Thr Ser Val Thr Ala Ala Asp Thr Ala Val Tyr
                405                 410                 415

Phe Cys Ala Arg Ser Gly Gly Thr Tyr Ser Ala Phe Asp Ile Trp Gly
            420                 425                 430

Gln Gly Thr Met Val Thr Val Ser Ser Gly Gly Gly Ser Gly Gly
            435                 440                 445

Gly Gly Ser Gly Gly Gly Ser Gly Gly Gly Ser Glu Ile Val
            450                 455                 460

Leu Thr Gln Ser Pro Gly Thr Leu Ser Leu Ser Pro Gly Glu Arg Ser
465                 470                 475                 480

Thr Leu Ser Cys Arg Ala Ser Gln Ser Phe Thr Ser Asn Tyr Leu Ala
                485                 490                 495

Trp Tyr Gln Gln Arg Pro Gly Gln Ala Pro Arg Leu Leu Ile Tyr Gly
            500                 505                 510

Ala Ser Thr Arg Ala Ile Gly Ile Pro Asp Arg Phe Ser Gly Ser Gly
            515                 520                 525

Ser Gly Thr Asp Phe Thr Leu Thr Ile Ser Arg Leu Glu Pro Glu Asp
            530                 535                 540

Phe Ala Val Tyr Tyr Cys Gln Gln Tyr Gly Ser Ser Pro Trp Thr Phe
545                 550                 555                 560

Gly Gln Gly Thr Lys Val Glu Ile Lys Thr Thr Thr Pro Ala Pro Arg
                565                 570                 575

Pro Pro Thr Pro Ala Pro Thr Ile Ala Ser Gln Pro Leu Ser Leu Arg
            580                 585                 590

Pro Glu Ala Cys Arg Pro Ala Ala Gly Gly Ala Val His Thr Arg Gly
            595                 600                 605

Leu Asp Phe Ala Cys Asp Ile Tyr Ile Trp Ala Pro Leu Ala Gly Thr
            610                 615                 620

Cys Gly Val Leu Leu Leu Ser Leu Val Ile Thr Leu Tyr Cys Lys Arg
625                 630                 635                 640

Gly Arg Lys Lys Leu Leu Tyr Ile Phe Lys Gln Pro Phe Met Arg Pro
                645                 650                 655

Val Gln Thr Thr Gln Glu Glu Asp Gly Cys Ser Cys Arg Phe Pro Glu
            660                 665                 670

Glu Glu Glu Gly Gly Cys Glu Leu Arg Val Lys Phe Ser Arg Ser Ala
            675                 680                 685

Asp Ala Pro Ala Tyr Gln Gln Gly Gln Asn Gln Leu Tyr Asn Glu Leu
            690                 695                 700

Asn Leu Gly Arg Arg Glu Glu Tyr Asp Val Leu Asp Lys Arg Arg Gly
705                 710                 715                 720

Arg Asp Pro Glu Met Gly Gly Lys Pro Arg Arg Lys Asn Pro Gln Glu
                725                 730                 735

Gly Leu Tyr Asn Glu Leu Gln Lys Asp Lys Met Ala Glu Ala Tyr Ser
            740                 745                 750

Glu Ile Gly Met Lys Gly Glu Arg Arg Arg Gly Lys Gly His Asp Gly
            755                 760                 765
```

Leu Tyr Gln Gly Leu Ser Thr Ala Thr Lys Asp Thr Tyr Asp Ala Leu
            770                 775                 780

His Met Gln Ala Leu Pro Pro Arg
785                 790

<210> SEQ ID NO 153
<211> LENGTH: 822
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Met Ala Leu Pro Val Thr Ala Leu Leu Leu Pro Leu Ala Leu Leu Leu
1               5                   10                  15

His Ala Ala Arg Pro Gly Lys Pro Ile Pro Asn Pro Leu Leu Gly Leu
            20                  25                  30

Asp Ser Thr Gly Gly Gly Gly Ser Gly Gly Gly Gly Ser Gly Gly Gly
        35                  40                  45

Gly Ser Gly Gly Gly Gly Ser Asp Ile Val Met Thr Gln Thr Pro Ala
    50                  55                  60

Ser Val Ser Glu Pro Val Gly Gly Ser Val Thr Ile Lys Cys Gln Ala
65                  70                  75                  80

Ser Gln Ser Phe Tyr Asn Leu Leu Ala Trp Tyr Gln Gln Lys Pro Gly
                85                  90                  95

Gln Pro Pro Lys Leu Leu Ile Tyr Asp Ala Ser Asp Leu Ala Ser Gly
            100                 105                 110

Val Pro Ser Arg Phe Lys Gly Ser Gly Ser Gly Thr Asp Phe Thr Leu
        115                 120                 125

Thr Ile Ser Asp Leu Glu Cys Ala Asp Ala Ala Tyr Tyr Cys Gln
    130                 135                 140

Ser Ala Asp Gly Ser Ser Tyr Ala Phe Gly Gly Gly Thr Glu Val Val
145                 150                 155                 160

Val Lys Gly Gly Gly Gly Ser Gly Gly Gly Gly Ser Gly Gly Gly Gly
                165                 170                 175

Gly Ser Pro Met Ala Lys Lys Gly Gly Gly Ser Gly Gly Gly Gly
            180                 185                 190

Ser Gly Gly Gly Ser Gln Glu Gln Leu Glu Ser Gly Gly Gly
        195                 200                 205

Leu Val Lys Pro Glu Gly Ser Leu Thr Leu Thr Cys Thr Ala Ser Gly
    210                 215                 220

Val Ser Phe Ser Ser Ser Tyr Trp Ile Tyr Trp Val Arg Gln Ala Pro
225                 230                 235                 240

Gly Lys Gly Leu Glu Trp Ile Ala Cys Ile Tyr Thr Gly Ser Ser Gly
                245                 250                 255

Ser Thr Tyr Tyr Ala Ser Trp Ala Lys Gly Arg Phe Thr Val Ser Glu
            260                 265                 270

Thr Ser Ser Thr Thr Val Thr Leu Gln Met Thr Ser Leu Thr Ala Ala
        275                 280                 285

Asp Thr Ala Thr Tyr Phe Cys Ala Arg Ala Ser Ala Trp Thr Tyr Gly
    290                 295                 300

Met Asp Leu Trp Gly Pro Gly Thr Leu Val Thr Val Ser Ser Gly Gly
305                 310                 315                 320

Gly Gly Ser Gly Gly Gly Gly Ser Gly Gly Gly Gly Ser Pro Met Ala
                325                 330                 335

```
Lys Lys Gly Gly Gly Ser Gly Gly Gly Ser Gly Gly Gly
            340             345             350
Ser Gln Val Gln Leu Gln Glu Ser Gly Pro Gly Leu Val Lys Pro Ser
            355             360             365
Glu Thr Leu Ser Leu Thr Cys Thr Val Ser Gly Ser Ile Ser Tyr
            370             375             380
Tyr Ser Trp Thr Trp Val Arg Gln Pro Ala Gly Gln Gly Leu Glu Trp
385             390             395             400
Ile Gly Arg Ile His Ile Ser Gly Val Thr Asn His Asn Pro Ser Leu
            405             410             415
Lys Ser Arg Val Ser Met Ser Ile Asp Thr Ser Arg Thr Gln Phe Ser
            420             425             430
Leu Arg Leu Thr Ser Val Thr Ala Ala Asp Thr Ala Val Tyr Phe Cys
            435             440             445
Ala Arg Ser Gly Gly Thr Tyr Ser Ala Phe Asp Ile Trp Gly Gln Gly
            450             455             460
Thr Met Val Thr Val Ser Ser Gly Gly Gly Ser Gly Gly Gly Gly
465             470             475             480
Ser Gly Gly Gly Ser Gly Gly Gly Ser Glu Ile Val Leu Thr
            485             490             495
Gln Ser Pro Gly Thr Leu Ser Leu Ser Pro Gly Glu Arg Ser Thr Leu
            500             505             510
Ser Cys Arg Ala Ser Gln Ser Phe Thr Ser Asn Tyr Leu Ala Trp Tyr
            515             520             525
Gln Gln Arg Pro Gly Gln Ala Pro Arg Leu Leu Ile Tyr Gly Ala Ser
            530             535             540
Thr Arg Ala Ile Gly Ile Pro Asp Arg Phe Ser Gly Ser Gly Ser Gly
545             550             555             560
Thr Asp Phe Thr Leu Thr Ile Ser Arg Leu Glu Pro Glu Asp Phe Ala
            565             570             575
Val Tyr Tyr Cys Gln Gln Tyr Gly Ser Ser Pro Trp Thr Phe Gly Gln
            580             585             590
Gly Thr Lys Val Glu Ile Lys Thr Thr Thr Pro Ala Pro Arg Pro Pro
            595             600             605
Thr Pro Ala Pro Thr Ile Ala Ser Gln Pro Leu Ser Leu Arg Pro Glu
            610             615             620
Ala Cys Arg Pro Ala Ala Gly Gly Ala Val His Thr Arg Gly Leu Asp
625             630             635             640
Phe Ala Cys Asp Ile Tyr Ile Trp Ala Pro Leu Ala Gly Thr Cys Gly
            645             650             655
Val Leu Leu Leu Ser Leu Val Ile Thr Leu Tyr Cys Lys Arg Gly Arg
            660             665             670
Lys Lys Leu Leu Tyr Ile Phe Lys Gln Pro Phe Met Arg Pro Val Gln
            675             680             685
Thr Thr Gln Glu Glu Asp Gly Cys Ser Cys Arg Phe Pro Glu Glu Glu
            690             695             700
Glu Gly Gly Cys Glu Leu Arg Val Lys Phe Ser Arg Ser Ala Asp Ala
705             710             715             720
Pro Ala Tyr Gln Gln Gly Gln Asn Gln Leu Tyr Asn Glu Leu Asn Leu
            725             730             735
Gly Arg Arg Glu Glu Tyr Asp Val Leu Asp Lys Arg Arg Gly Arg Asp
            740             745             750
```

```
Pro Glu Met Gly Gly Lys Pro Arg Arg Lys Asn Pro Gln Glu Gly Leu
            755                 760                 765

Tyr Asn Glu Leu Gln Lys Asp Lys Met Ala Glu Ala Tyr Ser Glu Ile
770                 775                 780

Gly Met Lys Gly Glu Arg Arg Arg Gly Lys Gly His Asp Gly Leu Tyr
785                 790                 795                 800

Gln Gly Leu Ser Thr Ala Thr Lys Asp Thr Tyr Asp Ala Leu His Met
            805                 810                 815

Gln Ala Leu Pro Pro Arg
            820

<210> SEQ ID NO 154
<211> LENGTH: 817
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Met Ala Leu Pro Val Thr Ala Leu Leu Leu Pro Leu Ala Leu Leu Leu
1               5                   10                  15

His Ala Ala Arg Pro Gly Lys Pro Ile Pro Asn Pro Leu Leu Gly Leu
            20                  25                  30

Asp Ser Thr Gly Gly Gly Gly Ser Gly Gly Gly Gly Ser Gly Gly Gly
            35                  40                  45

Gly Ser Gly Gly Gly Gly Ser Asp Ile Val Met Thr Gln Thr Pro Ala
50                  55                  60

Ser Val Ser Glu Pro Val Gly Gly Ser Val Thr Ile Lys Cys Gln Ala
65                  70                  75                  80

Ser Gln Ser Phe Tyr Asn Leu Leu Ala Trp Tyr Gln Gln Lys Pro Gly
                85                  90                  95

Gln Pro Pro Lys Leu Leu Ile Tyr Asp Ala Ser Asp Leu Ala Ser Gly
            100                 105                 110

Val Pro Ser Arg Phe Lys Gly Ser Gly Ser Gly Thr Asp Phe Thr Leu
            115                 120                 125

Thr Ile Ser Asp Leu Glu Cys Ala Asp Ala Ala Tyr Tyr Cys Gln
            130                 135                 140

Ser Ala Asp Gly Ser Ser Tyr Ala Phe Gly Gly Gly Thr Glu Val Val
145                 150                 155                 160

Val Lys Gly Gly Gly Gly Ser Gly Gly Gly Gly Ser Gly Gly Gly
                165                 170                 175

Gly Ser Pro Met Ala Lys Lys Gly Gly Gly Ser Gly Gly Gly Gly
            180                 185                 190

Ser Gly Gly Gly Ser Gln Glu Gln Leu Glu Glu Ser Gly Gly Gly
            195                 200                 205

Leu Val Lys Pro Glu Gly Ser Leu Thr Leu Thr Cys Thr Ala Ser Gly
            210                 215                 220

Val Ser Phe Ser Ser Ser Tyr Trp Ile Tyr Trp Val Arg Gln Ala Pro
225                 230                 235                 240

Gly Lys Gly Leu Glu Trp Ile Ala Cys Ile Tyr Thr Gly Ser Ser Gly
                245                 250                 255

Ser Thr Tyr Tyr Ala Ser Trp Ala Lys Gly Arg Phe Thr Val Ser Glu
            260                 265                 270

Thr Ser Ser Thr Thr Val Thr Leu Gln Met Thr Ser Leu Thr Ala Ala
            275                 280                 285
```

```
Asp Thr Ala Thr Tyr Phe Cys Ala Arg Ala Ser Ala Trp Thr Tyr Gly
    290                 295                 300

Met Asp Leu Trp Gly Pro Gly Thr Leu Val Thr Val Ser Ser Gly Gly
305                 310                 315                 320

Gly Gly Ser Gly Gly Gly Ser Pro Met Ala Lys Lys Gly Gly
            325                 330                 335

Gly Ser Gly Gly Gly Ser Gly Gly Gly Ser Gln Val Gln Leu
        340                 345                 350

Gln Glu Ser Gly Pro Gly Leu Val Lys Pro Ser Glu Thr Leu Ser Leu
        355                 360                 365

Thr Cys Thr Val Ser Gly Gly Ser Ile Ser Tyr Tyr Trp Ser Trp
    370                 375                 380

Val Arg Gln Pro Ala Gly Gln Gly Leu Glu Trp Ile Gly Arg Ile His
385                 390                 395                 400

Ile Ser Gly Val Thr Asn His Asn Pro Ser Leu Lys Ser Arg Val Ser
                405                 410                 415

Met Ser Ile Asp Thr Ser Arg Thr Gln Phe Ser Leu Arg Leu Thr Ser
                420                 425                 430

Val Thr Ala Ala Asp Thr Ala Val Tyr Phe Cys Ala Arg Ser Gly Gly
            435                 440                 445

Thr Tyr Ser Ala Phe Asp Ile Trp Gly Gln Gly Thr Met Val Thr Val
    450                 455                 460

Ser Ser Gly Gly Gly Gly Ser Gly Gly Gly Ser Gly Gly Gly Gly
465                 470                 475                 480

Ser Gly Gly Gly Gly Ser Glu Ile Val Leu Thr Gln Ser Pro Gly Thr
                485                 490                 495

Leu Ser Leu Ser Pro Gly Glu Arg Ser Thr Leu Ser Cys Arg Ala Ser
            500                 505                 510

Gln Ser Phe Thr Ser Asn Tyr Leu Ala Trp Tyr Gln Gln Arg Pro Gly
        515                 520                 525

Gln Ala Pro Arg Leu Leu Ile Tyr Gly Ala Ser Thr Arg Ala Ile Gly
        530                 535                 540

Ile Pro Asp Arg Phe Ser Gly Ser Gly Ser Gly Thr Asp Phe Thr Leu
545                 550                 555                 560

Thr Ile Ser Arg Leu Glu Pro Glu Asp Phe Ala Val Tyr Tyr Cys Gln
                565                 570                 575

Gln Tyr Gly Ser Ser Pro Trp Thr Phe Gly Gln Gly Thr Lys Val Glu
            580                 585                 590

Ile Lys Thr Thr Thr Pro Ala Pro Arg Pro Pro Thr Pro Ala Pro Thr
        595                 600                 605

Ile Ala Ser Gln Pro Leu Ser Leu Arg Pro Glu Ala Cys Arg Pro Ala
    610                 615                 620

Ala Gly Gly Ala Val His Thr Arg Gly Leu Asp Phe Ala Cys Asp Ile
625                 630                 635                 640

Tyr Ile Trp Ala Pro Leu Ala Gly Thr Cys Gly Val Leu Leu Leu Ser
                645                 650                 655

Leu Val Ile Thr Leu Tyr Cys Lys Arg Gly Arg Lys Lys Leu Leu Tyr
            660                 665                 670

Ile Phe Lys Gln Pro Phe Met Arg Pro Val Gln Thr Thr Gln Glu Glu
        675                 680                 685

Asp Gly Cys Ser Cys Arg Phe Pro Glu Glu Glu Gly Gly Cys Glu
    690                 695                 700
```

Leu Arg Val Lys Phe Ser Arg Ser Ala Asp Ala Pro Ala Tyr Gln Gln
705                 710                 715                 720

Gly Gln Asn Gln Leu Tyr Asn Glu Leu Asn Leu Gly Arg Arg Glu Glu
            725                 730                 735

Tyr Asp Val Leu Asp Lys Arg Arg Gly Arg Asp Pro Glu Met Gly Gly
        740                 745                 750

Lys Pro Arg Arg Lys Asn Pro Gln Glu Gly Leu Tyr Asn Glu Leu Gln
    755                 760                 765

Lys Asp Lys Met Ala Glu Ala Tyr Ser Glu Ile Gly Met Lys Gly Glu
770                 775                 780

Arg Arg Arg Gly Lys Gly His Asp Gly Leu Tyr Gln Gly Leu Ser Thr
785                 790                 795                 800

Ala Thr Lys Asp Thr Tyr Asp Ala Leu His Met Gln Ala Leu Pro Pro
                805                 810                 815

Arg

<210> SEQ ID NO 155
<211> LENGTH: 812
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Met Ala Leu Pro Val Thr Ala Leu Leu Leu Pro Leu Ala Leu Leu Leu
1               5                   10                  15

His Ala Ala Arg Pro Gly Lys Pro Ile Pro Asn Pro Leu Leu Gly Leu
            20                  25                  30

Asp Ser Thr Gly Gly Gly Gly Ser Gly Gly Gly Gly Ser Gly Gly Gly
        35                  40                  45

Gly Ser Gly Gly Gly Gly Ser Asp Ile Val Met Thr Gln Thr Pro Ala
    50                  55                  60

Ser Val Ser Glu Pro Val Gly Gly Ser Val Thr Ile Lys Cys Gln Ala
65                  70                  75                  80

Ser Gln Ser Phe Tyr Asn Leu Leu Ala Trp Tyr Gln Gln Lys Pro Gly
                85                  90                  95

Gln Pro Pro Lys Leu Leu Ile Tyr Asp Ala Ser Asp Leu Ala Ser Gly
            100                 105                 110

Val Pro Ser Arg Phe Lys Gly Ser Gly Ser Gly Thr Asp Phe Thr Leu
        115                 120                 125

Thr Ile Ser Asp Leu Glu Cys Ala Asp Ala Ala Thr Tyr Tyr Cys Gln
    130                 135                 140

Ser Ala Asp Gly Ser Ser Tyr Ala Phe Gly Gly Gly Thr Glu Val Val
145                 150                 155                 160

Val Lys Gly Gly Gly Gly Ser Gly Gly Gly Gly Ser Gly Gly Gly Gly
                165                 170                 175

Gly Ser Pro Met Ala Lys Lys Gly Gly Gly Ser Gly Gly Gly Gly Gly
            180                 185                 190

Ser Gly Gly Gly Ser Gln Glu Gln Leu Glu Glu Ser Gly Gly Gly
        195                 200                 205

Leu Val Lys Pro Glu Gly Ser Leu Thr Leu Thr Cys Thr Ala Ser Gly
    210                 215                 220

Val Ser Phe Ser Ser Tyr Trp Ile Tyr Trp Val Arg Gln Ala Pro
225                 230                 235                 240

```
Gly Lys Gly Leu Glu Trp Ile Ala Cys Ile Tyr Thr Gly Ser Ser Gly
                245                 250                 255

Ser Thr Tyr Tyr Ala Ser Trp Ala Lys Gly Arg Phe Thr Val Ser Glu
            260                 265                 270

Thr Ser Thr Thr Val Thr Leu Gln Met Thr Ser Leu Thr Ala Ala
        275                 280                 285

Asp Thr Ala Thr Tyr Phe Cys Ala Arg Ala Ser Ala Trp Thr Tyr Gly
    290                 295                 300

Met Asp Leu Trp Gly Pro Gly Thr Leu Val Thr Val Ser Ser Gly Gly
305                 310                 315                 320

Gly Gly Ser Gly Gly Gly Ser Pro Met Ala Lys Lys Gly Gly Gly
            325                 330                 335

Gly Ser Gly Gly Gly Ser Gln Val Gln Leu Gln Glu Ser Gly Pro
        340                 345                 350

Gly Leu Val Lys Pro Ser Glu Thr Leu Ser Leu Thr Cys Thr Val Ser
            355                 360                 365

Gly Gly Ser Ile Ser Tyr Tyr Ser Trp Thr Trp Val Arg Gln Pro Ala
370                 375                 380

Gly Gln Gly Leu Glu Trp Ile Gly Arg Ile His Ile Ser Gly Val Thr
385                 390                 395                 400

Asn His Asn Pro Ser Leu Lys Ser Arg Val Ser Met Ser Ile Asp Thr
                405                 410                 415

Ser Arg Thr Gln Phe Ser Leu Arg Leu Thr Ser Val Thr Ala Ala Asp
            420                 425                 430

Thr Ala Val Tyr Phe Cys Ala Arg Ser Gly Gly Thr Tyr Ser Ala Phe
        435                 440                 445

Asp Ile Trp Gly Gln Gly Thr Met Val Thr Val Ser Ser Gly Gly Gly
    450                 455                 460

Gly Ser Gly Gly Gly Gly Ser Gly Gly Gly Ser Gly Gly Gly Gly
465                 470                 475                 480

Ser Glu Ile Val Leu Thr Gln Ser Pro Gly Thr Leu Ser Leu Ser Pro
                485                 490                 495

Gly Glu Arg Ser Thr Leu Ser Cys Arg Ala Ser Gln Ser Phe Thr Ser
            500                 505                 510

Asn Tyr Leu Ala Trp Tyr Gln Gln Arg Pro Gly Gln Ala Pro Arg Leu
        515                 520                 525

Leu Ile Tyr Gly Ala Ser Thr Arg Ala Ile Gly Ile Pro Asp Arg Phe
    530                 535                 540

Ser Gly Ser Gly Ser Gly Thr Asp Phe Thr Leu Thr Ile Ser Arg Leu
545                 550                 555                 560

Glu Pro Glu Asp Phe Ala Val Tyr Tyr Cys Gln Gln Tyr Gly Ser Ser
                565                 570                 575

Pro Trp Thr Phe Gly Gln Gly Thr Lys Val Glu Ile Lys Thr Thr Thr
            580                 585                 590

Pro Ala Pro Arg Pro Pro Thr Pro Ala Pro Thr Ile Ala Ser Gln Pro
        595                 600                 605

Leu Ser Leu Arg Pro Glu Ala Cys Arg Pro Ala Ala Gly Gly Ala Val
    610                 615                 620

His Thr Arg Gly Leu Asp Phe Ala Cys Asp Ile Tyr Ile Trp Ala Pro
625                 630                 635                 640

Leu Ala Gly Thr Cys Gly Val Leu Leu Leu Ser Leu Val Ile Thr Leu
                645                 650                 655

Tyr Cys Lys Arg Gly Arg Lys Lys Leu Leu Tyr Ile Phe Lys Gln Pro
```

```
                    660                 665                 670
Phe Met Arg Pro Val Gln Thr Thr Gln Glu Glu Asp Gly Cys Ser Cys
                675                 680                 685
Arg Phe Pro Glu Glu Glu Gly Gly Cys Glu Leu Arg Val Lys Phe
            690                 695                 700
Ser Arg Ser Ala Asp Ala Pro Ala Tyr Gln Gln Gly Gln Asn Gln Leu
705                 710                 715                 720
Tyr Asn Glu Leu Asn Leu Gly Arg Arg Glu Glu Tyr Asp Val Leu Asp
                725                 730                 735
Lys Arg Arg Gly Arg Asp Pro Glu Met Gly Gly Lys Pro Arg Arg Lys
                740                 745                 750
Asn Pro Gln Glu Gly Leu Tyr Asn Glu Leu Gln Lys Asp Lys Met Ala
                755                 760                 765
Glu Ala Tyr Ser Glu Ile Gly Met Lys Gly Glu Arg Arg Arg Gly Lys
                770                 775                 780
Gly His Asp Gly Leu Tyr Gln Gly Leu Ser Thr Ala Thr Lys Asp Thr
785                 790                 795                 800
Tyr Asp Ala Leu His Met Gln Ala Leu Pro Pro Arg
                805                 810

<210> SEQ ID NO 156
<211> LENGTH: 807
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

Met Ala Leu Pro Val Thr Ala Leu Leu Leu Pro Leu Ala Leu Leu Leu
1               5                   10                  15
His Ala Ala Arg Pro Gly Lys Pro Ile Pro Asn Pro Leu Leu Gly Leu
                20                  25                  30
Asp Ser Thr Gly Gly Gly Gly Ser Gly Gly Gly Gly Ser Gly Gly Gly
            35                  40                  45
Gly Ser Gly Gly Gly Gly Ser Asp Ile Val Met Thr Gln Thr Pro Ala
        50                  55                  60
Ser Val Ser Glu Pro Val Gly Gly Ser Val Thr Ile Lys Cys Gln Ala
65                  70                  75                  80
Ser Gln Ser Phe Tyr Asn Leu Leu Ala Trp Tyr Gln Gln Lys Pro Gly
                85                  90                  95
Gln Pro Pro Lys Leu Leu Ile Tyr Asp Ala Ser Asp Leu Ala Ser Gly
                100                 105                 110
Val Pro Ser Arg Phe Lys Gly Ser Gly Ser Gly Thr Asp Phe Thr Leu
            115                 120                 125
Thr Ile Ser Asp Leu Glu Cys Ala Asp Ala Ala Tyr Tyr Cys Gln
130                 135                 140
Ser Ala Asp Gly Ser Ser Tyr Ala Phe Gly Gly Thr Glu Val Val
145                 150                 155                 160
Val Lys Gly Gly Gly Gly Ser Gly Gly Gly Gly Ser Gly Gly Gly
            165                 170                 175
Gly Ser Pro Met Ala Lys Lys Gly Gly Gly Ser Gly Gly Gly Gly
                180                 185                 190
Ser Gly Gly Gly Gly Ser Gln Glu Gln Leu Glu Glu Ser Gly Gly Gly
                195                 200                 205
```

-continued

```
Leu Val Lys Pro Glu Gly Ser Leu Thr Leu Thr Cys Thr Ala Ser Gly
    210                 215                 220

Val Ser Phe Ser Ser Tyr Trp Ile Tyr Trp Val Arg Gln Ala Pro
225                 230                 235                 240

Gly Lys Gly Leu Glu Trp Ile Ala Cys Ile Tyr Thr Gly Ser Ser Gly
                245                 250                 255

Ser Thr Tyr Tyr Ala Ser Trp Ala Lys Gly Arg Phe Thr Val Ser Glu
            260                 265                 270

Thr Ser Ser Thr Thr Val Thr Leu Gln Met Thr Ser Leu Thr Ala Ala
        275                 280                 285

Asp Thr Ala Thr Tyr Phe Cys Ala Arg Ala Ser Ala Trp Thr Tyr Gly
290                 295                 300

Met Asp Leu Trp Gly Pro Gly Thr Leu Val Thr Val Ser Ser Gly Gly
305                 310                 315                 320

Gly Gly Ser Pro Met Ala Lys Lys Gly Gly Gly Ser Gly Gly Gly
                325                 330                 335

Gly Ser Gln Val Gln Leu Gln Glu Ser Gly Pro Gly Leu Val Lys Pro
            340                 345                 350

Ser Glu Thr Leu Ser Leu Thr Cys Thr Val Ser Gly Gly Ser Ile Ser
        355                 360                 365

Tyr Tyr Ser Trp Thr Trp Val Arg Gln Pro Ala Gly Gln Gly Leu Glu
370                 375                 380

Trp Ile Gly Arg Ile His Ile Ser Gly Val Thr Asn His Asn Pro Ser
385                 390                 395                 400

Leu Lys Ser Arg Val Ser Met Ser Ile Asp Thr Ser Arg Thr Gln Phe
                405                 410                 415

Ser Leu Arg Leu Thr Ser Val Thr Ala Ala Asp Thr Ala Val Tyr Phe
            420                 425                 430

Cys Ala Arg Ser Gly Gly Thr Tyr Ser Ala Phe Asp Ile Trp Gly Gln
        435                 440                 445

Gly Thr Met Val Thr Val Ser Ser Gly Gly Gly Ser Gly Gly Gly
450                 455                 460

Gly Ser Gly Gly Gly Gly Ser Gly Gly Gly Gly Ser Glu Ile Val Leu
465                 470                 475                 480

Thr Gln Ser Pro Gly Thr Leu Ser Leu Ser Pro Gly Glu Arg Ser Thr
                485                 490                 495

Leu Ser Cys Arg Ala Ser Gln Ser Phe Thr Ser Asn Tyr Leu Ala Trp
            500                 505                 510

Tyr Gln Gln Arg Pro Gly Gln Ala Pro Arg Leu Leu Ile Tyr Gly Ala
        515                 520                 525

Ser Thr Arg Ala Ile Gly Ile Pro Asp Arg Phe Ser Gly Ser Gly Ser
530                 535                 540

Gly Thr Asp Phe Thr Leu Thr Ile Ser Arg Leu Glu Pro Glu Asp Phe
545                 550                 555                 560

Ala Val Tyr Tyr Cys Gln Gln Tyr Gly Ser Ser Pro Trp Thr Phe Gly
                565                 570                 575

Gln Gly Thr Lys Val Glu Ile Lys Thr Thr Thr Pro Ala Pro Arg Pro
            580                 585                 590

Pro Thr Pro Ala Pro Thr Ile Ala Ser Gln Pro Leu Ser Leu Arg Pro
        595                 600                 605

Glu Ala Cys Arg Pro Ala Ala Gly Gly Ala Val His Thr Arg Gly Leu
610                 615                 620

Asp Phe Ala Cys Asp Ile Tyr Ile Trp Ala Pro Leu Ala Gly Thr Cys
```

```
                625                 630                 635                 640
Gly Val Leu Leu Leu Ser Leu Val Ile Thr Leu Tyr Cys Lys Arg Gly
                        645                 650                 655

Arg Lys Lys Leu Leu Tyr Ile Phe Lys Gln Pro Phe Met Arg Pro Val
                660                 665                 670

Gln Thr Thr Gln Glu Glu Asp Gly Cys Ser Cys Arg Phe Pro Glu Glu
            675                 680                 685

Glu Glu Gly Gly Cys Glu Leu Arg Val Lys Phe Ser Arg Ser Ala Asp
690                 695                 700

Ala Pro Ala Tyr Gln Gln Gly Gln Asn Gln Leu Tyr Asn Glu Leu Asn
705                 710                 715                 720

Leu Gly Arg Arg Glu Glu Tyr Asp Val Leu Asp Lys Arg Arg Gly Arg
                725                 730                 735

Asp Pro Glu Met Gly Gly Lys Pro Arg Arg Lys Asn Pro Gln Glu Gly
                740                 745                 750

Leu Tyr Asn Glu Leu Gln Lys Asp Lys Met Ala Glu Ala Tyr Ser Glu
            755                 760                 765

Ile Gly Met Lys Gly Glu Arg Arg Gly Lys Gly His Asp Gly Leu
770                 775                 780

Tyr Gln Gly Leu Ser Thr Ala Thr Lys Asp Thr Tyr Asp Ala Leu His
785                 790                 795                 800

Met Gln Ala Leu Pro Pro Arg
                805

<210> SEQ ID NO 157
<211> LENGTH: 817
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

Met Ala Leu Pro Val Thr Ala Leu Leu Leu Pro Leu Ala Leu Leu Leu
1               5                   10                  15

His Ala Ala Arg Pro Gly Lys Pro Ile Pro Asn Pro Leu Leu Gly Leu
                20                  25                  30

Asp Ser Thr Gly Gly Gly Gly Ser Gly Gly Gly Gly Ser Gly Gly Gly
            35                  40                  45

Gly Ser Gly Gly Gly Gly Ser Asp Ile Val Met Thr Gln Thr Pro Ala
50                  55                  60

Ser Val Ser Glu Pro Val Gly Gly Ser Val Thr Ile Lys Cys Gln Ala
65                  70                  75                  80

Ser Gln Ser Phe Tyr Asn Leu Leu Ala Trp Tyr Gln Gln Lys Pro Gly
                85                  90                  95

Gln Pro Pro Lys Leu Leu Ile Tyr Asp Ala Ser Asp Leu Ala Ser Gly
                100                 105                 110

Val Pro Ser Arg Phe Lys Gly Ser Gly Ser Gly Thr Asp Phe Thr Leu
            115                 120                 125

Thr Ile Ser Asp Leu Glu Cys Ala Asp Ala Ala Tyr Tyr Cys Gln
130                 135                 140

Ser Ala Asp Gly Ser Ser Tyr Ala Phe Gly Gly Gly Thr Glu Val Val
145                 150                 155                 160

Val Lys Gly Gly Gly Gly Ser Gly Gly Gly Gly Ser Gly Gly Gly Gly
                165                 170                 175
```

```
Gly Ser Gly Gly Gly Ser Gln Glu Gln Leu Glu Glu Ser Gly Gly
            180                 185                 190

Gly Leu Val Lys Pro Glu Gly Ser Leu Thr Leu Thr Cys Thr Ala Ser
        195                 200                 205

Gly Val Ser Phe Ser Ser Ser Tyr Trp Ile Tyr Trp Val Arg Gln Ala
    210                 215                 220

Pro Gly Lys Gly Leu Glu Trp Ile Ala Cys Ile Tyr Thr Gly Ser Ser
225                 230                 235                 240

Gly Ser Thr Tyr Tyr Ala Ser Trp Ala Lys Gly Arg Phe Thr Val Ser
                245                 250                 255

Glu Thr Ser Ser Thr Thr Val Thr Leu Gln Met Thr Ser Leu Thr Ala
            260                 265                 270

Ala Asp Thr Ala Thr Tyr Phe Cys Ala Arg Ala Ser Ala Trp Thr Tyr
        275                 280                 285

Gly Met Asp Leu Trp Gly Pro Gly Thr Leu Val Thr Val Ser Ser Gly
    290                 295                 300

Gly Gly Gly Ser Gly Gly Gly Ser Gly Ser Ser Pro Leu Gly Leu
305                 310                 315                 320

Ala Gly Ser Gly Gly Gly Gly Ser Gly Gly Gly Ser Pro Met Ala
                325                 330                 335

Lys Lys Gly Gly Gly Gly Ser Gly Gly Gly Ser Gln Val Gln Leu
            340                 345                 350

Gln Glu Ser Gly Pro Gly Leu Val Lys Pro Ser Glu Thr Leu Ser Leu
        355                 360                 365

Thr Cys Thr Val Ser Gly Gly Ser Ile Ser Tyr Tyr Ser Trp Thr Trp
    370                 375                 380

Val Arg Gln Pro Ala Gly Gln Gly Leu Glu Trp Ile Gly Arg Ile His
385                 390                 395                 400

Ile Ser Gly Val Thr Asn His Asn Pro Ser Leu Lys Ser Arg Val Ser
                405                 410                 415

Met Ser Ile Asp Thr Ser Arg Thr Gln Phe Ser Leu Arg Leu Thr Ser
            420                 425                 430

Val Thr Ala Ala Asp Thr Ala Val Tyr Phe Cys Ala Arg Ser Gly Gly
        435                 440                 445

Thr Tyr Ser Ala Phe Asp Ile Trp Gly Gln Gly Thr Met Val Thr Val
    450                 455                 460

Ser Ser Gly Gly Gly Gly Ser Gly Gly Gly Gly Ser Gly Gly Gly Gly
465                 470                 475                 480

Ser Gly Gly Gly Gly Ser Glu Ile Val Leu Thr Gln Ser Pro Gly Thr
                485                 490                 495

Leu Ser Leu Ser Pro Gly Glu Arg Ser Thr Leu Ser Cys Arg Ala Ser
            500                 505                 510

Gln Ser Phe Thr Ser Asn Tyr Leu Ala Trp Tyr Gln Gln Arg Pro Gly
        515                 520                 525

Gln Ala Pro Arg Leu Leu Ile Tyr Gly Ala Ser Thr Arg Ala Ile Gly
    530                 535                 540

Ile Pro Asp Arg Phe Ser Gly Ser Gly Ser Gly Thr Asp Phe Thr Leu
545                 550                 555                 560

Thr Ile Ser Arg Leu Glu Pro Glu Asp Phe Ala Val Tyr Tyr Cys Gln
                565                 570                 575

Gln Tyr Gly Ser Ser Pro Trp Thr Phe Gly Gln Gly Thr Lys Val Glu
            580                 585                 590

Ile Lys Thr Thr Thr Pro Ala Pro Arg Pro Pro Thr Pro Ala Pro Thr
```

```
                    595                 600                 605
Ile Ala Ser Gln Pro Leu Ser Leu Arg Pro Glu Ala Cys Arg Pro Ala
610                 615                 620

Ala Gly Gly Ala Val His Thr Arg Gly Leu Asp Phe Ala Cys Asp Ile
625                 630                 635                 640

Tyr Ile Trp Ala Pro Leu Ala Gly Thr Cys Gly Val Leu Leu Leu Ser
                    645                 650                 655

Leu Val Ile Thr Leu Tyr Cys Lys Arg Gly Arg Lys Lys Leu Leu Tyr
                660                 665                 670

Ile Phe Lys Gln Pro Phe Met Arg Pro Val Gln Thr Thr Gln Glu Glu
            675                 680                 685

Asp Gly Cys Ser Cys Arg Phe Pro Glu Glu Glu Gly Gly Cys Glu
690                 695                 700

Leu Arg Val Lys Phe Ser Arg Ser Ala Asp Ala Pro Ala Tyr Gln Gln
705                 710                 715                 720

Gly Gln Asn Gln Leu Tyr Asn Glu Leu Asn Leu Gly Arg Arg Glu Glu
                725                 730                 735

Tyr Asp Val Leu Asp Lys Arg Gly Arg Asp Pro Glu Met Gly Gly
                740                 745                 750

Lys Pro Arg Arg Lys Asn Pro Gln Glu Gly Leu Tyr Asn Glu Leu Gln
                755                 760                 765

Lys Asp Lys Met Ala Glu Ala Tyr Ser Glu Ile Gly Met Lys Gly Glu
770                 775                 780

Arg Arg Arg Gly Lys Gly His Asp Gly Leu Tyr Gln Gly Leu Ser Thr
785                 790                 795                 800

Ala Thr Lys Asp Thr Tyr Asp Ala Leu His Met Gln Ala Leu Pro Pro
                    805                 810                 815

Arg

<210> SEQ ID NO 158
<211> LENGTH: 817
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Met Ala Leu Pro Val Thr Ala Leu Leu Leu Pro Leu Ala Leu Leu Leu
1               5                   10                  15

His Ala Ala Arg Pro Gly Lys Pro Ile Pro Asn Pro Leu Leu Gly Leu
                20                  25                  30

Asp Ser Thr Gly Gly Gly Gly Ser Gly Gly Gly Ser Gly Gly Gly
            35                  40                  45

Gly Ser Gly Gly Gly Ser Asp Ile Val Met Thr Gln Thr Pro Ala
50                  55                  60

Ser Val Ser Glu Pro Val Gly Gly Ser Val Thr Ile Lys Cys Gln Ala
65                  70                  75                  80

Ser Gln Ser Phe Tyr Asn Leu Leu Ala Trp Tyr Gln Gln Lys Pro Gly
                85                  90                  95

Gln Pro Pro Lys Leu Leu Ile Tyr Asp Ala Ser Asp Leu Ala Ser Gly
                100                 105                 110

Val Pro Ser Arg Phe Lys Gly Ser Gly Ser Gly Thr Asp Phe Thr Leu
                115                 120                 125

Thr Ile Ser Asp Leu Glu Cys Ala Asp Ala Ala Ala Tyr Tyr Cys Gln
```

```
                130               135               140
Ser Ala Asp Gly Ser Ser Tyr Ala Phe Gly Gly Gly Thr Glu Val Val
145                 150                 155                 160
Val Lys Gly Gly Gly Gly Ser Gly Gly Gly Ser Gly Gly Gly
                165                 170                 175
Gly Ser Gly Gly Gly Gly Ser Gln Glu Gln Leu Glu Glu Ser Gly Gly
                180                 185                 190
Gly Leu Val Lys Pro Glu Gly Ser Leu Thr Leu Thr Cys Thr Ala Ser
                195                 200                 205
Gly Val Ser Phe Ser Ser Ser Tyr Trp Ile Tyr Trp Val Arg Gln Ala
                210                 215                 220
Pro Gly Lys Gly Leu Glu Trp Ile Ala Cys Ile Tyr Thr Gly Ser Ser
225                 230                 235                 240
Gly Ser Thr Tyr Tyr Ala Ser Trp Ala Lys Gly Arg Phe Thr Val Ser
                245                 250                 255
Glu Thr Ser Ser Thr Thr Val Thr Leu Gln Met Thr Ser Leu Thr Ala
                260                 265                 270
Ala Asp Thr Ala Thr Tyr Phe Cys Ala Arg Ala Ser Ala Trp Thr Tyr
                275                 280                 285
Gly Met Asp Leu Trp Gly Pro Gly Thr Leu Val Thr Val Ser Ser Gly
290                 295                 300
Gly Gly Gly Ser Gly Gly Gly Ser Gly Gly Ser Val His Met Pro
305                 310                 315                 320
Leu Gly Phe Leu Gly Pro Gly Gly Gly Gly Ser Pro Met Ala
                325                 330                 335
Lys Lys Gly Gly Gly Ser Gly Gly Gly Gly Ser Gln Val Gln Leu
                340                 345                 350
Gln Glu Ser Gly Pro Gly Leu Val Lys Pro Ser Glu Thr Leu Ser Leu
                355                 360                 365
Thr Cys Thr Val Ser Gly Gly Ser Ile Ser Tyr Tyr Ser Trp Thr Trp
                370                 375                 380
Val Arg Gln Pro Ala Gly Gln Gly Leu Glu Trp Ile Gly Arg Ile His
385                 390                 395                 400
Ile Ser Gly Val Thr Asn His Asn Pro Ser Leu Lys Ser Arg Val Ser
                405                 410                 415
Met Ser Ile Asp Thr Ser Arg Thr Gln Phe Ser Leu Arg Leu Thr Ser
                420                 425                 430
Val Thr Ala Ala Asp Thr Ala Val Tyr Phe Cys Ala Arg Ser Gly Gly
                435                 440                 445
Thr Tyr Ser Ala Phe Asp Ile Trp Gly Gln Gly Thr Met Val Thr Val
                450                 455                 460
Ser Ser Gly Gly Gly Gly Ser Gly Gly Gly Gly Ser Gly Gly Gly Gly
465                 470                 475                 480
Ser Gly Gly Gly Gly Ser Glu Ile Val Leu Thr Gln Ser Pro Gly Thr
                485                 490                 495
Leu Ser Leu Ser Pro Gly Glu Arg Ser Thr Leu Ser Cys Arg Ala Ser
                500                 505                 510
Gln Ser Phe Thr Ser Asn Tyr Leu Ala Trp Tyr Gln Gln Arg Pro Gly
                515                 520                 525
Gln Ala Pro Arg Leu Leu Ile Tyr Gly Ala Ser Thr Arg Ala Ile Gly
                530                 535                 540
Ile Pro Asp Arg Phe Ser Gly Ser Gly Ser Gly Thr Asp Phe Thr Leu
545                 550                 555                 560
```

```
Thr Ile Ser Arg Leu Glu Pro Glu Asp Phe Ala Val Tyr Tyr Cys Gln
                565                 570                 575

Gln Tyr Gly Ser Ser Pro Trp Thr Phe Gly Gln Gly Thr Lys Val Glu
            580                 585                 590

Ile Lys Thr Thr Thr Pro Ala Pro Arg Pro Pro Thr Pro Ala Pro Thr
        595                 600                 605

Ile Ala Ser Gln Pro Leu Ser Leu Arg Pro Glu Ala Cys Arg Pro Ala
    610                 615                 620

Ala Gly Gly Ala Val His Thr Arg Gly Leu Asp Phe Ala Cys Asp Ile
625                 630                 635                 640

Tyr Ile Trp Ala Pro Leu Ala Gly Thr Cys Gly Val Leu Leu Leu Ser
                645                 650                 655

Leu Val Ile Thr Leu Tyr Cys Lys Arg Gly Arg Lys Lys Leu Leu Tyr
            660                 665                 670

Ile Phe Lys Gln Pro Phe Met Arg Pro Val Gln Thr Thr Gln Glu Glu
        675                 680                 685

Asp Gly Cys Ser Cys Arg Phe Pro Glu Glu Glu Glu Gly Gly Cys Glu
    690                 695                 700

Leu Arg Val Lys Phe Ser Arg Ser Ala Asp Ala Pro Ala Tyr Gln Gln
705                 710                 715                 720

Gly Gln Asn Gln Leu Tyr Asn Glu Leu Asn Leu Gly Arg Arg Glu Glu
                725                 730                 735

Tyr Asp Val Leu Asp Lys Arg Arg Gly Arg Asp Pro Glu Met Gly Gly
            740                 745                 750

Lys Pro Arg Arg Lys Asn Pro Gln Glu Gly Leu Tyr Asn Glu Leu Gln
        755                 760                 765

Lys Asp Lys Met Ala Glu Ala Tyr Ser Glu Ile Gly Met Lys Gly Glu
    770                 775                 780

Arg Arg Arg Gly Lys Gly His Asp Gly Leu Tyr Gln Gly Leu Ser Thr
785                 790                 795                 800

Ala Thr Lys Asp Thr Tyr Asp Ala Leu His Met Gln Ala Leu Pro Pro
                805                 810                 815

Arg

<210> SEQ ID NO 159
<211> LENGTH: 817
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Met Ala Leu Pro Val Thr Ala Leu Leu Leu Pro Leu Ala Leu Leu Leu
1               5                   10                  15

His Ala Ala Arg Pro Gly Lys Pro Ile Pro Asn Pro Leu Leu Gly Leu
            20                  25                  30

Asp Ser Thr Gly Gly Gly Gly Ser Gly Gly Gly Ser Gly Gly Gly Gly
        35                  40                  45

Gly Ser Gly Gly Gly Gly Ser Asp Ile Val Met Thr Gln Thr Pro Ala
    50                  55                  60

Ser Val Ser Glu Pro Val Gly Gly Ser Val Thr Ile Lys Cys Gln Ala
65                  70                  75                  80

Ser Gln Ser Phe Tyr Asn Leu Leu Ala Trp Tyr Gln Gln Lys Pro Gly
                85                  90                  95
```

-continued

```
Gln Pro Pro Lys Leu Leu Ile Tyr Asp Ala Ser Asp Leu Ala Ser Gly
                100                 105                 110

Val Pro Ser Arg Phe Lys Gly Ser Gly Ser Gly Thr Asp Phe Thr Leu
            115                 120                 125

Thr Ile Ser Asp Leu Glu Cys Ala Asp Ala Ala Tyr Tyr Cys Gln
130                 135                 140

Ser Ala Asp Gly Ser Ser Tyr Ala Phe Gly Gly Gly Thr Glu Val Val
145                 150                 155                 160

Val Lys Gly Gly Gly Gly Ser Gly Gly Gly Ser Gly Gly Gly
                165                 170                 175

Gly Ser Gly Gly Gly Ser Gln Glu Gln Leu Glu Glu Ser Gly Gly
            180                 185                 190

Gly Leu Val Lys Pro Glu Gly Ser Leu Thr Leu Thr Cys Thr Ala Ser
            195                 200                 205

Gly Val Ser Phe Ser Ser Ser Tyr Trp Ile Tyr Trp Val Arg Gln Ala
    210                 215                 220

Pro Gly Lys Gly Leu Glu Trp Ile Ala Cys Ile Tyr Thr Gly Ser Ser
225                 230                 235                 240

Gly Ser Thr Tyr Tyr Ala Ser Trp Ala Lys Gly Arg Phe Thr Val Ser
            245                 250                 255

Glu Thr Ser Ser Thr Thr Val Thr Leu Gln Met Thr Ser Leu Thr Ala
            260                 265                 270

Ala Asp Thr Ala Thr Tyr Phe Cys Ala Arg Ala Ser Ala Trp Thr Tyr
        275                 280                 285

Gly Met Asp Leu Trp Gly Pro Gly Thr Leu Val Thr Val Ser Ser Gly
        290                 295                 300

Gly Gly Gly Ser Gly Gly Gly Ser Gly Gly Ser Pro Leu Gly Val
305                 310                 315                 320

Arg Gly Lys Gly Gly Gly Gly Ser Gly Gly Gly Ser Pro Met Ala
            325                 330                 335

Lys Lys Gly Gly Gly Gly Ser Gly Gly Gly Gly Ser Gln Val Gln Leu
            340                 345                 350

Gln Glu Ser Gly Pro Gly Leu Val Lys Pro Ser Glu Thr Leu Ser Leu
        355                 360                 365

Thr Cys Thr Val Ser Gly Gly Ser Ile Ser Tyr Tyr Ser Trp Thr Trp
    370                 375                 380

Val Arg Gln Pro Ala Gly Gln Gly Leu Glu Trp Ile Gly Arg Ile His
385                 390                 395                 400

Ile Ser Gly Val Thr Asn His Asn Pro Ser Leu Lys Ser Arg Val Ser
            405                 410                 415

Met Ser Ile Asp Thr Ser Arg Thr Gln Phe Ser Leu Arg Leu Thr Ser
            420                 425                 430

Val Thr Ala Ala Asp Thr Ala Val Tyr Phe Cys Ala Arg Ser Gly Gly
        435                 440                 445

Thr Tyr Ser Ala Phe Asp Ile Trp Gly Gln Gly Thr Met Val Thr Val
        450                 455                 460

Ser Ser Gly Gly Gly Gly Ser Gly Gly Gly Gly Ser Gly Gly Gly Gly
465                 470                 475                 480

Ser Gly Gly Gly Gly Ser Glu Ile Val Leu Thr Gln Ser Pro Gly Thr
            485                 490                 495

Leu Ser Leu Ser Pro Gly Glu Arg Ser Thr Leu Ser Cys Arg Ala Ser
        500                 505                 510
```

Gln Ser Phe Thr Ser Asn Tyr Leu Ala Trp Tyr Gln Gln Arg Pro Gly
515                 520                 525

Gln Ala Pro Arg Leu Leu Ile Tyr Gly Ala Ser Thr Arg Ala Ile Gly
530                 535                 540

Ile Pro Asp Arg Phe Ser Gly Ser Gly Ser Gly Thr Asp Phe Thr Leu
545                 550                 555                 560

Thr Ile Ser Arg Leu Glu Pro Glu Asp Phe Ala Val Tyr Tyr Cys Gln
                565                 570                 575

Gln Tyr Gly Ser Ser Pro Trp Thr Phe Gly Gln Gly Thr Lys Val Glu
            580                 585                 590

Ile Lys Thr Thr Thr Pro Ala Pro Arg Pro Pro Thr Pro Ala Pro Thr
        595                 600                 605

Ile Ala Ser Gln Pro Leu Ser Leu Arg Pro Glu Ala Cys Arg Pro Ala
    610                 615                 620

Ala Gly Gly Ala Val His Thr Arg Gly Leu Asp Phe Ala Cys Asp Ile
625                 630                 635                 640

Tyr Ile Trp Ala Pro Leu Ala Gly Thr Cys Gly Val Leu Leu Leu Ser
                645                 650                 655

Leu Val Ile Thr Leu Tyr Cys Lys Arg Gly Arg Lys Lys Leu Leu Tyr
                660                 665                 670

Ile Phe Lys Gln Pro Phe Met Arg Pro Val Gln Thr Thr Gln Glu Glu
            675                 680                 685

Asp Gly Cys Ser Cys Arg Phe Pro Glu Glu Glu Glu Gly Gly Cys Glu
        690                 695                 700

Leu Arg Val Lys Phe Ser Arg Ser Ala Asp Ala Pro Ala Tyr Gln Gln
705                 710                 715                 720

Gly Gln Asn Gln Leu Tyr Asn Glu Leu Asn Leu Gly Arg Arg Glu Glu
                725                 730                 735

Tyr Asp Val Leu Asp Lys Arg Arg Gly Arg Asp Pro Glu Met Gly Gly
                740                 745                 750

Lys Pro Arg Arg Lys Asn Pro Gln Glu Gly Leu Tyr Asn Glu Leu Gln
            755                 760                 765

Lys Asp Lys Met Ala Glu Ala Tyr Ser Glu Ile Gly Met Lys Gly Glu
770                 775                 780

Arg Arg Arg Gly Lys Gly His Asp Gly Leu Tyr Gln Gly Leu Ser Thr
785                 790                 795                 800

Ala Thr Lys Asp Thr Tyr Asp Ala Leu His Met Gln Ala Leu Pro Pro
                805                 810                 815

Arg

<210> SEQ ID NO 160
<211> LENGTH: 817
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Met Ala Leu Pro Val Thr Ala Leu Leu Leu Pro Leu Ala Leu Leu Leu
1               5                   10                  15

His Ala Ala Arg Pro Gly Lys Pro Ile Pro Asn Pro Leu Leu Gly Leu
                20                  25                  30

Asp Ser Thr Gly Gly Gly Gly Ser Gly Gly Gly Ser Gly Gly Gly
            35                  40                  45

Gly Ser Gly Gly Gly Ser Asp Ile Val Met Thr Gln Thr Pro Ala
50                    55                    60

Ser Val Ser Glu Pro Val Gly Ser Val Thr Ile Lys Cys Gln Ala
65               70                    75                    80

Ser Gln Ser Phe Tyr Asn Leu Leu Ala Trp Tyr Gln Lys Pro Gly
                85                    90                    95

Gln Pro Pro Lys Leu Leu Ile Tyr Asp Ala Ser Asp Leu Ala Ser Gly
            100                   105                   110

Val Pro Ser Arg Phe Lys Gly Ser Gly Ser Gly Thr Asp Phe Thr Leu
            115                   120                   125

Thr Ile Ser Asp Leu Glu Cys Ala Asp Ala Ala Tyr Tyr Cys Gln
130                   135                   140

Ser Ala Asp Gly Ser Ser Tyr Ala Phe Gly Gly Gly Thr Glu Val Val
145                   150                   155                   160

Val Lys Gly Gly Gly Gly Ser Gly Gly Gly Ser Gly Gly Gly
                165                   170                   175

Gly Ser Gly Gly Gly Ser Gln Glu Gln Leu Glu Glu Ser Gly Gly
            180                   185                   190

Gly Leu Val Lys Pro Glu Gly Ser Leu Thr Leu Thr Cys Thr Ala Ser
            195                   200                   205

Gly Val Ser Phe Ser Ser Tyr Trp Ile Tyr Trp Val Arg Gln Ala
210                   215                   220

Pro Gly Lys Gly Leu Glu Trp Ile Ala Cys Ile Tyr Thr Gly Ser Ser
225                   230                   235                   240

Gly Ser Thr Tyr Tyr Ala Ser Trp Ala Lys Gly Arg Phe Thr Val Ser
                245                   250                   255

Glu Thr Ser Ser Thr Thr Val Thr Leu Gln Met Thr Ser Leu Thr Ala
            260                   265                   270

Ala Asp Thr Ala Thr Tyr Phe Cys Ala Arg Ala Ser Ala Trp Thr Tyr
            275                   280                   285

Gly Met Asp Leu Trp Gly Pro Gly Thr Leu Val Thr Val Ser Ser Gly
290                   295                   300

Gly Gly Gly Ser Gly Gly Gly Gly Ser Gly Gly Ser Ser Pro Leu Gly
305                   310                   315                   320

Leu Ala Gly Ser Gly Gly Gly Ser Arg Gln Ala Arg Val Val
            325                   330                   335

Asn Gly Gly Gly Gly Ser Gly Gly Gly Ser Gln Val Gln Leu
                340                   345                   350

Gln Glu Ser Gly Pro Gly Leu Val Lys Pro Ser Glu Thr Leu Ser Leu
355                   360                   365

Thr Cys Thr Val Ser Gly Gly Ser Ile Ser Tyr Tyr Ser Trp Thr Trp
370                   375                   380

Val Arg Gln Pro Ala Gly Gln Gly Leu Glu Trp Ile Gly Arg Ile His
385                   390                   395                   400

Ile Ser Gly Val Thr Asn His Asn Pro Ser Leu Lys Ser Arg Val Ser
                405                   410                   415

Met Ser Ile Asp Thr Ser Arg Thr Gln Phe Ser Leu Arg Leu Thr Ser
            420                   425                   430

Val Thr Ala Ala Asp Thr Ala Val Tyr Phe Cys Ala Arg Ser Gly Gly
            435                   440                   445

Thr Tyr Ser Ala Phe Asp Ile Trp Gly Gln Gly Thr Met Val Thr Val
450                   455                   460

Ser Ser Gly Gly Gly Gly Ser Gly Gly Gly Gly Ser Gly Gly Gly Gly

```
                465                 470                 475                 480
Ser Gly Gly Gly Ser Glu Ile Val Leu Thr Gln Ser Pro Gly Thr
                485                 490                 495

Leu Ser Leu Ser Pro Gly Glu Arg Ser Thr Leu Ser Cys Arg Ala Ser
            500                 505                 510

Gln Ser Phe Thr Ser Asn Tyr Leu Ala Trp Tyr Gln Arg Pro Gly
            515                 520                 525

Gln Ala Pro Arg Leu Leu Ile Tyr Gly Ala Ser Thr Arg Ala Ile Gly
        530                 535                 540

Ile Pro Asp Arg Phe Ser Gly Ser Gly Ser Gly Thr Asp Phe Thr Leu
545                 550                 555                 560

Thr Ile Ser Arg Leu Glu Pro Glu Asp Phe Ala Val Tyr Tyr Cys Gln
                565                 570                 575

Gln Tyr Gly Ser Ser Pro Trp Thr Phe Gly Gln Gly Thr Lys Val Glu
            580                 585                 590

Ile Lys Thr Thr Thr Pro Ala Pro Arg Pro Pro Thr Pro Ala Pro Thr
        595                 600                 605

Ile Ala Ser Gln Pro Leu Ser Leu Arg Pro Glu Ala Cys Arg Pro Ala
610                 615                 620

Ala Gly Gly Ala Val His Thr Arg Gly Leu Asp Phe Ala Cys Asp Ile
625                 630                 635                 640

Tyr Ile Trp Ala Pro Leu Ala Gly Thr Cys Gly Val Leu Leu Leu Ser
                645                 650                 655

Leu Val Ile Thr Leu Tyr Cys Lys Arg Gly Arg Lys Lys Leu Leu Tyr
            660                 665                 670

Ile Phe Lys Gln Pro Phe Met Arg Pro Val Gln Thr Thr Gln Glu Glu
        675                 680                 685

Asp Gly Cys Ser Cys Arg Phe Pro Glu Glu Glu Glu Gly Gly Cys Glu
            690                 695                 700

Leu Arg Val Lys Phe Ser Arg Ser Ala Asp Ala Pro Ala Tyr Gln Gln
705                 710                 715                 720

Gly Gln Asn Gln Leu Tyr Asn Glu Leu Asn Leu Gly Arg Arg Glu Glu
                725                 730                 735

Tyr Asp Val Leu Asp Lys Arg Arg Gly Arg Asp Pro Glu Met Gly Gly
            740                 745                 750

Lys Pro Arg Arg Lys Asn Pro Gln Glu Gly Leu Tyr Asn Glu Leu Gln
        755                 760                 765

Lys Asp Lys Met Ala Glu Ala Tyr Ser Glu Ile Gly Met Lys Gly Glu
770                 775                 780

Arg Arg Arg Gly Lys Gly His Asp Gly Leu Tyr Gln Gly Leu Ser Thr
785                 790                 795                 800

Ala Thr Lys Asp Thr Tyr Asp Ala Leu His Met Gln Ala Leu Pro Pro
                805                 810                 815

Arg

<210> SEQ ID NO 161
<211> LENGTH: 817
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

Met Ala Leu Pro Val Thr Ala Leu Leu Leu Pro Leu Ala Leu Leu Leu
```

-continued

```
1               5                   10                  15
His Ala Ala Arg Pro Gly Lys Pro Ile Pro Asn Pro Leu Leu Gly Leu
            20                  25                  30

Asp Ser Thr Gly Gly Gly Ser Gly Gly Gly Ser Gly Gly Gly
            35                  40                  45

Gly Ser Gly Gly Gly Ser Asp Ile Val Met Thr Gln Thr Pro Ala
50                  55                  60

Ser Val Ser Glu Pro Val Gly Ser Val Thr Ile Lys Cys Gln Ala
65                  70                  75                  80

Ser Gln Ser Phe Tyr Asn Leu Leu Ala Trp Tyr Gln Gln Lys Pro Gly
                85                  90                  95

Gln Pro Pro Lys Leu Leu Ile Tyr Asp Ala Ser Asp Leu Ala Ser Gly
            100                 105                 110

Val Pro Ser Arg Phe Lys Gly Ser Gly Ser Gly Thr Asp Phe Thr Leu
            115                 120                 125

Thr Ile Ser Asp Leu Glu Cys Ala Asp Ala Ala Tyr Tyr Cys Gln
130                 135                 140

Ser Ala Asp Gly Ser Ser Tyr Ala Phe Gly Gly Gly Thr Glu Val Val
145                 150                 155                 160

Val Lys Gly Gly Gly Gly Ser Gly Gly Gly Ser Gly Gly Gly
            165                 170                 175

Gly Ser Gly Gly Gly Ser Gln Glu Gln Leu Glu Glu Ser Gly Gly
            180                 185                 190

Gly Leu Val Lys Pro Glu Gly Ser Leu Thr Leu Thr Cys Thr Ala Ser
            195                 200                 205

Gly Val Ser Phe Ser Ser Ser Tyr Trp Ile Tyr Trp Val Arg Gln Ala
210                 215                 220

Pro Gly Lys Gly Leu Glu Trp Ile Ala Cys Ile Tyr Thr Gly Ser Ser
225                 230                 235                 240

Gly Ser Thr Tyr Tyr Ala Ser Trp Ala Lys Gly Arg Phe Thr Val Ser
            245                 250                 255

Glu Thr Ser Ser Thr Thr Val Thr Leu Gln Met Thr Ser Leu Thr Ala
            260                 265                 270

Ala Asp Thr Ala Thr Tyr Phe Cys Ala Arg Ala Ser Ala Trp Thr Tyr
            275                 280                 285

Gly Met Asp Leu Trp Gly Pro Gly Thr Leu Val Thr Val Ser Ser Gly
            290                 295                 300

Gly Gly Gly Ser Gly Gly Gly Gly Ser Gly Gly Ser Val His Met Pro
305                 310                 315                 320

Leu Gly Phe Leu Gly Pro Gly Gly Ser Arg Gln Ala Arg Val Val
            325                 330                 335

Asn Gly Gly Gly Gly Ser Gly Gly Gly Gly Ser Gln Val Gln Leu
            340                 345                 350

Gln Glu Ser Gly Pro Gly Leu Val Lys Pro Ser Glu Thr Leu Ser Leu
            355                 360                 365

Thr Cys Thr Val Ser Gly Gly Ser Ile Ser Tyr Tyr Ser Trp Thr Trp
370                 375                 380

Val Arg Gln Pro Ala Gly Gln Gly Leu Glu Trp Ile Gly Arg Ile His
385                 390                 395                 400

Ile Ser Gly Val Thr Asn His Asn Pro Ser Leu Lys Ser Arg Val Ser
                405                 410                 415

Met Ser Ile Asp Thr Ser Arg Thr Gln Phe Ser Leu Arg Leu Thr Ser
            420                 425                 430
```

```
Val Thr Ala Ala Asp Thr Ala Val Tyr Phe Cys Ala Arg Ser Gly Gly
            435                 440                 445

Thr Tyr Ser Ala Phe Asp Ile Trp Gly Gln Gly Thr Met Val Thr Val
    450                 455                 460

Ser Ser Gly Gly Gly Gly Ser Gly Gly Gly Gly Ser Gly Gly Gly Gly
465                 470                 475                 480

Ser Gly Gly Gly Ser Glu Ile Val Leu Thr Gln Ser Pro Gly Thr
                485                 490                 495

Leu Ser Leu Ser Pro Gly Glu Arg Ser Thr Leu Ser Cys Arg Ala Ser
            500                 505                 510

Gln Ser Phe Thr Ser Asn Tyr Leu Ala Trp Tyr Gln Gln Arg Pro Gly
    515                 520                 525

Gln Ala Pro Arg Leu Leu Ile Tyr Gly Ala Ser Thr Arg Ala Ile Gly
530                 535                 540

Ile Pro Asp Arg Phe Ser Gly Ser Gly Ser Gly Thr Asp Phe Thr Leu
545                 550                 555                 560

Thr Ile Ser Arg Leu Glu Pro Glu Asp Phe Ala Val Tyr Tyr Cys Gln
                565                 570                 575

Gln Tyr Gly Ser Ser Pro Trp Thr Phe Gly Gln Gly Thr Lys Val Glu
            580                 585                 590

Ile Lys Thr Thr Thr Pro Ala Pro Arg Pro Pro Thr Pro Ala Pro Thr
    595                 600                 605

Ile Ala Ser Gln Pro Leu Ser Leu Arg Pro Glu Ala Cys Arg Pro Ala
610                 615                 620

Ala Gly Gly Ala Val His Thr Arg Gly Leu Asp Phe Ala Cys Asp Ile
625                 630                 635                 640

Tyr Ile Trp Ala Pro Leu Ala Gly Thr Cys Gly Val Leu Leu Leu Ser
                645                 650                 655

Leu Val Ile Thr Leu Tyr Cys Lys Arg Gly Arg Lys Lys Leu Leu Tyr
            660                 665                 670

Ile Phe Lys Gln Pro Phe Met Arg Pro Val Gln Thr Thr Gln Glu Glu
    675                 680                 685

Asp Gly Cys Ser Cys Arg Phe Pro Glu Glu Glu Glu Gly Gly Cys Glu
690                 695                 700

Leu Arg Val Lys Phe Ser Arg Ser Ala Asp Ala Pro Ala Tyr Gln Gln
705                 710                 715                 720

Gly Gln Asn Gln Leu Tyr Asn Glu Leu Asn Leu Gly Arg Arg Glu Glu
                725                 730                 735

Tyr Asp Val Leu Asp Lys Arg Arg Gly Arg Asp Pro Glu Met Gly Gly
            740                 745                 750

Lys Pro Arg Arg Lys Asn Pro Gln Glu Gly Leu Tyr Asn Glu Leu Gln
    755                 760                 765

Lys Asp Lys Met Ala Glu Ala Tyr Ser Glu Ile Gly Met Lys Gly Glu
770                 775                 780

Arg Arg Arg Gly Lys Gly His Asp Gly Leu Tyr Gln Gly Leu Ser Thr
785                 790                 795                 800

Ala Thr Lys Asp Thr Tyr Asp Ala Leu His Met Gln Ala Leu Pro Pro
                805                 810                 815

Arg

<210> SEQ ID NO 162
<211> LENGTH: 817
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 162

```
Met Ala Leu Pro Val Thr Ala Leu Leu Leu Pro Leu Ala Leu Leu Leu
1               5                   10                  15

His Ala Ala Arg Pro Gly Lys Pro Ile Pro Asn Pro Leu Leu Gly Leu
            20                  25                  30

Asp Ser Thr Gly Gly Gly Gly Ser Gly Gly Gly Ser Gly Gly Gly
        35                  40                  45

Gly Ser Gly Gly Gly Gly Ser Asp Ile Val Met Thr Gln Thr Pro Ala
    50                  55                  60

Ser Val Ser Glu Pro Val Gly Ser Val Thr Ile Lys Cys Gln Ala
65              70                  75                  80

Ser Gln Ser Phe Tyr Asn Leu Leu Ala Trp Tyr Gln Gln Lys Pro Gly
                85                  90                  95

Gln Pro Pro Lys Leu Leu Ile Tyr Asp Ala Ser Asp Leu Ala Ser Gly
            100                 105                 110

Val Pro Ser Arg Phe Lys Gly Ser Gly Ser Gly Thr Asp Phe Thr Leu
        115                 120                 125

Thr Ile Ser Asp Leu Glu Cys Ala Asp Ala Ala Tyr Tyr Cys Gln
130                 135                 140

Ser Ala Asp Gly Ser Ser Tyr Ala Phe Gly Gly Gly Thr Glu Val Val
145                 150                 155                 160

Val Lys Gly Gly Gly Gly Ser Gly Gly Gly Ser Gly Gly Gly
                165                 170                 175

Gly Ser Gly Gly Gly Gly Ser Gln Glu Gln Leu Glu Glu Ser Gly Gly
        180                 185                 190

Gly Leu Val Lys Pro Glu Gly Ser Leu Thr Leu Thr Cys Thr Ala Ser
    195                 200                 205

Gly Val Ser Phe Ser Ser Ser Tyr Trp Ile Tyr Trp Val Arg Gln Ala
210                 215                 220

Pro Gly Lys Gly Leu Glu Trp Ile Ala Cys Ile Tyr Thr Gly Ser Ser
225                 230                 235                 240

Gly Ser Thr Tyr Tyr Ala Ser Trp Ala Lys Gly Arg Phe Thr Val Ser
                245                 250                 255

Glu Thr Ser Ser Thr Val Thr Leu Gln Met Thr Ser Leu Thr Ala
            260                 265                 270

Ala Asp Thr Ala Thr Tyr Phe Cys Ala Arg Ala Ser Ala Trp Thr Tyr
        275                 280                 285

Gly Met Asp Leu Trp Gly Pro Gly Thr Leu Val Thr Val Ser Ser Gly
    290                 295                 300

Gly Gly Ser Gly Gly Gly Ser Gly Gly Ser Pro Leu Gly Val
305                 310                 315                 320

Arg Gly Lys Gly Gly Ser Gly Gly Ser Arg Gln Ala Arg Val Val
                325                 330                 335

Asn Gly Gly Gly Gly Ser Gly Gly Gly Ser Gln Val Gln Leu
            340                 345                 350

Gln Glu Ser Gly Pro Gly Leu Val Lys Pro Ser Glu Thr Leu Ser Leu
        355                 360                 365

Thr Cys Thr Val Ser Gly Gly Ser Ile Ser Tyr Tyr Ser Trp Thr Trp
370                 375                 380
```

```
Val Arg Gln Pro Ala Gly Gln Gly Leu Glu Trp Ile Gly Arg Ile His
385                 390                 395                 400

Ile Ser Gly Val Thr Asn His Asn Pro Ser Leu Lys Ser Arg Val Ser
                405                 410                 415

Met Ser Ile Asp Thr Ser Arg Thr Gln Phe Ser Leu Arg Leu Thr Ser
            420                 425                 430

Val Thr Ala Ala Asp Thr Ala Val Tyr Phe Cys Ala Arg Ser Gly Gly
        435                 440                 445

Thr Tyr Ser Ala Phe Asp Ile Trp Gly Gln Gly Thr Met Val Thr Val
    450                 455                 460

Ser Ser Gly Gly Gly Gly Ser Gly Gly Gly Gly Ser Gly Gly Gly Gly
465                 470                 475                 480

Ser Gly Gly Gly Gly Ser Glu Ile Val Leu Thr Gln Ser Pro Gly Thr
            485                 490                 495

Leu Ser Leu Ser Pro Gly Glu Arg Ser Thr Leu Ser Cys Arg Ala Ser
            500                 505                 510

Gln Ser Phe Thr Ser Asn Tyr Leu Ala Trp Tyr Gln Gln Arg Pro Gly
    515                 520                 525

Gln Ala Pro Arg Leu Leu Ile Tyr Gly Ala Ser Thr Arg Ala Ile Gly
530                 535                 540

Ile Pro Asp Arg Phe Ser Gly Ser Gly Ser Gly Thr Asp Phe Thr Leu
545                 550                 555                 560

Thr Ile Ser Arg Leu Glu Pro Glu Asp Phe Ala Val Tyr Tyr Cys Gln
                565                 570                 575

Gln Tyr Gly Ser Ser Pro Trp Thr Phe Gly Gln Gly Thr Lys Val Glu
            580                 585                 590

Ile Lys Thr Thr Thr Pro Ala Pro Arg Pro Pro Thr Pro Ala Pro Thr
        595                 600                 605

Ile Ala Ser Gln Pro Leu Ser Leu Arg Pro Glu Ala Cys Arg Pro Ala
    610                 615                 620

Ala Gly Gly Ala Val His Thr Arg Gly Leu Asp Phe Ala Cys Asp Ile
625                 630                 635                 640

Tyr Ile Trp Ala Pro Leu Ala Gly Thr Cys Gly Val Leu Leu Leu Ser
                645                 650                 655

Leu Val Ile Thr Leu Tyr Cys Lys Arg Gly Arg Lys Lys Leu Leu Tyr
            660                 665                 670

Ile Phe Lys Gln Pro Phe Met Arg Pro Val Gln Thr Thr Gln Glu Glu
        675                 680                 685

Asp Gly Cys Ser Cys Arg Phe Pro Glu Glu Glu Glu Gly Gly Cys Glu
    690                 695                 700

Leu Arg Val Lys Phe Ser Arg Ser Ala Asp Ala Pro Ala Tyr Gln Gln
705                 710                 715                 720

Gly Gln Asn Gln Leu Tyr Asn Glu Leu Asn Leu Gly Arg Arg Glu Glu
                725                 730                 735

Tyr Asp Val Leu Asp Lys Arg Arg Gly Arg Asp Pro Glu Met Gly Gly
            740                 745                 750

Lys Pro Arg Arg Lys Asn Pro Gln Glu Gly Leu Tyr Asn Glu Leu Gln
        755                 760                 765

Lys Asp Lys Met Ala Glu Ala Tyr Ser Glu Ile Gly Met Lys Gly Glu
    770                 775                 780

Arg Arg Arg Gly Lys Gly His Asp Gly Leu Tyr Gln Gly Leu Ser Thr
785                 790                 795                 800

Ala Thr Lys Asp Thr Tyr Asp Ala Leu His Met Gln Ala Leu Pro Pro
```

Arg

<210> SEQ ID NO 163
<211> LENGTH: 817
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

```
Met Ala Leu Pro Val Thr Ala Leu Leu Leu Pro Leu Ala Leu Leu Leu
1               5                   10                  15

His Ala Ala Arg Pro Gly Lys Pro Ile Pro Asn Pro Leu Leu Gly Leu
                20                  25                  30

Asp Ser Thr Gly Gly Gly Gly Ser Gly Gly Gly Ser Gly Gly Gly
            35                  40                  45

Gly Ser Gly Gly Gly Gly Ser Asp Ile Val Met Thr Gln Thr Pro Ala
    50                  55                  60

Ser Val Ser Glu Pro Val Gly Gly Ser Val Thr Ile Lys Cys Gln Ala
65                  70                  75                  80

Ser Gln Ser Phe Tyr Asn Leu Leu Ala Trp Tyr Gln Gln Lys Pro Gly
                85                  90                  95

Gln Pro Pro Lys Leu Leu Ile Tyr Asp Ala Ser Asp Leu Ala Ser Gly
                100                 105                 110

Val Pro Ser Arg Phe Lys Gly Ser Gly Ser Gly Thr Asp Phe Thr Leu
            115                 120                 125

Thr Ile Ser Asp Leu Glu Cys Ala Asp Ala Ala Tyr Tyr Cys Gln
            130                 135                 140

Ser Ala Asp Gly Ser Ser Tyr Ala Phe Gly Gly Gly Thr Glu Val Val
145                 150                 155                 160

Val Lys Gly Gly Gly Gly Ser Gly Gly Gly Gly Ser Gly Gly
                165                 170                 175

Gly Ser Gly Gly Gly Gly Ser Gln Glu Gln Leu Glu Glu Ser Gly Gly
            180                 185                 190

Gly Leu Val Lys Pro Glu Gly Ser Leu Thr Leu Thr Cys Thr Ala Ser
            195                 200                 205

Gly Val Ser Phe Ser Ser Ser Tyr Trp Ile Tyr Trp Val Arg Gln Ala
            210                 215                 220

Pro Gly Lys Gly Leu Glu Trp Ile Ala Cys Ile Tyr Thr Gly Ser Ser
225                 230                 235                 240

Gly Ser Thr Tyr Tyr Ala Ser Trp Ala Lys Gly Arg Phe Thr Val Ser
                245                 250                 255

Glu Thr Ser Ser Thr Thr Val Thr Leu Gln Met Thr Ser Leu Thr Ala
            260                 265                 270

Ala Asp Thr Ala Thr Tyr Phe Cys Ala Arg Ala Ser Ala Trp Thr Tyr
            275                 280                 285

Gly Met Asp Leu Trp Gly Pro Gly Thr Leu Val Thr Val Ser Ser Gly
            290                 295                 300

Gly Gly Gly Ser Gly Gly Gly Ser Gly Gly Gly Ser Gly Gly
305                 310                 315                 320

Ser Gly Ser Gly Gly Gly Ser Gly Gly Gly Ser Gly Gly
                325                 330                 335

Gly Ser Gly Gly Gly Gly Ser Gly Gly Gly Gly Ser Gln Val Gln Leu
```

```
                340               345               350
    Gln Glu Ser Gly Pro Gly Leu Val Lys Pro Ser Glu Thr Leu Ser Leu
            355               360               365
    Thr Cys Thr Val Ser Gly Gly Ser Ile Ser Tyr Tyr Ser Trp Thr Trp
            370               375               380
    Val Arg Gln Pro Ala Gly Gln Gly Leu Glu Trp Ile Gly Arg Ile His
    385               390               395               400
    Ile Ser Gly Val Thr Asn His Asn Pro Ser Leu Lys Ser Arg Val Ser
                    405               410               415
    Met Ser Ile Asp Thr Ser Arg Thr Gln Phe Ser Leu Arg Leu Thr Ser
                420               425               430
    Val Thr Ala Ala Asp Thr Ala Val Tyr Phe Cys Ala Arg Ser Gly Gly
                435               440               445
    Thr Tyr Ser Ala Phe Asp Ile Trp Gly Gln Gly Thr Met Val Thr Val
            450               455               460
    Ser Ser Gly Gly Gly Gly Ser Gly Gly Gly Gly Ser Gly Gly Gly Gly
    465               470               475               480
    Ser Gly Gly Gly Gly Ser Glu Ile Val Leu Thr Gln Ser Pro Gly Thr
                    485               490               495
    Leu Ser Leu Ser Pro Gly Glu Arg Ser Thr Leu Ser Cys Arg Ala Ser
                500               505               510
    Gln Ser Phe Thr Ser Asn Tyr Leu Ala Trp Tyr Gln Gln Arg Pro Gly
            515               520               525
    Gln Ala Pro Arg Leu Leu Ile Tyr Gly Ala Ser Thr Arg Ala Ile Gly
            530               535               540
    Ile Pro Asp Arg Phe Ser Gly Ser Gly Ser Gly Thr Asp Phe Thr Leu
    545               550               555               560
    Thr Ile Ser Arg Leu Glu Pro Glu Asp Phe Ala Val Tyr Tyr Cys Gln
                    565               570               575
    Gln Tyr Gly Ser Ser Pro Trp Thr Phe Gly Gln Gly Thr Lys Val Glu
                580               585               590
    Ile Lys Thr Thr Thr Pro Ala Pro Arg Pro Pro Thr Pro Ala Pro Thr
            595               600               605
    Ile Ala Ser Gln Pro Leu Ser Leu Arg Pro Glu Ala Cys Arg Pro Ala
            610               615               620
    Ala Gly Gly Ala Val His Thr Arg Gly Leu Asp Phe Ala Cys Asp Ile
    625               630               635               640
    Tyr Ile Trp Ala Pro Leu Ala Gly Thr Cys Gly Val Leu Leu Leu Ser
                    645               650               655
    Leu Val Ile Thr Leu Tyr Cys Lys Arg Gly Arg Lys Lys Leu Leu Tyr
                660               665               670
    Ile Phe Lys Gln Pro Phe Met Arg Pro Val Gln Thr Thr Gln Glu Glu
            675               680               685
    Asp Gly Cys Ser Cys Arg Phe Pro Glu Glu Glu Glu Gly Gly Cys Glu
            690               695               700
    Leu Arg Val Lys Phe Ser Arg Ser Ala Asp Ala Pro Ala Tyr Gln Gln
    705               710               715               720
    Gly Gln Asn Gln Leu Tyr Asn Glu Leu Asn Leu Gly Arg Arg Glu Glu
                    725               730               735
    Tyr Asp Val Leu Asp Lys Arg Arg Gly Arg Asp Pro Glu Met Gly Gly
                740               745               750
    Lys Pro Arg Arg Lys Asn Pro Gln Glu Gly Leu Tyr Asn Glu Leu Gln
            755               760               765
```

```
Lys Asp Lys Met Ala Glu Ala Tyr Ser Glu Ile Gly Met Lys Gly Glu
            770                 775                 780

Arg Arg Arg Gly Lys Gly His Asp Gly Leu Tyr Gln Gly Leu Ser Thr
785                 790                 795                 800

Ala Thr Lys Asp Thr Tyr Asp Ala Leu His Met Gln Ala Leu Pro Pro
                805                 810                 815

Arg

<210> SEQ ID NO 164
<211> LENGTH: 807
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

Met Ala Leu Pro Val Thr Ala Leu Leu Leu Pro Leu Ala Leu Leu Leu
1               5                   10                  15

His Ala Ala Arg Pro Gly Lys Pro Ile Pro Asn Pro Leu Leu Gly Leu
            20                  25                  30

Asp Ser Thr Gly Gly Gly Gly Ser Gly Gly Gly Gly Ser Gly Gly Gly
        35                  40                  45

Gly Ser Gly Gly Gly Gly Ser Asp Ile Val Met Thr Gln Thr Pro Ala
    50                  55                  60

Ser Val Ser Glu Pro Val Gly Gly Ser Val Thr Ile Lys Cys Gln Ala
65                  70                  75                  80

Ser Gln Ser Phe Tyr Asn Leu Leu Ala Trp Tyr Gln Lys Pro Gly
                85                  90                  95

Gln Pro Pro Lys Leu Leu Ile Tyr Asp Ala Ser Asp Leu Ala Ser Gly
            100                 105                 110

Val Pro Ser Arg Phe Lys Gly Ser Gly Ser Gly Thr Asp Phe Thr Leu
        115                 120                 125

Thr Ile Ser Asp Leu Glu Cys Ala Asp Ala Ala Tyr Tyr Cys Gln
130                 135                 140

Ser Ala Asp Gly Ser Ser Tyr Ala Phe Gly Gly Gly Thr Glu Val Val
145                 150                 155                 160

Val Lys Gly Gly Gly Gly Ser Gly Gly Gly Ser Gly Gly Gly
            165                 170                 175

Gly Ser Gly Gly Gly Gly Ser Gln Glu Gln Leu Glu Glu Ser Gly Gly
            180                 185                 190

Gly Leu Val Lys Pro Glu Gly Ser Leu Thr Leu Thr Cys Thr Ala Ser
            195                 200                 205

Gly Val Ser Phe Ser Ser Ser Tyr Trp Ile Tyr Trp Val Arg Gln Ala
        210                 215                 220

Pro Gly Lys Gly Leu Glu Trp Ile Ala Cys Ile Tyr Thr Gly Ser Ser
225                 230                 235                 240

Gly Ser Thr Tyr Tyr Ala Ser Trp Ala Lys Gly Arg Phe Thr Val Ser
                245                 250                 255

Glu Thr Ser Ser Thr Thr Val Thr Leu Gln Met Thr Ser Leu Thr Ala
            260                 265                 270

Ala Asp Thr Ala Thr Tyr Phe Cys Ala Arg Ala Ser Ala Trp Thr Tyr
        275                 280                 285

Gly Met Asp Leu Trp Gly Pro Gly Thr Leu Val Thr Val Ser Ser Gly
            290                 295                 300
```

-continued

```
Gly Gly Ser Gly Gly Ser Gly Ser Gly Gly Gly Ser Gly Gly
305                 310             315             320
Gly Gly Ser Gly Gly Gly Ser Gly Gly Gly Ser Gly Gly Gly
                325             330             335
Gly Ser Gln Val Gln Leu Gln Glu Ser Gly Pro Gly Leu Val Lys Pro
        340                 345                 350
Ser Glu Thr Leu Ser Leu Thr Cys Thr Val Ser Gly Gly Ser Ile Ser
        355                 360                 365
Tyr Tyr Ser Trp Thr Trp Val Arg Gln Pro Ala Gly Gln Gly Leu Glu
370             375                 380
Trp Ile Gly Arg Ile His Ile Ser Gly Val Thr Asn His Asn Pro Ser
385                 390                 395                 400
Leu Lys Ser Arg Val Ser Met Ser Ile Asp Thr Ser Arg Thr Gln Phe
            405                 410                 415
Ser Leu Arg Leu Thr Ser Val Thr Ala Ala Asp Thr Ala Val Tyr Phe
            420                 425                 430
Cys Ala Arg Ser Gly Gly Thr Tyr Ser Ala Phe Asp Ile Trp Gly Gln
            435                 440                 445
Gly Thr Met Val Thr Val Ser Ser Gly Gly Gly Ser Gly Gly Gly
450                 455                 460
Gly Ser Gly Gly Gly Gly Ser Gly Gly Gly Gly Ser Glu Ile Val Leu
465                 470                 475                 480
Thr Gln Ser Pro Gly Thr Leu Ser Leu Ser Pro Gly Glu Arg Ser Thr
                485                 490                 495
Leu Ser Cys Arg Ala Ser Gln Ser Phe Thr Ser Asn Tyr Leu Ala Trp
            500                 505                 510
Tyr Gln Gln Arg Pro Gly Gln Ala Pro Arg Leu Leu Ile Tyr Gly Ala
            515                 520                 525
Ser Thr Arg Ala Ile Gly Ile Pro Asp Arg Phe Ser Gly Ser Gly Ser
530                 535                 540
Gly Thr Asp Phe Thr Leu Thr Ile Ser Arg Leu Glu Pro Glu Asp Phe
545                 550                 555                 560
Ala Val Tyr Tyr Cys Gln Gln Tyr Gly Ser Ser Pro Trp Thr Phe Gly
                565                 570                 575
Gln Gly Thr Lys Val Glu Ile Lys Thr Thr Thr Pro Ala Pro Arg Pro
            580                 585                 590
Pro Thr Pro Ala Pro Thr Ile Ala Ser Gln Pro Leu Ser Leu Arg Pro
            595                 600                 605
Glu Ala Cys Arg Pro Ala Ala Gly Gly Ala Val His Thr Arg Gly Leu
            610                 615                 620
Asp Phe Ala Cys Asp Ile Tyr Ile Trp Ala Pro Leu Ala Gly Thr Cys
625                 630                 635                 640
Gly Val Leu Leu Leu Ser Leu Val Ile Thr Leu Tyr Cys Lys Arg Gly
            645                 650                 655
Arg Lys Lys Leu Leu Tyr Ile Phe Lys Gln Pro Phe Met Arg Pro Val
            660                 665                 670
Gln Thr Thr Gln Glu Glu Asp Gly Cys Ser Cys Arg Phe Pro Glu Glu
            675                 680                 685
Glu Glu Gly Gly Cys Glu Leu Arg Val Lys Phe Ser Arg Ser Ala Asp
            690                 695                 700
Ala Pro Ala Tyr Gln Gln Gly Gln Asn Gln Leu Tyr Asn Glu Leu Asn
705                 710                 715                 720
```

```
Leu Gly Arg Arg Glu Glu Tyr Asp Val Leu Asp Lys Arg Arg Gly Arg
                725                 730                 735

Asp Pro Glu Met Gly Gly Lys Pro Arg Arg Lys Asn Pro Gln Glu Gly
            740                 745                 750

Leu Tyr Asn Glu Leu Gln Lys Asp Lys Met Ala Glu Ala Tyr Ser Glu
        755                 760                 765

Ile Gly Met Lys Gly Glu Arg Arg Arg Gly Lys Gly His Asp Gly Leu
    770                 775                 780

Tyr Gln Gly Leu Ser Thr Ala Thr Lys Asp Thr Tyr Asp Ala Leu His
785                 790                 795                 800

Met Gln Ala Leu Pro Pro Arg
                805
```

<210> SEQ ID NO 165
<211> LENGTH: 797
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165

```
Met Ala Leu Pro Val Thr Ala Leu Leu Leu Pro Leu Ala Leu Leu Leu
1               5                   10                  15

His Ala Ala Arg Pro Gly Lys Pro Ile Pro Asn Pro Leu Leu Gly Leu
            20                  25                  30

Asp Ser Thr Gly Gly Gly Gly Ser Gly Gly Gly Ser Gly Gly Gly
        35                  40                  45

Gly Ser Gly Gly Gly Gly Ser Asp Ile Val Met Thr Gln Thr Pro Ala
50                  55                  60

Ser Val Ser Glu Pro Val Gly Gly Ser Val Thr Ile Lys Cys Gln Ala
65                  70                  75                  80

Ser Gln Ser Phe Tyr Asn Leu Leu Ala Trp Tyr Gln Gln Lys Pro Gly
                85                  90                  95

Gln Pro Pro Lys Leu Leu Ile Tyr Asp Ala Ser Asp Leu Ala Ser Gly
            100                 105                 110

Val Pro Ser Arg Phe Lys Gly Ser Gly Ser Gly Thr Asp Phe Thr Leu
        115                 120                 125

Thr Ile Ser Asp Leu Glu Cys Ala Asp Ala Ala Tyr Tyr Cys Gln
    130                 135                 140

Ser Ala Asp Gly Ser Ser Tyr Ala Phe Gly Gly Gly Thr Glu Val Val
145                 150                 155                 160

Val Lys Gly Gly Gly Gly Ser Gly Gly Gly Ser Gly Gly Gly
                165                 170                 175

Gly Ser Gly Gly Gly Gly Ser Gln Glu Gln Leu Glu Glu Ser Gly Gly
            180                 185                 190

Gly Leu Val Lys Pro Glu Gly Ser Leu Thr Leu Thr Cys Thr Ala Ser
        195                 200                 205

Gly Val Ser Phe Ser Ser Ser Tyr Trp Ile Tyr Trp Val Arg Gln Ala
    210                 215                 220

Pro Gly Lys Gly Leu Glu Trp Ile Ala Cys Ile Tyr Thr Gly Ser Ser
225                 230                 235                 240

Gly Ser Thr Tyr Tyr Ala Ser Trp Ala Lys Gly Arg Phe Thr Val Ser
                245                 250                 255

Glu Thr Ser Ser Thr Thr Val Thr Leu Gln Met Thr Ser Leu Thr Ala
            260                 265                 270
```

```
Ala Asp Thr Ala Thr Tyr Phe Cys Ala Arg Ala Ser Ala Trp Thr Tyr
        275                 280                 285

Gly Met Asp Leu Trp Gly Pro Gly Thr Leu Val Thr Val Ser Ser Gly
        290                 295                 300

Gly Gly Gly Ser Gly Gly Gly Ser Gly Gly Gly Ser Gly Gly
305                 310                 315                 320

Gly Gly Ser Gly Gly Gly Ser Gln Val Gln Leu Gln Glu Ser Gly
            325                 330                 335

Pro Gly Leu Val Lys Pro Ser Glu Thr Leu Ser Leu Thr Cys Thr Val
            340                 345                 350

Ser Gly Gly Ser Ile Ser Tyr Tyr Ser Trp Thr Trp Val Arg Gln Pro
        355                 360                 365

Ala Gly Gln Gly Leu Glu Trp Ile Gly Arg Ile His Ile Ser Gly Val
        370                 375                 380

Thr Asn His Asn Pro Ser Leu Lys Ser Arg Val Ser Met Ser Ile Asp
385                 390                 395                 400

Thr Ser Arg Thr Gln Phe Ser Leu Arg Leu Thr Ser Val Thr Ala Ala
            405                 410                 415

Asp Thr Ala Val Tyr Phe Cys Ala Arg Ser Gly Gly Tyr Ser Ala
            420                 425                 430

Phe Asp Ile Trp Gly Gln Gly Thr Met Val Thr Val Ser Ser Gly Gly
        435                 440                 445

Gly Gly Ser Gly Gly Gly Ser Gly Gly Gly Ser Gly Gly Gly
450                 455                 460

Gly Ser Glu Ile Val Leu Thr Gln Ser Pro Gly Thr Leu Ser Leu Ser
465                 470                 475                 480

Pro Gly Glu Arg Ser Thr Leu Ser Cys Arg Ala Ser Gln Ser Phe Thr
            485                 490                 495

Ser Asn Tyr Leu Ala Trp Tyr Gln Gln Arg Pro Gly Gln Ala Pro Arg
        500                 505                 510

Leu Leu Ile Tyr Gly Ala Ser Thr Arg Ala Ile Gly Ile Pro Asp Arg
        515                 520                 525

Phe Ser Gly Ser Gly Ser Gly Thr Asp Phe Thr Leu Thr Ile Ser Arg
        530                 535                 540

Leu Glu Pro Glu Asp Phe Ala Val Tyr Tyr Cys Gln Gln Tyr Gly Ser
545                 550                 555                 560

Ser Pro Trp Thr Phe Gly Gln Gly Thr Lys Val Glu Ile Lys Thr Thr
            565                 570                 575

Thr Pro Ala Pro Arg Pro Pro Thr Pro Ala Pro Thr Ile Ala Ser Gln
            580                 585                 590

Pro Leu Ser Leu Arg Pro Glu Ala Cys Arg Pro Ala Ala Gly Gly Ala
            595                 600                 605

Val His Thr Arg Gly Leu Asp Phe Ala Cys Asp Ile Tyr Ile Trp Ala
        610                 615                 620

Pro Leu Ala Gly Thr Cys Gly Val Leu Leu Leu Ser Leu Val Ile Thr
625                 630                 635                 640

Leu Tyr Cys Lys Arg Gly Arg Lys Lys Leu Leu Tyr Ile Phe Lys Gln
            645                 650                 655

Pro Phe Met Arg Pro Val Gln Thr Thr Gln Glu Glu Asp Gly Cys Ser
            660                 665                 670

Cys Arg Phe Pro Glu Glu Glu Glu Gly Gly Cys Glu Leu Arg Val Lys
            675                 680                 685
```

```
Phe Ser Arg Ser Ala Asp Ala Pro Ala Tyr Gln Gln Gly Gln Asn Gln
        690                 695                 700

Leu Tyr Asn Glu Leu Asn Leu Gly Arg Arg Glu Glu Tyr Asp Val Leu
705                 710                 715                 720

Asp Lys Arg Arg Gly Arg Asp Pro Glu Met Gly Gly Lys Pro Arg Arg
                725                 730                 735

Lys Asn Pro Gln Glu Gly Leu Tyr Asn Glu Leu Gln Lys Asp Lys Met
            740                 745                 750

Ala Glu Ala Tyr Ser Glu Ile Gly Met Lys Gly Glu Arg Arg Arg Gly
        755                 760                 765

Lys Gly His Asp Gly Leu Tyr Gln Gly Leu Ser Thr Ala Thr Lys Asp
770                 775                 780

Thr Tyr Asp Ala Leu His Met Gln Ala Leu Pro Pro Arg
785                 790                 795

<210> SEQ ID NO 166
<211> LENGTH: 660
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166

Met Ala Leu Pro Val Thr Ala Leu Leu Leu Pro Leu Ala Leu Leu Leu
1               5                   10                  15

His Ala Ala Arg Pro Gly Tyr Pro Tyr Asp Val Pro Asp Tyr Ala Gln
            20                  25                  30

Phe Ser Val Leu Gly Pro Ser Gly Pro Ile Leu Ala Met Val Gly Glu
        35                  40                  45

Asp Ala Asp Leu Pro Cys His Leu Phe Pro Thr Met Ser Ala Glu Thr
    50                  55                  60

Met Glu Leu Lys Trp Val Ser Ser Ser Leu Arg Gln Val Val Asn Val
65                  70                  75                  80

Tyr Ala Asp Gly Lys Glu Val Glu Asp Arg Gln Ser Ala Pro Tyr Arg
                85                  90                  95

Gly Arg Thr Ser Ile Leu Arg Asp Gly Ile Thr Ala Gly Lys Ala Ala
            100                 105                 110

Leu Arg Ile His Asn Val Thr Ala Ser Asp Ser Gly Lys Tyr Leu Cys
        115                 120                 125

Tyr Phe Gln Asp Gly Asp Phe Tyr Glu Lys Ala Leu Val Glu Leu Lys
    130                 135                 140

Val Ala Gly Gly Gly Ser Gly Gly Gly Gly Ser Gly Gly Gly Gly Ser
145                 150                 155                 160

Gly Gly Gly Ser Gly Ser Gly Gly Gly Ser Gly Gly Gly Gly Gly Ser
                165                 170                 175

Gly Gly Gly Gly Ser Gly Gly Gly Ser Gly Gly Gly Gly Ser Gln
            180                 185                 190

Val Gln Leu Gln Glu Ser Gly Pro Gly Leu Val Lys Pro Ser Glu Thr
        195                 200                 205

Leu Ser Leu Thr Cys Thr Val Ser Gly Gly Ser Ile Ser Tyr Tyr Ser
    210                 215                 220

Trp Thr Trp Val Arg Gln Pro Ala Gly Gln Gly Leu Glu Trp Ile Gly
225                 230                 235                 240

Arg Ile His Ile Ser Gly Val Thr Asn His Asn Pro Ser Leu Lys Ser
                245                 250                 255
```

-continued

```
Arg Val Ser Met Ser Ile Asp Thr Ser Arg Thr Gln Phe Ser Leu Arg
            260                 265                 270

Leu Thr Ser Val Thr Ala Ala Asp Thr Ala Val Tyr Phe Cys Ala Arg
        275                 280                 285

Ser Gly Gly Thr Tyr Ser Ala Phe Asp Ile Trp Gly Gln Gly Thr Met
    290                 295                 300

Val Thr Val Ser Ser Gly Gly Gly Ser Gly Gly Gly Ser Gly
305                 310                 315                 320

Gly Gly Ser Gly Gly Gly Ser Glu Ile Val Leu Thr Gln Ser
            325                 330                 335

Pro Gly Thr Leu Ser Leu Ser Pro Gly Glu Arg Ser Thr Leu Ser Cys
        340                 345                 350

Arg Ala Ser Gln Ser Phe Thr Ser Asn Tyr Leu Ala Trp Tyr Gln Gln
    355                 360                 365

Arg Pro Gly Gln Ala Pro Arg Leu Leu Ile Tyr Gly Ala Ser Thr Arg
370                 375                 380

Ala Ile Gly Ile Pro Asp Arg Phe Ser Gly Ser Gly Ser Gly Thr Asp
385                 390                 395                 400

Phe Thr Leu Thr Ile Ser Arg Leu Glu Pro Glu Asp Phe Ala Val Tyr
            405                 410                 415

Tyr Cys Gln Gln Tyr Gly Ser Ser Pro Trp Thr Phe Gly Gln Gly Thr
        420                 425                 430

Lys Val Glu Ile Lys Thr Thr Thr Pro Ala Pro Arg Pro Pro Thr Pro
    435                 440                 445

Ala Pro Thr Ile Ala Ser Gln Pro Leu Ser Leu Arg Pro Glu Ala Cys
    450                 455                 460

Arg Pro Ala Ala Gly Gly Ala Val His Thr Arg Gly Leu Asp Phe Ala
465                 470                 475                 480

Cys Asp Ile Tyr Ile Trp Ala Pro Leu Ala Gly Thr Cys Gly Val Leu
            485                 490                 495

Leu Leu Ser Leu Val Ile Thr Leu Tyr Cys Lys Arg Gly Arg Lys Lys
        500                 505                 510

Leu Leu Tyr Ile Phe Lys Gln Pro Phe Met Arg Pro Val Gln Thr Thr
    515                 520                 525

Gln Glu Glu Asp Gly Cys Ser Cys Arg Phe Pro Glu Glu Glu Glu Gly
530                 535                 540

Gly Cys Glu Leu Arg Val Lys Phe Ser Arg Ser Ala Asp Ala Pro Ala
545                 550                 555                 560

Tyr Gln Gln Gly Gln Asn Gln Leu Tyr Asn Glu Leu Asn Leu Gly Arg
            565                 570                 575

Arg Glu Glu Tyr Asp Val Leu Asp Lys Arg Arg Gly Arg Asp Pro Glu
        580                 585                 590

Met Gly Gly Lys Pro Arg Arg Lys Asn Pro Gln Glu Gly Leu Tyr Asn
    595                 600                 605

Glu Leu Gln Lys Asp Lys Met Ala Glu Ala Tyr Ser Glu Ile Gly Met
    610                 615                 620

Lys Gly Glu Arg Arg Arg Gly Lys Gly His Asp Gly Leu Tyr Gln Gly
625                 630                 635                 640

Leu Ser Thr Ala Thr Lys Asp Thr Tyr Asp Ala Leu His Met Gln Ala
            645                 650                 655

Leu Pro Pro Arg
            660
```

<210> SEQ ID NO 167
<211> LENGTH: 656
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 167

Met Ala Leu Pro Val Thr Ala Leu Leu Leu Pro Leu Ala Leu Leu Leu
1               5                   10                  15

His Ala Ala Arg Pro Gly Tyr Pro Tyr Asp Val Pro Asp Tyr Ala Ala
                20                  25                  30

Leu Gly Ser Asp Leu His Val Asp Val Lys Gly Tyr Lys Asp Gly Gly
            35                  40                  45

Ile His Leu Glu Cys Arg Ser Thr Gly Trp Tyr Pro Gln Pro Gln Ile
    50                  55                  60

Gln Trp Ser Asn Asn Lys Gly Glu Asn Ile Pro Thr Val Glu Ala Pro
65                  70                  75                  80

Val Val Ala Asp Gly Val Gly Leu Tyr Ala Val Ala Ala Ser Val Ile
                85                  90                  95

Met Arg Gly Ser Ser Gly Glu Gly Val Ser Cys Thr Ile Arg Ser Ser
                100                 105                 110

Leu Leu Gly Leu Glu Lys Thr Ala Ser Ile Ser Ile Ala Asp Pro Phe
            115                 120                 125

Phe Arg Ser Ala Gln Arg Trp Ile Ala Ala Leu Ala Gly Thr Gly Gly
    130                 135                 140

Gly Gly Ser Gly Gly Gly Ser Gly Gly Gly Ser Gly Gly Gly Gly Ser
145                 150                 155                 160

Gly Ser Gly Gly Gly Gly Ser Gly Gly Gly Ser Gly Gly Gly Gly Gly
                165                 170                 175

Ser Gly Gly Gly Gly Ser Gly Gly Gly Ser Gln Val Gln Leu Gln
                180                 185                 190

Glu Ser Gly Pro Gly Leu Val Lys Pro Ser Glu Thr Leu Ser Leu Thr
            195                 200                 205

Cys Thr Val Ser Gly Gly Ser Ile Ser Tyr Tyr Ser Trp Thr Trp Val
    210                 215                 220

Arg Gln Pro Ala Gly Gln Gly Leu Glu Trp Ile Gly Arg Ile His Ile
225                 230                 235                 240

Ser Gly Val Thr Asn His Asn Pro Ser Leu Lys Ser Arg Val Ser Met
                245                 250                 255

Ser Ile Asp Thr Ser Arg Thr Gln Phe Ser Leu Arg Leu Thr Ser Val
            260                 265                 270

Thr Ala Ala Asp Thr Ala Val Tyr Phe Cys Ala Arg Ser Gly Gly Thr
    275                 280                 285

Tyr Ser Ala Phe Asp Ile Trp Gly Gln Gly Thr Met Val Thr Val Ser
    290                 295                 300

Ser Gly Gly Gly Gly Ser Gly Gly Gly Gly Ser Gly Gly Gly Gly Ser
305                 310                 315                 320

Gly Gly Gly Gly Ser Glu Ile Val Leu Thr Gln Ser Pro Gly Thr Leu
                325                 330                 335

Ser Leu Ser Pro Gly Glu Arg Ser Thr Leu Ser Cys Arg Ala Ser Gln
            340                 345                 350

Ser Phe Thr Ser Asn Tyr Leu Ala Trp Tyr Gln Gln Arg Pro Gly Gln
    355                 360                 365

-continued

Ala Pro Arg Leu Leu Ile Tyr Gly Ala Ser Thr Arg Ala Ile Gly Ile
    370                 375                 380

Pro Asp Arg Phe Ser Gly Ser Gly Ser Gly Thr Asp Phe Thr Leu Thr
385                 390                 395                 400

Ile Ser Arg Leu Glu Pro Glu Asp Phe Ala Val Tyr Tyr Cys Gln Gln
                405                 410                 415

Tyr Gly Ser Ser Pro Trp Thr Phe Gly Gln Gly Thr Lys Val Glu Ile
            420                 425                 430

Lys Thr Thr Thr Pro Ala Pro Arg Pro Pro Thr Pro Ala Pro Thr Ile
        435                 440                 445

Ala Ser Gln Pro Leu Ser Leu Arg Pro Glu Ala Cys Arg Pro Ala Ala
    450                 455                 460

Gly Gly Ala Val His Thr Arg Gly Leu Asp Phe Ala Cys Asp Ile Tyr
465                 470                 475                 480

Ile Trp Ala Pro Leu Ala Gly Thr Cys Gly Val Leu Leu Leu Ser Leu
                485                 490                 495

Val Ile Thr Leu Tyr Cys Lys Arg Gly Arg Lys Lys Leu Leu Tyr Ile
            500                 505                 510

Phe Lys Gln Pro Phe Met Arg Pro Val Gln Thr Thr Gln Glu Glu Asp
        515                 520                 525

Gly Cys Ser Cys Arg Phe Pro Glu Glu Glu Glu Gly Gly Cys Glu Leu
530                 535                 540

Arg Val Lys Phe Ser Arg Ser Ala Asp Ala Pro Ala Tyr Gln Gln Gly
545                 550                 555                 560

Gln Asn Gln Leu Tyr Asn Glu Leu Asn Leu Gly Arg Arg Glu Glu Tyr
                565                 570                 575

Asp Val Leu Asp Lys Arg Arg Gly Arg Asp Pro Glu Met Gly Gly Lys
            580                 585                 590

Pro Arg Arg Lys Asn Pro Gln Glu Gly Leu Tyr Asn Glu Leu Gln Lys
        595                 600                 605

Asp Lys Met Ala Glu Ala Tyr Ser Glu Ile Gly Met Lys Gly Glu Arg
    610                 615                 620

Arg Arg Gly Lys Gly His Asp Gly Leu Tyr Gln Gly Leu Ser Thr Ala
625                 630                 635                 640

Thr Lys Asp Thr Tyr Asp Ala Leu His Met Gln Ala Leu Pro Pro Arg
                645                 650                 655

<210> SEQ ID NO 168
<211> LENGTH: 771
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 168

Met Ala Leu Pro Val Thr Ala Leu Leu Leu Pro Leu Ala Leu Leu Leu
1               5                   10                  15

His Ala Ala Arg Pro Gly Tyr Pro Tyr Asp Val Pro Asp Tyr Ala Gln
            20                  25                  30

Phe Ser Val Leu Gly Pro Ser Gly Pro Ile Leu Ala Met Val Gly Glu
        35                  40                  45

Asp Ala Asp Leu Pro Cys His Leu Phe Pro Thr Met Ser Ala Glu Thr
    50                  55                  60

Met Glu Leu Lys Trp Val Ser Ser Ser Leu Arg Gln Val Val Asn Val

```
                65                  70                  75                  80

Tyr Ala Asp Gly Lys Glu Val Glu Asp Arg Gln Ser Ala Pro Tyr Arg
                    85                  90                  95

Gly Arg Thr Ser Ile Leu Arg Asp Gly Ile Thr Ala Gly Lys Ala Ala
                100                 105                 110

Leu Arg Ile His Asn Val Thr Ala Ser Asp Ser Gly Lys Tyr Leu Cys
                115                 120                 125

Tyr Phe Gln Asp Gly Asp Phe Tyr Glu Lys Ala Leu Val Glu Leu Lys
            130                 135                 140

Val Ala Ala Leu Gly Ser Asp Leu His Val Asp Val Lys Gly Tyr Lys
145                 150                 155                 160

Asp Gly Gly Ile His Leu Glu Cys Arg Ser Thr Gly Trp Tyr Pro Gln
                    165                 170                 175

Pro Gln Ile Gln Trp Ser Asn Asn Lys Gly Glu Asn Ile Pro Thr Val
                180                 185                 190

Glu Ala Pro Val Val Ala Asp Gly Val Gly Leu Tyr Ala Val Ala Ala
                195                 200                 205

Ser Val Ile Met Arg Gly Ser Ser Gly Glu Gly Val Ser Cys Thr Ile
        210                 215                 220

Arg Ser Ser Leu Leu Gly Leu Glu Lys Thr Ala Ser Ile Ser Ile Ala
225                 230                 235                 240

Asp Pro Phe Phe Arg Ser Ala Gln Arg Trp Ile Ala Ala Leu Ala Gly
                    245                 250                 255

Thr Gly Gly Gly Gly Ser Gly Gly Gly Ser Gly Gly Gly Gly Ser Gly
                260                 265                 270

Gly Gly Ser Gly Ser Gly Gly Gly Ser Gly Gly Gly Gly Gly Ser Gly
            275                 280                 285

Gly Gly Gly Ser Gly Gly Gly Ser Gly Gly Gly Gly Gly Ser Gln Val
        290                 295                 300

Gln Leu Gln Glu Ser Gly Pro Gly Leu Val Lys Pro Ser Glu Thr Leu
305                 310                 315                 320

Ser Leu Thr Cys Thr Val Ser Gly Gly Ser Ile Ser Tyr Tyr Ser Trp
                    325                 330                 335

Thr Trp Val Arg Gln Pro Ala Gly Gln Gly Leu Glu Trp Ile Gly Arg
                340                 345                 350

Ile His Ile Ser Gly Val Thr Asn His Asn Pro Ser Leu Lys Ser Arg
            355                 360                 365

Val Ser Met Ser Ile Asp Thr Ser Arg Thr Gln Phe Ser Leu Arg Leu
        370                 375                 380

Thr Ser Val Thr Ala Ala Asp Thr Ala Val Tyr Phe Cys Ala Arg Ser
385                 390                 395                 400

Gly Gly Thr Tyr Ser Ala Phe Asp Ile Trp Gly Gln Gly Thr Met Val
                    405                 410                 415

Thr Val Ser Ser Gly Gly Gly Gly Ser Gly Gly Gly Gly Ser Gly Gly
                420                 425                 430

Gly Gly Ser Gly Gly Gly Gly Ser Glu Ile Val Leu Thr Gln Ser Pro
            435                 440                 445

Gly Thr Leu Ser Leu Ser Pro Gly Glu Arg Ser Thr Leu Ser Cys Arg
        450                 455                 460

Ala Ser Gln Ser Phe Thr Ser Asn Tyr Leu Ala Trp Tyr Gln Gln Arg
465                 470                 475                 480

Pro Gly Gln Ala Pro Arg Leu Leu Ile Tyr Gly Ala Ser Thr Arg Ala
                    485                 490                 495
```

```
Ile Gly Ile Pro Asp Arg Phe Ser Gly Ser Gly Ser Gly Thr Asp Phe
            500                 505                 510

Thr Leu Thr Ile Ser Arg Leu Glu Pro Glu Asp Phe Ala Val Tyr Tyr
        515                 520                 525

Cys Gln Gln Tyr Gly Ser Ser Pro Trp Thr Phe Gly Gln Gly Thr Lys
    530                 535                 540

Val Glu Ile Lys Thr Thr Pro Ala Pro Arg Pro Pro Thr Pro Ala
545                 550                 555                 560

Pro Thr Ile Ala Ser Gln Pro Leu Ser Leu Arg Pro Glu Ala Cys Arg
                565                 570                 575

Pro Ala Ala Gly Gly Ala Val His Thr Arg Gly Leu Asp Phe Ala Cys
            580                 585                 590

Asp Ile Tyr Ile Trp Ala Pro Leu Ala Gly Thr Cys Gly Val Leu Leu
            595                 600                 605

Leu Ser Leu Val Ile Thr Leu Tyr Cys Lys Arg Gly Arg Lys Lys Leu
        610                 615                 620

Leu Tyr Ile Phe Lys Gln Pro Phe Met Arg Pro Val Gln Thr Thr Gln
625                 630                 635                 640

Glu Glu Asp Gly Cys Ser Cys Arg Phe Pro Glu Glu Glu Glu Gly Gly
                645                 650                 655

Cys Glu Leu Arg Val Lys Phe Ser Arg Ser Ala Asp Ala Pro Ala Tyr
            660                 665                 670

Gln Gln Gly Gln Asn Gln Leu Tyr Asn Glu Leu Asn Leu Gly Arg Arg
        675                 680                 685

Glu Glu Tyr Asp Val Leu Asp Lys Arg Arg Gly Arg Asp Pro Glu Met
    690                 695                 700

Gly Gly Lys Pro Arg Arg Lys Asn Pro Gln Glu Gly Leu Tyr Asn Glu
705                 710                 715                 720

Leu Gln Lys Asp Lys Met Ala Glu Ala Tyr Ser Glu Ile Gly Met Lys
                725                 730                 735

Gly Glu Arg Arg Arg Gly Lys Gly His Asp Gly Leu Tyr Gln Gly Leu
            740                 745                 750

Ser Thr Ala Thr Lys Asp Thr Tyr Asp Ala Leu His Met Gln Ala Leu
        755                 760                 765

Pro Pro Arg
    770

<210> SEQ ID NO 169
<211> LENGTH: 908
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 169

Met Ala Leu Pro Val Thr Ala Leu Leu Leu Pro Leu Ala Leu Leu Leu
1               5                   10                  15

His Ala Ala Arg Pro Gly Tyr Pro Tyr Asp Val Pro Asp Tyr Ala Gly
            20                  25                  30

Phe His Thr Ile Asn Ala Thr Trp Trp Ala Asn Ile Thr Leu Val Gly
        35                  40                  45

Pro Pro Asp Thr Pro Val Thr Trp Tyr Asp Thr Gln Gly Leu Trp Phe
    50                  55                  60

Cys Asn Gly Ser Arg Val Lys Asn Pro Gln Ile Arg His Thr Cys Asn
```

```
              65                  70                  75                  80
Asp Gln Asn Leu Thr Leu Ile His Val Asn Lys Thr Tyr Glu Arg Thr
                  85                  90                  95

Tyr Met Gly Tyr Asn Arg Gln Gly Thr Lys Lys Glu Asp Tyr Lys Val
                 100                 105                 110

Val Val Ile Pro Pro Pro Ala Thr Val Lys Pro Gln Pro Glu Pro
            115                 120                 125

Glu Tyr Val Phe Val Tyr Met Gly Glu Asn Lys Thr Leu Glu Gly Pro
130                 135                 140

Pro Gly Thr Pro Val Thr Trp Phe Asn Gln Asp Gly Lys Lys Phe Cys
145                 150                 155                 160

Glu Gly Glu Lys Val Leu His Pro Glu Phe Asn His Thr Cys Asp Lys
                165                 170                 175

Gln Asn Leu Ile Leu Leu Phe Val Asn Phe Thr His Asp Gly Ala Tyr
                180                 185                 190

Leu Gly Tyr Asn His Gln Gly Thr Gln Arg Thr His Tyr Glu Val Thr
            195                 200                 205

Val Leu Asp Leu Phe Pro Asp Ser Gly Gln Met Lys Ile Glu Asn His
210                 215                 220

Ser Glu Glu Thr Glu Gln Lys Asn Asp Glu His His Asn Trp Gln Lys
225                 230                 235                 240

Gln Gly Gly Gln Lys Gln Gly Gln Lys Thr Asn Gln Thr Lys Val
                245                 250                 255

Asn Asp Arg Arg Lys Thr Ala Gln Lys Arg Pro Ser Lys Leu Lys Pro
                260                 265                 270

Ala Thr Ile Glu Ala Met Leu Val Thr Val Thr Ala Gly Ser Asn Leu
            275                 280                 285

Thr Leu Val Gly Pro Lys Ala Glu Gly Lys Val Thr Trp Phe Asp Gly
            290                 295                 300

Asp Leu Lys Arg Pro Cys Glu Pro Asn Tyr Arg Leu Arg His Glu Cys
305                 310                 315                 320

Asn Asn Gln Asn Leu Thr Leu Ile Asn Val Thr Lys Asp Tyr Glu Gly
                325                 330                 335

Thr Tyr Tyr Gly Thr Asn Asp Lys Asp Glu Gly Lys Arg Tyr Arg Val
                340                 345                 350

Lys Val Asn Thr Thr Asn Ser Gln Ser Val Lys Ile Gln Pro Tyr Thr
                355                 360                 365

Arg Gln Thr Thr Pro Asp Gln Glu His Lys Phe Glu Leu Gln Phe Glu
370                 375                 380

Thr Asn Gly Asn Tyr Asp Ser Lys Ile Pro Gly Gly Gly Ser Gly
385                 390                 395                 400

Gly Gly Gly Ser Gly Gly Ser Gly Gly Ser Gly Ser Gly Gly
                405                 410                 415

Gly Gly Ser Gly Gly Gly Ser Gly Gly Gly Ser Gly Gly Gly
            420                 425                 430

Gly Ser Gly Gly Gly Ser Gln Val Gln Leu Gln Glu Ser Gly Pro
            435                 440                 445

Gly Leu Val Lys Pro Ser Glu Thr Leu Ser Leu Thr Cys Thr Val Ser
            450                 455                 460

Gly Gly Ser Ile Ser Tyr Tyr Ser Trp Thr Trp Val Arg Gln Pro Ala
465                 470                 475                 480

Gly Gln Gly Leu Glu Trp Ile Gly Arg Ile His Ile Ser Gly Val Thr
                485                 490                 495
```

```
Asn His Asn Pro Ser Leu Lys Ser Arg Val Ser Met Ser Ile Asp Thr
            500                 505                 510

Ser Arg Thr Gln Phe Ser Leu Arg Leu Thr Ser Val Thr Ala Ala Asp
            515                 520                 525

Thr Ala Val Tyr Phe Cys Ala Arg Ser Gly Gly Thr Tyr Ser Ala Phe
            530                 535                 540

Asp Ile Trp Gly Gln Gly Thr Met Val Thr Val Ser Ser Gly Gly Gly
545                 550                 555                 560

Gly Ser Gly Gly Gly Gly Ser Gly Gly Gly Gly Ser Gly Gly Gly Gly
            565                 570                 575

Ser Glu Ile Val Leu Thr Gln Ser Pro Gly Thr Leu Ser Leu Ser Pro
            580                 585                 590

Gly Glu Arg Ser Thr Leu Ser Cys Arg Ala Ser Gln Ser Phe Thr Ser
            595                 600                 605

Asn Tyr Leu Ala Trp Tyr Gln Gln Arg Pro Gly Gln Ala Pro Arg Leu
            610                 615                 620

Leu Ile Tyr Gly Ala Ser Thr Arg Ala Ile Gly Ile Pro Asp Arg Phe
625                 630                 635                 640

Ser Gly Ser Gly Ser Gly Thr Asp Phe Thr Leu Thr Ile Ser Arg Leu
            645                 650                 655

Glu Pro Glu Asp Phe Ala Val Tyr Tyr Cys Gln Gln Tyr Gly Ser Ser
            660                 665                 670

Pro Trp Thr Phe Gly Gln Gly Thr Lys Val Glu Ile Lys Thr Thr Thr
            675                 680                 685

Pro Ala Pro Arg Pro Pro Thr Pro Ala Pro Thr Ile Ala Ser Gln Pro
            690                 695                 700

Leu Ser Leu Arg Pro Glu Ala Cys Arg Pro Ala Ala Gly Gly Ala Val
705                 710                 715                 720

His Thr Arg Gly Leu Asp Phe Ala Cys Asp Ile Tyr Ile Trp Ala Pro
            725                 730                 735

Leu Ala Gly Thr Cys Gly Val Leu Leu Leu Ser Leu Val Ile Thr Leu
            740                 745                 750

Tyr Cys Lys Arg Gly Arg Lys Lys Leu Leu Tyr Ile Phe Lys Gln Pro
            755                 760                 765

Phe Met Arg Pro Val Gln Thr Thr Gln Glu Glu Asp Gly Cys Ser Cys
770                 775                 780

Arg Phe Pro Glu Glu Glu Gly Gly Cys Glu Leu Arg Val Lys Phe
785                 790                 795                 800

Ser Arg Ser Ala Asp Ala Pro Ala Tyr Gln Gln Gly Gln Asn Gln Leu
            805                 810                 815

Tyr Asn Glu Leu Asn Leu Gly Arg Arg Glu Glu Tyr Asp Val Leu Asp
            820                 825                 830

Lys Arg Arg Gly Arg Asp Pro Glu Met Gly Gly Lys Pro Arg Arg Lys
            835                 840                 845

Asn Pro Gln Glu Gly Leu Tyr Asn Glu Leu Gln Lys Asp Lys Met Ala
            850                 855                 860

Glu Ala Tyr Ser Glu Ile Gly Met Lys Gly Glu Arg Arg Arg Gly Lys
865                 870                 875                 880

Gly His Asp Gly Leu Tyr Gln Gly Leu Ser Thr Ala Thr Lys Asp Thr
            885                 890                 895

Tyr Asp Ala Leu His Met Gln Ala Leu Pro Pro Arg
            900                 905
```

<210> SEQ ID NO 170
<211> LENGTH: 745
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 170

```
Met Ala Leu Pro Val Thr Ala Leu Leu Leu Pro Leu Ala Leu Leu Leu
1               5                   10                  15

His Ala Ala Arg Pro Gly Tyr Pro Tyr Asp Val Pro Asp Tyr Ala His
            20                  25                  30

Asp Ala Cys Ile Pro Val Val Gly Lys Ile Gly Thr Asn Val Thr Leu
        35                  40                  45

Asn Ala Val Asp Phe His Pro Gly Asp His Val Arg Trp Ser Tyr Gly
    50                  55                  60

Pro Gly Gly Ala Gly Tyr Met Leu Cys Val Tyr Thr Gly Ser Trp Thr
65                  70                  75                  80

Glu Tyr Lys Lys Pro Asp Ile Ile Phe Lys Cys Leu Ser Asn Asn Ser
                85                  90                  95

Leu Leu Leu Ile Asn Val Thr Val Asn Tyr Thr Asn Thr Tyr Arg Thr
            100                 105                 110

Leu Thr Ser Leu Asn Asn Trp Val His Asn Gln His His His Lys Phe
        115                 120                 125

Pro Gly Trp Asn Leu Asp Thr Cys Tyr Ser Leu Thr Val Asn Glu Asn
    130                 135                 140

Gly Thr Phe Pro Thr Thr Thr Lys Lys Pro Thr Thr Thr Arg
145                 150                 155                 160

Thr Thr Thr Thr Thr Thr Thr Lys Lys Thr Thr Thr Thr Arg Thr Thr
                165                 170                 175

Thr Ala Ala Lys Lys Thr Thr Ile Ser Thr Thr His His Lys His Ser
            180                 185                 190

Ser Pro Lys Lys Ser Ser Thr Pro Asn Ser His Val Glu His His Val
        195                 200                 205

Gly Phe Glu Ala Thr Ala Ala Glu Thr Pro Leu Gln Pro Ser Pro Gln
    210                 215                 220

His Gln His Val Ala Thr His Gly Gly Gly Ser Gly Gly Gly Gly
225                 230                 235                 240

Ser Gly Gly Gly Ser Gly Gly Gly Ser Gly Gly Gly Gly Ser
                245                 250                 255

Gly Gly Gly Gly Ser Gly Gly Gly Ser Gly Gly Gly Gly Ser Gly
            260                 265                 270

Gly Gly Gly Ser Gln Val Gln Leu Gln Glu Ser Gly Pro Gly Leu Val
        275                 280                 285

Lys Pro Ser Glu Thr Leu Ser Leu Thr Cys Thr Val Ser Gly Gly Ser
    290                 295                 300

Ile Ser Tyr Tyr Ser Trp Thr Trp Val Arg Gln Pro Ala Gly Gln Gly
305                 310                 315                 320

Leu Glu Trp Ile Gly Arg Ile His Ile Ser Gly Val Thr Asn His Asn
                325                 330                 335

Pro Ser Leu Lys Ser Arg Val Ser Met Ser Ile Asp Thr Ser Arg Thr
            340                 345                 350

Gln Phe Ser Leu Arg Leu Thr Ser Val Thr Ala Ala Asp Thr Ala Val
        355                 360                 365
```

```
Tyr Phe Cys Ala Arg Ser Gly Thr Tyr Ser Ala Phe Asp Ile Trp
            370                 375                 380

Gly Gln Gly Thr Met Val Thr Val Ser Ser Gly Gly Gly Ser Gly
385                 390                 395                 400

Gly Gly Gly Ser Gly Gly Gly Ser Gly Gly Gly Ser Glu Ile
                405                 410                 415

Val Leu Thr Gln Ser Pro Gly Thr Leu Ser Leu Ser Pro Gly Glu Arg
            420                 425                 430

Ser Thr Leu Ser Cys Arg Ala Ser Gln Ser Phe Thr Ser Asn Tyr Leu
            435                 440                 445

Ala Trp Tyr Gln Gln Arg Pro Gly Gln Ala Pro Arg Leu Leu Ile Tyr
        450                 455                 460

Gly Ala Ser Thr Arg Ala Ile Gly Ile Pro Asp Arg Phe Ser Gly Ser
465                 470                 475                 480

Gly Ser Gly Thr Asp Phe Thr Leu Thr Ile Ser Arg Leu Glu Pro Glu
            485                 490                 495

Asp Phe Ala Val Tyr Tyr Cys Gln Gln Tyr Gly Ser Ser Pro Trp Thr
            500                 505                 510

Phe Gly Gln Gly Thr Lys Val Glu Ile Lys Thr Thr Thr Pro Ala Pro
        515                 520                 525

Arg Pro Pro Thr Pro Ala Pro Thr Ile Ala Ser Gln Pro Leu Ser Leu
530                 535                 540

Arg Pro Glu Ala Cys Arg Pro Ala Ala Gly Gly Ala Val His Thr Arg
545                 550                 555                 560

Gly Leu Asp Phe Ala Cys Asp Ile Tyr Ile Trp Ala Pro Leu Ala Gly
            565                 570                 575

Thr Cys Gly Val Leu Leu Leu Ser Leu Val Ile Thr Leu Tyr Cys Lys
            580                 585                 590

Arg Gly Arg Lys Lys Leu Leu Tyr Ile Phe Lys Gln Pro Phe Met Arg
        595                 600                 605

Pro Val Gln Thr Thr Gln Glu Glu Asp Gly Cys Ser Cys Arg Phe Pro
610                 615                 620

Glu Glu Glu Glu Gly Gly Cys Glu Leu Arg Val Lys Phe Ser Arg Ser
625                 630                 635                 640

Ala Asp Ala Pro Ala Tyr Gln Gln Gly Gln Asn Gln Leu Tyr Asn Glu
            645                 650                 655

Leu Asn Leu Gly Arg Arg Glu Glu Tyr Asp Val Leu Asp Lys Arg Arg
            660                 665                 670

Gly Arg Asp Pro Glu Met Gly Gly Lys Pro Arg Arg Lys Asn Pro Gln
        675                 680                 685

Glu Gly Leu Tyr Asn Glu Leu Gln Lys Asp Lys Met Ala Glu Ala Tyr
690                 695                 700

Ser Glu Ile Gly Met Lys Gly Glu Arg Arg Arg Gly Lys Gly His Asp
705                 710                 715                 720

Gly Leu Tyr Gln Gly Leu Ser Thr Ala Thr Lys Asp Thr Tyr Asp Ala
            725                 730                 735

Leu His Met Gln Ala Leu Pro Pro Arg
            740                 745

<210> SEQ ID NO 171
<211> LENGTH: 245
<212> TYPE: PRT
<213> ORGANISM: Artificial Sequence
<220> FEATURE:
```

<223> OTHER INFORMATION: Description of Artificial Sequence: Synthetic
polypeptide

<400> SEQUENCE: 171

```
Asp Ile Leu Leu Thr Gln Ser Pro Ala Thr Leu Ser Leu Ser Pro Gly
1               5                   10                  15

Glu Arg Ala Thr Leu Ser Cys Arg Ala Ser Gln Asn Ile Gly Thr Ser
            20                  25                  30

Ile Gln Trp Tyr Gln Gln Lys Pro Gly Gln Ala Pro Arg Leu Leu Ile
        35                  40                  45

Arg Ser Ser Ser Glu Ser Ile Ser Gly Ile Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Asn Thr Trp Pro Phe
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Ser Gly Gly Gly Gly Ser Glu
        115                 120                 125

Val Gln Leu Val Glu Ser Gly Ala Glu Val Lys Lys Pro Gly Ala Ser
    130                 135                 140

Val Lys Val Ser Cys Lys Ala Ser Gly Tyr Thr Phe Thr Asn Tyr Ile
145                 150                 155                 160

Ile His Trp Val Lys Gln Glu Pro Gly Gln Gly Leu Glu Trp Ile Gly
                165                 170                 175

Tyr Phe Asn Pro Tyr Asn His Gly Thr Lys Tyr Asn Glu Lys Phe Lys
            180                 185                 190

Gly Arg Ala Thr Leu Thr Ala Asp Lys Ser Ile Ser Thr Ala Tyr Met
        195                 200                 205

Glu Leu Ser Ser Leu Arg Ser Glu Asp Thr Ala Val Tyr Tyr Cys Ala
    210                 215                 220

Arg Ser Gly Pro Tyr Ala Trp Phe Asp Thr Trp Gly Gln Gly Thr Thr
225                 230                 235                 240

Val Thr Val Ser Ser
                245
```

<210> SEQ ID NO 172
<211> LENGTH: 25
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 172

```
Gly Ser Ser Pro Leu Gly Leu Ala Gly Ser Gly Gly Gly Ser Gly
1               5                   10                  15

Gly Gly Gly Ser Pro Met Ala Lys Lys
            20                  25
```

<210> SEQ ID NO 173
<211> LENGTH: 25
<212> TYPE: PRT
<213> ORGANISM: Artificial Sequence
<220> FEATURE:
<223> OTHER INFORMATION: Description of Artificial Sequence: Synthetic
peptide

```
<400> SEQUENCE: 173

Gly Gly Ser Val His Met Pro Leu Gly Phe Leu Gly Pro Gly Ser
1               5                   10                  15

Gly Gly Gly Ser Pro Met Ala Lys Lys
            20                  25

<210> SEQ ID NO 174
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Gly Gly Ser Pro Leu Gly Val Arg Gly Lys Gly Gly Gly Ser Gly
1               5                   10                  15

Gly Gly Gly Ser Pro Met Ala Lys Lys
            20                  25

<210> SEQ ID NO 175
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Gly Gly Ser Ser Pro Leu Gly Leu Ala Gly Ser Gly Ser Gly Gly
1               5                   10                  15

Ser Arg Gln Ala Arg Val Val Asn Gly
            20                  25

<210> SEQ ID NO 176
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Gly Gly Ser Val His Met Pro Leu Gly Phe Leu Gly Pro Gly Gly
1               5                   10                  15

Ser Arg Gln Ala Arg Val Val Asn Gly
            20                  25

<210> SEQ ID NO 177
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Gly Gly Ser Pro Leu Gly Val Arg Gly Lys Gly Gly Ser Gly Gly
1               5                   10                  15

Ser Arg Gln Ala Arg Val Val Asn Gly
            20                  25

<210> SEQ ID NO 178
<211> LENGTH: 5
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Gly Gly Gly Gly Ser
1               5

<210> SEQ ID NO 179
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Glu Leu Pro Thr Gln Gly Thr Phe Ser Asn Val Ser Thr Asn Val Ser
1               5                   10                  15

<210> SEQ ID NO 180
<211> LENGTH: 528
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 180

Met Ala Leu Pro Val Thr Ala Leu Leu Leu Pro Leu Ala Leu Leu Leu
1               5                   10                  15

His Ala Ala Arg Pro Gly Gly Gly Ser Cys Pro Tyr Ser Asn Pro
                20                  25                  30

Ser Leu Cys Gly Gly Gly Gly Ser Gln Val Gln Leu Gln Glu Ser Gly
            35                  40                  45

Pro Gly Leu Val Lys Pro Ser Glu Thr Leu Ser Leu Thr Cys Thr Val
        50                  55                  60

Ser Gly Gly Ser Ile Ser Tyr Tyr Ser Trp Thr Trp Val Arg Gln Pro
65                  70                  75                  80

Ala Gly Gln Gly Leu Glu Trp Ile Gly Arg Ile His Ile Ser Gly Val
                85                  90                  95

Thr Asn His Asn Pro Ser Leu Lys Ser Arg Val Ser Met Ser Ile Asp
                100                 105                 110

Thr Ser Arg Thr Gln Phe Ser Leu Arg Leu Thr Ser Val Thr Ala Ala
            115                 120                 125

Asp Thr Ala Val Tyr Phe Cys Ala Arg Ser Gly Gly Thr Tyr Ser Ala
        130                 135                 140

Phe Asp Ile Trp Gly Gln Gly Thr Met Val Thr Val Ser Ser Gly Gly
145                 150                 155                 160

Gly Gly Ser Gly Gly Gly Gly Ser Gly Gly Gly Gly Ser Gly Gly Gly
                165                 170                 175

Gly Ser Glu Ile Val Leu Thr Gln Ser Pro Gly Thr Leu Ser Leu Ser
            180                 185                 190

Pro Gly Glu Arg Ser Thr Leu Ser Cys Arg Ala Ser Gln Ser Phe Thr
        195                 200                 205

Ser Asn Tyr Leu Ala Trp Tyr Gln Gln Arg Pro Gly Gln Ala Pro Arg
    210                 215                 220

Leu Leu Ile Tyr Gly Ala Ser Thr Arg Ala Ile Gly Ile Pro Asp Arg
```

```
                225                 230                 235                 240
Phe Ser Gly Ser Gly Ser Gly Thr Asp Phe Thr Leu Thr Ile Ser Arg
                245                 250                 255
Leu Glu Pro Glu Asp Phe Ala Val Tyr Tyr Cys Gln Gln Tyr Gly Ser
                260                 265                 270
Ser Pro Trp Thr Phe Gly Gln Gly Thr Lys Val Glu Ile Lys Gly Gly
            275                 280                 285
Gly Gly Ser Cys Pro Tyr Ser Asn Pro Ser Leu Cys Gly Gly Gly Gly
        290                 295                 300
Ser Thr Thr Thr Pro Ala Pro Arg Pro Pro Thr Pro Ala Pro Thr Ile
305                 310                 315                 320
Ala Ser Gln Pro Leu Ser Leu Arg Pro Glu Ala Cys Arg Pro Ala Ala
                325                 330                 335
Gly Gly Ala Val His Thr Arg Gly Leu Asp Phe Ala Cys Asp Ile Tyr
                340                 345                 350
Ile Trp Ala Pro Leu Ala Gly Thr Cys Gly Val Leu Leu Leu Ser Leu
            355                 360                 365
Val Ile Thr Leu Tyr Cys Lys Arg Gly Arg Lys Lys Leu Leu Tyr Ile
        370                 375                 380
Phe Lys Gln Pro Phe Met Arg Pro Val Gln Thr Thr Gln Glu Glu Asp
385                 390                 395                 400
Gly Cys Ser Cys Arg Phe Pro Glu Glu Glu Glu Gly Gly Cys Glu Leu
                405                 410                 415
Arg Val Lys Phe Ser Arg Ser Ala Asp Ala Pro Ala Tyr Gln Gln Gly
            420                 425                 430
Gln Asn Gln Leu Tyr Asn Glu Leu Asn Leu Gly Arg Arg Glu Glu Tyr
        435                 440                 445
Asp Val Leu Asp Lys Arg Arg Gly Arg Asp Pro Glu Met Gly Gly Lys
    450                 455                 460
Pro Arg Arg Lys Asn Pro Gln Glu Gly Leu Tyr Asn Glu Leu Gln Lys
465                 470                 475                 480
Asp Lys Met Ala Glu Ala Tyr Ser Glu Ile Gly Met Lys Gly Glu Arg
                485                 490                 495
Arg Arg Gly Lys Gly His Asp Gly Leu Tyr Gln Gly Leu Ser Thr Ala
            500                 505                 510
Thr Lys Asp Thr Tyr Asp Ala Leu His Met Gln Ala Leu Pro Pro Arg
        515                 520                 525

<210> SEQ ID NO 181
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 181

Gly Gly Gly Gly Ser Gly Gly Gly Ser Gly Gly Ser Gly Ser
1               5                   10                  15

Gly Gly Gly Gly Ser Gly Gly Ser Gly Gly Ser Gly Gly Gly
            20                  25                  30

Ser Gly Ser Gly Gly Gly Ser Gly Gly Gly Ser
        35                  40                  45

<210> SEQ ID NO 182
<211> LENGTH: 45
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 182

Gly Gly Gly Gly Ser Gly Gly Gly Ser Gly Gly Gly Ser Gly Gly
1               5                   10                  15

Gly Ser Gly Ser Gly Gly Gly Ser Gly Gly Gly Ser Gly Gly
            20                  25                  30

Gly Gly Ser Gly Gly Gly Gly Ser Gly Gly Gly Ser
            35                  40                  45

<210> SEQ ID NO 183
<211> LENGTH: 226
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 183

Gln Phe Ser Val Leu Gly Pro Ser Gly Pro Ile Leu Ala Met Val Gly
1               5                   10                  15

Glu Asp Ala Asp Leu Pro Cys His Leu Phe Pro Thr Met Ser Ala Glu
            20                  25                  30

Thr Met Glu Leu Lys Trp Val Ser Ser Ser Leu Arg Gln Val Val Asn
        35                  40                  45

Val Tyr Ala Asp Gly Lys Glu Val Glu Asp Arg Gln Ser Ala Pro Tyr
    50                  55                  60

Arg Gly Arg Thr Ser Ile Leu Arg Asp Gly Ile Thr Ala Gly Lys Ala
65                  70                  75                  80

Ala Leu Arg Ile His Asn Val Thr Ala Ser Asp Ser Gly Lys Tyr Leu
                85                  90                  95

Cys Tyr Phe Gln Asp Gly Asp Phe Tyr Glu Lys Ala Leu Val Glu Leu
            100                 105                 110

Lys Val Ala Ala Leu Gly Ser Asp Leu His Val Asp Val Lys Gly Tyr
        115                 120                 125

Lys Asp Gly Gly Ile His Leu Glu Cys Arg Ser Thr Gly Trp Tyr Pro
    130                 135                 140

Gln Pro Gln Ile Gln Trp Ser Asn Asn Lys Gly Glu Asn Ile Pro Thr
145                 150                 155                 160

Val Glu Ala Pro Val Val Ala Asp Gly Val Gly Leu Tyr Ala Val Ala
                165                 170                 175

Ala Ser Val Ile Met Arg Gly Ser Ser Gly Glu Gly Val Ser Cys Thr
            180                 185                 190

Ile Arg Ser Ser Leu Leu Gly Leu Glu Lys Thr Ala Ser Ile Ser Ile
        195                 200                 205

Ala Asp Pro Phe Phe Arg Ser Ala Gln Arg Trp Ile Ala Ala Leu Ala
    210                 215                 220

Gly Thr
225

<210> SEQ ID NO 184
<211> LENGTH: 4
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 184

Gly Gly Gly Ser
1

<210> SEQ ID NO 185
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Ser Gly Gly Gly Gly
1               5

<210> SEQ ID NO 186
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Ser Gly Gly Gly Gly Ser
1               5

<210> SEQ ID NO 187
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Tyr Pro Tyr Asp Val Pro Asp Tyr Ala
1               5
```

PROTEASE-ACTIVATING CD45-GATE CAR

CROSS REFERENCE TO RELATED APPLICATIONS

The present application claims the benefit of priority to U.S. Provisional Application No. 63/128,667, filed on Dec. 21, 2020; and U.S. Provisional Application No. 63/289,984, filed on Dec. 15, 2021, the contents of both of which are hereby incorporated by reference in their entireties.

SEQUENCE LISTING

This application contains a Sequence Listing which has been submitted electronically in ASCII format and is hereby incorporated by reference in its entirety. Said ASCII copy, created on Dec. 19, 2021, is named AT-043_03US_SL.txt and is 556,722 bytes in size.

TECHNICAL FIELD

The present disclosure relates generally to the use of immune cells (e.g., T cells) engineered to express a chimeric antigen receptor (CAR) to treat a disease.

BACKGROUND

Tumor specificity is one of the major hurdles for the development of cancer therapy, such as CAR T cell therapy, in solid tumor indications. This differentiates solid tumor targets from many hematologic targets (e.g. CD19, CD20, BCMA), in that expression of these hematologic targets is heavily restricted to the hematologic lineage. Although their expression can be found on healthy hematologic cells and this can lead to the destruction of both healthy and cancerous cells, repopulation of normal hematologic cells from their progenitor stem cells makes these targets acceptable. However, many solid tumor targets exhibit an appreciable level of expression in some healthy organs or tissues, and the collateral destruction of these healthy tissues by CAR T cells may lead to severe adverse side effects and even death in patients ("on-target off-tumor toxicity"). Hence, it is useful to develop effective strategies and improve the anti-tumor specificity of CAR T cells to address potential on-target off-tumor toxicities. There exists a need for a cell-based cancer therapy, such as CAR T cells, with reduced on-target off-tumor toxicity.

SUMMARY

The present disclosure provides, among other things, chimeric antigen receptors (CARs) modified to improve target specificity in CAR T cell therapy, and related nucleic acids, expression vectors, cells, compositions and methods of treatment of cancer and other conditions amenable to CAR T cell therapy. The present disclosure provides a modification to CARs, the CD45 gate, that at least partially suppresses the modified CAR's activation in the presence of the CAR's antigen, thereby reducing the CAR's activity relative to the CAR not so modified or relative to the CAR not modified. This suppression and reduction in activity is partially or fully relieved when the modified CAR is in the presence of certain proteases, as occurs at the site of a tumor that is the CAR T cell therapy target. Disclosed herein are at least the following aspects and embodiments of the disclosure. Also provided is an anti-MUC16 CAR, including an anti-MUC16 CAR for use as a component of the protease-activating CD45-gate CAR disclosed herein.

CD45 is a phosphatase that plays a dynamic role in regulating T cell activation (1). It was found to directly activate TCR signaling by dephosphorylating other kinases, e.g. LCK, which activates these kinases and the downstream TCR signaling (2). CD45 is also able to directly dephosphorylate CD3zeta, which leads to the deactivation of TCR signaling (3).

Accordingly, in one aspect, provided herein is a protease-activating CD45-gate effector polypeptide comprising a CD45 recruiting domain connected to an effector entity optionally by a linker. In some embodiments, the effector entity can be reversibly modulated by CD45. In some embodiments, the effector entity is activated when the CD45 recruiting domain is released from the protease-activating CD45-gate effector by protease cleavage. In some embodiments, the CD45 recruiter is released by protease cleavage at the linker. In some embodiments, the effector entity comprises a chimeric antigen receptor (CAR). In some embodiments, the effector entity comprises a T cell receptor (TCR). In some embodiments, the CD45 recruiting domain (e.g. an anti-CD45 scFv) is prepared, using no more than ordinary skill in the art, from the CD45 antibodies disclosed in, for example, WO2005/026210, WO20131048804, WO2017009473, WO2020092654, EP1664122B1, and U.S. Pat. No. 6,106,834.

In one aspect, provided herein is a protease-activating CD45-gate chimeric antigen receptor (CD45-gate CAR) comprising an extracellular domain, a transmembrane domain, and an intracellular domain, wherein the extracellular domain comprises: a CD45 recruiting domain, a linker comprising one or more protease cleavage sites that can be cleaved by at least one protease, and an antigen binding domain. In some embodiments of the protease-activating CD45-gate CAR, the intracellular domain comprises at least one signaling domain that can be reversibly inactivated by CD45. In an embodiment, the linker is between the CD45 recruiting domain and the antigen binding domain. In an embodiment, the CD45 recruiting domain comprises one or more linkers. In an embodiment, the CD45 recruiting domain comprises an anti-CD45 antibody comprising a heavy chain variable domain ($V_H$) and a light chain variable domain ($V_L$). In some embodiments, the linker is between the $V_H$ and $V_L$ of the anti-CD45 antibody. In some embodiments, the protease-activating CD45-gate CAR comprises additional flexible regions e.g. placed between domains.

In a further aspect, provided herein is a protease-activating CD45-gate chimeric antigen receptor (CD45-gate CAR) comprising an extracellular domain, a transmembrane domain, and an intracellular domain, wherein the extracellular domain comprises:
 a CD45 recruiting domain,
 an antigen binding domain, and
 a linker connecting the carboxy terminus of the CD45 recruiting domain to the amino terminus of the antigen binding domain, wherein the linker comprises at least one protease cleavage site that is recognized by a protease,
 and further wherein the intracellular domain comprises at least one (e.g. one or more than one) signaling domain that can be reversibly inactivated by CD45.

In some embodiments, the CD45 recruiting domain comprises one or more of an anti-CD45 antibody antigen binding domain, an anti-CD45 NANOBODY®, an anti-CD45 scFv, a viral protein binder of CD45, a truncated viral protein binder of CD45, an anti-CD45 Fab, an anti-CD45 camelid VHH, a CD45-binding protein, an endogenous CD45 binder, or a truncated endogenous CD45 binder. In some embodiments, the CD45 recruiting domain comprises one or more of a peptide or protein that interacts with CD45, for example, full-length or truncated UL11, full-length or truncated sec49K, and full-length or truncated BTN3A1. In some embodiments, the CD45 recruiting domain comprises a truncated BTN3A1, e.g. a truncated BTN3A1 having the amino acid sequence of SEQ ID NO: 14 or of SEQ ID NO: 15.

In some embodiments, the CD45 recruiting domain comprises an anti-CD45 scFv. In some embodiments, the CD45 recruiting domain comprises an anti-CD45 antibody antigen binding domain. In some embodiments, the CD45 recruiting domain comprises one or more of truncated UL11, truncated sec49K, and truncated BTN3A1. In some embodiments, the CD45 recruiting domain comprises the amino acid sequence of SEQ ID NO: 3, SEQ ID NO: 4, SEQ ID NO: 5, SEQ ID NO: 6, SEQ ID NO: 12, SEQ ID NO: 13, SEQ ID NO: 14 or SEQ ID NO: 15.

In some embodiments, the antigen binding domain specifically binds BCMA, MUC16 (also known as CA125), EGFR, EGFRvIII, MUC1, Flt-3, WT-1, CD20, CD23, CD30, CD38, CD70, CD33, CD133, MHC-WT1, TSPAN10, MHC-PRAME, MHC-NY-ESO1, HER2 (ERBB2), CAIX (Carbonic anhydrase IX), LIV1, ADAM10, CHRNA2, LeY, NKG2D, CS1, CD44v6, ROR1, CD19, Claudin-18.2 (Claudin-18A2, or Claudin18 isoform 2), PSCA, DLL3 (Delta-like protein 3, *Drosophila* Delta homolog 3, Delta3), Mud 7 (Mucin17, Muc3, Muc3), FAP alpha (Fibroblast Activation Protein alpha), Ly6G6D (Lymphocyte antigen 6 complex locus protein G6d, c6orf23, G6D, MEGT1, NG25), PSMA, MSLN, or RNF43 (E3 ubiquitin-protein ligase RNF43, RING finger protein 43).

In some embodiments, the antigen binding domain specifically binds MUC16. In some embodiments, the antigen binding domain specifically binds MUC16 and the protease-activating CD45-gate CAR comprises the amino acid sequence of any of SEQ ID NOs: 11, 56, 75-79, and 121-170, each of which can have or not have the signal sequence of SEQ ID NO:1. In some embodiments, the antigen binding domain specifically binds MUC16 and the protease-activating CD45-gate CAR comprises the amino acid sequence of SEQ ID NO: 75, with or without the signal sequence of SEQ ID NO:1. In some embodiments, the antigen binding domain specifically binds MUC16 and the protease-activating CD45-gate CAR comprises the amino acid sequence of SEQ ID NO: 76, with or without the signal sequence of SEQ ID NO:1. In some embodiments, the extracellular domain comprises the amino acid sequence of any one of SEQ ID NOs: 3, 4, 5, 6, 12, 13, 14, 15, 56, and 56 without the signal sequence of SEQ ID NO:1.

In some embodiments, the antigen binding domain specifically binds to an antigen expressed by a certain type of tumor and the protease cleavage sites can be recognized and cleaved by a protease that the same type of tumor expresses. In some embodiments, the protease-activating CD45-gate CAR both (1) can specifically recognize and bind to an antigen expressed by a tumor and (2) comprises a CD45 recruiting domain-CAR linker that can be cleaved by a protease that the tumor secretes and/or that is present and/or active in the tumor microenvironment.

In some embodiments, the antigen binding domain specifically binds to a breast cancer tumor antigen or a colorectal cancer tumor antigen and one or more of the at least one protease cleavage sites can be recognized and cleaved by uPA. In some embodiments, the protease-activating CD45-gate CAR's antigen binding domain specifically recognizes and binds to an antigen characteristic of any of cervical, breast, ovarian and colorectal cancers and at least one of its protease cleavage sites can be recognized and cleaved by MMP-2 and/or MMP-9. In some embodiments, the protease-activating CD45-gate CAR's antigen binding domain specifically recognizes and binds to an antigen characteristic of any of breast and ovarian cancers and at least one of its protease cleavage sites can be recognized and cleaved by matriptase.

In some embodiments, the linker comprises a GS sequence on either or both ends of each of the one or more protease cleavage sites. In some embodiments, the GS sequence is a polypeptide that consist of only glycine and serine residues. In some embodiments, each GS sequence comprises a series of linked GS peptides, a GS peptide being, for example, a peptide having an amino acid sequence comprising only glycine and serine residues, e.g. a peptide having an amino acid sequence comprising one or more glycine residues followed by one or more serine residues, for example, a peptide having an amino acid sequence of GS, GGS, GGGS (SEQ ID NO: 184), or GGGGS (SEQ ID NO:178), wherein the linked GS peptides are linked in any order and in any combination. In some embodiments, the GS sequence comprises any combination of 1, 2, 3, 4, 5, 6, 7, 8, 9 or 10 GS peptides or comprises between 1 and 15 GS peptides in any order and combination.

In some embodiments, the linker of the protease-activating CD45-gate CAR disclosed herein has a length of 15-100 amino acids, 30-100 amino acids, 15-75 amino acids, 20-50 amino acids, 20 amino acids, 25 amino acids, 30 amino acids, 35 amino acids, 40 amino acids, 45 amino acids, or 50 amino acids, or about 20 amino acids, about 25 amino acids, about 30 amino acids, about 35 amino acids, about 40 amino acids, about 45 amino acids, or about 50 amino acids.

In some embodiments of the protease-activating CD45-gate CAR disclosed herein, the linker comprises one or more protease cleavage sites that comprise the amino acid sequence of SEQ ID NO: 32, 91-98, 103-105 or SEQ ID NO: 106. In some embodiments, the linker comprises one or more amino acid sequences of SEQ ID NO: 53, 89, or 90. In some embodiments, the linker comprises one or more amino acid sequences of SEQ ID NO: 8-10, 99-102, 107-120, 172-176 or SEQ ID NO: 177. In some embodiments, the linker comprises two or more protease cleavage sites and each cleavage site is the same as or different from any of the other cleavage sites. In some embodiments, the number of protease cleavage sites is 1, 2, 3, 4, 5, 6, 7, 8, 9, 10, or is between 1 and 15. In some embodiments, when the linker comprises more than one protease cleavage site, each protease cleavage site is independently the same as or different from one or more of the other protease cleavage sites.

In some embodiments, the linker comprises one protease cleavage site (e.g. any of the protease cleavage sites disclosed herein, e.g. a cleavage site having the amino acid sequence of, for example, any of SEQ ID NOs: 32, 89-98 and 103-106) (SEQ ID NOs: 89 and 90 each have two protease cleavage sites, a MMP2/9 site and a MTSP site). In some embodiments, the protease cleavage site comprises the amino acid sequence of SEQ ID NO: 32 [LVPRGS]. In some embodiments, the protease cleavage site comprises the amino acid sequence of SEQ ID NO: 91. In some embodiments, the protease cleavage site comprises the amino acid sequence of SEQ ID NO: 92. In some embodiments, the protease cleavage site comprises the amino acid sequence of SEQ ID NO:93. In some embodiments, the protease cleavage site comprises the amino acid sequence of SEQ ID NO:94. In some embodiments, the protease cleavage site comprises the amino acid sequence of SEQ ID NO:95. In some embodiments, the protease cleavage site comprises the amino acid sequence of SEQ ID NO:96. In some embodiments, the protease cleavage site comprises the amino acid sequence of SEQ ID NO:97. In some embodiments, the protease cleavage site comprises the amino acid sequence of SEQ ID NO:98. In some embodiments, the protease cleavage site comprises the amino acid sequence of SEQ ID NO: 103. In some embodiments, the protease cleavage site comprises the amino acid sequence of SEQ ID NO:104. In some embodiments, the protease cleavage site comprises the amino acid of any one of SEQ ID NOs: 89, 90, 91, 92, 93, 94, 95, 96, 97, 98, 103, 104, 105, and 106. In some embodiments, the linker comprises multiple protease cleavage sites (for example, any of the protease cleavage sites known and/or disclosed herein, e.g. a cleavage site having the amino acid sequence of any of SEQ ID NOs: 32, 89-98 and 103-104), such as two, three, four, five, six or more protease cleavage sites, e.g. up to ten or up to fifteen protease cleavage sites, and each cleavage site is the same as or different from any of the other cleavage sites. In some embodiments, one or more than one of the multiple protease cleavage sites comprises the amino acid sequence of SEQ ID NO: 32 (amino acid sequence LVPRGS). In some embodiments, the CD45 recruiting domain comprises one or more than one protease cleavage sites. In some embodiments, the linker amino acid sequence is or comprises the amino acid sequence of any one or more of (e.g. 1, 2, 3, 4, 5, 6 or more) of SEQ ID NOs: 99-102, 172-177, and 108-120. In some embodiments, the linker comprises one copy or more than one copy (e.g. 1, 2, 3, 4, 5, 6 or more) of the amino acid sequence of any of SEQ ID NOs: 89-98 and 103-106.

In some embodiments, the protease cleavage site, or one or more of the multiple protease cleavage sites, is recognized by one or more (e.g. 1, 2, 3, 4, 5, 6, 7, 8, 9, 10, or 15, or any range between any two of these values) of thrombin, trypsin, plasmin, prostate-specific antigen (PSA), urokinase plasminogen activator (uPA), urokinase plasminogen activator receptor (uPAR), matrix metalloproteinase (MMP), matriptase (MT-SP1), legumain, a disintegrin and metalloproteinase (ADAM), and transmembrane Serine Protease (TMPRSS). Alternatively stated, in some embodiments, the protease that recognizes the protease cleavage site, or that recognizes one or more of the multiple protease cleavage sites, is one or more of thrombin, trypsin, plasmin, prostate-specific antigen (PSA), urokinase plasminogen activator (uPA), urokinase plasminogen activator receptor (uPAR), matrix metalloproteinase (MMP), matriptase (MT-SP1), legumain, a disintegrin and metalloproteinase (ADAM), transmembrane Serine Protease (TMPRSS), Granzyme B, activated protein C, Caspase, Cathepsin, Chymase, Elastase, Guanidinobenzoatase, HtrA1, Human Neutrophil Elastase, Lactoferrin, Marapsin, NS3/4A, PACE4, tissue plasminogen activator (tPA), DESC1, DPP-4, FAP, Hepsin, Matriptase-2, secretase, kallikrein-related peptidase (KLK), and tryptase, or a serine protease, a cysteine-type lysosomal protease, a metalloproteinase, a coagulation factor protease, or an aspartyl-type lysosomal protease. In some embodiments, the protease cleavage site comprises an amino acid sequence that is cleaved by a protease or type of protease listed herein. In some embodiments, the protease cleavage site or one or more of the multiple protease cleavage sites is recognized by an endogenous protease or by a protease which is present in a tumor microenvironment. In some embodiments, the protease that recognizes the protease cleavage site, or that recognizes one or more of the multiple protease cleavage sites, is a protease which is present in a tumor microenvironment.

In some embodiments, the linker comprises, in any order, including e.g. from the amino to the carboxy terminus and from the carboxy to the amino terminus, any of the following combinations of cleavage sites: for example, uPA and MMP, uPA and matriptase, MMP and matriptase, matriptase and MMP and uPA. In some embodiments, the linker further comprises one or more spacer sequences at either or both ends of one or more of each protease cleavage site to provide flexibility. In some embodiments, the linker further comprises one or more of a GS sequence, e.g. a GS sequence as disclosed herein (e.g. any one or more of SEQ ID NOs: 52, 54, 57), at either or both ends of one or more of each protease cleavage site. In some embodiments, the CD45-gate CAR comprises one or more of the linkers disclosed herein (e.g. SEQ ID NOs: 7-10, 99-102, 172-177, 108-120), e.g. 1, 2, 3, 4, 5, 15, or any intervening integer value or any range between any two such values. The linkers can be placed, e.g., between the CD45 recruiting domain, e.g., an anti-CD45 scFv, and an antigen binding domain, e.g., an antigen binding domain of a CAR. In some embodiments, the CD45 recruiting domain comprises an anti-CD45 antibody such as scFv, and the linkers can be placed between $V_L$ and $V_H$ or between $V_H$ and $V_L$ of the CD45 binding domain. In some embodiments, the antigen binding domain comprises 53B6 as disclosed herein. In some embodiments, the GS sequence provides a spacer sequence that creates flexibility between functional domains. In some embodiments, either region or both regions flanking the protease cleavage site, or the spacer sequence providing flexibility is not a GS sequence, as many flexible sequences that may function equally well are known in the art. See for example, Whitlow M. et al., An improved linker for single-chain Fv with reduced aggregation and enhanced proteolytic stability. Protein Eng. 1993 November; 6(8):989-95. doi: 10.1093/protein/6.8.989. PMID: 8309948. In some embodiments, the spacer sequence creates flexibility and does not interfere with the activities of each functional domain. In some embodiments, the linker can be any suitable length, e.g. from 15-100 amino acids, 30-100 amino acids, 20-80 amino acids, 20-50 amino acids, or 25, 30, 35, 40, 45, 50, or 55 amino acids in length, or about 25, about 30, about 35, about 40, about 45, about 50, or about 55 amino acids in length.

In some embodiments, the protease cleavage site or one or more of the multiple protease cleavage sites is recognized by one or more of a serine protease, a cysteine-type lysosomal protease, an aspartyl-type lysosomal protease and a metalloproteinase. In some embodiments, a protease that recognizes the protease cleavage site, or that recognizes one or more of the multiple protease cleavage sites, is one or more of a serine protease, a cysteine-type lysosomal protease, an aspartyl-type lysosomal protease and a metalloproteinase.

In some embodiments, the linker comprises between 1 and 15 or between 1 and 10 or 1, 2, 3, 4, 5, 6, 7, 8, 9 or 10 cleavage sites, each one of which may be the same as or different from one or more of the other cleavage sites, and/or the number of proteases that recognize the protease cleavage site or sites is between 1 and 15 or between 1 and 10 or is 1, 2, 3, 4, 5, 6, 7, 8, 9 or 10.

In some embodiments, the linker comprises an amino GS peptide, a peptide comprising a protease cleavage site, and a carboxy GS peptide. In some embodiments, the linker comprises the amino acid sequence of SEQ ID NO: 9, which comprises an amino GS peptide (SEQ ID NO: 52), a cleavage peptide (e.g. SEQ ID NO: 53) comprising a protease cleavage site, and a carboxy GS peptide (SEQ ID NO: 54). In some embodiments, the linker comprises the same amino and carboxy GS peptides and a different cleavage peptide comprising the same or a different protease cleavage site.

In some embodiments, the linker of the protease-activating CD45-gate CAR disclosed herein comprises the amino acid sequence of any one or more of SEQ ID NOs: 9, 10, 102, 172-177, and 108-120. In some embodiments, the linker comprises one or more protease cleavage sites having an amino acid sequence selected from the group consisting of SEQ ID NOs: 32, 89-98 and 103-104, optionally wherein the number of protease cleavage sites is 1, 2, 3, 4, 5, 6, 7, 8, 9, 10, or between 1 and 15, and, when the linker comprises more than one protease cleavage site, each protease cleavage site is independently the same as or different from one or more of the other protease cleavage sites.

In some embodiments, the linker of the protease-activating CD45-gate CAR disclosed herein comprises, on either or both ends of, and contiguous with, one or more of the protease cleavage sites, one or more sets of contiguous GS sequences, wherein each GS sequence has an amino acid sequence of GS, GGS, GGGS (SEQ ID NO: 184), or GGGGS (SEQ ID NO:178), and the sets of contiguous GS sequences comprise GS sequences in any combination, optionally wherein a set of contiguous GS sequences comprises any combination of 1, 2, 3, 4, 5, 6, 7, 8, 9 or 10 GS sequences or comprises between 1 and 15 GS sequences in any combination. Exemplary embodiments of linkers comprising such sets of contiguous GS sequences include SEQ ID NOs: 9, 10, 102, 172-177, and 107-120.

In some embodiments, the protease-activating CD45-gate CAR comprises more than one linker comprising a protease cleavage site, wherein each linker has an amino acid sequence independently selected from SEQ ID NOs: 9, 10, 102, 172-177, and 107-120, and optionally wherein the number of linkers is 2, 3, 4, 5, or an integer value between 2 and 10. Exemplary embodiments of protease-activating CD45-gate CARs comprising more than one linker include SEQ ID NOs: 125-128 and 142-145.

In some embodiments, the extracellular domain comprises a stalk domain between the antigen binding domain and the transmembrane domain.

In some embodiments, the intracellular signaling domain comprises an activating domain. In some embodiments, the intracellular signaling domain comprises a costimulatory domain. In some embodiments, the intracellular signaling domain comprises an activating domain and a costimulatory domain. In some embodiments, the intracellular signaling domain comprises an activating domain such as an ITAM-containing domain. In some embodiments, the intracellular signaling domain comprises the CD3 zeta intracellular domain. In some embodiments, the intracellular signaling domain comprises a CD3 zeta domain that comprises the amino acid sequence of SEQ ID NO: 34 or a fragment thereof.

In some embodiments, an intracellular signaling domain for use in a protease-activating CD45-gate CAR can be the cytoplasmic sequences of, for example without limitation, the T cell receptor and co-receptors that act in concert to initiate signal transduction following antigen receptor engagement, as well as any derivative or variant of these sequences and any synthetic sequence that has the same functional capability.

In some embodiments, the intracellular domain comprises or further comprises at least one costimulatory domain. In some embodiments, the at least one costimulatory domain is a cytoplasmic signaling region or domain of CD28, OX-40, 4-1BB/CD137, CD2, CD7, CD27, CD30, CD40, programmed death-1 (PD-1), inducible T cell costimulator (ICOS), lymphocyte function-associated antigen-1 (LFA-1 (CD1 la/CD 18), CD3 gamma, CD3 delta, CD3 epsilon, CD247, CD276 (B7-H3), LIGHT, (TNFSFI4), NKG2C, Ig alpha (CD79a), DAP-10, Fc gamma receptor, MHC class I molecule, TNF receptor proteins, an Immunoglobulin protein, cytokine receptor, integrins, Signaling Lymphocytic Activation Molecules (SLAM proteins), activating NK cell receptors, BTLA, a Toll ligand receptor, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL-2R beta, IL-2R gamma, IL-7R alpha, ITGA4, VLA1, CD49a, ITGA4, CD49D, ITGA6, VLA-6, CD49f, ITGAD, CD1 Id, ITGAE, CD103, ITGAL, CD1 la, LFA-1, IT GAM, CD1 lb, ITGAX, CD1 lc, ITGB1, CD29, ITGB2, CD 18, LFA-1, ITGB7, NKG2D, TNFR2, TRANCE/RANKL, DNAMI (CD226), SLAMF4 (CD244, 2B4), CD84, CD96 (Tactile), CEACAM1, CRT AM, Ly9 (CD229), CD 160 (BY55), PSGL1, CD100 (SEMA4D), CD69, SLAMF6 (NTB-A, Lyl08), SLAM (SLAMFI, CD150, IPO-3), BLAME (SLAMF8), SELPLG (CD162), LTBR, LAT, GADS, SLP-76, PAG/Cbp, CD 19a, a ligand that specifically binds with CD83, or any combination thereof.

In some embodiments, the protease-activating CD45-gate CAR comprises a signal sequence. In some embodiments, the signal sequence is the CD8 signal sequence. In some embodiments, the signal sequence comprises the amino acid sequence of SEQ ID NOs: 1 or 44.

In some embodiments, the amino acid sequence of the protease-activating CD45-gate CAR is or comprises the amino acid sequence of any one of SEQ ID NOs: 16-31 and 121-170, or is or comprises the amino acid sequence of any one of SEQ ID NOs: 16-31 and 121-170 but which lacks any one or more of: the signal sequence, hemagglutinin (HA) tag, and/or V5 tag.

In an alternative aspect of the protease-activating CD45-gate CAR disclosed herein, the CD45 recruiting domain itself comprises one or more than one protease cleavage sites (e.g. protease cleavage sites as disclosed herein), and the linker that joins the CD45 recruiting domain to the antigen binding domain either comprises no protease cleavage site or comprises one or more than one protease cleavage sites (e.g. protease cleavage sites as disclosed herein). In an embodiment, protease cleavage produces a CAR attached to a fragment of the CD45 protein, and the protease cleavage partially or wholly relieves the CD45-induced inhibition of the CAR's activity.

Also provided herein is a CAR that specifically recognizes and binds to MUC16. In an embodiment, the anti-MUC16 CAR comprises the amino acid sequence of any of SEQ ID NO: 11, 75, 76, 77, 78, and 79.

The present disclosure further provides a protease-activating CD45-gate T cell receptor (TCR). In an embodiment, the protease-activating CD45-gate TCR comprises a modified TCR a, 3, 7, or 6 polypeptide, wherein the modification comprises a CD45 recruiting domain joined by a protease-cleavable linker peptide to the amino terminus of the TCR a, 3, 7, or 6 polypeptide. In an embodiment, the protease-activating CD45-gate TCR comprises a modified single-chain TCR, wherein the modification comprises a CD45 recruiting domain joined by a protease-cleavable linker peptide to the amino terminus of a single-chain TCR. In an embodiment, the polypeptide is a CD45-TCR a, J, 7, or 6 polypeptide. In an embodiment, the polypeptide is a CD45- single chain TCR. In another aspect, provided herein is a nucleic acid that encodes the CD45-gate TCR disclosed herein.

In another aspect, provided herein is a nucleic acid encoding the extracellular domain of the protease-activating CD45-gate CAR disclosed herein. In some embodiments, the encoded extracellular domain comprises a CD45 recruiting domain such as but not limited to a CD45 recruiting domain disclosed herein, the extracellular domain of a CAR such as but not limited to a CAR disclosed herein, and a linker connecting the carboxy terminus of the CD45 recruiting domain to the amino terminus of the CAR extracellular domain, such as but not limited to a linker disclosed herein.

In another aspect, provided herein is a nucleic acid that encodes the CD45-gate CAR disclosed herein.

Also provided herein is a nucleic acid that encodes a polypeptide that comprises the amino acid sequence of any of SEQ ID NOs: 11, 56, 75, 76, 77, 78, 79 and 121-170. In some embodiments, the polypeptide is an anti-MUC16 CAR as disclosed herein. In some embodiments, the polypeptide is a protease-activating CD45-gate CAR as disclosed herein.

In another aspect, provided herein is a vector comprising a nucleic acid as disclosed herein. In an embodiment, the vector is an expression vector. In an embodiment, the vector is a viral vector, a retroviral vector, a DNA vector, a plasmid, a RNA vector, an adenoviral vector, an adenovirus associated vector, a lentiviral vector, or any combination thereof.

In a further aspect, provided herein is an engineered cell e.g. an engineered immune cell comprising a protease-activating CD45-gate CAR as disclosed herein.

In a further aspect, provided herein is an engineered immune cell comprising a nucleic acid as disclosed herein.

In another aspect, provided herein is an engineered immune cell comprising a vector as disclosed herein.

In various embodiments, any of the engineered cells e.g. any of the engineered immune cells disclosed herein functionally express a protease-activating CD45-gate CAR as disclosed herein. In various embodiments, any of the engineered cells e.g. any of the engineered immune cells disclosed herein functionally express a protease-activating CD45-gate CAR that comprises the amino acid sequence of any of SEQ ID NOs: 11, 56, 75, 76, 77, 78, 79, and 121-170. Also provided herein are engineered cells e.g. engineered immune cells that functionally express a MUC16-specific CAR that comprises the amino acid sequence of any of SEQ ID NOs: 11, 56, 75, 76, 77, 78, 79 and 121-170. In various embodiments, any of the engineered cells e.g. any of the engineered immune cells disclosed herein is an isolated cell.

In various embodiments, the engineered cell e.g. engineered immune cell disclosed herein functionally expresses the protease-activating CD45-gate CAR disclosed herein from a nucleic acid encoding the protease-activating CD45-gate CAR. In various embodiments, the engineered cell e.g. engineered immune cell disclosed herein functionally expresses CD45, e.g. functionally expresses the cell's endogenous CD45 gene or functionally expresses CD45, or a fragment or variant of CD45, from an exogenous nucleic acid that encodes CD45 and that was introduced into the cell. In various embodiments, the engineered cell e.g. engineered immune cell disclosed herein functionally expresses the anti-MUC16 CAR disclosed herein from a nucleic acid encoding the anti-MUC16 CAR. In some embodiments, the anti-MUC16 CAR is a protease-activating CD45-gate MUC16CAR.

In various embodiments, the engineered immune cell disclosed herein is an engineered B cell, mast cell, myeloic-derived phagocyte, T cell e.g. an alpha/beta and/or gamma/delta T cell, tumor infiltrating lymphocyte (TIL), NK cell, TCR-expressing cell, dendritic cell, or NK-T cell. In some embodiments, the cell is and/or is derived from an autologous T cell. In some embodiments, the cell is and/or is derived from an allogeneic T cell or an iPSC (induced pluripotent stem cell). In some embodiments, the cell is and/or is derived from an iPSC-derived T cell.

In an embodiment, an engineered immune cell as disclosed herein comprises or further comprises one or more genomic modifications of one or more of the endogenous CD52 gene and the endogenous TCR genes, e.g. the TCRα gene. In an embodiment, an engineered immune cell as disclosed herein is a T cell.

In another aspect, provided herein is a population of immune cells comprising one or more of the engineered immune cells disclosed herein. In an embodiment, the population comprises about or at least about $1\times10^4$, about or at least about $1\times10^5$, about or at least about $1\times10^6$, about or at least about $1\times10^7$, or about or at least about $1\times10^8$ engineered cells, e.g. engineered immune cells, as disclosed herein, optionally wherein the population does not comprise more than about $1\times10^{10}$ or more than about $1\times10^9$ or more than about $5\times10^9$ engineered cells, e.g. engineered immune cells, as disclosed herein. In an embodiment, a population of immune cells as disclosed herein is enriched for the engineered immune cell as disclosed herein. In various embodiments, the population of immune cells is at least 50%, e.g. 50%, 55%, 60%, 65%, 70%, 75%, 80%, 85%, 90%, 95%, or more than 95% engineered cells that are T cells, e.g., alpha/beta T cells and gamma/delta T cells, B cells, natural killer (NK) cells, natural killer T (NKT) cells, mast cells, and/or myeloic-derived phagocytes. In various embodiments, the population of immune cells is at least 50%, e.g. 50%, 55%, 60%, 65%, 70%, 75%, 80%, 85%, 90%, 95%, or more than 95% engineered T cells.

In another aspect, provided herein is a composition comprising an engineered cell e.g. an engineered immune cell as disclosed herein or a population of cells as disclosed herein, and a pharmaceutically acceptable carrier.

Also provided herein is the use of any of the engineered immune cells e.g. engineered T cells provided herein in the manufacture of a medicament for the treatment of cancer or for inhibiting tumor growth or progression in a subject in need thereof. Also provided herein is any of the engineered immune cells e.g. engineered T cells provided herein for use as a medicament and for use in treating any disease or condition amenable to treatment by CAR T cell therapy. In some embodiments, the disease or condition is a cancer, autoimmune disease, or infection. In some embodiments, the disease or condition is a form of cancer.

In another aspect, provided herein is a method of treating a condition in a patient comprising administering to the patient an engineered immune cell as disclosed herein. In an embodiment of the method, the engineered immune cell is an allogeneic engineered immune cell derived from a donor other than the patient.

In another aspect, provided herein is a method of treating a condition in a patient comprising administering to the patient a population of engineered immune cells as disclosed herein. In an embodiment of the method, the engineered immune cells of the population are derived from one or more allogeneic immune cells from a donor other than the patient.

In another aspect, provided herein is a method of treating a condition in a patient comprising administering to the patient a pharmaceutical composition as disclosed herein. In an embodiment of the method, the composition comprises one or more engineered allogeneic immune cells derived from a donor other than the patient.

In embodiments of the methods of treating a condition in a patient disclosed herein, the condition may be any disease or condition amenable to treatment by CAR T cell therapy. In some embodiments, the disease or condition is a cancer, autoimmune disease, or infection. In some embodiments, the disease or condition is a form of cancer. In some embodiments, the cancer is a hematological malignancy or non-solid tumor. In some embodiments, the cancer is a solid cancer or solid tumor. In some embodiments, the cancer is a hematological malignancy that is acute lymphoblastic leukemia (ALL), acute myeloid leukemia (AML), chronic myelogenous leukemia (CML), chronic eosinophilic leukemia (CEL), myelodysplasia syndrome (MDS), non-Hodgkin's lymphoma (NHL), or multiple myeloma (MM). In some embodiments, the cancer is a solid cancer that is biliary cancer, bladder cancer, bone or soft tissue carcinoma, brain tumor, breast cancer, cervical cancer, colon cancer, colorectal adenocarcinoma, colorectal cancer, desmoid tumor, embryonal cancer, endometrial cancer, esophageal cancer, gastric cancer, gastric adenocarcinoma, glioblastoma multiforme, gynecological tumor, head and neck squamous cell carcinoma, hepatic cancer, lung cancer, malignant melanoma, osteosarcoma, ovarian cancer, pancreatic cancer, pancreatic ductal adenocarcinoma, primary astrocytic tumor, primary thyroid cancer, prostate cancer, renal cancer, renal cell carcinoma, rhabdomyosarcoma, skin cancer, soft tissue sarcoma, testicular germ-cell tumor, urothelial cancer, uterine sarcoma, or uterine cancer.

In another aspect, provided herein is a method of reducing on-target off-tumor toxicity of CAR T cells comprising administering to a patient a cell as disclosed herein, a population of cells as disclosed herein, or a composition as disclosed herein, wherein the on-target, off-tumor toxicity is lower than the on-target, off-tumor toxicity of control cells, a population of control cells or a composition of control cells, respectively, administered under the same conditions, wherein the control cells, population of control cells, or control cells of the composition comprise a CAR that lacks at least one of a CD45 recruiting domain and a linker that comprises a protease cleavage site.

In another aspect, provided herein is a method of increasing the efficiency of CAR T cells or CAR T cell therapy comprising administering to a patient a cell as disclosed herein, a population of cells as disclosed herein, or a composition as disclosed herein, wherein the efficiency is greater than the efficiency of control cells, a population of control cells or a composition of control cells, respectively, administered under the same conditions, wherein the control cells, population of control cells, or control cells of the composition comprise a CAR that lacks at least one of a CD45 recruiting domain and a linker that comprises a protease cleavage site.

In another aspect, provided herein is a method of increasing the efficacy of CAR T cell therapy comprising administering to a patient a cell as disclosed herein, a population of cells as disclosed herein, or a composition as disclosed herein, wherein the efficacy is greater than the efficacy of control cells, a population of control cells or a composition of control cells, respectively, administered under the same conditions, wherein the control cells, population of control cells, or control cells of the composition comprise a CAR that lacks at least one of a CD45 recruiting domain and a linker that comprises a protease cleavage site.

In another aspect, provided herein is a method of increasing the efficacy of CAR T cell therapy against a solid tumor comprising administering to a patient having a solid tumor a cell as disclosed herein, a population of cells as disclosed herein, or a composition as disclosed herein, wherein the efficacy against the solid tumor is greater than the efficacy against the solid tumor of control cells, a population of control cells or a composition of control cells, respectively, administered under the same conditions, wherein the control cells, population of control cells, or control cells of the composition comprise a CAR that lacks at least one of a CD45 recruiting domain and a linker that comprises a protease cleavage site.

In another aspect, provided herein is a method of reducing the incidence of side effects in CAR T cell therapy comprising administering to a patient a cell as disclosed herein, a population of cells as disclosed herein, or a composition as disclosed herein, wherein the incidence of side effects is lower than the incidence of side effects when control cells, a population of control cells or a composition of control cells, respectively, are administered under the same conditions, wherein the control cells, population of control cells, or control cells of the composition comprise a CAR that lacks at least one of a CD45 recruiting domain and a linker that comprises a protease cleavage site.

In another aspect, provided herein is a method of effecting reversible colocalization of CD45 and a CD45-gate CAR in a CAR T cell, the reversible colocalization comprising a CD45-gate CAR recruiting domain binding to a CD45 protein on a CAR T cell surface, resulting in colocalization, which binding and colocalization can be disrupted by a protease cleaving a protease cleavage site in the CD45-gate CAR's linker, thereby reversing the colocalization, the method comprising the steps of:
  (a) providing a T cell that expresses CD45,
  (b) introducing a nucleic acid encoding a protease-activating CD45-gate CAR as disclosed herein into the T cell,
  (c) maintaining the T cell under conditions in which both CD45 and the CAR are functionally expressed at the cell surface, resulting in a CD45-gate CAR recruiting domain binding to a CD45 protein on the CAR T cell surface and colocalization of the CAR and the CD45 protein, which colocalization can be reversed by a protease cleaving a protease cleavage site in the CD45-gate CAR's linker, wherein the cleaving produces a functional CAR no longer connected by the linker to the CD45-gate CAR recruiting domain.

In another aspect, provided herein is a method of effecting reversible reduction of CAR activity by a CD45 protein in a CAR T cell, the reversible reduction of CAR activity comprising a CD45-gate CAR recruiting domain binding to a CD45 protein on a CAR T cell surface, resulting in inactivation of the chimeric antigen receptor by the CD45, which inactivation can be disrupted by a protease cleaving a protease cleavage site in the CD45-gate CAR's linker, resulting in the disassociation of the chimeric antigen receptor and the CD45 protein and ending the inactivation of the chimeric antigen receptor by the CD45, the method comprising the steps of:
  (a) providing a T cell that expresses CD45,
  (b) introducing a nucleic acid encoding a CD45-gate CAR into the T cell, (c) maintaining the T cell under conditions in which both CD45 and the CAR are functionally expressed at the cell surface,
  resulting in a CD45-gate CAR recruiting domain binding to a CD45 protein on the CAR T cell surface, association of the CAR and the CD45 protein, and reduction of the CAR's activity by the CD45 protein, which activity reduction can be reversed by a protease cleaving a protease cleavage site in the CD45-gate CAR's linker, thereby ending the association of the CAR and the CD45 protein, and ending the CD45 protein's reduction of or inhibition of CAR activity, wherein the cleaving produces a functional CAR no longer connected by the linker to the CD45-gate CAR recruiting domain.

In another aspect, provided herein is a method of treating with CAR T cell therapy a patient who has a tumor characterized by a protease-rich tumor microenvironment, comprising administering to the patient a cell as disclosed herein, a population of cells as disclosed herein, or a composition as disclosed herein, wherein CAR T cell activity is lower outside the protease-rich tumor microenvironment than in the protease-rich tumor microenvironment.

In another aspect, provided herein is a method of regulating cytotoxic activity of a CAR T cell that comprises a CAR as disclosed herein, the method comprising inhibiting the cytotoxic activity of the CAR T cell by associating the CAR with CD45 of the CAR T cell, and activating the cytotoxic activity of the CAR T cell by subjecting and/or exposing the CAR T cell to a protease that recognizes and cleaves the protease cleavage site.

In embodiments of the methods of treating a condition in a patient disclosed herein, the cell, population of cells or composition can be administered to the subject on one occasion or can be administered to the subject on two or more occasions spaced at least about 1, 2, 3, 4, 5, 6, 7, or more days apart. In some embodiments, the disorder can be a viral disease, a bacterial disease, a cancer, an inflammatory disease, an immune disease, or an aging-associated disease.

Also provided herein are chimeric antigen receptors (CARs) that bind to MUC16 ("MUC16-specific CARs" or "anti-MUC16 CARs" or "MUC16 CARs"). It is demonstrated that the expression of MUC16 specific CARs in T cells is effective to activate the T cells upon contact with MUC16. The MUC16 specific CARs provided herein bind human MUC16 and exhibit cytotoxic activity upon contact with MUC16-expressing cells.

Accordingly, in another aspect, provided herein is a MUC16 specific chimeric antigen receptor (CAR) comprising an extracellular ligand-binding domain, a first transmembrane domain, and an intracellular signaling domain, wherein the extracellular domain comprises a single chain variable fragment (scFv) binding to the extracellular domain of MUC16.

The extracellular domain of MUC16 specific CARs comprises a scFv, wherein the scFv comprises a heavy chain variable ($V_H$) region and a light chain variable ($V_L$) region, the $V_H$ and $V_L$ regions each comprising three complementarity determining regions (CDRs) specific for MUC16.

In some embodiments, the $V_H$ region comprises (i) a $V_H$ complementarity determining region one (CDR1) having the amino acid sequence shown in SEQ ID NO: 60 or 63; (ii) a $V_H$ complementarity determining region two (CDR2) having the amino acid sequence shown in SEQ ID NO: 61 or 64; and (iii) a $V_H$ complementarity determining region three (CDR3) having the amino acid sequence shown in SEQ ID NO: 62 or 65; and/or the $V_L$ region comprises (i) a $V_L$ complementarity determining region one (CDR1) having the amino acid sequence shown in SEQ ID NO: 66 or 69; (ii) a $V_L$ complementarity determining region two (CDR2) having the amino acid sequence shown in SEQ ID NO: 67 or 70; and (iii) a $V_L$ complementarity determining region three (CDR3) having the amino acid sequence shown in SEQ ID NO: 68 or 71.

In some embodiments, provided are MUC16 specific CARs comprising a scFv, wherein the scFv comprises a $V_H$ region having the sequence shown in SEQ ID NO: 58.

In some embodiments, provided are MUC16 specific CARs comprising a scFV, wherein the scFv comprises a $V_L$ region having the sequence shown in SEQ ID NO: 59.

In some embodiments, provided are MUC16 specific CARs comprising a scFV comprising a $V_H$ region and a $V_L$ region, wherein the $V_H$ region has the sequence shown in SEQ ID NO: 58, and the $V_L$ region has the sequence shown in SEQ ID NO: 59.

In some embodiments, the $V_H$ region comprises the sequence shown in SEQ ID NO: 58, or a variant thereof with one or several conservative amino acid substitutions in residues that are not within a CDR and/or the $V_L$ region comprises the amino acid sequence shown in SEQ ID NO: 59, or a variant thereof with one or several amino acid substitutions in amino acids that are not within a CDR.

In some embodiments, the $V_H$ region comprises the amino acid sequence shown in SEQ ID NO: 58 and the $V_L$ region comprises the amino acid sequence shown in SEQ ID NO: 59.

In some embodiments, each CDR is defined in accordance with the Kabat definition, the Chothia definition, the combination of the Kabat definition and the Chothia definition, the AbM definition, or the contact definition of CDR.

In some embodiments, the MUC16 specific CAR intracellular signaling domain comprises a CD3ζ signalling domain. In some embodiments, the intracellular signaling domain comprises a 4-1BB domain. In some embodiments, the MUC16 specific CAR comprises a second intracellular signaling domain. In some embodiments, the second intracellular signaling domain comprises a 4-1BB domain.

In some embodiments, the MUC16 specific CARs disclosed herein may comprise a stalk domain between the extracellular ligand-binding domain and the first transmembrane domain. In some embodiments, the stalk domain is selected from the group consisting of: a CD8α hinge, an IgG1 hinge, and an FcγRIIIα hinge. In some embodiments, the stalk domain is a human CD8α hinge, a human IgG1 hinge, or a human FcγRIIIα hinge.

In some embodiments, the MUC16 specific CARs disclosed herein may comprise one or more epitopes or mimotopes specific for one or more monoclonal antibodies. In some embodiments, the one or more epitopes or mimotopes specific for a monoclonal antibody includes a CD20 epitope or mimotope. In some embodiments, the CD20 epitope or mimotope comprises the amino acid sequence shown in SEQ ID NO: 50 or SEQ ID NO: 51.

In some embodiments, the MUC16 specific CAR comprises the amino acid sequence shown in any of SEQ ID NO: 11, 75, 76, 77, 78, and 79, with or without a signal sequence. In some embodiments, the MUC16 specific CAR comprises the amino acid sequence shown in SEQ ID NO: 75, with or without a signal sequence. In some embodiments, the MUC16 specific CAR comprises the amino acid sequence shown in SEQ ID NO: 76, with or without a signal sequence.

In some embodiments, the first transmembrane domain comprises a CD8α chain transmembrane domain.

In some embodiments, the MUC16 specific CAR can comprise another extracellular ligand-binding domain which is not specific for MUC16.

In some embodiments, the extracellular ligand-binding domain(s), the first transmembrane domain, and intracellular signaling domain(s) are on a single polypeptide.

In some embodiments, the CAR can comprise a second transmembrane domain, wherein the first transmembrane domain and the extracellular ligand-binding domain(s) are on a first polypeptide, and wherein the second transmembrane domain and the intracellular signaling domain(s) are on a second polypeptide. In an exemplary embodiment, the first transmembrane domain comprises a transmembrane domain from the α chain of the high-affinity IgE receptor (FcεRI) and the second transmembrane domain comprises a transmembrane domain from the γ or β chain of FcεRI.

In some embodiments, the CAR can comprise a third polypeptide comprising a third transmembrane domain fused to an intracellular signaling domain from a co-stimulatory molecule, wherein the third transmembrane domain comprises a transmembrane domain from the γ or β chain of FcεRI.

In another aspect, provided herein is an isolated polynucleotide comprising a nucleic acid sequence encoding the MUC16 specific CAR described herein.

In another aspect, provided herein is an expression vector comprising the polynucleotide encoding the MUC16 specific CAR described herein.

In another aspect, provided herein is an engineered immune cell expressing at its cell surface membrane a MUC16 specific CAR described herein. In some embodiments, the engineered immune cell can comprise another CAR which is not specific for MUC16. In some embodiments, the engineered immune cell can comprise a polynucleotide encoding a suicide polypeptide. In some embodiments, the suicide polypeptide is RQR8.

In some embodiments, the engineered immune cell is derived from an inflammatory T-lymphocyte, a cytotoxic T-lymphocyte, a regulatory T-lymphocyte, or a helper T-lymphocyte. In some embodiments, the engineered immune cell is an inflammatory T-lymphocyte, a cytotoxic T-lymphocyte, a regulatory T-lymphocyte, or a helper T-lymphocyte.

In some embodiments, the engineered immune cell can comprise a disruption of one or more endogenous genes, wherein the endogenous gene encodes TCRα, TCRβ, CD52, glucocorticoid receptor (GR), deoxycytidine kinase (dCK), or an immune checkpoint protein such as for example programmed death-1 (PD-1).

In some embodiments, the engineered immune cell is obtained from a healthy donor. In some embodiments, the engineered immune cell is obtained from an individual afflicted with a disease or disorder.

In another aspect, provided herein is an engineered immune cell expressing at its cell surface membrane a MUC16 specific CAR as described herein for use as a medicament. In another aspect, provided herein is a MUC16 specific antibody for use as a medicament. In some embodiments, the medicament comprising the MUC16 specific CAR expressing immune cells or MUC16 specific antibodies is for use in treatment of a MUC16 associated disease or disorder.

In one aspect, provided herein is a population of cells comprising engineered immune cells expressing MUC16 specific CARs described herein, wherein (ii) said population of cells comprises a percentage of stem cell memory and central memory cells greater than 20%, 30% or 40%, and/or (iii) said population of cells achieves a percentage lysis of MUC16 expressing cells greater than 10%, 20%, 30% or 40%.

In another aspect, provided herein is a method of engineering an immune cell expressing any one of the MUC16 specific CARs described herein, the method comprising: providing an immune cell; and introducing into the cell at least one polynucleotide encoding said MUC16 specific CAR; whereby said immune cell expresses said MUC16 specific CAR.

In some embodiments, the method comprises providing an immune cell;
  introducing into the cell at least one polynucleotide encoding said MUC16 specific CAR; and introducing at least one polynucleotide encoding a CAR which is not specific for MUC16.

In another aspect, provided herein is a method of treating a subject suffering from a MUC16 associated disease or disorder, the method comprising: providing an immune cell expressing at the surface a MUC16 specific CAR as described herein; and administering said immune cells to said subject. The disclosure also provides methods of treating subjects suffering from a MUC16 associated disease or disorder, the method comprising providing MUC16 specific antibodies described herein and administering said antibodies to said subject.

In some embodiments, provided herein is a pharmaceutical composition comprising an engineered immune cell expressing MUC16 specific CARs as described herein. In other embodiments, the disclosure provides pharmaceutical compositions comprising any of the MUC16 specific antibodies described herein.

In another aspect, provided herein is a method of treating a condition associated with malignant cells expressing MUC16 in a subject comprising administering to a subject in need thereof an effective amount of the pharmaceutical composition comprising an engineered immune cell as described herein. In some embodiments, the condition is a cancer.

In another aspect, provided herein is a method of inhibiting tumor growth or progression in a subject who has malignant cells expressing MUC16, comprising administering to the subject in need thereof an effective amount of the pharmaceutical composition comprising an engineered immune cell as described herein or a MUC16 specific antibody as described herein to the subject.

In another aspect, provided herein is a method of inhibiting metastasis of malignant cells expressing MUC16 in a subject, comprising administering to the subject in need thereof an effective amount of the pharmaceutical composition comprising an engineered immune cell as described herein or a MUC16 specific antibody as described herein to the subject.

In another aspect, provided herein is a method of inducing tumor regression in a subject who has malignant cells expressing MUC16, comprising administering to the subject in need thereof an effective amount of the pharmaceutical composition comprising an engineered immune cell as described herein or a MUC16 specific antibody as described herein to the subject.

In some embodiments, any of the above methods further comprises administering one or more additional therapies, such as for example, a monoclonal antibody and/or a chemotherapeutic. In some embodiments, the monoclonal antibody can be, for example, an antibody that binds to a checkpoint inhibitor such as, for example, an anti-PD-1 antibody or an anti-PD-L1 antibody. In some embodiments, any of the above methods further comprises administering a Receptor Tyrosine Kinase inhibitor, an mTOR inhibitor, an epigenetic modulator, a proteasome inhibitor, an immunomodulatory agent such as lenalidomide, a Hedgehog inhibitor or an Isocitrate Dehydrogenase (IDH) inhibitors, to the subject.

BRIEF DESCRIPTION OF THE DRAWINGS

FIG. 1A (left side) illustrates a potential mechanism of action for an exemplary protease-activating CD45-gate CAR. In the cell membrane of a T cell, for example, a linker peptide tethers (i.e. joins or connects) a CD45 recruiter domain to a CAR. The linker peptide comprises at least one protease site. The recruiter recognizes and binds to a CD45 protein, thus holding the CAR and CD45 protein in relatively close proximity to each other. This close proximity permits the CD45 to inactivate the CD3zeta domain. Thus, the CAR activity is reduced even when it binds to its target antigen, so long as the linker peptide is intact. When a protease cleaves the linker peptide (FIG. 1A, right side) (e.g. when the CAR T cell is in the environment of a tumor that expresses the protease that recognizes the protease site in the linker), the CAR is "released" from the CD45 and ceases to be inactivated by the CD45. The CAR T cell thus selectively becomes active primarily in the vicinity of its target tumor, thereby reducing on-target off-tumor toxicity. FIG. 1B presents schematic representations of the domains of exemplary CARs/CAR constructs. Upper: An exemplary CAR preprotein comprises a CD8 signal sequence and a CAR polypeptide. Lower: An exemplary protease-activating CD45-gate CAR preprotein comprises a CD8 signal sequence, optional hemagglutinin (HA) tag, CD45 recruiter domain, linker comprising glycine-serine (GS) rich sequences flanking a thrombin protease cleavage site, and a CAR.

FIG. 2A. Percentage of CAR+ cells at days 8 and 15 of production. FIG. 2B. Cell number at day 15 of production. NTD, not transduced.

FIG. 4A. Ovcar3 (MUC16$^{High}$), 1st round—48H cytotoxicity. FIG. 4B. Ovcar3 (MUC16$^{High}$), 2nd round—2×48H cytotoxicity. NTD: not transduced; Ovcar3 (MUC16$^{High}$): cell line that expresses a high density of the target antigen MUC16.

FIG. 5A. Cov644 (MUC16$^{Low}$) 1st round—48H cytotoxicity. FIG. 5B. Cov644 (MUC16$^{Low}$), 2nd round—2×48H cytotoxicity. NTD: not transduced; Cov644 (MUC16$^{Low}$): cell line that expresses a low density of the target antigen MUC16.

FIGS. 8A-8C. 1×10$^7$ luciferase-expressing ovarian target cells (OVCAR3, COV644, FUOV$_1$) with different MUC16 surface protein expression levels (indicated in parentheses) were co-cultured with 53B6 CAR+ T cells for 72 hours at various Effector:Target (E:T) ratio. Empty vector (EV) control T cells were also included in the study. Percent target cell survival after being exposed to T cells was determined by comparing to target cells alone.

FIG. 11. Schematic diagram of exemplary CD45-gate CAR constructs. TPS3, TPS4 etc. refer to linkers of various lengths (e.g. TPS6 20aa, TPS5 25aa, etc.) as shown in Table 2; MMP=matrix metalloproteinase; uPA=urokinase plasminogen activator (uPA); ✓ indicates presence of the indicated site; white rectangle between 53B6vL and 41BB ICD indicates the transmembrane and hinge region.

FIG. 12A. The percentages of CAR transduction are comparable across all CD45-gate CAR T cells. FIG. 12B. The overall expansion of T cells remains similar among all the clones and is comparable to non-transduced control (NTD), indicting no obvious fratricide. FIG. 12C. Overall, CD45-gate CAR T cells show higher percentage of stem-cell memory subset (CD45RO-/

CD62L+) than naked CAR T cells. FIG. 12D. CD45-gate CAR T cells exhibit less tonic signaling (e.g., CD25+/41BB+) than naked CAR T cells, suggesting a potential benefit of CD45-gate CARs in controlling T cell exhaustion. All cleavable linkers in FIGS. 12A-12D have a length of 45 amino acids and their sequences (e.g. TPS3 (45 aa), TPS4 (45aa), TPS6 (45 aa)) are set forth in Table 2. TPS3 (45aa) has the same amino acid sequence as SEQ ID NO:9, referred to in Table 2 as "GSTPS1 (45 aa)" (also known as "TPS1").

FIG. 13A. The percentages of CAR transduction are comparable for all TPS linkers except TPS10. FIG. 13B. CD45-gate does not cause obvious fratricide. FIG. 13C. CD45-gate CARs show more stem-cell memory phenotype than non-transduced T cells and T cells transduced with 53B6 (anti-MUC) CAR (non-CD45-gate). FIG. 13D. CD45-gate CARs show higher mean fluorescence intensity (MFI, top panel), but show less tonic signaling than T cells transduced with 53B6 (bottom panel). FIG. 13A shows the results of flow cytometry. All cleavable linkers in FIGS. 13A-13D have a length of 45 amino acids.

FIG. 14A. Flow cytometry results confirming the surface expression of matriptase (anti-matriptase antibody used at 3 μg/mL: R&D Systems Cat. No. BAF3946) for each cell line. Vertical axis: site scatter area (SSC-A). FIG. 14B. Surface-expressed matriptase activity was assessed through the detection of a V5 tag that is attached to the N-terminus of Muc16 CAR 53B6 via a matriptase cleavable linker TPS6 45aa, as described in Example 1. Minimal protease activity was detected in vitro despite matriptase expression, as evidenced by the fact that the V5 signal coincides with Muc16 CAR signal in OVCAR3, MDA MB 231, and H292. This indicates that V5 is not cleaved off by matriptase. Recombinant human matriptase cleaved the V5 signal. FIG. 14C. Validation of the expression of the target protein MUC16 by flow cytometry for two additional cell lines, H292-Muc16 and MDA MB 231-Muc16, for use as CAR target cells. FIG. 14D. ELISA kit (R7D, DUPA00) results, detecting soluble urokinase (uPA) secretion in conditioned media for each cell line. FIG. 14E. Summary table of target cells and protease expression.

FIGS. 15A-15F. TPS3 and TPS4 show response to endogenous proteases (-Matriptase) in a Jurkat NFAT reporter assay while TPS6 mainly responds to exogenous matriptase (+Matriptase). A Jurkat-NFAT-luciferase reporter cell line transduced with lentivirus encoding CD45-gate CARs was used to evaluate the activity of CD45-gate CARs in the presence of endogenous matriptase only (-Matriptase) or in the presence of exogenous matriptase (+Matriptase). Exposure to MUC16 positive target cells led to the activation of 53B6 CAR, while no activation was detected with a CD45-gate CAR with a non-cleavable linker. However, the activation can be restored via the cleavable linkers upon exposure to endogenous or exogenous proteases. TPS3 and TPS4 show response to endogenous proteases in a Jurkat NFAT reporter assay while TPS6 mainly responds to exogenous matriptase. All cleavable linkers in FIGS. 15A-15C have a length of 45 amino acids. The following construct names in FIGS. 15D-15F have the amino acid sequence of the following SEQ ID NOs, respectively: 1102 (2×TPS3): SEQ ID NO:9; 1399 (TPS4): SEQ ID NO:137; 1401 (TPS6): SEQ ID NO:138; 1241 (2×TPS6): SEQ ID NO:144; 1466 (2×TPS6): SEQ ID NO:153; 1467 (2×TPS6): SEQ ID NO:154; 1468 (2×TPS6): SEQ ID NO:155; 1469 (2×TPS6): SEQ ID NO:156. This shows that the CD45-gate functions with linkers of different lengths.

FIG. 17A. Activity measured in the absence of exogenous matriptase. FIG. 17B. Activity measured in the presence of exogenous matriptase. Activity ranking: TPS12>TPS4, TPS9, TPS11, TPS13>TPS3, TPS8>TPS6, TPS10. All cleavable linkers in FIGS. 17A-17B have a length of 45 amino acids.

FIG. 18A. Schematic summary of the experimental scheme for in vivo analysis. FIG. 18B. CD45-Gate CARs with cleavable TPS3 or TPS4 linker showed anti-tumor activity while the CD45-Gate CAR with TPS6 linker did not show activity in this assay. CD45-gate CAR with non-cleavable GS linker had no CAR activity. FIG. 18C. Treatment with CD45-gate CAR T cells had no effect on the body weight of the mice and no toxicities were observed with any of the cells used. All cleavable linkers in FIGS. 18B-18C have a length of 45 amino acids.

FIG. 19A. Schematic summary of the experimental scheme for in vivo analysis. FIG. 19B. CD45-Gate CAR with cleavable TPS4 linker showed anti-tumor activity. CD45-gate CAR with non-cleavable GS linker (aCD45-GS-53B6; this is the same construct as "GS non-cleavable" in FIGS. 12A-15C and 16A-18C; the non-cleavable linker has a length of 30 amino acids) had no CAR activity. FIG. 19C. Treatment with CD45-gate CAR T cells had no effect on the body weight of the mice and no toxicities were observed with any of the cells used. All cleavable linkers in FIGS. 19B-19C have a length of 45 amino acids.

FIG. 20A, OvCAR3 (Mucl6$^{High}$) and FIG. 20B, Cov644

Figure 1A:
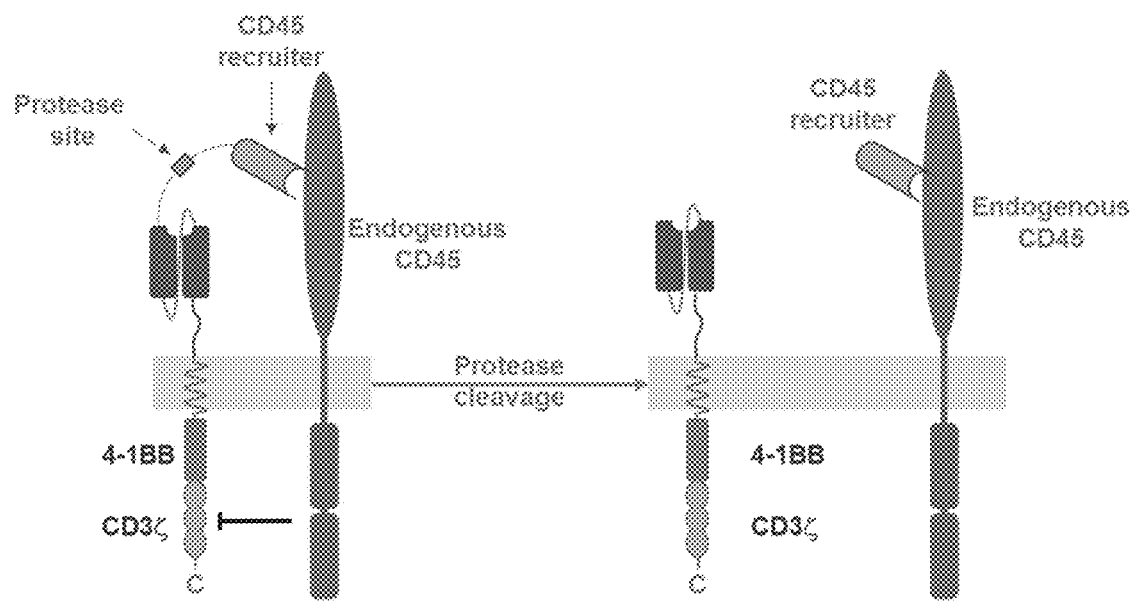
FIGS. 1A-1B.

(Muc16$^{Low}$) 1st round—48H cytotoxicity. The constructs comprised the following domains as indicated by each construct's name: 53B6, which has the amino acid sequence of SEQ ID NO: 11; CD45, which has the amino acid sequence of SEQ ID NO: 3; GS45, which has the amino acid sequence of SEQ ID NO: 182; BTN3A1(IgV), which has the amino acid sequence of SEQ ID NO: 14; BTN3A1, which has the amino acid sequence of SEQ ID NO: 183; sec49k, which has the amino acid sequence of SEQ ID NO: 12; UL11, which has the amino acid sequence of SEQ ID NO: 13. The constructs have the following amino acid sequences: BTN3A1(IgV)-GS45-53B6: SEQ ID NO: 166; BTN3A1-GS45-53B6: SEQ ID NO: 168; sec49k-GS45-53B6: SEQ ID NO: 169; UL11-GS45-53B6: SEQ ID NO: 170.

DETAILED DESCRIPTION

The present disclosure provides a protease-activating CD45-gate CAR e.g. a chimeric antigen receptor modified to comprise a removable CD45-recruiting domain, which specifically binds to CD45. The disclosure further provides related nucleic acids, engineered cells, compositions, and methods. The CD45 binding domain is linked, joined to or tethered to the antigen binding domain of a CAR by a peptide linker that comprises at least one protease cleavage site. The CAR's antigen binding domain can specifically bind to an antigen expressed by a target cell such as a tumor cell. Whilst not wishing to be bound by theory, it is hypothesized that when the protease-activating CD45-gate CAR is functionally expressed in a cell that also functionally expresses CD45, the protease-activating CD45-gate CAR will bind to the CD45 protein. This binding is thought to hold CD45 in close proximity to the protease-activating CD45-gate CAR. This is thought to permit the CD45, a phosphatase, to dephosphorylate the CAR's intracellular signalling domain, thereby at least partially suppressing the CAR's activity. When the CAR binds to its antigen under this condition, it is not activated to the same extent that it would have been in the absence of the CD45 gate. Thus the CAR is in a "suppressed" or "reduced activity" state. The protease-activating CD45-gate CAR's extracellular linker protease cleavage site can be recognized and cleaved by a protease present in the microenvironment of one or more tumor cells that the CAR targets. In this circumstance, the protease disconnects the CAR from the CD45 recruiting domain. This permits the CAR to disassociate from the CD45, thus ending the CD45-mediated suppression of the CAR's activation. Under this condition, when the CAR binds to its antigen, it can become activated up to the same extent that it would have been if it had never comprised a CD45 gate. Thus, the partial suppression of the CAR's activity is at least partially relieved, in other words the protease-activating CD45-gate CAR is at least partially activated, when the protease-activating CD45-gate CAR-expressing cell is in the presence of its target cell. The protease-activating CD45-gate CAR thus is expected to provide more selective CAR activation than a CAR that lacks the gate.

General Techniques

The practice of the disclosure will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995). Gene editing techniques using TALENs, CRISPR/Cas9, and megaTAL nucleases, for example, are within the skill of the art and explained fully in the literature, such as T. Gaj et al., Genome-Editing Technologies: Principles and Applications, *Cold Spring Harb Perspect Biol* 2016; 8:a023754 and citations therein, C. Sommer et al, Mol. Ther. 27: 1126-38 (2019) (PMID: 31005597), C. Sommer et al., Mol. Ther. 28: 2237-51 (PMID: 32592688).

Definitions

As used herein "autologous" means that cells, a cell line, or population of cells used for treating subjects are originating from said subject.

As used herein "allogeneic" means that cells or population of cells used for treating subjects are not originating from said subject but from a donor.

As used herein, the term "endogenous" refers to any material from or produced inside an organism, cell, tissue or system.

As used herein, the term "exogenous" refers to any material introduced from or produced outside an organism, cell, tissue or system.

As used herein, "immune cell" refers to a cell of hematopoietic origin functionally involved in the initiation and/or execution of innate and/or adaptative immune response. Examples of immune cells include T cells, e.g., alpha/beta T cells and gamma/delta T cells, B cells, natural killer (NK) cells, natural killer T (NKT) cells, mast cells, and myeloic-derived phagocytes.

As used herein, the term "expression" refers to the transcription and/or translation of a particular nucleotide sequence driven by a promoter.

As used herein, "expression vector" refers to a vector comprising a recombinant polynucleotide comprising expression control sequences operatively linked to a nucleotide sequence to be expressed. Expression vectors include all those known in the art, including cosmids, plasmids (e.g., naked or contained in liposomes) and viruses (e.g., lentiviruses, retroviruses, adenoviruses, and adeno-associated viruses) that incorporate the recombinant polynucleotide.

As used herein, "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter).

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

"Promoter" and "promoter sequence" are used interchangeably and refer to a DNA sequence capable of controlling the expression of a coding sequence or functional RNA. In general, a coding sequence is located 3' to a promoter sequence. It is understood by those skilled in the art that different promoters may direct the expression of a gene in different tissues or cell types, or at different stages of development, or in response to different environmental or physiological conditions.

In any of the vectors of the present disclosure, the vector optionally comprises a promoter disclosed herein.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this disclosure.

The term "extracellular ligand-binding domain" as used herein refers to an oligo- or polypeptide that is capable of binding a ligand. Preferably, the domain will be capable of interacting with a cell surface molecule. For example, the extracellular ligand-binding domain may be chosen to recognize a ligand that acts as a cell surface marker on target cells associated with a particular disease state. The term "stalk domain" is used herein to refer to any oligo- or polypeptide that functions to link the transmembrane domain to the extracellular ligand-binding domain. In particular, stalk domains are used to provide more flexibility and accessibility for the extracellular ligand-binding domain.

The term "intracellular signaling domain" refers to the portion of a protein which transduces the effector signal function signal and directs the cell to perform a specialized function.

A "co-stimulatory molecule" as used herein refers to the cognate binding partner on a T cell that specifically binds with a co-stimulatory ligand, thereby mediating a co-stimulatory response by the cell, such as, but not limited to proliferation. Co-stimulatory molecules include, but are not limited to an MHC class I molecule, BTLA and Toll ligand receptor. Examples of costimulatory molecules include CD27, CD28, CD8, 4-1 BB (CD137), OX40, CD30, CD40, PD-1, ICOS, lymphocyte function-associated antigen-1 (LFA-1), CD2, CD7, LIGHT, NKG2C, B7-H3 and a ligand that specifically binds with CD83 and the like.

A "co-stimulatory ligand" refers to a molecule on an antigen presenting cell that specifically binds a cognate co-stimulatory signal molecule on a T cell, thereby providing a signal which, in addition to the primary signal provided by, for instance, binding of a TCR/CD3 complex with an MHC molecule loaded with peptide, mediates a T cell response, including, but not limited to, proliferation activation, differentiation and the like. A co-stimulatory ligand can include but is not limited to CD7, B7-1 (CD80), B7-2 (CD86), PD-L1, PD-L2, 4-1 BBL, OX40L, inducible costimulatory ligand (ICOS-L), intercellular adhesion molecule (ICAM, CD30L, CD40, CD70, CD83, HLA-G, MICA, M1 CB, HVEM, lymphotoxin R receptor, 3/TR6, ILT3, ILT4, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as but not limited to, CD27, CD28, 4-1 BB, OX40, CD30, CD40, PD-1, ICOS, lymphocyte function-associated antigen-1 (LFA-1), CD2, CD7, LTGHT, NKG2C, B7-H3, a ligand that specifically binds with CD83.

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also antigen-binding fragments thereof (such as Fab, Fab', F(ab')2, and Fv), and any other modified configuration of the immunoglobulin molecule that comprises an antigen recognition site including, for example without limitation, single chain (scFv) and domain antibodies (including, for example, shark and camelid antibodies), and fusion proteins comprising an antibody. An antibody includes an antibody of any class, such as IgG, IgA, or IgM (or sub-class thereof), and the antibody need not be of any particular class. Depending on the antibody amino acid sequence of the constant region of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant regions that correspond to the different classes of immunoglobulins are called alpha, delta, epsilon, gamma, and mu, respectively. The subunit structures and three-dimensional configurations of different classes of immunoglobulins are well known.

The term "antigen-binding fragment" or "antigen binding portion" of an antibody, as used herein, refers to one or more fragments of an intact antibody that retain the ability to specifically bind to a given antigen. Antigen binding functions of an antibody can be performed by fragments of an intact antibody. Examples of binding fragments encompassed within the term "antigen binding fragment" of an antibody include Fab; Fab'; F(ab')2; an Fd fragment consisting of the $V_H$ and CH1 domains; an Fv fragment consisting of the $V_L$ and VH domains of a single arm of an antibody; a single domain antibody (dAb) fragment (Ward et al., Nature 341:544-546, 1989), and an isolated complementarity determining region (CDR).

An antibody, an antibody conjugate, or a polypeptide that "specifically binds" to a target is a term well understood in the art, and methods to determine such specific binding are also well known in the art. A molecule is said to exhibit "specific binding" if it reacts or associates more frequently, more rapidly, with greater duration and/or with greater affinity with a particular cell or substance than it does with alternative cells or substances. An antibody "specifically binds" to a target if it binds with greater affinity, avidity, more readily, and/or with greater duration than it binds to other substances. It is also understood that by reading this definition, for example, an antibody (or moiety or epitope or mimotope) that specifically binds to a first target may or may not specifically bind to a second target. As such, "specific binding" does not necessarily require (although it can include) exclusive binding.

A "variable region" of an antibody refers to the variable region of the antibody light chain or the variable region of the antibody heavy chain, either alone or in combination. As known in the art, the variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda MD)); and (2) an approach based on crystallographic studies of antigen-antibody complexes (Al-lazikani et al., 1997, J. Molec. Biol. 273:927-948). As used herein, a CDR may refer to CDRs defined by either approach or by a combination of both approaches.

A "CDR" of a variable domain are amino acid residues within the variable region that are identified in accordance with the definitions of the Kabat, Chothia, the accumulation of both Kabat and Chothia, AbM, contact, and/or conformational definitions or any method of CDR determination well known in the art. Antibody CDRs may be identified as the hypervariable regions originally defined by Kabat et al. See, e.g., Kabat et al., 1992, Sequences of Proteins of Immunological Interest, 5th ed., Public Health Service, NIH, Washington D.C. The positions of the CDRs may also be identified as the structural loop structures originally described by Chothia and others. See, e.g., Chothia et al., Nature 342:877-883, 1989. Other approaches to CDR identification include the "AbM definition," which is a compromise between Kabat and Chothia and is derived using Oxford Molecular's AbM antibody modeling software (now Accelrys®), or the "contact definition" of CDRs based on observed antigen contacts, set forth in MacCallum et al., J. Mol. Biol., 262:732-745, 1996. In another approach, referred to herein as the "conformational definition" of CDRs, the positions of the CDRs may be identified as the residues that make enthalpic contributions to antigen binding. See, e.g., Makabe et al., Journal of Biological Chemistry, 283:1 156-1 166, 2008. Still other CDR boundary definitions may not strictly follow one of the above approaches, but will nonetheless overlap with at least a portion of the Kabat CDRs, although they may be shortened or lengthened in light of prediction or experimental findings that particular residues or groups of residues or even entire CDRs do not significantly impact antigen binding. As used herein, a CDR may refer to CDRs defined by any approach known in the art, including combinations of approaches. The methods used herein may utilize CDRs defined according to any of these approaches. For any given embodiment containing more than one CDR, the CDRs may be defined in accordance with any of Kabat, Chothia, extended, AbM, contact, and/or conformational definitions.

Antibodies of the disclosure can be produced using techniques well known in the art, e.g., recombinant technologies, phage display technologies, synthetic technologies or combinations of such technologies or other technologies readily known in the art (see, for example, Jayasena, S. D., Clin. Chem., 45: 1628-50, 1999 and Fellouse, F. A., et al, J. Mol. Biol., 373(4):924-40, 2007).

As known in the art, "polynucleotide," or "nucleic acid," as used interchangeably herein, refer to chains of nucleotides of any length, and include DNA and RNA. The nucleotides can be deoxyribonucleotides, ribonucleotides, modified nucleotides or bases, and/or their analogs, or any substrate that can be incorporated into a chain by DNA or RNA polymerase. A polynucleotide may comprise modified nucleotides, such as methylated nucleotides and their analogs. If present, modification to the nucleotide structure may be imparted before or after assembly of the chain. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha- or beta-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), (O)NR2 ("amidate"), P(O)R, P(O)OR', CO or CH2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

As used herein, "transfection" refers to the uptake of exogenous or heterologous RNA or DNA by a cell. A cell has been "transfected" by exogenous or heterologous RNA or DNA when such RNA or DNA has been introduced inside the cell. A cell has been "transformed" by exogenous or heterologous RNA or DNA when the transfected RNA or DNA effects a phenotypic change. The transforming RNA or DNA can be integrated (covalently linked) into chromosomal DNA making up the genome of the cell.

As used herein, "transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

As used herein, "substantially pure" refers to material which is at least 50% pure (i.e., free from contaminants), more preferably, at least 90% pure, more preferably, at least 95% pure, yet more preferably, at least 98% pure, and most preferably, at least 99% pure. The term "compete", as used herein with regard to an antibody, means that a first antibody, or an antigen binding fragment (or portion) thereof, binds to an epitope or mimotope in a manner sufficiently similar to the binding of a second antibody, or an antigen binding portion thereof, such that the result of binding of the first antibody with its cognate epitope or mimotope is detectably decreased in the presence of the second antibody compared to the binding of the first antibody in the absence of the second antibody. The alternative, where the binding of the second antibody to its epitope or mimotope is also detectably decreased in the presence of the first antibody, can, but need not be the case. That is, a first antibody can inhibit the binding of a second antibody to its epitope or mimotope without that second antibody inhibiting the binding of the first antibody to its respective epitope or mimotope. However, where each antibody detectably inhibits the binding of the other antibody with its cognate epitope or mimotope or ligand, whether to the same, greater, or lesser extent, the antibodies are said to "cross-compete" with each other for binding of their respective epitope(s) or mimotope(s). Both competing and cross-competing antibodies are encompassed by the disclosure. Regardless of the mechanism by which such competition or cross-competition occurs (e.g., steric hindrance, conformational change, or binding to a common epitope or mimotope, or portion thereof), the skilled artisan would appreciate, based upon the teachings provided herein, that such competing and/or cross-competing antibodies are encompassed and can be useful for the methods disclosed herein.

As used herein, "treatment" is an approach for obtaining beneficial or desired clinical results. For purposes of this disclosure, beneficial or desired clinical results include, but are not limited to, one or more of the following: reducing the proliferation of (or destroying) neoplastic or cancerous cells, inhibiting metastasis of neoplastic cells, shrinking or decreasing the size of tumor, remission of a disease (e.g., cancer), decreasing symptoms resulting from a disease (e.g., cancer), increasing the quality of life of those suffering from a disease (e.g., cancer), decreasing the dose of other medications required to treat a disease (e.g., cancer), delaying the progression of a disease (e.g., cancer), curing a disease (e.g., cancer), and/or prolong survival of subjects having a disease (e.g., cancer).

"Ameliorating" means a lessening or improvement of one or more symptoms as compared to not administering a treatment. "Ameliorating" also includes shortening or reduction in duration of a symptom. As used herein, an "effective dosage" or "effective amount" of drug, compound, or pharmaceutical composition is an amount sufficient to effect any one or more beneficial or desired results. For prophylactic use, beneficial or desired results include eliminating or reducing the risk, lessening the severity, or delaying the outset of the disease, including biochemical, histological and/or behavioral symptoms of the disease, its complications and intermediate pathological phenotypes presenting during development of the disease. For therapeutic use, beneficial or desired results include clinical results such as reducing incidence or amelioration of one or more symptoms of various diseases or conditions (such as for example cancer), decreasing the dose of other medications required to treat the disease, enhancing the effect of another medication, and/or delaying the progression of the disease. An effective dosage can be administered in one or more administrations. For purposes of this disclosure, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

As used herein, a "subject" is any mammal, e.g a human, or a monkey. Mammals include, but are not limited to, farm animals, sport animals, pets, primates, horses, dogs, cats, mice and rats. In an exemplary embodiment, the subject is a human. In an exemplary embodiment, the subject is a monkey, e.g. a cynomolgus monkey.

As used herein, "vector" means a construct, which is capable of delivering, and, preferably, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "pharmaceutically acceptable carrier" or "pharmaceutically acceptable excipient" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline (PBS) or normal (0.9%) saline. Compositions of the disclosure comprising such carriers are formulated by well-known conventional methods (see, for example, Remington's Pharmaceutical Sciences, 18th edition, A. Gennaro, ed., Mack Publishing Co., Easton, PA, 1990; and Remington, The Science and Practice of Pharmacy 21 st Ed. Mack Publishing, 2005).

As used herein, "alloreactivity" refers to the ability of T cells to recognize MHC complexes that were not encountered during thymic development. Alloreactivity manifests itself clinically as host versus graft rejection and graft versus host disease.

Reference to "about" a value or parameter herein includes (and describes) embodiments that are directed to that value or parameter per se. For example, description referring to "about X" includes description of "X." Numeric ranges are inclusive of the numbers defining the range.

It is understood that wherever embodiments are described herein with the language "comprising," otherwise analogous embodiments described in terms of "consisting of" and/or "consisting essentially of" are also provided.

Where aspects or embodiments of the disclosure are described in terms of a Markush group or other grouping of alternatives, the disclosure encompasses not only the entire group listed as a whole, but each member of the group individually and all possible subgroups of the main group, but also the main group absent one or more of the group members. The disclosure also envisages the explicit exclusion of one or more of any of the group members in the claimed disclosure.

Unless otherwise defined, all technical and scientific terms used herein have the same meaning as commonly understood by one of ordinary skill in the art to which this disclosure belongs. In case of conflict, the present specification, including definitions, will control. Throughout this specification and claims, the word "comprise," or variations such as "comprises" or "comprising" will be understood to imply the inclusion of a stated integer or group of integers but not the exclusion of any other integer or group of integers. Unless otherwise required by context, singular terms shall include pluralities and plural terms shall include the singular.

Exemplary methods and materials are described herein, although methods and materials similar or equivalent to those described herein can also be used in the practice or testing of the disclosure. The materials, methods, and examples are illustrative only and not intended to be limiting.

An "antigen binding protein" comprises one or more antigen binding domains. An "antigen binding domain" as used herein means any polypeptide that binds a specified target antigen. In some embodiments, the antigen binding domain binds to an antigen on a tumor cell. In some embodiments, the antigen binding domain binds to an antigen on a cell involved in a hyperproliferative disease or to a viral or bacterial antigen.

Antigen binding domains include, but are not limited to, antibody binding regions that are immunologically functional fragments. The term "immunologically functional fragment" (or "fragment") of an antigen binding domain is a species of antigen binding domain comprising a portion (regardless of how that portion is obtained or synthesized) of an antibody that lacks at least some of the amino acids present in a full-length chain, but which is still capable of specifically binding to a target antigen. Such fragments are biologically active in that they bind to the target antigen and can compete with other antigen binding domains, including intact antibodies, for binding to a given epitope or mimotope.

Immunologically functional immunoglobulin fragments include, but are not limited to, scFv fragments, Fab fragments (Fab', F(ab')2, and the like), one or more complementarity determining regions ("CDRs"), a diabody (heavy chain variable domain on the same polypeptide as a light chain variable domain, connected via a short peptide linker that is too short to permit pairing between the two domains on the same chain), domain antibodies, bivalent antigen binding domains (comprises two antigen binding sites), multispecific antigen binding domains, and single-chain antibodies. These fragments can be derived from any mammalian source, including but not limited to human, mouse, rat, camelid or rabbit. As will be appreciated by one of skill in the art, an antigen binding domain can include non-protein components.

The variable regions typically exhibit the same general structure of relatively conserved framework regions (FR) joined by the 3 hypervariable regions (CDRs). The CDRs from the two chains of each pair typically are aligned by the framework regions, which can enable binding to a specific epitope or mimotope. From N-terminal to C-terminal, both light and heavy chain variable regions typically comprise the domains FR1, CDR1, FR2, CDR2, FR3, CDR3 and FR4. By convention, CDR regions in the heavy chain are typically referred to as HC CDR1, CDR2, and CDR3. The CDR regions in the light chain are typically referred to as LC CDR1, CDR2, and CDR3.

In some embodiments, antigen binding domains comprise one or more complementary binding regions (CDRs) present in the full-length light or heavy chain of an antibody, and in some embodiments comprise a single heavy chain and/or light chain or portion thereof. These fragments can be produced by recombinant DNA techniques or can be produced by enzymatic or chemical cleavage of antigen binding domains, including intact antibodies.

In some embodiments, the antigen binding domain is an antibody or fragment thereof, including one or more of the complementarity determining regions (CDRs) thereof. In some embodiments, the antigen binding domain is a single chain variable fragment (scFv), comprising light chain CDRs CDR1, CDR2 and CDR3, and heavy chain CDRs CDR1, CDR2 and CDR3.

The assignment of amino acids to each of the framework, CDR, and variable domains is typically in accordance with numbering schemes of Kabat numbering (see, e.g., Kabat et al. in Sequences of Proteins of Immunological Interest, 5th Ed., NIH Publication 91-3242, Bethesda Md. 1991), Chothia numbering (see, e.g., Chothia & Lesk, (1987), J Mol Biol 196: 901-917; Al-Lazikani et al., (1997) J Mol Biol 273: 927-948; Chothia et al., (1992) J Mol Biol 227: 799-817; Tramontano et al., (1990) J Mol Biol 215(1): 175-82; and U.S. Pat. No. 7,709,226), contact numbering, or the AbM scheme (Antibody Modeling program, Oxford Molecular).

In some embodiments, the antigen binding domain is a recombinant antigen receptor. The term "recombinant antigen receptor" as used herein refers broadly to a non-naturally occurring surface receptor that comprises an extracellular antigen-binding domain or an extracellular ligand-binding domain, a transmembrane domain and an intracellular domain. In some embodiments, the recombinant antigen receptor is a chimeric antigen receptor (CAR). Chimeric antigen receptors (CARs) are well-known in the art. A CAR is a fusion protein that comprises an extracellular domain comprising an antigen recognition moiety (also referred to herein as an antigen binding domain), a transmembrane domain and an intracellular domain comprising one or more T cell activation domains (see, e.g., Eshhar et al., Proc. Natl. Acad. Sci. USA, 90(2): 720-724 (1993), and Sadelain et al., Curr. Opin. Immunol, 21(2): 215-223 (2009)). A hinge region or domain typically is situated between the CAR's antigen recognition domain and the transmembrane domain.

In some embodiments, the intracellular domain of a recombinant antigen receptor comprises a co-stimulatory domain and/or an ITAM-containing domain. In some embodiments, the intracellular domain of a recombinant antigen receptor comprises an intracellular protein or a functional variant thereof (e.g., truncation(s), insertion(s), deletion(s) or substitution(s)).

The term "extracellular ligand-binding domain" or "extracellular antigen-binding domain" as used herein refers to a polypeptide that is capable of binding a ligand or an antigen or capable of interacting with a cell surface molecule, such as a ligand or a surface antigen. For example, the extracellular ligand-binding or antigen-binding domain may be chosen to recognize a ligand that acts as a cell surface marker on target cells associated with a particular disease state, e.g., a tumor-specific antigen. In some embodiments, the antigen-binding domain comprises an antibody, or an antigen binding fragment or an antigen binding portion of an antibody. In some embodiments, the antigen binding domain comprises an Fv or scFv, an Fab or scFab, an F(ab')2 or a scF(ab')2, an Fd, a monobody, an affibody, a camelid antibody, a VHH antibody, a single domain antibody, or a darpin. In some embodiments, the ligand-binding domain comprises a partner of a binding pair, such as a ligand that binds to a surface receptor, or an ectodomain of a surface receptor that binds to a ligand.

The terms "stalk domain" and "hinge domain" are used interchangeably herein to refer to any polypeptide that functions to link the transmembrane domain to the extracellular ligand-binding domain. In particular, stalk domains are used to provide more flexibility and accessibility for the extracellular ligand-binding domain.

The term "intracellular signaling domain" refers to the portion of a protein which transduces the effector signal function signal and directs the cell to perform a specialized function.

Vectors

Expression vectors and administration of polynucleotide compositions are further described herein.

In another aspect, the disclosure provides a method of making any of the polynucleotides described herein.

Polynucleotides complementary to any such sequences are also encompassed by the disclosure. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the disclosure, and a polynucleotide may, but need not, be linked to other molecules and/or support materials.

Polynucleotides may comprise a native sequence (i.e., an endogenous sequence that encodes an antibody or a portion thereof) or may comprise a variant of such a sequence. Polynucleotide variants contain one or more substitutions, additions, deletions and/or insertions such that the immunoreactivity of the encoded polypeptide is not diminished, relative to a native immunoreactive molecule. The effect on the immunoreactivity of the encoded polypeptide may generally be assessed as described herein. Variants preferably exhibit at least about 70% identity, more preferably, at least about 80% identity, yet more preferably, at least about 90% identity, and most preferably, at least about 95% identity to a polynucleotide sequence that encodes a native antibody or a portion thereof. Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, or 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, WI), using default parameters. This program embodies several alignment schemes described in the following references: Dayhoff, M. O., 1978, A model of evolutionary change in proteins—Matrices for detecting distant relationships. In Dayhoff, M. O. (ed.) Atlas of Protein Sequence and Structure, National Biomedical Research Foundation, Washington DC Vol. 5, Suppl. 3, pp. 345-358; Hein J., 1990, Unified Approach to Alignment and Phylogenes pp. 626-645 Methods in Enzymology vol. 183, Academic Press, Inc., San Diego, CA; Higgins, D. G. and Sharp, P. M., 1989, CABIOS 5:151-153; Myers, E. W. and Muller W., 1988, CABIOS 4:1 1-17; Robinson, E. D., 1971, Comb. Theor. 1 1:105; Santou, N., Nes, M., 1987, Mol. Biol. Evol. 4:406-425; Sneath, P. H. A. and Sokal, R. R., 1973, Numerical Taxonomy the Principles and Practice of Numerical Taxonomy, Freeman Press, San Francisco, CA; Wilbur, W. J. and Lipman, D. J., 1983, Proc. Natl. Acad. Sci. USA 80:726-730.

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native antibody (or a complementary sequence).

Suitable "moderately stringent conditions" include prewashing in a solution of 5×SSC, 0.5% SDS, 1.0 mM EDTA (pH 8.0); hybridizing at 50° C.-65° C., 5×SSC, overnight; followed by washing twice at 65° C. for 20 minutes with each of 2×, 0.5× and 0.2×SSC containing 0.1% SDS.

As used herein, "highly stringent conditions" or "high stringency conditions" are those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 g/m), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. The skilled artisan will recognize how to adjust the temperature, ionic strength, etc. as necessary to accommodate factors such as probe length and the like.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the disclosure. Further, alleles of the genes comprising the polynucleotide sequences provided herein are within the scope of the disclosure. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

The polynucleotides of this disclosure can be obtained using chemical synthesis, recombinant methods, or PCR. Methods of chemical polynucleotide synthesis are well known in the art and need not be described in detail herein. One of skill in the art can use the sequences provided herein and a commercial DNA synthesizer to produce a desired DNA sequence.

For preparing polynucleotides using recombinant methods, a polynucleotide comprising a desired sequence can be inserted into a suitable vector, and the vector in turn can be introduced into a suitable host cell for replication and amplification, as further discussed herein. Polynucleotides may be inserted into host cells by any means known in the art. Cells are transformed by introducing an exogenous polynucleotide by direct uptake, endocytosis, transfection, F-mating or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art. See, e.g., Sambrook et al., 1989.

Alternatively, PCR allows reproduction of DNA sequences. PCR technology is well known in the art and is described in U.S. Pat. Nos. 4,683,195, 4,800,159, 4,754,065 and 4,683,202, as well as PCR: The Polymerase Chain Reaction, Mullis et al. eds., Birkauswer Press, Boston, 1994.

RNA can be obtained by using the isolated DNA in an appropriate vector and inserting it into a suitable host cell. When the cell replicates and the DNA is transcribed into RNA, the RNA can then be isolated using methods well known to those of skill in the art, as set forth in Sambrook et al., 1989, supra, for example.

Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Strategene, and Invitrogen.

Expression vectors generally are replicable polynucleotide constructs that contain a polynucleotide according to the disclosure. It is implied that an expression vector must be replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO 87/04462. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

A polynucleotide encoding a protease-activating CD45-gate CAR disclosed herein, its extracellular domain, or another fragment of the protease-activating CD45-gate CAR may exist in an expression cassette or expression vector (e.g., a plasmid for introduction into a bacterial host cell, or a viral vector such as a baculovirus vector for transfection of an insect host cell, or a plasmid or viral vector such as a lentivirus for transfection of a mammalian host cell). In some embodiments, a polynucleotide or vector can include a nucleic acid sequence encoding ribosomal skip sequences such as, for example without limitation, a sequence encoding a 2A peptide. 2A peptides, which were identified in the Aphthovirus subgroup of picornaviruses, cause a ribosomal "skip" from one codon to the next without the formation of a peptide bond between the two amino acids encoded by the codons (see (Donnelly and Elliott 2001; Atkins, Wills et al. 2007; Doronina, Wu et al. 2008)). By "codon" is meant three nucleotides on an mRNA (or on the sense strand of a DNA molecule) that are translated by a ribosome into one amino acid residue. Thus, two polypeptides can be synthesized from a single, contiguous open reading frame within an mRNA when the polypeptides are separated by a 2A oligopeptide sequence that is in frame. Such ribosomal skip mechanisms are well known in the art and are known to be used by several vectors for the expression of several proteins encoded by a single messenger RNA.

To direct transmembrane polypeptides into the secretory pathway of a host cell, in some embodiments, a secretory signal sequence (also known as a leader sequence, prepro sequence or pre sequence) is provided in a polynucleotide sequence or vector sequence. The secretory signal sequence is operably linked to the transmembrane nucleic acid sequence, i.e., the two sequences are joined in the correct reading frame and positioned to direct the newly synthesized polypeptide into the secretory pathway of the host cell. Secretory signal sequences are commonly positioned 5' to the nucleic acid sequence encoding the polypeptide of interest, although certain secretory signal sequences may be positioned elsewhere in the nucleic acid sequence of interest (see, e.g., Welch et al., U.S. Pat. No. 5,037,743; Holland et al., U.S. Pat. No. 5,143,830). Those skilled in the art will recognize that, in view of the degeneracy of the genetic code, considerable sequence variation is possible among these polynucleotide molecules. In some embodiments, nucleic acid sequences of the disclosure are codon-optimized for expression in mammalian cells, preferably for expression in human cells. Codon-optimization refers to the exchange in a sequence of interest of codons that are generally rare in highly expressed genes of a given species for codons that are generally frequent in highly expressed genes of such species, such codons encoding the same amino acids as the codons that are being exchanged.

Methods of preparing immune cells for use in immunotherapy are provided herein. In some embodiments, the methods comprise introducing a protease-activating CD45-gate CAR into immune cells, and expanding the cells. In some embodiments, the disclosure relates to a method of engineering an immune cell comprising: providing an immune cell and expressing at the surface of the cell at least one protease-activating CD45-gate CAR. In some embodiments, the method comprises: transfecting the cell with at least one polynucleotide encoding a protease-activating CD45-gate CAR, and expressing the at least one polynucleotide in the cell.

In some embodiments, the polynucleotide encoding the protease-activating CD45-gate CAR is present in an expression vector for stable expression in the cells. In some embodiments, the polynucleotide is present in a viral vector for stable expression in the cells. In some embodiments, the viral vector may be, for example, a lentiviral vector or adenoviral vector.

In some embodiments, polynucleotides encoding polypeptides according to the present disclosure can be mRNA which is introduced directly into the cells, for example by electroporation. In some embodiments, cytoPulse technology can be used to transiently permeabilize living cells for delivery of material into the cells. Parameters can be modified in order to determine conditions for high transfection efficiency with minimal mortality.

Also provided herein are methods of transfecting an immune cell e.g. a T cell. In some embodiments, the method comprises: contacting a T cell with RNA and applying to the T cell an agile pulse sequence consisting of: (a) an electrical pulse with a voltage range from about 2250 to 3000 V per centimeter; (b) a pulse width of 0.1 ms; (c) a pulse interval of about 0.2 to 10 ms between the electrical pulses of step (a) and (b); (d) an electrical pulse with a voltage range from about 2250 to 3000 V per centimeter with a pulse width of about 100 ms and a pulse interval of about 100 ms between the electrical pulse of step (b) and the first electrical pulse of step (c); and (e) four electrical pulses with a voltage of about 325 V with a pulse width of about 0.2 ms and a pulse interval of 2 ms between each of 4 electrical pulses. In some embodiments, a method of transfecting a T cell comprises contacting said T cell with RNA and applying to the T cell an agile pulse sequence comprising: (a) an electrical pulse with a voltage of about 2250, 2300, 2350, 2400, 2450, 2500, 2550, 2400, 2450, 2500, 2600, 2700, 2800, 2900 or 3000V per centimeter; (b) a pulse width of 0.1 ms; (c) and a pulse interval of about 0.2, 0.5, 1, 2, 3, 4, 5, 6, 7, 8, 9 or 10 ms between the electrical pulses of step (a) and (b); (d) one electrical pulse with a voltage range from about 2250 to 3000 V per centimeter, e.g. of 2250, 2300, 2350, 2400, 2450, 2500, 2550, 2400, 2450, 2500, 2600, 2700, 2800, 2900 or 3000V per centimeter with a pulse width of 100 ms and a pulse interval of 100 ms between the electrical pulse of step (b) and the first electrical pulse of step (c); and (e) 4 electrical pulses with a voltage of about 325 V with a pulse width of about 0.2 ms and a pulse interval of about 2 ms between each of 4 electrical pulses. Any values included in the value range described above are disclosed in the present application. Electroporation medium can be any suitable medium known in the art. In some embodiments, the electroporation medium has conductivity in a range spanning about 0.01 to about 1.0 milliSiemens.

In some embodiments, the method can further comprise a step of genetically modifying a cell by inactivating or reducing the expression level of at least one gene expressing, for example without limitation, a component of the TCR, a target for an immunosuppressive agent, an HLA gene, and/or an immune checkpoint protein such as, for example, PDCD1 or CTLA-4. By inactivating a gene it is intended that the gene of interest is not expressed in a functional protein form. In some embodiments, the gene to be inactivated is selected from the group consisting of, for example without limitation, TCRα, TCRβ, β2-microglobulin ("02m"), CD52, GR, deoxycytidine kinase (DCK), PD-1, and CTLA-4. In some embodiments the method comprises inactivating or reducing the expression level of one or more genes by introducing into the cells a rare-cutting endonuclease able to selectively inactivate a gene by selective DNA cleavage. In some embodiments the rare-cutting endonuclease can be, for example, a transcription activator-like effector nuclease (TALE-nuclease or TALEN), a megaTAL nuclease or a Cas9 endonuclease.

In another aspect, a step of genetically modifying immune cells e.g. T cells can comprise: modifying immune cells e.g. T cells by inactivating at least one gene expressing a target for an immunosuppressive agent, and; expanding the cells, optionally in the presence of the immunosuppressive agent. An immunosuppressive agent is an agent that suppresses immune function by one of several mechanisms of action. An immunosuppressive agent can diminish the extent and/or voracity of an immune response. Non-limiting examples of immunosuppressive agents include calcineurin inhibitors, targets of rapamycin, interleukin-2 α-chain blockers, inhibitors of inosine monophosphate dehydrogenase, inhibitors of dihydrofolic acid reductase, corticosteroids, and immunosuppressive antimetabolites. Some cytotoxic immunosuppressants act by inhibiting DNA synthesis. Others may act through activation of T cells or by inhibiting the activation of helper cells. The methods according to the disclosure allow conferring immunosuppressive resistance to e.g. T cells for immunotherapy by inactivating the target of the immunosuppressive agent in the T cells. As non-limiting examples, targets for an immunosuppressive agent can be a receptor for an immunosuppressive agent such as for example without limitation CD52, glucocorticoid receptor (GR), FKBP family gene members, and cyclophilin family gene members.

Compositions and methods for expressing a protease-activating CD45-gate CAR are provide herein. Also provided are uses of such compositions and methods for improving the functional activities of immune cells e.g. T cells, such as CAR-T cells. The methods and compositions provided herein are useful for improving activation specificity and therapeutic efficacy of immune cells e.g. T cells such as CAR-T cells.

Immune cells e.g. T cells provided herein express a protease-activating CD45-gate CAR as disclosed herein. Advantageously, the immune cells provided herein exhibit improved in vivo activation specificity relative to cells that express a non-gated CAR e.g. that express the same or comparable CAR except it lacks a functional protease cleavage site.

Protease-Activating CD45-Gate CAR

In one aspect, provided herein is a protease-activating CD45-gate chimeric antigen receptor (CD45-gate CAR) comprising an extracellular domain, a transmembrane domain, and an intracellular domain, wherein the extracellular domain comprises:
 a CD45 recruiting domain,
 an antigen binding domain, and
 a linker connecting the carboxy terminus of the CD45 recruiting domain to the amino terminus of the antigen binding domain, wherein the linker comprises at least one protease cleavage site that is recognized by a protease, and further wherein the intracellular domain comprises at least one signaling domain that can be reversibly inactivated by CD45.

In some embodiments, the extracellular domain comprises a stalk domain that joins the extracellular domain to the transmembrane domain.

In some embodiments, the intracellular signaling domain comprises an activating domain. In some embodiments, the intracellular signaling domain comprises a costimulatory domain. In some embodiments, the intracellular signaling domain comprises an activating domain and a costimulatory domain. In some embodiments, the intracellular signaling domain comprises an activating domain such as an ITAM-containing domain. In some embodiments, the intracellular signaling domain comprises the CD3 zeta intracellular domain. In some embodiments, the intracellular signaling domain comprises a CD3 zeta domain that comprises the amino acid sequence of SEQ ID NO: 34 or a fragment thereof.

In some embodiments the intracellular signaling domain comprises one, two or three ITAM domains selected from the group consisting of wildtype or variants of a CD37 ITAM, a CD36 ITAM, a CD3E ITAM, a CD3ζ 1 ITAM, a CD3ζ 2 ITAM, and a CD3ζ 3 ITAM, provided that, if three ITAM domains are selected that are wildtype ITAM domains, the three ITAM domains are not CD3ζ 1, CD3ζ 2 and CD3ζ 3; see U.S. Provisional Patent Appl. No. 63/054,701, incorporated herein by reference in its entirety.

In some embodiments, the intracellular domain comprises or further comprises at least one costimulatory domain. In some embodiments, the at least one costimulatory domain is a signaling region of CD28, OX-40, 4-1BB/CD137, CD2, CD7, CD27, CD30, CD40, programmed death-1 (PD-1), inducible T cell costimulator (ICOS), lymphocyte function-associated antigen-1 (LFA-1 (CD1 la/CD 18), CD3 gamma, CD3 delta, CD3 epsilon, CD247, CD276 (B7-H3), LIGHT, (TNFSF14), NKG2C, Ig alpha (CD79a), DAP-10, Fc gamma receptor, MHC class I molecule, TNF receptor proteins, an Immunoglobulin protein, cytokine receptor, integrins, Signaling Lymphocytic Activation Molecules (SLAM proteins), activating NK cell receptors, BTLA, a Toll ligand receptor, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL-2R beta, IL-2R gamma, IL-7R alpha, ITGA4, VLA1, CD49a, ITGA4, CD49D, ITGA6, VLA-6, CD49f, ITGAD, CD1 Id, ITGAE, CD103, ITGAL, CD1 la, LFA-1, IT GAM, CD1 lb, ITGAX, CD1 lc, ITGB1, CD29, ITGB2, CD 18, LFA-1, ITGB7, NKG2D, TNFR2, TRANCE/RANKL, DNAMI (CD226), SLAMF4 (CD244, 2B4), CD84, CD96 (Tactile), CEACAM1, CRT AM, Ly9 (CD229), CD 160 (BY55), PSGL1, CD100 (SEMA4D), CD69, SLAMF6 (NTB-A, Lyl08), SLAM (SLAMFI, CD150, IPO-3), BLAME (SLAMF8), SELPLG (CD162), LTBR, LAT, GADS, SLP-76, PAG/Cbp, CD 19a, a ligand that specifically binds with CD83, or any combination thereof.

In some embodiments, the CD45 recruiting domain comprises one or more of an anti-CD45 antibody antigen binding domain, an anti-CD45 NANOBODY®, an anti-CD45 scFv, a truncated viral protein binder of CD45, an anti-CD45 Fab, an anti-CD45 camelid VHH, a CD45-binding protein, or a truncated endogenous CD45 binder. In some embodiments, the CD45 recruiting domain comprises one or more of truncated UL11, truncated sec49K, and truncated BTN3A1.

In some embodiments, the linker comprises one protease cleavage site. In some embodiments, the protease cleavage site comprises any of the amino acid sequences of SEQ ID NO: 32 and SEQ ID NOs: 89-102 (Table 2), which comprise (e.g. SEQ ID NOs: 99-102), or can be modified to comprise (e.g. any of SEQ ID NOs: 89-98), a GS linker at the amino and/or carboxy terminus when incorporated into the linker. In some embodiments, the linker comprises multiple protease cleavage sites, such as two, three, four, five, six or more protease cleavage sites, e.g. up to ten or up to fifteen protease cleavage sites, and each cleavage site is the same as or different from any of the other cleavage sites. In some embodiments, the linker is or comprises the amino acid sequence of any one or more of (e.g. 2, 3, 4, 5 copies of) of SEQ ID NOs: 99-102, 172-177, and 108-120. In some embodiments, the linker comprises one copy or more than one copy (e.g. 2, 3, 4, 5, 6, 10 or 15) of the amino acid sequence of any of SEQ ID NOs: 89-98, 103 and 104.

In some embodiments, the protease cleavage site or one or more of the multiple protease cleavage sites is recognized by one or more of thrombin, trypsin, plasmin, prostate-specific antigen (PSA), urokinase plasminogen activator (uPA), urokinase plasminogen activator receptor (uPAR), matrix metalloproteinase (MMP), matriptase (MT-SP1), legumain, a disintegrin and metalloproteinase (ADAM), and transmembrane Serine Protease (TMPRSS). Alternatively stated, in some embodiments, the protease that recognizes the protease cleavage site, or that recognizes one or more of the multiple protease cleavage sites, is one or more of thrombin, trypsin, plasmin, prostate-specific antigen (PSA), urokinase plasminogen activator (uPA), urokinase plasminogen activator receptor (uPAR), matrix metalloproteinase (MMP), matriptase (MT-SP1), legumain, a disintegrin and metalloproteinase (ADAM), transmembrane Serine Protease (TMPRSS), Granzyme B, activated protein C, Caspase, Cathepsin, Chymase, Elastase, Guanidinobenzoatase, HtrA1, Human Neutrophil Elastase, Lactoferrin, Marapsin, NS3/4A, PACE4, tissue plasminogen activator (tPA), DESC1, DPP-4, FAP, Hepsin, Matriptase-2, secretase, kallikrein-related peptidase (KLK), and tryptase, or a serine protease, a cysteine-type lysosomal protease, a metalloproteinase, a coagulation factor protease, or an aspartyl-type lysosomal protease. In some embodiments, the protease cleavage site comprises an amino acid sequence that is cleaved by a protease or type of protease listed herein. In some embodiments, the protease cleavage site or one or more of the multiple protease cleavage sites is recognized by an endogenous protease. In some embodiments, the protease that recognizes the protease cleavage site, or that recognizes one or more of the multiple protease cleavage sites, is an endogenous protease.

In some embodiments, the protease cleavage site or one or more of the multiple protease cleavage sites is recognized by one or more of a serine protease, a cysteine-type lysosomal protease, an aspartyl-type lysosomal protease and a metalloproteinase. In some embodiments, the protease that recognizes the protease cleavage site, or that recognizes one or more of the multiple protease cleavage sites, is one or more of a serine protease, a cysteine-type lysosomal protease, an aspartyl-type lysosomal protease and a metalloproteinase.

In some embodiments, the linker comprises an amino GS peptide, a peptide comprising a protease cleavage site, and a carboxy GS peptide. In some embodiments, the linker comprises the amino acid sequence of SEQ ID NO: 9, which comprises an amino GS peptide (SEQ ID NO: 52), a TPS cleavage peptide (SEQ ID NO: 53) comprising a protease cleavage site, and a carboxy GS peptide (SEQ ID NO: 54). In some embodiments, the linker comprises the same amino and carboxy GS peptides and a different cleavage peptide comprising the same or a (LHF) different protease cleavage site. Information on additional exemplary linkers is set forth in the tables below, which show the linker name, SEQ ID NO: protease cleavage sites that each linker comprises and their corresponding SEQ ID NOs: and the length (in amino acids ("a.a.") of each linker. For example, the linker TPS4 45aa (SEQ ID NO: 107) comprises an MMP cleavage site having an amino acid sequence of SEQ ID NO: 93 and a matriptase cleavage site having an amino acid sequence of SEQ ID NO: 91. As shown in Table 2, TPS4 45aa (SEQ ID NO: 107) further comprises a GS peptide at the amino and carboxy termini. Additional linker information can be found at, for example, M. Geiger et al., Protease-activation using anti-idiotypic masks enables tumor specificity of afolate receptor 1-T cell bispecific antibody, Nature Commun 11: 3196 (2020); E. J. Kwon et al., Ultrasensitive tumour-penetrating nanosensors of protease activity, Nature Biomed Eng 1:0054 (2017); WO 2016/118629 A1, US 20170204139A1; WO 2013/130683 A2, US 2013 0165389A1.

TABLE 1A

| Linker | Matriptase site | MMP site | Length |
|---|---|---|---|
| TPS1 45aa (SEQ ID NO: 9) | LSGRSDNH* (SEQ ID NO: 97) | SPLGLAGS (SEQ ID NO: 103) | 45 a.a. |
| TPS3 45aa (SEQ ID NO: 9) | LSGRSDNH* (SEQ ID NO: 97) | SPLGLAGS (SEQ ID NO: 103) | 45 a.a. |
| TPS6 45aa (SEQ ID NO: 113) | PMAKK (SEQ ID NO: 95) | | 45 a.a. |

*The sequence "LSGRSDNH" (SEQ ID NO 97) can be cleaved by both matriptase and uPA.

TABLE 1B

| Linker | MMP site | Matriptase site | Length |
|---|---|---|---|
| TPS4 45aa (SEQ ID NO: 107) | VHMPLGFLGP (SEQ ID NO: 93) | RQARVVNG (SEQ ID NO: 91) | 45 a.a. |
| TPS8 45aa (SEQ ID NO: 115) | SPLGLAGS (SEQ ID NO: 103) | PMAKK (SEQ ID NO: 95) | 45 a.a. |
| TPS9 45aa (SEQ ID NO: 116) | VHMPLGFLGP (SEQ ID NO: 93) | PMAKK (SEQ ID NO: 95) | 45 a.a. |
| TPS10 45aa (SEQ ID NO: 117) | PLGVRGK (SEQ ID NO: 104) | PMAKK (SEQ ID NO: 95) | 45 a.a. |
| TPS11 45aa (SEQ ID NO: 118) | SPLGLAGS (SEQ ID NO: 103) | RQARVVNG (SEQ ID NO: 91) | 45 a.a. |
| TPS12 45aa (SEQ ID NO: 119) | VHMPLGFLGP (SEQ ID NO: 93) | RQARVVNG (SEQ ID NO: 91) | 45 a.a. |

TABLE 1B-continued

| Linker | MMP site | Matriptase site | Length |
|---|---|---|---|
| TPS13 45aa (SEQ ID NO: 120) | PLGVRGK (SEQ ID NO: 104) | RQARVVNG (SEQ ID NO: 91) | 45 a.a. |

In some embodiments, the antigen binding domain specifically binds BCMA, MUC16 (also known as CA125), EGFR, EGFRvIII, MUC1, Flt-3, WT-1, CD20, CD23, CD30, CD38, CD70, CD33, CD133, MHC-WT1, TSPAN10, MHC-PRAME, MHC-NY-ESO1, HER2 (ERBB2), CAIX (Carbonic anhydrase IX), LIV1, ADAM10, CHRNA2, LeY, NKG2D, CS1, CD44v6, ROR1, CD19, Claudin-18.2 (Claudin-18A2, or Claudin18 isoform 2), PSCA, DLL3 (Delta-like protein 3, Drosophila Delta homolog 3, Delta3), Mud 7 (Mucin17, Muc3, Muc3), FAP alpha (Fibroblast Activation Protein alpha), Ly6G6D (Lymphocyte antigen 6 complex locus protein G6d, c6orf23, G6D, MEGT1, NG25), PSMA, MSLN, or RNF43 (E3 ubiquitin-protein ligase RNF43, RING finger protein 43). CARs and/or antibodies that target the antigens are disclosed, for example, in the following: BCMA- WO201616630, WO2020150339, WO2019196713, WO2016014565, WO2017025038; MUC16: U.S. Pat. No. 9,169,328, WO2016149368, WO2020023888; EGFRvIII: WO2017125830, WO2016016341; Flt3: WO2018222935, WO2020010284, WO2017173410; CD20: WO2018145649, WO2020010235, WO2020123691; CD38: WO2017025323; CD70: WO2019152742, WO2018152181; CD33: WO2016014576; CD133: WO2018072025; CS1: WO2019030240; ROR1: WO2016115559; CD19: WO2002077029, U.S. Pat. No. 11,077,144; Claudin: WO2018006882, WO2021008463; DLL3: WO2020180591; WT1: US20160152725A1, U.S. Pat. No. 7,622,119B2; CD23: U.S. Pat. No. 6,011,138A, CN1568198A; CD30: U.S. Ser. No. 10/815,301B2, U.S. Ser. No. 10/808,035B2; PRAME: US20180148503A1, WO2020186204A1; LIV1: US20200231699A1; NKG2D: WO2021179353A1, US20210269501A1; FAP Alpha: US20200246383A1, US20210115102A1; PSMA: US20210277141A1, WO2020108646A1; MSLN: CN109680002A, CN109628492A.

In some embodiments, the antigen binding domain specifically binds MUC16. In some embodiments, the antigen binding domain specifically binds MUC16 and the protease-activating CD45-gate CAR comprises the amino acid sequence of any of SEQ ID NOs: 11, 56, 75, 76, 77, 78, 79, and 121-170, with or without a signal sequence. In some embodiments, the antigen binding domain specifically binds MUC16 and comprises the amino acid sequence of SEQ ID NO: 75 or 76, with or without a signal sequence. In some embodiments, the antigen binding domain specifically binds to an antigen expressed by a certain type of tumor and the protease cleavage sites can be recognized and cleaved by a protease that the same type of tumor expresses. In some embodiments, the protease-activating CD45-gate CAR both (1) can specifically recognize and bind to an antigen expressed by a tumor and (2) comprises a CD45-CAR linker that can be cleaved by a protease that the tumor secretes and/or that is present and/or active in the tumor microenvironment.

In some embodiments, the antigen binding domain specifically binds to a breast cancer tumor antigen or a colorectal cancer tumor antigen and one or more of the at least one protease cleavage sites can be recognized and cleaved by uPA. In some embodiments, the protease-activating CD45-gate CAR's antigen binding domain specifically recognizes and binds to an antigen characteristic of any of cervical, breast, ovarian and colorectal cancers and at least one of its protease cleavage sites can be recognized and cleaved by MMP-2 and/or MMP-9. In some embodiments, the protease-activating CD45-gate CAR's antigen binding domain specifically recognizes and binds to an antigen characteristic of any of breast and ovarian cancers and at least one of its protease cleavage sites can be recognized and cleaved by matriptase.

In some embodiments, the protease-activating CD45-gate CAR comprises a signal sequence. In some embodiments, the signal sequence is the CD8 signal sequence. In some embodiments, the signal sequence comprises the amino acid sequence of SEQ ID NOs: 1 or 44.

Also provided herein is a CAR that specifically recognizes and binds to MUC16 (also known as CA125). In an embodiment, the anti-MUC16 CAR comprises the amino acid sequence of any of SEQ ID NOs: 11, 56, 75, 76, 77, 78, 79, and 121-170, or a variant thereof that does not comprise a signal sequence, or a conservative variant thereof.

MUC16 has been found to be an overexpressed antigen in several cancers, including ovarian, breast, pancreatic, non-small-cell lung cancer, intrahepatic cholangiocarcinoma-mass forming type, adenocarcinoma of the uterine cervix, and adenocarcinoma of the gastric tract. See, e.g., Haridas et al., FASEB J. 28: 4183-99 (2014). The present disclosure therefore provides, in some embodiments, a method of treating any of ovarian cancer, breast cancer, pancreatic cancer, non-small-cell lung cancer, intrahepatic cholangiocarcinoma-mass forming type, adenocarcinoma of the uterine cervix, and adenocarcinoma of the gastric tract comprising administering to a patient who has that condition one or more engineered immune cells that functionally express a MUC16-specific CAR disclosed herein e.g. one comprising the amino acid sequence of any of SEQ ID NOs: 11, 56, 75, 76, 77, 78, 79, and 121-170, and variants thereof described herein or that functionally express a protease-activating CD45-gate MUC16-specific CAR disclosed herein (e.g. one comprising the amino acid sequence of SEQ ID NOs: 11, 16, 18, 20-31, 56, 75, 76, 77, 78, 79, or 121-170, or a variant thereof described herein).

In various embodiments, the protease-activating CD45-gate CAR protein disclosed herein comprises the amino acid sequence of, e.g., any one or more of SEQ ID NOs: 1-178 and conservative variants thereof. In certain embodiments, the protease-activating CD45-gate CAR comprises an amino acid sequence which comprises at least 70%, for example at least 80%, or at least 90%, 95%, 97%, or 99% sequence identity with any one or more of SEQ ID NOs: 1-178.

In some embodiments, the protease-activating CD45-gate CAR disclosed herein comprises any one of the amino acid sequences of SEQ ID NOs: 11, 16, 17 (control sequence-contains no protease cleavage site), 18, 19 (control sequence-contains no protease cleavage site), 20, 21, 22, 23, 24, 25, 26, 27, 28, 29, 30, 31, 56, 75, 76, 77, 78, 79, and 121-170. Some of these sequences contain one or both of the HA (tag) (SEQ ID NO: 2) and V5 peptide motif (SEQ ID NO: 55). In some embodiments of the protease-activating CD45-gate CAR of the disclosure, either or both of the HA (tag) and V5 peptide motif, and/or the signal peptide, are excluded from the protease-activating CD45-gate CAR. The present disclosure therefore provides a protease-activating CD45-gate CAR that comprises a variant of the amino acid sequence of any one of SEQ ID NOs: 11, 16-31, 56, 75-79 and 121-170 wherein the variant excludes (does not comprise) the amino acid sequence of the HA tag of SEQ ID NO: 2 and/or the amino acid sequence of the V5 peptide motif of SEQ ID NO: 55 and/or the amino acid sequence of CD8ss SEQ ID NO: 1, or an amino acid sequence which comprises at least 70%, for example at least 80%, or at least 90%, 95%, 97%, 99% or 100% sequence identity therewith. Some embodiments of the protease-activating CD45-gate CAR disclosed herein contain one, two, or all three of the HA (tag) (SEQ ID NO: 2), V5 peptide motif (SEQ ID NO: 55) and CD8 signal sequence (SEQ ID NO: 1).

In some embodiments, the protease-activating CD45-gate CAR comprises a CD45 recruiting domain, a CAR, and a linker connecting the carboxy terminus of the CD45 recruiting domain to the amino terminus of the antigen binding domain of the CAR. In some embodiments, the protease-activating CD45-gate CAR comprises a CD45 recruiting domain, a CAR, and a linker connecting the carboxy terminus of the CD45 recruiting domain to the amino terminus of the antigen binding domain of the CAR wherein the CAR comprises the amino acid sequence of SEQ ID NO: 11.

In some embodiments, the protease-activating CD45-gate CAR extracellular CD45 recruiting domain comprises the amino acid sequence of SEQ ID NOs: 3, 4, 12, 13, 14, or 15.

In some embodiments, the protease-activating CD45-gate CAR extracellular CD45 recruiting domain together with the protease-cleavable linker comprises the amino acid sequence of SEQ ID NOs: 5 or 6.

In some embodiments, the protease-activating CD45-gate CAR extracellular protease-cleavable linker comprises the amino acid sequence of SEQ ID NOs: 8, 9, or 10 and/or the protease cleavage site having the amino acid sequence of SEQ ID NOs: 32 (thrombin cleavage site) or 53 (TPS cleavage site) and/or either or both of SEQ ID NOs: 52 or 54 (sequences flanking the cleavage site). In some embodiments, the protease-activating CD45-gate CAR comprises a non-cleavable linker; in some embodiments, the non-cleavable linker comprises the amino acid sequence of SEQ ID NO: 7.

In some embodiments, the protease-activating CD45-gate CAR extracellular antigen binding domain comprises the amino acid sequence of SEQ ID NO: 56.

In some embodiments, the protease-activating CD45-gate CAR transmembrane domain comprises the amino acid sequence of SEQ ID NO: 39. In some embodiments, the CAR's transmembrane and intracellular domain comprises the amino acid sequence of SEQ ID NO: 41.

In some embodiments, the protease-activating CD45-gate CAR intracellular domain comprises one or more of the amino acid sequences of SEQ ID NOs: 33, 40 and 43.

In some embodiments, the protease-activating CD45-gate CAR hinge domain comprises the amino acid sequence of SEQ ID NOs: 36, 37 or 38.

In some embodiments, the protease-activating CD45-gate CAR disclosed herein comprises an N-terminal signal sequence. In some embodiments, the signal sequence has the amino acid sequence of SEQ ID NOs: 1 or 44. In some embodiments, a nucleic acid that encodes the protease-activating CD45-gate CAR encodes the signal sequence, and, during processing within the cell, the signal sequence is removed, leaving the remainder of the encoded amino acid sequence in the mature form of the protein. This mature form of protease-activating CD45-gate CAR is within the scope of the disclosure. In some embodiments, the protease-activating CD45-gate CAR disclosed herein does not comprise an N-terminal signal sequence.

In another aspect, provided herein is a nucleic acid encoding the extracellular domain of the protease-activating CD45-gate CAR disclosed herein. In another aspect, provided herein is a nucleic acid that encodes the protease-activating CD45-gate CAR disclosed herein. In certain embodiments, a nucleic acid of the disclosure encodes a protease-activating CD45-gate CAR that comprises an amino acid sequence which comprises at least 70%, for example at least 80%, or at least 90%, 95%, 97%, or 99% sequence identity with one or more of the amino acid sequences of SEQ ID NOs: 1-56. In certain embodiments, a nucleic acid of the disclosure encodes a protease-activating CD45-gate CAR that comprises an amino acid sequence which comprises at least 70%, for example at least 80%, or at least 90%, 95%, 97%, or 99% sequence identity with the amino acid sequence of SEQ ID NOs: 11, 16, 17 (control sequence-contains no protease cleavage site), 18, 19 (control sequence-contains no protease cleavage site), 20, 21, 22, 23, 24, 25, 26, 27, 28, 29, 30, 31, 56, 75, 76, 77, 78, 79, and 121-170, or a variant thereof that does not comprise an HA tag and/or a V5 sequence.

Also provided herein is a nucleic acid that encodes the amino acid sequence of any of SEQ ID NOs: 11, 56, 75, 76, 77, 78, 79, and 121-170. Also provided herein is a nucleic acid that encodes the amino acid sequence of SEQ ID NO: 56. In certain embodiments, a nucleic acid of the disclosure encodes an anti-MUC16 CAR that comprises an amino acid sequence which comprises at least 70%, for example at least 80%, or at least 90%, 95%, 97%, or 99% sequence identity with the amino acid sequence of SEQ ID NOs: 11, 56, 75, 76, 77, 78, 79, and 121-170.

In another aspect, provided herein is a vector comprising the nucleic acid disclosed herein. In an embodiment, the vector is an expression vector. In an embodiment, the vector is a viral vector, a retroviral vector, a DNA vector, a plasmid, a RNA vector, an adenoviral vector, an adenovirus associated vector, a lentiviral vector, or any combination thereof.

In a further aspect, provided herein is an engineered cell e.g. an engineered immune cell comprising the protease-activating CD45-gate CAR disclosed herein. In a further aspect, provided herein is an engineered immune cell comprising the nucleic acid disclosed herein. In another aspect, provided herein is an engineered immune cell comprising the vector disclosed herein.

In another aspect, an immune cell e.g. T cell of the disclosure comprises e.g. expresses a polypeptide that consists of or comprises one or more amino acid sequences listed in Table 2. In some embodiments, an immune cell e.g. T cell of the disclosure comprises e.g. expresses a nucleic acid that encodes one or more amino acid sequences listed in Table 2.

In various embodiments, any of the engineered cells e.g. any of the engineered immune cells disclosed herein functionally express the protease-activating CD45-gate CAR disclosed herein. In various embodiments, any of the engineered cells e.g. any of the engineered immune cells disclosed herein functionally express a protease-activating CD45-gate CAR that comprises the amino acid sequence of SEQ ID NO: 11, 56, 75, 76, 77, 78, 79, and 121-170 or a variant thereof that lacks an N-terminal signal sequence. Also provided herein are engineered cells e.g. engineered immune cells that functionally express a CAR that comprises the amino acid sequence of SEQ ID NO: 11, 56, 75, 76, 77, 78, 79, and 121-170 or a variant thereof that lacks an N-terminal signal sequence. In various embodiments, any of the engineered cells e.g. any of the engineered immune cells disclosed herein is an isolated cell.

In various embodiments, the engineered cell e.g. engineered immune cell disclosed herein functionally expresses the protease-activating CD45-gate CAR disclosed herein from a nucleic acid encoding the protease-activating CD45-gate CAR. In various embodiments, the engineered cell e.g. engineered immune cell disclosed herein functionally expresses CD45, e.g. functionally expresses the cell's endogenous CD45 gene or functionally expresses CD45 from an exogenous nucleic acid that encodes CD45 and was introduced into cell. Table 2: Exemplary Protein Sequences

TABLE 2

Exemplary Protein Sequences

| SEQ ID NO: | Name | Amino Acid Sequence |
|---|---|---|
| 1 | CD8ss | MALPVTALLLPLALLLHAARP |
| 2 | HA(tag) | GYPYDVPDYA |
| 3 | CD45-Gate1 (4131) | DIVMTQTPASVSEPVGGSVTIKCQASQSFYNLLAWYQQKPGQPPKLLIYDASDL ASGVPSRFKGSGSGTDFTLTISDLECADAAAYYCQSADGSSYAFGGGTEVVVKG GGGGSGGGGSGGGGSGGGGSQEQLEESGGGLVKPEGSLTLTCTASGVSFSSSYW IYWVRQAPGKGLEWIACIYTGSSGSTYYASWAKGRFTVSETSSTTVTLQMTSLT AADTATYFCARASAWTYGMDLWGPGTLVTVSS |
| 4 | CD45-Gate2 (4122) | DIVMTQTPASVSEPVGGTVTIMCQASQSISNWLAWYQQKPGQPPKLLIYQASKL ASGVPSRFKGSGSGTEYTLTISDLECADAATYYCQSYYDSGSNVFFAFGGGTKV VVEGGGGSGGGGSGGGGSGGGGSLSLEESGGDLVKPGASLTLTCTASGFSFSA GYWICWVRQAPGKGLEWIACTYAGRSGSTYYANWVNGRFTIPKTSSTTVTLQMT SLSGADTASYFCARGNAGVAVGALWGPGTLVTVSS |
| 5 | CD45-Gate1 withTPS | DIVMTQTPASVSEPVGGSVTIKCQASQSFYNLLAWYQQKPGQPPKLLIYDASDL ASGVPSRFKGSGSGTDFTLTISDLECADAAAYYCQSADGSSYAFGGGTEVVVKG GGGGSGGGGSLSGRSDNHSPLGLAGSGGGGSGGGGSQEQLEESGGGLVKPEGSL TLTCTASGVSFSSSYWIYWVRQAPGKGLEWIACIYTGSSGSTYYASWAKGRFTV SETSSTTVTLQMTSLTAADTATYFCARASAWTYGMDLWGPGTLVTVSS |
| 6 | CD45-Gate2 withTPS | DIVMTQTPASVSEPVGGTVTIMCQASQSISNWLAWYQQKPGQPPKLLIYQASKL ASGVPSRFKGSGSGTEYTLTISDLECADAATYYCQSYYDSGSNVFFAFGGGTKV VVEGGGGSGGGGSLSGRSDNHSPLGLAGSGGGGSGGGGSLSLEESGGDLVKPG ASLTLTCTASGFSFSAGYWICWVRQAPGKGLEWIACTYAGRSGSTYYANWVNGR FTIPKTSSTTVTLQMTSLSGADTASYFCARGNAGVAVGALWGPGTLVTVSS |

TABLE 2-continued

Exemplary Protein Sequences

| SEQ ID NO: Name | Amino Acid Sequence |
|---|---|
| 171 CD45-Gate3 (RB/RO) | DILLTQSPATLSLSPGERATLSCRASQNIGTSIQWYQQKPGQAPRLLIRSSSES ISGIPSRFSGSGSGTDFTLTISSLEPEDFAVYYCQQSNTWPFTFGQGTKLEIKG GGGSGGGGSGGGGSGGGGSEVQLVESGAEVKKPGASVKVSCKASGYTFTNYITH WVKQEPGQGLEWIGYFNPYNHGTKYNEKFKGRATLTADKSISTAYMELSSLRSE DTAVYYCARSGPYAWFDTWGQGTTVTVSS |
| 11 MUC16 CAR1 (53B6) | QVQLQESGPGLVKPSETLSLTCTVSGGSISYYSWTWVRQPAGQGLEWIGRIHIS GVTNHNPSLKSRVSMSIDTSRTQFSLRLTSVTAADTAVYFCARSGGTYSAFDIW GQGTMVTVSSGGGGSGGGGSGGGGSGGGGSEIVLTQSPGTLSLSPGERSTLSCR ASQSFTSNYLAWYQQRPGQAPRLLIYGASTRAIGIPDRFSGSGSGTDFTLTISR LEPEDFAVYYCQQYGSSPWTFGQGTKVEIKTTTPAPRPPTPAPTIASQPLSLRP EACRPAAGGAVHTRGLDFACDIYIWAPLAGTCGVLLLSLVITLYCKRGRKKLLY IFKQPFMRPVQTTQEEDGCSCRFPEEEEGGCELRVKFSRSADAPAYQQGQNQLY NELNLGRREEYDVLDKRRGRDPEMGGKPRRKNPQEGLYNELQKDKMAEAYSEIG MKGERRRGKGHDGLYQGLSTATKDTYDALHMQALPPR |
| 12 Sec49k | GPHTINATWWANITLVGPPDTPVTWYDTQGLWFCNGSRVKNPQIRHTCNDQNLT LIHVNKTYERTYMGYNRQGTKKEDYKVVVIPPPPATVKPQPEPEYVEVYMGENK TLEGPPGTPVTWFNQDGKKFCEGEKVLHPEFNHTCDKQNLILLFVNFTHDGAYL GYNHQGTQRTHYEVTVLDLFPDSGQMKIENHSEETEQKNDEHHNWQKQGGQKQG GQKTNQTKVNDRRKTAQKRPSKLKPATIEAMLVTVTAGSNLTLVGPKAEGKVTW FDGDLKRPCEPNYRLRHECNNQNLTLINVTKDYEGTYYGTNDKDEGKRYRVKVN TTNSQSVKIQPYTRQTTPDQEHKFELQFETNGNYDSKIP |
| 13 UL11 | HDACIPVVGKIGTNVTLNAVDFHPGDHVRWSYGPGGAGYMLCVYTGSWTEYKKP DIIFKCLSNNSLLLINVTVNYTNTYRTLTSLNNWVHNQHHHKFPGWNLDTCYSL TVNENGTFPTTTTKKPTTTTRTTTTTTKKTTTTRTTTAAKKTTISTTHHKHSS PKKSSTPNSHVEHHVGFEATAAETPLQPSPQHQHVATH |
| 14 BTN3A1-IgV | QFSVLGPSGPILAMVGEDADLPCHLEPTMSAETMELKWVSSSLRQVVNVYADGK EVEDRQSAPYRGRTSILRDGITAGKAALRIHNVTASDSGKYLCYFQDGDFYEKA LVELKVA |
| 15 BTN3A1-IgC | ALGSDLHVDVKGYKDGGIHLECRSTGWYPQPQIQWSNNKGENIPTVEAPVVADG VGLYAVAASVIMRGSSGEGVSCTIRSSLLGLEKTASISIADPFFRSAQRWIAAL AGT |
| 183 BTN3A1 | QFSVLGPSGPILAMVGEDADLPCHLFPTMSAETMELKWVSSSLRQVVNVYADGK EVEDRQSAPYRGRTSILRDGITAGKAALRIHNVTASDSGKYLCYFQDGDFYEKA LVELKVAALGSDLHVDVKGYKDGGIHLECRSTGWYPQPQIQWSNNKGENIPTVE APVVADGVGLYAVAASVIMRGSSGEGVSCTIRSSLLGLEKTASISIADPFFRSA QRWIAALAGT |
| 160 975-N-HA-4131scFv-V5-2G4STMB-53B6 | MALPVTALLLPLALLLHAARPGYPYDVPDYADIVMTQTPASVSEPVGGSVTIKC QASQSFYNLLAWYQQKPGQPPKLLIYDASDLASGVPSRFKGSGSGTDFTLTISD LECADAAAYYCQSADGSSYAFGGGTEVVVKGGGGSGGGGSGGGGSGGGGSQEEQ LEESGGGLVKPEGSLTLTCTASGVSFSSSYWIYWVRQAPGKGLEWIACIYTGSS GSTYYASWAKGRFTVSETSSTTVTLQMTSLTAADTATYFCARASAWTYGMDLWG PGTLVTVSSGGGGSGGGGSLVPRGSKPIPNPLLGLDSTLVPRGSGGGGSGGGGS QVQLQESGPGLVKPSETLSLTCTVSGGSISYYSWTWVRQPAGQGLEWIGRIHIS GVTNHNPSLKSRVSMSIDTSRTQFSLRLTSVTAADTAVYFCARSGGTYSAFDIW GQGTMVTVSSGGGGSGGGGSGGGGSGGGGSEIVLTQSPGTLSLSPGERSTLSCR ASQSFTSNYLAWYQQRPGQAPRLLIYGASTRAIGIPDRFSGSGSGTDFTLTISR LEPEDFAVYYCQQYGSSPWTFGQGTKVEIKTTTPAPRPPTPAPTIASQPLSLRP EACRPAAGGAVHTRGLDFACDIYIWAPLAGTCGVLLLSLVITLYCKRGRKKLLY IFKQPFMRPVQTTQEEDGCSCRFPEEEEGGCELRVKFSRSADAPAYQQGQNQLY NELNLGRREEYDVLDKRRGRDPEMGGKPRRKNPQEGLYNELQKDKMAEAYSEIG MKGERRRGKGHDGLYQGLSTATKDTYDALHMQALPPR |
| 170 976-N-HA-4131scFv-V5-3G4S-53B6 | MALPVTALLLPLALLLHAARPGYPYDVPDYADIVMTQTPASVSEPVGGSVTIKC QASQSFYNLLAWYQQKPGQPPKLLIYDASDLASGVPSRFKGSGSGTDFTLTISD LECADAAAYYCQSADGSSYAFGGGTEVVVKGGGGSGGGGSGGGGSGGGGSQEEQ LEESGGGLVKPEGSLTLTCTASGVSFSSSYWIYWVRQAPGKGLEWIACIYTGSS GSTYYASWAKGRFTVSETSSTTVTLQMTSLTAADTATYFCARASAWTYGMDLWG PGTLVTVSSGGGGSGGGGSGGGGSKPIPNPLLGLDSTGGGSGGGGSGGGGS QVQLQESGPGLVKPSETLSLTCTVSGGSISYYSWTWVRQPAGQGLEWIGRIHIS GVTNHNPSLKSRVSMSIDTSRTQFSLRLTSVTAADTAVYFCARSGGTYSAFDIW GQGTMVTVSSGGGGSGGGGSGGGGSGGGGSEIVLTQSPGTLSLSPGERSTLSCR ASQSFTSNYLAWYQQRPGQAPRLLIYGASTRAIGIPDRFSGSGSGTDFTLTISR LEPEDFAVYYCQQYGSSPWTFGQGTKVEIKTTTPAPRPPTPAPTIASQPLSLRP EACRPAAGGAVHTRGLDFACDIYIWAPLAGTCGVLLLSLVITLYCKRGRKKLLY IFKQPFMRPVQTTQEEDGCSCRFPEEEEGGCELRVKFSRSADAPAYQQGQNQLY NELNLGRREEYDVLDKRRGRDPEMGGKPRRKNPQEGLYNELQKDKMAEAYSEIG MKGERRRGKGHDGLYQGLSTATKDTYDALHMQALPPR |

TABLE 2-continued

Exemplary Protein Sequences

| SEQ ID NO: | Name | Amino Acid Sequence |
|---|---|---|
| 18 | 0977-N-HA-4122scFv-V5-2G4STMB-53B6 | MALPVTALLLPLALLLHAARPGYPYDVPDYADIVMTQTPASVSEPVGGTVTIMC QASQSISNWLAWYQQKPGQPPKLLIYQASKLASGVPSRFKGSGSGTEYTLTISD LECADAATYYCQSYYDSGSNVFFAFGGGTKVVEGGGGSGGGGSGGGGSGGGG SLSLEESGGDLVKPGASLTLTCTASGFSFSAGYWICWVRQAPGKGLEWIACTYA GRSGSTYYANWVNGRFTIPKTSSTTVTLQMTSLSGADTASYFCARGNAGVAVGA LWGPGTLVTVSSGGGGSGGGGSLVPRGSKPIPNPLLGLDSTLVPRGSGGGSGG GGSQVQLQESGPGLVKPSETLSLTCTVSGGSISYYSWTWVRQPAGQGLEWIGRI HISGVTNHNPSLKSRVSMSIDTSRTQFSLRLTSVTAADTAVYFCARSGGTYSAF DIWGQGTMVTVSSGGGGSGGGGSGGGGSGGGGSEIVLTQSPGTLSLSPGERSTL SCRASQSFTSNYLAWYQQRPGQAPRLLIYGASTRAIGIPDRFSGSGSGTDFTLT ISRLEPEDFAVYYCQQYGSSPWTFGQGTKVEIKTTTPAPRPPTPAPTIASQPLS LRPEACRPAAGGAVHTRGLDFACDIYIWAPLAGTCGVLLLSLVITLYCKRGRKK LLYIFKQPFMRPVQTTQEEDGCSCRFPEEEEGGCELRVKFSRSADAPAYQQGQN QLYNELNLGRREEYDVLDKRRGRDPEMGGKPRRKNPQEGLYNELQKDKMAEAYS EIGMKGERRRGKHDGLYQGLSTATKDTYDALHMQALPPR |
| 19 | 0978-N-HA-4122scFv-V5-3G4S-53B6 | MALPVTALLLPLALLLHAARPGYPYDVPDYADIVMTQTPASVSEPVGGTVTIMC QASQSISNWLAWYQQKPGQPPKLLIYQASKLASGVPSRFKGSGSGTEYTLTISD LECADAATYYCQSYYDSGSNVFFAFGGGTKVVEGGGGSGGGGSGGGGSGGGG SLSLEESGGDLVKPGASLTLTCTASGFSFSAGYWICWVRQAPGKGLEWIACTYA GRSGSTYYANWVNGRFTIPKTSSTTVTLQMTSLSGADTASYFCARGNAGVAVGA LWGPGTLVTVSSGGGGSGGGGSGGGGSGSKPIPNPLLGLDSTGGGSGSGGGSGG GGSQVQLQESGPGLVKPSETLSLTCTVSGGSISYYSWTWVRQPAGQGLEWIGRI HISGVTNHNPSLKSRVSMSIDTSRTQFSLRLTSVTAADTAVYFCARSGGTYSAF DIWGQGTMVTVSSGGGGSGGGGSGGGGSGGGGSEIVLTQSPGTLSLSPGERSTL SCRASQSFTSNYLAWYQQRPGQAPRLLIYGASTRAIGIPDRFSGSGSGTDFTLT ISRLEPEDFAVYYCQQYGSSPWTFGQGTKVEIKTTTPAPRPPTPAPTIASQPLS LRPEACRPAAGGAVHTRGLDFACDIYIWAPLAGTCGVLLLSLVITLYCKRGRKK LLYIFKQPFMRPVQTTQEEDGCSCRFPEEEEGGCELRVKFSRSADAPAYQQGQN QLYNELNLGRREEYDVLDKRRGRDPEMGGKPRRKNPQEGLYNELQKDKMAEAYS EIGMKGERRRGKHDGLYQGLSTATKDTYDALHMQALPPR |
| 20 | 01082-N-HA-4131scFv-TPS1-53B6 | MALPVTALLLPLALLLHAARPGYPYDVPDYADIVMTQTPASVSEPVGGSVTIKC QASQSFYNLLAWYQQKPGQPPKLLIYDASDLASGVPSRFKGSGSGTDFTLTISD LECADAAAYYCQSADGSSYAFGGGTEVVVKGGGGSGGGGSGGGGSGGGGSQEQ LEESGGGLVKPEGSLTLTCTASGVSFSSSYWIYWVRQAPGKGLEWIACIYTGSS GSTYYASWAKGRFTVSETSSTTVTLQMTSLTAADTATYFCARASAWTYGMDLWG PGTLVTVSSGGGGSGGGGSGGGGSGLSGRSDNHSPLGLAGSGGGGSGGGGSGGGGS QVQLQESGPGLVKPSETLSLTCTVSGGSISYYSWTWVRQPAGQGLEWIGRIHIS GVTNHNPSLKSRVSMSIDTSRTQFSLRLTSVTAADTAVYFCARSGGTYSAFDIW GQGTMVTVSSGGGGSGGGGSGGGGSGGGGSEIVLTQSPGTLSLSPGERSTLSCR ASQSFTSNYLAWYQQRPGQAPRLLIYGASTRAIGIPDRFSGSGSGTDFTLTISR LEPEDFAVYYCQQYGSSPWTFGQGTKVEIKTTTPAPRPPTPAPTIASQPLSLRP EACRPAAGGAVHTRGLDFACDIYIWAPLAGTCGVLLLSLVITLYCKRGRKKLLY IFKQPFMRPVQTTQEEDGCSCRFPEEEEGGCELRVKFSRSADAPAYQQGQNQLY NELNLGRREEYDVLDKRRGRDPEMGGKPRRKNPQEGLYNELQKDKMAEAYSEIG MKGERRRGKHDGLYQGLSTATKDTYDALHMQALPPR |
| 21 | 01092-N-HA-4122scFv-TPS1-53B6 | MALPVTALLLPLALLLHAARPGYPYDVPDYADIVMTQTPASVSEPVGGTVTIMC QASQSISNWLAWYQQKPGQPPKLLIYQASKLASGVPSRFKGSGSGTEYTLTISD LECADAATYYCQSYYDSGSNVFFAFGGGTKVVEGGGGSGGGGSGGGGSGGGG SLSLEESGGDLVKPGASLTLTCTASGFSFSAGYWICWVRQAPGKGLEWIACTYA GRSGSTYYANWVNGRFTIPKTSSTTVTLQMTSLSGADTASYFCARGNAGVAVGA LWGPGTLVTVSSGGGGSGGGGSGGGGSGLSGRSDNHSPLGLAGSGGGSGGGGSGG GGSQVQLQESGPGLVKPSETLSLTCTVSGGSISYYSWTWVRQPAGQGLEWIGRI HISGVTNHNPSLKSRVSMSIDTSRTQFSLRLTSVTAADTAVYFCARSGGTYSAF DIWGQGTMVTVSSGGGGSGGGGSGGGGSGGGGSEIVLTQSPGTLSLSPGERSTL SCRASQSFTSNYLAWYQQRPGQAPRLLIYGASTRAIGIPDRFSGSGSGTDFTLT ISRLEPEDFAVYYCQQYGSSPWTFGQGTKVEIKTTTPAPRPPTPAPTIASQPLS LRPEACRPAAGGAVHTRGLDFACDIYIWAPLAGTCGVLLLSLVITLYCKRGRKK LLYIFKQPFMRPVQTTQEEDGCSCRFPEEEEGGCELRVKFSRSADAPAYQQGQN QLYNELNLGRREEYDVLDKRRGRDPEMGGKPRRKNPQEGLYNELQKDKMAEAYS EIGMKGERRRGKHDGLYQGLSTATKDTYDALHMQALPPR |
| 22 | 01098-N-HA-4131scFv-V5-2XTPS1-53B6 | MALPVTALLLPLALLLHAARPGYPYDVPDYADIVMTQTPASVSEPVGGSVTIKC QASQSFYNLLAWYQQKPGQPPKLLIYDASDLASGVPSRFKGSGSGTDFTLTISD LECADAAAYYCQSADGSSYAFGGGTEVVVKGGGGSGGGGSGGGGSGGGGSQEQ LEESGGGLVKPEGSLTLTCTASGVSFSSSYWIYWVRQAPGKGLEWIACIYTGSS GSTYYASWAKGRFTVSETSSTTVTLQMTSLTAADTATYFCARASAWTYGMDLWG PGTLVTVSSGGGGSLSGRSDNHSPLGLAGSKPIPNPLLGLDSTLSGRSDNHSPL GLAGSGGGGSQVQLQESGPGLVKPSETLSLTCTVSGGSISYYSWTWVRQPAGQG LEWIGRIHISGVTNHNPSLKSRVSMSIDTSRTQFSLRLTSVTAADTAVYFCARS GGTYSAFDIWGQGTMVTVSSGGGGSGGGGSGGGGSGGGGSEIVLTQSPGTLSLS |

TABLE 2-continued

Exemplary Protein Sequences

| SEQ ID NO: | Name | Amino Acid Sequence |
|---|---|---|
| | | PGERSTLSCRASQSFTSNYLAWYQQRPGQAPRLLIYGASTRAIGIPDRFSGSGS GTDFTLTISRLEPEDFAVYYCQQYGSSPWTFGQGTKVEIKTTTPAPRPPTPAPT IASQPLSLRPEACRPAAGGAVHTRGLDFACDIYIWAPLAGTCGVLLLSLVITLY CKRGRKKLLYIFKQPFMRPVQTTQEEDGCSCRFPEEEEGGCELRVKFSRSADAP AYQQGQNQLYNELNLGRREEYDVLDKRRGRDPEMGGKPRRKNPQEGLYNELQKD KMAEAYSEIGMKGERRRGKGHDGLYQGLSTATKDTYDALHMQALPPR |
| 23 | 01099-N-HA- 4122scFv-V5- 2XTPS1-53B6 | MALPVTALLLPLALLLHAARPGYPYDVPDYADIVMTQTPASVSEPVGGTVTIMC QASQSISNWLAWYQQKPGQPPKLLIYQASKLASGVPSRFKGSGSGTEYTLTISD LECADAATYYCQSYYDSGSNVFFAFGGGTKVVVEGGGGSGGGGSGGGGSGGGG SLSLEESGGDLVKPGASLTLTCTASGFSFSAGYWICWVRQAPGKGLEWIACTYA GRSGSTYYANWVNGRFTIPKTSSTTVTLQMTSLSGADTASYFCARGNAGVAVGA LWGPGTLVTVSSGGGGSLSGRSDNHSPLGLAGSKPIPNPLLGLDSTLSGRSDNH SPLGLAGSGGGGSQVQLQESGPGLVKPSETLSLTCTVSGGSISYYSWTWVRQPA GQGLEWIGRIHISGVTNHNPSLKSRVSMSIDTSRTQFSLRLTSVTAADTAVYFC ARSGGTYSAFDIWGQGTMVTVSSGGGGSGGGGSGGGGSGGGGSEIVLTQSPGTL SLSPGERSTLSCRASQSFTSNYLAWYQQRPGQAPRLLIYGASTRAIGIPDRFSG SGSGTDFTLTISRLEPEDFAVYYCQQYGSSPWTFGQGTKVEIKTTTPAPRPPTP APTIASQPLSLRPEACRPAAGGAVHTRGLDFACDIYIWAPLAGTCGVLLLSLVI TLYCKRGRKKLLYIFKQPFMRPVQTTQEEDGCSCRFPEEEEGGCELRVKFSRSA DAPAYQQGQNQLYNELNLGRREEYDVLDKRRGRDPEMGGKPRRKNPQEGLYNEL QKDKMAEAYSEIGMKGERRRGKGHDGLYQGLSTATKDTYDALHMQALPPR |
| 24 | 01102-N-HA- 4131-VL-RS- VH-TPS1-53B6 | MALPVTALLLPLALLLHAARPGYPYDVPDYADIVMTQTPASVSEPVGGSVTIKC QASQSFYNLLAWYQQKPGQPPKLLIYDASDLASGVPSRFKGSGSGTDFTLTISD LECADAAAYYCQSADGSSYAFGGGTEVVVKGGGGSGGGGSLSGRSDNHSPLGL AGSGGGGSGGGGSGGGGSQEQLEESGGGLVKPEGSLTLTCTASGVSFSSSYWIYWVRQA PGKGLEWIACIYTGSSGSTYYASWAKGRFTVSETSSTTVTLQMTSLTAADTATY FCARASAWTYGMDLWGPGTLVTVSSGGGGSGGGGSGGGGSGLSGRSDNHSPLGLA GSGGGGSGGGGSGGGGSQVQLQESGPGLVKPSETLSLTCTVSGGSISYYSWTWVR QPAGQGLEWIGRIHISGVTNHNPSLKSRVSMSIDTSRTQFSLRLTSVTAADTAV YFCARSGGTYSAFDIWGQGTMVTVSSGGGGSGGGGSGGGGSGGGGSEIVLTQSP GTLSLSPGERSTLSCRASQSFTSNYLAWYQQRPGQAPRLLIYGASTRAIGIPDR FSGSGSGTDFTLTISRLEPEDFAVYYCQQYGSSPWTFGQGTKVEIKTTTPAPRP PTPAPTIASQPLSLRPEACRPAAGGAVHTRGLDFACDIYIWAPLAGTCGVLLLS LVITLYCKRGRKKLLYIFKQPFMRPVQTTQEEDGCSCRFPEEEEGGCELRVKFS RSADAPAYQQGQNQLYNELNLGRREEYDVLDKRRGRDPEMGGKPRRKNPQEGLY NELQKDKMAEAYSEIGMKGERRRGKGHDGLYQGLSTATKDTYDALHMQALPPR |
| 25 | 01103-N-HA- 4122-VL-RS- VH-TPS1-53B6 | MALPVTALLLPLALLLHAARPGYPYDVPDYADIVMTQTPASVSEPVGGTVTIMC QASQSISNWLAWYQQKPGQPPKLLIYQASKLASGVPSRFKGSGSGTEYTLTISD LECADAATYYCQSYYDSGSNVFFAFGGGTKVVVEGGGGSGGGGSLSGRSDNHS PLGLAGSGGGGSGGGGSLSLEESGGDLVKPGASLTLTCTASGFSFSAGYWICWV RQAPGKGLEWIACTYAGRSGSTYYANWVNGRFTIPKTSSTTVTLQMTSLSGADT ASYFCARGNAGVAVGALWGPGTLVTVSSGGGGSGGGGSGGGGSGGGGSLSGRSDNHSPL GLAGSGGGGSGGGGSGGGGSQVQLQESGPGLVKPSETLSLTCTVSGGSISYYSWT WVRQPAGQGLEWIGRIHISGVTNHNPSLKSRVSMSIDTSRTQFSLRLTSVTAAD TAVYFCARSGGTYSAFDIWGQGTMVTVSSGGGGSGGGGSGGGGSGGGGSEIVLT QSPGTLSLSPGERSTLSCRASQSFTSNYLAWYQQRPGQAPRLLIYGASTRAIGI PDRFSGSGSGTDFTLTISRLEPEDFAVYYCQQYGSSPWTFGQGTKVEIKTTTPA PRPPTPAPTIASQPLSLRPEACRPAAGGAVHTRGLDFACDIYIWAPLAGTCGVL LLSLVITLYCKRGRKKLLYIFKQPFMRPVQTTQEEDGCSCRFPEEEEGGCELRV KFSRSADAPAYQQGQNQLYNELNLGRREEYDVLDKRRGRDPEMGGKPRRKNPQE GLYNELQKDKMAEAYSEIGMKGERRRGKGHDGLYQGLSTATKDTYDALHMQALP PR |
| 26 | 01112-N-HA- 4131-VL-TMB- VH-V5- 2G4STMB-53B6 | MALPVTALLLPLALLLHAARPGYPYDVPDYADIVMTQTPASVSEPVGGSVTIKC QASQSFYNLLAWYQQKPGQPPKLLIYDASDLASGVPSRFKGSGSGTDFTLTISD LECADAAAYYCQSADGSSYAFGGGTEVVVKGGGGSGGGGSLVPRGSGGGGSGG GGSQEQLEESGGGLVKPEGSLTLTCTASGVSFSSSYWIYWVRQAPGKGLEWIAC IYTGSSGSTYYASWAKGRFTVSETSSTTVTLQMTSLTAADTATYFCARASAWTY GMDLWGPGTLVTVSSGGGGSGGGGSLVPRGSKPIPNPLLGLDSTLVPRGSGGGG SGGGGSQVQLQESGPGLVKPSETLSLTCTVSGGSISYYSWTWVRQPAGQGLEWI GRIHISGVTNHNPSLKSRVSMSIDTSRTQFSLRLTSVTAADTAVYFCARSGGTY SAFDIWGQGTMVTVSSGGGGSGGGGSGGGGSGGGGSEIVLTQSPGTLSLSPGER STLSCRASQSFTSNYLAWYQQRPGQAPRLLIYGASTRAIGIPDRFSGSGSGTDF TLTISRLEPEDFAVYYCQQYGSSPWTFGQGTKVEIKTTTPAPRPPTPAPTIASQ PLSLRPEACRPAAGGAVHTRGLDFACDIYIWAPLAGTCGVLLLSLVITLYCKRG RKKLLYIFKQPFMRPVQTTQEEDGCSCRFPEEEEGGCELRVKFSRSADAPAYQQ GQNQLYNELNLGRREEYDVLDKRRGRDPEMGGKPRRKNPQEGLYNELQKDKMAE AYSEIGMKGERRRGKGHDGLYQGLSTATKDTYDALHMQALPPR |

TABLE 2-continued

Exemplary Protein Sequences

| SEQ ID NO: | Name | Amino Acid Sequence |
|---|---|---|
| 27 | 01113-N-HA-4122-VL-TMB-VH-V5-2G4STMB-53B6 | MALPVTALLLPLALLLHAARPGYPYDVPDYADIVMTQTPASVSEPVGGTVTIMC QASQSISNWLAWYQQKPGQPPKLLIYQASKLASGVPSRFKGSGSGTEYTLTISD LECADAATYYCQSYYDSGSNVFFAFGGGTKVVVEGGGGSGGGGSLVPRGSGG GSGGGGSLSLEESGGDLVKPGASLTLTCTASGFSFSAGYWICWVRQAPGKGLEW IACTYAGRSGSTYYANWVNGRFTIPKTSSTTVTLQMTSLSGADTASYFCARGNA GVAVGALWGPGTLVTVSSGGGGSGGGGSLVPRGSKPIPNPLLGLDSTLVPRGSG GGGSGGGGSQVQLQESGPGLVKPSETLSLTCTVSGGSISYYSWTWVRQPAGQGL EWIGRIHISGVTNHNPSLKSRVSMSIDTSRTQFSLRLTSVTAADTAVYFCARSG GTYSAFDIWGQGTMVTVSSGGGGSGGGGSGGGGSGGGGSEIVLTQSPGTLSLSP GERSTLSCRASQSFTSNYLAWYQQRPGQAPRLLIYGASTRAIGIPDRFSGSGSG TDFTLTISRLEPEDFAVYYCQQYGSSPWTFGQGTKVEIKTTTPAPRPPTPAPTI ASQPLSLRPEACRPAAGGAVHTRGLDFACDIYIWAPLAGTCGVLLLSLVITLYC KRGRKKLLYIFKQPFMRPVQTTQEEDGCSCRFPEEEEGGCELRVKFSRSADAPA YQQGQNQLYNELNLGRREEYDVLDKRRGRDPEMGGKPRRKNPQEGLYNELQKDK MAEAYSEIGMKGERRRGKGHDGLYQGLSTATKDTYDALHMQALPPR |
| 28 | 01121-N-HA-sec49k-V5-2G4STMB-53B6 | MALPVTALLLPLALLLHAARPGYPYDVPDYAGFHTINATWWANITLVGPPDTPV TWYDTQGLWFCNGSRVKNPQIRHTCNDQNLTLIHVNKTYERTYMGYNRQGTKKE DYKVVVIPPPPATVKPQPEPEYVFVYMGENKTLEGPPGTPVTWFNQDGKKFCEG EKVLHPEFNHTCDKQNLILLFVNFTHDGAYLGYNHQGTQRTHYEVTVLDLFPDS GQMKIENHSEETEQKNDEHHNWQKQGGQKQGGQKTNQTKVNDRRKTAQKRPSKL KPATIEAMLVTVTAGSNLTLVGPKAEGKVTWEDGDLKRPCEPNYRLRHECNNQN LTLINVTKDYEGTYYGTNDKDEGKRYRVKVNTTNSQSVKIQPYTRQTTPDQEHK FELQFETNGNYDSKIPGGGGSGGGGSLVPRGSKPIPNPLLGLDSTLVPRGSGGG GSGGGGSQVQLQESGPGLVKPSETLSLTCTVSGGSISYYSWTWVRQPAGQGLEW IGRIHISGVTNHNPSLKSRVSMSIDTSRTQFSLRLTSVTAADTAVYFCARSGGT YSAFDIWGQGTMVTVSSGGGGSGGGGSGGGGSGGGGSEIVLTQSPGTLSLSPGE RSTLSCRASQSFTSNYLAWYQQRPGQAPRLLIYGASTRAIGIPDRFSGSGSGTD FTLTISRLEPEDFAVYYCQQYGSSPWTFGQGTKVEIKTTTPAPRPPTPAPTIAS QPLSLRPEACRPAAGGAVHTRGLDFACDIYIWAPLAGTCGVLLLSLVITLYCKR GRKKLLYIFKQPFMRPVQTTQEEDGCSCRFPEEEEGGCELRVKFSRSADAPAYQ QGQNQLYNELNLGRREEYDVLDKRRGRDPEMGGKPRRKNPQEGLYNELQKDKMA EAYSEIGMKGERRRGKGHDGLYQGLSTATKDTYDALHMQALPPR |
| 29 | 01122-N-HA-UL11-V5-2G4STMB-53B6 | MALPVTALLLPLALLLHAARPGYPYDVPDYAHDACIPVVGKIGTNVTLNAVDFH PGDHVRWSYGPGGAGYMLCVYTGSWTEYKKPDIIFKCLSNNSLLINVTVNYTN TYRTLTSLNNWVHNQHHHKFPGWNLDTCYSLTVNENGTEPTTTTKKPTTTTRTT TTTTTKKTTTTRTTTAAKKTTISTTHHKHSSPKKSSTPNSHVEHHVGFEATAAE TPLQPSPQHQVATHGGGGSGGGGSLVPRGSKPIPNPLLGLDSTLVPRGSGGGG SGGGGSQVQLQESGPGLVKPSETLSLTCTVSGGSISYYSWTWVRQPAGQGLEWI GRIHISGVTNHNPSLKSRVSMSIDTSRTQFSLRLTSVTAADTAVYFCARSGGTY SAFDIWGQGTMVTVSSGGGGSGGGGSGGGGSGGGGSEIVLTQSPGTLSLSPGER STLSCRASQSFTSNYLAWYQQRPGQAPRLLIYGASTRAIGIPDRFSGSGSGTDF TLTISRLEPEDFAVYYCQQYGSSPWTFGQGTKVEIKTTTPAPRPPTPAPTIASQ PLSLRPEACRPAAGGAVHTRGLDFACDIYIWAPLAGTCGVLLLSLVITLYCKRG RKKLLYIFKQPFMRPVQTTQEEDGCSCRFPEEEEGGCELRVKFSRSADAPAYQQ GQNQLYNELNLGRREEYDVLDKRRGRDPEMGGKPRRKNPQEGLYNELQKDKMAE AYSEIGMKGERRRGKGHDGLYQGLSTATKDTYDALHMQALPPR |
| 30 | 01207-N-HA-IgV-V5-2G4STMB-53B6 | MALPVTALLLPLALLLHAARPGYPYDVPDYAQFSVLGPSGPILAMVGEDADLPC HLEPTMSAETMELKWVSSSLRQVVNVYADGKEVEDRQSAPYRGRTSILRDGITA GKAALRIHNVTASDSGKYLCYFQDGDFYEKALVELKVAGGGGSGGGGSLVPRGS KPIPNPLLGLDSTLVPRGSGGGGSGGGGSQVQLQESGPGLVKPSETLSLTCTVS GGSISYYSWTWVRQPAGQGLEWIGRIHISGVTNHNPSLKSRVSMSIDTSRTQFS LRLTSVTAADTAVYFCARSGGTYSAFDIWGQGTMVTVSSGGGGSGGGGSGGGGS GGGGSEIVLTQSPGTLSLSPGERSTLSCRASQSFTSNYLAWYQQRPGQAPRLLI YGASTRAIGIPDRFSGSGSGTDFTLTISRLEPEDFAVYYCQQYGSSPWTFGQGT KVEIKTTTPAPRPPTPAPTIASQPLSLRPEACRPAAGGAVHTRGLDFACDIYIW APLAGTCGVLLLSLVITLYCKRGRKKLLYIFKQPFMRPVQTTQEEDGCSCRFPE EEEGGCELRVKFSRSADAPAYQQGQNQLYNELNLGRREEYDVLDKRRGRDPEMG GKPRRKNPQEGLYNELQKDKMAEAYSEIGMKGERRRGKGHDGLYQGLSTATKDT YDALHMQALPPR |
| 31 | 01208-N-HA-IgC-V5-2G4STMB-53B6 | MALPVTALLLPLALLLHAARPGYPYDVPDYAALGSDLHVDVKGYKDGGIHLECR STGWYPQPQIQWSNNKGENIPTVEAPVVADGVGLYAVAASVIMRGSSGEGVSCT IRSSLLGLEKTASISIADPFFRSAQRWIAALAGTGGGGSGGGGSLVPRGSKPIP NPLLGLDSTLVPRGSGGGGSGGGGSQVQLQESGPGLVKPSETLSLTCTVSGGSI SYYSWTWVRQPAGQGLEWIGRIHISGVTNHNPSLKSRVSMSIDTSRTQFSLRLT SVTAADTAVYFCARSGGTYSAFDIWGQGTMVTVSSGGGGSGGGGSGGGGSGGGGS SEIVLTQSPGTLSLSPGERSTLSCRASQSFTSNYLAWYQQRPGQAPRLLIYGAS TRAIGIPDRFSGSGSGTDFTLTISRLEPEDFAVYYCQQYGSSPWTFGQGTKVEI KTTTPAPRPPTPAPTIASQPLSLRPEACRPAAGGAVHTRGLDFACDIYIWAPLA GTCGVLLLSLVITLYCKRGRKKLLYIFKQPFMRPVQTTQEEDGCSCRFPEEEEG GCELRVKFSRSADAPAYQQGQNQLYNELNLGRREEYDVLDKRRGRDPEMGGKPR |

TABLE 2-continued

Exemplary Protein Sequences

| SEQ ID NO: | Name | Amino Acid Sequence |
|---|---|---|
| | | RKNPQEGLYNELQKDKMAEAYSEIGMKGERRRGKGHDGLYQGLSTATKDTYDAL HMQALPPR |
| 33 | 4-1BB intracellular signaling domain (ISD) | KRGRKKLLYIFKQPFMRPVQTTQEEDGCSCRFPEEEEGGCEL |
| 34 | CD3ζ intracellular signaling domain (ISD) | RVKFSRSADAPAYQQGQNQLYNELNLGRREEYDVLDKRRGRDPEMGGKPRRKNP QEGLYNELQKDKMAEAYSEIGMKGERRRGKGHDGLYQGLSTATKDTYDALHMQA LPPR |
| 35 | CD28-IC (CD28 co-stimulatory domain) | RSKRSRGGHSDYMNMTPRRPGPTRKHYQPYAPPRDFAAYRS |
| 36 | FcγRIIIα hinge | GLWSTISSFEPPGYQ |
| 37 | CD8α hinge | TTTPAPRPPTPTIASQPLSLRPEACRPAAGGAVRTRGLDFACD |
| 38 | IgG1 hinge | EPKSPDKTHTCPPCPAPPVAGPSVFLFPPKPKDTLMTkRTPEVTCVVVDVSHED PEVKFNWYVDGVEVHNAETKPREEQYNSTYRVVSVLTVLHQDWLNGKEYNCKVS NKALPAPIEKTISKAKGQPREPQVITLPPSRDELTKNQVSLTCLVKGFIPSDIA VEWESNGQPENNYKTTPPVLDSDGSFFLYSKLTVDKSRWQQGNVFSCSVMHEAL HNHYTQKSLSLSPGK |
| 39 | CD8α transmembrane (TM) domain | IYIWAPLAGTCGVLLLSLVITLYG |
| 40 | CD3ζ intracellular signaling domain (ISD) | RVKFSRSADAPAYQQGQNQLYNELNLGRREEYDVIDKRRGRDPEMGGKPRRKNP QEGLYNELQKDKMAEAYSEIGMKGERRRGKGEDGLYQGLSTATKDTYDALHMQA LPPP |
| 41 | FcεRI α-TM-IC (FcεRI α chain transmembrane and intracellular domain) | FFIPLLVVILFAVDTGLFISTQQQVTFLLKIKRTRKGERLLNPHPKPNTKNN |
| 42 | FcεRiβ-ΔITAM (FcεRi β chain without ITAM) | MDTESNRRANLALPQEPSSVPAFEVLEISPQEVSSGRELKSASSPPLHTWLTVL KKEQEFLGVTQILTAMICLCFGTVVCSVLDISHIEGDIFSSFKAGYPFWGAIFF SISGMLSIISERRNATYLVRGSLGANTASSIAGGTGITILIINLKKSLAYIHIH SCQKFFETKCFMSFSTEIVVMMLFLTILGLGSAVSLTICGAGEELKGNKVPE |
| 43 | CD23-IC (CD28 co-stimulatory domain) | RSKRSRGGHSDYMNMTPRRPGPTPKHYQPIPPPDFAAYRS |
| 44 | FgεRIγ-SP (signal peptide) | MIPAVVILLLLLVEQAAA |
| 45 | FcεRI γ-ΔITAM (FcεRI γ chain without ITAM) | LGEPQLCYILDAILFLIGIVLTLLICRLKIQVRKAAITSYEKS |
| 46 | GSG-P2A (GSG-P2A ribosomal skip polypeptide) | GSGATNFSLLKQAGDVEENPGP |
| 47 | GSG-T2A (GSG-T2A ribosomal skip polypeptide) | GSGERGSLLTCGDVEENPGP |

TABLE 2-continued

Exemplary Protein Sequences

| SEQ ID NO: | Name | Amino Acid Sequence |
|---|---|---|
| 48 | safety switch | CPYSNPSLCSGGGGSELPTQGTFSNVSTNVSPAKPTTTACPYSNPSLCSGGGGS PAPRPPTPAPTIASQPLSLRPEACRPAAGGAVHTRGLDFACDIYIWAPLAGTCG VLLLSLVITLYCNHRNRRRVCKCPRPVV |
| 49 | safety switch-amino term. | MGTSLLCWMALCLLGADHADACPYSNPSLCSGGGGSELPTQGTFSNVSTNVSPA KPTTTACPYSNPSLCSGGGGSPAPRPPTPAPTIASQPLSLRPEACRPAAGGAVH TRGLDFACDIYIWAPLAGTCGVLLLSLVITLYCNHRNRRRVCKCPRPVV |
| 50 | CD20 mimotope | CPYSNPSLC |
| 51 | 2xCD20 mimotope | GSGGGGSCPYSNPSLCSGGGGSCPYSNPSLCSGGGGS |
| 52 | aminoGS | GGGGSGGGGSGGGSG |
| 54 | carboxyGS | GGGSGGGGSGGGGS |
| 55 | V5 | KPIPNPLLGLDST |
| 56 | Leader-53B6 scEv | MALPVTALLLPLALLLHAARPQVQLQESGPGLVKPSETLSLTCTVSGGSISYYS WTWVRQPAGQGLEWIGRIHISGVTNHNPSLKSRVSMSIDTSRTQFSLRLTSVTA ADTAVYFCARSGGTYSAFDIWGQGTMVTVSSGGGGSGGGGSGGGGSGGGGSEIV LTQSPGTLSLSPGERSTLSCRASQSFTSNYLAWYQQRPGQAPRLLIYGASTRAI GIPDRFSGSGSGTDFTLTISRLEPEDFAVYYCQQYGSSPWTFGQGTKVEIK |
| 57 | GSlinker | GGGGSGGGGSGGGGS |
| 178 | GS sequence (1) | GGGGS |
| 181 | GS45 (GS sequence 2) | GGGGSGGGGSGGGSGSGGGGSGGGSGGGSGGGGSGGGGSGGGGS |
| 182 | GS45 (3) | GGGGSGGGGSGGGSGGGSGSGGGGSGGGGSGGGGSGGGGSGGGGS |

PROTEASE CLEAVAGE SITES:

| SEQ ID NO: | Name | Amino Acid Sequence |
|---|---|---|
| 32 | TMB cleavage site | LVPRGS |
| 53 | TPS cleavage | LSGRSDNHSPLGLAGS |
| 89 | MMP2/9/MTSP site (1) | VHMPLGFLGPRQARVVNG |
| 90 | MMP2/9/MTSP site (2) | VHMPLGFLGPGSARVVNG |
| 91 | MTSP (matriptase) site (1) | RQARVVNG |
| 92 | MTSP site (2) | RQARVGSG |
| 93 | MMP2/9 (1) | VHMPLGFLGP |
| 94 | MMP2/9 (2) | VHMPLSFLGP |
| 95 | MTSP (3) | PMAKK |
| 96 | MTSP (4) | PMAKGS |
| 97 | MTSP (5) | LSGRSDNH |
| 98 | MTSP (6) | LSGRSDSH |
| 103 | MMP (site 3) | SPLGLAGS |
| 104 | MMP (site 4) | PLGVRGK |
| 105 | MTSP (7) | PMAKG |
| 106 | MTSP (8) | GSARVVNG |

TABLE 2-continued

Exemplary Protein Sequences

| SEQ ID NO:Name | Amino Acid Sequence |
|---|---|

LINKER SEQUENCES WITH PROTEASE CLEAVAGE SITES

7 GS (45aa)  GGGGSGGGGSGGGSGSKPIPNPLLGLDSTGGGSGSGGGGSGGGGS

8 GSTMB (45aa)  GGGGSGGGGSLVPRGSKPIPNPLLGLDSTLVPRGSGGGGSGGGGS

9 GSTPS1 (45aa) (also referred to as TPS1 (45aa); same sequence as TPS3 (45aa) and TPS2 (45aa))  GGGGSGGGGSGGGSGLSGRSDNHSPLGLAGSGGGGSGGGGSGGGGS 10 GSTPS2 (55aa) (also referred to as "TPS2 (55aa)")  GGGGSLSGRSDNHSPLGLAGSKPIPNPLLGLDSTLSGRSDNHSPLGLAGSGGGGS 99 TPS4 (25aa)  GGGGSVHMPLGFLGPRQARVVNGGS 100 TPS5 (25aa)  GGGGSVHMPLGFLGPGSARVVNGGS 101 TPS6 (25aa)  GGGGSGGGGSPMAKKGGGGSGGGGS 102 TPS7 (25aa)  GGGGSGGGGSPMAKGSGGGSGGGGS 107 TPS4 (45aa)  GGGGSGGGGSGGGGSVHMPLGFLGPRQARVVNGGSGGGGSGGGGS 172 TPS8 (25aa)  GSSPLGLAGSGGGGSGGGGSPMAKK 173 TPS9 (25aa)  GGSVHMPLGFLGPGGSGGGSPMAKK 174 TPS10 (25aa)  GGSPLGVRGKGGGGSGGGGSPMAKK 175 TPS11 (25aa)  GGSSPLGLAGSGSGGGSRQARVVNG 176 TPS12 (25aa)  GGSVHMPLGFLGPGGGSRQARVVNG 177 TPS13 (25aa)  GGSPLGVRGKGGSGGGSRQARVVNG 108 TPS5 45aa  GGGGSGGGGSGGGGSVHMPLGFLGPGSARVVNGGSGGGGSGGGGS 109 TPS6 20aa  GGGGSPMAKKGGGGSGGGGS 110 TPS6 25aa  GGGGSGGGGSPMAKKGGGGSGGGGS 111 TPS6 30aa  GGGGSGGGGSPMAKKGGGGSGGGGSGGGGS 112 TPS6 35aa  GGGGSGGGGSGGGGSPMAKKGGGGSGGGGSGGGGS 113 TPS6 45aa  GGGGSGGGGSGGGGSGGGGSPMAKKGGGGSGGGGSGGGGSGGGGS 114 TPS7 45aa  GGGGSGGGGSGGGGSGGGGSPMAKGSGGGSGGGGSGGGGSGGGGS 115 TPS8 45aa  GGGGSGGGGSGSSPLGLAGSGGGGSGGGGSPMAKKGGGGSGGGGS 116 TPS9 45aa  GGGGSGGGGSGGSVHMPLGFLGPGGSGGGSPMAKKGGGGSGGGGS 117 TPS10 45aa  GGGGSGGGGSGGSPLGVRGKGGGGSGGGGSPMAKKGGGGSGGGGS 118 TPS11 45aa  GGGGSGGGGSGGSSPLGLAGSGSGGGSRQARVVNGGGGGSGGGGS 119 TPS12 45aa  GGGGSGGGGSGGSVHMPLGFLGPGGGSRQARVVNGGGGGSGGGGS 120 TPS13 45aa  GGGGSGGGGSGGSPLGVRGKGGSGGGSRQARVVNGGGGGSGGGGS TABLE 2-continued Exemplary Protein Sequences SEQ
ID
NO: Name        Amino Acid Sequence Exemplary protease-activating CD45-gate MUC16-specific CARs 121 N-HA-        MALPVTALLLPLALLLHAARPGYPYDVPDYADIVMTQTPASVSEPVGGSVTIKC
    4131scFv-   QASQSFYNLLAWYQQKPGQPPKLLIYDASDLASGVPSRFKGSGSGTDFTLTISD
    TPS4-53B6   LECADAAAYYCQSADGSSYAFGGGTEVVVKGGGGGSGGGGSGGGGSGGGGSQEQ
                LEESGGGLVKPEGSLTLTCTASGVSFSSSYWIYWVRQAPGKGLEWIACIYTGSS
                GSTYYASWAKGRFTVSETSSTTVTLQMTSLTAADTATYFCARASAWTYGMDLWG
                PGTLVTVSSGGGGSGGGGSGGGGSVHMPLGFLGPRQARVVNGGSGGGGSGGGGS
                QVQLQESGPGLVKPSETLSLTCTVSGGSISYYSWTWVRQPAGQGLEWIGRIHIS
                GVTNHNPSLKSRVSMSIDTSRTQFSLRLTSVTAADTAVYFCARSGGTYSAFDIW
                GQGTMVTVSSGGGGSGGGGSGGGGSGGGGSEIVLTQSPGTLSLSPGERSTLSCR
                ASQSFTSNYLAWYQQRPGQAPRLLIYGASTRAIGIPDRFSGSGSGTDFTLTISR
                LEPEDFAVYYCQQYGSSPWTFGQGTKVEIKTTTPAPRPPTPAPTIASQPLSLRP
                EACRPAAGGAVHTRGLDFACDIYIWAPLAGTCGVLLLSLVITLYCKRGRKKLLY
                IFKQPFMRPVQTTQEEDGCSCRFPEEEEGGCELRVKFSRSADAPAYQQGQNQLY
                NELNLGRREEYDVLDKRRGRDPEMGGKPRRKNPQEGLYNELQKDKMAEAYSEIG
                MKGERRRGKGHDGLYQGLSTATKDTYDALHMQALPPR 122 N-HA-        MALPVTALLLPLALLLHAARPGYPYDVPDYADIVMTQTPASVSEPVGGSVTIKC
    4131scFv-   QASQSFYNLLAWYQQKPGQPPKLLIYDASDLASGVPSRFKGSGSGTDFTLTISD
    TPS5-53B6   LECADAAAYYCQSADGSSYAFGGGTEVVVKGGGGGSGGGGSGGGGSGGGGSQEQ
                LEESGGGLVKPEGSLTLTCTASGVSFSSSYWIYWVRQAPGKGLEWIACIYTGSS
                GSTYYASWAKGRFTVSETSSTTVTLQMTSLTAADTATYFCARASAWTYGMDLWG
                PGTLVTVSSGGGGSGGGGSGGGGSVHMPLGFLGPGSARVVNGGSGGGGSGGGGS
                QVQLQESGPGLVKPSETLSLTCTVSGGSISYYSWTWVRQPAGQGLEWIGRIHIS
                GVTNHNPSLKSRVSMSIDTSRTQFSLRLTSVTAADTAVYFCARSGGTYSAFDIW
                GQGTMVTVSSGGGGSGGGGSGGGGSGGGGSEIVLTQSPGTLSLSPGERSTLSCR
                ASQSFTSNYLAWYQQRPGQAPRLLIYGASTRAIGIPDRFSGSGSGTDFTLTISR
                LEPEDFAVYYCQQYGSSPWTFGQGTKVEIKTTTPAPRPPTPAPTIASQPLSLRP
                EACRPAAGGAVHTRGLDFACDIYIWAPLAGTCGVLLLSLVITLYCKRGRKKLLY
                IFKQPFMRPVQTTQEEDGCSCRFPEEEEGGCELRVKFSRSADAPAYQQGQNQLY
                NELNLGRREEYDVLDKRRGRDPEMGGKPRRKNPQEGLYNELQKDKMAEAYSEIG
                MKGERRRGKGHDGLYQGLSTATKDTYDALHMQALPPR 123 N-HA-        MALPVTALLLPLALLLHAARPGYPYDVPDYADIVMTQTPASVSEPVGGSVTIKC
    4131scFv-   QASQSFYNLLAWYQQKPGQPPKLLIYDASDLASGVPSRFKGSGSGTDFTLTISD
    TPS6-53B6   LECADAAAYYCQSADGSSYAFGGGTEVVVKGGGGGSGGGGSGGGGSGGGGSQEQ
                LEESGGGLVKPEGSLTLTCTASGVSFSSSYWIYWVRQAPGKGLEWIACIYTGSS
                GSTYYASWAKGRFTVSETSSTTVTLQMTSLTAADTATYFCARASAWTYGMDLWG
                PGTLVTVSSGGGGSGGGGSGGGGSGGGGSPMAKKGGGGSGGGGSGGGGSGGGGS
                QVQLQESGPGLVKPSETLSLTCTVSGGSISYYSWTWVRQPAGQGLEWIGRIHIS
                GVTNHNPSLKSRVSMSIDTSRTQFSLRLTSVTAADTAVYFCARSGGTYSAFDIW
                GQGTMVTVSSGGGGSGGGGSGGGGSGGGGSEIVLTQSPGTLSLSPGERSTLSCR
                ASQSFTSNYLAWYQQRPGQAPRLLIYGASTRAIGIPDRFSGSGSGTDFTLTISR
                LEPEDFAVYYCQQYGSSPWTFGQGTKVEIKTTTPAPRPPTPAPTIASQPLSLRP
                EACRPAAGGAVHTRGLDFACDIYIWAPLAGTCGVLLLSLVITLYCKRGRKKLLY
                IFKQPFMRPVQTTQEEDGCSCRFPEEEEGGCELRVKFSRSADAPAYQQGQNQLY
                NELNLGRREEYDVLDKRRGRDPEMGGKPRRKNPQEGLYNELQKDKMAEAYSEIG
                MKGERRRGKGHDGLYQGLSTATKDTYDALHMQALPPR 124 N-HA-        MALPVTALLLPLALLLHAARPGYPYDVPDYADIVMTQTPASVSEPVGGSVTIKC
    4131scFv-   QASQSFYNLLAWYQQKPGQPPKLLIYDASDLASGVPSRFKGSGSGTDFTLTISD
    TPS7-53B6   LECADAAAYYCQSADGSSYAFGGGTEVVVKGGGGGSGGGGSGGGGSGGGGSQEQ
                LEESGGGLVKPEGSLTLTCTASGVSFSSSYWIYWVRQAPGKGLEWIACIYTGSS
                GSTYYASWAKGRFTVSETSSTTVTLQMTSLTAADTATYFCARASAWTYGMDLWG
                PGTLVTVSSGGGGSGGGGSGGGGSGGGGSPMAKGSGGGGSGGGGSGGGGSGGGGS
                QVQLQESGPGLVKPSETLSLTCTVSGGSISYYSWTWVRQPAGQGLEWIGRIHIS
                GVTNHNPSLKSRVSMSIDTSRTQFSLRLTSVTAADTAVYFCARSGGTYSAFDIW
                GQGTMVTVSSGGGGSGGGGSGGGGSGGGGSEIVLTQSPGTLSLSPGERSTLSCR
                ASQSFTSNYLAWYQQRPGQAPRLLIYGASTRAIGIPDRFSGSGSGTDFTLTISR
                LEPEDFAVYYCQQYGSSPWTFGQGTKVEIKTTTPAPRPPTPAPTIASQPLSLRP
                EACRPAAGGAVHTRGLDFACDIYIWAPLAGTCGVLLLSLVITLYCKRGRKKLLY
                IFKQPFMRPVQTTQEEDGCSCRFPEEEEGGCELRVKFSRSADAPAYQQGQNQLY
                NELNLGRREEYDVLDKRRGRDPEMGGKPRRKNPQEGLYNELQKDKMAEAYSEIG
                MKGERRRGKGHDGLYQGLSTATKDTYDALHMQALPPR 125 N-HA-        MALPVTALLLPLALLLHAARPGYPYDVPDYADIVMTQTPASVSEPVGGSVTIKC
    4131scFv-   QASQSFYNLLAWYQQKPGQPPKLLIYDASDLASGVPSRFKGSGSGTDFTLTISD
    2XTPS4-53B6 LECADAAAYYCQSADGSSYAFGGGTEVVVKGGGGGSGGGGSVHMPLGFLGPRQA
                RVVNGGSGGGGSQEQLEESGGGLVKPEGSLTLTCTASGVSFSSSYWIYWVRQAP
                GKGLEWIACIYTGSSGSTYYASWAKGRFTVSETSSTTVTLQMTSLTAADTATYF
                CARASAWTYGMDLWGPGTLVTVSSGGGGSGGGGSGGGGSVHMPLGFLGPRQARV
                VNGGSGGGGSGGGGSQVQLQESGPGLVKPSETLSLTCTVSGGSISYYSWTWVRQ TABLE 2-continued Exemplary Protein Sequences

| SEQ ID NO:Name | Amino Acid Sequence |
|---|---|
| | PAGQGLEWIGRIHISGVTNHNPSLKSRVSMSIDTSRTQFSLRLTSVTAADTAVY<br>FCARSGGTYSAFDIWGQGTMVTVSSGGGGSGGGGSGGGGSGGGGSEIVLTQSPG<br>TLSLSPGERSTLSCRASQSFTSNYLAWYQQRPGQAPRLLIYGASTRAIGIPDRF<br>SGSGSGTDFTLTISRLEPEDFAVYYCQQYGSSPWTFGQGTKVEIKTTTPAPRPP<br>TPAPTIASQPLSLRPEACRPAAGGAVHTRGLDFACDIYIWAPLAGTCGVLLLSL<br>VITLYCKRGRKKLLYIFKQPFMRPVQTTQEEDGCSCRFPEEEEGGCELRVKFSR<br>SADAPAYQQGQNQLYNELNLGRREEYDVLDKRRGRDPEMGGKPRRKNPQEGLYN<br>ELQKDKMAEAYSEIGMKGERRRGKGHDGLYQGLSTATKDTYDALHMQALPPR |
| 126 N-HA-<br>4131scFv-<br>2XTPS5-53B6 | MALPVTALLLPLALLLHAARPGYPYDVPDYADIVMTQTPASVSEPVGGSVTIKC<br>QASQSFYNLLAWYQQKPGQPPKLLIYDASDLASGVPSRFKGSGSGTDFTLTISD<br>LECADAAAYYCQSADGSSYAFGGGTEVVVKGGGGGSGGGGSVHMPLGFLGPGSA<br>RVVNGGSGGGGSQEQLEESGGGLVKPEGSLTLTCTASGVSFSSSYWIYWVRQAP<br>GKGLEWIACIYTGSSGSTYYASWAKGRFTVSETSSTTVTLQMTSLTAADTATYF<br>CARASAWTYGMDLWGPGTLVTVSSGGGGSGGGGSGGGGSVHMPLGFLGPGSARV<br>VNGGSGGGGSGGGGSQVQLQESGPGLVKPSETLSLTCTVSGGSISYYSWTWVRQ<br>PAGQGLEWIGRIHISGVTNHNPSLKSRVSMSIDTSRTQFSLRLTSVTAADTAVY<br>FCARSGGTYSAFDIWGQGTMVTVSSGGGGSGGGGSGGGGSGGGGSEIVLTQSPG<br>TLSLSPGERSTLSCRASQSFTSNYLAWYQQRPGQAPRLLIYGASTRAIGIPDRF<br>SGSGSGTDFTLTISRLEPEDFAVYYCQQYGSSPWTFGQGTKVEIKTTTPAPRPP<br>TPAPTIASQPLSLRPEACRPAAGGAVHTRGLDFACDIYIWAPLAGTCGVLLLSL<br>VITLYCKRGRKKLLYIFKQPFMRPVQTTQEEDGCSCRFPEEEEGGCELRVKFSR<br>SADAPAYQQGQNQLYNELNLGRREEYDVLDKRRGRDPEMGGKPRRKNPQEGLYN<br>ELQKDKMAEAYSEIGMKGERRRGKGHDGLYQGLSTATKDTYDALHMQALPPR |
| 127 N-HA-<br>4131scFv-<br>2XTP56-53B6 | MALPVTALLLPLALLLHAARPGYPYDVPDYADIVMTQTPASVSEPVGGSVTIKC<br>QASQSFYNLLAWYQQKPGQPPKLLIYDASDLASGVPSRFKGSGSGTDFTLTISD<br>LECADAAAYYCQSADGSSYAFGGGTEVVVKGGGGGSGGGGSPMAKKGGGG<br>GSGGGGSGGGGSQEQLEESGGGLVKPEGSLTLTCTASGVSFSSSYWIYWVRQAP<br>GKGLEWIACIYTGSSGSTYYASWAKGRFTVSETSSTTVTLQMTSLTAADTATYF<br>CARASAWTYGMDLWGPGTLVTVSSGGGGSGGGGSGGGGSGGGGSPMAKKGGGGS<br>GGGGSGGGGSGGGGSQVQLQESGPGLVKPSETLSLTCTVSGGSISYYSWTWVRQ<br>PAGQGLEWIGRIHISGVTNHNPSLKSRVSMSIDTSRTQFSLRLTSVTAADTAVY<br>FCARSGGTYSAFDIWGQGTMVTVSSGGGGSGGGGSGGGGSGGGGSEIVLTQSPG<br>TLSLSPGERSTLSCRASQSFTSNYLAWYQQRPGQAPRLLIYGASTRAIGIPDRF<br>SGSGSGTDFTLTISRLEPEDFAVYYCQQYGSSPWTFGQGTKVEIKTTTPAPRPP<br>TPAPTIASQPLSLRPEACRPAAGGAVHTRGLDFACDIYIWAPLAGTCGVLLLSL<br>VITLYCKRGRKKLLYIFKQPFMRPVQTTQEEDGCSCRFPEEEEGGCELRVKFSR<br>SADAPAYQQGQNQLYNELNLGRREEYDVLDKRRGRDPEMGGKPRRKNPQEGLYN<br>ELQKDKMAEAYSEIGMKGERRRGKGHDGLYQGLSTATKDTYDALHMQALPPR |
| 128 N-HA-<br>4131scFv-<br>2XTP57-53B6 | MALPVTALLLPLALLLHAARPGYPYDVPDYADIVMTQTPASVSEPVGGSVTIKC<br>QASQSFYNLLAWYQQKPGQPPKLLIYDASDLASGVPSRFKGSGSGTDFTLTISD<br>LECADAAAYYCQSADGSSYAFGGGTEVVVKGGGGGSGGGGSGGGGSPMAKGSGG<br>GSGGGGSGGGGSQEQLEESGGGLVKPEGSLTLTCTASGVSFSSSYWIYWVRQAP<br>GKGLEWIACIYTGSSGSTYYASWAKGRFTVSETSSTTVTLQMTSLTAADTATYF<br>CARASAWTYGMDLWGPGTLVTVSSGGGGSGGGGSGGGGSGGGGSPMAKGSGGGS<br>GGGGSGGGGSGGGGSQVQLQESGPGLVKPSETLSLTCTVSGGSISYYSWTWVRQ<br>PAGQGLEWIGRIHISGVTNHNPSLKSRVSMSIDTSRTQFSLRLTSVTAADTAVY<br>FCARSGGTYSAFDIWGQGTMVTVSSGGGGSGGGGSGGGGSGGGGSEIVLTQSPG<br>TLSLSPGERSTLSCRASQSFTSNYLAWYQQRPGQAPRLLIYGASTRAIGIPDRF<br>SGSGSGTDFTLTISRLEPEDFAVYYCQQYGSSPWTFGQGTKVEIKTTTPAPRPP<br>TPAPTIASQPLSLRPEACRPAAGGAVHTRGLDFACDIYIWAPLAGTCGVLLLSL<br>VITLYCKRGRKKLLYIFKQPFMRPVQTTQEEDGCSCRFPEEEEGGCELRVKFSR<br>SADAPAYQQGQNQLYNELNLGRREEYDVLDKRRGRDPEMGGKPRRKNPQEGLYN<br>ELQKDKMAEAYSEIGMKGERRRGKGHDGLYQGLSTATKDTYDALHMQALPPR |
| 129 N-HA-BTN3A1-<br>V5-2G4STMB-<br>53B6 | MALPVTALLLPLALLLHAARPGYPYDVPDYAQFSVLGPSGPILAMVGEDADLPC<br>HLFPTMSAETMELKWVSSSLRQVVNVYADGKEVEDRQSAPYRGRTSILRDGITA<br>GKAALRIHNVTASDSGKYLCYFQDGDFYEKALVELKVAALGSDLHVDVKGYKDG<br>GIHLECRSTGWYPQPQIQWSNNKGENIPTVEAPVVADGVGLYAVAASVIMRGSS<br>GEGVSCTIRSSLLGLEKTASISIADPFFRSAQRWIAALAGTGGGGSGGGGSLVP<br>RGSKPIPNPLLGLDSTLVPRGSGGGGSGGGGSQVQLQESGPGLVKPSETLSLTC<br>TVSGGSISYYSWTWVRQPAGQGLEWIGRIHISGVTNHNPSLKSRVSMSIDTSRT<br>QFSLRLTSVTAADTAVYFCARSGGTYSAFDIWGQGTMVTVSSGGGGSGGGGSGG<br>GGSGGGGSEIVLTQSPGTLSLSPGERSTLSCRASQSFTSNYLAWYQQRPGQAPR<br>LLIYGASTRAIGIPDRFSGSGSGTDFTLTISRLEPEDFAVYYCQQYGSSPWTFG<br>QGTKVEIKTTTPAPRPPTPAPTIASQPLSLRPEACRPAAGGAVHTRGLDFACDI<br>YIWAPLAGTCGVLLLSLVITLYCKRGRKKLLYIFKQPFMRPVQTTQEEDGCSCR<br>FPEEEEGGCELRVKFSRSADAPAYQQGQNQLYNELNLGRREEYDVLDKRRGRDP<br>EMGGKPRRKNPQEGLYNELQKDKMAEAYSEIGMKGERRRGKGHDGLYQGLSTAT<br>KDTYDALHMQALPPR |

TABLE 2-continued

Exemplary Protein Sequences

| SEQ ID NO: | Name | Amino Acid Sequence |
|---|---|---|
| 130 | N-HA-RORB-V5-2G4STMB-53B6 | MALPVTALLLPLALLLHAARPGYPYDVPDYADILLTQSPATLSLSPGERATLSC<br>RASQNIGTSIQWYQQKPGQAPRLLIRSSSESISGIPSRFSGSGSGTDFTLTISS<br>LEPEDFAVYYCQQSNTWPFTFGQGTKLEIKGGGGSGGGGSGGGGSGGGGSEVQL<br>VESGAEVKKPGASVKVSCKASGYTFTNYIIHWVKQEPGQGLEWIGYFNPYNHGT<br>KYNEKFKGRATLTADKSISTAYMELSSLRSEDTAVYYCARSGPYAWFDTWGQGT<br>TVTVSSGGGGSGGGGSLVPRGSKPIPNPLLGLDSTLVPRGSGGGGSGGGGSQVQ<br>LQESGPGLVKPSETLSLTCTVSGGSISYYSWTWVRQPAGQGLEWIGRIHISGVT<br>NHNPSLKSRVSMSIDTSRTQFSLRLTSVTAADTAVYFCARSGGTYSAFDIWGQG<br>TMVTVSSGGGGSGGGGSGGGGSGGGGSEIVLTQSPGTLSLSPGERSTLSCRASQ<br>SFTSNYLAWYQQRPGQAPRLLIYGASTRAIGIPDRFSGSGSGTDFTLTISRLEP<br>EDFAVYYCQQYGSSPWTFGQGTKVEIKTTTPAPRPPTPAPTIASQPLSLRPEAC<br>RPAAGGAVHTRGLDFACDIYIWAPLAGTCGVLLLSLVITLYCKRGRKKLLYIFK<br>QPFMRPVQTTQEEDGCSCRFPEEEEGGCELRVKFSRSADAPAYQQGQNQLYNEL<br>NLGRREEYDVLDKRRGRDPEMGGKPRRKNPQEGLYNELQKDKMAEAYSEIGMKG<br>ERRRGKGHDGLYQGLSTATKDTYDALHMQALPPR |
| 131 | N-HA-RORB-V5-3G45-53B6 | MALPVTALLLPLALLLHAARPGYPYDVPDYADILLTQSPATLSLSPGERATLSC<br>RASQNIGTSIQWYQQKPGQAPRLLIRSSSESISGIPSRFSGSGSGTDFTLTISS<br>LEPEDFAVYYCQQSNTWPFTFGQGTKLEIKGGGGSGGGGSGGGGSGGGGSEVQL<br>VESGAEVKKPGASVKVSCKASGYTFTNYIIHWVKQEPGQGLEWIGYFNPYNHGT<br>KYNEKFKGRATLTADKSISTAYMELSSLRSEDTAVYYCARSGPYAWFDTWGQGT<br>TVTVSSGGGGSGGGGSGGGSGSKPIPNPLLGLDSTGGGSGSGGGSGGGGSQVQ<br>LQESGPGLVKPSETLSLTCTVSGGSISYYSWTWVRQPAGQGLEWIGRIHISGVT<br>NHNPSLKSRVSMSIDTSRTQFSLRLTSVTAADTAVYFCARSGGTYSAFDIWGQG<br>TMVTVSSGGGGSGGGGSGGGGSGGGGSEIVLTQSPGTLSLSPGERSTLSCRASQ<br>SFTSNYLAWYQQRPGQAPRLLIYGASTRAIGIPDRFSGSGSGTDFTLTISRLEP<br>EDFAVYYCQQYGSSPWTFGQGTKVEIKTTTPAPRPPTPAPTIASQPLSLRPEAC<br>RPAAGGAVHTRGLDFACDIYIWAPLAGTCGVLLLSLVITLYCKRGRKKLLYIFK<br>QPFMRPVQTTQEEDGCSCRFPEEEEGGCELRVKFSRSADAPAYQQGQNQLYNEL<br>NLGRREEYDVLDKRRGRDPEMGGKPRRKNPQEGLYNELQKDKMAEAYSEIGMKG<br>ERRRGKGHDGLYQGLSTATKDTYDALHMQALPPR |
| 132 | N-HA-RORB-TPS4-53B6 | MALPVTALLLPLALLLHAARPGYPYDVPDYADILLTQSPATLSLSPGERATLSC<br>RASQNIGTSIQWYQQKPGQAPRLLIRSSSESISGIPSRFSGSGSGTDFTLTISS<br>LEPEDFAVYYCQQSNTWPFTFGQGTKLEIKGGGGSGGGGSGGGGSGGGGSEVQL<br>VESGAEVKKPGASVKVSCKASGYTFTNYIIHWVKQEPGQGLEWIGYFNPYNHGT<br>KYNEKFKGRATLTADKSISTAYMELSSLRSEDTAVYYCARSGPYAWFDTWGQGT<br>TVTVSSGGGGSGGGGSGGGGSVHMPLGELGPRQARVVNGGSGGGGSGGGGSQVQ<br>LQESGPGLVKPSETLSLTCTVSGGSISYYSWTWVRQPAGQGLEWIGRIHISGVT<br>NHNPSLKSRVSMSIDTSRTQFSLRLTSVTAADTAVYFCARSGGTYSAFDIWGQG<br>TMVTVSSGGGGSGGGGSGGGGSGGGGSEIVLTQSPGTLSLSPGERSTLSCRASQ<br>SFTSNYLAWYQQRPGQAPRLLIYGASTRAIGIPDRFSGSGSGTDFTLTISRLEP<br>EDFAVYYCQQYGSSPWTFGQGTKVEIKTTTPAPRPPTPAPTIASQPLSLRPEAC<br>RPAAGGAVHTRGLDFACDIYIWAPLAGTCGVLLLSLVITLYCKRGRKKLLYIFK<br>QPFMRPVQTTQEEDGCSCRFPEEEEGGCELRVKFSRSADAPAYQQGQNQLYNEL<br>NLGRREEYDVLDKRRGRDPEMGGKPRRKNPQEGLYNELQKDKMAEAYSEIGMKG<br>ERRRGKGHDGLYQGLSTATKDTYDALHMQALPPR |
| 133 | N-HA-RORB-TPS6-53B6 | MALPVTALLLPLALLLHAARPGYPYDVPDYADILLTQSPATLSLSPGERATLSC<br>RASQNIGTSIQWYQQKPGQAPRLLIRSSSESISGIPSRFSGSGSGTDFTLTISS<br>LEPEDFAVYYCQQSNTWPFTFGQGTKLEIKGGGGSGGGGSGGGGSGGGGSEVQL<br>VESGAEVKKPGASVKVSCKASGYTFTNYIIHWVKQEPGQGLEWIGYFNPYNHGT<br>KYNEKFKGRATLTADKSISTAYMELSSLRSEDTAVYYCARSGPYAWFDTWGQGT<br>TVTVSSGGGGSGGGGSGGGGSGGGGSPMAKKGGGGSGGGGSGGGGSGGGGSQVQ<br>LQESGPGLVKPSETLSLTCTVSGGSISYYSWTWVRQPAGQGLEWIGRIHISGVT<br>NHNPSLKSRVSMSIDTSRTQFSLRLTSVTAADTAVYFCARSGGTYSAFDIWGQG<br>TMVTVSSGGGGSGGGGSGGGGSGGGGSEIVLTQSPGTLSLSPGERSTLSCRASQ<br>SFTSNYLAWYQQRPGQAPRLLIYGASTRAIGIPDRFSGSGSGTDFTLTISRLEP<br>EDFAVYYCQQYGSSPWTFGQGTKVEIKTTTPAPRPPTPAPTIASQPLSLRPEAC<br>RPAAGGAVHTRGLDFACDIYIWAPLAGTCGVLLLSLVITLYCKRGRKKLLYIFK<br>QPFMRPVQTTQEEDGCSCRFPEEEEGGCELRVKFSRSADAPAYQQGQNQLYNEL<br>NLGRREEYDVLDKRRGRDPEMGGKPRRKNPQEGLYNELQKDKMAEAYSEIGMKG<br>ERRRGKGHDGLYQGLSTATKDTYDALHMQALPPR |
| 134 | N-HA-RORB-2XTP54-53B6 | MALPVTALLLPLALLLHAARPGYPYDVPDYADILLTQSPATLSLSPGERATLSC<br>RASQNIGTSIQWYQQKPGQAPRLLIRSSSESISGIPSRFSGSGSGTDFTLTISS<br>LEPEDFAVYYCQQSNTWPFTFGQGTKLEIKGGGGSGGGGSVHMPLGFLGPRQAR<br>VVNGGSGGGGSEVQLVESGAEVKKPGASVKVSCKASGYTFTNYIIHWVKQEPGQ<br>GLEWIGYFNPYNHGTKYNEKFKGRATLTADKSISTAYMELSSLRSEDTAVYYCA<br>RSGPYAWFDTWGQGTTVTVSSGGGGSGGGGSGGGGSVHMPLGELGPRQARVVNG<br>GSGGGGSGGGGSQVQLQESGPGLVKPSETLSLTCTVSGGSISYYSWTWVRQPAG<br>QGLEWIGRIHISGVTNHNPSLKSRVSMSIDTSRTQFSLRLTSVTAADTAVYFCA<br>RSGGTYSAFDIWGQGTMVTVSSGGGGSGGGGSGGGGSGGGGSEIVLTQSPGTLS<br>LSPGERSTLSCRASQSFTSNYLAWYQQRPGQAPRLLIYGASTRAIGIPDRFSGS |

TABLE 2-continued

Exemplary Protein Sequences

| SEQ ID NO:Name | Amino Acid Sequence |
|---|---|
| | GSGTDFTLTISRLEPEDFAVYYCQQYGSSPWTFGQGTKVEIKTTTPAPRPPTPA PTIASQPLSLRPEACRPAAGGAVHTRGLDFACDIYIWAPLAGTCGVLLLSLVIT LYCKRGRKKLLYIFKQPFMRPVQTTQEEDGCSCRFPEEEEGGCELRVKFSRSAD APAYQQGQNQLYNELNLGRREEYDVLDKRRGRDPEMGGKPRRKNPQEGLYNELQ KDKMAEAYSEIGMKGERRRGKGHDGLYQGLSTATKDTYDALHMQALPPR |
| 135N-HA-RORB-2XTP56-53B6 | MALPVTALLLPLALLLHAARPGYPYDVPDYADILLTQSPATLSLSPGERATLSC RASQNIGTSIQWYQQKPGQAPRLLIRSSSESISGIPSRFSGSGSGTDFTLTISS LEPEDFAVYYCQQSNTWPFTFGQGTKLEIKGGGGSGGGGSGGGGSPMAKKGGGG SGGGGSGGGGSEVQLVESGAEVKKPGASVKVSCKASGYTFTNYIIHWVKQEPGQ GLEWIGYFNPYNHGTKYNEKFKGRATLTADKSISTAYMELSSLRSEDTAVYYCA RSGPYAWFDTWGQGTTVTVSSGGGGSGGGGSGGGGSGGGGSPMAKKGGGGSGGG GSGGGGSGGGGSQVQLQESGPGLVKPSETLSLTCTVSGGSISYYSWTWVRQPAG QGLEWIGRIHISGVTNHNPSLKSRVSMSIDTSRTQFSLRLTSVTAADTAVYFCA RSGGTYSAFDIWGQGTMVTVSSGGGGSGGGGSGGGGSGGGGSEIVLTQSPGTLS LSPGERSTLSCRASQSFTSNYLAWYQQRPGQAPRLLIYGASTRAIGIPDRFSGS GSGTDFTLTISRLEPEDFAVYYCQQYGSSPWTFGQGTKVEIKTTTPAPRPPTPA PTIASQPLSLRPEACRPAAGGAVHTRGLDFACDIYIWAPLAGTCGVLLLSLVIT LYCKRGRKKLLYIFKQPFMRPVQTTQEEDGCSCRFPEEEEGGCELRVKFSRSAD APAYQQGQNQLYNELNLGRREEYDVLDKRRGRDPEMGGKPRRKNPQEGLYNELQ KDKMAEAYSEIGMKGERRRGKGHDGLYQGLSTATKDTYDALHMQALPPR |
| 136V5-GS20-4131scFv-TPS1-53B6 | MALPVTALLLPLALLLHAARPGKPIPNPLLGLDSTGGGGSGGGGSGGGGSGGGG SDIVMTQTPASVSEPVGGSVTIKCQASQSFYNLLAWYQQKPGQPPKLLIYDASD LASGVPSRFKGSGSGTDFTLTISDLECADAAAYYCQSADGSSYAFGGGTEVVVK GGGGGSGGGGSGGGGSGGGGSQEQLEESGGGLVKPEGSLTLTCTASGVSFSSSY WIYWVRQAPGKGLEWIACIYTGSSGSTYYASWAKGRFTVSETSSTTVTLQMTSL TAADTATYFCARASAWTYGMDLWGPGTLVTVSSGGGGSGGGGSGGGGSGLSGRSD NHSPLGLAGSGGGSGGGGSGGGGSQVQLQESGPGLVKPSETLSLTCTVSGGSIS YYSWTWVRQPAGQGLEWIGRIHISGVTNHNPSLKSRVSMSIDTSRTQFSLRLTS VTAADTAVYFCARSGGTYSAFDIWGQGTMVTVSSGGGGSGGGGSGGGGSGGGGS EIVLTQSPGTLSLSPGERSTLSCRASQSFTSNYLAWYQQRPGQAPRLLIYGAST RAIGIPDRFSGSGSGTDFTLTISRLEPEDFAVYYCQQYGSSPWTFGQGTKVEIK TTTPAPRPPTPAPTIASQPLSLRPEACRPAAGGAVHTRGLDFACDIYIWAPLAG TCGVLLLSLVITLYCKRGRKKLLYIFKQPFMRPVQTTQEEDGCSCRFPEEEEGG CELRVKFSRSADAPAYQQGQNQLYNELNLGRREEYDVLDKRRGRDPEMGGKPRR KNPQEGLYNELQKDKMAEAYSEIGMKGERRRGKGHDGLYQGLSTATKDTYDALH MQALPPR |
| 137V5-GS20-4131scFv-TPS4-53B6 | MALPVTALLLPLALLLHAARPGKPIPNPLLGLDSTGGGGSGGGGSGGGGSGGGG SDIVMTQTPASVSEPVGGSVTIKCQASQSFYNLLAWYQQKPGQPPKLLIYDASD LASGVPSRFKGSGSGTDFTLTISDLECADAAAYYCQSADGSSYAFGGGTEVVVK GGGGGSGGGGSGGGGSGGGGSQEQLEESGGGLVKPEGSLTLTCTASGVSFSSSY WIYWVRQAPGKGLEWIACIYTGSSGSTYYASWAKGRFTVSETSSTTVTLQMTSL TAADTATYFCARASAWTYGMDLWGPGTLVTVSSGGGGSGGGGSGGGGSVHMPLG FLGPRQARVVNGGSGGGGSGGGGSQVQLQESGPGLVKPSETLSLTCTVSGGSIS YYSWTWVRQPAGQGLEWIGRIHISGVTNHNPSLKSRVSMSIDTSRTQFSLRLTS VTAADTAVYFCARSGGTYSAFDIWGQGTMVTVSSGGGGSGGGGSGGGGSGGGGS EIVLTQSPGTLSLSPGERSTLSCRASQSFTSNYLAWYQQRPGQAPRLLIYGAST RAIGIPDRFSGSGSGTDFTLTISRLEPEDFAVYYCQQYGSSPWTFGQGTKVEIK TTTPAPRPPTPAPTIASQPLSLRPEACRPAAGGAVHTRGLDFACDIYIWAPLAG TCGVLLLSLVITLYCKRGRKKLLYIFKQPFMRPVQTTQEEDGCSCRFPEEEEGG CELRVKFSRSADAPAYQQGQNQLYNELNLGRREEYDVLDKRRGRDPEMGGKPRR KNPQEGLYNELQKDKMAEAYSEIGMKGERRRGKGHDGLYQGLSTATKDTYDALH MQALPPR |
| 138V5-G520-4131scFv-TPS6-53B6 | MALPVTALLLPLALLLHAARPGKPIPNPLLGLDSTGGGGSGGGGSGGGGSGGGG SDIVMTQTPASVSEPVGGSVTIKCQASQSFYNLLAWYQQKPGQPPKLLIYDASD LASGVPSRFKGSGSGTDFTLTISDLECADAAAYYCQSADGSSYAFGGGTEVVVK GGGGGSGGGGSGGGGSGGGGSQEQLEESGGGLVKPEGSLTLTCTASGVSFSSSY WIYWVRQAPGKGLEWIACIYTGSSGSTYYASWAKGRFTVSETSSTTVTLQMTSL TAADTATYFCARASAWTYGMDLWGPGTLVTVSSGGGGSGGGGSGGGGSGGGGSP MAKKGGGGSGGGGSGGGGSGGGGSQVQLQESGPGLVKPSETLSLTCTVSGGSIS YYSWTWVRQPAGQGLEWIGRIHISGVTNHNPSLKSRVSMSIDTSRTQFSLRLTS VTAADTAVYFCARSGGTYSAFDIWGQGTMVTVSSGGGGSGGGGSGGGGSGGGGS EIVLTQSPGTLSLSPGERSTLSCRASQSFTSNYLAWYQQRPGQAPRLLIYGAST RAIGIPDRFSGSGSGTDFTLTISRLEPEDFAVYYCQQYGSSPWTFGQGTKVEIK TTTPAPRPPTPAPTIASQPLSLRPEACRPAAGGAVHTRGLDFACDIYIWAPLAG TCGVLLLSLVITLYCKRGRKKLLYIFKQPFMRPVQTTQEEDGCSCRFPEEEEGG CELRVKFSRSADAPAYQQGQNQLYNELNLGRREEYDVLDKRRGRDPEMGGKPRR KNPQEGLYNELQKDKMAEAYSEIGMKGERRRGKGHDGLYQGLSTATKDTYDALH MQALPPR |

TABLE 2-continued

Exemplary Protein Sequences

| SEQ ID NO: Name | Amino Acid Sequence |
|---|---|
| 139 V5-G520-4131scFv-2XTPS6-53B6 | MALPVTALLLPLALLLHAARPGKPIPNPLLGLDSTGGGGSGGGGSGGGGSGGGG<br>SDIVMTQTPASVSEPVGGSVTIKCQASQSFYNLLAWYQQKPGQPPKLLIYDASD<br>LASGVPSRFKGSGSGTDFTLTISDLECADAAAYYCQSADGSSYAFGGGTEVVVK<br>GGGGGSGGGGSGGGGSPMAKKGGGGSGGGGSGGGGSQEQLEESGGGLVKPEGSL<br>TLTCTASGVSFSSSYWIYWVRQAPGKGLEWIACIYTGSSGSTYYASWAKGRFTV<br>SETSSTTVTLQMTSLTAADTATYFCARASAWTYGMDLWGPGTLVTVSSGGGGSG<br>GGGSGGGGSGGGGSPMAKKGGGGSGGGGSGGGGSQVQLQESGPGLVKPS<br>ETLSLTCTVSGGSISYYSWTWVRQPAGQGLEWIGRIHISGVTNHNPSLKSRVSM<br>SIDTSRTQFSLRLTSVTAADTAVYFCARSGGTYSAFDIWGQGTMVTVSSGGGGS<br>GGGGSGGGGSGGGGSEIVLTQSPGTLSLSPGERSTLSCRASQSFTSNYLAWYQQ<br>RPGQAPRLLIYGASTRAIGIPDRFSGSGSGTDFTLTISRLEPEDFAVYYCQQYG<br>SSPWTFGQGTKVEIKTTTPAPRPPTPAPTIASQPLSLRPEACRPAAGGAVHTRG<br>LDFACDIYIWAPLAGTCGVLLLSLVITLYCKRGRKKLLYIFKQPFMRPVQTTQE<br>EDGCSCRFPEEEEGGCELRVKFSRSADAPAYQQGQNQLYNELNLGRREEYDVLD<br>KRRGRDPEMGGKPRRKNPQEGLYNELQKDKMAEAYSEIGMKGERRRGKGHDGLY<br>QGLSTATKDTYDALHMQALPPR |
| 140 V5-GS20-4131scFv-G545-53B6 | MALPVTALLLPLALLLHAARPGKPIPNPLLGLDSTGGGGSGGGGSGGGGSGGGG<br>SDIVMTQTPASVSEPVGGSVTIKCQASQSFYNLLAWYQQKPGQPPKLLIYDASD<br>LASGVPSRFKGSGSGTDFTLTISDLECADAAAYYCQSADGSSYAFGGGTEVVVK<br>GGGGGSGGGGSGGGGSGGGGSQEQLEESGGGLVKPEGSLTLTCTASGVSFSSSY<br>WIYWVRQAPGKGLEWIACIYTGSSGSTYYASWAKGRFTVSETSSTTVTLQMTSL<br>TAADTATYFCARASAWTYGMDLWGPGTLVTVSSGGGGSGGGGSGGGGSGGGGS<br>GGGSGGGGSGGGGSGSGGGGSGGGGSQVQLQESGPGLVKPSETLSLTCTVSGGSIS<br>YYSWTWVRQPAGQGLEWIGRIHISGVTNHNPSLKSRVSMSIDTSRTQFSLRLTS<br>VTAADTAVYFCARSGGTYSAFDIWGQGTMVTVSSGGGGSGGGGSGGGGSGGGGS<br>EIVLTQSPGTLSLSPGERSTLSCRASQSFTSNYLAWYQQRPGQAPRLLIYGAST<br>RAIGIPDRFSGSGSGTDFTLTISRLEPEDFAVYYCQQYGSSPWTFGQGTKVEIK<br>TTTPAPRPPTPAPTIASQPLSLRPEACRPAAGGAVHTRGLDFACDIYIWAPLAG<br>TCGVLLLSLVITLYCKRGRKKLLYIFKQPFMRPVQTTQEEDGCSCRFPEEEEGG<br>CELRVKFSRSADAPAYQQGQNQLYNELNLGRREEYDVLDKRRGRDPEMGGKPRR<br>KNPQEGLYNELQKDKMAEAYSEIGMKGERRRGKGHDGLYQGLSTATKDTYDALH<br>MQALPPR |
| 141 4131scFv-V5-2XTPS1-53B6 | MALPVTALLLPLALLLHAARPGYPYDVPDYADIVMTQTPASVSEPVGGSVTIKC<br>QASQSFYNLLAWYQQKPGQPPKLLIYDASDLASGVPSRFKGSGSGTDFTLTISD<br>LECADAAAYYCQSADGSSYAFGGGTEVVVKGGGGGSGGGGSLSGRSDNHSPLGL<br>AGSGGGGSGGGGSQEQLEESGGGLVKPEGSLTLTCTASGVSFSSSYWIYWVRQA<br>PGKGLEWIACIYTGSSGSTYYASWAKGRFTVSETSSTTVTLQMTSLTAADTATY<br>FCARASAWTYGMDLWGPGTLVTVSSGGGGSGGGGSKPIPNPLLGLDSTGGGSGL<br>SGRSDNHSPLGLAGSGGGSGGGGSGGGGSQVQLQESGPGLVKPSETLSLTCTVS<br>GGSISYYSWTWVRQPAGQGLEWIGRIHISGVTNHNPSLKSRVSMSIDTSRTQFS<br>LRLTSVTAADTAVYFCARSGGTYSAFDIWGQGTMVTVSSGGGGSGGGGSGGGGS<br>GGGGSEIVLTQSPGTLSLSPGERSTLSCRASQSFTSNYLAWYQQRPGQAPRLLI<br>YGASTRAIGIPDRFSGSGSGTDFTLTISRLEPEDFAVYYCQQYGSSPWTFGQGT<br>KVEIKTTTPAPRPPTPAPTIASQPLSLRPEACRPAAGGAVHTRGLDFACDIYIW<br>APLAGTCGVLLLSLVITLYCKRGRKKLLYIFKQPFMRPVQTTQEEDGCSCRFPE<br>EEEGGCELRVKFSRSADAPAYQQGQNQLYNELNLGRREEYDVLDKRRGRDPEMG<br>GKPRRKNPQEGLYNELQKDKMAEAYSEIGMKGERRRGKGHDGLYQGLSTATKDT<br>YDALHMQALPPR |
| 142 4131scFv-V5-2XTPS4-53B6 | MALPVTALLLPLALLLHAARPGYPYDVPDYADIVMTQTPASVSEPVGGSVTIKC<br>QASQSFYNLLAWYQQKPGQPPKLLIYDASDLASGVPSRFKGSGSGTDFTLTISD<br>LECADAAAYYCQSADGSSYAFGGGTEVVVKGGGGGSGGGGSVHMPLGELGPRQA<br>RVVNGGSGGGGSQEQLEESGGGLVKPEGSLTLTCTASGVSFSSSYWIYWVRQAP<br>GKGLEWIACIYTGSSGSTYYASWAKGRFTVSETSSTTVTLQMTSLTAADTATYF<br>CARASAWTYGMDLWGPGTLVTVSSGGGGSGGGGSKPIPNPLLGLDSTGGGGSVH<br>MPLGFLGPRQARVVNGGSGGGGSGGGGSQVQLQESGPGLVKPSETLSLTCTVSG<br>GSISYYSWTWVRQPAGQGLEWIGRIHISGVTNHNPSLKSRVSMSIDTSRTQFSL<br>RLTSVTAADTAVYFCARSGGTYSAFDIWGQGTMVTVSSGGGGSGGGGSGGGGSG<br>GGGSEIVLTQSPGTLSLSPGERSTLSCRASQSFTSNYLAWYQQRPGQAPRLLIY<br>GASTRAIGIPDRFSGSGSGTDFTLTISRLEPEDFAVYYCQQYGSSPWTFGQGTK<br>VEIKTTTPAPRPPTPAPTIASQPLSLRPEACRPAAGGAVHTRGLDFACDIYIWA<br>PLAGTCGVLLLSLVITLYCKRGRKKLLYIFKQPFMRPVQTTQEEDGCSCRFPEE<br>EEGGCELRVKFSRSADAPAYQQGQNQLYNELNLGRREEYDVLDKRRGRDPEMGG<br>KPRRKNPQEGLYNELQKDKMAEAYSEIGMKGERRRGKGHDGLYQGLSTATKDTY<br>DALHMQALPPR |
| 143 4131scFv-V5-2XTPS5-53B6 | MALPVTALLLPLALLLHAARPGYPYDVPDYADIVMTQTPASVSEPVGGSVTIKC<br>QASQSFYNLLAWYQQKPGQPPKLLIYDASDLASGVPSRFKGSGSGTDFTLTISD<br>LECADAAAYYCQSADGSSYAFGGGTEVVVKGGGGGSGGGGSVHMPLGELGPSA<br>RVVNGGSGGGGSQEQLEESGGGLVKPEGSLTLTCTASGVSFSSSYWIYWVRQAP<br>GKGLEWIACIYTGSSGSTYYASWAKGRFTVSETSSTTVTLQMTSLTAADTATYF<br>CARASAWTYGMDLWGPGTLVTVSSGGGGSGGGGSKPIPNPLLGLDSTGGGGSVH |

TABLE 2-continued

Exemplary Protein Sequences

| SEQ ID NO: | Name | Amino Acid Sequence |
|---|---|---|
| | | MPLGFLGPGSARVVNGGSGGGGSGGGGSQVQLQESGPGLVKPSETLSLTCTVSG
GSISYYSWTWVRQPAGQGLEWIGRIHISGVTNHNPSLKSRVSMSIDTSRTQFSL
RLTSVTAADTAVYFCARSGGTYSAFDIWGQGTMVTVSSGGGGSGGGGSGGGGSG
GGGSEIVLTQSPGTLSLSPGERSTLSCRASQSFTSNYLAWYQQRPGQAPRLLIY
GASTRAIGIPDRFSGSGSGTDFTLTISRLEPEDFAVYYCQQYGSSPWTFGQGTK
VEIKTTTPAPRPPTPAPTIASQPLSLRPEACRPAAGGAVHTRGLDFACDIYIWA
PLAGTCGVLLLSLVITLYCKRGRKKLLYIFKQPFMRPVQTTQEEDGCSCRFPEE
EEGGCELRVKFSRSADAPAYQQGQNQLYNELNLGRREEYDVLDKRRGRDPEMGG
KPRRKNPQEGLYNELQKDKMAEAYSEIGMKGERRRGKGHDGLYQGLSTATKDTY
DALHMQALPPR |
| 144 | 4131scFv-V5-2XTPS6-53B6 | MALPVTALLLPLALLLHAARPGYPYDVPDYADIVMTQTPASVSEPVGGSVTIKC
QASQSFYNLLAWYQQKPGQPPKLLIYDASDLASGVPSRFKGSGSGTDFTLTISD
LECADAAAYYCQSADGSSYAFGGGTEVVVKGGGGSGGGGSGGGGSPMAKKGGG
GSGGGGSGGGGSQEQLEESGGGLVKPEGSLTLTCTASGVSFSSSYWIYWVRQAP
GKGLEWIACIYTGSSGSTYYASWAKGRFTVSETSSTTVTLQMTSLTAADTATYF
CARASAWTYGMDLWGPGTLVTVSSGGGGSGGGGSKPIPNPLLGLDSTGGGGSPM
AKKGGGGSGGGGSGGGGSGGGGSQVQLQESGPGLVKPSETLSLTCTVSGGSISY
YSWTWVRQPAGQGLEWIGRIHISGVTNHNPSLKSRVSMSIDTSRTQFSLRLTSV
TAADTAVYFCARSGGTYSAFDIWGQGTMVTVSSGGGGSGGGGSGGGGSGGGGSE
IVLTQSPGTLSLSPGERSTLSCRASQSFTSNYLAWYQQRPGQAPRLLIYGASTR
AIGIPDRFSGSGSGTDFTLTISRLEPEDFAVYYCQQYGSSPWTFGQGTKVEIKT
TTPAPRPPTPAPTIASQPLSLRPEACRPAAGGAVHTRGLDFACDIYIWAPLAGT
CGVLLLSLVITLYCKRGRKKLLYIFKQPFMRPVQTTQEEDGCSCRFPEEEEGGC
ELRVKFSRSADAPAYQQGQNQLYNELNLGRREEYDVLDKRRGRDPEMGGKPRRK
NPQEGLYNELQKDKMAEAYSEIGMKGERRRGKGHDGLYQGLSTATKDTYDALHM
QALPPR |
| 145 | 4131scFv-V5-2XTPS7-53B6 | MALPVTALLLPLALLLHAARPGYPYDVPDYADIVMTQTPASVSEPVGGSVTIKC
QASQSFYNLLAWYQQKPGQPPKLLIYDASDLASGVPSRFKGSGSGTDFTLTISD
LECADAAAYYCQSADGSSYAFGGGTEVVVKGGGGSGGGGSGGGGSPMAKGSGG
GSGGGGSGGGGSQEQLEESGGGLVKPEGSLTLTCTASGVSFSSSYWIYWVRQAP
GKGLEWIACIYTGSSGSTYYASWAKGRFTVSETSSTTVTLQMTSLTAADTATYF
CARASAWTYGMDLWGPGTLVTVSSGGGGSGGGGSKPIPNPLLGLDSTGGGGSPM
AKGSGGGSGGGGSGGGGSGGGGSQVQLQESGPGLVKPSETLSLTCTVSGGSISY
YSWTWVRQPAGQGLEWIGRIHISGVTNHNPSLKSRVSMSIDTSRTQFSLRLTSV
TAADTAVYFCARSGGTYSAFDIWGQGTMVTVSSGGGGSGGGGSGGGGSGGGGSE
IVLTQSPGTLSLSPGERSTLSCRASQSFTSNYLAWYQQRPGQAPRLLIYGASTR
AIGIPDRFSGSGSGTDFTLTISRLEPEDFAVYYCQQYGSSPWTFGQGTKVEIKT
TTPAPRPPTPAPTIASQPLSLRPEACRPAAGGAVHTRGLDFACDIYIWAPLAGT
CGVLLLSLVITLYCKRGRKKLLYIFKQPFMRPVQTTQEEDGCSCRFPEEEEGGC
ELRVKFSRSADAPAYQQGQNQLYNELNLGRREEYDVLDKRRGRDPEMGGKPRRK
NPQEGLYNELQKDKMAEAYSEIGMKGERRRGKGHDGLYQGLSTATKDTYDALHM
QALPPR |
| 146 | N-HA-4131scFv-G530-53B6 | MALPVTALLLPLALLLHAARPGYPYDVPDYADIVMTQTPASVSEPVGGSVTIKC
QASQSFYNLLAWYQQKPGQPPKLLIYDASDLASGVPSRFKGSGSGTDFTLTISD
LECADAAAYYCQSADGSSYAFGGGTEVVVKGGGGSGGGGSGGGGSGGGGSQEQ
LEESGGGLVKPEGSLTLTCTASGVSFSSSYWIYWVRQAPGKGLEWIACIYTGSS
GSTYYASWAKGRFTVSETSSTTVTLQMTSLTAADTATYFCARASAWTYGMDLWG
PGTLVTVSSGGGGSGGGGSGGGGSGGGGSGGGGSGGGGSQVQLQESGPGLVKPS
ETLSLTCTVSGGSISYYSWTWVRQPAGQGLEWIGRIHISGVTNHNPSLKSRVSM
SIDTSRTQFSLRLTSVTAADTAVYFCARSGGTYSAFDIWGQGTMVTVSSGGGGS
GGGGSGGGGSGGGGSEIVLTQSPGTLSLSPGERSTLSCRASQSFTSNYLAWYQQ
RPGQAPRLLIYGASTRAIGIPDRFSGSGSGTDFTLTISRLEPEDFAVYYCQQYG
SSPWTFGQGTKVEIKTTTPAPRPPTPAPTIASQPLSLRPEACRPAAGGAVHTRG
LDFACDIYIWAPLAGTCGVLLLSLVITLYCKRGRKKLLYIFKQPFMRPVQTTQE
EDGCSCRFPEEEEGGCELRVKFSRSADAPAYQQGQNQLYNELNLGRREEYDVLD
KRRGRDPEMGGKPRRKNPQEGLYNELQKDKMAEAYSEIGMKGERRRGKGHDGLY
QGLSTATKDTYDALHMQALPPR |
| 147 | N-HA-4131scFv-GS20-53B6 | MALPVTALLLPLALLLHAARPGYPYDVPDYADIVMTQTPASVSEPVGGSVTIKC
QASQSFYNLLAWYQQKPGQPPKLLIYDASDLASGVPSRFKGSGSGTDFTLTISD
LECADAAAYYCQSADGSSYAFGGGTEVVVKGGGGSGGGGSGGGGSGGGGSQEQ
LEESGGGLVKPEGSLTLTCTASGVSFSSSYWIYWVRQAPGKGLEWIACIYTGSS
GSTYYASWAKGRFTVSETSSTTVTLQMTSLTAADTATYFCARASAWTYGMDLWG
PGTLVTVSSGGGGSGGGGSGGGGSGGGGGGSQVQLQESGPGLVKPSETLSLTCTVS
GGSISYYSWTWVRQPAGQGLEWIGRIHISGVTNHNPSLKSRVSMSIDTSRTQFS
LRLTSVTAADTAVYFCARSGGTYSAFDIWGQGTMVTVSSGGGGSGGGGSGGGGS
GGGGSEIVLTQSPGTLSLSPGERSTLSCRASQSFTSNYLAWYQQRPGQAPRLLI
YGASTRAIGIPDRFSGSGSGTDFTLTISRLEPEDFAVYYCQQYGSSPWTFGQGT
KVEIKTTTPAPRPPTPAPTIASQPLSLRPEACRPAAGGAVHTRGLDFACDIYIW |

TABLE 2-continued

Exemplary Protein Sequences

| SEQ ID NO:Name | Amino Acid Sequence |
|---|---|
| | APLAGTCGVLLLSLVITLYCKRGRKKLLYIFKQPFMRPVQTTQEEDGCSCRFPE EEEGGCELRVKFSRSADAPAYQQGQNQLYNELNLGRREEYDVLDKRRGRDPEMG GKPRRKNPQEGLYNELQKDKMAEAYSEIGMKGERRRGKGHDGLYQGLSTATKDT YDALHMQALPPR |
| 148 N-HA-4131scFv-GS10-53B6 | MALPVTALLLPLALLLHAARPGYPYDVPDYADIVMTQTPASVSEPVGGSVTIKC QASQSFYNLLAWYQQKPGQPPKLLIYDASDLASGVPSRFKGSGSGTDFTLTISD LECADAAAYYCQSADGSSYAFGGGTEVVVKGGGGGSGGGGSGGGGSGGGGSQEQ LEESGGGLVKPEGSLTLTCTASGVSFSSSYWIYWVRQAPGKGLEWIACIYTGSS GSTYYASWAKGRFTVSETSSTTVTLQMTSLTAADTATYFCARASAWTYGMDLWG PGTLVTVSSGGGGSGGGGSQVQLQESGPGLVKPSETLSLTCTVSGGSISYYSWT WVRQPAGQGLEWIGRIHISGVTNHNPSLKSRVSMSIDTSRTQFSLRLTSVTAAD TAVYFCARSGGTYSAFDIWGQGTMVTVSSGGGGSGGGGSGGGGSGGGGSEIVLT QSPGTLSLSPGERSTLSCRASQSFTSNYLAWYQQRPGQAPRLLIYGASTRAIGI PDRFSGSGSGTDFTLTISRLEPEDFAVYYCQQYGSSPWTFGQGTKVEIKTTTPA PRPPTPAPTIASQPLSLRPEACRPAAGGAVHTRGLDFACDIYIWAPLAGTCGVL LLSLVITLYCKRGRKKLLYIFKQPFMRPVQTTQEEDGCSCRFPEEEGGCELRV KFSRSADAPAYQQGQNQLYNELNLGRREEYDVLDKRRGRDPEMGGKPRRKNPQE GLYNELQKDKMAEAYSEIGMKGERRRGKGHDGLYQGLSTATKDTYDALHMQALP PR |
| 149 V5-GS20-4131scFv-TPS6-35-53B6 | MALPVTALLLPLALLLHAARPGKPIPNPLLGLDSTGGGGSGGGGSGGGGSGGGG SDIVMTQTPASVSEPVGGSVTIKCQASQSFYNLLAWYQQKPGQPPKLLIYDASD LASGVPSRFKGSGSGTDFTLTISDLECADAAAYYCQSADGSSYAFGGGTEVVVK GGGGGSGGGGSGGGGSGGGGSQEQLEESGGGLVKPEGSLTLTCTASGVSFSSSY WIYWVRQAPGKGLEWIACIYTGSSGSTYYASWAKGRFTVSETSSTTVTLQMTSL TAADTATYFCARASAWTYGMDLWGPGTLVTVSSGGGGSGGGGSGGGGSPMAKKG GGGSGGGGSGGGGSQVQLQESGPGLVKPSETLSLTCTVSGGSISYYSWTWVRQP AGQGLEWIGRIHISGVTNHNPSLKSRVSMSIDTSRTQFSLRLTSVTAADTAVYF CARSGGTYSAFDIWGQGTMVTVSSGGGGSGGGGSGGGGSGGGGSEIVLTQSPGT LSLSPGERSTLSCRASQSFTSNYLAWYQQRPGQAPRLLIYGASTRAIGIPDRES GSGSGTDFTLTISRLEPEDFAVYYCQQYGSSPWTFGQGTKVEIKTTTPAPRPPT PAPTIASQPLSLRPEACRPAAGGAVHTRGLDFACDIYIWAPLAGTCGVLLLSLV ITLYCKRGRKKLLYIFKQPFMRPVQTTQEEDGCSCRFPEEEGGCELRVKFSRS ADAPAYQQGQNQLYNELNLGRREEYDVLDKRRGRDPEMGGKPRRKNPQEGLYNE LQKDKMAEAYSEIGMKGERRRGKGHDGLYQGLSTATKDTYDALHMQALPPR |
| 150 V5-G520-4131scFv-TPS6-30-53B6 | MALPVTALLLPLALLLHAARPGKPIPNPLLGLDSTGGGGSGGGGSGGGGSGGGG SDIVMTQTPASVSEPVGGSVTIKCQASQSFYNLLAWYQQKPGQPPKLLIYDASD LASGVPSRFKGSGSGTDFTLTISDLECADAAAYYCQSADGSSYAFGGGTEVVVK GGGGGSGGGGSGGGGSGGGGSQEQLEESGGGLVKPEGSLTLTCTASGVSFSSSY WIYWVRQAPGKGLEWIACIYTGSSGSTYYASWAKGRFTVSETSSTTVTLQMTSL TAADTATYFCARASAWTYGMDLWGPGTLVTVSSGGGGSGGGGSPMAKKGGGGSG GGGSGGGGSQVQLQESGPGLVKPSETLSLTCTVSGGSISYYSWTWVRQPAGQGL EWIGRIHISGVTNHNPSLKSRVSMSIDTSRTQFSLRLTSVTAADTAVYFCARSG GTYSAFDIWGQGTMVTVSSGGGGSGGGGSGGGGSGGGGSEIVLTQSPGTLSLSP GERSTLSCRASQSFTSNYLAWYQQRPGQAPRLLIYGASTRAIGIPDRFSGSGSG TDFTLTISRLEPEDFAVYYCQQYGSSPWTFGQGTKVEIKTTTPAPRPPTPAPTI ASQPLSLRPEACRPAAGGAVHTRGLDFACDIYIWAPLAGTCGVLLLSLVITLYC KRGRKKLLYIFKQPFMRPVQTTQEEDGCSCRFPEEEGGCELRVKFSRSADAPA YQQGQNQLYNELNLGRREEYDVLDKRRGRDPEMGGKPRRKNPQEGLYNELQKDK MAEAYSEIGMKGERRRGKGHDGLYQGLSTATKDTYDALHMQALPPR |
| 151 V5-GS20-4131scFv-TPS6-25-53B6 | MALPVTALLLPLALLLHAARPGKPIPNPLLGLDSTGGGGSGGGGSGGGGSGGGG SDIVMTQTPASVSEPVGGSVTIKCQASQSFYNLLAWYQQKPGQPPKLLIYDASD LASGVPSRFKGSGSGTDFTLTISDLECADAAAYYCQSADGSSYAFGGGTEVVVK GGGGGSGGGGSGGGGSGGGGSQEQLEESGGGLVKPEGSLTLTCTASGVSFSSSY WIYWVRQAPGKGLEWIACIYTGSSGSTYYASWAKGRFTVSETSSTTVTLQMTSL TAADTATYFCARASAWTYGMDLWGPGTLVTVSSGGGGSGGGGSPMAKKGGGGSG GGGSQVQLQESGPGLVKPSETLSLTCTVSGGSISYYSWTWVRQPAGQGLEWIGR IHISGVTNHNPSLKSRVSMSIDTSRTQFSLRLTSVTAADTAVYFCARSGGTYSA FDIWGQGTMVTVSSGGGGSGGGGSGGGGSGGGGSEIVLTQSPGTLSLSPGERST LSCRASQSFTSNYLAWYQQRPGQAPRLLIYGASTRAIGIPDRFSGSGSGTDFTL TISRLEPEDFAVYYCQQYGSSPWTFGQGTKVEIKTTTPAPRPPTPAPTIASQPL SLRPEACRPAAGGAVHTRGLDFACDIYIWAPLAGTCGVLLLSLVITLYCKRGRK KLLYIFKQPFMRPVQTTQEEDGCSCRFPEEEGGCELRVKFSRSADAPAYQQGQ NQLYNELNLGRREEYDVLDKRRGRDPEMGGKPRRKNPQEGLYNELQKDKMAEAY SEIGMKGERRRGKGHDGLYQGLSTATKDTYDALHMQALPPR |
| 152 V5-GS20-4131scFv-TPS6-20-53B6 | MALPVTALLLPLALLLHAARPGKPIPNPLLGLDSTGGGGSGGGGSGGGGSGGGG SDIVMTQTPASVSEPVGGSVTIKCQASQSFYNLLAWYQQKPGQPPKLLIYDASD LASGVPSRFKGSGSGTDFTLTISDLECADAAAYYCQSADGSSYAFGGGTEVVVK GGGGGSGGGGSGGGGSGGGGSQEQLEESGGGLVKPEGSLTLTCTASGVSFSSSY WIYWVRQAPGKGLEWIACIYTGSSGSTYYASWAKGRFTVSETSSTTVTLQMTSL |

TABLE 2-continued

Exemplary Protein Sequences

| SEQ ID NO:Name | Amino Acid Sequence |
|---|---|
| | TAADTATYFCARASAWTYGMDLWGPGTLVTVSSGGGGSPMAKKGGGGSGGGGSQ VQLQESGPGLVKPSETLSLTCTVSGGSISYYSWTWVRQPAGQGLEWIGRIHISG VTNHNPSLKSRVSMSIDTSRTQFSLRLTSVTAADTAVYFCARSGGTYSAFDIWG QGTMVTVSSGGGGSGGGGSGGGGSGGGGSEIVLTQSPGTLSLSPGERSTLSCRA SQSFTSNYLAWYQQRPGQAPRLLIYGASTRAIGIPDRFSGSGSGTDFTLTISRL EPEDFAVYYCQQYGSSPWTFGQGTKVEIKTTTPAPRPPTPAPTIASQPLSLRPE ACRPAAGGAVHTRGLDFACDIYIWAPLAGTCGVLLLSLVITLYCKRGRKKLLYI FKQPFMRPVQTTQEEDGCSCRFPEEEEGGCELRVKFSRSADAPAYQQGQNQLYN ELNLGRREEYDVLDKRRGRDPEMGGKPRRKNPQEGLYNELQKDKMAEAYSEIGM KGERRRGKGHDGLYQGLSTATKDTYDALHMQALPPR |
| 153 V5-G520-4131scFv-2XTPS6-35-53B6 | MALPVTALLLPLALLLHAARPGKPIPNPLLGLDSTGGGGSGGGGSGGGGSGGGG SDIVMTQTPASVSEPVGGSVTIKCQASQSFYNLLAWYQQKPGQPPKLLIYDASD LASGVPSRFKGSGSGTDFTLTISDLECADAAAYYCQSADGSSYAFGGGTEVVVK GGGGGSGGGGSGGGGSPMAKKGGGGSGGGGSGGGGSQEQLEESGGGLVKPEGSL TLTCTASGVSFSSSYWIYWVRQAPGKGLEWIACIYTGSSGSTYYASWAKGRFTV SETSSTTVTLQMTSLTAADTATYFCARASAWTYGMDLWGPGTLVTVSSGGGGSG GGGSGGGGSPMAKKGGGGSGGGGSGGGGSQVQLQESGPGLVKPSETLSLTCTVS GGSISYYSWTWVRQPAGQGLEWIGRIHISGVTNHNPSLKSRVSMSIDTSRTQFS LRLTSVTAADTAVYFCARSGGTYSAFDIWGQGTMVTVSSGGGGSGGGGSGGGGS GGGGSEIVLTQSPGTLSLSPGERSTLSCRASQSFTSNYLAWYQQRPGQAPRLLI YGASTRAIGIPDRFSGSGSGTDFTLTISRLEPEDFAVYYCQQYGSSPWTFGQGT KVEIKTTTPAPRPPTPAPTIASQPLSLRPEACRPAAGGAVHTRGLDFACDIYIW APLAGTCGVLLLSLVITLYCKRGRKKLLYIFKQPFMRPVQTTQEEDGCSCRFPE EEEGGCELRVKFSRSADAPAYQQGQNQLYNELNLGRREEYDVLDKRRGRDPEMG GKPRRKNPQEGLYNELQKDKMAEAYSEIGMKGERRRGKGHDGLYQGLSTATKDT YDALHMQALPPR |
| 154 V5-G520-4131scFv-2XTPS6-30-53B6 | MALPVTALLLPLALLLHAARPGKPIPNPLLGLDSTGGGGSGGGGSGGGGSGGGG SDIVMTQTPASVSEPVGGSVTIKCQASQSFYNLLAWYQQKPGQPPKLLIYDASD LASGVPSRFKGSGSGTDFTLTISDLECADAAAYYCQSADGSSYAFGGGTEVVVK GGGGGSGGGGSGGGGSPMAKKGGGGSGGGGSGGGGSQEQLEESGGGLVKPEGSL TLTCTASGVSFSSSYWIYWVRQAPGKGLEWIACIYTGSSGSTYYASWAKGRFTV SETSSTTVTLQMTSLTAADTATYFCARASAWTYGMDLWGPGTLVTVSSGGGGSG GGGSPMAKKGGGGSGGGGSGGGGSQVQLQESGPGLVKPSETLSLTCTVSGGSIS YYSWTWVRQPAGQGLEWIGRIHISGVTNHNPSLKSRVSMSIDTSRTQFSLRLTS VTAADTAVYFCARSGGTYSAFDIWGQGTMVTVSSGGGGSGGGGSGGGGSGGGGS EIVLTQSPGTLSLSPGERSTLSCRASQSFTSNYLAWYQQRPGQAPRLLIYGAST RAIGIPDRFSGSGSGTDFTLTISRLEPEDFAVYYCQQYGSSPWTFGQGTKVEIK TTTPAPRPPTPAPTIASQPLSLRPEACRPAAGGAVHTRGLDFACDIYIWAPLAG TCGVLLLSLVITLYCKRGRKKLLYIFKQPFMRPVQTTQEEDGCSCRFPEEEEGG CELRVKFSRSADAPAYQQGQNQLYNELNLGRREEYDVLDKRRGRDPEMGGKPRR KNPQEGLYNELQKDKMAEAYSEIGMKGERRRGKGHDGLYQGLSTATKDTYDALH MQALPPR |
| 155 V5-GS20-4131scFv-2XTPS6-25-53B6 | MALPVTALLLPLALLLHAARPGKPIPNPLLGLDSTGGGGSGGGGSGGGGSGGGG SDIVMTQTPASVSEPVGGSVTIKCQASQSFYNLLAWYQQKPGQPPKLLIYDASD LASGVPSRFKGSGSGTDFTLTISDLECADAAAYYCQSADGSSYAFGGGTEVVVK GGGGGSGGGGSGGGGSPMAKKGGGGSGGGGSGGGGSQEQLEESGGGLVKPEGSL TLTCTASGVSFSSSYWIYWVRQAPGKGLEWIACIYTGSSGSTYYASWAKGRFTV SETSSTTVTLQMTSLTAADTATYFCARASAWTYGMDLWGPGTLVTVSSGGGGSG GGGSPMAKKGGGGSGGGGSQVQLQESGPGLVKPSETLSLTCTVSGGSISYYSWT WVRQPAGQGLEWIGRIHISGVTNHNPSLKSRVSMSIDTSRTQFSLRLTSVTAAD TAVYFCARSGGTYSAFDIWGQGTMVTVSSGGGGSGGGGSGGGGSGGGGSEIVLT QSPGTLSLSPGERSTLSCRASQSFTSNYLAWYQQRPGQAPRLLIYGASTRAIGI PDRFSGSGSGTDFTLTISRLEPEDFAVYYCQQYGSSPWTFGQGTKVEIKTTTPA PRPPTPAPTIASQPLSLRPEACRPAAGGAVHTRGLDFACDIYIWAPLAGTCGVL LLSLVITLYCKRGRKKLLYIFKQPFMRPVQTTQEEDGCSCRFPEEEEGGCELRV KFSRSADAPAYQQGQNQLYNELNLGRREEYDVLDKRRGRDPEMGGKPRRKNPQE GLYNELQKDKMAEAYSEIGMKGERRRGKGHDGLYQGLSTATKDTYDALHMQALP PR |
| 156 V5-GS20-4131scFv-2XTPS6-20-53B6 | MALPVTALLLPLALLLHAARPGKPIPNPLLGLDSTGGGGSGGGGSGGGGSGGGG SDIVMTQTPASVSEPVGGSVTIKCQASQSFYNLLAWYQQKPGQPPKLLIYDASD LASGVPSRFKGSGSGTDFTLTISDLECADAAAYYCQSADGSSYAFGGGTEVVVK GGGGGSGGGGSGGGGSPMAKKGGGGSGGGGSGGGGSQEQLEESGGGLVKPEGSL TLTCTASGVSFSSSYWIYWVRQAPGKGLEWIACIYTGSSGSTYYASWAKGRFTV SETSSTTVTLQMTSLTAADTATYFCARASAWTYGMDLWGPGTLVTVSSGGGGSP MAKKGGGGSGGGGSQVQLQESGPGLVKPSETLSLTCTVSGGSISYYSWTWVRQP AGQGLEWIGRIHISGVTNHNPSLKSRVSMSIDTSRTQFSLRLTSVTAADTAVYF CARSGGTYSAFDIWGQGTMVTVSSGGGGSGGGGSGGGGSGGGGSEIVLTQSPGT LSLSPGERSTLSCRASQSFTSNYLAWYQQRPGQAPRLLIYGASTRAIGIPDRFS GSGSGTDFTLTISRLEPEDFAVYYCQQYGSSPWTFGQGTKVEIKTTTPAPRPPT PAPTIASQPLSLRPEACRPAAGGAVHTRGLDFACDIYIWAPLAGTCGVLLLSLV |

TABLE 2-continued

Exemplary Protein Sequences

| SEQ ID NO:Name | Amino Acid Sequence |
|---|---|
| | ITLYCKRGRKKLLYIFKQPFMRPVQTTQEEDGCSCRFPEEEEGGCELRVKFSRS<br>ADAPAYQQGQNQLYNELNLGRREEYDVLDKRRGRDPEMGGKPRRKNPQEGLYNE<br>LQKDKMAEAYSEIGMKGERRRGKGHDGLYQGLSTATKDTYDALHMQALPPR |
| 157 V5-GS20-<br>4131scFv-<br>TPS8-53B6 | MALPVTALLLPLALLLHAARPGKPIPNPLLGLDSTGGGSGGGGSGGGGSGGGG<br>SDIVMTQTPASVSEPVGGSVTIKCQASQSFYNLLAWYQQKPGQPPKLLIYDASD<br>LASGVPSRFKGSGSGTDFTLTISDLECADAAAYYCQSADGSSYAFGGGTEVVVK<br>GGGGGSGGGGSGGGGSGGGGSQEQLEESGGGLVKPEGSLTLTCTASGVSFSSSY<br>WIYWVRQAPGKGLEWIACIYTGSSGSTYYASWAKGRFTVSETSSTTVTLQMTSL<br>TAADTATYFCARASAWTYGMDLWGPGTLVTVSSGGGGSGGGGSGSSPLGLAGSG<br>GGGSGGGGSPMAKKGGGGSGGGGSGVQLQESGPGLVKPSETLSLTCTVSGGSIS<br>YYSWTWVRQPAGQGLEWIGRIHISGVTNHNPSLKSRVSMSIDTSRTQFSLRLTS<br>VTAADTAVYFCARSGGTYSAFDIWGQGTMVTVSSGGGGSGGGGSGGGGSGGGGS<br>EIVLTQSPGTLSLSPGERSTLSCRASQSFTSNYLAWYQQRPGQAPRLLIYGAST<br>RAIGIPDRFSGSGSGTDFTLTISRLEPEDFAVYYCQQYGSSPWTFGQGTKVEIK<br>TTTPAPRPPTPAPTIASQPLSLRPEACRPAAGGAVHTRGLDFACDIYIWAPLAG<br>TCGVLLLSLVITLYCKRGRKKLLYIFKQPFMRPVQTTQEEDGCSCRFPEEEEGG<br>CELRVKFSRSADAPAYQQGQNQLYNELNLGRREEYDVLDKRRGRDPEMGGKPRR<br>KNPQEGLYNELQKDKMAEAYSEIGMKGERRRGKGHDGLYQGLSTATKDTYDALH<br>MQALPPR |
| 158 V5-GS20-<br>4131scFv-<br>TPS9-53B6 | MALPVTALLLPLALLLHAARPGKPIPNPLLGLDSTGGGSGGGGSGGGGSGGGG<br>SDIVMTQTPASVSEPVGGSVTIKCQASQSFYNLLAWYQQKPGQPPKLLIYDASD<br>LASGVPSRFKGSGSGTDFTLTISDLECADAAAYYCQSADGSSYAFGGGTEVVVK<br>GGGGGSGGGGSGGGGSGGGGSQEQLEESGGGLVKPEGSLTLTCTASGVSFSSSY<br>WIYWVRQAPGKGLEWIACIYTGSSGSTYYASWAKGRFTVSETSSTTVTLQMTSL<br>TAADTATYFCARASAWTYGMDLWGPGTLVTVSSGGGGSGGGGSGGSVHMPLGEL<br>GPGGSGGGSPMAKKGGGGSGGGGSGVQLQESGPGLVKPSETLSLTCTVSGGSIS<br>YYSWTWVRQPAGQGLEWIGRIHISGVTNHNPSLKSRVSMSIDTSRTQFSLRLTS<br>VTAADTAVYFCARSGGTYSAFDIWGQGTMVTVSSGGGGSGGGGSGGGGSGGGGS<br>EIVLTQSPGTLSLSPGERSTLSCRASQSFTSNYLAWYQQRPGQAPRLLIYGAST<br>RAIGIPDRFSGSGSGTDFTLTISRLEPEDFAVYYCQQYGSSPWTFGQGTKVEIK<br>TTTPAPRPPTPAPTIASQPLSLRPEACRPAAGGAVHTRGLDFACDIYIWAPLAG<br>TCGVLLLSLVITLYCKRGRKKLLYIFKQPFMRPVQTTQEEDGCSCRFPEEEEGG<br>CELRVKFSRSADAPAYQQGQNQLYNELNLGRREEYDVLDKRRGRDPEMGGKPRR<br>KNPQEGLYNELQKDKMAEAYSEIGMKGERRRGKGHDGLYQGLSTATKDTYDALH<br>MQALPPR |
| 159 V5-GS20-<br>4131scFv-<br>TPS10-53B6 | MALPVTALLLPLALLLHAARPGKPIPNPLLGLDSTGGGSGGGGSGGGGSGGGG<br>SDIVMTQTPASVSEPVGGSVTIKCQASQSFYNLLAWYQQKPGQPPKLLIYDASD<br>LASGVPSRFKGSGSGTDFTLTISDLECADAAAYYCQSADGSSYAFGGGTEVVVK<br>GGGGGSGGGGSGGGGSGGGGSQEQLEESGGGLVKPEGSLTLTCTASGVSFSSSY<br>WIYWVRQAPGKGLEWIACIYTGSSGSTYYASWAKGRFTVSETSSTTVTLQMTSL<br>TAADTATYFCARASAWTYGMDLWGPGTLVTVSSGGGGSGGGGSGGSPLGVRGKG<br>GGGSGGGGSPMAKKGGGGSGGGGSGVQLQESGPGLVKPSETLSLTCTVSGGSIS<br>YYSWTWVRQPAGQGLEWIGRIHISGVTNHNPSLKSRVSMSIDTSRTQFSLRLTS<br>VTAADTAVYFCARSGGTYSAFDIWGQGTMVTVSSGGGGSGGGGSGGGGSGGGGS<br>EIVLTQSPGTLSLSPGERSTLSCRASQSFTSNYLAWYQQRPGQAPRLLIYGAST<br>RAIGIPDRFSGSGSGTDFTLTISRLEPEDFAVYYCQQYGSSPWTFGQGTKVEIK<br>TTTPAPRPPTPAPTIASQPLSLRPEACRPAAGGAVHTRGLDFACDIYIWAPLAG<br>TCGVLLLSLVITLYCKRGRKKLLYIFKQPFMRPVQTTQEEDGCSCRFPEEEEGG<br>CELRVKFSRSADAPAYQQGQNQLYNELNLGRREEYDVLDKRRGRDPEMGGKPRR<br>KNPQEGLYNELQKDKMAEAYSEIGMKGERRRGKGHDGLYQGLSTATKDTYDALH<br>MQALPPR |
| 160 V5-GS20-<br>4131scFv-<br>TPS11-53B6 | MALPVTALLLPLALLLHAARPGKPIPNPLLGLDSTGGGSGGGGSGGGGSGGGG<br>SDIVMTQTPASVSEPVGGSVTIKCQASQSFYNLLAWYQQKPGQPPKLLIYDASD<br>LASGVPSRFKGSGSGTDFTLTISDLECADAAAYYCQSADGSSYAFGGGTEVVVK<br>GGGGGSGGGGSGGGGSGGGGSQEQLEESGGGLVKPEGSLTLTCTASGVSFSSSY<br>WIYWVRQAPGKGLEWIACIYTGSSGSTYYASWAKGRFTVSETSSTTVTLQMTSL<br>TAADTATYFCARASAWTYGMDLWGPGTLVTVSSGGGGSGGGGSGGSSPLGLAGS<br>GSGGGSRQARVVNGGGGSGGGGSQVQLQESGPGLVKPSETLSLTCTVSGGSIS<br>YYSWTWVRQPAGQGLEWIGRIHISGVTNHNPSLKSRVSMSIDTSRTQFSLRLTS<br>VTAADTAVYFCARSGGTYSAFDIWGQGTMVTVSSGGGGSGGGGSGGGGSGGGGS<br>EIVLTQSPGTLSLSPGERSTLSCRASQSFTSNYLAWYQQRPGQAPRLLIYGAST<br>RAIGIPDRFSGSGSGTDFTLTISRLEPEDFAVYYCQQYGSSPWTFGQGTKVEIK<br>TTTPAPRPPTPAPTIASQPLSLRPEACRPAAGGAVHTRGLDFACDIYIWAPLAG<br>TCGVLLLSLVITLYCKRGRKKLLYIFKQPFMRPVQTTQEEDGCSCRFPEEEEGG<br>CELRVKFSRSADAPAYQQGQNQLYNELNLGRREEYDVLDKRRGRDPEMGGKPRR<br>KNPQEGLYNELQKDKMAEAYSEIGMKGERRRGKGHDGLYQGLSTATKDTYDALH<br>MQALPPR |

TABLE 2-continued

Exemplary Protein Sequences

| SEQ ID NO: Name | Amino Acid Sequence |
|---|---|
| 161 V5-G520-4131scFv-TPS12-53B6 | MALPVTALLLPLALLLHAARPGKPIPNPLLGLDSTGGGGSGGGGSGGGGSGGGG<br>SDIVMTQTPASVSEPVGGSVTIKCQASQSFYNLLAWYQQKPGQPPKLLIYDASD<br>LASGVPSRFKGSGSGTDFTLTISDLECADAAAYYCQSADGSSYAFGGGTEVVVK<br>GGGGGSGGGGSGGGGSGGGGSQEQLEESGGGLVKPEGSLTLTCTASGVSFSSSY<br>WIYWVRQAPGKGLEWIACIYTGSSGSTYYASWAKGRFTVSETSSTTVTLQMTSL<br>TAADTATYFCARASAWTYGMDLWGPGTLVTVSSGGGGSGGGGSGGSVHMPLGFL<br>GPGGGSRQARVVNGGGGSGGGGSQVQLQESGPGLVKPSETLSLTCTVSGGSIS<br>YYSWTWVRQPAGQGLEWIGRIHISGVTNHNPSLKSRVSMSIDTSRTQFSLRLTS<br>VTAADTAVYFCARSGGTYSAFDIWGQGTMVTVSSGGGGSGGGGSGGGGSGGGGS<br>EIVLTQSPGTLSLSPGERSTLSCRASQSFTSNYLAWYQQRPGQAPRLLIYGAST<br>RAIGIPDRFSGSGSGTDFTLTISRLEPEDFAVYYCQQYGSSPWTFGQGTKVEIK<br>TTTPAPRPPTPAPTIASQPLSLRPEACRPAAGGAVHTRGLDFACDIYIWAPLAG<br>TCGVLLLSLVITLYCKRGRKKLLYIFKQPFMRPVQTTQEEDGCSCRFPEEEEGG<br>CELRVKFSRSADAPAYQQGQNQLYNELNLGRREEYDVLDKRRGRDPEMGGKPRR<br>KNPQEGLYNELQKDKMAEAYSEIGMKGERRRGKGHDGLYQGLSTATKDTYDALH<br>MQALPPR |
| 162 V5-G520-4131scFv-TPS13-53B6 | MALPVTALLLPLALLLHAARPGKPIPNPLLGLDSTGGGGSGGGGSGGGGSGGGG<br>SDIVMTQTPASVSEPVGGSVTIKCQASQSFYNLLAWYQQKPGQPPKLLIYDASD<br>LASGVPSRFKGSGSGTDFTLTISDLECADAAAYYCQSADGSSYAFGGGTEVVVK<br>GGGGGSGGGGSGGGGSGGGGSQEQLEESGGGLVKPEGSLTLTCTASGVSFSSSY<br>WIYWVRQAPGKGLEWIACIYTGSSGSTYYASWAKGRFTVSETSSTTVTLQMTSL<br>TAADTATYFCARASAWTYGMDLWGPGTLVTVSSGGGGSGGGGSGGGGSPLGVRGKG<br>GSGGGSRQARVVNGGGGSGGGGSQVQLQESGPGLVKPSETLSLTCTVSGGSIS<br>YYSWTWVRQPAGQGLEWIGRIHISGVTNHNPSLKSRVSMSIDTSRTQFSLRLTS<br>VTAADTAVYFCARSGGTYSAFDIWGQGTMVTVSSGGGGSGGGGSGGGGSGGGGS<br>EIVLTQSPGTLSLSPGERSTLSCRASQSFTSNYLAWYQQRPGQAPRLLIYGAST<br>RAIGIPDRFSGSGSGTDFTLTISRLEPEDFAVYYCQQYGSSPWTFGQGTKVEIK<br>TTTPAPRPPTPAPTIASQPLSLRPEACRPAAGGAVHTRGLDFACDIYIWAPLAG<br>TCGVLLLSLVITLYCKRGRKKLLYIFKQPFMRPVQTTQEEDGCSCRFPEEEEGG<br>CELRVKFSRSADAPAYQQGQNQLYNELNLGRREEYDVLDKRRGRDPEMGGKPRR<br>KNPQEGLYNELQKDKMAEAYSEIGMKGERRRGKGHDGLYQGLSTATKDTYDALH<br>MQALPPR |
| 163 V5-G520-4131scFv-G545-53B6 | MALPVTALLLPLALLLHAARPGKPIPNPLLGLDSTGGGGSGGGGSGGGGSGGGG<br>SDIVMTQTPASVSEPVGGSVTIKCQASQSFYNLLAWYQQKPGQPPKLLIYDASD<br>LASGVPSRFKGSGSGTDFTLTISDLECADAAAYYCQSADGSSYAFGGGTEVVVK<br>GGGGGSGGGGSGGGGSGGGGSQEQLEESGGGLVKPEGSLTLTCTASGVSFSSSY<br>WIYWVRQAPGKGLEWIACIYTGSSGSTYYASWAKGRFTVSETSSTTVTLQMTSL<br>TAADTATYFCARASAWTYGMDLWGPGTLVTVSSGGGGSGGGGSGGGGSGGGGSG<br>GGGSGGGGSGGGGSGGGGSGGGGSQVQLQESGPGLVKPSETLSLTCTVSGGSIS<br>YYSWTWVRQPAGQGLEWIGRIHISGVTNHNPSLKSRVSMSIDTSRTQFSLRLTS<br>VTAADTAVYFCARSGGTYSAFDIWGQGTMVTVSSGGGGSGGGGSGGGGSGGGGS<br>EIVLTQSPGTLSLSPGERSTLSCRASQSFTSNYLAWYQQRPGQAPRLLIYGAST<br>RAIGIPDRFSGSGSGTDFTLTISRLEPEDFAVYYCQQYGSSPWTFGQGTKVEIK<br>TTTPAPRPPTPAPTIASQPLSLRPEACRPAAGGAVHTRGLDFACDIYIWAPLAG<br>TCGVLLLSLVITLYCKRGRKKLLYIFKQPFMRPVQTTQEEDGCSCRFPEEEEGG<br>CELRVKFSRSADAPAYQQGQNQLYNELNLGRREEYDVLDKRRGRDPEMGGKPRR<br>KNPQEGLYNELQKDKMAEAYSEIGMKGERRRGKGHDGLYQGLSTATKDTYDALH<br>MQALPPR |
| 164 v5-G520-4131scFv-G535-53B6 | MALPVTALLLPLALLLHAARPGKPIPNPLLGLDSTGGGGSGGGGSGGGGSGGGG<br>SDIVMTQTPASVSEPVGGSVTIKCQASQSFYNLLAWYQQKPGQPPKLLIYDASD<br>LASGVPSRFKGSGSGTDFTLTISDLECADAAAYYCQSADGSSYAFGGGTEVVVK<br>GGGGGSGGGGSGGGGSGGGGSQEQLEESGGGLVKPEGSLTLTCTASGVSFSSSY<br>WIYWVRQAPGKGLEWIACIYTGSSGSTYYASWAKGRFTVSETSSTTVTLQMTSL<br>TAADTATYFCARASAWTYGMDLWGPGTLVTVSSGGGGSGGGGSGGGGSGGGGSG<br>GGGSGGGGSGGGGSQVQLQESGPGLVKPSETLSLTCTVSGGSISYYSWTWVRQP<br>AGQGLEWIGRIHISGVTNHNPSLKSRVSMSIDTSRTQFSLRLTSVTAADTAVYF<br>CARSGGTYSAFDIWGQGTMVTVSSGGGGSGGGGSGGGGSGGGGSEIVLTQSPGT<br>LSLSPGERSTLSCRASQSFTSNYLAWYQQRPGQAPRLLIYGASTRAIGIPDRFS<br>GSGSGTDFTLTISRLEPEDFAVYYCQQYGSSPWTFGQGTKVEIKTTTPAPRPPT<br>PAPTIASQPLSLRPEACRPAAGGAVHTRGLDFACDIYIWAPLAGTCGVLLLSLV<br>ITLYCKRGRKKLLYIFKQPFMRPVQTTQEEDGCSCRFPEEEEGGCELRVKFSRS<br>ADAPAYQQGQNQLYNELNLGRREEYDVLDKRRGRDPEMGGKPRRKNPQEGLYNE<br>LQKDKMAEAYSEIGMKGERRRGKGHDGLYQGLSTATKDTYDALHMQALPPR |
| 165 V5-GS20-4131scFv-GS25-53B6 | MALPVTALLLPLALLLHAARPGKPIPNPLLGLDSTGGGGSGGGGSGGGGSGGGG<br>SDIVMTQTPASVSEPVGGSVTIKCQASQSFYNLLAWYQQKPGQPPKLLIYDASD<br>LASGVPSRFKGSGSGTDFTLTISDLECADAAAYYCQSADGSSYAFGGGTEVVVK<br>GGGGGSGGGGSGGGGSGGGGSQEQLEESGGGLVKPEGSLTLTCTASGVSFSSSY<br>WIYWVRQAPGKGLEWIACIYTGSSGSTYYASWAKGRFTVSETSSTTVTLQMTSL<br>TAADTATYFCARASAWTYGMDLWGPGTLVTVSSGGGGSGGGGSGGGGSGGGGSG<br>GGGSQVQLQESGPGLVKPSETLSLTCTVSGGSISYYSWTWVRQPAGQGLEWIGR |

TABLE 2-continued

Exemplary Protein Sequences

| SEQ ID NO:Name | Amino Acid Sequence |
|---|---|
| | IHISGVTNHNPSLKSRVSMSIDTSRTQFSLRLTSVTAADTAVYFCARSGGTYSA FDIWGQGTMVTVSSGGGGSGGGGSGGGGSGGGGSEIVLTQSPGTLSLSPGERST LSCRASQSFTSNYLAWYQQRPGQAPRLLIYGASTRAIGIPDRFSGSGSGTDFTL TISRLEPEDFAVYYCQQYGSSPWTFGQGTKVEIKTTTPAPRPPTPAPTIASQPL SLRPEACRPAAGGAVHTRGLDFACDIYIWAPLAGTCGVLLLSLVITLYCKRGRK KLLYIFKQPFMRPVQTTQEEDGCSCRFPEEEEGGCELRVKFSRSADAPAYQQGQ NQLYNELNLGRREEYDVLDKRRGRDPEMGGKPRRKNPQEGLYNELQKDKMAEAY SEIGMKGERRRGKGHDGLYQGLSTATKDTYDALHMQALPPR |
| 166 N-HA-IgV-G545-53B6 | MALPVTALLLPLALLLHAARPGYPYDVPDYAQFSVLGPSGPILAMVGEDADLPC HLFPTMSAETMELKWVSSSLRQVVNVYADGKEVEDRQSAPYRGRTSILRDGITA GKAALRIHNVTASDSGKYLCYFQDGDFYEKALVELKVAGGGGSGGGGSGGGGSG GSGSGGGGSGGGGSGGGGSGGGGSGGGGSQVQLQESGPGLVKPSETLSLTCTVS GGSISYYSWTWVRQPAGQGLEWIGRIHISGVTNHNPSLKSRVSMSIDTSRTQFS LRLTSVTAADTAVYFCARSGGTYSAFDIWGQGTMVTVSSGGGGSGGGGSGGGGS GGGGSEIVLTQSPGTLSLSPGERSTLSCRASQSFTSNYLAWYQQRPGQAPRLLI YGASTRAIGIPDRFSGSGSGTDFTLTISRLEPEDFAVYYCQQYGSSPWTFGQGT KVEIKTTTPAPRPPTPAPTIASQPLSLRPEACRPAAGGAVHTRGLDFACDIYIW APLAGTCGVLLLSLVITLYCKRGRKKLLYIFKQPFMRPVQTTQEEDGCSCRFPE EEEGGCELRVKFSRSADAPAYQQGQNQLYNELNLGRREEYDVLDKRRGRDPEMG GKPRRKNPQEGLYNELQKDKMAEAYSEIGMKGERRRGKGHDGLYQGLSTATKDT YDALHMQALPPR |
| 167 N-HA-IgC-G545-53B6 | MALPVTALLLPLALLLHAARPGYPYDVPDYAALGSDLHVDVKGYKDGGIHLECR STGWYPQPQIQWSNNKGENIPTVEAPVVADGVGLYAVAASVIMRGSSGEGVSCT IRSSLLGLEKTASISIADPFFRSAQRWIAALAGTGGGGSGGGGSGGGSGGGSGS GGGGSGGGGSGGGGSGGGGSGGGGSQVQLQESGPGLVKPSETLSLTCTVSGGSI SYYSWTWVRQPAGQGLEWIGRIHISGVTNHNPSLKSRVSMSIDTSRTQFSLRLT SVTAADTAVYFCARSGGTYSAFDIWGQGTMVTVSSGGGGSGGGGSGGGGSGGGG SEIVLTQSPGTLSLSPGERSTLSCRASQSFTSNYLAWYQQRPGQAPRLLIYGAS TRAIGIPDRFSGSGSGTDFTLTISRLEPEDFAVYYCQQYGSSPWTFGQGTKVEI KTTTPAPRPPTPAPTIASQPLSLRPEACRPAAGGAVHTRGLDFACDIYIWAPLA GTCGVLLLSLVITLYCKRGRKKLLYIFKQPFMRPVQTTQEEDGCSCRFPEEEEG GCELRVKFSRSADAPAYQQGQNQLYNELNLGRREEYDVLDKRRGRDPEMGGKPR RKNPQEGLYNELQKDKMAEAYSEIGMKGERRRGKGHDGLYQGLSTATKDTYDAL HMQALPPR |
| 168 N-HA-BTN3A1-G545-53B6 | MALPVTALLLPLALLLHAARPGYPYDVPDYAQFSVLGPSGPILAMVGEDADLPC HLFPTMSAETMELKWVSSSLRQVVNVYADGKEVEDRQSAPYRGRTSILRDGITA GKAALRIHNVTASDSGKYLCYFQDGDFYEKALVELKVAALGSDLHVDVKGYKDG GIHLECRSTGWYPQPQIQWSNNKGENIPTVEAPVVADGVGLYAVAASVIMRGSS GEGVSCTIRSSLLGLEKTASISIADPFFRSAQRWIAALAGTGGGGSGGGGSGGG SGGGGSGSGGGGSGGGGSGGGGSGGGGSGGGGSQVQLQESGPGLVKPSETLSLTC TVSGGSISYYSWTWVRQPAGQGLEWIGRIHISGVTNHNPSLKSRVSMSIDTSRT QFSLRLTSVTAADTAVYFCARSGGTYSAFDIWGQGTMVTVSSGGGGSGGGGSGG GGSGGGGSEIVLTQSPGTLSLSPGERSTLSCRASQSFTSNYLAWYQQRPGQAPR LLIYGASTRAIGIPDRFSGSGSGTDFTLTISRLEPEDFAVYYCQQYGSSPWTFG QGTKVEIKTTTPAPRPPTPAPTIASQPLSLRPEACRPAAGGAVHTRGLDFACDI YIWAPLAGTCGVLLLSLVITLYCKRGRKKLLYIFKQPFMRPVQTTQEEDGCSCR FPEEEEGGCELRVKFSRSADAPAYQQGQNQLYNELNLGRREEYDVLDKRRGRDP EMGGKPRRKNPQEGLYNELQKDKMAEAYSEIGMKGERRRGKGHDGLYQGLSTAT KDTYDALHMQALPPR |
| 169 N-HA-sec49k-GS45-53B6 | MALPVTALLLPLALLLHAARPGYPYDVPDYAGFHTINATWWANITLVGPPDTPV TWYDTQGLWFCNGSRVKNPQIRHTCNDQNLTLIHVNKTYERTYMGYNRQGTKKE DYKVVVIPPPPATVKPQPEPEYVFVYMGENKTLEGPPGTPVTWFNQDGKKFCEG EKVLHPEFNHTCDKQNLILLFVNPTHDGAYLGYNHQGTQRTHYEVTVLDLFPDS GQMKIENHSEETEQKNDEHHNWQKQGGQKQGGQKTNQTKVNDRRKTAQKRPSKL KPATIEAMLVTVTAGSNLTLVGPKAEGKVTWFDGDLKRPCEPNYRLRHECNNQN LTLINVTKDYEGTYYGTNDKDEGKRYRVKVNTTNSQSVKIQPYTRQTTPDQEHK FELQFETNGNYDSKIPGGGGSGGGGSGGGSGGGSGSGGGGSGGGGSGGGGSGGG GSGGGGSQVQLQESGPGLVKPSETLSLTCTVSGGSISYYSWTWVRQPAGQGLEW IGRIHISGVTNHNPSLKSRVSMSIDTSRTQFSLRLTSVTAADTAVYFCARSGGT YSAFDIWGQGTMVTVSSGGGGSGGGGSGGGGSGGGGSEIVLTQSPGTLSLSPGE RSTLSCRASQSFTSNYLAWYQQRPGQAPRLLIYGASTRAIGIPDRFSGSGSGTD FTLTISRLEPEDFAVYYCQQYGSSPWTFGQGTKVEIKTTTPAPRPPTPAPTIAS QPLSLRPEACRPAAGGAVHTRGLDFACDIYIWAPLAGTCGVLLLSLVITLYCKR GRKKLLYIFKQPFMRPVQTTQEEDGCSCRFPEEEEGGCELRVKFSRSADAPAYQ QGQNQLYNELNLGRREEYDVLDKRRGRDPEMGGKPRRKNPQEGLYNELQKDKMA EAYSEIGMKGERRRGKGHDGLYQGLSTATKDTYDALHMQALPPR |

TABLE 2-continued

Exemplary Protein Sequences

| SEQ ID NO: Name | Amino Acid Sequence |
|---|---|
| 170N-HA-UL11-GS45-53B6 | MALPVTALLLPLALLLHAARPGYPYDVPDYAHDACIPVVGKIGTNVTLNAVDFH<br>PGDHVRWSYGPGGAGYMLCVYTGSWTEYKKPDIIFKCLSNNSLLLINVTVNYTN<br>TYRTLTSLNNWVHNQHHHKFPGWNLDTCYSLTVNENGTFPTTTTKKPTTTTRTT<br>TTTTTKKTTTTRTTTAAKKTTISTTHHKHSSPKKSSTPNSHVEHHVGFEATAAE<br>TPLQPSPQHQHVATHGGGGSGGGGSGGGSGGGSGSGGGGSGGGGSGGGGSGGGG<br>SGGGGSQVQLQESGPGLVKPSETLSLTCTVSGGSISYYSWTWVRQPAGQGLEWI<br>GRIHISGVTNHNPSLKSRVSMSIDTSRTQFSLRLTSVTAADTAVYFCARSGGTY<br>SAFDIWGQGTMVTVSSGGGGSGGGGSGGGGSGGGGSEIVLTQSPGTLSLSPGER<br>STLSCRASQSFTSNYLAWYQQRPGQAPRLLIYGASTRAIGIPDRFSGSGSGTDF<br>TLTISRLEPEDFAVYYCQQYGSSPWTFGQGTKVEIKTTTPAPRPPTPAPTIASQ<br>PLSLRPEACRPAAGGAVHTRGLDFACDIYIWAPLAGTCGVLLLSLVITLYCKRG<br>RKKLLYIFKQPFMRPVQTTQEEDGCSCRFPEEEEGGCELRVKFSRSADAPAYQQ<br>GQNQLYNELNLGRREEYDVLDKRRGRDPEMGGKPRRKNPQEGLYNELQKDKMAE<br>AYSEIGMKGERRRGKGHDGLYQGLSTATKDTYDALHMQALPPR |

MUC16-Specific CARs

In another aspect, provided herein is a CAR that specifically binds to MUC16, wherein the CAR comprises an extracellular ligand-binding domain comprising: a $V_H$ region having the sequence shown in SEQ ID NO: 58, and/or a $V_L$ region having the sequence shown in SEQ ID NO: 59. In some embodiments, the $V_H$ and $V_L$ are linked together by a flexible linker. In some embodiments, a flexible linker comprises the amino acid sequence shown in SEQ ID NO: 57 ((GGGGS)$_3$).

In another aspect, provided is a MUC16 specific chimeric antigen receptor (CAR) comprising an extracellular ligand-binding domain, a first transmembrane domain, and an intracellular signaling domain, wherein the extracellular domain comprises a single chain Fv fragment (scFv) comprising a heavy chain variable ($V_H$) region and a light chain variable ($V_L$) region, wherein the $V_H$ region comprises (i) a $V_H$ complementarity determining region one (CDR1) having the amino acid sequence shown in SEQ ID NO:60 or 63; (ii) a VH complementarity determining region two (CDR2) having the amino acid sequence shown in SEQ ID NO: 61 or 64; and (iii) a $V_H$ complementarity determining region three (CDR3) having the amino acid sequence shown in SEQ ID NO:62 or 65.

In another aspect, provided is a MUC16 specific chimeric antigen receptor (CAR) comprising an extracellular ligand-binding domain, a first transmembrane domain, and an intracellular signaling domain, wherein the extracellular domain comprises a single chain Fv fragment (scFv) comprising a heavy chain variable ($V_H$) region and a light chain variable ($V_L$) region, wherein the $V_L$ region comprises (i) a $V_L$ complementarity determining region one (CDR1) having the amino acid sequence shown in SEQ ID NO: 66 or 69; (ii) a $V_L$ complementarity determining region two (CDR2) having the amino acid sequence shown in SEQ ID NO: 67 or 70; and (iii) a $V_L$ complementarity determining region three (CDR3) having the amino acid sequence shown in SEQ ID NO: 68 or 71.

In another aspect, provided is a MUC16 specific chimeric antigen receptor (CAR) comprising an extracellular ligand-binding domain, a first transmembrane domain, and an intracellular signaling domain, wherein the extracellular domain comprises a single chain Fv fragment (scFv) comprising a heavy chain variable ($V_H$) region and a light chain variable ($V_L$) region, wherein (a) the $V_H$ region comprises (i) a $V_H$ complementarity determining region one (CDR1) having the amino acid sequence shown in SEQ ID NO: 60 or 63; (ii) a VH complementarity determining region two (CDR2) having the amino acid sequence shown in SEQ ID NO: 61 or 64; and (iii) a $V_H$ complementarity determining region three (CDR3) having the amino acid sequence shown in SEQ ID NO: 62 or 65; and (b) the $V_L$ region comprises (i) a $V_L$ complementarity determining region one (CDR1) having the amino acid sequence shown in SEQ ID NO: 66; (ii) a $V_L$ complementarity determining region two (CDR2) having the amino acid sequence shown in SEQ ID NO:67; and (iii) a $V_L$ complementarity determining region three (CDR3) having the amino acid sequence shown in SEQ ID NO: 68.

Also provided herein are CDR portions of antigen binding domains of antibodies to MUC16 or CDR portions of extracellular ligand-binding domains of CARs to MUC16 (including Chothia, Kabat CDRs, and CDR contact regions). Determination of CDR regions is well within the skill of the art. It is understood that in some embodiments, CDRs can be a combination of the Kabat and Chothia CDR (also termed "combined CRs" or "extended CDRs"). In some embodiments, the CDRs are the Kabat CDRs. In other embodiments, the CDRs are the Chothia CDRs. In other words, in embodiments with more than one CDR, the CDRs may be any of Kabat, Chothia, combination CDRs, or combinations thereof.

TABLE 3

53B6 MUC16 CAR component sequences

| Clone | | SEQ ID NO: |
|---|---|---|
| | VH Sequence | |
| 53B6-VH | QVQLQESGPGLVKPSETLSLTCTVSGGSISYYSWTWVRQPA<br>GQGLEWIGRIHISGVTNHNPSLKSRVSMSIDTSRTQFSLRL<br>TSVTAADTAVYFCARSGGTYSAFDIWGQGTMVTVSS | 58 |

TABLE 3-continued

53B6 MUC16 CAR component sequences

| Clone | | SEQ ID NO: |
|---|---|---|
| | VL sequence | |
| 53B6-VL | EIVLTQSPGTLSLSPGERSTLSCRASQSFTSNYLAWYQQRP GQAPRLLIYGASTRAIGIPDRFSGSGSGTDFTLTISRLEPE DFAVYYCQQYGSSPWTFGQGTKVEIK | 59 |
| | CDRs for 53B6 VH (Kabat definition) | |
| CDR1 | YYSWT | 60 |
| CDR2 | RIHISGVTNHNPSLKS | 61 |
| CDR3 | SGGTYSAFDI | 62 |
| | CDRs for 53B6 VH (Chothia definition) | |
| CDR1 | SGGSISYY | 63 |
| CDR2 | HISGV | 64 |
| CDR3 | SGGTYSAFDI | 65 |
| | CDRs for 53B6 VL (Kabat definition) | |
| CDR1 | RASQSFTSNYLA | 66 |
| CDR2 | GASTRAI | 67 |
| CDR3 | QQYGSSPWT | 68 |
| | CDRs for 53B6 VL (Chothia definition) | |
| CDR1 | RASQSFTSNYLA | 69 |
| CDR2 | GASTRAI | 70 |
| CDR3 | QQYGSSPWT | 71 |
| | CAR Amino Acid Sequences | |
| CD8α signal sequence | MALPVTALLLPLALLLHAARP | 1 |
| GS linker 2 | GGGGSGGGGSGGGGSGGGGS | 72 |
| CD8α hinge and transmembrane regions | TTTPAPRPPTPAPTIASQPLSLRPEACRPAAGGAVHTRGLD FACDIYIWAPLAGTCGVLLLSLVIT | 73 |
| 41BB cytoplasmic signaling domain | KRGRKKLLYIFKQPFMRPVQTTQEEDGCSCRFPEEEEGGCE L | 33 |
| CD3ζ cytoplasmic signaling domain | RVKFSRSADAPAYQQGQNQLYNELNLGRREEYDVLDKRRGR DPEMGGKPRRKNPQEGLYNELQKDKMAEAYSEIGMKGERRR GKGHDGLYQGLSTATKDTYDALHMQALPPR | 34 |
| | Mimotope sequences | |
| Rituximab | | |
| Mimotope | CPYSNPSLC | 50 |
| QBEND-10 | | |
| Epitope | ELPTQGTFSNVSTNVSPAKPTTTA | 74 |
| Epitope | ELPTQGTFSNVSTNVS | 179 |

TABLE 4

53B6 CAR sequences

| Clone Name | Name/Component | Sequence | SEQ ID NO: |
|---|---|---|---|
| 53B6 | CD8α signal sequence, 53B6 scFv, CD8α hinge and transmembrane regions, 41BB cytoplasmic signaling domain, CD3ζ cytoplasmic signaling domain | *MALPVTALLLPLALLLHAARP*QVQLQESGPGLVKPS ETLSLTCTVSGGSISYYSWTWVRQPAGQGLEWIGRI HISGVTNHNPSLKSRVSMSIDTSRTQFSLRLTSVTA ADTAVYFCARSGGTYSAFDIWGQGTMVTVSSGGGGS GGGGSGGGGSGGGGSEIVLTQSPGTLSLSPGERSTL SCRASQSFTSNYLAWYQQRPGQAPRLLIYGASTRAI GIPDRFSGSGSGTDFTLTISRLEPEDFAVYYCQQYG SSPWTFGQGTKVEIKTTTPAPRPPTPAPTIASQPLS LRPEACRPAAGGAVHTRGLDFACDIYIWAPLAGTCG VLLLSLVITLYCKRGRKKLLYIFKQPFMRPVQTTQE EDGCSCRFPEEEEGGCELRVKFSRSADAPAYQQGQN QLYNELNLGRREEYDVLDKRRGRDPEMGGKPRRKNP QEGLYNELQKDKMAEAYSEIGMKGERRRGKGHDGLY QGLSTATKDTYDALHMQALPPR | 75 |
| 53B6-SR2 | CD8α signal sequence, 53B6 scFv, CD20 mimotope, CD20 mimotope, CD8α hinge and transmembrane regions, 41BB cytoplasmic signaling domain, CD3ζ cytoplasmic signaling domain | *MALPVTALLLPLALLLHAARP*QVQLQESGPGLVKPS ETLSLTCTVSGGSISYYSWTWVRQPAGQGLEWIGRI HISGVTNHNPSLKSRVSMSIDTSRTQFSLRLTSVTA ADTAVYFCARSGGTYSAFDIWGQGTMVTVSSGGGGS GGGGSGGGGSGGGGSEIVLTQSPGTLSLSPGERSTL SCRASQSFTSNYLAWYQQRPGQAPRLLIYGASTRAI GIPDRFSGSGSGTDFTLTISRLEPEDFAVYYCQQYG SSPWTFGQGTKVEIKGSGGGGS<u>CPYSNPSLC</u>SGGGG SCPYSNPSLCSGGGGSTTTPAPRPPTPAPTIASQPL SLRPEACRPAAGGAVHTRGLDFACDIYIWAPLAGTC GVLLLSLVITLYCKRGRKKLLYIFKQPFMRPVQTTQ EEDGCSCRFPEEEEGGCELRVKFSRSADAPAYQQGQ NQLYNELNLGRREEYDVLDKRRGRDPEMGGKPRRKN PQEGLYNELQKDKMAEAYSEIGMKGERRRGKGHDGL YQGLSTATKDTYDALHMQALPPR | 76 |
| 53B6-RSR | CD8α signal sequence, CD20 mimotope, 53B6 scFv, CD20 mimotope, CD8α hinge and transmembrane regions, 41BB cytoplasmic signaling domain, CD3ζ cytoplasmic signaling domain | *MALPVTALLLPLALLLHAARP*GGGGS<u>CPYSNPSLC</u>G GGGSQVQLQESGPGLVKPSETLSLTC<del>T</del>VSGGSISYY SWTWVRQPAGQGLEWIGRIHISGVTNHNPSLKSRVS MSIDTSRTQFSLRLTSVTAADTAVYFCARSGGTYSA FDIWGQGTMVTVSSGGGGSGGGGSGGGGSGGGGSEI VLTQSPGTLSLSPGERSTLSCRASQSFTSNYLAWYQ QRPGQAPRLLIYGASTRAIGIPDRFSGSGSGTDFTL TISRLEPEDFAVYYCQQYGSSPWTFGQGTKVEIKGG GGS<u>CPYSNPSLC</u>TTTPAPRPPTPAPTIASQPLSLRP EACRPAAGGAVHTRGLDFACDIYIWAPLAGTCGVLL LSLVITLYCKRGRKKLLYIFKQPFMRPVQTTQEEDG CSCRFPEEEEGGCELRVKFSRSADAPAYQQGQNQLY NELNLGRREEYDVLDKRRGRDPEMGGKPRRKNPQEG LYNELQKDKMAEAYSEIGMKGERRRGKGHDGLYQGL STATKDTYDALHMQALPPR | 77 |
| 53B6-R2S | CD8α signal sequence, CD20 mimotope, CD20 mimotope, 53B6 scFv, CD8α hinge and transmembrane regions, 41BB cytoplasmic signaling domain, CD3ζ cytoplasmic signaling domain | *MALPVTALLLPLALLLHAARP*GGGGS<u>CPYSNPSLC</u>G GGGSCPYSNPSLCGGGGSQVQLQESGPGLVKPSETL SLTC<del>T</del>VSGGSISYYSWTWVRQPAGQGLEWIGRIHIS GVTNHNPSLKSRVSMSIDTSRTQFSLRLTSVTAADT AVYFCARSGGTYSAFDIWGQGTMVTVSSGGGGSGGG GSGGGGSGGGGSEIVLTQSPGTLSLSPGERSTLSCR ASQSFTSNYLAWYQQRPGQAPRLLIYGASTRAIGIP DRFSGSGSGTDFTLTISRLEPEDFAVYYCQQYGSSP WTFGQGTKVEIKTTTPAPRPPTPAPTIASQPLSLRP EACRPAAGGAVHTRGLDFACDIYIWAPLAGTCGVLL LSLVITLYCKRGRKKLLYIFKQPFMRPVQTTQEEDG CSCRFPEEEEGGCELRVKFSRSADAPAYQQGQNQLY NELNLGRREEYDVLDKRRGRDPEMGGKPRRKNPQEG LYNELQKDKMAEAYSEIGMKGERRRGKGHDGLYQGL STATKDTYDALHMQALPPR | 78 |
| 53B6-QR3 | CD8α signal sequence, CD20 mimotope, 53B6 scFv, CD20 mimotope, QBEND-10 epitope, CD20 mimotope, hinge and transmembrane regions of human CD8α | *MALPVTALLLPLALLLHAARP*GGGGS<u>CPYSNPSLC</u>S GGGGSGGGGSQVQLQESGPGLVKPSETLSLTCTVSG GSISYYSWTWVRQPAGQGLEWIGRIHISGVTNHNPS LKSRVSMSIDTSRTQFSLRLTSVTAADTAVYFCARS GGTYSAFDIWGQGTMVTVSSGGGGSGGGGSGGGGSG GGGSEIVLTQSPGTLSLSPGERSTLSCRASQSFTSN YLAWYQQRPGQAPRLLIYGASTRAIGIPDRFSGSGS GTDFTLTISRLEPEDFAVYYCQQYGSSPWTFGQGTK VEIKGSGGGGS<u>CPYSNPSLC</u>SGGGGSELPTQGTFSN VSTNVSPAKPTTTA<u>CPYSNP</u>SLCTTTPAPRPPTPAP TIASQPLSLRPEACRPAAGGAVHTRGLDFACDIYIW APLAGTCGVLLLSLVITLYCKRGRKKLLYIFKQPFM | 79 |

TABLE 4-continued

53B6 CAR sequences

| Clone Name | Name/Component | Sequence | SEQ ID NO: |
|---|---|---|---|
| | molecule, 41BB signaling domain, CD3ζ signaling domain | RPVQTTQEEDGCSCRFPEEEEGGCELLRVKFSRSAD APAYQQGQNQLYNELNLGRREEYDVLDKRRGRDPEM GGKPRRKNPQEGLYNELQKDKMAEAYSEIGMKGERR RGKGHDGLYQGLSTATKDTYDALHMQALPPR | |
| 53B6-RSR (2) | CD8α signal sequence, CD20 mimotope, 53B6 scFv, CD20 mimotope, CD8α hinge and transmembrane regions, 41BB cytoplasmic signaling domain, CD3ζ cytoplasmic signaling domain | MALPVTALLLPLALLLHAARPGGGGSCPYSNPSLCG GGGSQVQLQESGPGLVKPSETLSLTCTVSGGSISYY SWTWVRQPAGQGLEWIGRIHISGVTNHNPSLKSRVS MSIDTSRTQFSLRLTSVTAADTAVYFCARSGGTYSA FDIWGQGTMVTVSSGGGGSGGGGSGGGGSGGGGSEI VLTQSPGTLSLSPGERSTLSCRASQSFTSNYLAWYQ QRPGQAPRLLIYGASTRAIGIPDRFSGSGSGTDFTL TISRLEPEDFAVYYCQQYGSSPWTFGQGTKVEIKGG GGSCPYSNPSLCGGGGSTTTPAPRPPTPAPTIASQP LSLRPEACRPAAGGAVHTRGLDFACDIYIWAPLAGT CGVLLLSLVITLYCKRGRKKLLYIFKQPFMRPVQTT QEEDGCSCRFPEEEEGGCELRVKFSRSADAPAYQQG QNQLYNELNLGRREEYDVLDKRRGRDPEMGGKPRRK NPQEGLYNELQKDKMAEAYSEIGMKGERRRGKGHDG LYQGLSTATKDTYDALHMQALPPR | 180 |

The disclosure encompasses modifications to the CARs and polypeptides shown in Table 4, including functionally equivalent CARs having modifications which do not significantly affect their properties and variants which have enhanced or decreased activity and/or affinity. For example, the amino acid sequence may be mutated to obtain an antibody with the desired binding affinity to MUC16. Modification of polypeptides is routine practice in the art and need not be described in detail herein. Examples of modified polypeptides include polypeptides with conservative substitutions of amino acid residues, one or more deletions or additions of amino acids which do not significantly deleteriously change the functional activity, or which mature (enhance) the affinity of the polypeptide for its ligand, or use of chemical analogs.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to an epitope or mimotope tag. Other insertional variants of the antibody molecule include the fusion to the N- or C-terminus of the antibody of an enzyme or a polypeptide which increases the half-life of the antibody in the blood circulation.

Substitution variants have at least one amino acid residue in the antibody molecule removed and a different residue inserted in its place. The sites of greatest interest for substitutional mutagenesis include the hypervariable regions, but FR alterations are also contemplated. Conservative substitutions are shown in Table 6 under the heading of "conservative substitutions." If such substitutions result in a change in biological activity, then more substantial changes, denominated "exemplary substitutions" in Table 6, or as further described below in reference to amino acid classes, may be introduced and the products screened.

In some embodiments, provided herein is a CAR, which specifically binds to MUC16, wherein the CAR comprises a $V_H$ region comprising a sequence shown in SEQ ID NO: 58; and/or a $V_L$ region comprising a sequence shown in SEQ ID NO: 59.

In some embodiments, the provided herein are CARs comprising CDR portions of antibodies to MUC16 antibodies based on CDR contact regions. CDR contact regions are regions of an antibody that imbue specificity to the antibody for an antigen. In general, CDR contact regions include the residue positions in the CDRs and Vernier zones which are constrained in order to maintain proper loop structure for the antibody to bind a specific antigen. See, e.g., Makabe et al., J. Biol. Chem., 283:1156-1166, 2007. Determination of CDR contact regions is well within the skill of the art.

The binding affinity ($K_D$) of the ligand binding domain of the MUC16 specific CAR as described herein to MUC16 (such as human MUC16 (e.g., Uniprot accession number: Q8WXI7)) can be for example about 0.1 to about 1000 nM, for example between about 0.5 nM to about 500 nM, or for example between about 1nM to about 250 nM. In some embodiments, the binding affinity is about any of 1000 nm, 750 nm, 500 nm, 400 nm, 300 nm, 250 nm, 200 nM, 100 nM, 90 nM, 80 nM, 70 nM, 60 nM, 50 nM, 45 nM, 40 nM, 35 nM, 30 nM, 25 nM, 20 nM, 19 nm, 18 nm, 17 nm, 16 nm, 15 nM, 10 nM, 8 nM, 7.5 nM, 7 nM, 6.5 nM, 6 nM, 5.5 nM, 5 nM, 4 nM, 3 nM, 2 nM, 1 nM, 0.5 nM, 0.3 nM or 0.1 nM.

In some embodiments, the binding affinity is less than about any of 1000 nm, 900 nm, 800 nm, 250 nM, 200 nM, 100 nM, 50 nM, 30 nM, 20 nM, 10 nM, 7.5 nM, 7 nM, 6.5 nM, 6 nM, 5 nM.

Monoclonal Antibody-Specific Epitopes and Mimotopes

In some embodiments, the extracellular domain of any one of the MUC16 specific CARs disclosed herein may comprise one or more epitopes or mimotopes specific for (i.e., specifically recognized by) a monoclonal antibody. These epitopes or mimotopes are also referred to herein as mAb-specific epitopes or mimotopes. In these embodiments, the extracellular domain comprises the $V_H$ and $V_L$ polypeptides that specifically bind to MUC16 and one or more epitopes or mimotopes that bind to one or more monoclonal antibodies (mAbs). CARs comprising the mAb-specific epitopes or mimotopes can be single-chain or multi-chain.

The inclusion of epitopes or mimotopes specific for monoclonal antibodies in the extracellular domain of the CARs described herein allows sorting and depletion of engineered immune cells expressing the CARs. In some embodiments, this feature also promotes recovery of endogenous MUC16 expressing cells that were depleted by administration of engineered immune cells expressing the CARs.

Accordingly, in some embodiments, the present disclosure relates to a method for sorting and/or depleting the engineered immune cells endowed with the CARs comprising mAb-specific epitopes or mimotopes and a method for promoting recovery of endogenous MUC16 expressing cells, such as bone marrow progenitor cells.

Several epitope- or mimotope-monoclonal antibody couples can be used to generate CARs comprising monoclonal antibody specific epitopes or mimotopes; in particular, those already approved for medical use, such as CD20 epitope or mimotope/rituximab as a non-limiting example.

In some embodiments, the monoclonal antibody specific for the epitope or mimotope may be conjugated with a cytotoxic drug. It is also possible to promote CDC cytotoxicity by using engineered antibodies on which are grafted component(s) of the complement system. In some embodiments, activation of the CAR-T cells can be modulated by depleting the cells using an antibody which recognizes the epitope or mimotope.

The disclosure also encompasses methods for sorting the engineered immune cells endowed with the MUC16 specific CARs expressing the mAb-specific epitope(s) or mimotope(s) and therapeutic methods where the activation of the engineered immune cells endowed with these CARs is modulated by depleting the cells using an antibody that targets the external ligand binding domain of said CARs.

CARs comprising one or more epitopes or mimotopes specifically recognized by a monoclonal antibody are disclosed in WO2016/120216, which is hereby incorporated by reference in its entirety. The one or more epitopes or mimotopes can be selected from any number of epitopes and mimotopes known in the art. In some embodiments, the one or more epitopes or mimotopes can be a target of a monoclonal antibody approved for medical use, such as, for example without limitation, the CD20 epitope or mimotope recognized by rituximab. In some embodiments, the one or more epitopes or mimotopes comprises any one or more of the amino acid sequences shown in SEQ ID NOs: 50, 51 and 74.

In some embodiments, the epitope or mimotope can be located between the scFv and the hinge of a CAR. In some embodiments, two instances of the same epitope or mimotope, separated by linkers, may be used in the CAR. For example, a polypeptide comprising 2 copies of the mimotope shown in SEQ ID NO: 50, separated by linkers, as shown in GSGGGGSCPYSNPSLCSGGGGSCPYSNPSLCSGGGGS (SEQ ID NO: 51), can be used within a CAR, located between the light chain variable region and the hinge.

In some embodiments, the extracellular binding domain of the CAR comprising the $V_H$ and $V_L$ polypeptides and the mAb-specific epitope(s) or mimotope(s) may have different structures depending on the position of insertion of the epitope(s) or mimotope(s) and the use of linkers. For example, the extracellular binding domain of the MUC16 specific CAR comprising mAb-specific epitopes or mimotopes may have one of the following structures (a mimotope may substitute for an epitope in the following structures):

$V_1$-$L_1$-$V_2$-$(L)_x$-Epitope1-$(L)_x$-;
$V_1$-$L_1$-$V_2$-$(L)_x$-Epitope1-$(L)_x$-Epitope2-$(L)_x$-;
$V_1$-$L_1$-$V_2$-$(L)_x$-Epitope1-$(L)_x$-Epitope2-$(L)_x$-Epitope3-$(L)_x$-;
$(L)_x$-Epitope1-$(L)_x$-$V_1$-$L_1$-$V_2$;
$(L)_x$-Epitope1-$(L)_x$-Epitope2-$(L)_x$-$V_1$-$L_1$-$V_2$;

Epitope1-$(L)_x$-Epitope2-$(L)_x$-Epitope3-$(L)_x$-$V_1$-$L_1$-$V_2$;
$(L)_x$-Epitope1-$(L)_x$-$V_1$-$L_1$-$V_2$-$(L)_x$-Epitope2-$(L)_x$;
$(L)_x$-Epitope1-$(L)_x$-$V_1$-$L_1$-$V_2$-$(L)_x$-Epitope2-$(L)_x$-Epitope3-$(L)_x$-;
$(L)_x$-Epitope1-$(L)_x$-$V_1$-$L_1$-$V_2$-$(L)_x$-Epitope2-$(L)_x$-Epitope3-$(L)_x$-Epitope4-$(L)_x$-;
$(L)_x$-Epitope1-$(L)_x$-Epitope2-$(L)_x$-$V_1$-$L_1$-$V_2$-$(L)_x$-Epitope3-$(L)_x$-;
$(L)_x$-Epitope1-$(L)_x$-Epitope2-$(L)_x$-$V_1$-$L_1$-$V_2$-$(L)_x$-Epitope3-$(L)_x$-Epitope4-$(L)_x$-;
$V_1$-$(L)_x$-Epitope1-$(L)_x$-$V_2$;
$V_1$-$(L)_x$-Epitope1-$(L)_x$-$V_2$-$(L)_x$-Epitope2-$(L)_x$;
$V_1$-$(L)_x$-Epitope1-$(L)_x$-$V_2$-$(L)_x$-Epitope2-$(L)_x$-Epitope3-$(L)_x$;
$V_1$-$(L)_x$-Epitope1-$(L)_x$-$V_2$-$(L)_x$-Epitope2-$(L)_x$-Epitope3-$(L)_x$-Epitope4-$(L)_x$;
$(L)_x$-Epitope1-$(L)_x$-$V_1$-$(L)_x$-Epitope2-$(L)_x$-$V_2$; or,
$(L)_x$-Epitope1-$(L)_x$-$V_1$-$(L)_x$-Epitope2-$(L)_x$-$V_2$-$(L)_x$-Epitope3-$(L)_x$;

wherein, $V_1$ is $V_L$ and $V_2$ is $V_H$ or $V_1$ is $V_H$ and $V_2$ is $V_L$ $L_1$ is a linker suitable to link the $V_H$ chain to the $V_L$ chain;

L is a linker comprising glycine and serine residues, and each occurrence of L in the extracellular binding domain can be identical or different to other occurrence of L in the same extracellular binding domain, for example SGGGG (SEQ ID NO: 185), GGGGS (SEQ ID NO: 178) or SGGGGS (SEQ ID NO: 186) (all of which occur, e.g., in SEQ ID NO:52), and, x is 0 or 1 and each occurrence of x is selected independently from the others; and, Epitope 1, Epitope 2, Epitope 3 and Epitope 4 are mAb-specific epitopes and can be identical or different.

In some embodiments, the extracellular binding domain of the CAR comprises the following sequence:

$V_1$-$L_1$-$V_2$-$(L)_x$-Epitope1-$(L)_x$-Epitope2-$(L)_x$-; or,
$(L)_x$-Epitope1-$(L)_x$-$V_1$-$L_1$-$V_2$-$(L)_x$-Epitope2-$(L)_x$-Epitope3-$(L)_x$-Epitope4-$(L)_x$-. wherein $V_1$, $V_2$, $L_1$, L, x and Epitope 1, Epitope 2, Epitope 3 and Epitope 4 are as defined above.

In some embodiments, any one of the MUC16 specific CARs disclosed herein may comprise one or more mAb-specific epitopes or mimotopes selected from a CD52 epitope or mimotope, a CD20 epitope or mimotope, a CD3 epitope or mimotope, a CD41 epitope or mimotope, a CD25 epitope or mimotope, a CD30 epitope or mimotope, an EGFR epitope or mimotope, a TNFα epitope or mimotope, a VEGF epitope or mimotope, a complement protein C5 epitope or mimotope, a CD11a epitope or mimotope, a CD33 epitope or mimotope, an alpha-4 integrin epitope or mimotope, an IgE Fc region epitope or mimotope, an RSV protein F epitope or mimotope, an IL-6 receptor epitope or mimotope, a HER2 receptor epitope or mimotope, an integrin $α_4β_7$ epitope or mimotope, a BAFF (B-cell activatin factor) epitope or mimotope, an IL-1β epitope or mimotope, a RANKL epitope or mimotope, a CTLA4 epitope or mimotope, a CD34 epitope or mimotope, an IL-12 epitope or mimotope, and/or an IL-23 epitope or mimotope.

In some embodiments, the MUC16 specific CARs disclosed herein may comprise one or more mAb-specific epitopes or mimotopes selected from epitopes and mimotopes specifically recognized by alemtuzumab, ibritumomab tiuxetan, muromonab-CD3, tositumomab, abciximab, basiliximab, brentuximab vedotin, cetuximab, infliximab, rituximab, bevacizumab, certolizumab pegol, daclizumab, eculizumab, efalizumab, gemtuzumab, natalizumab, omalizumab, palivizumab, ranibizumab, tocilizumab, trastuzumab, vedolizumab, adalimumab, belimumab, canakinumab, denosumab, golimumab, ipilimumab, ofatumumab, panitumumab, QBEND-10 and/or ustekinumab.

In some embodiments, the MUC16 specific CARs comprise one or more mAb-specific epitopes or mimotopes selected from the epitopes and mimotopes disclosed in Table 5:

TABLE 5

Examples of mAb-specific epitopes and mimotopes that can be used in the extracellular binding domain of the MUC16 specific CARs of the disclosure such as for example mimotopes and epitopes with their corresponding mAb.

| | | |
|---|---|---|
| Rituximab | | |
| Mimotope | SEQ ID NO: 50 | CPYSNPSLC |
| Palivizumab | | |
| Epitope | SEQ ID NO: 80 | NSELLSLINDMP ITNDQKKLMSNN |
| Cetuximab | | |
| Mimotope 1 | SEQ ID NO: 81 | CQFDLSTRRLKC |
| Mimotope 2 | SEQ ID NO: 82 | CQYNLSSRALKC |
| Mimotope 3 | SEQ ID NO: 83 | CVWQRWQKSYVC |
| Mimotope 4 | SEQ ID NO: 84 | CMWDRFSRWYKC |
| Nivolumab | | |
| Epitope 1 | SEQ ID NO: 85 | SFVLNWYRMSPS NQTDKLAAFPED R |
| Epitope 2 | SEQ ID NO: 86 | SGTYLCGAISLA PKAQIKE |
| QBEND-10 | | |
| Epitope | SEQ ID NO: 87 | ELPTQGTFSNVS TNVSPAKPTTTA |
| Alemtuzumab | | |
| Epitope | SEQ ID NO: 88 | GQNDTSQTSSPS |

The intracellular signaling domain of a CAR as disclosed herein is responsible for intracellular signaling following the binding of extracellular ligand-binding domain to the target resulting in the activation of the immune cell and immune response. The intracellular signaling domain has the ability to activate at least one of the normal effector functions of the immune cell in which the CAR is expressed. For example, the effector function of a T cell can be a cytolytic activity or helper activity including the secretion of cytokines.

Expression of Proteins in Cells and Related Embodiments

In some embodiments, an immune cell e.g. T cell of the disclosure comprises and/or expresses a polypeptide that comprises any one or more of the sequences listed in Tables 1-3 (SEQ ID NOs: 1-79). In some embodiments, an immune cell e.g. T cell of the disclosure comprises and/or expresses a nucleic acid e.g. a vector that encodes such a polypeptide.

In some embodiments, an immune cell e.g. T cell of the disclosure comprises and/or expresses a polypeptide that comprises the amino acid sequence of MUC16 CAR1 (53B6) (SEQ ID NO: 11). In some embodiments, an immune cell e.g. T cell of the disclosure comprises and/or expresses a polypeptide that comprises the amino acid sequence of Sec49k (SEQ ID NO: 12). In some embodiments, an immune cell e.g. T cell of the disclosure comprises and/or expresses a polypeptide that comprises the amino acid sequence of UL11 (SEQ ID NO: 13). In some embodiments, an immune cell e.g. T cell of the disclosure comprises and/or expresses a polypeptide that comprises the amino acid sequence of BTN3A1-IgV (SEQ ID NO: 14). In some embodiments, an immune cell e.g. T cell of the disclosure comprises and/or expresses a polypeptide that comprises the amino acid sequence of BTN3A1-IgC (SEQ ID NO: 15).

In some embodiments, an immune cell e.g. T cell of the disclosure comprises and/or expresses a nucleic acid e.g. a vector that encodes a protease-activating CD45-gate CAR disclosed herein. In some embodiments, an immune cell e.g. T cell of the disclosure comprises and/or expresses a nucleic acid e.g. a vector that comprises a nucleic acid sequence that encodes the amino acid sequence of a MUC16 CAR (53B6) (any of SEQ ID NOs: 11, 56, 75, 76, 77, 78, 79, and 121-170). In some embodiments, an immune cell e.g. T cell of the disclosure comprises and/or expresses a nucleic acid e.g. a vector that comprises a nucleic acid sequence that encodes the amino acid sequence of Sec49k (SEQ ID NO: 12). In some embodiments, an immune cell e.g. T cell of the disclosure comprises and/or expresses a nucleic acid e.g. a vector that comprises a nucleic acid sequence that encodes the amino acid sequence of UL11 (SEQ ID NO: 13). In some embodiments, an immune cell e.g. T cell of the disclosure comprises and/or expresses a nucleic acid e.g. a vector that comprises a nucleic acid sequence that encodes the amino acid sequence of BTN3A1-IgV (SEQ ID NO: 14). In some embodiments, an immune cell e.g. T cell of the disclosure comprises and/or expresses a nucleic acid e.g. a vector that comprises a nucleic acid sequence that encodes the amino acid sequence of BTN3A1-IgC (SEQ ID NO: 15).

The disclosure encompasses modifications to the proteins of the disclosure embodiments shown in Table 2, including functionally equivalent proteins having modifications which do not significantly affect their properties and variants which have enhanced or decreased activity and/or affinity. Modification of polypeptides is routine practice in the art and need not be described in detail herein. Examples of modified polypeptides include polypeptides with conservative substitutions of amino acid residues, one or more deletions or additions of amino acids which do not significantly deleteriously change the functional activity, or which mature (enhance) the affinity of the polypeptide for its ligand, or use of chemical analogs.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to an epitope or mimotope tag.

Substitution variants have at least one amino acid residue in the protein removed and a different residue inserted in its place. Conservative substitutions are shown in Table 6 under the heading of "conservative substitutions." If such substitutions result in a change in biological activity, then more substantial changes, denominated "exemplary substitutions" in Table 6, or as further described below in reference to amino acid classes, may be introduced and the products screened.

TABLE 6

Amino Acid Substitutions

| Original residue (naturally occurring amino acid) | Conservative substitutions | Exemplary subsitutions |
|---|---|---|
| Ala (A) | Val | Val; Leu; Ile |
| Arg (R) | Lys | Lys; Gln; Asn |
| Asn (N) | Gln | Gln; His; Asp; Lys; Arg |
| Asp (D) | Glu | Glu; Asn |
| Cys (C) | Ser | Ser; Ala |
| Gln (Q) | Asn | Asn; Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

Protease-activating CD45-gate CAR protein and protease-activating CD45-gate CAR protein derivatives may be synthesized in situ in the cell after introduction of polynucleotides encoding the proteins into the cell. Alternatively, protease-activating CD45-gate CAR protein and protease-activating CD45-gate CAR protein derivative proteins may be produced outside of cells, and then introduced into cells. Methods for introducing a polynucleotide construct into cells are known in the art. In some embodiments, stable transformation methods can be used to integrate the polynucleotide construct into the genome of the cell. In other embodiments, transient transformation methods can be used to transiently express the polynucleotide construct, and the polynucleotide construct not integrated into the genome of the cell. In other embodiments, virus-mediated methods can be used. The polynucleotides may be introduced into a cell by any suitable means such as for example, recombinant viral vectors (e.g. retroviruses e.g. lentiviruses, adenoviruses), liposomes, and the like. Transient transformation methods include, for example without limitation, microinjection, electroporation or particle bombardment. Polynucleotides may be included in vectors, such as for example plasmid vectors or viral vectors.

In some embodiments, an immune cell e.g. T cell of the disclosure can comprise at least one protease-activating CD45-gate CAR protein or protease-activating CD45-gate CAR protein derivative. In some embodiments, an immune cell e.g. T cell can comprise at least one protease-activating CD45-gate CAR protein or protease-activating CD45-gate CAR protein derivative and one or more additional CARs (gated or not gated), and each CAR may comprise different extracellular ligand-binding domains.

In some embodiments of an immune cell e.g. T cell provided herein, a CAR that the T cell expresses can comprise an extracellular ligand-binding domain (e.g., a single chain variable fragment (scFv)), a transmembrane domain, and an intracellular signaling domain. In some embodiments, the extracellular ligand-binding domain, transmembrane domain, and intracellular signaling domain are in one polypeptide, i.e., in a single chain. Multichain CARs and polypeptides are also provided herein. In some embodiments, the multichain CARs comprise: a first polypeptide comprising a transmembrane domain and at least one extracellular ligand-binding domain, and a second polypeptide comprising a transmembrane domain and at least one intracellular signaling domain, wherein the polypeptides assemble together to form a multichain CAR. The CAR can be modified as described herein to comprise a CD45 recruiting domain that is linked to the amino terminus of the CAR's extracellular ligand-binding domain.

The extracellular ligand-binding domain specifically binds to a target of interest. In some embodiments, the target of interest can be any molecule of interest, including, for example, without limitation, BCMA, MUC16 (also known as CA125), EGFR, EGFRvIII, MUC1, Flt-3, WT-1, CD20, CD23, CD30, CD38, CD70, CD33, CD133, MHC-WT1, TSPAN10, MHC-PRAME, MHC-NY-ESO1, HER2 (ERBB2), CAIX (Carbonic anhydrase IX), LIV1, ADAM10, CHRNA2, LeY, NKG2D, CS1, CD44v6, ROR1, CD19, Claudin-18.2 (Claudin-18A2, or Claudin18 isoform 2), PSCA, DLL3 (Delta-like protein 3, Drosophila Delta homolog 3, Delta3), Mud 7 (Mucin17, Muc3, Muc3), FAP alpha (Fibroblast Activation Protein alpha), Ly6G6D (Lymphocyte antigen 6 complex locus protein G6d, c6orf23, G6D, MEGT1, NG25), PSMA, MSLN, or RNF43 (E3 ubiquitin-protein ligase RNF43, RING finger protein 43).

In some embodiments, the extracellular ligand-binding domain comprises an scFv comprising the light chain variable ($V_L$) region and the heavy chain variable ($V_H$) region of a target antigen specific monoclonal antibody joined by a flexible linker. Single chain variable region fragments are made by linking light and/or heavy chain variable regions by using a short linking peptide (Bird et al., Science 242:423-426, 1988). An example of a linking peptide is the GS linker having the amino acid sequence (GGGGS)3 (SEQ ID NO: 57), which bridges approximately 3.5 nm between the carboxy terminus of one variable region and the amino terminus of the other variable region. Linkers of other sequences have been designed and used (Bird et al., 1988, supra). In general, linkers can be short, flexible polypeptides and preferably comprised of about 20 or fewer amino acid residues. Linkers can in turn be modified for additional functions, such as attachment of drugs or attachment to solid supports. The single chain variants can be produced either recombinantly or synthetically. For synthetic production of scFv, an automated synthesizer can be used. For recombinant production of scFv, a suitable plasmid or other vector containing a polynucleotide that encodes the scFv can be introduced into a suitable host cell, either eukaryotic, such as yeast, plant, insect or mammalian cells, or prokaryotic, such as E. coli. Polynucleotides encoding the scFv of interest can be made by routine manipulations such as ligation of polynucleotides. The resultant scFv can be isolated using standard protein purification techniques known in the art.

In some embodiments, a flexible linker as described herein is modified to comprise a protease cleavage site and the modified linker connects the CD45 recruiting domain of the protease-activating CD45-gate CAR described herein to the antigen binding domain of the protease-activating CD45-gate CAR. An example of such a modified linker comprises the amino acid sequence of SEQ ID NO: 9.

The intracellular signaling domain of a protease-activating CD45-gate CAR according to the disclosure is responsible for intracellular signaling following the binding of extracellular ligand-binding domain to the target resulting in the activation of the immune cell and immune response. The intracellular signaling domain has the ability to activate at least one of the normal effector functions of the immune cell in which the protease-activating CD45-gate CAR is expressed. For example, the effector function of a T cell can be a cytolytic activity or helper activity including the secretion of cytokines.

In some embodiments, an intracellular signaling domain for use in a protease-activating CD45-gate CAR can be the cytoplasmic sequences of, for example without limitation, the T cell receptor and co-receptors that act in concert to initiate signal transduction following antigen receptor engagement, as well as any derivative or variant of these sequences and any synthetic sequence that has the same functional capability. Intracellular signaling domains comprise two distinct classes of cytoplasmic signaling sequences: those that initiate antigen-dependent primary activation, and those that act in an antigen-independent manner to provide a secondary or co-stimulatory signal. Primary cytoplasmic signaling sequences can comprise signaling motifs which are known as immunoreceptor tyrosine-based activation motifs or ITAMs. ITAMs are well defined signaling motifs found in the intracytoplasmic tail of a variety of receptors that serve as binding sites for syk/zap70 class tyrosine kinases. Examples of ITAM used in the protease-activating CD45-gate CARs of the disclosure can include as non-limiting examples those derived from TCRζ, FcRγ, FcRβ, FcRε, CD3γ, CD3δ, CD3ε, CD5, CD22, CD79a, CD79b and CD66d. In some embodiments, the intracellular signaling domain of the CAR can comprise the CD3ζ signaling domain (e.g. comprising or consisting of the amino acid sequence of SEQ ID NO: 34).

In some embodiments the intracellular signaling domain of the protease-activating CD45-gate CAR of the disclosure comprises a domain of a co-stimulatory molecule. In some embodiments, the intracellular signaling domain of a protease-activating CD45-gate CAR of the disclosure comprises a part of a co-stimulatory molecule selected from the group consisting of a fragment of 41BB (GenBank: AAA53133, e.g. comprising or consisting of the amino acid sequence of SEQ ID NO: 33) and CD28 (NP_006130.1, e.g. comprising or consisting of the amino acid sequence of SEQ ID NO: 35). In some embodiments, the intracellular signaling domain of the CAR of the disclosure comprises an amino acid sequence which comprises at least 70%, preferably at least 80%, more preferably at least 90%, 95%, 97%, or 99% sequence identity with one or more of the amino acid sequences shown in SEQ ID NOs: 33-35.

CARs generally are expressed on the surface membrane of the cell. Thus, the protease-activating CD45-gate CAR disclosed herein can comprise a transmembrane domain. Suitable transmembrane domains for a protease-activating CD45-gate CAR disclosed herein have the ability to (a) be expressed at the surface of a cell, for example an immune cell such as, for example without limitation, lymphocyte cells (e.g. T cells) or Natural killer (NK) cells, and (b) interact with the ligand-binding domain and intracellular signaling domain for directing a cellular response of an immune cell against a predefined target cell. The transmembrane domain can be derived either from a natural or from a synthetic source. The transmembrane domain can be derived from any membrane-bound or transmembrane protein. As non-limiting examples, the transmembrane polypeptide can be a domain of the T cell receptor such as α, β, γ or δ, polypeptide constituting CD3 complex, IL-2 receptor e.g. p55 (α chain), p75 (β chain or γ chain), subunit chain of Fc receptors, in particular Fcγ receptor III or CD proteins. Alternatively, the transmembrane domain can be synthetic and can comprise predominantly hydrophobic residues such as leucine and valine. In some embodiments said transmembrane domain is derived from the human CD8α chain (e.g., NP_001139345.1). The protease-activating CD45-gate CAR can further comprise a stalk domain between the extracellular ligand-binding domain and said transmembrane domain. A stalk domain may comprise up to 300 amino acids, for example, from 10 to 100 amino acids or 25 to 50 amino acids. The stalk region may be derived from all or part of naturally occurring molecules, such as from all or part of the extracellular region of CD8, CD4, or CD28, or from all or part of an antibody constant region. Alternatively the stalk domain may be a synthetic sequence that corresponds to a naturally occurring stalk sequence, or may be an entirely synthetic stalk sequence. In some embodiments said stalk domain is a part of human CD8α chain (e.g., NP_001139345.1). In another particular embodiment, the transmembrane domain comprises a part of the human CD8α chain. In some embodiments, protease-activating CD45-gate CARs disclosed herein can comprise a CD45 recruiting domain, a protease-cleavable linker, an extracellular ligand-binding domain, CD8α human stalk and transmembrane domains, the CD3ζ signaling domain, and 4-1BB signaling domain. In some embodiments, a nucleic acid encoding a protease-activating CD45-gate CAR as disclosed herein can be introduced into an immune cell as a transgene via a vector e.g. a plasmid vector. In some embodiments, the vector e.g. plasmid vector can also contain, for example, a selection marker which provides for identification and/or selection of cells which received the vector.

Protease-activating CD45-gate CAR polypeptides may be synthesized in situ in the cell after introduction of polynucleotides encoding the protease-activating CD45-gate CAR polypeptides into the cell. Alternatively, protease-activating CD45-gate CAR polypeptides may be produced outside of cells, and then introduced into cells. Methods for introducing a polynucleotide construct into cells are known in the art. In some embodiments, stable transformation methods can be used to integrate the polynucleotide construct into the genome of the cell. In other embodiments, transient transformation methods can be used to transiently express the polynucleotide construct, and the polynucleotide construct not integrated into the genome of the cell. In other embodiments, virus-mediated methods can be used. The polynucleotides may be introduced into a cell by any suitable means such as for example, recombinant viral vectors (e.g. retroviruses (e.g. lentiviruses), adenoviruses), liposomes, and the like. Transient transformation methods include, for example without limitation, microinjection, electroporation or particle bombardment. Polynucleotides may be included in vectors, such as for example plasmid vectors or viral vectors.

Methods of generating engineered immune cells expressing any of the protease-activating CD45-gate CARs provided herein is described in WO/2016/166630, incorporated by reference in its entirety.

Also provided herein are immune cells e.g. T cells such as isolated T cells obtained according to any one of the methods described herein and modified e.g. engineered to comprise and express the nucleic acids, vectors and polypeptides disclosed herein. Any immune cell capable of expressing heterologous DNAs can be used for the purpose of expressing the protease-activating CD45-gate CAR protein or protease-activating CD45-gate CAR protein derivative and optionally any additional CAR of interest. In some embodiments, the immune cell is a T cell. In some embodiments, an immune cell can be derived from, for example without limitation, a stem cell. The stem cells can be adult stem cells, non-human embryonic stem cells, more particularly non-human stem cells, cord blood stem cells, progenitor cells, bone marrow stem cells, induced pluripotent stem cells, totipotent stem cells or hematopoietic stem cells. Representative human cells are CD34+ cells. The isolated cell can also be a dendritic cell, killer dendritic cell, a mast cell, a NK-cell, a B-cell or a T cell selected from the group consisting of inflammatory T-lymphocytes, cytotoxic T-lymphocytes, regulatory T-lymphocytes or helper T-lymphocytes. In some embodiments, the cell can be derived from the group consisting of CD4+ T-lymphocytes and CD8+ T-lymphocytes.

In some embodiments, the engineered immune cell disclosed herein is an engineered B cell, mast cell, myeloic-derived phagocyte, T cell e.g. an alpha/beta and/or gamma/delta T cell, tumor infiltrating lymphocyte (TIL), NK cell, TCR-expressing cell, dendritic cell, or NK-T cell. In some embodiments, the cell is and/or is derived from an autologous T cell. In some embodiments, the cell is and/or is derived from an allogeneic T cell.

In some embodiments, the immune cells e.g. T cells such as isolated T cells are further modified e.g. genetically modified by methods described herein (e.g. known gene editing techniques that employ, for example, TALENs, CRISPR/Cas9, or megaTAL nucleases).

Prior to expansion and genetic modification, a source of cells can be obtained from a subject through a variety of non-limiting methods. Cells can be obtained from a number of non-limiting sources, including peripheral blood mononuclear cells, bone marrow, lymph node tissue, cord blood, thymus tissue, tissue from a site of infection, ascites, pleural effusion, spleen tissue, and tumors. In some embodiments, any number of T cell lines available and known to those skilled in the art, may be used. In some embodiments, cells can be derived from a healthy donor, from a subject diagnosed with cancer or from a subject diagnosed with an infection. In some embodiments, cells can be part of a mixed population of cells which present different phenotypic characteristics.

In some embodiments, an isolated cell or engineered immune cell according to the present disclosure comprises one inactivated gene selected from the group consisting of CD52, GR, PD-1, CTLA-4, LAG3, Tim3, BTLA, BY55, TIGIT, B7H5, LAIR1, SIGLEC10, 2B4, HLA, TCRα and TCRβ and/or expresses a CAR, a multi-chain CAR and/or a pTa transgene. In some embodiments, an isolated cell comprises polynucleotides encoding polypeptides comprising a multi-chain CAR. In some embodiments, the isolated cell according to the present disclosure comprises two inactivated genes selected from the group consisting of: CD52 and GR, CD52 and TCRα, CDR52 and TCRβ, GR and TCRα, GR and TCRβ, TCRα and TCRβ, PD-1 and TCRα, PD-1 and TCRβ, CTLA-4 and TCRα, CTLA-4 and TCRβ, LAG3 and TCRα, LAG3 and TCRβ, Tim3 and TCRα, Tim3 and TCRβ, BTLA and TCRα, BTLA and TCRβ, BY55 and TCRα, BY55 and TCRβ, TIGIT and TCRα, TIGIT and TCRβ, B7H5 and TCRα, B7H5 and TCRβ, LAIR1 and TCRα, LAIR1 and TCRβ, SIGLEC10 and TCRα, SIGLEC10 and TCRβ, 2B4 and TCRα, 2B4 and TCRβ and/or expresses a CAR (e.g. the protease-activating CD45-gate CAR of the present disclosure or the anti-MUC16 CAR of the present disclosure), a multi-chain CAR and a pTα transgene.

Gene inactivation can be carried out by methods practiced by those with skill in the art. The methods include, but are not limited to gene inactivation by use of zinc fingers, TALEN®s, and CRISPR/Cas-based system.

In some embodiments, the protease-activating CD45-gate CAR-containing immune cell has an inactivated CD52 gene. In some embodiments only one copy of the CD52 gene is inactivated.

In some embodiments, the protease-activating CD45-gate CAR-containing immune cell has an inactivated TCRα gene.

In some embodiments, the protease-activating CD45-gate CAR-containing immune cell has an inactivated TCRβ gene.

In some embodiments, TALEN® is used for gene inactivation. In such embodiments, the efficiency of gene inactivation with TALEN® is not 100%, and resulting TCRαβ-negative T-cells are enriched by depleting residual TCRαβ-positive T cells before cryopreservation. However, CD52-negative cells are not purified, resulting in a cell product with varying frequencies of CD52-negative cells, typically between 60-80%. Accordingly in some embodiments, the genotype of the protease-activating CD45-gate CAR T cells of the disclosure is protease-activating CD45-gate CAR+_TCRαβ-_CD52+/− T-cells.

In some embodiments, TCR is rendered not functional in the cells according to the disclosure by inactivating TCRα gene and/or TCRβ gene(s). In some embodiments, a method to obtain modified cells derived from an individual is provided, wherein the cells can proliferate independently of the major histocompatibility complex (MHC) signaling pathway. Modified cells, which can proliferate independently of the MHC signaling pathway, susceptible to be obtained by this method are encompassed in the scope of the present disclosure. Modified cells disclosed herein can be used in for treating subjects in need thereof against Host versus Graft (HvG) rejection and Graft versus Host Disease (GvHD); therefore in the scope of the present disclosure is a method of treating subjects in need thereof against Host versus Graft (HvG) rejection and Graft versus Host Disease (GvHD) comprising treating said subject by administering to said subject an effective amount of modified cells comprising inactivated TCRα and/or TCRβ genes.

In some embodiments, the immune cells are engineered to be resistant to one or more chemotherapy drugs. The chemotherapy drug can be, for example, a purine nucleotide analogue (PNA), thus making the immune cell suitable for cancer treatment combining adoptive immunotherapy and chemotherapy. Exemplary PNAs include, for example, clofarabine, fludarabine, and cytarabine, alone or in combination. PNAs are metabolized by deoxycytidine kinase (dCK) into mono-, di-, and tri-phosphate PNA. Their tri-phosphate forms compete with ATP for DNA synthesis, act as pro-apoptotic agents, and are potent inhibitors of ribonucleotide reductase (RNR), which is involved in trinucleotide production. Provided herein are protease-activating CD45-gate CAR-T cells comprising an inactivated dCK gene. In some embodiments, the dCK knockout cells are made by transfection of T cells using polynucleotides encoding specific TAL-nuclease directed against dCK genes by, for example, electroporation of mRNA. The dCK knockout protease-activating CD45-gate CAR-T cells are resistant to PNAs, including for example clorofarabine and/or fludarabine, and maintain T cell cytotoxic activity toward cells that express the ligand of the protease-activating CD45-gate CAR.

In some embodiments, isolated cells or cell lines of the disclosure can comprise a pTα or a functional variant thereof. In some embodiments, an isolated cell or cell line can be further genetically modified by inactivating the TCRα gene.

In some embodiments, the CAR-T cell (e.g. protease-activating CD45-gate CAR-expressing T cell) comprises a polynucleotide encoding a safety switch, such as for example RQR8. See, e.g., WO2013153391A, which is hereby incorporated by reference in its entirety. In CAR-T cells comprising the polynucleotide, the safety switch polypeptide is expressed at the surface of a CAR-T cell. In some embodiments, the safety switch polypeptide comprises the amino acid sequence shown in SEQ ID NO: 48.

(SEQ ID NO: 48)
CPYSNPSLCSGGGGSELPTQGTFSNVSTNVSPAKPTTTACPYSNPSLCSG

GGGSPAPRPPTPAPTIASQPLSLRPEACRPAAGGAVHTRGLDFACDIYIW

APLAGTCGVLLLSLVITLYCNHRNRRRVCKCPRPVV

The safety switch polypeptide may also comprise a signal peptide at the amino terminus. In some embodiments, the safety switch polypeptide comprises the amino acid sequence shown in SEQ ID NO: 49.

(SEQ ID NO: 49)
MGTSLLCWMALCLLGADHADACPYSNPSLCSGGGGSELPTQGTFSNVSTN

VSPAKPTTTACPYSNPSLCSGGGGSPAPRPPTPAPTIASQPLSLRPEACR

PAAGGAVHTRGLDFACDIYIWAPLAGTCGVLLLSLVITLYCNHRNRRRVC

KCPRPVV

When the safety switch polypeptide is expressed at the surface of a CAR-T cell, binding of rituximab to the R epitopes or mimotopes of the polypeptide causes lysis of the cell. More than one molecule of rituximab may bind per polypeptide expressed at the cell surface. Each R epitope or mimotope of the polypeptide may bind a separate molecule of rituximab. Deletion of protease-activating CD45-gate CAR-T cells may occur in vivo, for example by administering rituximab to a subject. The decision to delete the transferred cells may arise from undesirable effects being detected in the subject which are attributable to the transferred cells, such as for example, when unacceptable levels of toxicity are detected.

In some embodiments, the CAR-T cell comprises a selected epitope or mimotope within the scFv or extracellular domain (e.g. stalk domain) of the protease-activating CD45-gate CAR, the selected epitope or mimotope having a specificity to be recognized by a specific antibody. See, e.g., PCT application PCT/EP2016/051467, WO2016/120216, "mAb-DRIVEN CHIMERIC ANTIGEN RECEPTOR SYSTEMS FOR SORTING/DEPLETING ENGINEERED IMMUNE CELLS," filed on Jan. 25, 2016, which is hereby incorporated by reference in its entirety. Such an epitope or mimotope facilitates sorting and/or depleting the CAR-T cells. The epitope or mimotope can be selected from any number of epitopes and mimotopes known in the art. In some embodiments, the epitope or mimotope can be a target of a monoclonal antibody approved for medical use, such as, for example without limitation, a CD20 epitope or mimotope recognized by rituximab. In some embodiments, the epitope or mimotope comprises the amino acid sequence shown in SEQ ID NO: 50.

(SEQ ID NO: 50)
CPYSNPSLC

In some embodiments, the epitope or mimotope is located within the CAR. For example without limitation, the epitope or mimotope can be located between the scFv and the hinge of a CAR. In some embodiments, two instances of the same epitope or mimotope, separate by linkers, may be used in the CAR. For example, the polypeptide comprising the amino acid sequence shown in SEQ ID NO: 51 can be used within a CAR, located between the light chain variable region and the hinge.

(SEQ ID NO: 51)
GSGGGGSCPYSNPSLCSGGGGSCPYSNPSLCSGGGGS

In some embodiments, the epitope- or mimotope-specific antibody may be conjugated with a cytotoxic drug. It is also possible to promote CDC cytotoxicity by using engineered antibodies on which are grafted component(s) of the complement system. In some embodiments, activation of the CAR-T cells can be modulated by depleting the cells using an antibody which recognizes the epitope or mimotope.

Adverse events also may be minimized by transducing the immune cells (containing one or more CARs) with a suicide gene. It may also be desired to incorporate an inducible "on" or "accelerator" switch into the immune cells. Suitable techniques include use of inducible caspase-9 (U.S. Appl. 2011/0286980) or a thymidine kinase, before, after or at the same time, as the cells are transduced with the CAR construct of the present disclosure. Additional methods for introducing suicide genes and/or "on" switches include TALENS, zinc fingers, RNAi, siRNA, shRNA, antisense technology, and other techniques known in the art.

In accordance with the disclosure, additional on-off or other types of control switch techniques may be incorporated herein. These techniques may employ the use of dimerization domains and optional activators of such domain dimerization. These techniques include, e.g., those described by Wu et al., Science 2014 350 (6258) utilizing FKBP/Rapalog dimerization systems in certain cells, the contents of which are incorporated by reference herein in their entirety. Additional dimerization technology is described in, e.g., Fegan et al. Chem. Rev. 2010, 110, 3315-3336 as well as U.S. Pat. Nos. 5,830,462; 5,834,266; 5,869,337; and 6,165,787, the contents of which are also incorporated by reference herein in their entirety. Additional dimerization pairs may include cyclosporine-A/cyclophilin, receptor, estrogen/estrogen receptor (optionally using tamoxifen), glucocorticoids/glucocorticoid receptor, tetracycline/tetracycline receptor, vitamin D/vitamin D receptor. Further examples of dimerization technology can be found in e.g., WO 2014/127261, WO 2015/090229, US 2014/0286987, US2015/0266973, US2016/0046700, U.S. Pat. No. 8,486,693, US 2014/0171649, and US 2012/0130076, the contents of which are further incorporated by reference herein in their entirety.

Also provided herein are cell lines obtained from a modified e.g. transformed immune cell e.g. T cell according to any of the methods described herein. In some embodiments, an immune cell e.g. T cell according to the disclosure comprises a polynucleotide encoding a protease-activating CD45-gate CAR protein or protease-activating CD45-gate CAR protein derivative. In some embodiments, an immune cell e.g. T cell according to the disclosure comprises a polynucleotide encoding a protease-activating CD45-gate CAR protein or protease-activating CD45-gate CAR protein derivative and a polynucleotide encoding an additional CAR.

The immune cells e.g. T cells of the disclosure can be activated and expanded, either prior to or after modification of the cells, using methods as generally described, for example without limitation, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005. Immune cells e.g. T cells can be expanded in vitro or in vivo. Generally, the immune cells of the disclosure can be expanded, for example, by contact with an agent that stimulates a CD3 TCR complex and a co-stimulatory molecule on the surface of the immune cells to create an activation signal for the cell. For example, chemicals such as calcium ionophore A23187, phorbol 12-myristate 13-acetate (PMA), or mitogenic lectins like phytohemagglutinin (PHA) can be used to create an activation signal for the immune cell e.g. T cell.

In some embodiments, T cell populations may be stimulated in vitro by contact with, for example, an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. Conditions appropriate for T cell culture include an appropriate medium (e.g., Minimal Essential Media or RPMI Media 1640 or, X-vivo 5, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-2, IL-15, a TGFβ, and TNF, or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM V, DMEM, MEM, α-MEM, F-12, X-Vivo 10, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% CO2). Immune cells e.g. T cells that have been exposed to varied stimulation times may exhibit different characteristics.

In some embodiments, the cells of the disclosure can be expanded by co-culturing with tissue or cells. The cells can also be expanded in vivo, for example in the subject's blood after administrating the cell into the subject.

In another aspect, the disclosure provides compositions (such as pharmaceutical compositions) comprising any of the cells of the disclosure or any of the populations of cells of the disclosure. In some embodiments, the composition comprises a T cell comprising a polynucleotide encoding a protease-activating CD45-gate CAR protein or protease-activating CD45-gate CAR protein derivative, which may further comprise a polynucleotide encoding a second CAR. The compositions comprise, for example, an immune cell e.g. T cell of the disclosure, e.g. an immune cell that expresses a protease-activating CD45-gate CAR and/or protease-activating CD45-gate CAR protein derivative, or comprise a population of cells that comprises an immune cell e.g. T cell of the disclosure, and one or more pharmaceutically acceptable carriers or excipients.

In some embodiments, primary cells isolated from a donor are manipulated as described herein to provide a population of cells of which a subpopulation (e.g. a proportion less than 100%, such as 10%, 20%, 30%) of the resulting cells comprise all of the desired modifications. Such a resulting population comprising a mixture of cells that comprise all of the modifications and cells that do not can be used in the methods of treatment of the disclosure and to prepare the compositions of the disclosure. Alternatively, this population of cells (the "starting population") can be manipulated by known methods e.g. cell sorting and/or expansion of cells that have the desired modifications, to provide a population of cells that is enriched for those cells comprising one or more of the desired modifications (e.g. enriched for cells that express the desired antigen binding protein, for cells that express a protease-activating CD45-gate CAR protein and/or protease-activating CD45-gate CAR protein derivative), that is, that comprises a higher percentage of such modified cells than did the starting population. The population enriched for the modified cells can then be used in the methods of treatment of the disclosure and to prepare the compositions of the disclosure, for example. In some embodiments, the enriched population of cells contains or contains at least 40%, 50%, 60%, 70%, 80%, 90%, 95%, or 99% cells that have one or more of the modifications. In other embodiments, the proportion of cells of the enriched population of cells that comprise one or more of the modifications is at least 30% higher than the proportion of cells of the starting population of cells that comprise the desired modifications.

In some embodiments, a population of immune cells comprises one or more of the engineered immune cells disclosed herein. In an embodiment, the population comprises about or at least about $1\times10^4$, about or at least about $1\times10^5$, about or at least about $1\times10^6$, about or at least about $1\times10^7$, or about or at least about $1\times10^8$ engineered cells, e.g. engineered immune cells, as disclosed herein, optionally wherein the population does not comprise more than about $1\times10^{10}$ or more than about $1\times10^9$ or more than about $5\times10^9$ engineered cells, e.g. engineered immune cells, as disclosed herein. In an embodiment, a population of immune cells as disclosed herein is enriched for the engineered immune cell as disclosed herein. In various embodiments, the population of immune cells is at least 50%, e.g. 50%, 55%, 60%, 65%, 70%, 75%, 80%, 85%, 90%, 95%, or more than 95% engineered cells that are T cells, e.g., alpha/beta T cells and gamma/delta T cells, B cells, natural killer (NK) cells, natural killer T (NKT) cells, mast cells, and/or myeloic-derived phagocytes. In various embodiments, the population of immune cells is at least 50%, e.g. 50%, 55%, 60%, 65%, 70%, 75%, 80%, 85%, 90%, 95%, or more than 95% engineered T cells.

Methods of Treating

Immune cells e.g. T cells obtained by the methods described above, or cell lines derived from such immune cells or T cells, can be used as a medicament. In some embodiments, such a medicament can be used for treating a disorder such as for example a viral disease, a bacterial disease, a cancer, an inflammatory disease, an immune disease, an autoimmune disease, an infection, or an aging-associated disease. In some embodiments, the cancer is a hematological malignancy or non-solid tumor. In some embodiments, the cancer is a solid cancer or solid tumor. In some embodiments, the cancer is a solid cancer or solid tumor. In some embodiments, the cancer is a hematological malignancy that is acute lymphoblastic leukemia (ALL), acute myeloid leukemia (AML), chronic myelogenous leukemia (CML), chronic eosinophilic leukemia (CEL), myelodysplasia syndrome (MDS), non-Hodgkin's lymphoma (NHL), or multiple myeloma (MM). In some embodiments, the cancer is a solid cancer that is biliary cancer, bladder cancer, bone or soft tissue carcinoma, brain tumor, breast cancer, cervical cancer, colon cancer, colorectal adenocarcinoma, colorectal cancer, desmoid tumor, embryonal cancer, endometrial cancer, esophageal cancer, gastric cancer, gastric adenocarcinoma, glioblastoma multiforme, gynecological tumor, head and neck squamous cell carcinoma, hepatic cancer, lung cancer, malignant melanoma, osteosarcoma, ovarian cancer, pancreatic cancer, pancreatic ductal adenocarcinoma, primary astrocytic tumor, primary thyroid cancer, prostate cancer, renal cancer, renal cell carcinoma, rhabdomyosarcoma, skin cancer, soft tissue sarcoma, testicular germ-cell tumor, urothelial cancer, uterine sarcoma, or uterine cancer. In some embodiments, the cancer can be selected from the group consisting of gastric cancer, sarcoma, osteosarcoma, rhabdomyosarcoma, tissue sarcoma, uterine sarcoma, lymphoma, leukemia, head and neck cancer, thymic cancer, epithelial cancer, salivary cancer, liver cancer, stomach cancer, thyroid cancer, lung cancer, ovarian cancer, breast cancer, prostate cancer, esophageal cancer, pancreatic cancer, glioma, leukemia, multiple myeloma, renal cell carcinoma, bladder cancer, cervical cancer, choriocarcinoma, colon cancer, oral cancer, skin cancer, and melanoma. In some embodiments, the subject is a previously treated adult subject with locally advanced or metastatic melanoma, squamous cell head and neck cancer (SCHNC), ovarian carcinoma, sarcoma, or relapsed or refractory classic Hodgkin's Lymphoma (cHL). In an embodiment, the condition is ovarian cancer and the protease-activating CD45-gate CAR comprises the amino acid sequence of any of SEQ ID NOs: 11, 56, 75, 76, 77, 78, 79, and 121-170.

In some embodiments, immune cells e.g. T cells according to the disclosure, or cell line derived from the immune cells e.g. T cells, can be used in the manufacture of a medicament for treatment of a disorder in a subject in need thereof. In some embodiments, the disorder can be, for example, a cancer, an autoimmune disorder, or an infection.

Also provided herein are methods for treating subjects. In some embodiments the method comprises administering or providing an immune cell e.g. T cell of the disclosure to a subject in need thereof. In some embodiments, the method comprises a step of administering the immune cells e.g. T cells of the disclosure to a subject in need thereof.

In another aspect, provided herein is a method of treating a condition in a patient comprising administering to the patient an engineered immune cell as disclosed herein. In an embodiment of the method, the engineered immune cell is an allogeneic engineered immune cell derived from a donor other than the patient.

In another aspect, provided herein is a method of treating a condition in a patient comprising administering to the patient a population of immune cells as disclosed herein. In an embodiment of the method, the immune cells of the population are derived from one or more allogeneic immune cells from a donor other than the patient.

In another aspect, provided herein is a method of treating a condition in a patient comprising administering to the patient a pharmaceutical composition as disclosed herein. In an embodiment of the method, the composition comprises one or more engineered allogeneic immune cells derived from a donor other than the patient.

In some embodiments, immune cells e.g. T cells of the disclosure can undergo robust in vivo cell expansion and can persist for an extended amount of time. Methods of treatment of the disclosure can be ameliorating, curative or prophylactic. The method of the disclosure may be either part of an autologous immunotherapy or part of an allogenic immunotherapy treatment. The disclosure is particularly suitable for allogeneic immunotherapy. Immune cells e.g. T cells from donors can be transformed into non-alloreactive cells using standard protocols and reproduced as needed, thereby producing e.g. CAR-T cells which may be administered to one or several subjects. Such CAR-T cell therapy can be made available as an "off the shelf" therapeutic product.

In another aspect, the disclosure provides a method of inhibiting tumor growth or progression in a subject who has a tumor, comprising administering to the subject an effective amount of immune cells e.g. T cells as described herein. In another aspect, the disclosure provides a method of inhibiting or preventing metastasis of cancer cells in a subject, comprising administering to the subject in need thereof an effective amount of immune cells e.g. T cells as described herein. In another aspect, the disclosure provides a method of inducing tumor regression in a subject who has a tumor, comprising administering to the subject an effective amount of immune cells e.g. T cells as described herein.

In some embodiments, the immune cells e.g. T cells provided herein can be administered parenterally in a subject. In some embodiments, the subject is a human.

In some embodiments, the method can further comprise administering an effective amount of a second therapeutic agent. In some embodiments, the second therapeutic agent is, for example, crizotinib, palbociclib, an anti-CTLA4 antibody, an anti-4-1BB antibody, a PD-1 antibody, or a PD-L1 antibody.

Also provided is the use of any of the immune cells e.g. T cells provided herein in the manufacture of a medicament for the treatment of cancer or for inhibiting tumor growth or progression in a subject in need thereof.

Also provided herein are uses and methods as described herein wherein the condition is ovarian cancer and the protease-activating CD45-gate CAR comprises the amino acid sequence of any of SEQ ID NOs: 11, 56, 75, 76, 77, 78, 79, and 121-170. Also provided herein are uses and methods as described herein wherein the condition is ovarian cancer and a CAR comprising the amino acid sequence of any of SEQ ID NOs: 11, 56, 75, 76, 77, 78, 79, and 121-170 is used in addition to or instead of the protease-activating CD45-gate CAR.

The degree to which the gate modulates the protease-activating CD45-gate CAR's activity can be assessed in various ways. One way is to measure the cytotoxicity of a T cell that expresses the protease-activating CD45-gate CAR in comparison to various controls, such as a T cell that expresses a protein that is the same as the protease-activating CD45-gate CAR but that lacks a protease cleavage site in the linker that connects the CD45 recruiting domain to the ligand binding domain (non-cleavable gate), a T cell that expresses a protein that comprises the same CAR but that has no CD45 recruiting domain (non-gated CAR), and a T cell that has not been transduced. The cytotoxicity of these cells can be measured by incubating them with target cells that express the ligand that the CAR antigen binding domain recognizes. The assay can be adjusted by varying the ratio of the effector CAR T cell to the target ligand-expressing cell. When the effector and target cells are incubated together under the appropriate conditions, while not wishing to be bound by theory, it is expected that the CAR T cells will exhibit high cytotoxicity and both the cleavable and non-cleavable CD45-gate CAR T cells will exhibit lower cytotoxicity because the gate at least partially inactivates the CAR. It is expected that the non-transduced cells will exhibit no cytotoxicity. This form of assay serves to confirm that, under the conditions of the assay, the gate can at least partially inactivate the CAR when the CAR's ligand is present but the protease is absent. It thus mimics the in vivo condition in which the protease-activating CD45-gate CAR T cell encounters its antigen off-tumor. In such an assay, in some embodiments, the protease-activating CD45-gate CAR cytotoxicity is reduced by or by at least about 20%, 30%, 40%, 50%, 60%, 70%, 80%, or 90% relative to the non-gated CAR. The degree of reduction observed depends on the conditions of the assay.

To mimic the in vivo condition in which the protease-activating CD45-gate CAR T cell encounters antigen at the tumor site, the same assay can be repeated in the presence of a protease that can cleave the linker that connects the CD45 recruiting domain to the ligand binding domain. It is expected that the protease will not affect the non-gated CAR T cells' cytotoxicity. It is also expected that the cleavable protease-activating CD45-gate CAR will show reduced cytotoxicity in the absence of the protease and will show higher cytotoxicity in the presence of the protease as compared with in the absence of the protease, because, while not wishing to be bound by theory, in the presence of the protease, the gate that inhibited CAR activation has been removed by cleavage of the linker. It is expected that the non-cleavable gate CAR cytotoxicity will not be affected by the presence of the protease. It is expected that its cytotoxicity will be reduced both in the absence of and in the presence of the protease, because, while not wishing to be bound by theory, the gate inhibits the CAR's activation under both conditions. In such an assay, in some embodiments, in the absence of protease, the protease-activating CD45-gate CAR cytotoxicity is reduced by or by at least about 20%, 30%, 40%, 50%, 60%, 70%, 80%, or 90% relative to the non-gated CAR and, in the presence of protease, the cells' cytotoxicity is significantly higher. The degrees of reduction and increase observed depend on the conditions of the assay.

In another aspect, provided herein is a method of reducing on-target off-tumor toxicity of CAR T cells comprising administering to a patient a cell as disclosed herein, a population of cells as disclosed herein, or a composition as disclosed herein, wherein the on-target, off-tumor toxicity is lower than the on-target, off-tumor toxicity of control cells, a population of control cells or a composition of control cells, respectively, administered under the same conditions, wherein the control cells, population of control cells, or control cells of the composition comprise a CAR that lacks at least one of a CD45 recruiting domain and a linker that comprises a protease cleavage site.

In another aspect, provided herein is a method of increasing the efficiency of CAR T cells or CAR T cell therapy comprising administering to a patient a cell as disclosed herein, a population of cells as disclosed herein, or a composition as disclosed herein, wherein the efficiency is greater than the efficiency of control cells, a population of control cells or a composition of control cells, respectively, administered under the same conditions, wherein the control cells, population of control cells, or control cells of the composition comprise a CAR that lacks at least one of a CD45 recruiting domain and a linker that comprises a protease cleavage site.

In another aspect, provided herein is a method of increasing the efficacy of CAR T cell therapy comprising administering to a patient a cell as disclosed herein, a population of cells as disclosed herein, or a composition as disclosed herein, wherein the efficacy is greater than the efficacy of control cells, a population of control cells or a composition of control cells, respectively, administered under the same conditions, wherein the control cells, population of control cells, or control cells of the composition comprise a CAR that lacks at least one of a CD45 recruiting domain and a linker that comprises a protease cleavage site.

In another aspect, provided herein is a method of increasing the efficacy of CAR T cell therapy against a solid tumor comprising administering to a patient having a solid tumor a cell as disclosed herein, a population of cells as disclosed herein, or a composition as disclosed herein, wherein the efficacy against the solid tumor is greater than the efficacy against the solid tumor of control cells, a population of control cells or a composition of control cells, respectively, administered under the same conditions, wherein the control cells, population of control cells, or control cells of the composition comprise a CAR that lacks at least one of a CD45 recruiting domain and a linker that comprises a protease cleavage site.

In another aspect, provided herein is a method of reducing the incidence of side effects in CAR T cell therapy comprising administering to a patient a cell as disclosed herein, a population of cells as disclosed herein, or a composition as disclosed herein, wherein the incidence of side effects is lower than the incidence of side effects when control cells, a population of control cells or a composition of control cells, respectively, are administered under the same conditions, wherein the control cells, population of control cells, or control cells of the composition comprise a CAR that lacks at least one of a CD45 recruiting domain and a linker that comprises a protease cleavage site.

In another aspect, provided herein is a method of effecting reversible colocalization of CD45 and a CD45-gate CAR in a CAR T cell, the reversible colocalization comprising a CD45-gate CAR recruiting domain binding to a CD45 protein on a CAR T cell surface, resulting in colocalization, which binding and colocalization can be disrupted by a protease cleaving a protease cleavage site in the CD45-gate CAR's linker, thereby reversing the colocalization, the method comprising the steps of:
  (a) providing a T cell that expresses CD45,
  (b) introducing a nucleic acid encoding a protease-activating CD45-gate CAR as disclosed herein into the T cell,
  (c) maintaining the T cell under conditions in which both CD45 and the CAR are functionally expressed at the cell surface,
  resulting in a CD45-gate CAR recruiting domain binding to a CD45 protein on the CAR T cell surface and colocalization of the CAR and the CD45 protein, which colocalization can be reversed by a protease cleaving a protease cleavage site in the CD45-gate CAR's linker, wherein the cleaving produces a functional CAR no longer connected by the linker to the CD45-gate CAR recruiting domain.

In another aspect, provided herein is a method of effecting reversible reduction of CAR activity by a CD45 protein in a CAR T cell, the reversible reduction of CAR activity comprising a CD45-gate CAR recruiting domain binding to a CD45 protein on a CAR T cell surface, resulting in inactivation of the chimeric antigen receptor by the CD45, which inactivation can be disrupted by a protease cleaving a protease cleavage site in the CD45-gate CAR's linker, resulting in the disassociation of the chimeric antigen receptor and the CD45 protein and ending the inactivation of the chimeric antigen receptor by the CD45, the method comprising the steps of:
 (a) providing a T cell that expresses CD45,
 (b) introducing a nucleic acid encoding a CD45-gate CAR into the T cell,
 (c) maintaining the T cell under conditions in which both CD45 and the CAR are functionally expressed at the cell surface,
 resulting in a CD45-gate CAR recruiting domain binding to a CD45 protein on the CAR T cell surface, association of the CAR and the CD45 protein, and reduction of the CAR's activity by the CD45 protein, which activity reduction can be reversed by a protease cleaving a protease cleavage site in the CD45-gate CAR's linker, thereby ending the association of the CAR and the CD45 protein, and ending the CD45 protein's reduction of CAR activity, wherein the cleaving produces a functional CAR no longer connected by the linker to the CD45-gate CAR recruiting domain.

In another aspect, provided herein is a method of treating with CAR T cell therapy a patient who has a tumor characterized by a protease-rich tumor microenvironment, comprising administering to the patient a cell as disclosed herein, a population of cells as disclosed herein, or a composition as disclosed herein, wherein CAR T cell activity is lower outside the protease-rich tumor microenvironment than in the protease-rich tumor microenvironment.

In another aspect, provided herein is a method of regulating cytotoxic activity of a CAR T cell that comprises a CAR as disclosed herein, the method comprising inhibiting the cytotoxic activity of the CAR T cell by associating the CAR with CD45 of the CAR T cell, and activating the cytotoxic activity of the CAR T cell by subjecting and/or exposing the CAR T cell to a protease that recognizes and cleaves the protease cleavage site.

In embodiments of the methods of treating a condition in a patient disclosed herein, the cell, population of cells or composition can be administered to the subject on one occasion or can be administered to the subject on two or more occasions spaced at least about 1, 2, 3, 4, 5, 6, 7, or more days apart. In some embodiments, the disorder can be a viral disease, a bacterial disease, a cancer, an inflammatory disease, an immune disease, or an aging-associated disease.

In some embodiments, the treatment can be in combination with one or more therapies against cancer selected from the group of antibodies therapy, chemotherapy, cytokines therapy, dendritic cell therapy, gene therapy, hormone therapy, laser light therapy and radiation therapy.

In some embodiments, treatment can be administered to or administrated into subjects undergoing an immunosuppressive treatment. Indeed, the disclosure may rely on cells or a population of cells which have been made resistant to at least one immunosuppressive agent due to the inactivation of a gene encoding a receptor for such immunosuppressive agent. In this aspect, the immunosuppressive treatment may help the selection and expansion of the T cells according to the disclosure within the subject.

The administration of the cells or population of cells according to the disclosure may be carried out in any convenient manner, including by aerosol inhalation, injection, ingestion, transfusion, implantation or transplantation. The compositions described herein may be administered to a subject subcutaneously, intradermally, intratumorally, intranodally, intramedullary, intramuscularly, by intravenous or intralymphatic injection, or intraperitoneally. In one embodiment, the cell compositions of the disclosure are administered by intravenous injection.

In some embodiments, the administration of the cells or population of cells can comprise administration of, for example, about $10^4$ to about 10 cells per kg body weight including all integer values of cell numbers within those ranges. In some embodiments the administration of the cells or population of cells can comprise administration of about 10 to about $10^6$ cells per kg body weight including all integer values of cell numbers within those ranges. The cells or population of cells can be administered in one or more doses. In some embodiments, an effective amount of cells can be administered as a single dose. In some embodiments, an effective amount of cells can be administered as more than one dose over a period time. Timing of administration is within the judgment of the managing physician and depends on the clinical condition of the subject. The cells or population of cells may be obtained from any source, such as a blood bank or a donor. While individual needs vary, determination of optimal ranges of effective amounts of a given cell type for a particular disease or conditions is within the skill of the art. An effective amount means an amount which provides a therapeutic or prophylactic benefit. The dosage administered will be dependent upon the age, health and weight of the recipient, the kind of concurrent treatment, if any, the frequency of treatment and the nature of the effect desired. In some embodiments, an effective amount of cells or composition comprising those cells are administered parenterally. In some embodiments, administration can be an intravenous administration. In some embodiments, administration can be directly done by injection within a tumor.

In some embodiments of the disclosure, cells are administered to a subject in conjunction with (e.g., before, simultaneously or following) any number of relevant treatment modalities, including but not limited to treatment with agents such as monoclonal antibody therapy, CCR2 antagonist (e.g., INC-8761), antiviral therapy, cidofovir and interleukin-2, Cytarabine (also known as ARA-C) or nataliziimab treatment for MS subjects or efaliztimab treatment for psoriasis subjects or other treatments for PML subjects. In some embodiments, protease-activating CD45-gate CAR-T cells are administered to a subject in conjunction with one or more of the following: an anti-PD-1 antibody (e.g., nivolumab, pembrolizumab, or PF-06801591), an anti-PD-L1 antibody (e.g., avelumab, atezolizumab, or durvalumab), an anti-OX40 antibody (e.g., PF-04518600), an anti-4-1 BB antibody (e.g., PF-05082566), an anti-MCSF antibody (e.g., PD-0360324), an anti-GITR antibody, and/or an anti-TIGIT antibody. In further embodiments, the immune cells e.g. T cells of the disclosure may be used in combination with chemotherapy, radiation, immunosuppressive agents, such as cyclosporin, azathioprine, methotrexate, mycophenolate, and FK506, antibodies, or other immunoablative agents such as CAMPATH, anti-CD3 antibodies or other antibody therapies, cytoxin, fludaribine, cyclosporin, FK506, rapamycin, mycoplienolic acid, steroids, FR901228, cytokines, and/or irradiation. These drugs inhibit either the calcium dependent phosphatase calcineurin (cyclosporine and FK506) or inhibit the p70S6 kinase that is important for growth factor induced signaling (rapamycin) (Henderson, Naya et al. Immunology. 1991 July; 73(3): 316-321; Liu, Albers et al. Biochemistry 1992 April 28; 31(16):3896-901; Bierer, Hollander et al. Curr Opin Immunol. 1993 October; 5(5):763-73).

In a further embodiment, the cell compositions of the disclosure are administered to a subject in conjunction with (e.g., before, simultaneously or following) bone marrow transplantation, T cell ablative therapy using either chemotherapy agents such as fludarabine, external-beam radiation therapy (XRT), cyclophosphamide, or antibodies such as OKT3 or CAMPATH. In some embodiments, the cell compositions of the disclosure are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of expanded immune cells of the disclosure. In some embodiments, expanded cells are administered before or following surgery.

Kits

The disclosure also provides kits for use in the instant methods. Kits of the disclosure include one or more containers comprising a composition of the disclosure or an immune cell e.g. a T cell of the disclosure or a population of cells comprising an immune cell e.g. a T cell of the disclosure. In various embodiments, the immune cell e.g. T cell comprises one or more polynucleotide(s) encoding a protease-activating CD45-gate CAR protein as described herein or a protease-activating CD45-gate CAR protein derivative. The kit further comprises instructions for use in accordance with any of the methods of the disclosure described herein. Generally, these instructions comprise a description of administration of the composition, immune cell e.g. T cell or population of cells for the above described therapeutic treatments. In some embodiments the engineered immune cells are formulated in a solution comprising about 5% DMSO. Further, the engineered immune cells can be provided in a frozen state.

The instructions relating to the use of the kit components generally include information as to dosage, dosing schedule, and route of administration for the intended treatment. The containers may be unit doses, bulk packages (e.g., multi-dose packages) or sub-unit doses. Instructions supplied in the kits of the disclosure are typically written instructions on a label or package insert (e.g., a paper sheet included in the kit), but machine-readable instructions (e.g., instructions carried on a magnetic or optical storage disk) are also acceptable.

The kits of this disclosure are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an immune cell e.g. T cell according to the disclosure. The container may further comprise a second pharmaceutically active agent.

Kits may optionally provide additional components such as buffers and interpretive information. Normally, the kit comprises a container and a label or package insert(s) on or associated with the container.

EXAMPLES

The following examples are offered for illustrative purposes only, and are not intended to limit the scope of the disclosure in any way. Indeed, various modifications of the disclosure in addition to those shown and described herein will become apparent to those skilled in the art from the foregoing description and fall within the scope of the appended claims.

Example 1: Synthesis and Demonstration of CD45-Gate CAR

CD45-Gate CAR Structure

Figure 1B:
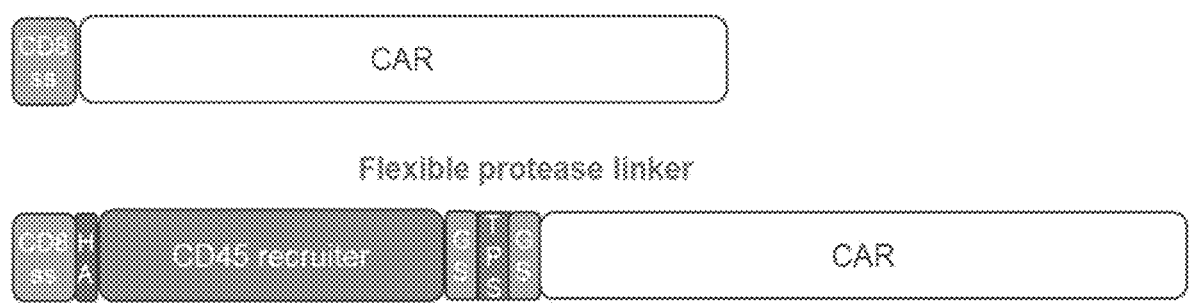

FIG. 1A shows a schematic representation of a protease-activating CD45-gate CAR. To investigate how the protease-activating CD45-gate can regulate the function of CAR T cells, we used a 2nd generation CAR ("53B6") that specifically targets MUC16-expressing cells. A generic CAR protein is comprised of an extracellular target-binding domain, a transmembrane domain, and an intracellular signaling domain that, for example, comprises an activation domain (e.g. CD3zeta cytoplasmic domain) and optionally also a costimulatory domain (e.g. 4-1BB signalling domain). In general, the extracellular domain of the CD45-gate CAR disclosed herein comprises, in addition, a CD45 recruiting domain ("recruiter"), fused via a flexible linker, which linker comprises, in certain embodiments, one or more protease-cleavable sites, to the N-terminus of a generic CAR, as illustrated in FIGS. 1A and 1B (bottom construct). As diagrammed in FIG. 1B (bottom construct), an additional N-HA tag (comprising the sequence YPYDVPDYA (SEQ ID NO: 187), a variant of SEQ ID NO: 2 without the initial G) was introduced as well for detection of the CD45-gate CAR, and the CD8 signal peptide was fused to the N-terminus of each protein to enable trafficking and surface expression. Non-gated, non-N-HA-tagged 53B6 (FIG. 1B, top construct) was used as a control in some of the experiments.

CD45-Gate CAR Expression in T Cells

Figure 2A:
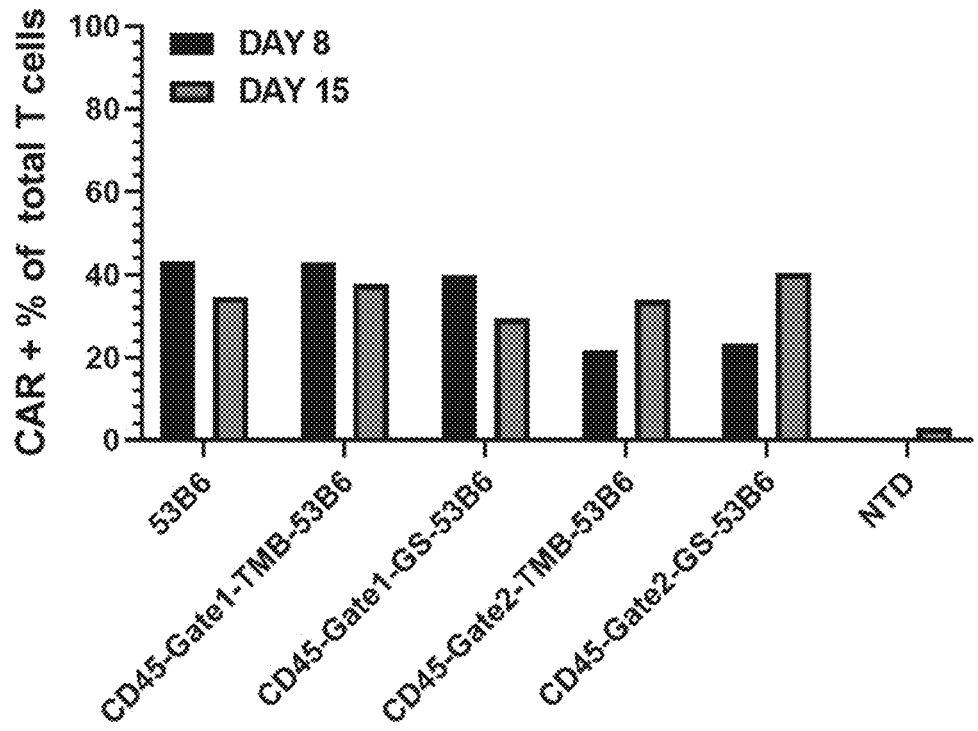
FIGS. 2A-2B. CAR T cells comprising vectors encoding protease-activating CD45-gate CARs grow and express the transgenic protein. T cells were transduced with a vector that encodes a CAR that is not a protease-activating CD45-gate CAR (53B6, an anti-MUC16 CAR), with a vector that encodes a protease-activating CD45-gate CAR (CD45-Gate1-TMB-53B6, CD45-Gate2-TMB-53B6), or with a vector that encodes analogs of the protease-activating CD45-gate CARs that comprise a non-cleavable linker (CD45-Gate1-GS-53B6, CD45-Gate2-GS-53B6). The linker of the cleavable protein comprised: GS-region-thrombin cleavage site-V5 peptide-thrombin cleavage site-GS-region. The linker of the non-cleavable protein comprised: GS-region-V5 peptide-GS-region.
Figure 2B:
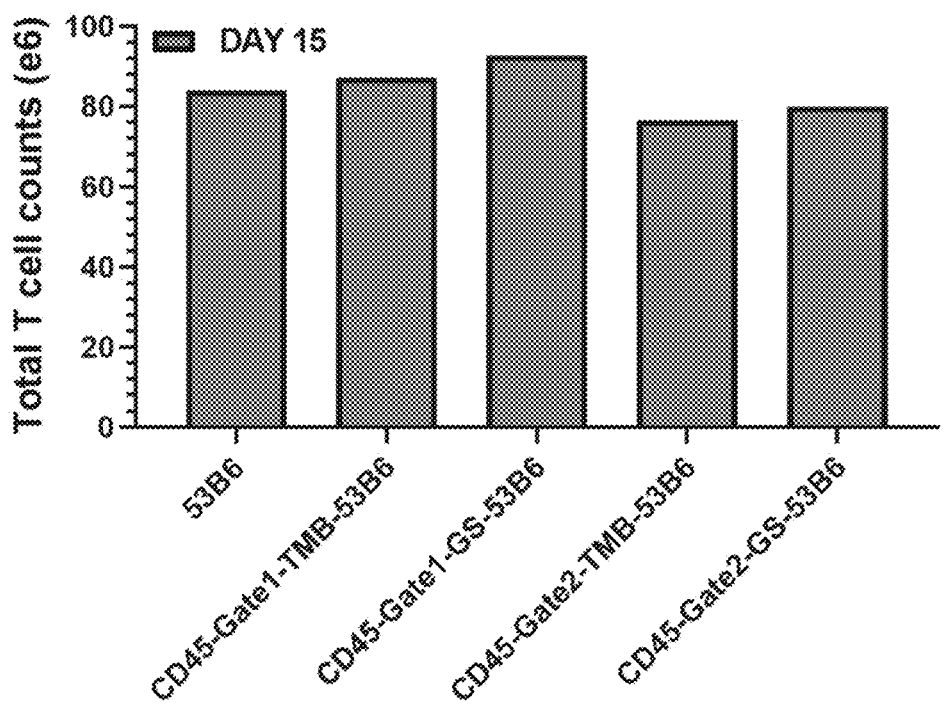

To evaluate CAR T cells that functionally express the protease-activating CD45-gate CAR, two variants of the CD45-gate were prepared, one comprising a first anti-CD45 scFv as the CD45 recruiter and the other comprising a second, different anti-CD45 scFv as the CD45 recruiter. A flexible protease-cleavable linker, which contained two thrombin protease cleavage sites flanking a V5 peptide motif, which can be used to detect the linker (SEQ ID NO: 8, GGGGSGGGGSLVPRGSKPIPNPLLGLDSTLVPRG-SGGGGSGGGGS), joined the CD45 recruiter to the N-terminus of the CAR. These two protease-activating CD45-gate CAR clones are designated "CD45-Gate1-TMB-53B6" (comprising amino acid sequence of SEQ ID NO: 16) and "CD45-Gate2-TMB-53B6" ("TMB" indicating the thrombin-cleavable linker) (comprising amino acid sequence of SEQ ID NO: 18), where the exemplary anti-MUC16 CAR clone 53B6 was used to demonstrate the proof of concept of such a protease-activating CD45-gate CAR. In parallel, a non-cleavable linker of the same length (SEQ ID NO: 7, GGGGSGGGGSGGGGSGSKPIPNPLLGLDSTGGGSGS-GGGGSGGGGS) was used to generate additional control CARs, designated "CD45-Gate1-GS-53B6" (comprising amino acid sequence of SEQ ID NO: 17) and "CD45-Gate2-GS-53B6" (comprising amino acid sequence of SEQ ID NO:

19), both of which are not expected to be cleaved by a protease. CAR T cells expressing either the non-gate 53B6 CAR or the CD45-gate 53B6 CARs were generated with lentiviral vectors as previously described (14,15). In brief (and using the methods described in Example 2 below, CAR-T Production), primary T cells from a healthy donor were transduced with lentiviruses (MOI of 5) expressing the different CAR molecules and the percentage of CAR+ cells were recorded at day 8 and day 15. As the data in FIG. 2A show, CARs with the CD45-gate1 ("CD45-Gate1-TMB-53B6" and "CD45-Gate1-GS-53B6") show CAR+ rate comparable to that of the 53B6 CAR throughout the production. The CD45-gate2 CARs ("CD45-Gate2-TMB-53B6" and "CD45-Gate2-GS-53B6") exhibit lower transduction rate initially, but are able to match up to the CAR+ percentage in the end of the production (data for FIG. 2A were obtained as described below under Example 2 with respect to FIG. 7A, Flow Cytometry Analysis). The overall growth of T cells remains similar among all the clones (see FIG. 2B). These data together indicate that, although CD45 is expressed on the surface of CAR T cells, surprisingly the CD45-gate CAR can be produced and expressed in the T cells successfully without causing severe fratricide.

CD45-Gate CAR Protease Cleavage and Ligand Binding

Figure 3A:
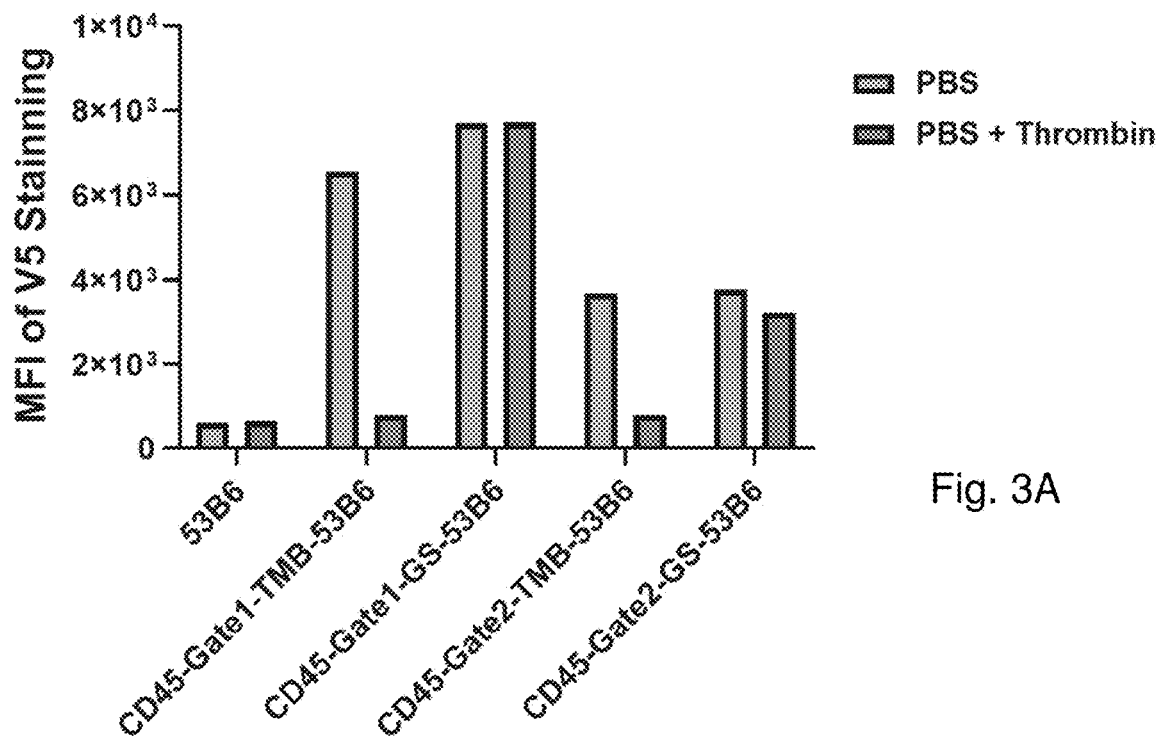
FIG. 3A. Exposing the CAR T cells of FIGS. 2A-2B to thrombin resulted in reduced detection of the V5 tag in the cleavable CARs but not in the non-cleavable CARs.

To evaluate whether the CD45-gate can be released by the corresponding protease, the detection of V5 tag that is imbedded in the cleavable or non-cleavable linkers was assessed. The protease cleavage was carried out by incubating the CAR T cells in PBS with 2 microgram/ml of thrombin at 370 for 30 mins. The successful cleavage of the protease linker was verified by the removal of V5 tag after cleavage. As the data in FIG. 3A show, the removal of V5 tag was only observed in the clone of CD45-Gate1-TMB-53B6 and CD45-Gate2-TMB-53B6 after cleavage, indicating that the CD45-gate can be released from CAR by the specific cleavage by the protease.

Next, whether the CD45-gate directly blocks the ligand binding was evaluated by assessing the binding of soluble MUC16 ligand to each CAR clone, before or after protease cleavage. It was observed that 53B6, CD45-Gate1-TMB-53B6, CD45-Gate1-GS-53B6 show very similar ligand-binding intensity, regardless of protease cleavage (see data in FIG. 3B). CD45-Gate2-TMB-53B6 and CD45-Gate2-GS-53B6 exhibited decreased ligand-binding intensity, likely due to inferior expression of the modified CAR molecule (see data in FIG. 3B). Nonetheless, the binding was not affected by protease cleavage and the release of CD45-gate. Overall, these data demonstrate that CD45 gate does not block binding to soluble target.

CD45-Gate CAR T Cell Cytotoxicity

Figure 4A:
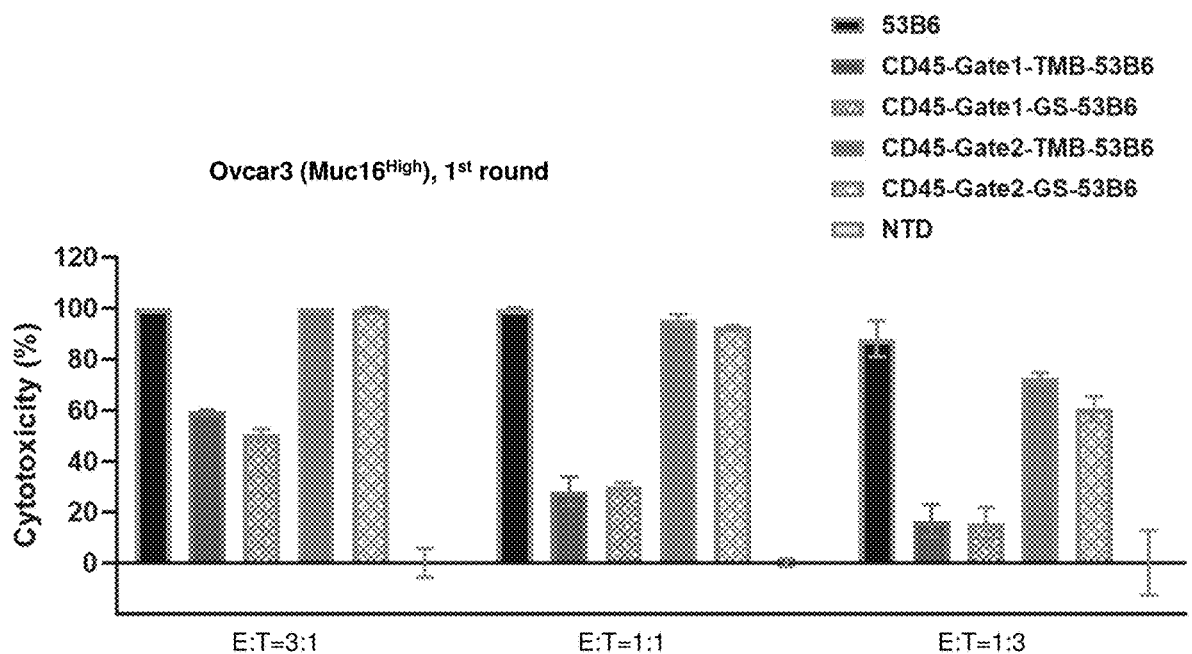
FIGS. 4A-4B. Results of cytotoxicity assays used to assess inhibitory activity of CD45 gate. Assays were performed in R10 medium without thrombin or other exogenous protein present.
Figure 4B:
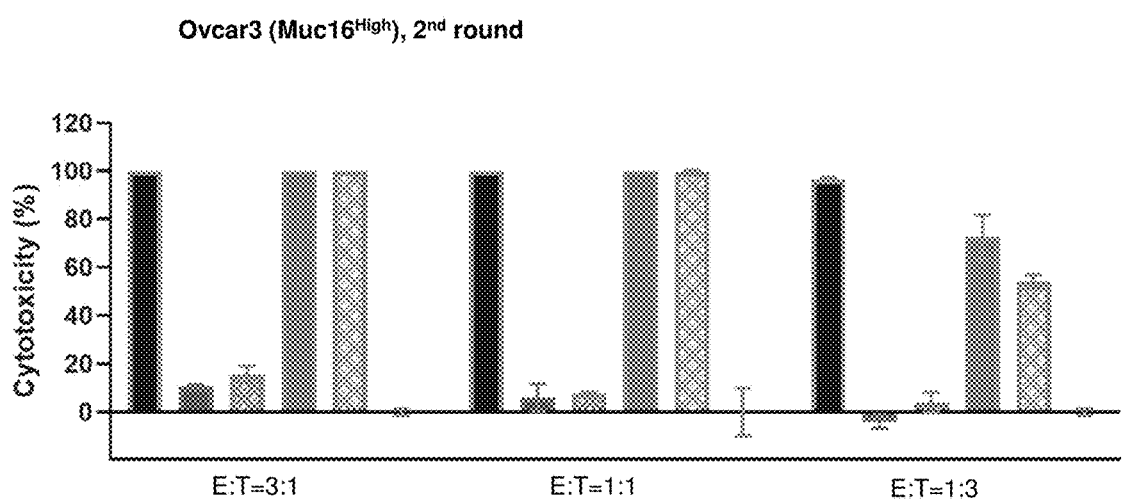
Figure 5A:
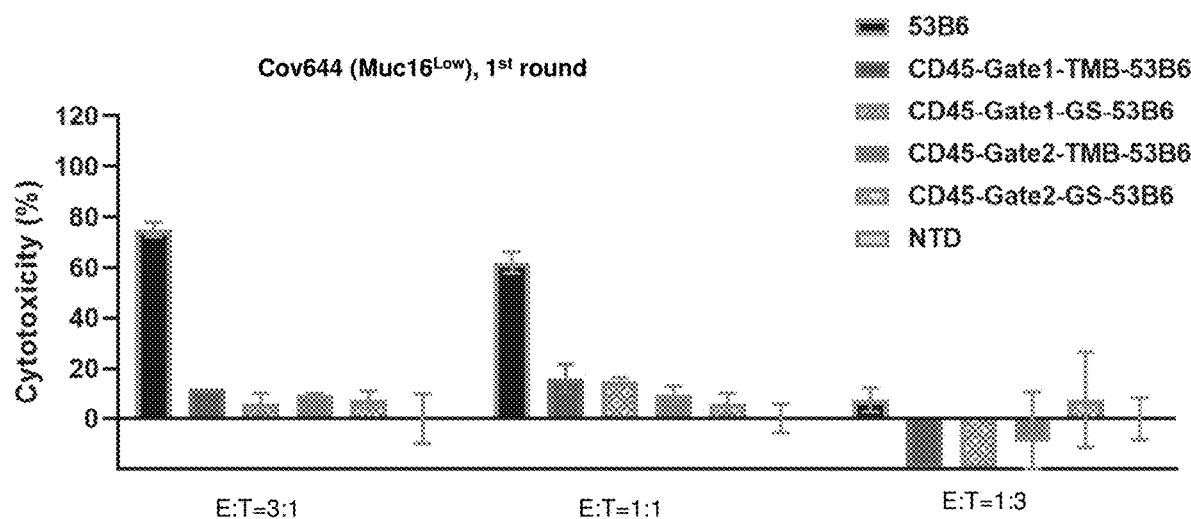
FIGS. 5A-5B. Results of cytotoxicity assays used to assess inhibitory activity of CD45 gate. Assays were performed in R10 medium without thrombin or other exogenous protein present.
Figure 5B:
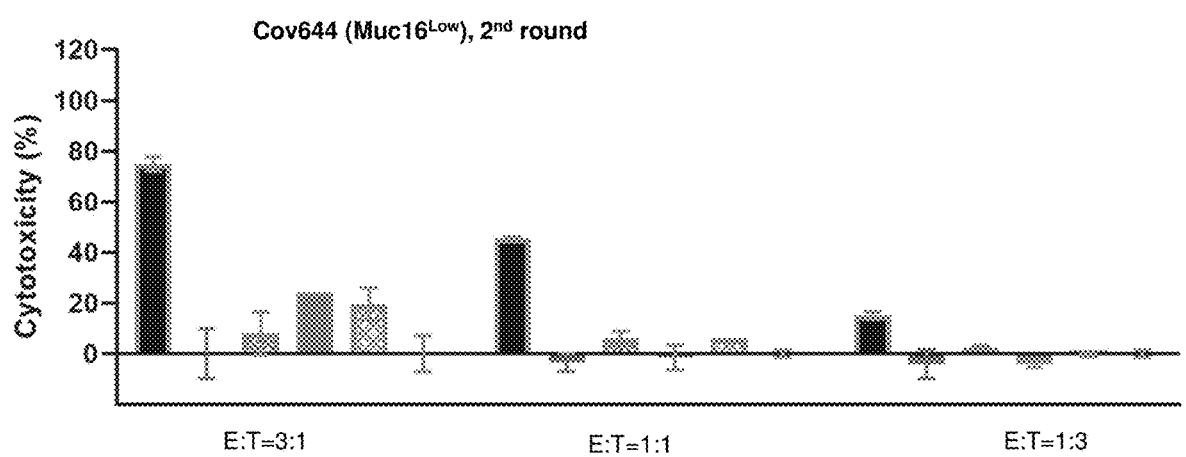

To understand whether the CD45-gate can regulate the CAR function, two target cell lines, Ovcar3 (MUC16High) and Cov644 (MUC16Low), were used to assess the cytotoxicity of each clone. Both target cells are incorporated with luciferase gene for facile quantification of viable cells. In brief, CAR T cells were normalized to the same CAR+ percentage and incubated with 10,000 target cells at E:T (Effector:Target) ratio of 3:1, 1:1, or 1:3 in 200 μl of RPMI medium with 10% of FBS. After the 48-hour co-culture, 100 μl of the supernatant containing CAR T cells was transferred to new wells with 10,000 fresh target cells, while the remaining samples were used to quantify the viable target cells by luciferase assay. After another 48-hour co-culture, the second round of cytotoxicity assessment was carried out in the same way. As FIGS. 4A-4B show, CD45-Gate1 moderately inhibited the CAR function to kill the Ovcar3 (MUC16High) target cells in the first round of cytotoxicity assay and the inhibition became more pronounced in the second round. However, the CD45-Gate2 showed very limited inhibition of the CAR activity; a reduction in cytotoxic activity was observed only at low E:T ratio (FIGS. 4A and 4B). In contrast, both CD45-Gate1 and CD45-Gate2 substantially inhibited the CAR cytotoxicity against the Cov644 (MUC16Low) target cells (FIGS. 5A-5B). These data together illustrate that the CD45-gate can effectively control CAR function and the level or degree of inhibition can be affected by and vary with the antigen density.

Regulation of CD45-Gate CAR T Cell Cytotoxicity

Figure 6A:
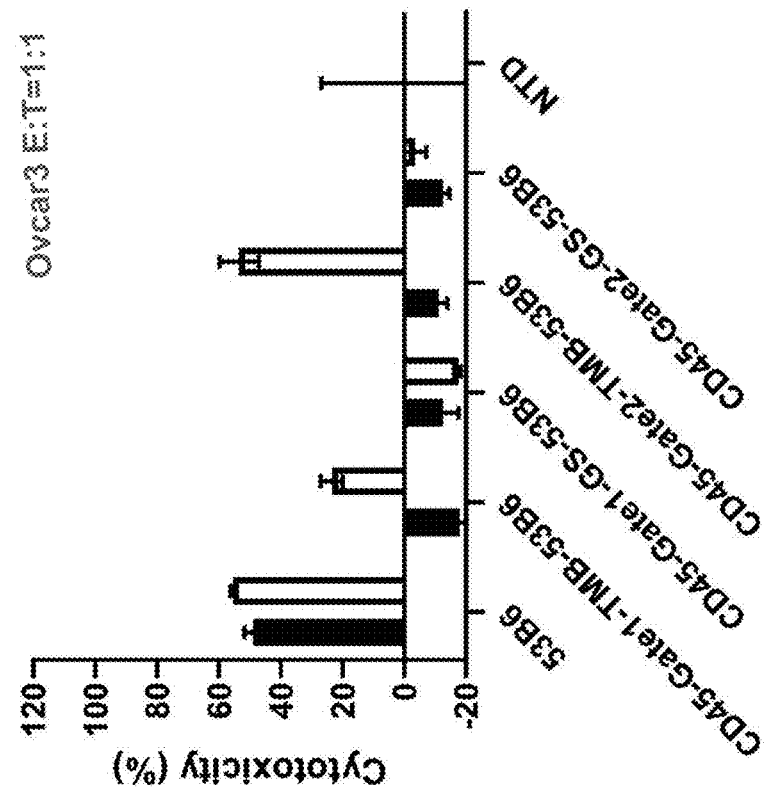
FIGS. 6A-6B. Results of cytotoxicity assays used to assess reversibility of CD45 gate inhibitory activity. Assays were performed in serum-free medium. Black bars: no protease present. White bars: protease (thrombin) present. E:T: ratio of number of effector cells to number of target cells; NTD: not transduced.
Figure 6B:
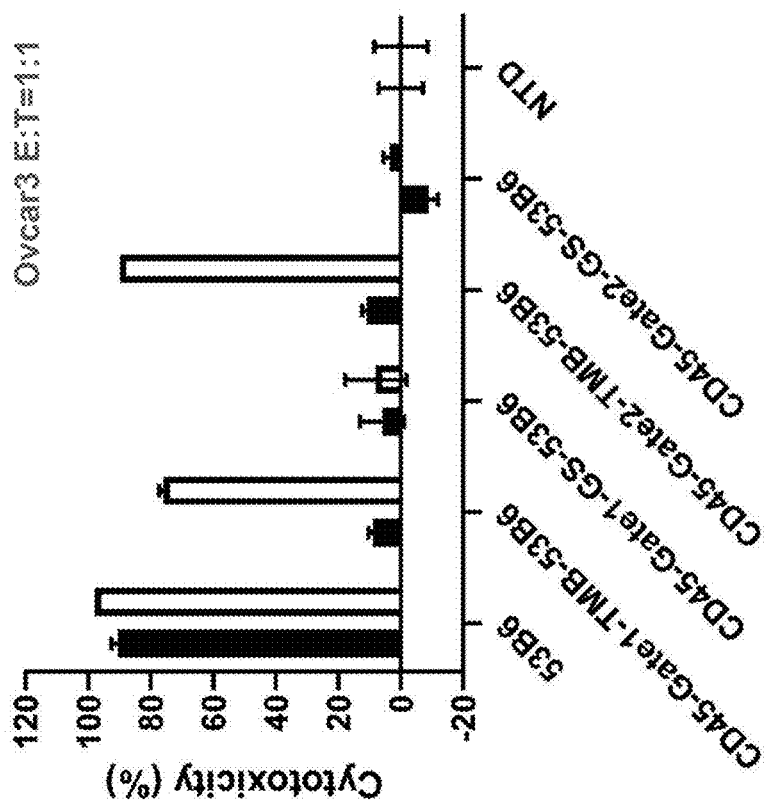

Next, whether the protease cleavage and the removal of CD45-gate from CAR can restore its cytotoxicity was evaluated. To test this, the cytotoxicity assay was carried out with the MUC16High Ovcar3 target cells similarly as above, except that serum-free medium was used in the assay to allow thrombin activity. The cytotoxicity of each clone was evaluated against the target cells at E:T of 1:1, with or without thrombin protease (final concentration of 2 μg/ml). In this condition, the regular 53B6 CAR T cells still can efficiently kill the target cells, albeit that the activity was weaker than their previous performance in the serum-rich medium. There is no change in 53B6 CAR activity when thrombin is introduced into the culture (FIG. 6A). Importantly, data from the clone of CD45-Gate1-TMB-53B6 and CD45-Gate2-TMB-53B6 demonstrates that the CD45-gate effectively inhibited the CAR activity and the cytotoxicity was mostly restored when the protease was present. In contrast, the CD45-gate in the clone of CD45-Gate1-GS-53B6 or CD45-Gate2-GS-53B6 could not be efficiently released and thus the CAR activity remained inhibited despite the presence of the protease.

Example 2. Expression and Activity of Anti-MUC16 CAR

CAR T Production

T cells were isolated from human peripheral blood mononuclear cells (PBMCs) obtained by density gradient centrifugation (Ficoll Paque, GE Healthcare, Pittsburgh, PA) using a Pan T cell isolation kit (Miltenyi Biotec, Auburn, CA) and cryopreserved.

To make lentivirus encoding 53B6 CAR, HEK-293T cells were plated at 0.45 million cells per mL in 2 mL of DMEM (Gibco) supplemented with 10% FBS (Hyclone or JR Scientific) per well of a 6-well plate on Day 0. On Day 1, the lentivirus was prepared by mixing together lentiviral packaging vectors 1.5 μg psPAX2, 0.5 μg pMD2G, and 1 μg of the appropriate transfer CAR vector in 250 μL Opti-MEM (Gibco) per well of the 6-well plate ("DNA mix"). 10 μL Lipofectamine 2000 (Invitrogen) in 250 μL Opti-MEM was incubated at room temperature for 5 minutes and then added to the DNA mix. The mixture was incubated at room temperature for 20 minutes and the total volume of 500 μL was slowly added to the sides of the wells containing HEK-293T. Purified T cells were activated in T cell transduction media (X-Vivo-15 medium [Lonza] with 10% FBS) supplemented with 20 ng/ml of human IL-2 (Miltenyi Biotec) and human T cell TransAct reagent (Miltenyi Biotec), as recommended by the manufacturer. On Day 2, the media from each well of the 6-well plate was replaced with 2 mL per well of T cell transduction media. On Day 3, T cells were resuspended at 0.33 million cells per mL in 1 mL of T cell transduction media. The lentiviral supernatant from HEK293T cells was harvested and passed through 0.45 micron filter (EMD Millipore) to remove cell debris, and then added to 0.5 million activated T cells along with 20 ng/ml human IL-2. Alternatively, to enhance the transduction efficiency, lentiviruses can be prepared with scaled up ratio as previous protocol and concentrated with Lenti-X™ Concentrator (Takara), following the manufacturer's protocol. Activated T cells were transduced at approximately MOI of 5 to generate CAR T cells.

On Day 5, 4.5 mL of T cell expansion media (X-Vivo-15 with 5% human AB serum [Gemini Bio]) was added to each well of a Grex-24 (Wilson Wolf) plate. IL-2 (20 ng/ml) was supplemented every 2-3 days. On Day 9 and Day 13, transduction efficiency was determined by detecting the percentage of T cells that recognize recombinant MUC16 protein (in-house) using flow cytometry. On Day 14, 53B6 CAR-T cells were cryopreserved.

Figure 7A:
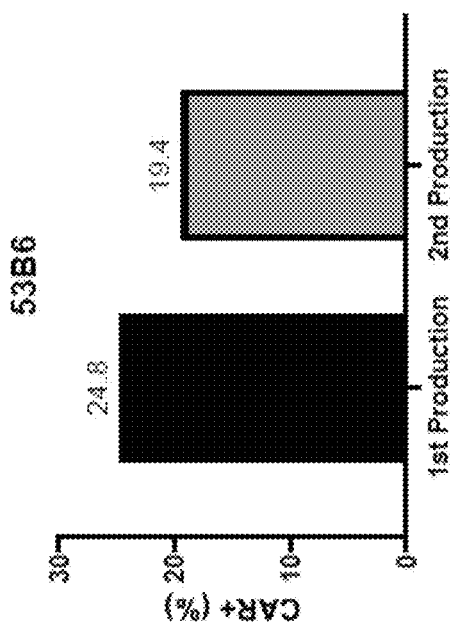
FIG. 7A. 53B6 CAR T cells were successfully generated from two different T cell donors using lentiviral transfer vector containing the 53B6 scFv that targets the MUC16 protein. CAR+ T cell population was detected with recombinant MUC16 protein (SEA1-4) using flow cytometry.
Figure 7A:
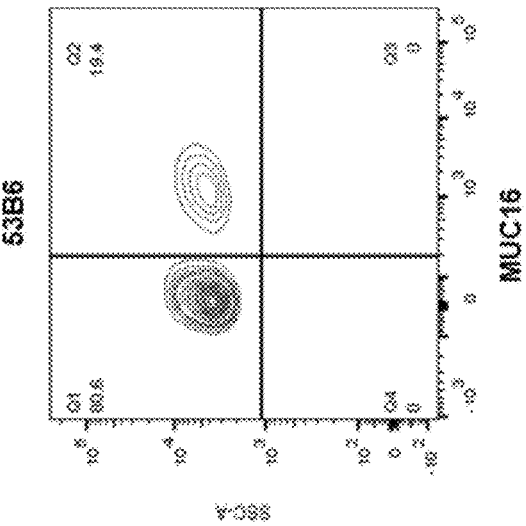
Figure 7A:
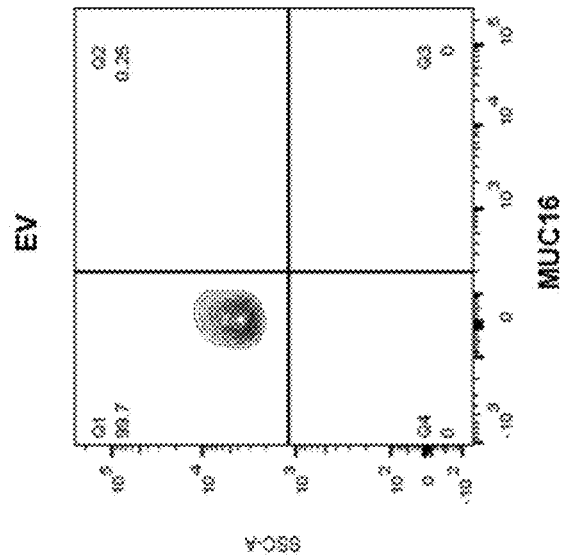
Figure 7B:
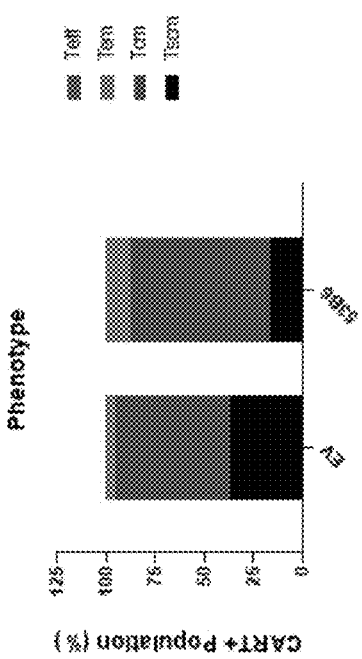
FIG. 7B. Phenotypes were assigned according to CD62L and CD45RO expression within the CAR+ T cell population as follows: stem cell memory (Tscm; CD45RO-/CD62L+), central memory (Tcm; CD45RO+/CD62L+), effector memory (Tem; CD45RO+/CD62L-), effector cells (Teff; CD45RO-/CD62L-). SEA=sperm protein, enterokinase, agrin; EV: empty vector.
Figure 7B:
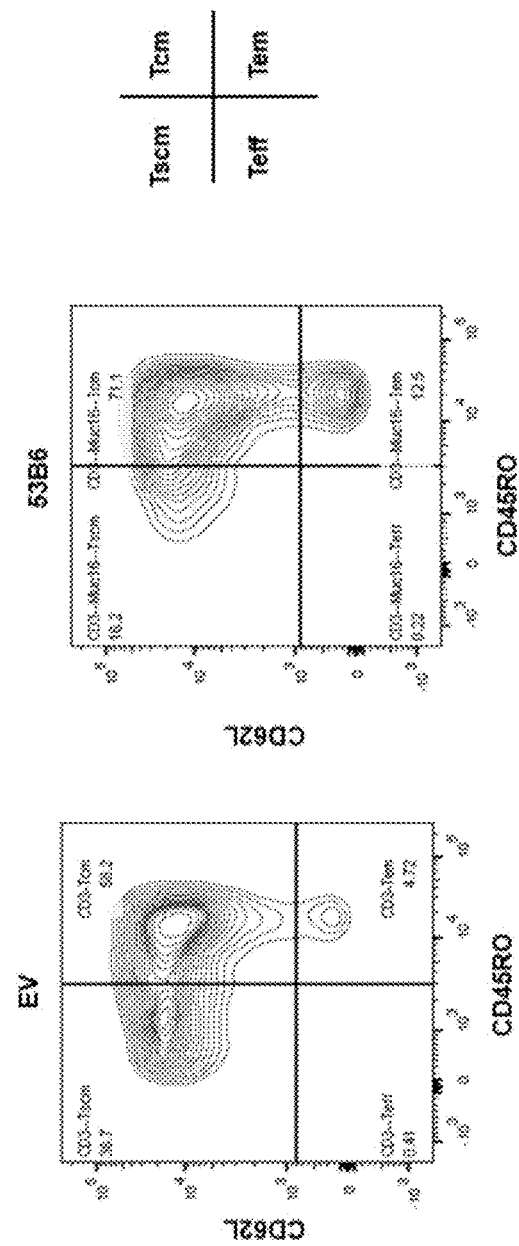

Flow Cytometry Analysis (FIGS. 7A-7B)

To determine the percentage of T cells that were successfully transduced with 53B6 CAR, T cells were first incubated with 3 µg/ml biotinylated recombinant MUC16 protein (in house) in FACS buffer (PBS+0.5% BSA with 2 mM EDTA) for 30 minutes at 4° C. The cells were then washed with FACS buffer, stained with streptavidin-PE labelled protein (Thermo Fisher, Cat #21627) at 1:250 ratio and analyzed using flow cytometry. As example, FIG. 7A shows that 53B6 CAR T cells were successfully generated from multiple productions using different T cell donors. The flow cytometry plot of 53B6 CAR T cells was from one of the productions. Empty vector (EV) control T cells were included in the studies.

Figure 3B:
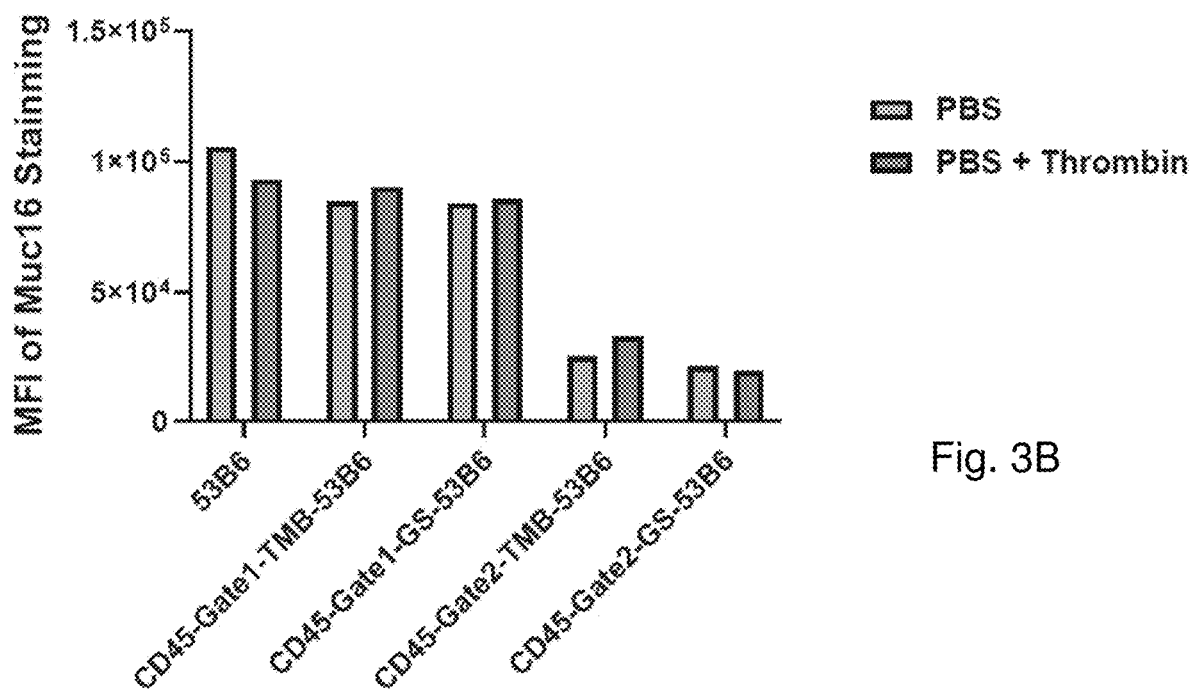
FIG. 3B. The ability of the CAR T cells of FIGS. 2A-2B to bind to soluble MUC16 was not significantly affected by the presence or absence of the CD45 gate.

Alternatively, another recombinant MUC16 conjugated with Alexa Fluor®647 were used to directly stain CAR T cells at approximately final concentration of 3 µg/ml to evaluate the binding of 53B6 CAR in FIGS. 2A and 3B.

Phenotypes (FIG. 7B) of the CAR T cells were also determined on Day 13 according to CD62L (Biolegend) and CD45RO (Biolegend) expression within the CAR+ T cell population as follows: stem cell memory (Tscm; CD45RO-/CD62L+), central memory (Tcm; CD45RO+/CD62L+), effector memory (Tem; CD45RO+/CD62L-), effector cells (Teff; CD45RO-/CD62L-). Lineage markers using antibodies toward CD3 (BD Biosciences), CD4 (Biolegend) and CD8 (Biolegend) were also included in the stain.

Cytotoxicity Assay (FIGS. 8A-8C and FIGS. 9A-9B)

Short Term Killing Assay

This example describes experiments used to determine the specificity and in vitro activity of 53B6 CAR.

OVCAR3, COV644 and FUOV$_1$ ovarian cell lines were purchased from ATCC or Sigma, and surface expression of MUC16 protein was determined using a quantitative analysis kit (Agilent Cat. #K007811-8), according to manufacturer's recommendation. To determine the activity of 53B6 CAR T cells, $1\times10^4$ luciferase-expressing ovarian target cells were co-cultured in RPMI 1640 medium (Gibco) supplemented with 10% FBS with 53B6 CAR+ T cells at defined Effector:Target (E:T) ratio in 96-well assay plates (Corning). Empty vector (EV) control T cells were also included in the study. Cell viability was measured after 72 hours using One-Glo reagent (Promega). Each condition was assayed in replicate wells. Percent target cell survival after being exposed to T cells was determined by comparing to target cells alone. Average percentage of live cells and standard deviation are shown (FIGS. 8A-8C).

Long Term Serial Killing Assay

A serial killing assay involves repeated exposure of CAR T cells to their target causing the CAR T cells to undergo proliferation and in certain cases, differentiation and exhaustion.

Figure 9A:
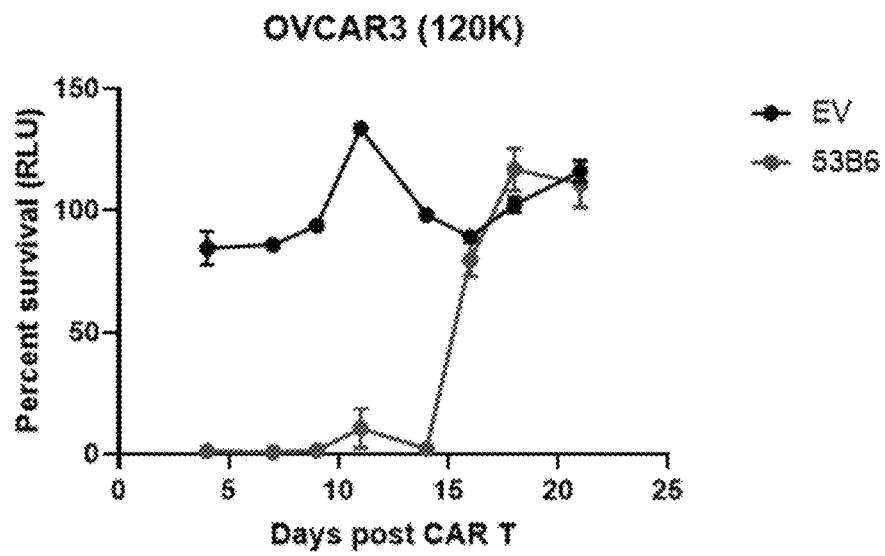
FIGS. 9A-9B. 1×10$^7$ luciferase-expressing OVCAR3 target cells were co-cultured with 53B6 CAR+ T cells at Effector:Target ratio of 1:1 in a serial killing assay, where the T cells are exposed to fresh target cells every 2-3 days. Empty vector (EV) control T cells were also included in the study. Percent target cell survival after being exposed to T cells was determined by comparing to target cells alone. Data presented are the activity of 53B6 CAR T cells from two different donors.
Figure 9B:
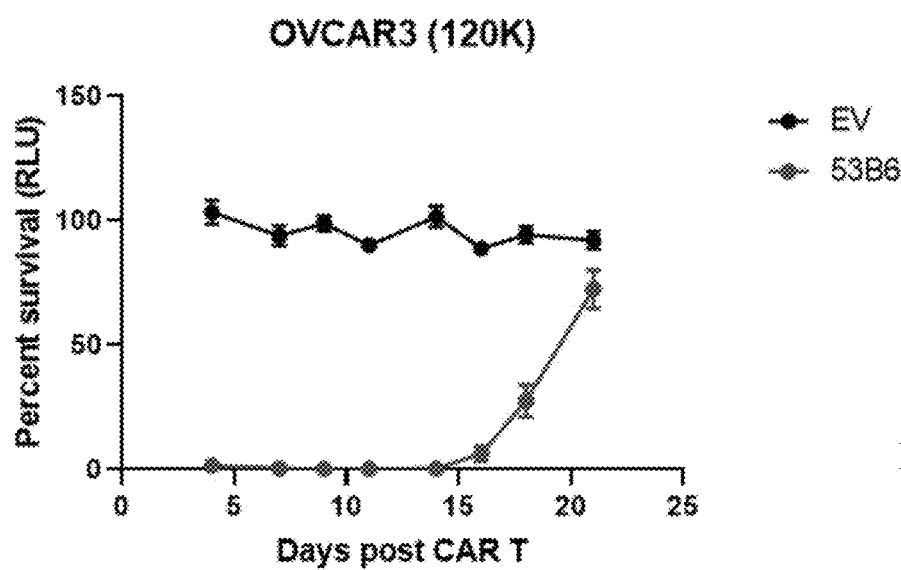

To determine the persistent killing of 53B6 CAR T cells, $1\times10^4$ luciferase-expressing OVCAR3 target cells were co-cultured in RPMI 1640 medium (Gibco) supplemented with 10% FBS with 53B6 CAR+ T cells at Effector:Target ratio of 1:1 in a serial killing assay using 96-well assay plates. Every 2-3 days thereafter, 100 µl medium from each well were transferred to freshly plated target cells ($1\times10^4$ cells per well) and percent target cell survival of the previously plated target cells after being exposed to CAR T cells was determined by comparing to target cells alone using One-Glo reagent. Each condition was assayed in 3 to 6 replicates. Empty vector (EV) control T cells were also included in the study. Average percentage of live cells and standard deviation are shown. Data presented are the activity of 53B6 CAR T cells from two different donors (FIGS. 9A-9B).

Figure 10A:
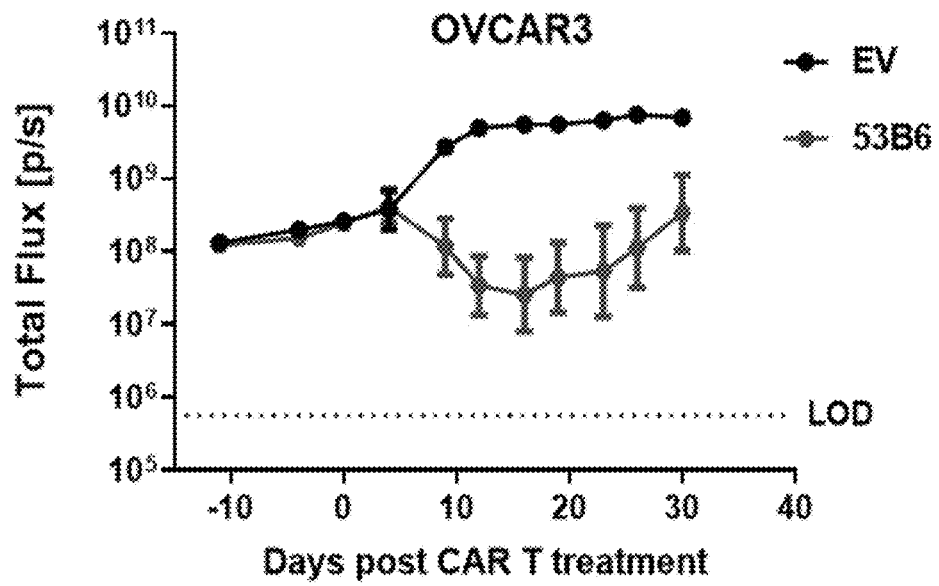
FIGS. 10A-10B. 53B6 anti-MUC16 CAR T cells display anti-tumor activity against two different orthotopic ovarian tumor models. NSG mice (n=5) intra-peritoneally (IP) injected with 3×10$^6$ luciferase-labeled OVCAR3 (FIG. 10A) or COV644 (FIG. 10B) cells received IP injection of 1×10$^6$ or 3×10$^6$ 53B6 CAR+ T cells, respectively, 14 days later. Tumor burden was monitored by bioluminescence, and the results demonstrated anti-tumor activity in both models. Empty-vector (EV) control T cells were also included in the study. LOD=Limit of Detection, based on bioluminescence imaging of non-tumor bearing mice.
Figure 10B:
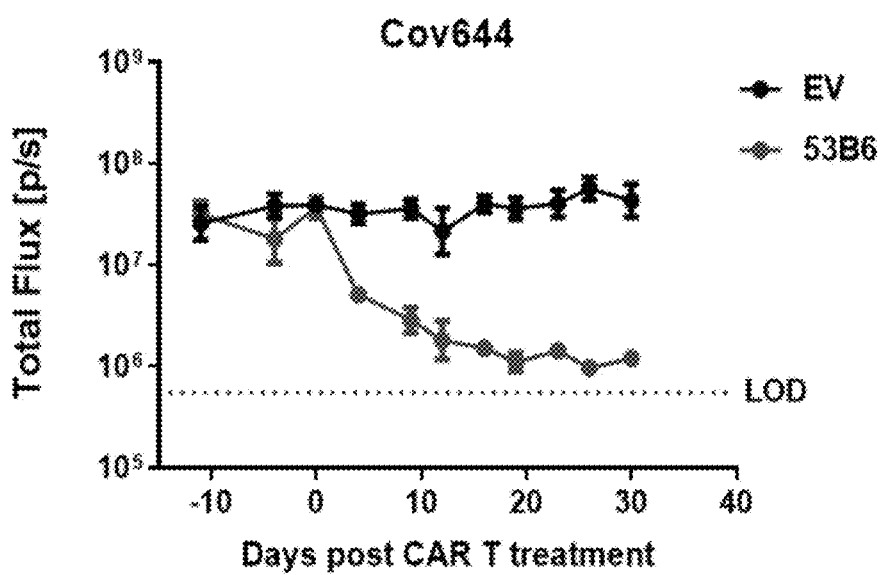

In Vivo Activity (FIGS. 10A-10B)

To test the anti-tumor activity of 53B6 CAR T cells, two different orthotopic ovarian tumor models were used. Luciferase-labeled OVCAR3 and COV644 ovarian cells were cultured in complete growth medium (RPMI 1640 supplemented with 10% FBS). Cells were collected and diluted to $15\times10^6$ viable cells/ml in PBS, and cell suspension was kept on ice until inoculation. NSG mice (Jackson Laboratory), aged 7-8 weeks old, were injected intra-peritoneally (IP) with 200 µl ($3\times10^6$ target cells per mouse) of OVCAR3 or COV644. Tumor burden was monitored using the IVIS Spectrum (Perkin Elmer), where the animals were injected intra-peritoneally with 200 µl of luciferin (15 mg/ml; Pierce) and bioluminescent intensity was measured. Mice were randomized into groups of 5 based on total body bioluminescence about two weeks post tumor implantation. 53B6 CAR T cells were then thawed and resuspended in PBS. OVCAR3-tumor bearing mice received $1\times10^6$ 53B6 CAR+ T cells per animal, whereas COV644-tumor bearing mice received $3\times10^6$ 53B6 CAR+ T cells per animal. Empty-vector control T cells were also included in the study. All animals infused with T cells were dosed via ip injection in a volume of 200 µl/mouse. The in vivo activity of the 53B6 CAR T cells against the tumor was monitored by bioluminescence, and the results demonstrated anti-tumor activity in both models (FIGS. 10A-10B).

Example 3. Test of CD45-Gate CAR T Cell Activity 3.1. Production of New CD45-Gate CAR T (Effector) Cells (FIGS. 12A-12D and FIGS. 13A-13D)

CAR T cells expressing a CD45-gate MUC16 CAR comprising a TPS linker selected from a panel of TPS linkers (similar to the CD45-gate CARs diagrammed in FIG. 11), were successfully generated and characterized using flow cytometry according to methods described in Example 2 and below. In addition to cells expressing CARs comprising one of the cleavable TPS linkers, cells expressing a CAR comprising a non-cleavable GS linker were prepared as a negative control expected not to exhibit CAR activity because the CD45-gate cannot be released by proteases. Cells expressing a non-gated MUC16 CAR (53B6) were included as a second, positive control expected to be active in the presence or absence of proteases.

Figure 12B:
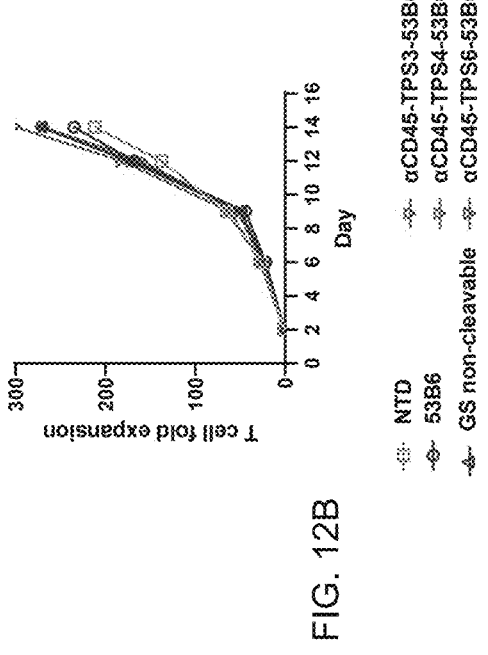
FIGS. 12A-12D. Production of new CD45-gate CART cells. CD45-gate CAR T cells containing a selective panel of TPS linkers were successfully generated and characterized using flow cytometry according to methods described in Example 2. Autoactivation and memory phenotypes of the CAR T cells were also determined using flow cytometry by analyzing the expression of CD45/41BB and CD45RO/CD62L on Day 9 and Day 14, respectively.
Figure 12A:
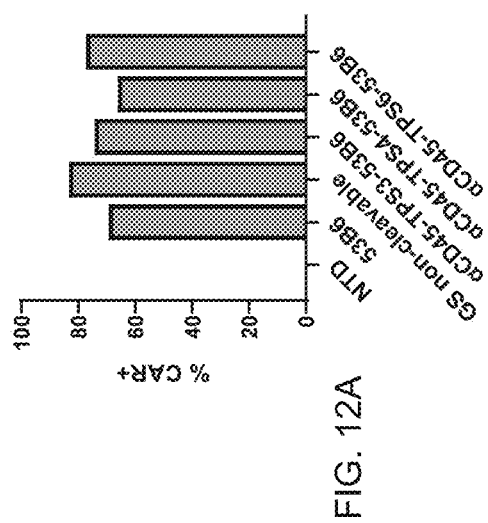
Figure 12D:
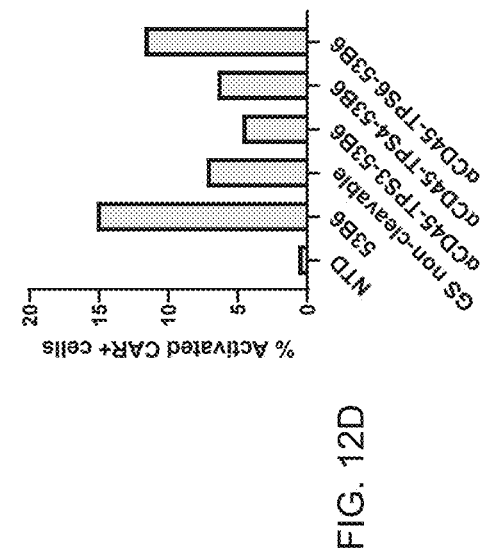
Figure 12C:
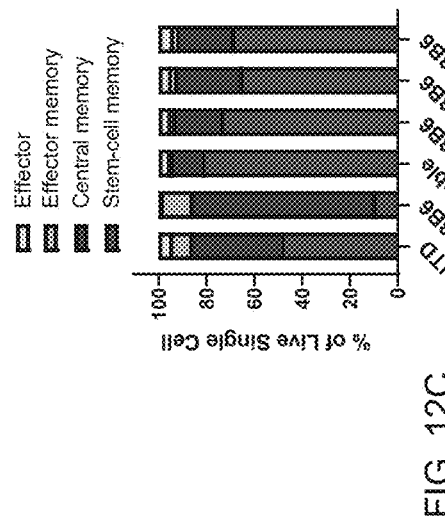
Figure 13B:
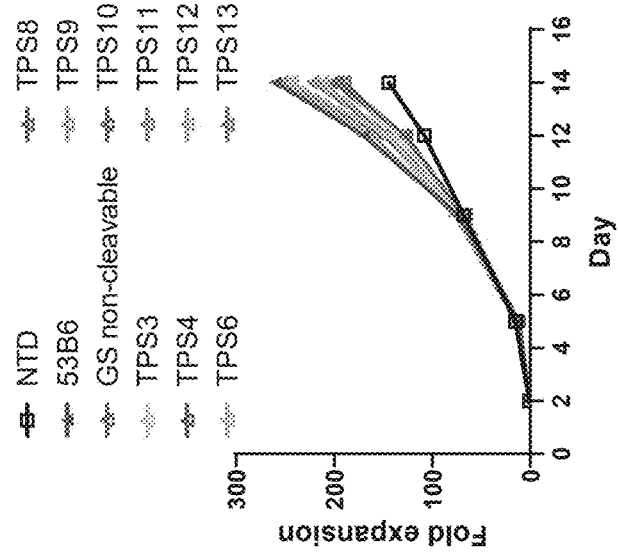
FIGS. 13A-13D. CD45-gate CAR T cells containing different TPS linkers were generated.
Figure 13A:
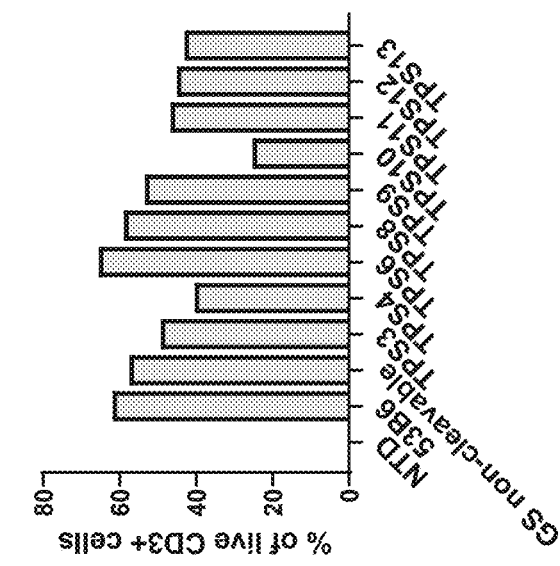
Figure 13D:
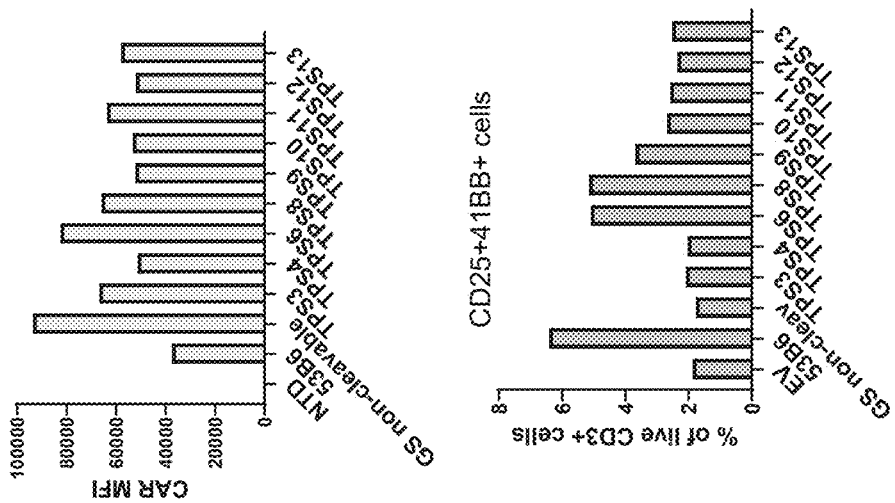
Figure 13C:
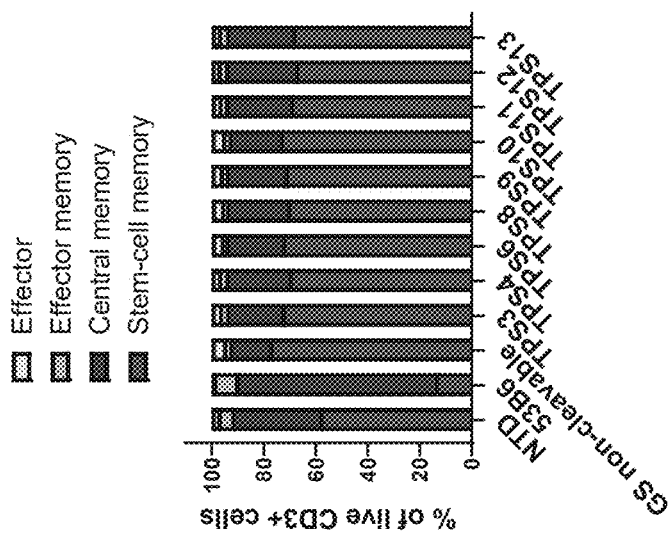

Each CAR+ T cell population was detected with AlexaFluor 647-conjugated recombinant MUC16 protein (SEA1-4) using flow cytometry (FIG. 12A). The overall expansion of T cells remains similar among all the clones and is comparable to non-transduced control (NTD), indicating no obvious fratricide (FIG. 12B). Autoactivation and memory phenotypes of the CAR T cells were also determined using flow cytometry by analyzing the expression of CD25/41BB and CD45RO/CD62L on Day 9 and Day 14, respectively. Overall, CD45-gate CAR T cells contain a higher percentage of stem-cell memory subset (CD45RO-/CD62L+, FIG. 12C) and exhibit less tonic signaling (CD25+/41BB+, FIG. 12D) than naked CAR T cells, suggesting a potential benefit of CD45-gate CARs in controlling T cell exhaustion. At the end of the production (Day 14-16), all T cells were cryopreserved in 90% FBS/10% DMSO using rate-controlled freezing chambers and stored in liquid nitrogen.

A second set of CAR T cell populations, each expressing a CD45-gate MUC16 CAR comprising a TPS linker selected from a second panel of TPS linkers, were generated successfully and characterized according to methods described in Example 2 and this section (results shown in FIGS. 13A-13D). The success in generating CD45-gate CAR T cells was surprising because T cells express endogenous CD45, however no noticeable fratricide was observed that would have hindered the production of the CD45-gate CAR T cells.

3.2. Generation and Analysis of Reagent Cell Lines (FIGS. 14A-14E)

Figure 14A:
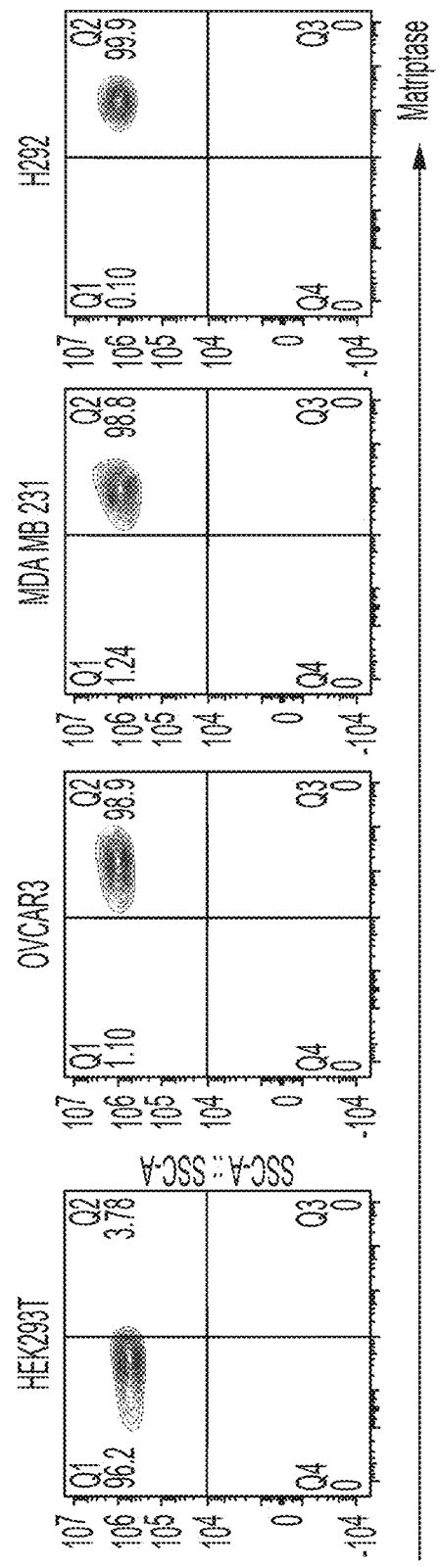
FIGS. 14A-14E. Generation and analysis of reagent cell lines. Target cells were developed in-house based on three cell lines that are positive for tumor-associated proteases, including an ovarian cancer cell line OVCAR3, a breast cancer cell line MDA-MB-231, and a lung carcinoma cell line NCI-H292.
Figure 14B:
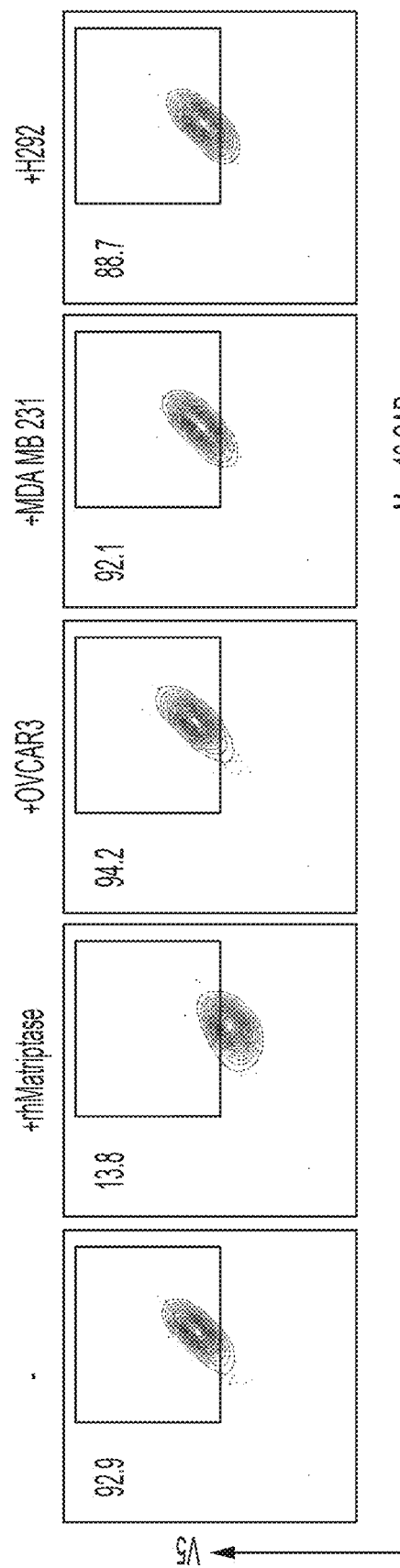
Figure 14C:
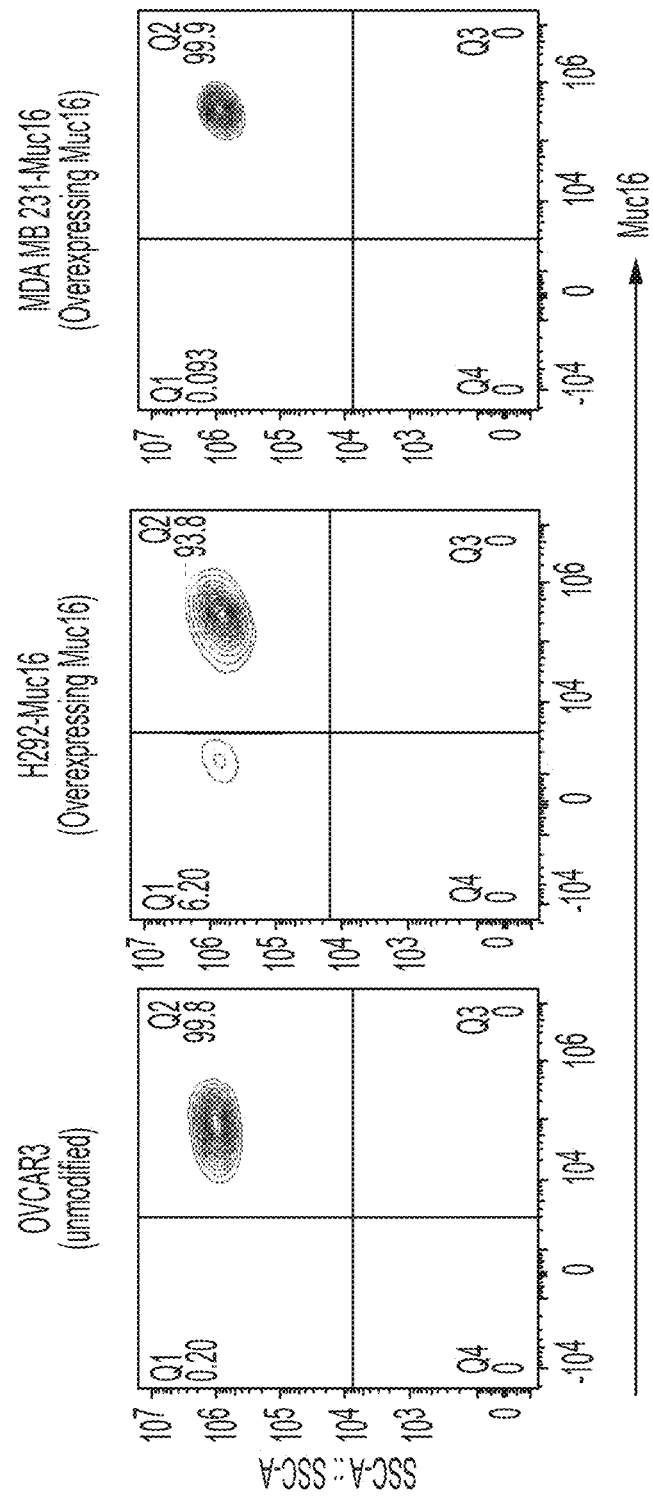
Figures 14D, 14E:
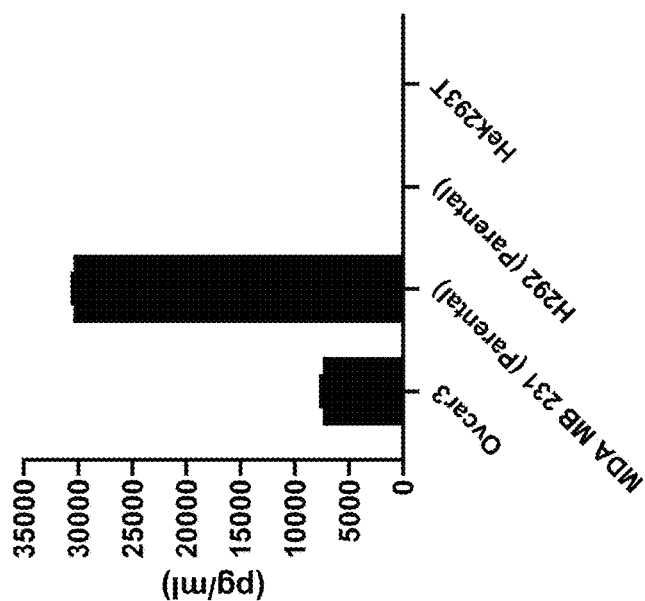

Target cell lines were developed in house based on three cell lines that are positive for (i.e. express active) tumor-associated proteases, including an ovarian cancer cell line OVCAR3, a breast cancer cell line MDA-MB-231, and a lung carcinoma cell line NCI-H292. The surface expression of matriptase (3 µg/mL; R&D, BAF3946) was confirmed using flow cytometry (FIG. 14A) and the secretion of urokinase (uPA) was detected in conditioned media by an ELISA kit (R&D, DUPA00) (FIG. 14D). In addition, the activity of surface expressed matriptase was assessed through the detection of a V5 tag that is attached to CAR via a matriptase cleavable linker TPS6, as previously described in Example 1 (FIG. 14B). Compared to the recombinant matriptase which effectively mediated linker cleavage and removal of V5 tag, the endogenous matriptase showed limited activity, which is, without wishing to be bound by specific mechanisms, believed to be due to the lack of activation of matriptase in the in vitro assay settings. For example, FIG. 14B shows that in this experiment in vitro matriptase is not active, consistent with the CD45-Gate CAR with TPS6 also not being active.

To study the target-mediated CAR activation, MDA-MB-231 and H292 cell lines engineered to overexpress human MUC16 SEA1-4 and OVCAR3 cell line expressing endogenous MUC16 were used as target cells. The expression of the target protein MUC16 was validated by flow cytometry (FIG. 14C). All three cell lines were then engineered to co-express a firefly luciferase and a nuclear GFP using a 2A peptide to enable sensitive measurement of tumor killing using luminescence reading or Incucyte imaging.

3.3 In Vitro Analysis of CD45-Gate CAR T Cell Activity, Protease Dependence and Sensitivity (FIGS. 15A-15F and FIGS. 16A-16F)

A Jurkat-NFAT reporter cell line was used to evaluate the activity of CD45-gate CARs. The Jurkat-NFAT reporter cell line contains a nuclear factor of activated T-cell (NFAT) promoter upstream of a luciferase gene, which allows the quantitative measurement of signaling activation upon stimulation. To generate CAR reporter cells, Jurkat-NFAT cells were transduced with lentivirus encoding CD45-gate CARs and expression was analyzed after 6 days using recombinant MUC16 protein (SEA1-4). Transduced cells were then cocultured with target cells (1×10⁴/well) at a 1:1 E:T ratio in 96-well white flat-bottom plates. Wells containing only Jurkat cells also were included as negative controls. All cocultures were performed in CTS OpTmizer T cell expansion SFM (Gibco) with or without human recombinant matriptase (0.2 µg/mL, R&D, 3946-SEB-010). After overnight incubation at 37° C., the reporter gene activation was detected by luminescence and normalized to the untreated control signal when no target cells were added.

As shown in FIGS. 15A-15F, exposure to MUC16 positive target cells led to the activation of 53B6 CAR while no activation was detected with a CD45-gate CAR with non-cleavable linker. However, the activation can be restored via the cleavable linkers upon exposure to endogenous ("−Matriptase" in FIGS. 15A-15C) or exogenous proteases ("+Matriptase" in FIGS. 15A-15C). This shows that the CD45-gate suppresses CAR activity and the suppression can be protease-sensitive when the linker comprises one or more protease sites. The data comprise clones 1241 (2×TPS6), 1466 (2×TPS6), 1467 (2×TPS6), 1468 (2×TPS6), and 1469 (2×TPS6), each of which utilizes linkers with various lengths (45, 35, 30, 25, 20-mers) and yet they enable highly similar functionality. The following constructs were used in FIGS. 15D-15F:

- 0975 (TMB) refers to SEQ ID NO: 16 (N-HA-4131scFv-V5-2G4STMB-53B6, comprising the linker GSTMB (45 aa) having the amino acid sequence of SEQ ID NO: 8
- 0976 (NC) refers to SEQ ID NO: 17 (non-cleavable)
- 1102 (2×TPS3) refers to SEQ ID NO: 24 (N-HA-4131-VL-RS-VH-TPS1-53B6, comprising the linker GSTPS1 (45 aa), having the amino acid sequence of SEQ ID NO: 9, and comprising the linker TPS cleavage, having the amino acid sequence of SEQ ID NO: 53 flanked on both ends by GS sequences
- 1399 (TPS4) refers to SEQ ID NO: 137, a construct containing the elements V5-GS20-4131scFv-TPS4-53B6, comprising the linker TPS4 45 aa (SEQ ID NO: 107) and a GS sequence
- 1401 (TPS6) refers to SEQ ID NO: 138, a construct containing the elements V5-GS20-4131scFv-TPS6-53B6, comprising the linker TPS6 45 aa having the amino acid sequence of SEQ ID NO: 113
- 1241 (2×TPS6) refers to SEQ ID NO: 144, a construct containing the elements N-HA-4131scFv-2×TPS6-53B6, comprising the linker TPS6 35aa having the amino acid sequence of SEQ ID NO: 112 and a second linker comprising the cleavage site MTSP (3) (SEQ ID NO: 95) flanked on both ends by a GS sequence
- 1466 (2×TPS6) refers to SEQ ID NO: 153, a construct containing the elements V5-GS20-4131scFv-2×TPS6-35-53B6, comprising 2 copies of the linker TPS6 35 aa, each copy having the amino acid sequence of SEQ ID NO: 112
- 1467 (2×TPS6) refers to SEQ ID NO: 154, a construct containing the elements V5-GS20-4131scFv-2×TPS6-30-53B6, comprising the linker TPS6 35 aa (SEQ ID NO: 112) and the linker TPS6 30 aa (SEQ ID NO: 111)
- 1468 (2×TPS6) refers to SEQ ID NO: 155, a construct containing the elements V5-GS20-4131scFv-2×TPS6-25-53B6, comprising the linker TPS6 35 aa (SEQ ID NO:112) and the linker TPS6 25 aa (SEQ ID NO: 110)
- 1469 (2×TPS6) refers to SEQ ID NO: 156, a construct containing the elements V5-GS20-4131scFv-2×TPS6-20-53B6, comprising the linker TPS6 35aa (SEQ ID NO: 112) and the linker TPS6 20aa (SEQ ID NO: 109)

3.4. Cytotoxicity of CD45-Gate CAR T Cells

Figure 16A:
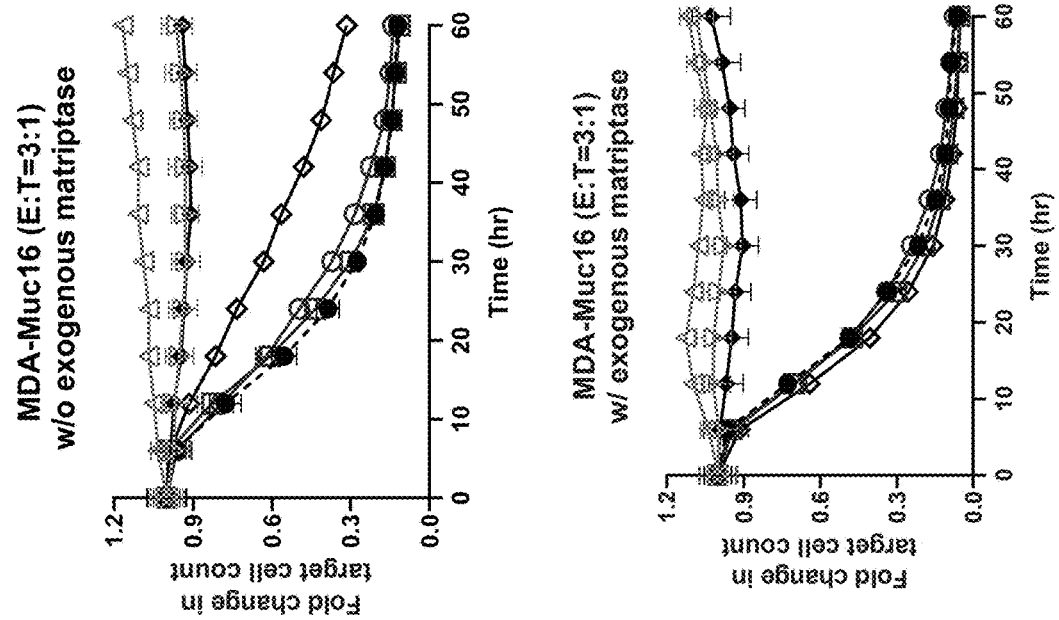
FIGS. 16A-16F. The short-term cytotoxicity of CD45-gate CAR T cells against target cell lines MDA-MB-231-Muc16, H292-Muc16, and OVCAR3 was evaluated using a nuclear GFP assay. Average fold change in target cell count and standard deviation are shown in each of FIGS. 16A-16F (E:T=3:1 for each cell line). Top panels: CD45-gate CARs with various TPS linkers showed a spectrum of activity in the presence of endogenous proteases, with some of the linkers (e.g., TPS4) exhibiting activity comparable to conventional 53B6 CAR. Bottom panels: all CD45-gate CARs with TPS linkers showed cytotoxic activities in the presence of exogenous matriptase. Incorporation of a non-cleavable GS linker in a CD45-gate CAR effectively inhibited CAR function. All cleavable linkers in FIGS. 16A-16F have a length of 45 amino acids.
Figure 16B:
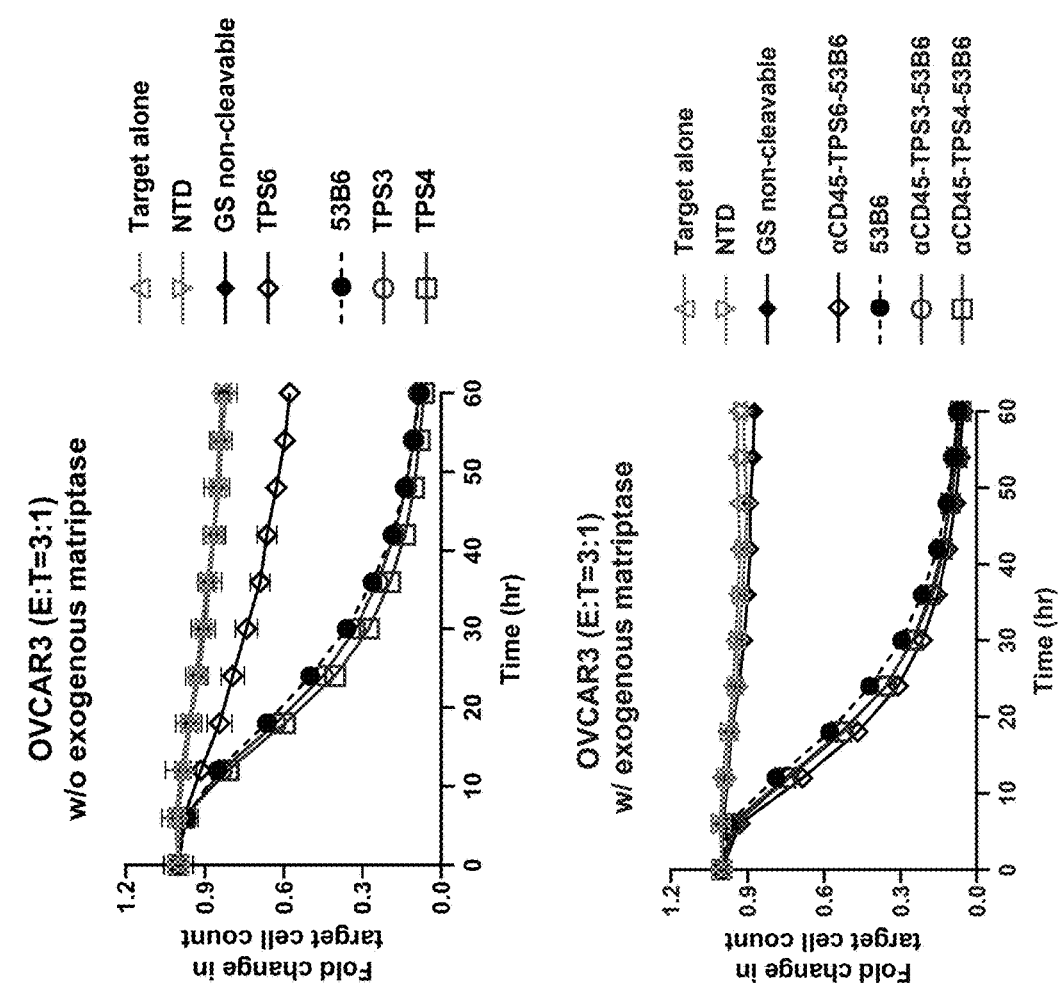
Figure 16C:
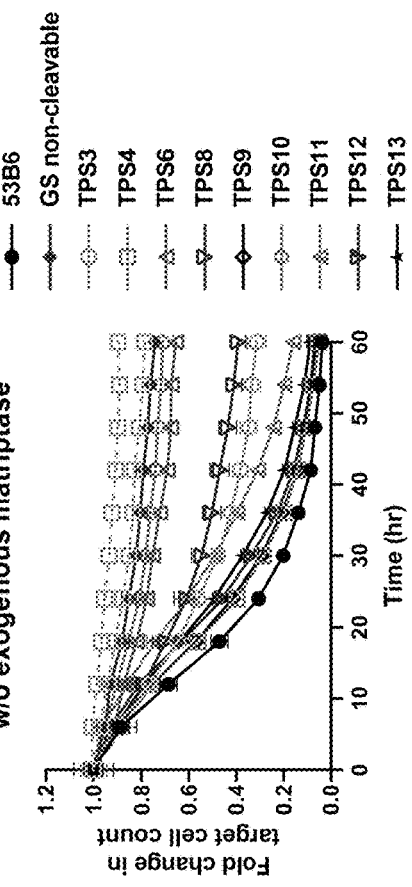
Figure 16C:
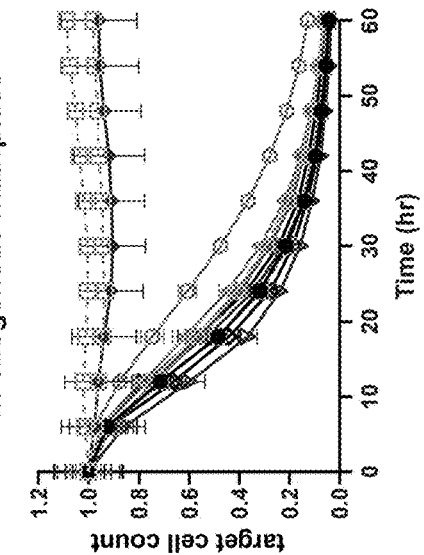
Figure 16D:
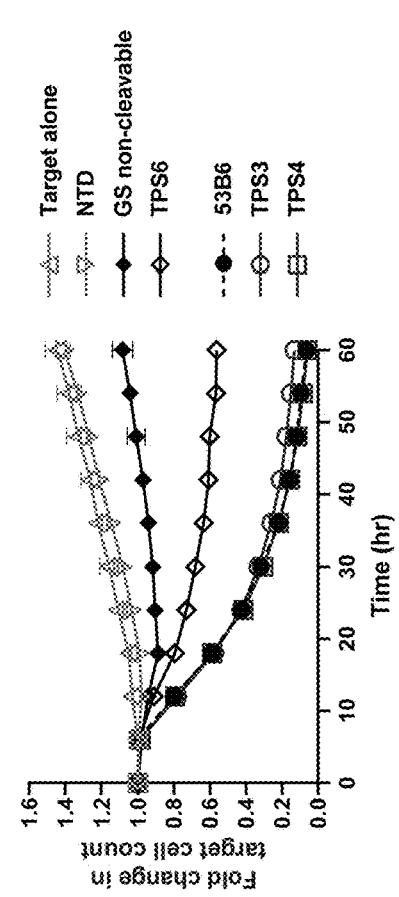
Figure 16D:
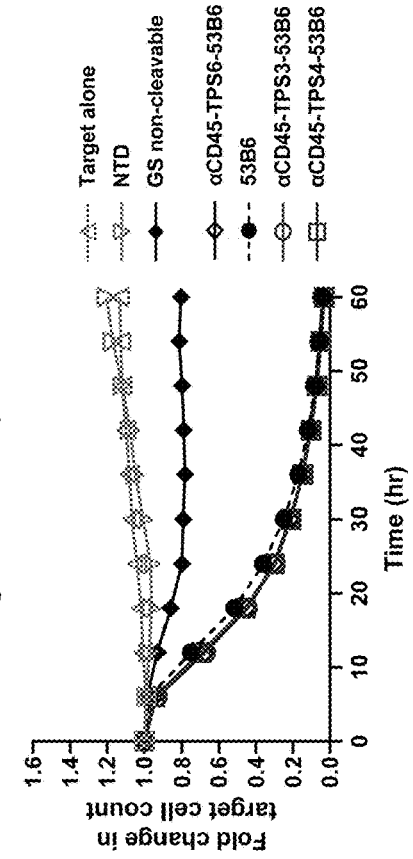
Figure 16E:
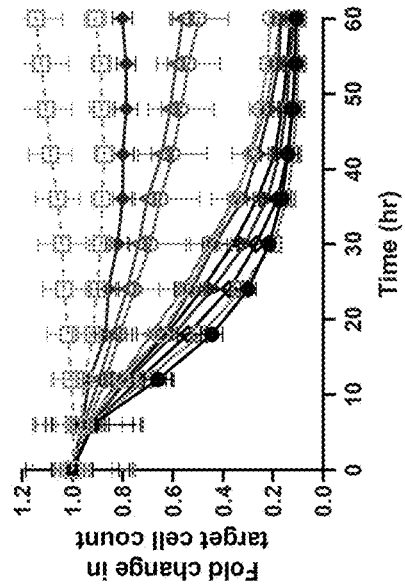
Figure 16E:
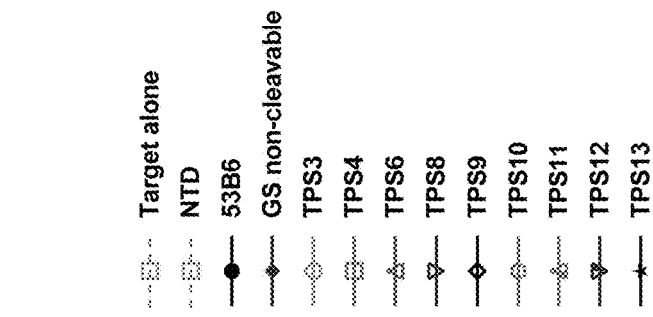
Figure 16F:
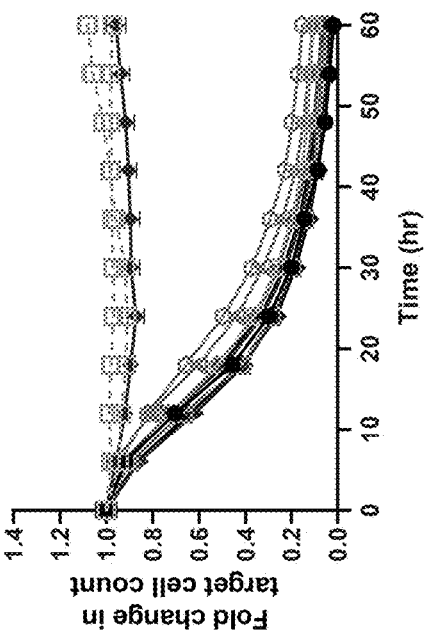
Figure 16F:
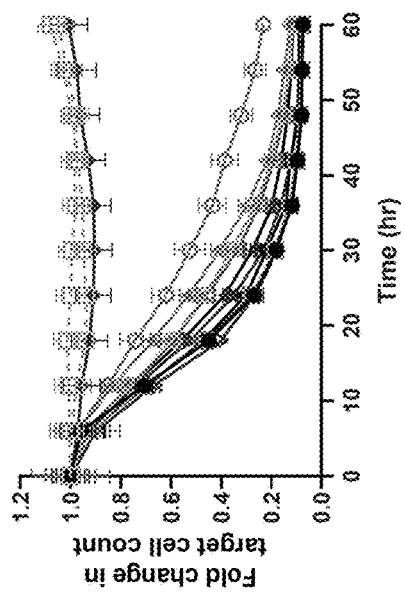

The short-term cytotoxicity of CD45-gate CAR T cells were characterized using Incucyte. For kinetic analysis of tumor cell killing, target cells MDA-MB-231-MUC16, H292-MUC16 and OVCAR3 cells engineered to express nuclear GFP were plated at a concentration of $1\times10^4$ cells per well in 96-well black flat-bottom plates. The following day, T cells were thawed and added at an effector:target (E:T) ratio of 3:1. All cocultures were performed in CTS OpTmizer T cell expansion SFM (Serum-Free Medium; Gibco) with or without human recombinant matriptase (0.2 µg/mL, R&D, 3946-SEB-010). The number of viable target cells was monitored by fluorescent imaging every 6 hours over 60 hours using the IncuCyte Live Cell Analysis System (Essen BioScience). Live-cell numbers were quantified by IncuCyte S3 software (Essen BioScience) and normalized to the initial counts at time 0 (time zero). Average fold change in target cell count and standard deviation are shown in FIGS. 16A-16F. CD45-gate CARs with non-cleavable GS linker effectively inhibited CAR function. In the presence of endogenous proteases ("w/o [without] exogenous matriptase") (top panels of FIGS. 16A-16F), CD45-gate CARs with various TPS linkers showed a spectrum of activity, with some of the linkers (e.g., TPS4) exhibiting activity comparable to that of non-gated 53B6 CAR. In the presence of exogenous matriptase ("w/[with] exogenous matriptase") (bottom panels of FIGS. 16A-16F), all CD45-gate CARs with TPS linkers showed cytotoxic activities. FIGS. 16A-16C show results using linkers from the first set of linkers (TPS3, TPS4, TPS6) plus controls; FIGS. 16D-16F show results using linkers from the first and second sets of linkers (TPS3, TPS4, TPS6, TPS8-TPS13) plus controls.

Figure 17A:
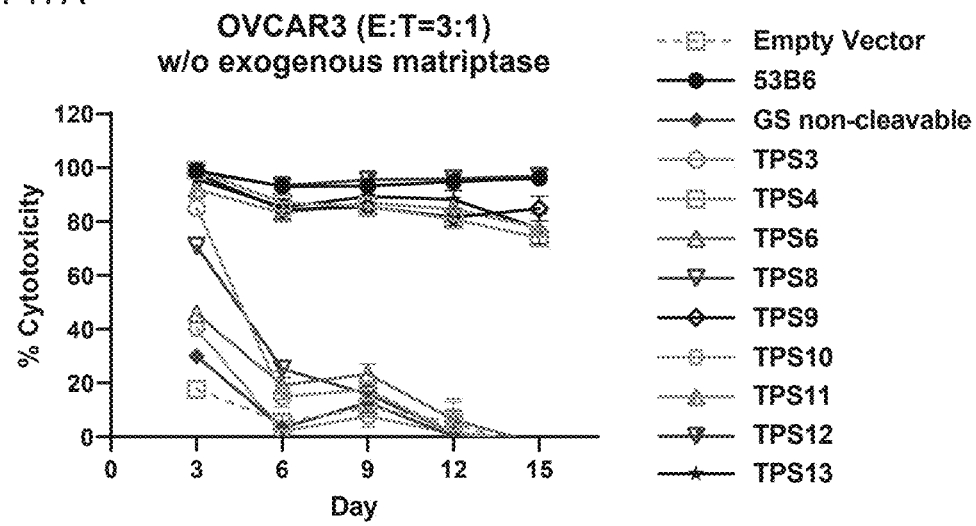
FIGS. 17A-17B. CARs with TPS linkers maintained long-term cytotoxicity in the presence of endogenous/exogenous proteases.
Figure 17B:
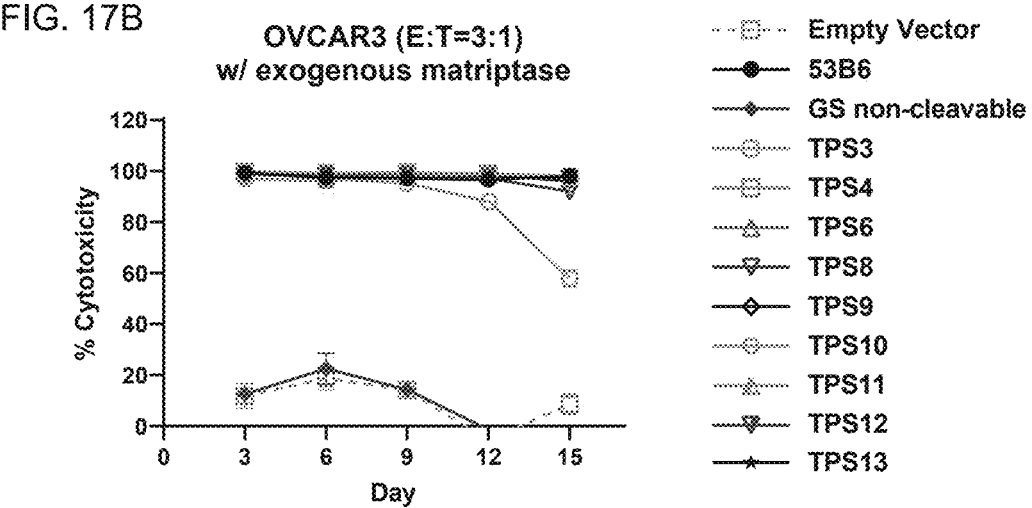

3.5 Long-Term Killing Assay (FIGS. 17A-17B)

To determine the persistent killing of CD45-gate CAR T cells upon repeated exposure to target, luciferase-expressing OVCAR3 cells were plated in CTS OpTmizer T cell expansion SFM (Gibco) at a concentration of $1\times10^4$ cells per well in 96-well white flat-bottom plates. The following day, T cells were thawed and added at a E:T ratio of 3:1. All cocultures were performed with or without human recombinant matriptase (0.2 µg/mL, R&D, 3946-SEB-010). Every 2-3 days, half of the supernatant containing CAR T cells from each well was transferred to freshly plated target cells ($1\times10^4$/well) and target cell viability was measured by luminescence using One-Glo assay (Promega) as previously described. Data presented are the cytotoxicity of CD45-gate CAR T cells, showing that those with cleavable linkers maintained long-term cytotoxicity in the presence of endogenous (FIG. 17A) or exogenous (FIG. 17B) proteases.

In Vivo Assay (FIGS. 18A-18C and FIGS. 19A-19C)

Figure 18A:
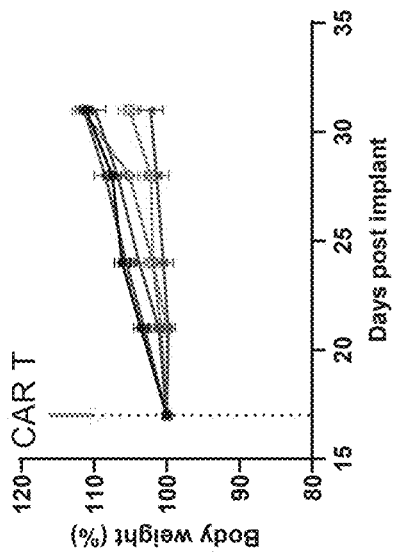
FIGS. 18A-18C. Evaluation of CD45-gate CART cells (MDA-MB-231-Muc16) in a breast cancer xenograft model in 7-8 weeks old NSG mice.

In vivo anti-tumor efficacy of CD45-gate CAR T cells was evaluated in a breast cancer xenograft model (FIG. 18A shows schematic outline of experiment). 7-8 weeks old NSG mice (Jackson Laboratory) were injected subcutaneously (SC) with 200 µl of MDA-MB-231-MUC16 cells ($5\times10^6$ cells mixed with Matrigel at 1:1 ratio). Mice were randomized into 6 groups (n=7-8) when average tumor size reached 290 mm³ on day 17. Each animal received 5 million CAR+ cells via tail vein injection. Total T cell numbers were kept constant across all groups by normalizing with non-transduced T cells. Tumors were measured twice a week and tumor volume was calculated as length (mm)×width (mm)×height (mm)/2. Statistical analysis of observed differences was performed by one-way ANOVA followed by Dunnett's test for multiple comparisons.

Figure 18C:
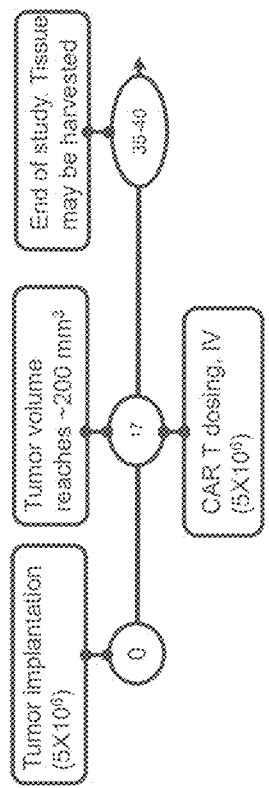
Figure 18B:
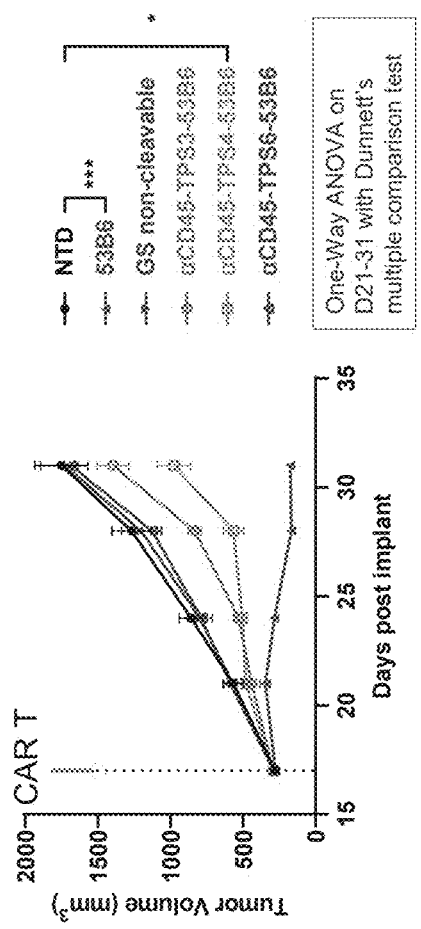

As shown in FIG. 18B, anti-tumor CAR activity cannot be activated in a CD45-gate CAR that comprises only a non-cleavable GS linker in the MDA-MB-231 model. In contrast, anti-tumor CAR activity can be activated in CD45-gate CARs with cleavable linkers (e.g., TPS4). Tumor growth was reduced in mice treated with the CD45-gate CAR aCD45-TPS4-53B6.

Treatment with CD45-gate CAR T cells had no effect on the body weight of the mice (FIG. 18C).

Figure 19A:
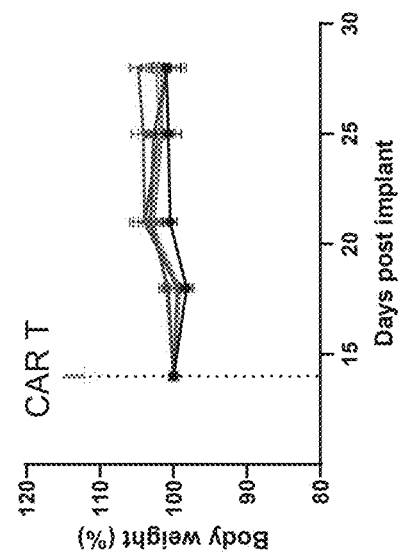
FIGS. 19A-19C. Evaluation of CD45-gate CART cells (NCI-H292-MUC16) in a non-small cell lung cancer xenograft model in NShG mice.

In vivo anti-tumor efficacy of CD45-gate CAR T cells was also evaluated in a non-small cell lung cancer xenograft model (FIG. 19A shows schematic outline of experiment). NSG mice (Jackson Laboratory) were injected subcutaneously (SC) with 200 µl of NCI-H292-MUC16 cells ($6\times10^6$ cells mixed with Matrigel at 1:1 ratio). Mice were randomized into 6 groups (n=6-7) when average tumor size reached 150 mm³ on day 14. CAR T cells were then thawed and infused immediately ($5\times10^6$ CAR+ cells per animal) via tail vein injection. Total T cell numbers were kept constant across all groups by normalizing with non-transduced T cells. Tumors were measured twice a week and tumor volume was calculated as length (mm)×width (mm)×height (mm)/2. Statistical analysis of observed differences was performed by one-way ANOVA followed by Dunnett's test for multiple comparisons. Without wishing to be limited to specific mechanisms, the results likely reflect the various levels of protease activity at the tumor site in this in vivo tumor model.

Figure 19B:
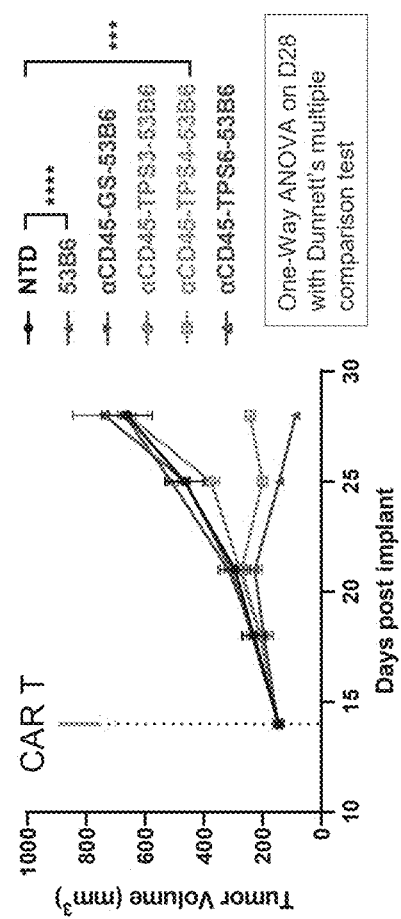
Figure 19C:
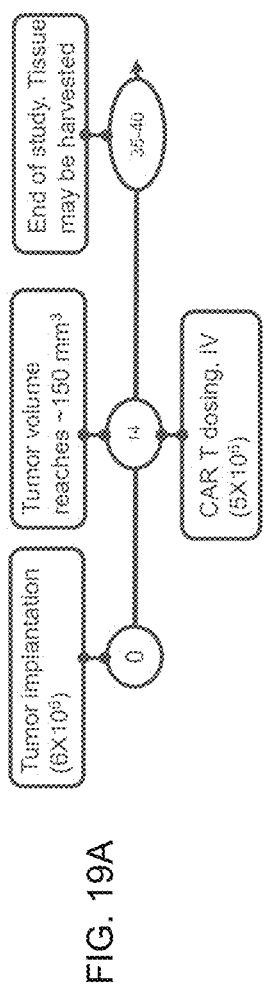
Figure 20A:
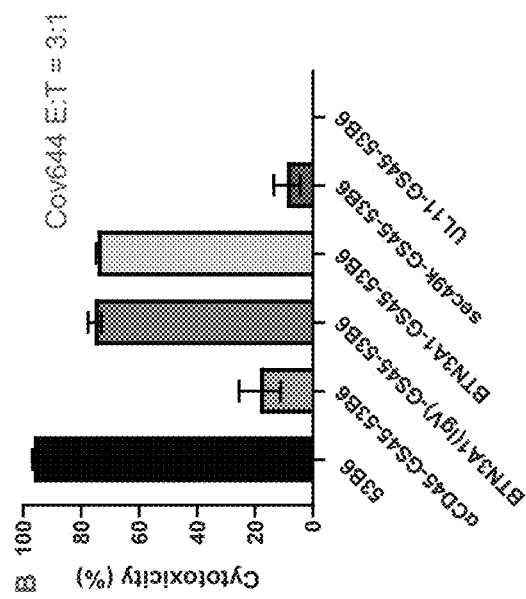
FIGS. 20A-20B. Evaluation of other CD45 ligands in protease-activating CD45-gate CAR. T cells were transduced with a vector that encodes a CAR that is not a protease-activating CD45-Gate CAR (53B6, an anti-Muc16 CAR), or with a vector that encodes the antibody-based CD45-Gate CAR (CD45-GS45-53B6), and other alternative CD45-Gate CARs that comprise a non-cleavable linker (BTN3A1(IgV)-GS45-53B6, BTN3A1-GS45-53B6, sec49k-GS45-53B6, UL11-GS45-53B6). The linker of the non-cleavable protein comprised a 45-mer G4S linker. Results of cytotoxicity assays used to assess inhibitory activity of CD45 gate. Assays were performed in R10 medium without thrombin or other exogenous protein present.
Figure 20B:
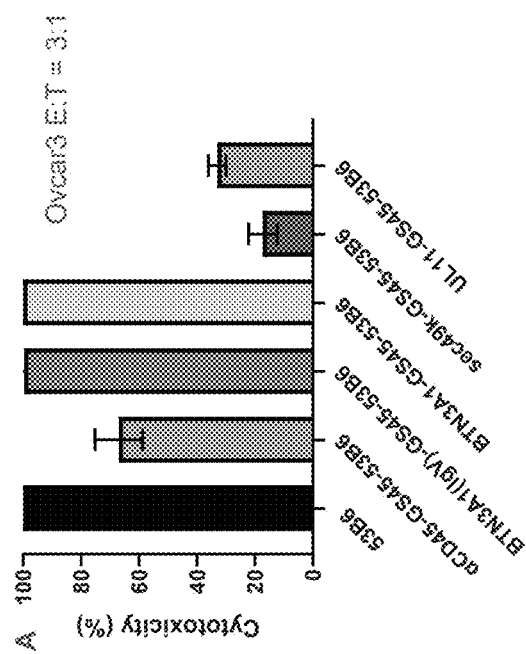

As shown in FIG. 19B, a CD45-gate CAR with a non-cleavable GS linker lacked any CAR anti-tumor activity in the H292 model. In contrast, a CD45-gate CAR with a cleavable linker (TPS4) showed anti-tumor activity.

Treatment with CD45-gate CAR T cells had no effect on the body weight of the mice (FIG. 19C), indicating that the CD45-gate CAR T cells did not lead to general toxicity in vivo.

REFERENCES

1. Ledbetter J A, Tonks N K, Fischer E H, Clark E A. CD45 regulates signal transduction and lymphocyte activation by specific association with receptor molecules on T or B cells. Proc Natl Acad Sci USA. 1988. doi:10.1073/pnas.85.22.8628
2. McNeill L, Salmond R J, Cooper J C, et al. The Differential Regulation of Lck Kinase Phosphorylation Sites by CD45 Is Critical for T Cell Receptor Signaling Responses. Immunity. 2007. doi:10.1016/j.immuni.2007.07.015
3. Felberg J, Johnson P. Characterization of Recombinant CD45 Cytoplasmic Domain Proteins. J Biol Chem. 1998. doi:10.1074/jbc.273.28.17839
4. Davis S J, van der Merwe P A. The kinetic-segregation model: TCR triggering and beyond. Nat Immunol. 2006. doi:10.1038/ni1369
5. Chang V T, Fernandes R A, Ganzinger K A, et al. Initiation of T cell signaling by CD45 segregation at "close contacts." Nat Immunol. 2016. doi:10.1038/ni.3392
6. Razvag Y, Neve-Oz Y, Sajman J, Reches M, Sherman E. Nanoscale kinetic segregation of TCR and CD45 in engaged microvilli facilitates early T cell activation. Nat Commun. 2018. doi:10.1038/s41467-018-03127-w
7. Thiel N, Zischke J, Elbasani E, Kay-Fedorov P, Messerle M. Viral interference with functions of the cellular receptor tyrosine phosphatase CD45. Viruses. 2015. doi:10.3390/v7031540
8. Payne K K, Mine J A, Biswas S, et al. BTN3A1 governs antitumor responses by coordinating ab and gd T cells. Science (80-). 2020. doi:10.1126/science.aay2767

9. Bakalar M H, Joffe A M, Schmid E M, Son S, Podolski M, Fletcher D A. Size-Dependent Segregation Controls Macrophage Phagocytosis of Antibody-Opsonized Targets. Cell. 2018. doi:10.1016/j.cell.2018.05.059
10. Weidle U H, Tiefenthaler G, Georges G. Proteases as activators for cytotoxic prodrugs in antitumor therapy. Cancer Genomics and Proteomics. 2014.
11. Gialeli C, Theocharis A D, Karamanos N K. Roles of matrix metalloproteinases in cancer progression and their pharmacological targeting. FEBS J. 2011. doi:10.1111/j.1742-4658.2010.07919.x
12. Geiger M, Stubenrauch K G, Sam J, et al. Protease-activation using anti-idiotypic masks enables tumor specificity of a folate receptor 1-T cell bispecific antibody. Nat Commun. 2020. doi:10.1038/s41467-020-16838-w
13. Desnoyers L R, Vasiljeva O, Richardson J H, et al. Tumor-specific activation of an EGFR-targeting probody enhances therapeutic index. Sci Transl Med. 2013. doi: 10.1126/scitranslmed.3006682
14. Sommer C, Cheng H Y, Nguyen D, et al. Allogeneic FLT3 CAR T Cells with an Off-Switch Exhibit Potent Activity against AML and Can Be Depleted to Expedite Bone Marrow Recovery. Mol Ther. 2020. doi:10.1016/j.ymthe.2020.06.022
15. Sommer C, Boldajipour B, Kuo T C, et al. Preclinical Evaluation of Allogeneic CAR T Cells Targeting BCMA for the Treatment of Multiple Myeloma. Mol Ther. 2019. doi:10.1016/j.ymthe.2019.04.00

What is claimed is:

1. A protease-activating CD45-gate chimeric antigen receptor (CD45-gate CAR) comprising an extracellular domain, a transmembrane domain, and an intracellular domain, wherein the extracellular domain comprises:
   a CD45 recruiting domain comprising an anti-CD45 antibody, or an antigen binding fragment thereof,
   an antigen binding domain, and
   a linker comprising one or more protease cleavage sites that is cleavable by at least one protease.

2. The protease-activating CD45-gate CAR of claim 1, wherein the intracellular domain comprises at least one signaling domain that is reversibly inactivated by CD45.

3. The protease-activating CD45-gate CAR of claim 1, wherein the linker is between the CD45 recruiting domain and the antigen binding domain.

4. The protease-activating CD45-gate CAR of claim 1, wherein the CD45 recruiting domain comprises one or more linkers.

5. The CD45-gate CAR of claim 1, wherein the linker connects the carboxy terminus of the CD45 recruiting domain to the amino terminus of the antigen binding domain, and further wherein the intracellular domain comprises at least one signaling domain that is reversibly inactivated by CD45.

6. The protease-activating CD45-gate CAR of claim 1, wherein the CD45 recruiting domain comprises one or more of an anti-CD45 antibody antigen binding fragment.

7. The protease-activating CD45-gate CAR of claim 6, wherein the anti-CD45 antibody antigen binding fragment comprises an anti-CD45 scFv.

8. The protease-activating CD45-gate CAR of claim 1, wherein the CD45 recruiting domain comprises the amino acid sequence of SEQ ID NO: 3, SEQ ID NO: 4, SEQ ID NO: 5, or SEQ ID NO: 6, without the signal sequence of SEQ ID NO:1.

9. The protease-activating CD45-gate CAR of claim 1, wherein the antigen binding domain specifically binds BCMA, MUC16, EGFR, EGFRvIII, MUC1, Flt-3, WT-1, CD20, CD23, CD30, CD38, CD70, CD33, CD133, MHC-WT1, TSPAN10, MHC-PRAME, MHC-NY-ESO1, HER2, (Carbonic anhydrase IX, LIV1, ADAM10, CHRNA2, LeY, NKG2D, CS1, CD44v6, ROR1, CD19, Claudin-18.2.

10. The protease-activating CD45 gate CAR of claim 1, wherein the linker comprising at least one protease cleavage site has a length of 15-100 amino acids.

11. The protease-activating CD45-gate CAR of claim 1, wherein the linker comprises one or more protease cleavage sites that are cleavable by at least one protease which is present in a tumor microenvironment.

12. The protease-activating CD45-gate CAR of claim 1, wherein the linker comprises at least one protease cleavage site that is cleavable by a serine protease, a cysteine-type lysosomal protease, a metalloproteinase, a coagulation factor protease, or an aspartyl-type lysosomal protease.

13. The protease-activating CD45-gate CAR of claim 1, wherein the linker comprises at least one protease cleavage site that is cleavable by matrix metalloproteinase (MMP), matriptase (MT-SP1), trypsin, plasmin, prostate-specific antigen (PSA), urokinase plasminogen activator (uPA), urokinase plasminogen activator receptor (uPAR), legumain, a disintegrin and metalloproteinase (ADAM), a transmembrane Serine Protease (TMPRSS), Granzyme B, activated protein C, Caspase, Cathepsin, Chymase, Elastase, Guanidinobenzoatase, HtrA1, Human Neutrophil Elastase, Lactoferrin, Marapsin, NS3/4A, PACE4, tissue plasminogen activator (tPA), thrombin, DESC1, DPP-4, FAP, Hepsin, Matriptase-2, secretase, kallikrein-related peptidase (KLK), and tryptase.

14. The protease-activating CD45-gate CAR of claim 1, wherein the linker comprises one or more protease cleavage sites, wherein the protease cleavage site comprises the amino acid sequence of SEQ ID NO: 32, 91-98, 103-105 or SEQ ID NO: 106.

15. The protease-activating CD45-gate CAR of claim 1, wherein the linker comprises one or more amino acid sequences of SEQ ID NO: 53, 89, or 90.

16. The protease-activating CD45-gate CAR of claim 1, wherein the linker comprises one or more amino acid sequences of SEQ ID NO: 8-10, 53, 89, 90, 99-102, 107-120, 172-176 or SEQ ID NO: 177.

17. The protease-activating CD45-gate CAR of claim 1, wherein the linker comprises two or more protease cleavage sites and each cleavage site is the same as or different from any of the other cleavage sites.

18. The protease-activating CD45-gate CAR of claim 1, wherein the intracellular domain comprises the cytoplasmic signaling domain of one or more of CD3 zeta, CD28, and CD2.

19. The protease-activating CD45-gate CAR of claim 1, wherein the intracellular domain comprises at least one costimulatory domain.

20. The protease-activating CD45-gate CAR of claim 19, wherein the at least one costimulatory domain is a signaling region of CD28, OX-40, 4-1BB/CD137, CD2, CD7, CD27, CD30, CD40, inducible T cell costimulator (ICOS), lymphocyte function-associated antigen-1 (LFA-1), CD3 gamma, CD3 delta, CD3 epsilon, CD247, CD276 (B7-H3), LIGHT (TNFSF14), NKG2C, Ig alpha (CD79a), DAP-10, Fc gamma receptor, MHC class I molecule, Signaling Lymphocytic Activation Molecules (SLAM proteins), BTLA, a Toll ligand receptor, ICAM-1, CDS, GITR, BAFFR, HVEM (LIGHTR), KIRDS2, NKp80 (KLRF1), NKp44, NKp30, NKp46, CD19, CD4, CD8alpha, CD8beta, IL-2R beta, IL-2R gamma, IL-7R alpha, ITGA4, VLA1, ITGA6, ITGAD, ITGAE, ITGAL, IT GAM, ITGAX, ITGB1, ITGB7, NKG2D, TNFR2, TRANCE/RANKL, DNAMI (CD226), CD84, CD96 (Tactile), CEACAM1, CRT AM, Ly9 (CD229), CD 160 (BY55), PSGL1, CD100 (SEMA4D), CD69, SELPLG (CD162), LTBR, LAT, GADS, SLP-76, PAG/Cbp, CD 19a, a ligand that specifically binds with CD83, or any combination thereof.

21. The protease-activating CD45-gate CAR of claim 1, further comprising a signal sequence optionally wherein the signal sequence is a CD8 signal sequence comprising the amino acid sequence of SEQ ID NO: 1.

22. The protease-activating CD45-gate CAR of claim 1, wherein the protease-activating CD45-gate CAR comprises the amino acid sequence of any one of SEQ ID NOs: 11, 16-31, 56, 75, 76, 77, 78, 79, and 121-170 or a variant thereof, wherein the variant does not comprise the amino acid sequence of the HA tag of SEQ ID NO: 2, does not comprise the amino acid sequence of the V5 peptide motif of SEQ ID NO: 55, or does not comprise the signal sequence of SEQ ID NO: 1.

23. A nucleic acid encoding the protease-activating CD45-gate CAR of claim 1.

24. An engineered immune cell comprising the nucleic acid of claim 23.

25. A vector comprising the nucleic acid of claim 23.

26. The vector of claim 25, wherein the vector is an expression vector.

27. An engineered immune cell comprising the vector of claim 25.

28. An engineered immune cell comprising the protease-activating CD45-gate CAR of claim 1.

29. The engineered immune cell of claim 28, wherein the immune cell is a T cell, an NK cell, or a dendritic cell.

30. The engineered immune cell of claim 29, wherein the T cell is a tumor infiltrating lymphocyte, an iPSC-derived T cell, a TCR-expressing cell, or an NK-T cell.

31. A population of cells comprising at least about $1 \times 10^4$, $1 \times 10^5$, $1 \times 10^6$, $1 \times 10^7$ or $1 \times 10^8$ of the engineered immune cell of claim 28.

32. A pharmaceutical composition comprising the engineered immune cell of claim 28 and a pharmaceutically acceptable carrier.

33. A method of treating cancer in a patient comprising administering to the patient the engineered immune cell of claim 28, and wherein the cancer expresses an antigen that is recognized and bound by the antigen binding domain of the CD45-gate CAR.

34. The method of claim 33, wherein the cancer is a solid tumor cancer or a liquid tumor cancer.

35. A method of treating a patient who has a tumor characterized by a protease-rich tumor microenvironment, comprising administering to the patient the engineered immune cell of claim 28, and wherein the tumor expresses an antigen that is recognized and bound by the antigen binding domain of the CD45-gate CAR.

* * * * *